(12) United States Patent
Sugimoto et al.

(10) Patent No.: US 9,777,005 B2
(45) Date of Patent: Oct. 3, 2017

(54) BICYCLIC HETEROCYCLIC COMPOUND CONTAINING A SUBSTITUTED PYRROLE RING

(71) Applicant: Takeda Pharmaceutical Company Limited, Osaka-shi, Osaka (JP)

(72) Inventors: Takahiro Sugimoto, Kanagawa (JP); Minoru Nakamura, Kanagawa (JP); Hiroki Sakamoto, Kanagawa (JP); Shinkichi Suzuki, Kanagawa (JP); Masami Yamada, Kanagawa (JP); Makoto Kamata, Kanagawa (JP); Takuto Kojima, Kanagawa (JP); Ikuo Fujimori, Kanagawa (JP); Kenichiro Shimokawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/443,598

(22) PCT Filed: Nov. 18, 2013

(86) PCT No.: PCT/JP2013/081084
§ 371 (c)(1),
(2) Date: May 18, 2015

(87) PCT Pub. No.: WO2014/077401
PCT Pub. Date: May 22, 2014

(65) Prior Publication Data
US 2015/0307497 A1    Oct. 29, 2015

(30) Foreign Application Priority Data

Nov. 19, 2012  (JP) ................ 2012-253708

(51) Int. Cl.
*C07D 221/02* (2006.01)
*A61K 31/44* (2006.01)
(Continued)

(52) U.S. Cl.
CPC ......... *C07D 487/04* (2013.01); *C07D 209/46* (2013.01); *C07D 401/06* (2013.01); *C07D 401/14* (2013.01); *C07D 403/10* (2013.01); *C07D 403/14* (2013.01); *C07D 405/12* (2013.01); *C07D 405/14* (2013.01); *C07D 409/14* (2013.01); *C07D 413/12* (2013.01);
(Continued)

(58) Field of Classification Search
None
See application file for complete search history.

(56) References Cited

U.S. PATENT DOCUMENTS 8,110,681 B2    2/2012  Heemskerk et al.
2008/0108659 A1  5/2008  Gandhi et al.
(Continued)

FOREIGN PATENT DOCUMENTS

EP    0 560 604    9/1993
GB    1 433 774    4/1976
(Continued)

OTHER PUBLICATIONS

Cornelison, TL. Human papillomavirus genotype 16 vaccines for cervical cancer prophylaxis and treatment. Curr. Opin. Oncol. 2000, vol. 12(5), p. 466.*
Karran, E. et al. The amyloid cascade hypothesis for Alzheimer's disease: an appraisal for the development of therapeutics. Nature. 2011, vol. 10, p. 698.*
Schmitz, C. et al. Hippocampal Neuron Loss Exceeds Amyloid Plaque Load in a Transgenic Mouse Model of Alzheimer's Disease. American Journal of Pathology. 2004, vol. 164, p. 1495.*
Zhao, et al., "6,7-Dihydroxy-1-oxoisoindoline-4-sulfonamide-containing HIV-1 integrase inhibitors", Bioorganic & Medicinal Chemistry Letters, vol. 22, No. 24, Oct. 27, 2012, pp. 7309-7313.
(Continued)

*Primary Examiner* — Noble Jarrell
*Assistant Examiner* — Ben S Michelson
(74) *Attorney, Agent, or Firm* — Hamre, Schumann, Mueller & Larson, P.C.

(57) ABSTRACT

Provided is a compound having a cholinergic muscarinic M1 receptor positive allosteric modulator activity, and useful as a prophylactic or therapeutic drug for Alzheimer's disease, schizophrenia, pain, sleep disorder and the like. The present invention relates to a compound represented by the formula

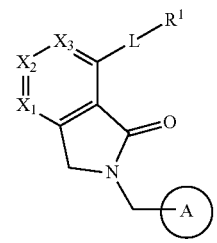

(I)

wherein ring A is a 4- to 7-membered ring optionally having substituent(s); L is —O—, —S—, —SO— or —SO$_2$—; R$^1$ is a C$_{1-6}$ alkyl group optionally having substituent(s) (provided that when L is —O—, R$^1$ is not a C$_{1-6}$ alkyl group optionally substituted by halogen atom(s)), or a cyclic group optionally having substituent(s); X$_1$ is —CRa═ or —N═; X$_2$ is —CRb═ or —N═; X$_3$ is —CRc═ or —N═; Ra, Rb and Rc are each a C$_{1-6}$ alkyl group, C$_{2-6}$ alkenyl group, C$_{1-6}$ alkoxy group, C$_{3-6}$ cycloalkyl group, C$_{3-6}$ cycloalkoxy group or C$_{6-14}$ aryl group, each of which optionally having substituent(s), H or halogen, or a salt thereof.

12 Claims, No Drawings

(51) Int. Cl.
| C07D 487/04 | (2006.01) |
| C07D 401/14 | (2006.01) |
| C07D 405/14 | (2006.01) |
| C07D 401/06 | (2006.01) |
| C07D 403/10 | (2006.01) |
| C07D 403/14 | (2006.01) |
| C07D 405/12 | (2006.01) |
| C07D 409/14 | (2006.01) |
| C07D 413/12 | (2006.01) |
| C07D 417/12 | (2006.01) |
| C07D 453/02 | (2006.01) |
| C07D 471/04 | (2006.01) |
| C07D 471/14 | (2006.01) |
| C07D 209/46 | (2006.01) |
| C07D 519/00 | (2006.01) |

(52) U.S. Cl.
CPC ......... *C07D 417/12* (2013.01); *C07D 453/02* (2013.01); *C07D 471/04* (2013.01); *C07D 471/14* (2013.01); *C07D 519/00* (2013.01)

(56) References Cited

U.S. PATENT DOCUMENTS

| 2009/0312323 | A1 | 12/2009 | Heemskerk et al. |
| 2011/0275630 | A1 | 11/2011 | Matulenko et al. |
| 2012/0083495 | A1 | 4/2012 | Heemskerk et al. |
| 2015/0126487 | A1 | 5/2015 | Sakamoto et al. |

FOREIGN PATENT DOCUMENTS

| JP | 64-061461 | 3/1989 |
| JP | 2-124871 | 5/1990 |
| JP | 2008-506692 | 3/2008 |
| JP | 2008-509926 | 5/2008 |
| JP | 2009-530306 | 8/2009 |
| WO | 91/05783 | 5/1991 |
| WO | 95/30647 | 11/1995 |
| WO | 01/19830 | 3/2001 |
| WO | WO 2005/021532 A1 * | 3/2005 |
| WO | 2006/019768 | 2/2006 |
| WO | 2006/020879 | 2/2006 |
| WO | 2007/059108 | 5/2007 |
| WO | 2007/067489 | 6/2007 |
| WO | 2007/100366 | 9/2007 |
| WO | 2007/139464 | 12/2007 |
| WO | 2008/002621 | 1/2008 |
| WO | 2009/051715 | 4/2009 |
| WO | 2009/053799 | 4/2009 |
| WO | 2009/094279 | 7/2009 |
| WO | 2009/102574 | 8/2009 |
| WO | 2009/102588 | 8/2009 |
| WO | 2009/117283 | 9/2009 |
| WO | 2009/134668 | 11/2009 |
| WO | 2010/019391 | 2/2010 |
| WO | 2010/042347 | 4/2010 |
| WO | 2010/047990 | 4/2010 |
| WO | 2010/059773 | 5/2010 |
| WO | 2010/096338 | 8/2010 |
| WO | 2010/123716 | 10/2010 |
| WO | 2011/006794 | 1/2011 |
| WO | 2011/025851 | 3/2011 |
| WO | 2011/041143 | 4/2011 |
| WO | 2011/049731 | 4/2011 |
| WO | 2011/062853 | 5/2011 |
| WO | 2011/075371 | 6/2011 |
| WO | 2011/084368 | 7/2011 |
| WO | 2011/084371 | 7/2011 |
| WO | 2011/137049 | 11/2011 |
| WO | 2011/149801 | 12/2011 |
| WO | 2011/159553 | 12/2011 |
| WO | 2011/159554 | 12/2011 |
| WO | 2011/163280 | 12/2011 |
| WO | 2012/003147 | 1/2012 |
| WO | 2013/063549 | 5/2013 |
| WO | 2013/129622 | 9/2013 |

OTHER PUBLICATIONS

Extended European Search Report issued in corresponding European Patent Application No. 13854399.6, Mar. 16, 2016, 7 pages.
Budzik, et al., "2' Biaryl amides as novel and subtype selective M1 agonists. Part II: Further optimization and profiling", Bioorganic & Medicinal Chemistry Letters, 2010, vol. 20, No. 12, pp. 3545-3549.
Bridges, et al., "Chemical lead optimization of a pan Gq mAChR M1, M3, M5 positive allosteric modulator (PAM) lead. Part II: Development of a potent and highly selective M1 PAM", Bioorganic & Medicinal Chemistry Letters, 2010, vol. 20, pp. 1972-1975.
Gordon, et al., "A facile, protic ionic liquid route to N-substituted 5-hydroxy-4-methyl-3-oxoisoindoline-1-carboxamides and N-substituted 3-oxoisoindoline-4-carboxylic acids", Green Chemistry, 2010, vol. 12, pp. 1000-1006.
Reddy, et al., "An Expeditious Synthesis of Some Novel N-Pyridyl-1,4-dihydro-4-oxo-3-quinoline Carboxylic Acids/Amides as Potential CB2 Cannabinoid Receptor Agonists", Asian Journal of Chemistry, vol. 23, No. 7, 2011, pp. 2981-2988.
Kuduk, et al., "Identification of Amides as Carboxylic Acid Surrogates for Quinolizidinone-Based M1 Positive Allosteric Modulators", ACS Medicinal Chemistry Letters, vol. 3, Oct. 13, 2012, pp. 1070-1074.
Wess, et al., "Muscarinic acetylcholine receptors: mutant mice provide new insights for drug development", Nature Reviews Drug Discovery, vol. 6, Sep. 2007, pp. 721-733.
Chen, et al., "Design, synthesis, and biological evaluation of novel quinoline derivatives as HIV-1 Tat-TAR interaction inhibitors", Bioorganic & Madicinal Chemistry, vol. 17, No. 5, 2009, pp. 1948-1956.
Stern, et al., "Pharmacomodulations around the 4-Oxo-1,4-dihydroquinoline-3-carboxamides, a Class of Potent CB2-Selective Cannabinoid Receptor Ligands: Consequences in Receptor Affinity and Functionality", Journal of Medicinal Chemistry, vol. 50, No. 22, 2007, pp. 5471-5484.
Tuccinardi, et al., "Structure-Based Virtual Screening: Identification of Novel CB2 Receptor Ligands", Letters in Drug Design & Discovery, vol. 4, No. 1, 2007, pp. 15-19.
Stern, et al., "Novel 4-Oxo-1,4-dihydroquinoline-3-carboxamide Derivatives as New CB2 Cannabinoid Receptors Agonists: Synthesis, Pharmacological Properties and Molecular Modeling", Journal of Medicinal Chemistry, vol. 49, No. 1, 2006, pp. 70-79.
Ward, et al., "Synthesis and Structure Activity Relationships of 4-Quinolonecarboxamides with 5-HT3 Antagonist Activity", Medicinal Chemistry Research, vol. 4, No. 4, 1993, pp. 267-272.
Gundel, et al., "Synthese and Reactions of [1.4]Diazepion[6.5-c]quinolines", Zeitschrift fur Naturforschung, 43b, 1998, pp. 769-777 with an English abstract.
Bohnert, et al., "Redox Reactions with Cyclopeptide-Like Quinoline Derivatives as Lipophilic NAD Model Compounds", Zeitschrift fur Naturforschung, 42b, 1987, pp. 1159-1166 with an English abstract.
Angelino, et al., :The Oxidation of 1-Alkyl(aryl)quinolinium Chlorides with Rabbit Liver Aldehyde Oxidase, Journal of Heterocyclic Chemistry, vol. 21, No. 1, 1984, pp. 107-112.
CAS Registry Nos. RN 1328835-66-0, RN 1329479-67-5, RN 1330047-24-9, RN 1330047-67-0, RN 1330126-62-9, RN 1329780-84-8, RN 1330126-45-8, RN 1329933-94-9, RN 1330242-66-4, RN 1401512-95-5, and RN 1401512-96-6, 3 pages.
Novelty Search Results, 163 pages.
International Search Report issued in International Application No. PCT/JP2013/055566, 4 pages, May 28, 2013.
Written Opinion of the International Searching Authority issued in International Application No. PCT/JP2013/055566, 6 pages, May 28, 2013.
International Search Report issued in International Application No. PCT/JP2013/081084, 9 pages, Apr. 8, 2014.

(56) References Cited

OTHER PUBLICATIONS

Extended European Search Report issued in the corresponding European Patent Application No. 13754154.6 dated Sep. 2, 2015 (9 pages).
Manera et al.: "New 1,8-naphthyridine and quinoline derivatives as CB2 selective agonists"; Bioorganic and Medicinal Chemistry Letters, vol. 17, No. 23, Nov. 2007, pp. 6505-6510 (6 pages).
Clementina Manera et al.: "Design, Synthesis and Biological Evaluation of New 1,8-Naphthyridin-4(1H)-on-3-carboxamide and Quinolin-4(1H)-on-3-carbonxamide Derivatives as CB2 Selective Agonists"; Journal of Medicinal Chemistry, vol. 49, No. 20, Oct. 2006, pp. 5947-5957 (11 pages).
Michelle Roche et al.: "Brain CB2 Receptors: Implications for Neuropsychiatric Disorders"; Pharmaceuticals, vol. 3, No. 8, Aug. 2010, pp. 2517-2553 (37 pages).

\* cited by examiner

BICYCLIC HETEROCYCLIC COMPOUND CONTAINING A SUBSTITUTED PYRROLE RING

TECHNICAL FIELD

The present invention relates to a nitrogen-containing heterocyclic compound having a cholinergic muscarinic M1 receptor positive allosteric modulator activity and useful as a medicament such as a prophylactic or therapeutic drug for Alzheimer's disease, schizophrenia, pain, sleep disorder and the like, and the like. As used herein, the positive allosteric modulator activity refers to an action to potentiate receptor function by binding to a moiety different from that of an endogenous activator (acetylcholine for this receptor).

BACKGROUND OF THE INVENTION

Acetylcholine is a neurotransmitter that transmits stimulation in the parasympathetic nerve and motor nerve. Acetylcholine receptor is classified into a ligand dependency ion channel (cholinergic nicotinic receptor) and a G-protein-conjugated receptor (cholinergic muscarinic receptor). The cholinergic muscarinic receptor is one kind of receptor for excitatory neurotransmitter acetylcholine, and was named based on the selective activation of the receptor by muscarine. The muscarinic receptor is further classified into subtypes of M1 to M5, and the M1 receptor is known to be widely distributed in the brain, and deeply involved particularly in learning, memory, sleep, neuropathic pain and the like. The importance of cholinergic muscarinic M1 receptor in brain physiology is well known, and a compound having an M1 receptor function enhancing action is expected to be useful as a prophylactic or therapeutic drug for mental diseases, neurodegenerative diseases, memory disorders, pain, sleep disorders and the like (non-patent document 1).

WO 2006/020879 (patent document 1) discloses the following compound as a metabotropic glutamate receptor potentiator:

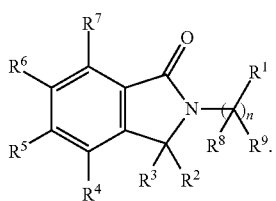

(I)

Bioorganic & Medicinal Chemistry Letters, 2010, 20, 1972-1975 (non-patent document 2) discloses the following compound and the like as a M1 receptor positive allosteric modulator:

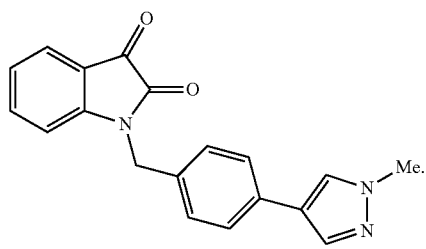 [SMILES: Cn1cc(-c2ccc(CN3C(=O)C(=O)c4ccccc43)cc2)cn1]

Green Chem., 2010, 12, 1000-1006 (non-patent document 3) discloses the following compounds:

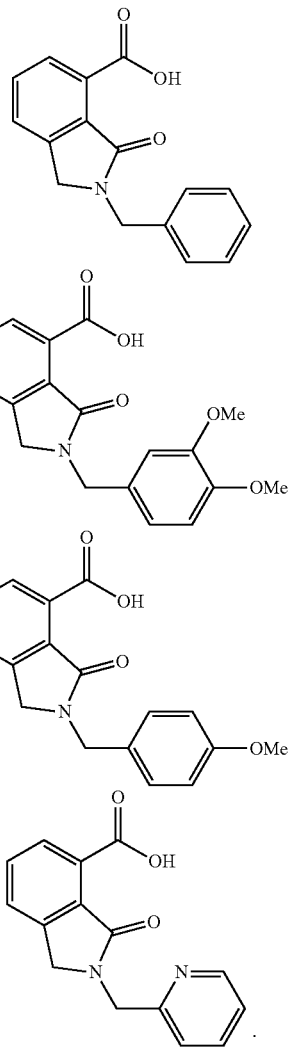

WO 2010/096338 (patent document 2) discloses the following compound as an M1 receptor positive allosteric modulator:

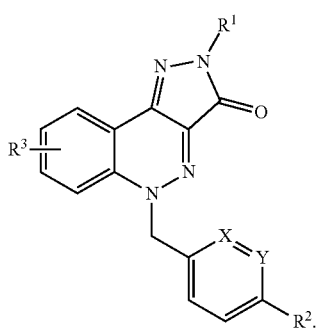

WO 95/30647 (patent document 3) discloses the following compound as a cholecystokinin (CCK) and gastrin receptor ligand:

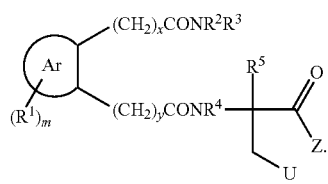

WO 2007/139464 (patent document 4) discloses the following compound as a compound useful for pain, gastrointestinal tract diseases, cancer, Parkinson's diseases, Alzheimer's diseases and the like:

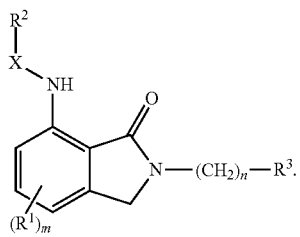

US 2008/0108659 (patent document 5) discloses the following compound as a compound having a poly(ADP-ribose)polymerase (PARP) inhibitory activity and useful for cancer, central nervous system diseases, inflammatory diseases and the like:

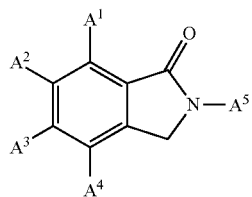

wherein $A^1$ is $C(O)NH_2$, and $A^5$ is phenyl, heteroaryl, cycloalkyl, heterocycloalkyl, alkyl and the like.

WO 2011/006794 (patent document 6) discloses the following compound as a compound having a poly(ADP-ribose)polymerase PARP-1 selective inhibitory activity and useful for cancer, cardiovascular disorders, central nervous disorders and the like:

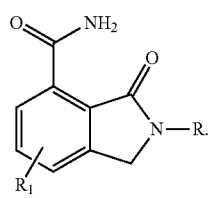

WO 2013/063549 (patent document 7) discloses the following compound as an M1 receptor positive allosteric modulator.

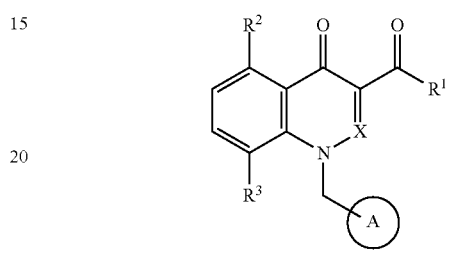

WO 2013/129622 (patent document 8) discloses the following compound as an M1 receptor positive allosteric modulator.

DOCUMENT LIST

Patent Documents patent document 1: WO 2006/020879
patent document 2: WO 2010/096338
patent document 3: WO 95/30647
patent document 4: WO 2007/139464
patent document 5: US 2008/0108659
patent document 6: WO 2011/006794
patent document 7: WO 2013/063549
patent document 8: WO 2013/129622

Non-Patent Documents non-patent document 1: Nature Reviews Drug Discovery, 2007, 6, 721-733
non-patent document 2: Bioorganic & Medicinal Chemistry Letters, 2010, 20, 1972-1975
non-patent document 3: Green Chem., 2010, 12, 1000-1006

SUMMARY OF THE INVENTION

Problems to be Solved by the Invention

The development of a compound having a cholinergic muscarinic M1 receptor (M1 receptor) positive allosteric modulator activity and useful as a prophylactic or therapeutic drug for Alzheimer's disease, schizophrenia, pain, sleep disorder and the like is desired. As used herein, the positive allosteric modulator activity means an action to bind to a site different from an endogenous active substance (acetylcholine in this receptor) and potentiate the receptor function.

Means of Solving the Problems

The present inventors have conducted intensive studies in an attempt to solve the aforementioned problems and found that a compound represented by the following formula (I) has a cholinergic muscarinic M1 receptor positive allosteric modulator activity, which resulted in the completion of the present invention.

Accordingly, the present invention relates to the following.

[1] A compound represented by the formula

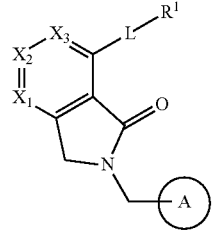

(I)

wherein
ring A is a 4- to 7-membered ring optionally having substituent(s);
L is —O—, —S—, —SO— or —SO$_2$—;
R$^1$ is a C$_{1-6}$ alkyl group optionally having substituent(s) (provided that when L is —O—, R$^1$ is not a C$_{1-6}$ alkyl group optionally substituted by halogen atom(s)), or a cyclic group optionally having substituent(s);
X$_1$ is —CRa═ or —N═;
X$_2$ is —CRb═ or —N═;
X$_3$ is —CRc═ or —N═;
Ra, Rb and Rc are each independently
a hydrogen atom,
a halogen atom,
a C$_{1-6}$ alkyl group optionally having substituent(s),
a C$_{2-6}$ alkenyl group optionally having substituent(s),
a C$_{1-6}$ alkoxy group optionally having substituent(s),
a C$_{3-6}$ cycloalkyl group optionally having substituent(s),
a C$_{3-6}$ cycloalkoxy group optionally having substituent(s) or
a C$_{6-14}$ aryl group optionally having substituent(s),
or a salt thereof (sometimes to be abbreviated as "compound (I)" in the present specification).

[2] The compound of the aforementioned [1], wherein L is —O—; and
R$^1$ is a cyclic group optionally having substituent(s) or a C$_{1-6}$ alkyl group having substituent(s) other than a halogen atom, or a salt thereof.

[2A] The compound of the aforementioned [2], wherein R$^1$ is a C$_{1-6}$ alkyl group having substituent(s) other than a halogen atom,
a C$_{3-8}$ cycloalkyl group optionally having substituent(s),
a phenyl group optionally having substituent(s),
a pyridyl group optionally having substituent(s),
a tetrahydropyranyl group optionally having substituent(s),
a tetrahydrothiopyranyl group optionally having substituent(s),
a pyrimidinyl group optionally having substituent(s),
a tetrahydronaphthyl group optionally having substituent(s),
a dihydrochromenyl group optionally having substituent(s),
a 6,7-dihydro-5H-cyclopentapyridyl group optionally having substituent(s),
a dihydrobenzofuryl group optionally having substituent(s), or
a pyrazolyl group optionally having substituent(s),
or a salt thereof.

[2B] The compound of the aforementioned [2], wherein ring A is
a benzene ring optionally having substituent(s),
a C$_{4-7}$ cycloalkane ring optionally having substituent(s),
a pyridine ring optionally having substituent(s),
a thiophene ring optionally having substituent(s),
a furan ring optionally having substituent(s), or
a piperidine ring optionally having substituent(s), or a salt thereof.

[2C] The compound of the aforementioned [2], wherein X$_1$, X$_2$ and X$_3$ are selected from the following combinations:
(1) X$_1$ is —CRa═, X$_2$ is —CRb═, and X$_3$ is —N═;
(2) X$_1$ is —N═, X$_2$ is —CRb═, and X$_3$ is —N═;
(3) X$_1$ is —CRa═, X$_2$ is —CRb═, and X$_3$ is —CRc═;
(4) X$_1$ is —CRa═, X$_2$ is —N═, and X$_3$ is —CRc═; and
(5) X$_1$ is —N═, X$_2$ is —CRb═, and X$_3$ is —CRc═; and
Ra, Rb and Rc are each independently
a hydrogen atom, a halogen atom, a C$_{1-6}$ alkyl group, a C$_{2-6}$ alkenyl group, or a phenyl group,
or a salt thereof.

[3] The compound of the aforementioned [2], wherein X$_1$, X$_2$ and X$_3$ are selected from the following combinations:
(1) X$_1$ is —CH═, X$_2$ is —CH═, and X$_3$ is —N═;
(2) X$_1$ is —N═, X$_2$ is —CH═, and X$_3$ is —N═; and
(3) X$_1$ is —CH═, X$_2$ is —CH═, and X$_3$ is —CH═;
or a salt thereof.

[3A] The compound of the aforementioned [2], wherein X$_1$ is —CH═, X$_2$ is —CH═, and X$_3$ is —N═, or a salt thereof.
[3B] The compound of the aforementioned [2], wherein X$_1$ is —N═, X$_2$ is —CH═, and X$_3$ is —N═, or a salt thereof.
[3C] The compound of the aforementioned [2], wherein each X$_1$, X$_2$ and X$_3$ is —CH═, or a salt thereof.
[3D] The compound of the aforementioned [2], wherein R$^1$ is
a C$_{1-6}$ alkyl group having substituent(s) other than a halogen atom,
a C$_{3-8}$ cycloalkyl group optionally having substituent(s),
a phenyl group optionally having substituent(s),
a pyridyl group optionally having substituent(s),
a tetrahydropyranyl group optionally having substituent(s),
a tetrahydrothiopyranyl group optionally having substituent(s),
a pyrimidinyl group optionally having substituent(s),
a tetrahydronaphthyl group optionally having substituent(s),
a dihydrochromenyl group optionally having substituent(s),
a 6,7-dihydro-5H-cyclopentapyridyl group optionally having substituent(s),
a dihydrobenzofuryl group optionally having substituent(s), or
a pyrazolyl group optionally having substituent(s), ring A is
a benzene ring optionally having substituent(s),
a C$_{4-7}$ cycloalkane ring optionally having substituent(s),
a pyridine ring optionally having substituent(s),
a thiophene ring optionally having substituent(s),
a furan ring optionally having substituent(s), or
a piperidine ring optionally having substituent(s),
X$_1$, X$_2$ and X$_3$ are selected from the following combinations:
(1) X$_1$ is —CRa═, X$_2$ is —CRb═, and X$_3$ is —N═;
(2) X$_1$ is —N═, X$_2$ is —CRb═, and X$_3$ is —N═;
(3) X$_1$ is —CRa═, X$_2$ is —CRb═, and X$_3$ is —CRc═;
(4) X$_1$ is —CRa═, X$_2$ is —N═, and X$_3$ is —CRc═; and
(5) X$_1$ is —N═, X$_2$ is —CRb═, and X$_3$ is —CRc═; and
Ra, Rb and Rc are each independently
a hydrogen atom, a halogen atom, a C$_{1-6}$ alkyl group, a C$_{2-6}$ alkenyl group, or a phenyl group,
or a salt thereof.

[3E] The compound of the aforementioned [2], wherein R$^1$ is (I) a C$_{3-8}$ cycloalkyl group, a C$_{6-14}$ aryl group, or a 4- to 10-membered heterocyclic group, each of which is optionally substituted by 1 to 3 substituents selected from
(1) a halogen atom,
(2) a cyano group, (3) a nitro group,
(4) an amino group,
(5) a hydroxy group,
(6) a $C_{1-6}$ alkyl group optionally having 1 to 5 substituents selected from (i) a halogen atom, (ii) a cyano group, (iii) a hydroxy group, (iv) a $C_{1-6}$ alkoxy group, and (v) an oxo group,
(7) a carbamoyl group,
(8) a $C_{1-6}$ alkoxy group optionally having 1 to 3 halogen atoms,
(9) a $C_{2-6}$ alkenyl group,
(10) a $C_{3-6}$ cycloalkyl group, and
(11) an oxo group; or
(II) a $C_{1-6}$ alkyl group substituted by 1 to 3 substituents selected from
(1) a cyano group,
(2) an amino group optionally substituted by 1 or 2 $C_{1-6}$ alkyl groups,
(3) a hydroxy group,
(4) a $C_{1-6}$ alkoxy-carbonyl group,
(5) a carboxy group,
(6) a carbamoyl group,
(7) a $C_{6-14}$ aryl-carbonyl group,
(8) a 4- to 10-membered heterocyclylcarbonyl group,
(9) a piperidylcarbonyl group,
(10) a $C_{1-6}$ alkoxy group,
(11) a $C_{6-14}$ aryl-$C_{1-6}$ alkoxy group,
(12) a $C_{6-14}$ aryloxy group,
(13) a $C_{3-6}$ cycloalkyl group optionally substituted by 1 to 3 $C_{1-6}$ alkyl groups,
(14) a $C_{6-14}$ aryl group optionally having 1 to 3 substituents selected from (a) a halogen atom, (b) a cyano group, (c) a $C_{1-6}$ alkyl group having 1 to 3 halogen atoms, (d) a $C_{1-6}$ alkoxy group, and (e) a $C_{6-14}$ aryl group, and
(15) a 4- to 10-membered heterocyclic group optionally having 1 to 3 substituents selected from a halogen atom, a cyano group, a $C_{1-6}$ alkoxy-carbonyl group, a $C_{1-6}$ alkyl group, and an oxo group;
ring A is a $C_{4-7}$ cycloalkane ring, a benzene ring, or a 4- to 7-membered heterocycle, each of which is optionally substituted by 1 to 3 substituents selected from
(1) a halogen atom,
(2) a cyano group,
(3) a carbamoyl group optionally having 1 or 2 substituents selected from
(a) a $C_{1-6}$ alkyl group optionally having 1 to 3 substituents selected from
(i) a halogen atom,
(ii) a phenyl group optionally having 1 to 3 halogen atoms,
(iii) a $C_{3-6}$ cycloalkyl group, and
(iv) a tetrahydrofuryl group, and
(b) a $C_{3-6}$ cycloalkyl group,
(4) a $C_{1-6}$ alkoxy-carbonyl group,
(5) a carboxy group,
(6) a $C_{1-6}$ alkoxy group optionally having 1 to 3 halogen atoms,
(7) a $C_{1-6}$ alkyl group optionally having 1 to 3 $C_{6-14}$ aryl groups having 1 to 3 halogen atoms,
(8) a $C_{2-6}$ alkenyl group optionally having 1 to 3 $C_{6-14}$ aryl groups optionally having 1 to 3 halogen atoms,
(9) a $C_{3-6}$ cycloalkyl group,
(10) a phenyl group having 1 to 3 $C_{1-6}$ alkoxy groups, and
(11) a 4- to 7-membered heterocyclic group optionally having 1 to 3 substituents selected from (a) a halogen atom, (b) a $C_{1-6}$ alkyl group optionally substituted by 1 to 3 substituents selected from a halogen atom and a $C_{3-6}$ cycloalkyl group, (c) a $C_{1-6}$ alkoxy group, (d) a benzyloxy group, (e) a hydroxy group, (f) a 4- to 7-membered heterocyclic group, and (g) an oxo group;
$X_1$, $X_2$ and $X_3$ are selected from the following combinations:
(1) $X_1$ is —CRa=, $X_2$ is —CRb=, and $X_3$ is —N=;
(2) $X_1$ is —N=, $X_2$ is —CRb=, and $X_3$ is —N=;
(3) $X_1$ is —CRa=, $X_2$ is —CRb=, and $X_3$ is —CRc=;
(4) $X_1$ is —CRa=, $X_2$ is —N=, and $X_3$ is —CRc=; and
(5) $X_1$ is —N=, $X_2$ is —CRb=, and $X_3$ is —CRc=; and
Ra, Rb and Rc are each independently
a hydrogen atom, a halogen atom, a $C_{1-6}$ alkyl group, a $C_{2-6}$ alkenyl group, or a $C_{6-14}$ aryl group,
or a salt thereof.

[3F] The compound of the aforementioned [2], wherein $R^1$ is (I) a $C_{3-8}$ cycloalkyl group, a phenyl group, a pyridyl group, a tetrahydropyranyl group, a 6,7-dihydro-5H-cyclopentapyridyl group, or a pyrazolyl group, each of which is optionally substituted by 1 to 3 substituents selected from
(1) a halogen atom,
(2) a cyano group,
(3) a nitro group,
(4) an amino group,
(5) a hydroxy group,
(6) a $C_{1-6}$ alkyl group optionally having 1 to 5 substituents selected from (i) a halogen atom, (ii) a cyano group, (iii) a hydroxy group, and (iv) a $C_{1-6}$ alkoxy group,
(7) a $C_{1-6}$ alkoxy group optionally having 1 to 3 halogen atoms,
(8) a $C_{2-6}$ alkenyl group, and
(9) a $C_{3-6}$ cycloalkyl group; or
(II) a $C_{1-6}$ alkyl group substituted by 1 to 3 substituents selected from
(1) a hydroxy group,
(2) a $C_{1-6}$ alkoxy-carbonyl group,
(3) a carboxy group,
(4) a piperidylcarbonyl group,
(5) a $C_{3-6}$ cycloalkyl group optionally substituted by 1 to 3 $C_{1-6}$ alkyl groups,
(6) a phenyl group substituted by 1 to 3 halogen atoms, and
(7) a tetrahydrofuryl group, a pyrrolidinyl group, a piperidyl group, a pyrazolyl group, a tetrahydropyranyl group, a pyridyl group, or a 7-oxabicyclo[2.2.1]heptyl group, each of which is optionally substituted by 1 to 3 substituents selected from a halogen atom and a $C_{1-6}$ alkoxy-carbonyl group;
ring A is a benzene ring, a $C_{4-7}$ cycloalkane ring, a pyridine ring, a thiophene ring, a furan ring, or a piperidine ring, each of which is optionally substituted by 1 to 3 substituents selected from
(1) a halogen atom,
(2) a cyano group,
(3) a carbamoyl group optionally monosubstituted by a $C_{1-6}$ alkyl group optionally substituted by 1 to 3 tetrahydrofuryl groups,
(4) a $C_{1-6}$ alkoxy-carbonyl group,
(5) a $C_{3-6}$ cycloalkyl group, and
(6) a pyrazolyl group, a piperidyl group, a pyridyl group, a pyridazinyl group, a triazolyl group, an imidazolyl group, an isoxazolyl group, a pyrazolopyridyl group, or a 4,5,6,7-tetrahydropyrazolopyridyl group, each of which optionally has 1 to 3 substituents selected from (i) a halogen atom, (ii) a $C_{1-6}$ alkyl group optionally substituted by 1 to 3 substituents selected from a halogen atom and a $C_{3-6}$ cycloalkyl group, and (iii) a tetrahydropyranyl group;
$X_1$, $X_2$ and $X_3$ are selected from the following combinations:

(1) $X_1$ is —CRa═, $X_2$ is —CRb═, and $X_3$ is —N═;
(2) $X_1$ is —N═, $X_2$ is —CRb═, and $X_3$ is —N═;
(3) $X_1$ is —CRa═, $X_2$ is —CRb═, and $X_3$ is —CRc═;
(4) $X_1$ is —CRa═, $X_2$ is —N═, and $X_3$ is —CRc═; and
(5) $X_1$ is —N═, $X_2$ is —CRb═, and $X_3$ is —CRc═; and
Ra, Rb and Rc are each independently
a hydrogen atom, a halogen atom, or a $C_{2-6}$ alkenyl group,
or a salt thereof.

[4] The compound of the aforementioned [2], wherein $R^1$ is
(I) a $C_{3-6}$ cycloalkyl group, a phenyl group, a pyridyl group, a tetrahydropyranyl group, a 6,7-dihydro-5H-cyclopentapyridyl group, or a pyrazolyl group, each of which is optionally substituted by 1 to 3 substituents selected from
  (1) a halogen atom,
  (2) a cyano group,
  (3) a nitro group,
  (4) an amino group,
  (5) a hydroxy group,
  (6) a $C_{1-6}$ alkyl group optionally having 1 to 5 substituents selected from (i) a halogen atom, (ii) a cyano group, (iii) a hydroxy group, and (iv) a $C_{1-6}$ alkoxy group,
  (7) a $C_{1-6}$ alkoxy group optionally having 1 to 3 halogen atoms,
  (8) a $C_{2-6}$ alkenyl group, and
  (9) a $C_{3-6}$ cycloalkyl group; or
(II) a $C_{1-6}$ alkyl group substituted by 1 to 3 substituents selected from
  (1) a hydroxy group,
  (2) a $C_{1-6}$ alkoxy-carbonyl group,
  (3) a carboxy group,
  (4) a piperidylcarbonyl group,
  (5) a $C_{3-6}$ cycloalkyl group optionally substituted by 1 to 3 $C_{1-6}$ alkyl groups,
  (6) a phenyl group substituted by 1 to 3 halogen atoms, and
  (7) a tetrahydrofuryl group, a pyrrolidinyl group, a piperidyl group, a pyrazolyl group, a tetrahydropyranyl group, a pyridyl group, or a 7-oxabicyclo[2.2.1]heptyl group, each of which optionally has 1 to 3 substituents selected from a halogen atom and a $C_{1-6}$ alkoxy-carbonyl group;
ring A is a benzene ring, a $C_{4-7}$ cycloalkane ring, a pyridine ring, a thiophene ring, a furan ring, or a piperidine ring, each of which is optionally substituted by 1 to 3 substituents selected from
(1) a halogen atom,
(2) a cyano group,
(3) a carbamoyl group optionally monosubstituted by a $C_{1-6}$ alkyl group optionally substituted by 1 to 3 tetrahydrofuryl groups,
(4) a $C_{1-6}$ alkoxy-carbonyl group,
(5) a $C_{3-6}$ cycloalkyl group, and
(6) a pyrazolyl group, a piperidyl group, a pyridyl group, a pyridazinyl group, a triazolyl group, an imidazolyl group, an isoxazolyl group, a pyrazolopyridyl group, or a 4,5,6,7-tetrahydropyrazolopyridyl group, each of which optionally has 1 to 3 substituents selected from (i) a halogen atom, (ii) a $C_{1-6}$ alkyl group optionally substituted by 1 to 3 substituents selected from a halogen atom and a $C_{3-6}$ cycloalkyl group, and (iii) a tetrahydropyranyl group;
$X_1$, $X_2$ and $X_3$ are selected from the following combinations:
(1) $X_1$ is —CH═, $X_2$ is —CH═, and $X_3$ is —N═;
(2) $X_1$ is —N═, $X_2$ is —CH═, and $X_3$ is —N═; and
(3) $X_1$ is —CH═, $X_2$ is —CH═, and $X_3$ is —CH═;
or a salt thereof.

[4A] The compound of the aforementioned [4], wherein $X_1$ is —CH═, $X_2$ is —CH═, and $X_3$ is —N═, or a salt thereof.

[4B] The compound of the aforementioned [4], wherein $X_1$ is —N═, $X_2$ is —CH═, and $X_3$ is —N═, or a salt thereof.
[4C] The compound of the aforementioned [4], wherein each of $X_1$, $X_2$ and $X_3$ is —CH═, or a salt thereof.

[5] The compound of the aforementioned [2], wherein $R^1$ is a $C_{3-8}$ cycloalkyl group, a phenyl group, a pyridyl group, or a tetrahydropyranyl group, each of which is optionally substituted by 1 to 3 substituents selected from
(1) a halogen atom,
(2) a cyano group,
(3) a hydroxy group,
(4) a $C_{1-6}$ alkyl group optionally having 1 to 5 substituents selected from (i) a halogen atom, (ii) a cyano group, (iii) a hydroxy group, and (iv) a $C_{1-6}$ alkoxy group,
(5) a $C_{1-6}$ alkoxy group optionally having 1 to 3 halogen atoms, and
(6) a $C_{3-6}$ cycloalkyl group;
ring A is a benzene ring or a pyridine ring, each of which is substituted by 1 to 3 substituents selected from
(1) a halogen atom,
(2) a carbamoyl group,
(3) a pyrazolyl group substituted by 1 to 3 $C_{1-6}$ alkyl groups, and
(4) a triazolyl group substituted by 1 or 2 $C_{1-6}$ alkyl groups; and
$X_1$, $X_2$ and $X_3$ are selected from the following combinations:
(1) $X_1$ is —CH═, $X_2$ is —CH═, and $X_3$ is —N═;
(2) $X_L$ is —N═, $X_2$ is —CH═, and $X_3$ is —N═; and
(3) $X_1$ is —CH═, $X_2$ is —CH═, and $X_3$ is —CH═;
or a salt thereof.

[5A] The compound of the aforementioned [5], wherein $X_1$ is —CH═, $X_2$ is —CH═, and $X_3$ is —N═, or a salt thereof.
[5B] The compound of the aforementioned [5], wherein $X_1$ is —N═, $X_2$ is —CH═, and $X_3$ is —N═, or a salt thereof.
[5C] The compound of the aforementioned [5], wherein each of $X_1$, $X_2$ and $X_3$ is —CH═, or a salt thereof.

[6] The compound of the aforementioned [2], wherein $R^1$ is a phenyl group or a pyridyl group, each of which is optionally substituted by 1 to 3 substituents selected from
(1) a halogen atom,
(2) a cyano group,
(3) a $C_{1-6}$ alkyl group optionally having 1 to 3 halogen atoms,
(4) a $C_{1-6}$ alkoxy group optionally having 1 to 3 halogen atoms, and
(5) a $C_{3-6}$ cycloalkyl group;
ring A is a benzene ring or a pyridine ring, each of which is substituted by 1 to 3 substituents selected from
(1) a halogen atom,
(2) a carbamoyl group,
(3) a pyrazolyl group substituted by 1 to 3 $C_{1-6}$ alkyl groups, and
(4) a triazolyl group substituted by 1 or 2 $C_{1-6}$ alkyl groups; and
$X_1$, $X_2$ and $X_3$ are selected from the following combinations:
(1) $X_1$ is —CH═, $X_2$ is —CH═, and $X_3$ is —N═;
(2) $X_1$ is —N═, $X_2$ is —CH═, and $X_3$ is —N═; and
(3) $X_1$ is —CH═, $X_2$ is —CH═, and $X_3$ is —CH═;
or a salt thereof.

[6A] The compound of the aforementioned [6], wherein $X_1$, $X_2$ and $X_3$ are selected from the following combinations:
(1) $X_1$ is —CH═, $X_2$ is —CH═, and $X_3$ is —N═; and
(2) $X_1$ is —N═, $X_2$ is —CH═, and $X_3$ is —N═; or a salt thereof.

[6B] The compound of the aforementioned [6], wherein $X_1$ is —CH═, $X_2$ is —CH═, and $X_3$ is —N═, or a salt thereof.

[6C] The compound of the aforementioned [6], wherein $X_1$ is —N=, $X_2$ is —CH=, and $X_3$ is —N=, or a salt thereof.
[6D] The compound of the aforementioned [6], wherein each of $X_1$, $X_2$ and $X_3$ is —CH=, or a salt thereof.
[7] The compound of the aforementioned [2], wherein $R^1$ is
(I) a $C_{1-6}$ alkyl group substituted by 1 to 3 substituents selected from
  (1) a phenyl group substituted by 1 to 3 halogen atoms, and
  (2) a tetrahydrofuryl group, or
(II) a $C_{3-8}$ cycloalkyl group, a phenyl group, a pyridyl group, or a tetrahydropyranyl group, each of which is substituted by 1 to 3 substituents selected from
  (1) a halogen atom,
  (2) a cyano group,
  (3) a hydroxy group, and
  (4) a $C_{1-6}$ alkyl group substituted by 1 to 3 halogen atoms;
ring A is a benzene ring or a pyridine ring, each of which is substituted by 1 to 3 substituents selected from
(1) a halogen atom,
(2) a carbamoyl group,
(3) a pyrazolyl group substituted by 1 to 3 $C_{1-6}$ alkyl groups, and
(4) a triazolyl group substituted by 1 or 2 $C_{1-6}$ alkyl groups; and
$X_1$, $X_2$ and $X_3$ are selected from the following combinations:
(1) $X_1$ is —CH=, $X_2$ is —CH=, and $X_3$ is —N=;
(2) $X_1$ is —N=, $X_2$ is —CH=, and $X_3$ is —N=; and
(3) each of $X_1$, $X_2$ and $X_3$ is —CH=;
or a salt thereof.
[8] The compound of the aforementioned [2], wherein $R^1$ is a phenyl group or a pyridyl group, each of which is substituted by 1 to 3 substituents selected from
(1) a halogen atom,
(2) a cyano group, and
(3) a $C_{1-6}$ alkyl group substituted by 1 to 3 halogen atoms;
ring A is a benzene ring or a pyridine ring, each of which is substituted by 1 to 3 substituents selected from
(1) a halogen atom,
(2) a carbamoyl group,
(3) a pyrazolyl group substituted by 1 to 3 $C_{1-6}$ alkyl groups, and
(4) a triazolyl group substituted by 1 or 2 $C_{1-6}$ alkyl groups; and
$X_1$, $X_2$ and $X_3$ are selected from the following combinations:
(1) $X_1$ is —CH=, $X_2$ is —CH=, and $X_3$ is —N=; and
(2) $X_1$ is —N=, $X_2$ is —CH=, and $X_3$ is —N=;
or a salt thereof.
[8A] The compound of the aforementioned [2], wherein $R^1$ is a phenyl group or a pyridyl group, each of which is substituted by 1 to 3 substituents selected from
(1) a halogen atom,
(2) a cyano group, and
(3) a $C_{1-6}$ alkyl group substituted by 1 to 3 halogen atoms;
ring A is a benzene ring substituted by 1 to 3 substituents selected from
(1) a halogen atom,
(2) a carbamoyl group,
(3) a pyrazolyl group substituted by 1 to 3 $C_{1-6}$ alkyl groups, and
(4) a triazolyl group substituted by 1 or 2 $C_{1-6}$ alkyl groups; and
$X_1$, $X_2$ and $X_3$ are selected from the following combinations:
(1) $X_1$ is —CH=, $X_2$ is —CH=, and $X_3$ is —N=; and
(2) $X_1$ is —N=, $X_2$ is —CH=, and $X_3$ is —N=;
or a salt thereof.

[8B] The compound of the aforementioned [8], wherein $X_1$ is —CH=, $X_2$ is —CH=, and $X_3$ is —N=, or a salt thereof.
[8C] The compound of the aforementioned [8], wherein $X_1$ is —N=, $X_2$ is —CH=, and $X_3$ is —N=, or a salt thereof.
[8D] The compound of the aforementioned [2], wherein $R^1$ is a phenyl group or a pyridyl group, each of which is optionally substituted by 1 to 3 $C_{1-6}$ alkyl groups optionally substituted by 1 to 5 substituents selected from
(1) a halogen atom,
(2) a cyano group,
(3) a hydroxy group, and
(4) a $C_{1-6}$ alkoxy group;
ring A is a benzene ring or a pyridine ring, each of which is substituted by 1 to 3 substituents selected from
(1) a halogen atom,
(2) a carbamoyl group,
(3) a pyrazolyl group substituted by 1 to 3 $C_{1-6}$ alkyl groups, and
(4) a triazolyl group substituted by 1 or 2 $C_{1-6}$ alkyl groups; and
$X_1$, $X_2$ and $X_3$ are selected from the following combinations:
(1) $X_1$ is —CH=, $X_2$ is —CH=, and $X_3$ is —N=;
(2) $X_1$ is —N=, $X_2$ is —CH=, and $X_3$ is —N=; and
(3) each of $X_1$, $X_2$ and $X_3$ is —CH=;
or a salt thereof.
[8E] The compound of the aforementioned [8D], wherein $X_1$ is —CH=, $X_2$ is —CH=, and $X_3$ is —N=, or a salt thereof.
[8F] The compound of the aforementioned [8D], wherein $X_1$ is —N=, $X_2$ is —CH=, and $X_3$ is —N=, or a salt thereof.
[9] 2-(4-(1-Methyl-1H-pyrazol-4-yl)benzyl)-7-((tetrahydrofuran-2-yl)methoxy)isoindolin-1-one, or a salt thereof.
[10] 3-Fluoro-2-((2-(4-(1-methyl-1H-pyrazol-4-yl)benzyl)-3-oxo-2,3-dihydro-1H-isoindol-4-yl)oxy)benzonitrile, or a salt thereof.
[11] 4-((2,4-Difluorobenzyl)oxy)-6-(4-(1-methyl-1H-1,2,3-triazol-4-yl)benzyl)-6,7-dihydro-5H-pyrrolo[3,4-d]pyrimidin-5-one, or a salt thereof.
[12] 4-((4-(2-Fluoro-4-(trifluoromethyl)phenoxy)-3-oxo-1,3-dihydro-2H-pyrrolo[3,4-c]pyridin-2-yl)methyl)benzamide, or a salt thereof.
[13] A medicament comprising the compound of any one of the aforementioned [1] to [12] or a salt thereof.
[14] The medicament of the aforementioned [13], which is a cholinergic muscarinic M1 receptor positive allosteric modulator.
[15] The medicament of the aforementioned [13], which is a prophylactic or therapeutic agent for Alzheimer's disease, schizophrenia, pain or a sleep disorder.
[16] The compound of any one of the aforementioned [1] to [12]
or a salt thereof for use in the prophylaxis or treatment of Alzheimer's disease, schizophrenia, pain or a sleep disorder.
[17] A method of cholinergic muscarinic M1 receptor positive allosteric modulation in a mammal, comprising administering an effective amount of the compound of any one of the aforementioned [1] to [12] or a salt thereof to said mammal.
[18] A method for the prophylaxis or treatment of Alzheimer's disease, schizophrenia, pain or a sleep disorder in a mammal, comprising administering an effective amount of the compound of any one of the aforementioned [1] to [12] or a salt thereof to said mammal.
[19] Use of the compound of any one of the aforementioned [1] to [12] or a salt thereof in the production of a prophylactic or therapeutic agent for Alzheimer's disease, schizophrenia, pain or a sleep disorder.

Effect of the Invention

The compound of the present invention has a cholinergic muscarinic M1 receptor positive allosteric modulator activity, and is useful as a prophylactic or therapeutic drug for, for example, Alzheimer's disease, schizophrenia, pain, sleep disorder and the like.

DETAILED DESCRIPTION OF THE INVENTION

The present invention is explained in detail in the following.

Examples of the "halogen atom" include a fluorine atom, a chlorine atom, a bromine atom and an iodine atom.

The "$C_{1-6}$ alkyl group" means a straight chain or branched chain $C_{1-6}$ alkyl group, and examples thereof include methyl, ethyl, propyl, isopropyl, butyl, isobutyl, sec-butyl, tert-butyl, pentyl, isopentyl, neopentyl, tert-pentyl, 1,2-dimethylpropyl, hexyl, 2-methylpentyl, 3-methylpentyl, 1,2-dimethylbutyl, 1,2,2-trimethylpropyl and the like.

The "$C_{1-6}$ alkyl group optionally having 1 to 3 halogen atoms" means a straight chain or branched chain $C_{1-6}$ alkyl group optionally having 1 to 3 halogen atoms (e.g., fluorine atom, chlorine atom, bromine atom, iodine atom), and examples thereof include methyl, ethyl, propyl, isopropyl, butyl, fluoromethyl, difluoromethyl, trifluoromethyl, 1,1-difluoroethyl, 2,2-difluoroethyl, 2,2,2-trifluoroethyl, chloromethyl, 2-chloroethyl, 2,2,2-trichloroethyl, bromomethyl, 2-bromoethyl and the like.

The "$C_{2-6}$ alkenyl group" means a straight chain or branched chain $C_{2-6}$ alkenyl group, and examples thereof include vinyl, allyl, 1-propenyl, 2-propenyl, 1-butenyl, 2-butenyl, 3-butenyl and the like.

The "$C_{1-6}$ alkoxy group" means a straight chain or branched chain $C_{1-6}$ alkoxy group, and examples thereof include methoxy, ethoxy, propoxy, isopropoxy, butoxy, isobutoxy, sec-butoxy, tert-butoxy, pentyloxy, isopentyloxy, neopentyloxy, tert-pentyloxy, 1,2-dimethylpropyloxy, hexyloxy, 2-methylpentyloxy, 3-methylpentyloxy, 1,2-dimethylbutyloxy, 1,2,2-trimethylpropyloxy and the like.

The "$C_{1-6}$ alkoxy group optionally having 1 to 3 halogen atoms" means a straight chain or branched chain $C_{1-6}$ alkoxy group optionally having 1 to 3 halogen atoms (e.g., fluorine atom, chlorine atom, bromine atom, iodine atom), and examples thereof include methoxy, ethoxy, propoxy, isopropoxy, butoxy, fluoromethoxy, difluoromethoxy, trifluoromethoxy, 1,1-difluoroethoxy, 2,2-difluoroethoxy, 2,2,2-trifluoroethoxy, chloromethoxy, 2-chloroethoxy, 2,2,2-trichloroethoxy, bromomethoxy, 2-bromoethoxy and the like.

Examples of the "$C_{3-6}$ cycloalkyl group" include cyclopropyl, cyclobutyl, cyclopentyl and cyclohexyl.

Examples of the "$C_{3-6}$ cycloalkoxy group" include cyclopropyloxy, cyclobutyloxy, cyclopentyloxy, and cyclohexyloxy.

Examples of the "$C_{6-14}$ aryl group" include phenyl, naphthyl (e.g., 1-naphthyl, 2-naphthyl), anthryl, phenanthryl and the like. Preferred is a $C_{6-10}$ aryl group such as phenyl, naphthyl and the like, and more preferred is phenyl.

Examples of the "4- to 7-membered ring" include a benzene ring, a $C_{4-7}$ cycloalkane ring, a $C_{4-7}$ cycloalkene ring, a 4- to 7-membered heterocycle and the like.

Examples of the "$C_{4-7}$ cycloalkane ring" include a cyclobutane ring, a cyclopentane ring, a cyclohexane ring, and a cycloheptane ring.

Examples of the "$C_{4-7}$ cycloalkene ring" include a cyclobutene ring, a cyclopentene ring, a cyclohexene ring, and a cycloheptene ring.

Examples of the "4- to 7-membered heterocycle" include a 4- to 7-membered (preferably 5- or 6-membered) heterocycle containing 1 to 4 (preferably 1 to 3, more preferably 1 or 2) hetero atoms selected from a nitrogen atom, a sulfur atom and an oxygen atom. Examples thereof include
5- or 6-membered aromatic heterocycles such as a thiophene ring, a furan ring, a pyrrole ring, an imidazole ring, a pyrazole ring, a thiazole ring, an isothiazole ring, an oxazole ring, an isoxazole ring, a pyridine ring, a pyrazine ring, a pyrimidine ring, a pyridazine ring, a 1,2,4-oxadiazole ring, a 1,3,4-oxadiazole ring, a 1,2,4-thiadiazole ring, a 1,3,4-thiadiazole ring, a 1,2,3-triazole ring, a 1,2,4-triazole ring, a tetrazole ring, a furazan ring, a pyran ring and the like;
4- to 7-membered non-aromatic heterocycles such as an azetidine ring, an oxetane ring, a pyrrolidine ring, a tetrahydrofuran ring, a tetrahydrothiophene ring, a piperidine ring, a tetrahydropyran ring, a morpholine ring, a thiomorpholine ring, a piperazine ring, an azepane ring, a diazepane ring (e.g., 1,4-diazepane ring), an oxazepane ring (e.g., 1,4-oxazepane ring), an oxazolidine ring, an isoxazolidine ring, a thiazolidine ring, an isothiazolidine ring, an imidazolidine ring, a pyrazolidine ring, an oxadiazolidine ring (e.g., 1,2,4-oxadiazolidine ring, 1,3,4-oxadiazolidine ring), a thiadiazolidine ring (e.g., 1,2,4-thiadiazolidine ring, 1,3,4-thiadiazolidine ring), a pyrroline ring, an oxazoline ring, an isoxazoline ring, a thiazoline ring, an isothiazoline ring, an imidazoline ring, a pyrazoline ring, an oxadiazoline ring (e.g., 1,2,4-oxadiazoline ring, 1,3,4-oxadiazoline ring), a thiadiazoline ring (e.g., 1,2,4-thiadiazoline ring, 1,3,4-thiadiazoline ring), a tetrahydropyridine ring (e.g., 1,2,3,6-tetrahydropyridine ring) and the like, and the like.

Examples of the "cyclic group" include a $C_{3-8}$ cycloalkyl group, a $C_{3-8}$ cycloalkenyl group, a $C_{6-14}$ aryl group, a tetrahydronaphthyl group, a heterocyclic group and the like.

Examples of the "$C_{3-8}$ cycloalkyl group" include cyclopropyl, cyclobutyl, cyclopentyl, cyclohexyl, cycloheptyl, and cyclooctyl.

Examples of the "$C_{3-8}$ cycloalkenyl group" include cyclopropenyl, cyclobutenyl, cyclopentenyl, cyclohexenyl, cycloheptenyl, and cyclooctenyl.

Examples of the "heterocyclic group" include a 4- to 14-membered (preferably 4- to 10-membered, more preferably 4- to 7-membered, further preferably 5- or 6-membered) (monocyclic, bicyclic or tricyclic, preferably monocyclic or bicyclic) heterocyclic group containing 1 to 4 (preferably 1 to 3, more preferably 1 or 2) hetero atoms selected from a nitrogen atom, a sulfur atom and an oxygen atom. Examples thereof include monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, furazanyl, pyranyl and the like;
fused polycyclic (preferably bicyclic or tricyclic) aromatic heterocyclic groups such as benzothienyl, benzofuranyl, benzimidazolyl, benzoxazolyl, benzothiazolyl, benzisothiazolyl, phenoxathiinyl, indolyl, isoindolyl, 1H-indazolyl, purinyl, 4H-quinolizinyl, isoquinolyl, quinolyl, phthalazinyl, naphthyridinyl, quinoxalinyl, quinazolinyl, cinnolinyl, carbazolyl, β-carbolinyl, phenanthridinyl, acrydinyl, phenazinyl, phenothiazinyl, phenoxazinyl, imidazopyridyl (e.g., imidazo[1,2-a]pyridyl) and the like;

nonaromatic heterocyclic groups such as azetidinyl, oxetanyl, pyrrolidinyl, tetrahydrofuryl, tetrahydrothienyl, piperidyl, tetrahydropyranyl, morpholinyl, thiomorpholinyl, piperazinyl, azepanyl, diazepanyl (e.g., 1,4-diazepanyl), oxazepanyl (e.g., 1,4-oxazepanyl), oxazolidinyl, isoxazolidinyl, thiazolidinyl, isothiazolidinyl, imidazolidinyl, pyrazolidinyl, oxadiazolidinyl (e.g., 1,2,4-oxadiazolidinyl, 1,3,4-oxadiazolidinyl), thiadiazolidinyl (e.g., 1,2,4-thiadiazolidinyl, 1,3,4-thiadiazolidinyl), pyrrolinyl, oxazolinyl, isoxazolinyl, thiazolinyl, isothiazolinyl, imidazolinyl, pyrazolinyl, oxadiazolinyl (e.g., 1,2,4-oxadiazolinyl, 1,3,4-oxadiazolinyl), thiadiazolinyl (e.g., 1,2,4-thiadiazolinyl, 1,3,4-thiadiazolinyl), tetrahydropyridyl (e.g., 1,2,3,6-tetrahydropyridyl), tetrahydroimidazopyridyl (e.g., 5,6,7,8-tetrahydroimidazo[1,5-a]pyridyl), dihydroisoindolyl (e.g., 2,3-dihydro-1H-isoindolyl), 1-azabicyclo[2.2.1]heptyl, tetrahydrothiopyranyl, dihydrochromenyl, 6,7-dihydro-5H-cyclopentapyridyl, dihydrobenzofuryl, 7-oxabicyclo[2.2.1]heptyl, 1,4-dioxanyl and the like; and the like.

Examples of the "4- to 10-membered heterocyclic group" include 4- to 10-membered heterocyclic groups from the aforementioned "heterocyclic groups". Examples thereof include tetrahydrofuryl, pyrrolidinyl, piperidyl, pyrazolyl, tetrahydropyranyl, oxetanyl, pyridyl, 5,6,7,8-tetrahydroimidazo[1,5-a]pyridyl, morpholinyl, imidazolyl, 2,3-dihydro-1H-isoindolyl, 1-azabicyclo[2.2.1]heptyl, pyrrolyl, 1,4-dioxanyl, 7-oxabicyclo[2.2.1]heptyl, thiazolyl and the like.

Examples of the "4- to 7-membered heterocyclic group" include a 4- to 7-membered (preferably 5- or 6-membered) heterocyclic group containing 1 to 4 (preferably 1 to 3, more preferably 1 or 2) hetero atoms selected from a nitrogen atom, a sulfur atom and an oxygen atom. Examples thereof include 5- or 6-membered aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, 1,2,3-triazolyl, 1,2,4-triazolyl, tetrazolyl, furazanyl, pyranyl and the like;

4- to 7-membered nonaromatic heterocyclic groups such as azetidinyl, oxetanyl, pyrrolidinyl, tetrahydrofuryl, tetrahydrothienyl, piperidyl, tetrahydropyranyl, morpholinyl, thiomorpholinyl, piperazinyl, azepanyl, diazepanyl (e.g., 1,4-diazepanyl), oxazepanyl (e.g., 1,4-oxazepanyl), oxazolidinyl, isoxazolidinyl, thiazolidinyl, isothiazolidinyl, imidazolidinyl, pyrazolidinyl, oxadiazolidinyl (e.g., 1,2,4-oxadiazolidinyl, 1,3,4-oxadiazolidinyl), thiadiazolidinyl (e.g., 1,2,4-thiadiazolidinyl, 1,3,4-thiadiazolidinyl), pyrrolinyl, oxazolinyl, isoxazolinyl, thiazolinyl, isothiazolinyl, imidazolinyl, pyrazolinyl, oxadiazolinyl (e.g., 1,2,4-oxadiazolinyl, 1,3,4-oxadiazolinyl), thiadiazolinyl (e.g., 1,2,4-thiadiazolinyl, 1,3,4-thiadiazolinyl), tetrahydropyridyl (e.g., 1,2,3,6-tetrahydropyridyl) and the like; and the like.

Examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl and the like.

Examples of the "$C_{6-14}$ aryl-carbonyl group" include benzoyl, naphthoyl (e.g., 1-naphthoyl, 2-naphthoyl) and the like. Preferred is a $C_{6-10}$ aryl-carbonyl group, and more preferred is benzoyl.

Examples of the "heterocyclylcarbonyl group" include a heterocyclecarbonyl group wherein the heterocycle moiety is a 4- to 7-membered heterocyclic group containing 1 to 4 hetero atoms selected from a nitrogen atom, a sulfur atom and an oxygen atom, such as azetidinylcarbonyl, pyrrolidinylcarbonyl, piperidylcarbonyl and the like.

Examples of the "4- to 10-membered heterocyclylcarbonyl group" include a heterocyclylcarbonyl group wherein the heterocycle moiety is a 4- to 10-membered heterocyclic group from the aforementioned "heterocyclic groups". Examples thereof include azetidinylcarbonyl, pyrrolidinylcarbonyl, piperidylcarbonyl and the like.

Examples of the $C_{6-14}$ aryl-$C_{1-6}$ alkoxy group" include benzyloxy, 2-phenylethyloxy, 1-phenylethyloxy, 3-phenylpropyloxy and the like. Preferred is a $C_{6-10}$ aryl-$C_{1-6}$ alkoxy group, and more preferred is benzyloxy.

Examples of the "$C_{6-14}$ aryloxy group" include phenoxy, naphthyloxy (e.g., 1-naphthyloxy, 2-naphthyloxy) and the like. Preferred is a $C_{6-10}$ aryloxy group, and more preferred is phenoxy.

Ring A is a 4- to 7-membered ring optionally having substituent(s).

Examples of the "4- to 7-membered ring" of the "4- to 7-membered ring optionally having substituent(s)" for ring A include a benzene ring, a $C_{4-7}$ cycloalkane ring (e.g., cyclohexane ring), a 4- to 7-membered heterocycle (preferably, 4- to 7-membered heterocycle containing 1 to 4 hetero atoms selected from a nitrogen atom, a sulfur atom and an oxygen atom, for example, a pyridine ring, a thiophene ring, a furan ring, a piperidine ring) and the like.

Examples of the "substituent" of the "4- to 7-membered ring optionally having substituent(s)" for ring A include 1 to 3 substituents selected from the following substituent group A.

[Substituent Group A]
(1) a halogen atom,
(2) a cyano group,
(3) a nitro group,
(4) an amino group,
(5) a hydroxy group,
(6) a carbamoyl group optionally having 1 or 2 substituents selected from
  (a) a $C_{1-6}$ alkyl group optionally having 1 to 3 substituents selected from
    (i) a halogen atom,
    (ii) a $C_{6-14}$ aryl group (e.g., phenyl) optionally having 1 to 3 halogen atoms,
    (iii) a $C_{3-6}$ cycloalkyl group, and
    (iv) a heterocyclic group (e.g., tetrahydrofuryl), and
  (b) a $C_{3-6}$ cycloalkyl group,
(7) a $C_{1-6}$ alkoxy-carbonyl group,
(8) a carboxy group,
(9) a $C_{1-6}$ alkoxy group optionally having 1 to 3 halogen atoms,
(10) a $C_{1-6}$ alkyl group optionally having 1 to 3 $C_{6-14}$ aryl groups (e.g., phenyl) optionally having 1 to 3 halogen atoms,
(11) a $C_{2-6}$ alkenyl group optionally having 1 to 3 $C_{6-14}$ aryl groups (e.g., phenyl) optionally having 1 to 3 halogen atoms,
(12) a $C_{3-6}$ cycloalkyl group,
(13) a $C_{6-14}$ aryl group (e.g., phenyl) optionally having 1 to 3 substituents selected from a halogen atom, a cyano group and a $C_{1-6}$ alkoxy group, and
(14) a heterocyclic group (preferably, a 4- to 10-membered (preferably 4- to 7-membered) heterocyclic group containing 1 to 4 hetero atoms selected from a nitrogen atom, a sulfur atom and an oxygen atom, for example, pyrazolyl, piperidyl, pyridyl, pyridazinyl, triazolyl, imidazolyl, furyl, pyrrolidinyl, thienyl, isoxazolyl, pyrimidinyl, thiazolyl, isothiazolyl, tetrahydropyridyl (e.g., 1,2,3,6-tetrahydropyridyl), pyrrolyl, pyrazolopyridyl, tetrahydropyrazolopyridyl) optionally having 1 to 3 substituents selected from (a) a halogen atom, (b) a $C_{1-6}$ alkyl group optionally substituted by 1 to 3 substituents selected from a halogen atom and a $C_{3-6}$ cycloalkyl group, (c) a $C_{1-6}$ alkoxy group, (d) a $C_{6-14}$ aryl-$C_{1-6}$ alkoxy group (e.g., benzyloxy), (e) a hydroxy group, (f) a 4- to 7-membered heterocyclic group (e.g., tetrahydropyranyl) and (g) an oxo group.

Ring A is preferably
a benzene ring optionally having substituent(s),
a $C_{4-7}$ cycloalkane ring (e.g., a cyclohexane ring) optionally having substituent(s), or
a 4- to 7-membered heterocycle (preferably, a 4- to 7-membered heterocycle containing 1 to 4 hetero atoms selected from a nitrogen atom, a sulfur atom and an oxygen atom, for example, a pyridine ring, a thiophene ring, a furan ring, a piperidine ring) optionally having substituent(s).

Ring A is more preferably
a benzene ring, a $C_{4-7}$ cycloalkane ring (e.g., a cyclohexane ring), or a 4- to 7-membered heterocycle (preferably, a 4- to 7-membered heterocycle containing 1 to 4 hetero atoms selected from a nitrogen atom, a sulfur atom and an oxygen atom, for example, a pyridine ring, a thiophene ring, a furan ring, a piperidine ring), each of which optionally has 1 to 3 substituents selected from
(1) a halogen atom,
(2) a cyano group,
(3) a carbamoyl group optionally having 1 or 2 substituents selected from
  (a) a $C_{1-6}$ alkyl group optionally having 1 to 3 substituents selected from
    (i) a halogen atom,
    (ii) a $C_{6-14}$ aryl group (e.g., phenyl) optionally having 1 to 3 halogen atoms,
    (iii) a $C_{3-6}$ cycloalkyl group, and
    (iv) a heterocyclic group (e.g., tetrahydrofuryl), and
  (b) a $C_{3-6}$ cycloalkyl group,
(4) a $C_{1-6}$ alkoxy-carbonyl group,
(5) a carboxy group,
(6) a $C_{1-6}$ alkoxy group optionally having 1 to 3 halogen atoms,
(7) a $C_{1-6}$ alkyl group optionally having 1 to 3 $C_{6-14}$ aryl groups (e.g., phenyl) optionally having 1 to 3 halogen atoms,
(8) a $C_{2-6}$ alkenyl group optionally having 1 to 3 $C_{6-14}$ aryl groups (e.g., phenyl) optionally having 1 to 3 halogen atoms,
(9) a $C_{3-6}$ cycloalkyl group,
(10) a $C_{6-14}$ aryl group (e.g., phenyl) optionally having 1 to 3 substituents selected from a halogen atom, a cyano group and a $C_{1-6}$ alkoxy group, and
(11) a heterocyclic group (preferably, a 4- to 10-membered (preferably 4- to 7-membered) heterocyclic group containing 1 to 4 hetero atoms selected from a nitrogen atom, a sulfur atom and an oxygen atom, for example, pyrazolyl, piperidyl, pyridyl, pyridazinyl, triazolyl, imidazolyl, furyl, pyrrolidinyl, thienyl, isoxazolyl, pyrimidinyl, thiazolyl, isothiazolyl, tetrahydropyridyl (e.g., 1,2,3,6-tetrahydropyridyl), pyrrolyl, thiadiazolyl, oxadiazolyl, pyrazolopyridyl, tetrahydropyrazolopyridyl) optionally having 1 to 3 substituents selected from (a) a halogen atom, (b) a $C_{1-6}$ alkyl group optionally substituted by 1 to 3 substituents selected from a halogen atom and a $C_{3-6}$ cycloalkyl group, (c) a $C_{1-6}$ alkoxy group, (d) a $C_{6-14}$ aryl-$C_{1-6}$ alkoxy group (e.g., benzyloxy), (e) a hydroxy group, (f) a 4- to 7-membered heterocyclic group (e.g., tetrahydropyranyl) and (g) an oxo group.

Ring A is further preferably
a benzene ring, a $C_{4-7}$ cycloalkane ring (e.g., a cyclohexane ring), or a 4- to 7-membered heterocycle (preferably, a 4- to 7-membered heterocycle containing 1 to 4 hetero atoms selected from a nitrogen atom, a sulfur atom and an oxygen atom, for example, a pyridine ring, a thiophene ring, a furan ring, a piperidine ring), each of which optionally has 1 to 3 substituents selected from
(1) a halogen atom,
(2) a carbamoyl group,
(3) a $C_{1-6}$ alkoxy group, and
(4) a heterocyclic group (preferably, a 4- to 7-membered heterocyclic group containing 1 to 4 hetero atoms selected from a nitrogen atom, a sulfur atom and an oxygen atom, for example, pyrazolyl, piperidyl, pyridyl, pyridazinyl, triazolyl, imidazolyl, furyl, pyrrolidinyl, thienyl, isoxazolyl, pyrimidinyl, thiazolyl, isothiazolyl, tetrahydropyridyl (e.g., 1,2,3,6-tetrahydropyridyl), pyrrolyl) optionally having 1 to 3 substituents selected from a $C_{1-6}$ alkyl group, a $C_{1-6}$ alkoxy group, a $C_{6-14}$ aryl-$C_{1-6}$ alkoxy group (e.g., benzyloxy), a hydroxy group, a heterocyclic group (e.g., tetrahydropyranyl) and an oxo group.

Ring A is further more preferably
a benzene ring, a $C_{4-7}$ cycloalkane ring (e.g., a cyclohexane ring), or a 4- to 7-membered heterocycle (preferably, a 4- to 7-membered heterocycle containing 1 to 4 hetero atoms selected from a nitrogen atom, a sulfur atom and an oxygen atom, for example, a piperidine ring), each of which optionally has 1 to 3 substituents selected from
(1) a halogen atom,
(2) a carbamoyl group, and
(3) a 5- or 6-membered aromatic heterocyclic group (preferably a 5- or 6-membered aromatic heterocyclic group containing 1 to 4 hetero atoms selected from a nitrogen atom, a sulfur atom and an oxygen atom, for example, pyrazolyl, pyridyl) optionally having 1 to 3 $C_{1-6}$ alkyl groups.

Ring A is particularly preferably a benzene ring having a 5- or 6-membered aromatic heterocyclic group optionally having 1 to 3 $C_{1-6}$ alkyl groups. The 5- or 6-membered aromatic heterocyclic group is preferably selected from pyrazolyl, pyridyl, pyridazinyl, triazolyl, imidazolyl, furyl, thienyl, isoxazolyl, pyrimidinyl, thiazolyl, isothiazolyl and pyrroly, and more preferably selected from pyrazolyl and pyridyl.

L is —O—, —S—, —SO— or —SO$_2$—. L is preferably —O— or —SO—, more preferably —O—.

$R^1$ is a $C_{1-6}$ alkyl group optionally having substituent(s) (provided that when L is —O—, $R^1$ is not a $C_{1-6}$ alkyl group optionally substituted by halogen atom(s)), or a cyclic group optionally having substituent(s).

Examples of the "substituent" of the "$C_{1-6}$ alkyl group optionally having substituent(s)" for $R^1$ include 1 to 3 substituents selected from the following substituent group B.

[Substituent Group B]
(1) a halogen atom,
(2) a cyano group,
(3) a nitro group,
(4) an amino group optionally substituted by 1 or 2 $C_{1-6}$ alkyl groups,
(5) a hydroxy group,
(6) a $C_{1-6}$ alkoxy-carbonyl group,
(7) a carboxy group,
(8) a carbamoyl group, (9) a $C_{6-14}$ aryl-carbonyl group (e.g., benzoyl),
(10) a heterocyclylcarbonyl group (e.g., azetidinylcarbonyl, piperidylcarbonyl),
(11) a $C_{1-6}$ alkoxy group,
(12) a $C_{6-14}$ aryl-$C_{1-6}$ alkoxy group (e.g., benzyloxy),
(13) a $C_{6-14}$ aryloxy group (e.g., phenoxy),
(14) a $C_{3-6}$ cycloalkyl group,
(15) a $C_{6-14}$ aryl group (e.g., phenyl) optionally having 1 to 3 substituents selected from (a) a halogen atom, (b) a cyano group, (c) a $C_{1-6}$ alkyl group optionally having 1 to 3 halogen atoms, (d) a $C_{1-6}$ alkoxy group and (e) a $C_{6-14}$ aryl group (e.g., phenyl), and
(16) a heterocyclic group (preferably a 4- to 10-membered heterocyclic group containing 1 to 4 hetero atoms selected from a nitrogen atom, a sulfur atom and an oxygen atom, for example, tetrahydrofuryl, pyrrolidinyl, piperidyl, pyrazolyl, tetrahydropyranyl, oxetanyl, pyridyl, tetrahydroimidazopyridyl (e.g., 5,6,7,8-tetrahydroimidazo[1,5-a]pyridyl), morpholinyl, imidazolyl, dihydroisoindolyl (e.g., 2,3-dihydro-1H-isoindolyl), 1-azabicyclo[2.2.1]heptyl, pyrrolyl, imidazopyridyl (e.g., imidazo[1,2-a]pyridyl), 1,4-dioxanyl, 7-oxabicyclo[2.2.1]heptyl, thiazolyl) optionally having 1 to 3 substituents selected from a halogen atom, a cyano group, a $C_{1-6}$ alkoxy-carbonyl group, a $C_{1-6}$ alkyl group, and an oxo group.

Examples of the "cyclic group" of the "cyclic group optionally having substituent(s)" for $R^1$ include a $C_{3-8}$ cycloalkyl group (e.g., cyclopentyl, cyclohexyl, cycloheptyl), a $C_{6-14}$ aryl group (e.g., phenyl), a tetrahydronaphthyl group, a heterocyclic group (preferably, a 4- to 10-membered (preferably 4- to 7-membered) heterocyclic group containing 1 to 4 hetero atoms selected from a nitrogen atom, a sulfur atom and an oxygen atom, for example, pyridyl, pyrazolyl, tetrahydropyranyl, tetrahydrothiopyranyl, pyrimidinyl, dihydrochromenyl, 6,7-dihydro-5H-cyclopentapyridyl, dihydrobenzofuryl) and the like.

Examples of the "substituent" of the "cyclic group optionally having substituent(s) for $R^1$ include 1 to 5 (preferably 1 to 3) substituents selected from the following substituent group C.

[Substituent Group C]
(1) a halogen atom,
(2) a cyano group,
(3) a nitro group,
(4) an amino group,
(5) a hydroxy group,
(6) a $C_{1-6}$ alkyl group optionally having 1 to 5 substituents selected from (i) a halogen atom, (ii) a cyano group, (iii) a hydroxy group, (iv) a $C_{1-6}$ alkoxy group and (v) an oxo group,
(7) a carbamoyl group,
(8) a $C_{1-6}$ alkoxy group optionally having 1 to 3 halogen atoms,
(9) a $C_{2-6}$ alkenyl group,
(10) a $C_{3-6}$ cycloalkyl group, and
(11) an oxo group.

$R^1$ is preferably
a $C_{1-6}$ alkyl group optionally having substituent(s) (provided that when L is —O—, $R^1$ is not a $C_{1-6}$ alkyl group optionally substituted by halogen atom(s)),
a $C_{3-8}$ cycloalkyl group (e.g., cyclopentyl, cyclohexyl, cycloheptyl) optionally having substituent(s),
a $C_{6-14}$ aryl group (e.g., phenyl) optionally having substituent(s), or
a heterocyclic group (preferably, a 4- to 7-membered heterocyclic group containing 1 to 4 hetero atoms selected from a nitrogen atom, a sulfur atom and an oxygen atom, for example, pyridyl, pyrazolyl, tetrahydropyranyl) optionally having substituent(s).

$R^1$ is more preferably
(A) a $C_{1-6}$ alkyl group having 1 to 3 substituents selected from
(1) a halogen atom,
(2) a hydroxy group,
(3) a $C_{1-6}$ alkoxy-carbonyl group,
(4) a carboxy group,
(5) a carbamoyl group,
(6) a $C_{6-14}$ aryl-carbonyl group (e.g., benzoyl),
(7) a heterocyclylcarbonyl group (e.g., azetidinylcarbonyl, piperidylcarbonyl),
(8) a $C_{1-6}$ alkoxy group,
(9) a $C_{6-14}$ aryl-$C_{1-6}$ alkoxy group (e.g., benzyloxy),
(10) a $C_{6-14}$ aryloxy group (e.g., phenoxy),
(11) a $C_{3-6}$ cycloalkyl group,
(12) a $C_{6-14}$ aryl group optionally having 1 to 3 substituents selected from (a) a halogen atom, (b) a cyano group, (c) a $C_{1-6}$ alkyl group optionally having 1 to 3 halogen atoms and (d) a $C_{6-14}$ aryl group, and
(13) a heterocyclic group (preferably a 4- to 10-membered heterocyclic group containing 1 to 4 hetero atoms selected from a nitrogen atom, a sulfur atom and an oxygen atom, for example, tetrahydrofuryl, pyrrolidinyl, piperidyl, pyrazolyl, tetrahydropyranyl, oxetanyl, pyridyl, tetrahydroimidazopyridyl (e.g., 5,6,7,8-tetrahydroimidazo[1,5-a]pyridyl), morpholinyl, imidazolyl, dihydroisoindolyl (e.g., 2,3-dihydro-1H-isoindolyl), 1-azabicyclo[2.2.1]heptyl, pyrrolyl, imidazopyridyl (e.g., imidazo[1,2-a]pyridyl)) optionally having 1 to 3 substituents selected from a halogen atom, a $C_{1-6}$ alkoxy-carbonyl group, a $C_{1-6}$ alkyl group and an oxo group, or (B) a $C_{3-8}$ cycloalkyl group (e.g., cyclopentyl, cyclohexyl, cycloheptyl),
a $C_{6-14}$ aryl group (e.g., phenyl), or
a heterocyclic group (preferably, a 4- to 7-membered heterocyclic group containing 1 to 4 hetero atoms selected from a nitrogen atom, a sulfur atom and an oxygen atom, for example, pyridyl, pyrazolyl, tetrahydropyranyl), each of which optionally has 1 to 5 (preferably 1 to 3) substituents selected from
(1) a halogen atom,
(2) a cyano group,
(3) a nitro group,
(4) an amino group,
(5) a hydroxy group,
(6) a carbamoyl group,
(7) a $C_{1-6}$ alkyl group optionally having 1 to 3 halogen atoms, and
(8) a $C_{1-6}$ alkoxy group.

Another preferable embodiment of $R^1$ is a $C_{1-6}$ alkyl group having 1 to 3 substituents selected from
(1) a halogen atom,
(2) a hydroxy group,
(3) a $C_{1-6}$ alkoxy-carbonyl group,
(4) a carboxy group,
(5) a carbamoyl group,
(6) a $C_{6-14}$ aryl-carbonyl group (e.g., benzoyl),
(7) a heterocyclylcarbonyl group (e.g., azetidinylcarbonyl, piperidylcarbonyl),
(8) a $C_{1-6}$ alkoxy group,
(9) a $C_{6-14}$ aryl-$C_{1-6}$ alkoxy group (e.g., benzyloxy),
(10) a $C_{6-14}$ aryloxy group (e.g., phenoxy),
(11) a $C_{3-6}$ cycloalkyl group,

(12) a $C_{6-14}$ aryl group optionally having 1 to 3 substituents selected from (a) a halogen atom, (b) a cyano group, (c) a $C_{1-6}$ alkyl group optionally having 1 to 3 halogen atoms and (d) a $C_{6-14}$ aryl group, and

(13) a heterocyclic group (preferably, a 4- to 10-membered heterocyclic group containing 1 to 4 hetero atoms selected from a nitrogen atom, a sulfur atom and an oxygen atom, for example, tetrahydrofuryl, pyrrolidinyl, piperidyl, pyrazolyl, tetrahydropyranyl, oxetanyl, pyridyl, tetrahydroimidazopyridyl (e.g., 5,6,7,8-tetrahydroimidazo[1,5-a]pyridyl), morpholinyl, imidazolyl, dihydroisoindolyl (e.g., 2,3-dihydro-1H-isoindolyl), 1-azabicyclo[2.2.1]heptyl, pyrrolyl, imidazopyridyl (e.g., imidazo[1,2-a]pyridyl)) optionally having 1 to 3 substituents selected from a halogen atom, a $C_{1-6}$ alkoxy-carbonyl group, a $C_{1-6}$ alkyl group and an oxo group (provided that when L is —O—, $R^1$ is not a $C_{1-6}$ alkyl group optionally substituted by halogen atom(s)).

A further preferable embodiment of $R^1$ is a $C_{1-6}$ alkyl group having 1 to 3 substituents selected from
(1) a hydroxy group,
(2) a $C_{1-6}$ alkoxy-carbonyl group,
(3) a carboxy group,
(4) a carbamoyl group,
(5) a $C_{6-14}$ aryl-carbonyl group (e.g., benzoyl),
(6) a heterocyclylcarbonyl group (e.g., azetidinylcarbonyl, piperidylcarbonyl),
(7) a $C_{1-6}$ alkoxy group,
(8) a $C_{6-14}$ aryl-$C_{1-6}$ alkoxy group (e.g., benzyloxy),
(9) a $C_{6-14}$ aryloxy group (e.g., phenoxy),
(10) a $C_{3-6}$ cycloalkyl group,
(11) a $C_{6-14}$ aryl group optionally having 1 to 3 substituents selected from (a) a halogen atom, (b) a cyano group, (c) a $C_{1-6}$ alkyl group optionally having 1 to 3 halogen atoms and (d) a $C_{6-14}$ aryl group, and
(12) a heterocyclic group (preferably a 4- to 10-membered heterocyclic group containing 1 to 4 hetero atoms selected from a nitrogen atom, a sulfur atom and an oxygen atom, for example, tetrahydrofuryl, pyrrolidinyl, piperidyl, pyrazolyl, tetrahydropyranyl, oxetanyl, pyridyl, tetrahydroimidazopyridyl (e.g., 5,6,7,8-tetrahydroimidazo[1,5-a]pyridyl), morpholinyl, imidazolyl, dihydroisoindolyl (e.g., 2,3-dihydro-1H-isoindolyl), 1-azabicyclo[2.2.1]heptyl, pyrrolyl, imidazopyridyl (e.g., imidazo[1,2-a]pyridyl)) optionally having 1 to 3 substituents selected from a halogen atom, a $C_{1-6}$ alkoxy-carbonyl group, a $C_{1-6}$ alkyl group and an oxo group.

$R^1$ is further more preferably tetrahydrofuran-2-ylmethyl.

Another preferable embodiment of $R^1$ is
a $C_{3-8}$ cycloalkyl group (e.g., cyclopentyl, cyclohexyl, cycloheptyl),
a $C_{6-14}$ aryl group (e.g., phenyl), or
a heterocyclic group (preferably, a 4- to 7-membered heterocyclic group containing 1 to 4 hetero atoms selected from a nitrogen atom, a sulfur atom and an oxygen atom, for example, pyridyl, pyrazolyl, tetrahydropyranyl), each of which optionally has 1 to 5 (preferably 1 to 3) substituents selected from
(1) a halogen atom,
(2) a cyano group,
(3) a nitro group,
(4) an amino group,
(5) a hydroxy group,
(6) a carbamoyl group,
(7) a $C_{1-6}$ alkyl group optionally having 1 to 3 halogen atoms, and
(8) a $C_{1-6}$ alkoxy group.

Another preferable embodiment of $R^1$ is a $C_{3-8}$ cycloalkyl group (e.g., cyclopentyl, cyclohexyl, cycloheptyl) optionally having 1 to 3 substituents selected from a halogen atom and a hydroxy group.

$R^1$ is further preferably 2-hydroxycyclohexyl.

Another preferable embodiment of $R^1$ is a $C_{6-14}$ aryl group (e.g., phenyl) optionally having 1 to 5 (preferably 1 to 3) substituents selected from
(1) a halogen atom,
(2) a cyano group,
(3) a nitro group,
(4) an amino group,
(5) a carbamoyl group,
(6) a $C_{1-6}$ alkyl group optionally having 1 to 3 halogen atoms, and
(7) a $C_{1-6}$ alkoxy group.

$R^1$ is further preferably a phenyl group having 1 to 3 substituents selected from a halogen atom and a cyano group. $R^1$ is further more preferably 2-cyano-6-fluorophenyl.

Another preferable embodiment of $R^1$ is a heterocyclic group (preferably a 4- to 7-membered heterocyclic group containing 1 to 4 hetero atoms selected from a nitrogen atom, a sulfur atom and an oxygen atom, for example, pyridyl, pyrazolyl, tetrahydropyranyl) optionally having 1 to 3 substituents selected from a halogen atom, a cyano group and a $C_{1-6}$ alkyl group.

Another preferable embodiment of $R^1$ is
(A) a $C_{1-6}$ alkyl group having 1 to 3 substituents selected from
 (1) a heterocyclylcarbonyl group (e.g., piperidylcarbonyl) and
 (2) a 5- or 6-membered heterocyclic group (preferably a 5- or 6-membered heterocyclic group containing 1 to 4 hetero atoms selected from a nitrogen atom, a sulfur atom and an oxygen atom, for example, tetrahydrofuryl, piperidyl, pyrazolyl) optionally having $C_{1-6}$ alkoxy-carbonyl group(s), or (B) a $C_{3-8}$ cycloalkyl group (e.g., cyclopentyl, cyclohexyl, cycloheptyl) or a phenyl group, each of which optionally has 1 to 3 substituents selected from
 (1) a halogen atom,
 (2) a cyano group,
 (3) an amino group, and
 (4) a hydroxy group.

$X_1$ is —CRa= or —N=;
$X_2$ is —CRb= or —N=;
$X_3$ is —CRc= or —N=; and
Ra, Rb and Rc are each independently
a hydrogen atom,
a halogen atom,
a $C_{1-6}$ alkyl group optionally having substituent(s),
a $C_{2-6}$ alkenyl group optionally having substituent(s),
a $C_{1-6}$ alkoxy group optionally having substituent(s),
a $C_{3-6}$ cycloalkyl group optionally having substituent(s),
a $C_{3-6}$ cycloalkoxy group optionally having substituent(s) or
a $C_{6-14}$ aryl group optionally having substituent(s).

Examples of the "substituent" of the aforementioned "$C_{1-6}$ alkyl group optionally having substituent(s)", "$C_{2-6}$ alkenyl group optionally having substituent(s)", "$C_{1-6}$ alkoxy group optionally having substituent(s)", "$C_{3-6}$ cycloalkyl group optionally having substituent(s)", "$C_{3-6}$ cycloalkoxy group optionally having substituent(s)" and "$C_{6-14}$ aryl group optionally having substituent(s)" include 1 to 3 substituents selected from substituent group A and substituent group B.

Preferable examples of the combination of $X_1$, $X_2$ and $X_3$ include the following combinations.
(1) $X_1$ is —CRa=, $X_2$ is —CRb=, and $X_3$ is —CRc=;
(2) $X_1$ is —N=, $X_2$ is —CRb=, and $X_3$ is —CRc=;
(3) $X_1$ is —CRa=, $X_2$ is —N=, and $X_3$ is —CRc=; and
(4) $X_1$ is —CRa=, $X_2$ is —CRb=, and $X_3$ is —N=.

Preferably, Ra, Rb and Rc are each independently a hydrogen atom, a halogen atom, a $C_{1-6}$ alkyl group, a $C_{2-6}$ alkenyl group or a $C_{6-14}$ aryl group.

More preferably, Ra is a hydrogen atom, a halogen atom, a $C_{1-6}$ alkyl group, a $C_{2-6}$ alkenyl group or a $C_{6-14}$ aryl group; Rb is a hydrogen atom or a halogen atom; and Rc is a hydrogen atom or a halogen atom.

Further preferably, Ra, Rb and Rc are each a hydrogen atom.

A compound wherein $R^1$ is a $C_{3-8}$ cycloalkyl group (e.g., cyclopentyl, cyclohexyl, cycloheptyl) having a hydroxyl group at the 2-position, and the relative configuration of the 1- and 2-positions of the cycloalkyl group is 1,2-trans is preferable.

Preferable embodiments of compound (I) are the following compounds.

[2a] The compound of the aforementioned [2], wherein $R^1$ is
a $C_{3-8}$ cycloalkyl group optionally having substituent(s),
a phenyl group optionally having substituent(s),
a pyridyl group having substituent(s),
a tetrahydropyranyl group having substituent(s),
a 6,7-dihydro-5H-cyclopentapyridyl group optionally having substituent(s),
a pyrazolyl group having substituent(s), or
a $C_{1-6}$ alkyl group having substituent(s) other than a halogen atom,
or a salt thereof.

[2b] The compound of the aforementioned [2], wherein the "$C_{1-6}$ alkyl group having substituent(s) other than a halogen atom" for $R^1$ is a $C_{1-6}$ alkyl group substituted by 1 to 3 substituents selected from
(1) a cyano group,
(2) an amino group optionally substituted by 1 or 2 $C_{1-6}$ alkyl groups,
(3) a hydroxy group,
(4) a $C_{1-6}$ alkoxy-carbonyl group,
(5) a carboxy group,
(6) a carbamoyl group,
(7) a $C_{6-14}$ aryl-carbonyl group (e.g., a benzoyl group),
(8) a 4- to 10-membered heterocyclylcarbonyl group (e.g., an azetidinylcarbonyl group),
(9) a piperidylcarbonyl group,
(10) a $C_{1-6}$ alkoxy group,
(11) a $C_{6-14}$ aryl-$C_{1-6}$ alkoxy group (e.g., a benzyloxy group),
(12) a $C_{6-14}$ aryloxy group (e.g., a phenoxy group),
(13) a $C_{3-6}$ cycloalkyl group optionally substituted by 1 to 3 $C_{1-6}$ alkyl groups,
(14) a $C_{6-14}$ aryl group (e.g., a phenyl group) optionally having 1 to 3 substituents selected from (a) a halogen atom, (b) a cyano group, (c) a $C_{1-6}$ alkyl group having 1 to 3 halogen atoms, (d) a $C_{1-6}$ alkoxy group, and (e) a $C_{6-14}$ aryl group (e.g., phenyl group), and
(15) a 4- to 10-membered heterocyclic group (e.g., a tetrahydrofuryl group, a pyrrolidinyl group, a piperidyl group, a pyrazolyl group, a tetrahydropyranyl group, an oxetanyl group, a pyridyl group, a 5,6,7,8-tetrahydroimidazo[1,5-a]pyridyl group, a morpholinyl group, an imidazolyl group, a 2,3-dihydro-1H-isoindolyl group, a 1-azabicyclo[2.2.1]heptyl group, a pyrrolyl group, a 1,4-dioxanyl group, a 7-oxabicyclo[2.2.1]heptyl group, or a thiazolyl group) optionally having 1 to 3 substituents selected from a halogen atom, a cyano group, a $C_{1-6}$ alkoxy-carbonyl group, a $C_{1-6}$ alkyl group, and an oxo group,
or a salt thereof.

[2c] The compound of the aforementioned [2], wherein the "$C_{1-6}$ alkyl group having substituent(s) other than a halogen atom" for $R^1$ is a $C_{1-6}$ alkyl group substituted by 1 to 3 substituents selected from
(1) a hydroxy group,
(2) a $C_{1-6}$ alkoxy-carbonyl group,
(3) a carboxy group,
(4) a piperidylcarbonyl group,
(5) a $C_{3-6}$ cycloalkyl group optionally substituted by 1 to 3 $C_{1-6}$ alkyl groups,
(6) a phenyl group substituted by 1 to 3 halogen atoms, and
(7) a tetrahydrofuryl group, a pyrrolidinyl group, a piperidyl group, a pyrazolyl group, a tetrahydropyranyl group, a pyridyl group, or a 7-oxabicyclo[2.2.1]heptyl group, each of which optionally has 1 to 3 substituents selected from a halogen atom and a $C_{1-6}$ alkoxy-carbonyl group,
or a salt thereof.

[2d] The compound of the aforementioned [2], wherein the "$C_{1-6}$ alkyl group having substituent(s) other than a halogen atom" for $R^1$ is a $C_{1-6}$ alkyl group substituted by 1 to 3 substituents selected from
(1) a phenyl group substituted by 1 to 3 halogen atoms, and
(2) a tetrahydrofuryl group,
or a salt thereof.

[2e] The compound of the aforementioned [2], wherein the "$C_{1-6}$ alkyl group having substituent(s) other than a halogen atom" for $R^1$ is a $C_{1-6}$ alkyl group substituted by one tetrahydrofuryl group, or a salt thereof.

[2f] The compound of the aforementioned [2], wherein the "cyclic group optionally having substituent(s)" for $R^1$ is a $C_{3-8}$ cycloalkyl group, a $C_{6-14}$ aryl group, or a 4- to 10-membered heterocyclic group, each of which is optionally substituted by 1 to 3 substituents selected from
(1) a halogen atom,
(2) a cyano group,
(3) a nitro group,
(4) an amino group,
(5) a hydroxy group,
(6) a $C_{1-6}$ alkyl group optionally having 1 to 5 substituents selected from (i) a halogen atom, (ii) a cyano group, (iii) a hydroxy group, (iv) a $C_{1-6}$ alkoxy group, and (v) an oxo group,
(7) a carbamoyl group,
(8) a $C_{1-6}$ alkoxy group optionally having 1 to 3 halogen atoms,
(9) a $C_{2-6}$ alkenyl group,
(10) a $C_{3-6}$ cycloalkyl group, and
(11) an oxo group,
or a salt thereof.

[2g] The compound of the aforementioned [2], wherein the "cyclic group optionally having substituent(s)" for $R^1$ is a $C_{3-8}$ cycloalkyl group, a phenyl group, a pyridyl group, a tetrahydropyranyl group, a tetrahydrothiopyranyl group, a pyrimidinyl group, a tetrahydronaphthyl group, a dihydrochromenyl group, a 6,7-dihydro-5H-cyclopentapyridyl group, a dihydrobenzofuryl group, or a pyrazolyl group, each of which is optionally substituted by 1 to 3 substituents selected from
(1) a halogen atom,
(2) a cyano group,
(3) a nitro group,
(4) an amino group, (5) a hydroxy group,
(6) a $C_{1-6}$ alkyl group optionally having 1 to 5 substituents selected from (i) a halogen atom, (ii) a cyano group, (iii) a hydroxy group, (iv) a $C_{1-6}$ alkoxy group, and (v) an oxo group,
(7) a carbamoyl group,
(8) a $C_{1-6}$ alkoxy group optionally having 1 to 3 halogen atoms,
(9) a $C_{2-6}$ alkenyl group,
(10) a $C_{3-6}$ cycloalkyl group, and
(11) an oxo group,
or a salt thereof.

[2h] The compound of the aforementioned [2], wherein the "cyclic group optionally having substituent(s)" for $R^1$ is a $C_{3-8}$ cycloalkyl group, a phenyl group, a pyridyl group, a tetrahydropyranyl group, a 6,7-dihydro-5H-cyclopentapyridyl group, or a pyrazolyl group, each of which is optionally substituted by 1 to 3 substituents selected from
(1) a halogen atom,
(2) a cyano group,
(3) a nitro group,
(4) an amino group,
(5) a hydroxy group,
(6) a $C_{1-6}$ alkyl group optionally having 1 to 5 substituents selected from (i) a halogen atom, (ii) a cyano group, (iii) a hydroxy group, and (iv) a $C_{1-6}$ alkoxy group,
(7) a $C_{1-6}$ alkoxy group optionally having 1 to 3 halogen atoms,
(8) a $C_{2-6}$ alkenyl group, and
(9) a $C_{3-6}$ cycloalkyl group,
or a salt thereof.

[2i] The compound of the aforementioned [2], wherein the "cyclic group optionally having substituent(s)" for $R^1$ is a $C_{3-8}$ cycloalkyl group, a phenyl group, a pyridyl group, or a tetrahydropyranyl group, each of which is optionally substituted by 1 to 3 substituents selected from
(1) a halogen atom,
(2) a cyano group,
(3) a hydroxy group, and
(4) a $C_{1-6}$ alkyl group substituted by 1 to 3 halogen atoms,
or a salt thereof.

[2j] The compound of the aforementioned [2], wherein $R^1$ is
(I) a $C_{1-6}$ alkyl group substituted by 1 to 3 substituents selected from
  (1) a phenyl group substituted by 1 to 3 halogen atoms, and
  (2) a tetrahydrofuryl group, or
(II) a $C_{3-8}$ cycloalkyl group, a phenyl group, a pyridyl group, or a tetrahydropyranyl group, each of which is optionally substituted by 1 to 3 substituents selected from
  (1) a halogen atom,
  (2) a cyano group,
  (3) a hydroxy group, and
  (4) a $C_{1-6}$ alkyl group substituted by 1 to 3 halogen atoms,
or a salt thereof.

[2k] The compound of the aforementioned [2], wherein ring A is
a benzene ring optionally having substituent(s),
a $C_{4-7}$ cycloalkane ring,
a pyridine ring having substituent(s),
a thiophene ring optionally having substituent(s),
a furan ring, or
a piperidine ring optionally having substituent(s),
or a salt thereof.

[2l] The compound of the aforementioned [2], wherein the "substituent" for ring A is
(1) a halogen atom,
(2) a cyano group,
(3) a carbamoyl group optionally having 1 or 2 substituents selected from
  (a) a $C_{1-6}$ alkyl group optionally having 1 to 3 substituents selected from
    (i) a halogen atom,
    (ii) a phenyl group optionally having 1 to 3 halogen atoms,
    (iii) a $C_{3-6}$ cycloalkyl group, and
    (iv) a tetrahydrofuryl group, and
  (b) a $C_{3-6}$ cycloalkyl group,
(4) a $C_{1-6}$ alkoxy-carbonyl group,
(5) a carboxy group,
(6) a $C_{1-6}$ alkoxy group optionally having 1 to 3 halogen atoms,
(7) a $C_{1-6}$ alkyl group optionally having 1 to 3 $C_{6-14}$ aryl groups (e.g., phenyl group) having 1 to 3 halogen atoms,
(8) a $C_{2-6}$ alkenyl group optionally having 1 to 3 $C_{6-14}$ aryl groups (e.g., phenyl groups) optionally having 1 to 3 halogen atoms,
(9) a $C_{3-6}$ cycloalkyl group,
(10) a phenyl group having 1 to 3 $C_{1-6}$ alkoxy groups, and
(11) a 4- to 7-membered heterocyclic group (e.g., a pyrazolyl group, a piperidyl group, a pyridyl group, a pyridazinyl group, a triazolyl group, an imidazolyl group, a furyl group, a pyrrolidinyl group, a thienyl group, an isoxazolyl group, a pyrimidinyl group, a thiazolyl group, an isothiazolyl group, a 1,2,3,6-tetrahydropyridyl group, a pyrrolyl group, a thiadiazolyl group, an oxadiazolyl group, a pyrazolopyridyl group, or a tetrahydropyrazolopyridyl group) optionally having 1 to 3 substituents selected from (a) a halogen atom, (b) a $C_{1-6}$ alkyl group optionally substituted by 1 to 3 substituents selected from a halogen atom and a $C_{3-6}$ cycloalkyl group, (c) a $C_{1-6}$ alkoxy group, (d) a benzyloxy group, (e) a hydroxy group, (f) a 4- to 7-membered heterocyclic group (e.g., a tetrahydropyranyl group), and (g) an oxo group,
or a salt thereof.

[2m] The compound of the aforementioned [2], wherein ring A is a benzene ring, a $C_{4-7}$ cycloalkane ring, a pyridine ring, a thiophene ring, a furan ring, or a piperidine ring, each of which is optionally substituted by 1 to 3 substituents selected from
(1) a halogen atom,
(2) a cyano group,
(3) a carbamoyl group optionally having 1 or 2 substituents selected from
  (a) a $C_{1-6}$ alkyl group optionally having 1 to 3 substituents selected from
    (i) a halogen atom,
    (ii) a phenyl group optionally having 1 to 3 halogen atoms,
    (iii) a $C_{3-6}$ cycloalkyl group, and
    (iv) a tetrahydrofuryl group, and
  (b) a $C_{3-6}$ cycloalkyl group,
(4) a $C_{1-6}$ alkoxy-carbonyl group,
(5) a carboxy group,
(6) a $C_{1-6}$ alkoxy group optionally having 1 to 3 halogen atoms,
(7) a $C_{1-6}$ alkyl group optionally having 1 to 3 phenyl groups having 1 to 3 halogen atoms,
(8) a $C_{2-6}$ alkenyl group optionally having 1 to 3 phenyl groups optionally having 1 to 3 halogen atoms,
(9) a $C_{3-6}$ cycloalkyl group,

(10) a phenyl group having 1 to 3 $C_{1-6}$ alkoxy groups, and
(11) a pyrazolyl group, a piperidyl group, a pyridyl group, a pyridazinyl group, a triazolyl group, an imidazolyl group, a furyl group, a pyrrolidinyl group, a thienyl group, an isoxazolyl group, a pyrimidinyl group, a thiazolyl group, an isothiazolyl group, a 1,2,3,6-tetrahydropyridyl group, a pyrrolyl group, a thiadiazolyl group, an oxadiazolyl group, a pyrazolopyridyl group, or a tetrahydropyrazolopyridyl group, each of which optionally has 1 to 3 Substituents selected from (a) a halogen atom, (b) a $C_{1-6}$ alkyl group optionally substituted by 1 to 3 substituents selected from a halogen atom and a $C_{3-6}$ cycloalkyl group, (c) a $C_{1-6}$ alkoxy group, (d) a benzyloxy group, (e) a hydroxy group, (f) a tetrahydropyranyl group, and (g) an oxo group,
or a salt thereof.

[2n] The compound of the aforementioned [2], wherein the "substituent" for ring A is selected from
(1) a halogen atom,
(2) a cyano group,
(3) a carbamoyl group optionally monosubstituted by a $C_{1-6}$ alkyl group optionally substituted by 1 to 3 tetrahydrofuryl groups,
(4) a $C_{1-6}$ alkoxy-carbonyl group,
(5) a $C_{3-6}$ cycloalkyl group, and
(6) a pyrazolyl group, a piperidyl group, a pyridyl group, a pyridazinyl group, a triazolyl group, an imidazolyl group, an isoxazolyl group, a pyrazolopyridyl group, or a 4,5,6,7-tetrahydropyrazolopyridyl group, each of which optionally has 1 to 3 substituents selected from (a) a halogen atom, (b) a $C_{1-6}$ alkyl group optionally substituted by 1 to 3 substituents selected from a halogen atom and a $C_{3-6}$ cycloalkyl group, and (c) a tetrahydropyranyl group,
or a salt thereof.

[2o] The compound of the aforementioned [2], wherein ring A is
a benzene ring,
a $C_{4-7}$ cycloalkane ring,
a pyridine ring,
a thiophene ring,
a furan ring, or
a piperidine ring, each of which is optionally substituted by 1 to 3 substituents selected from
(1) a halogen atom,
(2) a cyano group,
(3) a carbamoyl group optionally monosubstituted by a $C_{1-6}$ alkyl group optionally substituted by 1 to 3 tetrahydrofuryl groups,
(4) a $C_{1-6}$ alkoxy-carbonyl group,
(5) a $C_{3-6}$ cycloalkyl group, and
(6) a pyrazolyl group, a piperidyl group, a pyridyl group, a pyridazinyl group, a triazolyl group, an imidazolyl group, an isoxazolyl group, a pyrazolopyridyl group, or a 4,5,6,7-tetrahydropyrazolopyridyl group, each of which optionally has 1 to 3 substituents selected from (a) a halogen atom, (b) a $C_{1-6}$ alkyl group optionally substituted by 1 to 3 substituents selected from a halogen atom and a $C_{3-6}$ cycloalkyl group, and (c) a tetrahydropyranyl group,
or a salt thereof.

[2p] The compound of the aforementioned [2], wherein the "substituent" for ring A is selected from
(1) a halogen atom,
(2) a carbamoyl group, and
(3) a pyrazolyl group or a triazolyl group, each of which is substituted by 1 to 3 $C_{1-6}$ alkyl groups,
or a salt thereof.

[2q] The compound of the aforementioned [2], wherein ring A is a benzene ring or a pyridine ring, each of which is optionally substituted by 1 to 3 substituents selected from
(1) a halogen atom,
(2) a carbamoyl group, and
(3) a pyrazolyl group substituted by 1 to 3 $C_{1-6}$ alkyl groups, and
(4) a triazolyl group substituted by 1 or 2 $C_{1-6}$ alkyl groups,
or a salt thereof.

[2r] The compound of the aforementioned [2], wherein $X_1$, $X_2$ and $X_3$ are selected from the following combinations:
(1) $X_1$ is —CRa=, $X_2$ is —CRb=, and $X_3$ is —N=;
(2) $X_1$ is —N=, $X_2$ is —CRb=, and $X_3$ is —N=;
(3) $X_1$ is —CRa=, $X_2$ is —CRb=, and $X_3$ is —CRc=;
(4) $X_1$ is —CRa=, $X_2$ is —N=, and $X_3$ is —CRc=; and
(5) $X_1$ is —N=, $X_2$ is —CRb=, and $X_3$ is —CRc=; and Ra, Rb and Rc are each independently
a hydrogen atom, a halogen atom, or a $C_{2-6}$ alkenyl group,
or a salt thereof.

[2s] The compound of the aforementioned [2], wherein $R^1$ is
(I) a $C_{3-8}$ cycloalkyl group, a phenyl group, a pyridyl group, a tetrahydropyranyl group, a tetrahydrothiopyranyl group, a pyrimidinyl group, a tetrahydronaphthyl group, a dihydrochromenyl group, a 6,7-dihydro-5H-cyclopentapyridyl group, a dihydrobenzofuryl group, or a pyrazolyl group, each of which is optionally substituted by 1 to 3 substituents selected from
(1) a halogen atom,
(2) a cyano group,
(3) a nitro group,
(4) an amino group,
(5) a hydroxy group,
(6) a $C_{1-6}$ alkyl group optionally having 1 to 5 substituents selected from (i) a halogen atom, (ii) a cyano group, (iii) a hydroxy group, (iv) a $C_{1-6}$ alkoxy group, and (v) an oxo group,
(7) a carbamoyl group,
(8) a $C_{1-6}$ alkoxy group optionally having 1 to 3 halogen atoms,
(9) a $C_{2-6}$ alkenyl group,
(10) a $C_{3-6}$ cycloalkyl group, and
(11) an oxo group; or
(II) a $C_{2-6}$ alkyl group substituted by 1 to 3 substituents selected from
(1) a cyano group,
(2) an amino group optionally substituted by 1 or 2 $C_{1-6}$ alkyl groups,
(3) a hydroxy group,
(4) a $C_{1-6}$ alkoxy-carbonyl group,
(5) a carboxy group,
(6) a carbamoyl group,
(7) a benzoyl group,
(8) an azetidinylcarbonyl group,
(9) a piperidylcarbonyl group,
(10) a $C_{1-6}$ alkoxy group,
(11) a benzyloxy group,
(12) a phenoxy group,
(13) a $C_{3-6}$ cycloalkyl group optionally substituted by 1 to 3 $C_{1-6}$ alkyl groups,
(14) a phenyl group optionally having 1 to 3 substituents selected from (a) a halogen atom, (b) a cyano group, (c) a $C_{1-6}$ alkyl group having 1 to 3 halogen atoms, (d) a $C_{1-6}$ alkoxy group, and (e) a phenyl group, and
(15) a tetrahydrofuryl group, a pyrrolidinyl group, a piperidyl group, a pyrazolyl group, a tetrahydropyranyl group, an oxetanyl group, a pyridyl group, a 5,6,7,8-tetrahydroimidazo[1,5-a]pyridyl group, a morpholinyl group, an imidazolyl group, a 2,3-dihydro-1H-isoindolyl group, an 1-azabicyclo[2.2.1]heptyl group, a pyrrolyl group, a 1,4-dioxanyl group, a 7-oxabicyclo[2.2.1]heptyl group, or a thiazolyl group, each of which optionally has 1 to 3 substituents selected from a halogen atom, a cyano group, a $C_{1-6}$ alkoxy-carbonyl group, a $C_{1-6}$ alkyl group and an oxo group;

ring A is a benzene ring, a $C_{4-7}$ cycloalkane ring, a pyridine ring, a thiophene ring, a furan ring, or a piperidine ring, each of which is optionally substituted by 1 to 3 substituents selected from
(1) a halogen atom,
(2) a cyano group,
(3) a carbamoyl group optionally having 1 or 2 substituents selected from
    (a) a $C_{1-6}$ alkyl group optionally having 1 to 3 substituents selected from
        (i) a halogen atom,
        (ii) a phenyl group optionally having 1 to 3 halogen atoms,
        (iii) a $C_{3-6}$ cycloalkyl group, and
        (iv) a tetrahydrofuryl group, and
    (b) a $C_{3-6}$ cycloalkyl group,
(4) a $C_{1-6}$ alkoxy-carbonyl group,
(5) a carboxy group,
(6) a $C_{1-6}$ alkoxy group optionally having 1 to 3 halogen atoms,
(7) a $C_{1-6}$ alkyl group optionally having 1 to 3 phenyl groups having 1 to 3 halogen atoms,
(8) a $C_{2-6}$ alkenyl group optionally having 1 to 3 phenyl groups optionally having 1 to 3 halogen atoms,
(9) a $C_{3-6}$ cycloalkyl group,
(10) a phenyl group having 1 to 3 $C_{1-6}$ alkoxy groups, and
(11) a pyrazolyl group, a piperidyl group, a pyridyl group, a pyridazinyl group, a triazolyl group, an imidazolyl group, a furyl group, a pyrrolidinyl group, a thienyl group, an isoxazolyl group, a pyrimidinyl group, a thiazolyl group, an isothiazolyl group, a 1,2,3,6-tetrahydropyridyl group, a pyrrolyl group, a thiadiazolyl group, an oxadiazolyl group, a pyrazolopyridyl group, or a tetrahydropyrazolopyridyl group, each of which optionally has 1 to 3 substituents selected from (a) a halogen atom, (b) a $C_{1-6}$ alkyl group optionally substituted by 1 to 3 substituents selected from a halogen atom and a $C_{3-6}$ cycloalkyl group, (c) a $C_{1-6}$ alkoxy group, (d) a benzyloxy group, (e) a hydroxy group, (f) a tetrahydropyranyl group, and (g) an oxo group;

$X_1$, $X_2$ and $X_3$ are selected from the following combinations:
(1) $X_1$ is —CRa=, $X_2$ is —CRb=, and $X_3$ is —N=;
(2) $X_1$ is —N=, $X_2$ is —CRb=, and $X_3$ is —N=;
(3) $X_1$ is —CRa=, $X_2$ is —CRb=, and $X_3$ is —CRc=;
(4) $X_1$ is —CRa=, $X_2$ is —N=, and $X_3$ is —CRc=; and
(5) $X_1$ is —N=, $X_2$ is —CRb=, and $X_3$ is —CRc=; and Ra, Rb and Rc are each independently
a hydrogen atom, a halogen atom, or a $C_{2-6}$ alkenyl group, or a salt thereof.

As compound (I), the following compounds are preferable.

[Compound I-A]
A compound of the formula (I), wherein ring A is
a phenyl group,
a $C_{4-7}$ cycloalkyl group (e.g., cyclohexyl), or
a 4- to 7-membered heterocyclic group (preferably 4- to 7-membered heterocyclic group containing 1 to 4 hetero atoms selected from a nitrogen atom, a sulfur atom and an oxygen atom, for example, pyridyl, thienyl, furyl, piperidyl), each of which optionally has 1 to 3 substituents selected from
(1) a halogen atom,
(2) a cyano group,
(3) a carbamoyl group optionally having 1 or 2 substituents selected from
    (a) a $C_{1-6}$ alkyl group optionally having 1 to 3 substituents selected from
        (i) a halogen atom,
        (ii) a $C_{6-14}$ aryl group optionally having 1 to 3 halogen atoms,
        (iii) a $C_{3-6}$ cycloalkyl group, and
        (iv) a heterocyclic group (e.g., tetrahydrofuryl), and
    (b) a $C_{3-6}$ cycloalkyl group,
(4) a $C_{1-6}$ alkoxy-carbonyl group,
(5) a carboxy group,
(6) a $C_{1-6}$ alkoxy group optionally having 1 to 3 halogen atoms,
(7) a $C_{1-6}$ alkyl group optionally having 1 to 3 $C_{6-14}$ aryl groups optionally having 1 to 3 halogen atoms,
(8) a $C_{2-6}$ alkenyl group optionally having 1 to 3 $C_{6-14}$ aryl groups optionally having 1 to 3 halogen atoms,
(9) a $C_{3-6}$ cycloalkyl group,
(10) a $C_{6-14}$ aryl group optionally having 1 to 3 substituents selected from a halogen atom, a cyano group and a $C_{1-6}$ alkoxy group, and
(11) a heterocyclic group (preferably a 4- to 7-membered heterocyclic group containing 1 to 4 hetero atoms selected from a nitrogen atom, a sulfur atom and an oxygen atom, for example, pyrazolyl, piperidyl, pyridyl, pyridazinyl, triazolyl, imidazolyl, furyl, pyrrolidinyl, thienyl, isoxazolyl, pyrimidinyl, thiazolyl, isothiazolyl, tetrahydropyridyl (e.g., 1,2,3,6-tetrahydropyridyl), pyrrolyl) optionally having 1 to 3 substituents selected from a $C_{1-6}$ alkyl group, a $C_{1-6}$ alkoxy group, a $C_{6-14}$ aryl-$C_{1-6}$ alkoxy group (e.g., benzyloxy), a hydroxy group, a heterocyclic group (e.g., tetrahydropyranyl) and an oxo group;

L is —O—, —S—, —SO— or —SO$_2$—;

$R^1$ is
(A) a $C_{1-6}$ alkyl group having 1 to 3 substituents selected from
    (1) a halogen atom,
    (2) a hydroxy group,
    (3) a $C_{1-6}$ alkoxy-carbonyl group,
    (4) a carboxy group,
    (5) a carbamoyl group,
    (6) a $C_{6-14}$ aryl-carbonyl group (e.g., benzoyl),
    (7) a heterocyclylcarbonyl group (e.g., azetidinylcarbonyl, piperidylcarbonyl),
    (8) a $C_{1-6}$ alkoxy group,
    (9) a $C_{6-14}$ aryl-$C_{1-6}$ alkoxy group (e.g., benzyloxy),
    (10) a $C_{6-14}$ aryloxy group (e.g., phenoxy),
    (11) a $C_{3-6}$ cycloalkyl group,
    (12) a $C_{6-14}$ aryl group optionally having 1 to 3 substituents selected from (a) a halogen atom, (b) a cyano group, (c) a $C_{1-6}$ alkyl group optionally having 1 to 3 halogen atoms and (d) a $C_{6-14}$ aryl group, and
    (13) a heterocyclic group (preferably, a 4- to 10-membered heterocyclic group containing 1 to 4 hetero atoms selected from a nitrogen atom, a sulfur atom and an oxygen atom, for example, tetrahydrofuryl, pyrrolidinyl, piperidyl, pyrazolyl, tetrahydropyranyl, oxetanyl, pyridyl, tetrahydroimidazopyridyl (e.g., 5,6,7,8-tetrahydroimidazo[1,5-a]pyridyl), morpholinyl, imidazolyl, dihydroisoindolyl (e.g., 2,3-dihydro-1H-isoindolyl), 1-azabicyclo[2.2.1]heptyl, pyrrolyl, imidazopyridyl (e.g., imidazo[1,2-a]pyridyl)) optionally having 1 to 3 substituents selected from a halogen atom, a $C_{1-6}$ alkoxy-carbonyl group, a $C_{1-6}$ alkyl group and an oxo group, or (B) a $C_{3-8}$ cycloalkyl group (e.g., cyclopentyl, cyclohexyl, cycloheptyl), a $C_{6-14}$ aryl group (e.g., phenyl), or a heterocyclic group (preferably, 4- to 7-membered heterocyclic group containing 1 to 4 hetero atoms selected from a nitrogen atom, a sulfur atom and an oxygen atom, for example, pyridyl, pyrazolyl, tetrahydropyranyl), each of which optionally has 1 to 5 (preferably 1 to 3) substituents selected from
  (1) a halogen atom,
  (2) a cyano group,
  (3) a nitro group,
  (4) an amino group,
  (5) a hydroxy group,
  (6) a carbamoyl group,
  (7) a $C_{1-6}$ alkyl group optionally having 1 to 3 halogen atoms, and
  (8) a $C_{1-6}$ alkoxy group;

$X_1$ is —CRa= or —N=;
$X_2$ is —CRb= or —N=;
$X_3$ is —CRc= or —N=;

Ra is a hydrogen atom, a halogen atom, a $C_{1-6}$ alkyl group, a $C_{2-6}$ alkenyl group or a $C_{6-14}$ aryl group;
Rb is a hydrogen atom or a halogen atom; and
Rc is a hydrogen atom or a halogen atom,
or a salt thereof.

[Compound I-B]

A compound of the formula (I), wherein ring A is
a phenyl group,
a $C_{4-7}$ cycloalkyl group (e.g., cyclohexyl), or
a 4- to 7-membered heterocyclic group (preferably, a 4- to 7-membered heterocyclic group containing 1 to 4 hetero atoms selected from a nitrogen atom, a sulfur atom and an oxygen atom, for example, pyridyl, thienyl, furyl, piperidyl), each of which optionally has 1 to 3 substituents selected from
(1) a halogen atom,
(2) a cyano group,
(3) a carbamoyl group optionally having 1 or 2 substituents selected from
  (a) a $C_{1-6}$ alkyl group optionally having 1 to 3 substituents selected from
    (i) a halogen atom,
    (ii) a $C_{6-14}$ aryl group optionally having 1 to 3 halogen atoms,
    (iii) a $C_{3-6}$ cycloalkyl group, and
    (iv) a heterocyclic group (e.g., tetrahydrofuryl), and
  (b) a $C_{3-6}$ cycloalkyl group,
(4) a $C_{1-6}$ alkoxy-carbonyl group,
(5) a carboxy group,
(6) a $C_{1-6}$ alkoxy group optionally having 1 to 3 halogen atoms,
(7) a $C_{1-6}$ alkyl group optionally having 1 to 3 $C_{6-14}$ aryl groups optionally having 1 to 3 halogen atoms,
(8) a $C_{2-6}$ alkenyl group optionally having 1 to 3 $C_{6-14}$ aryl groups optionally having 1 to 3 halogen atoms,
(9) a $C_{3-6}$ cycloalkyl group,
(10) a $C_{6-14}$ aryl group optionally having 1 to 3 substituents selected from a halogen atom, a cyano group and a $C_{1-6}$ alkoxy group, and
(11) a heterocyclic group (preferably, a 4- to 7-membered heterocyclic group containing 1 to 4 hetero atoms selected from a nitrogen atom, a sulfur atom and an oxygen atom, for example, pyrazolyl, piperidyl, pyridyl, pyridazinyl, triazolyl, imidazolyl, furyl, pyrrolidinyl, thienyl, isoxazolyl, pyrimidinyl, thiazolyl, isothiazolyl, tetrahydropyridyl (e.g., 1,2,3,6-tetrahydropyridyl), pyrrolyl) optionally having 1 to 3 substituents selected from a $C_{1-6}$ alkyl group, a $C_{1-6}$ alkoxy group, a $C_{6-14}$ aryl-$C_{1-6}$ alkoxy group (e.g., benzyloxy), a hydroxy group, a heterocyclic group (e.g., tetrahydropyranyl) and an oxo group;

L is —O—, —S—, —SO— or —SO$_2$—;

$R^1$ is (A) a $C_{1-6}$ alkyl group having 1 to 3 substituents selected from
  (1) a hydroxy group,
  (2) a $C_{1-6}$ alkoxy-carbonyl group,
  (3) a carboxy group,
  (4) a carbamoyl group,
  (5) a $C_{6-14}$ aryl-carbonyl group (e.g., benzoyl),
  (6) a heterocyclylcarbonyl group (e.g., azetidinylcarbonyl, piperidylcarbonyl),
  (7) a $C_{1-6}$ alkoxy group,
  (8) a $C_{6-14}$ aryl-$C_{1-6}$ alkoxy group (e.g., benzyloxy),
  (9) a $C_{6-14}$ aryloxy group (e.g., phenoxy),
  (10) a $C_{3-6}$ cycloalkyl group,
  (11) a $C_{6-14}$ aryl group optionally having 1 to 3 substituents selected from (a) a halogen atom, (b) a cyano group, (c) a $C_{1-6}$ alkyl group optionally having 1 to 3 halogen atoms and (d) a $C_{6-14}$ aryl group, and
  (12) a heterocyclic group (preferably, a 4- to 10-membered heterocyclic group containing 1 to 4 hetero atoms selected from a nitrogen atom, a sulfur atom and an oxygen atom, for example, tetrahydrofuryl, pyrrolidinyl, piperidyl, pyrazolyl, tetrahydropyranyl, oxetanyl, pyridyl, tetrahydroimidazopyridyl (e.g., 5,6,7,8-tetrahydroimidazo[1,5-a]pyridyl), morpholinyl, imidazolyl, dihydroisoindolyl (e.g., 2,3-dihydro-1H-isoindolyl), 1-azabicyclo[2.2.1]heptyl, pyrrolyl, imidazopyridyl (e.g., imidazo[1,2-a]pyridyl)) optionally having 1 to 3 substituents selected from a halogen atom, a $C_{1-6}$ alkoxy-carbonyl group, a $C_{1-6}$ alkyl group and an oxo group, or (B) a $C_{3-8}$ cycloalkyl group (e.g., cyclopentyl, cyclohexyl, cycloheptyl), a $C_{6-14}$ aryl group (e.g., phenyl), or a heterocyclic group (preferably, a 4- to 7-membered heterocyclic group containing 1 to 4 hetero atoms selected from a nitrogen atom, a sulfur atom and an oxygen atom, for example, pyridyl, pyrazolyl, tetrahydropyranyl), each of which optionally has 1 to 5 (preferably 1 to 3) substituents selected from
  (1) a halogen atom,
  (2) a cyano group,
  (3) a nitro group,
  (4) an amino group,
  (5) a hydroxy group,
  (6) a carbamoyl group,
  (7) a $C_{1-6}$ alkyl group optionally having 1 to 3 halogen atoms, and
  (8) a $C_{1-6}$ alkoxy group;

$X_1$ is —CRa= or —N=;
$X_2$ is —CRb= or —N=;
$X_3$ is —CRc= or —N=;

Ra is a hydrogen atom, a halogen atom, a $C_{1-6}$ alkyl group, a $C_{2-6}$ alkenyl group or a $C_{6-14}$ aryl group;
Rb is a hydrogen atom or a halogen atom; and
Rc is a hydrogen atom or a halogen atom,
or a salt thereof.

[Compound I-C]

A compound of the formula (I), wherein ring A is
a phenyl group,
a $C_{4-7}$ cycloalkyl group (e.g., cyclohexyl), or a 4- to 7-membered heterocyclic group (preferably, a 4- to 7-membered heterocyclic group containing 1 to 4 hetero atoms selected from a nitrogen atom, a sulfur atom and an oxygen atom, for example, piperidyl), each of which optionally has 1 to 3 substituents selected from
(1) a halogen atom,
(2) a carbamoyl group, and
(3) a 5- or 6-membered aromatic heterocyclic group optionally having 1 to 3 $C_{1-6}$ alkyl groups (preferably, a 5- or 6-membered aromatic heterocyclic group containing 1 to 4 hetero atoms selected from a nitrogen atom, a sulfur atom and an oxygen atom, for example, pyrazolyl, pyridyl);
L is —O— or —SO—;
$R^1$ is
(A) a $C_{1-6}$ alkyl group having 1 to 3 substituents selected from
  (1) a heterocyclylcarbonyl group (e.g., piperidylcarbonyl) and
  (2) a 5- or 6-membered heterocyclic group (preferably, a 5- or 6-membered heterocyclic group containing 1 to 4 hetero atoms selected from a nitrogen atom, a sulfur atom and an oxygen atom, for example, tetrahydrofuryl, piperidyl, pyrazolyl) optionally having $C_{1-6}$ alkoxy-carbonyl group(s), or
(B) a $C_{3-8}$ cycloalkyl group (e.g., cyclopentyl, cyclohexyl, cycloheptyl) or a phenyl group, each of which optionally has 1 to 3 substituents selected from
  (1) a halogen atom,
  (2) a cyano group,
  (3) an amino group, and
  (4) a hydroxy group; and
$X_1$ is —CH=, $X_2$ is —CH=, and $X_3$ is —CH=,
$X_1$ is —N=, $X_2$ is —CH=, and $X_3$ is —CH=, or
$X_1$ is —CH=, $X_2$ is —CH=, and $X_3$ is —N=,
or a salt thereof.

When compound (I) is in a form of a salt, examples of such salt include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, examples of a preferable pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. compound (I) may be a compound labeled or substituted with an isotope (e.g., $^2$H, $^3$H, $^{11}$C, $^{14}$C, $^{18}$F, $^{35}$S, $^{125}$I). A compound labeled with or substituted by an isotope can be used, for example, as a tracer used for Positron Emission Tomography (PET) (PET tracer), and is useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are all encompassed in compound (I) of the present invention.

The production methods of the compound of the present invention are explained below.

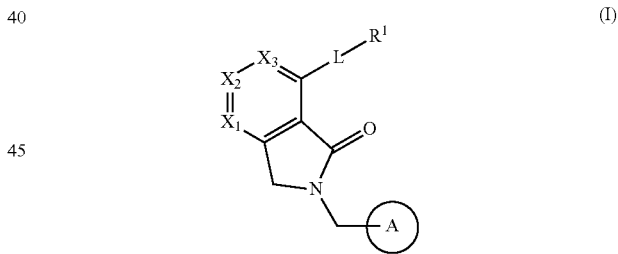

(I)

A compound represented by the above-mentioned of the formula (I) can be produced by, for example, the methods shown below or a method analogous thereto and the like. In the following, respective symbols relating to the compounds in the reaction schemes are as defined above, unless otherwise specified. In the following synthesis methods, the starting compound may be used as a salt, and as such salt, those exemplified as the salt of compound (I) can be used.

The starting compounds, reagents and reactants used for each reaction may be an easily available commercially product, or can also be produced by a method known per se, or a method analogous thereto, or the methods described in the Reference Examples and Examples.

In addition, the starting compounds and compounds obtained in respective steps can also be used for the next reaction in the form of a reaction mixture or an unpurified product, or can also be isolated from the reaction mixture according to a conventional method and can be purified easily by a separation means such as recrystallization, distillation, chromatography and the like.

Unless particularly indicated, the equivalent amount of the reagents and reactants used for each reaction is 0.001 equivalent to 100 equivalents relative to the substrate of each reaction. For example, the equivalent amounts of the reagents and reactants described in the Examples can be used.

Unless particularly indicated, two or more kinds of the respective acids, bases, oxidizing agents, reducing agents, additives, metal catalysts, catalysts, ligands and the like used in each reaction can be used in combination where necessary. For example, they can be used in the combinations described in the Examples.

Unless particularly indicated, the reaction time of each reaction is generally 5 min to 100 hr. For example, the reaction time described in the Examples can be employed.

Unless particularly indicated, the reaction temperature of each reaction is −100° C. to 300° C. For example, the reaction temperature described in the Examples can be employed.

Unless particularly indicated, each reaction can be performed under an atmospheric pressure or in a sealed tube. For example, the conditions described in the Examples can be employed.

Furthermore, each reaction can also be performed using, where necessary, a microwave irradiation apparatus (e.g., INITIATOR manufactured by Biotage etc.) and the like, under microwave irradiation.

When halogenation, acylation reaction, sulfonylation reaction, alkylation reaction, hydrolysis, amination reaction, amidation reaction, esterification reaction, etherification reaction, oxidation reaction, reduction reaction, protection reaction, deprotection, coupling reaction, addition reaction, elimination reaction, substitution reaction and the like are performed in the following reaction schemes, these reactions are performed according to a method known per se. Examples of the method include the methods described in ORGANIC FUNCTIONAL GROUP PREPARATIONS, 2nd edition, Academic Press Inc., 1989, Comprehensive Organic Transformations: A Guide to Functional Group Preparations, 2nd edition, Wiley-VCH, 1999, Shin Jikken Kagaku Koza (New Experimental Chemistry Course) (The Chemical Society of Japan ed.), Jikken Kagaku Kouza (Courses in Experimental Chemistry) (The Chemical Society of Japan ed.) and the like, and the like.

In each step mentioned below, $Y^1$—$Y^4$ are "leaving groups". Examples of the leaving group include alkali metal (e.g., lithium, sodium etc.), a halogen atom (e.g., fluorine, chlorine, bromine, iodine etc.), a $C_{1-6}$ alkoxy group (e.g., methoxy group etc.), a $C_{6-14}$ aryloxy group (e.g., phenoxy group etc.), an optionally substituted acyloxy group (e.g., acetyloxy group, benzoyloxy group etc.), an optionally halogenated $C_{1-6}$ alkylsulfonyloxy group [e.g., methanesulfonyloxy group, ethanesulfonyloxy group, trichloromethanesulfonyloxy group, trifluoromethanesulfonyloxy(triflate) group etc.], an optionally substituted $C_{6-14}$ arylsulfonyloxy group [for example, $C_{6-14}$ arylsulfonyloxy group optionally having 1 to 3 substituents selected from $C_{1-6}$ alkyl group (e.g., methyl group, ethyl group, propyl group, isopropyl group, butyl group, isobutyl group, sec-butyl group, tert-butyl group, pentyl group, hexyl group etc.), $C_{1-6}$ alkoxy group (e.g., methoxy group, ethoxy group, propoxy group, isopropoxy group, butoxy group, isobutoxy group, sec-butoxy group, pentyloxy group, hexyloxy group etc.) and a nitro group, and the like can be mentioned, and specific examples include benzenesulfonyloxy group, m-nitrobenzenesulfonyloxy group, p-toluenesulfonyloxy group, naphthylsulfonyloxy group etc.], a $C_{1-6}$ alkyloxonio group (e.g., dimethyloxonio group, diethyloxonio group etc.), a diazo group, a diazonio group, an optionally substituted $C_{6-14}$ aryliodonio group (e.g., phenyliodonio group), a boron functional group (e.g.,

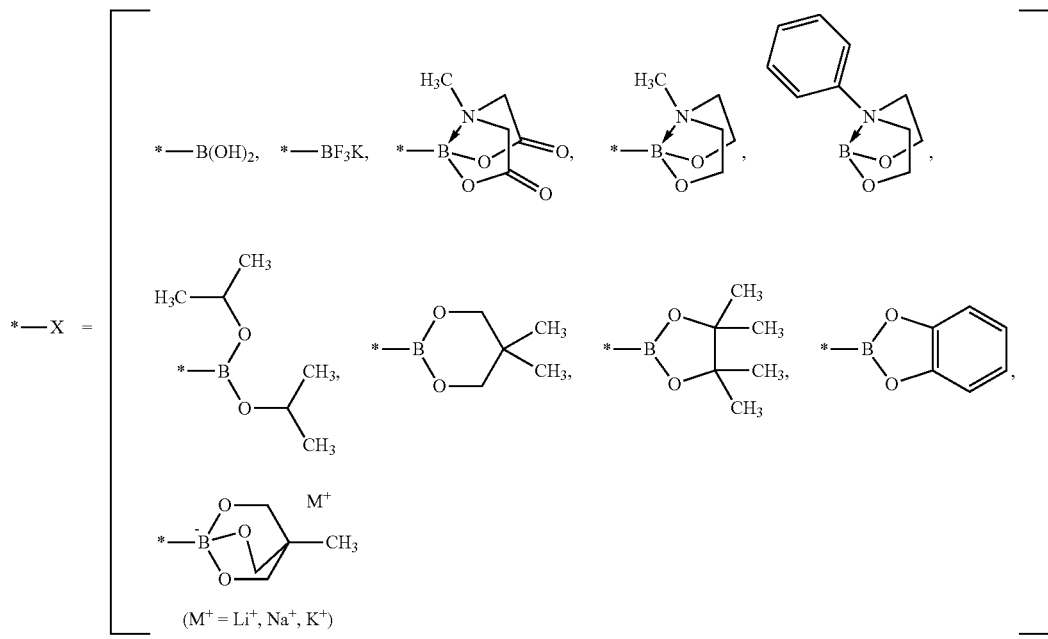

etc.), an optionally substituted $C_{1-6}$ alkylsilyl group (e.g., trimethylsilyl group etc.), an optionally substituted $C_{1-6}$ alkylstannyl group (e.g., tributylstannyl group etc.), an optionally substituted $C_{2-6}$ alkenylstannyl group, an optionally substituted $C_{6-14}$ arylstannyl group, a metal-containing substituent such as magnesium halide, zinc halide and the like, and the like.

Also, $Y^1$—$Y^4$ include substituents convertible to a leaving group, and they can be converted in a desired step to a leaving group by a reaction known per se. For example, when $Y^1$—$Y^4$ are methylthio groups, they can be converted to a methanesulfonyl group by an oxidation reaction, and the like.

In each step mentioned below, P is a "protecting group". When a starting compound has a hydroxy group, an amino group, a carboxy group, a carbonyl group, or a heterocyclic group as a substituent, a protecting group generally used in the peptide chemistry and the like may be introduced into these groups, and an object compound can be obtained by removing a protecting group as necessary after the reaction.

Examples of the hydroxyl-protecting group include a $C_{1-6}$ alkyl group (e.g., methyl, ethyl, propyl, isopropyl, butyl, tert-butyl), a phenyl group, a trityl group, a $C_{7-10}$ aralkyl group (e.g., benzyl), a formyl group, a $C_{1-6}$ alkyl-carbonyl group (e.g., acetyl, propionyl), a benzoyl group, a $C_{7-10}$ aralkyl-carbonyl group (e.g., benzylcarbonyl), a 2-tetrahydropyranyl group, a 2-tetrahydrofuranyl group, a silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups may be substituted by 1 to 3 substituents selected from a halogen atom (e.g., fluorine, chlorine, bromine, iodine), a $C_{1-6}$ alkyl group (e.g., methyl, ethyl, propyl), a $C_{1-6}$ alkoxy group (e.g., methoxy, ethoxy, propoxy), a nitro group and the like.

Examples of the amino-protecting group include a formyl group, a $C_{1-6}$ alkyl-carbonyl group (e.g., acetyl, propionyl), a $C_{1-6}$ alkoxy-carbonyl group (e.g., methoxycarbonyl, ethoxycarbonyl, tert-butoxycarbonyl), a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups may be substituted by 1 to 3 substituents selected from a halogen atom (e.g., fluorine, chlorine, bromine, iodine), a $C_{1-6}$ alkoxy group (e.g., methoxy, ethoxy, propoxy), a nitro group and the like.

Examples of the carboxy-protecting group include a $C_{1-6}$ alkyl group (e.g., methyl, ethyl, propyl, isopropyl, butyl, tert-butyl), a $C_{7-11}$ aralkyl group (e.g., benzyl), a phenyl group, a trityl group, a silyl group (e.g., trimethylsilyl, triethylsilyl, dimethylphenylsilyl, tert-butyldimethylsilyl, tert-butyldiethylsilyl, tert-butyldiphenylsilyl), a $C_{2-6}$ alkenyl group (e.g., 1-allyl) and the like. These groups may be substituted by 1 to 3 substituents selected from a halogen atom (e.g., fluorine, chlorine, bromine, iodine), a $C_{1-6}$ alkoxy group (e.g., methoxy, ethoxy, propoxy), a nitro group and the like.

Examples of the carbonyl-protecting group include cyclic acetal (e.g., 1,3-dioxane), acyclic acetal (e.g., di-$C_{1-6}$ alkyl acetal) and the like.

Examples of the heterocyclic-protecting group include a formyl group, a $C_{1-6}$ alkyl-carbonyl group (e.g., acetyl, propionyl), a $C_{1-6}$ alkoxy-carbonyl group (e.g., methoxycarbonyl, ethoxycarbonyl, tert-butoxycarbonyl), a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a N,N-dimethylaminomethylene group, a silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), a $C_{1-6}$ alkyl group (e.g., methyl, ethyl, propyl, isopropyl, butyl, tert-butyl), a phenyl group, a $C_{7-10}$ aralkyl group (e.g., benzyl), a 2-tetrahydropyranyl group, a 2-tetrahydrofuranyl group, and the like. These groups may be substituted by 1 to 3 substituents selected from a halogen atom (e.g., fluorine, chlorine, bromine, iodine), a $C_{1-6}$ alkoxy group (e.g., methoxy, ethoxy, propoxy), a nitro group and the like.

These protecting groups may be removed according to a method known per se, for example, the method described in Protective Groups in Organic Synthesis, John Wiley and Sons (1980) and the like. For example, a method using acid, base, ultraviolet rays, hydrazine, tetrabutylammonium fluoride, palladium acetate, palladium-carbon under a hydrogen atmosphere, trialkylsilyl halide (e.g., trimethylsilyl iodide, trimethylsilyl bromide and the like) and the like, a reduction method and the like are used.

Each step mentioned below can be performed without solvent or by dissolving or suspending in a suitable solvent, and is not particularly limited as long as the reaction proceeds. In addition, two or more kinds of solvents may be used after mixing at an appropriate ratio. Among the examples of the solvents to be used in the production method of the compound of the present invention, the following solvents are specifically used.

alcohols: methanol, ethanol, 1-propanol, 2-propanol, tert-butyl alcohol, 2-methoxyethanol and the like ethers: diethyl ether, diisopropyl ether, diphenyl ether, tetrahydrofuran, 1,4-dioxane, 1,2-dimethoxyethane and the like aromatic hydrocarbons: benzene, chlorobenzene, toluene, xylene, (trifluoromethyl)benzene and the like saturated hydrocarbons: cyclohexane, n-hexane, heptane, pentane, petroleum ether and the like amides: N,N-dimethylformamide, N,N-dimethylacetamide, N-methylpyrrolidone, hexamethylphosphoric triamide and the like halogenated hydrocarbons: dichloromethane, chloroform, carbon tetrachloride, 1,2-dichloroethane and the like nitriles: acetonitrile, propionitrile and the like sulfoxides: dimethyl sulfoxide and the like aromatic organic bases: pyridine, lutidine and the like acid anhydrides: acetic anhydride and the like organic acids: formic acid, acetic acid, propionic acid, trifluoroacetic acid, methanesulfonic acid and the like inorganic acids: hydrochloric acid, sulfuric acid and the like esters: methyl acetate, ethyl acetate, butyl acetate and the like ketones: acetone, methyl ethyl ketone and the like In addition, water as a solvent may be mixed at an appropriate ratio as long as the reaction proceeds.

Examples of the base or acid scavenger to be used in the production method of the compound of the present invention include the following, which are not particularly limited as long as the reaction proceeds.

inorganic bases: sodium hydroxide, potassium hydroxide, magnesium hydroxide, calcium chloride and the like basic salts: sodium carbonate, potassium carbonate, cesium carbonate, calcium carbonate, sodium hydrogen carbonate, tripotassium phosphate, dipotassium hydrogen phosphate, potassium dihydrogen phosphate and the like organic bases: triethylamine, diethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole and the like metal alkoxides: sodium methoxide, sodium ethoxide, potassium tert-butoxide and the like
alkali metal hydrides: sodium hydride, potassium hydride and the like
metal amides: sodium amide, lithium diisopropylamide, lithium hexamethyldisilazide and the like
organic lithiums: methyllithium, n-butyllithium, sec-butyllithium, tert-butyllithium and the like Examples of the acid or acidic catalyst to be used in the production method of the compound of the present invention include the following, which are not particularly limited as long as the reaction proceeds.
inorganic acids: hydrochloric acid, sulfuric acid, nitric acid, hydrobromic acid, phosphoric acid and the like
organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like
Lewis acids: boron trifluoride ether complex, zinc chloride, zinc iodide, anhydrous aluminum chloride, titanium tetrachloride, tetra(isopropoxy)titanium, anhydrous zinc chloride, anhydrous iron chloride, lanthanoid triflate and the like While the yield of the above-mentioned compound represented by the formula (I), which is obtained by each method below, may vary depending on the reaction conditions to be used, compound (I) can be easily obtained with high purity from these products by conventional separation and purification means (recrystallization, column chromatography and the like)

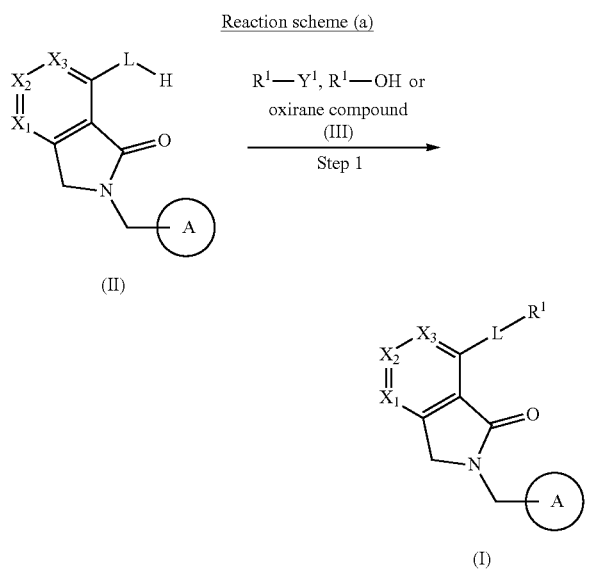

wherein $Y^1$ is a leaving group, OH is a hydroxy group, and other symbols are as defined above.

Reaction scheme (a) shows a production method of compound (I) from compounds (II) and (III).

The starting compounds (II) and (III) shown by the above-mentioned reaction (a) may be commercially available reagents or can be produced by a method known per se, the method shown in Reference Examples or a method analogous thereto.

In reaction scheme (a), when compound (III) is represented by $R^1-Y^1$ having a leaving group $Y^1$, this reaction is performed in the presence of a base, an additive and a metal catalyst as necessary, in a solvent that does not adversely influence the reaction. The amount of compound (III) to be used is generally about 1 to about 20 molar equivalents, preferably about 1 to about 10 molar equivalents, relative to compound (II).

Examples of the "base" include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like.

The amount of the base to be used is preferably about 1 to about 5 molar equivalents relative to compound (III).

Reaction scheme (a) may be performed in the copresence of an additive and a metal catalyst where necessary.

Examples of the "additive" include inorganic salts such as sodium iodide, potassium iodide, lithium chloride and the like, ammonium salts such as tetrabutylammonium iodide and the like, molecular sieves such as molecular sieve 3A, molecular sieve 4A and the like.

The amount in weight ratio of the "additive" to be used is about 0.1- to about 500-fold, preferably about 0.1- to about 30-fold, relative to compound (II).

Examples of the "metal catalyst" include metals such as nickel, palladium, copper and the like, metal salts thereof, a metal complex consisting of these and ligand, and the like. Examples of these reagents include tetrakis(triphenylphosphine)palladium(0), bis(triphenylphosphine)palladium(II) dichloride, [1,1'-bis(diphenylphosphino)ferrocene]palladium(II)dichloride, [1,1'-bis(diphenylphosphino)ferrocene]palladium(II)dichloride-dichloromethane adduct, tris(dibenzylideneacetone)dipalladium(0), bis(di-tert-butyl(4-dimethylaminophenyl)phosphine)dichloropalladium(II), chloro(2-dicyclohexylphosphino-2',4',6'-triisopropyl-1,1'-biphenyl) [2-(2-aminoethyl)phenyl]palladium(II), chloro-(2-dicyclohexylphosphino-2',6'-diisopropoxy-1,1'-biphenyl) [2-(2-aminoethyl)phenyl]palladium(II)-methyl-tert-butyl ether adduct, chloro[2-(dicyclohexylphosphino)-3,6-dimethoxy-2',4',6'-triisopropyl-1,1'-biphenyl][2-(2-aminoethyl)phenyl]palladium(II)-methyl-tert-butyl ether adduct, chloro[2-(di-tert-butylphosphino)-2',4',6'-triisopropyl-1,1'-biphenyl][2-(2-aminoethyl)phenyl])palladium(II), trans-dichlorobis(tri-o-tolylphosphine)palladium(II), palladium (II) trifluoroacetate, palladium(II) acetate, nickel(II) acetylacetonate, 1,2-bis(diphenylphosphino)ethane nickel chloride complex, copper iodide, copper bromide, copper chloride, copper acetate, copper oxide and the like.

The amount of the "metal catalyst" to be used is generally about 0.0001 to about 1000 wt %, preferably about 0.01 to about 200 wt %, relative to compound (II). When such metal catalyst is used, the reaction may be performed under a nitrogen, argon or oxygen atmosphere to perform the reaction smoothly.

Furthermore, a ligand may be added to the reaction system. Examples of the ligand include phosphine ligand [e.g., triphenylphosphine, 2,2'-bis(diphenylphosphino)-1,1'-binaphthyl, 2-dicyclohexylphosphino-2',6'-diisopropoxy-1,1'-biphenyl, 2-(dicyclohexylphosphino)-3,6-dimethoxy-2',4',6'-triisopropyl-1,1'-biphenyl, 2-di-tert-butylphosphino-3,4,5,6-tetramethyl-2',4',6'-triisopropyl-1,1'-biphenyl, 2-(di-tert-butylphosphino)biphenyl, 2-(dicyclohexylphosphino)biphenyl, 2-dicyclohexylphosphino-2',6'-dimethoxy-1,1'-biphenyl, 2-dicyclohexylphosphino-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, 4,5-bis(diphenylphosphino)-9,9-dimethylxanthene etc.], amine ligand (N,N'-dimethylethylenediamine, trans-1,2-diaminocyclohexane, trans-N,N'-dimethyl-1,2-cyclohexanediamine, 1,10-phenanthroline, 4,7-dimethoxy-1,10-phenanthroline, 3,4,7,8-tetramethyl-1,10-phenanthroline etc.), diketone ligand (2-acetylcyclohexanone, 2-isobutyrylhexanone, 2,2,6,6-tetramethyl-3,5-heptanedione etc.), salicylaldoxime, proline and the like.

The amount of the "ligand" to be used is generally about 0.0001 to about 1000 wt %, preferably about 0.01 to about 200 wt %, relative to compound (II).

It is advantageous to perform this reaction without a solvent or in a solvent inert to the reaction. While the solvent is not particularly limited as long as the reaction proceeds, for example, solvents such as alcohols such as methanol, ethanol, 1-propanol, 2-propanol, 1-butanol, 2-methyl-2-propanol, 2-methyl-2-butanol and the like, ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl)benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, nitrogen-containing aromatic hydrocarbons such as pyridine, lutidine, quinoline and the like, water and the like, a mixed solvent thereof and the like are preferable.

The reaction temperature is generally about −50° C. to about 150° C., preferably about −10° C. to about 100° C.

The reaction time is generally about 0.5 to about 20 hr.

In reaction scheme (a), when compound (III) is represented by $R^1$—OH, this reaction is performed by a method known per se, for example, the method described in Synthesis, page 1, 1981 and the like, or a method analogous thereto. That is, this reaction is generally performed in the presence of an organic phosphorus compound and an azo reagent in a solvent that does not adversely influence the reaction.

The amount of $R^1$—OH to be used, which corresponds to compound (III), is generally about 1 to about 10 molar equivalents, preferably about 1 to about 5 molar equivalents, relative to compound (II).

Examples of the "organic phosphorus compound" include triphenylphosphine, tri(n-butyl)phosphine and the like.

Examples of the "azo reagent" include diethyl azodicarboxylate, diisopropyl azodicarboxylate, azodicarbonyldipiperazine (diazene-1,2-diylbis(piperidin-1-ylmethanone)) and the like.

The amount of the organic phosphorus compound and azo reagent to be used is preferably about 1 to about 5 molar equivalents relative to compound (III).

It is advantageous to perform this reaction without a solvent or in a solvent inert to the reaction. The solvent is not particularly limited as long as the reaction proceeds and, for example, solvents such as ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl)benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, nitrogen-containing aromatic hydrocarbons such as pyridine, lutidine, quinoline and the like, water and the like, a mixed solvent thereof and the like are preferable.

The reaction temperature is generally about −50° C. to about 150° C., preferably about −10° C. to about 100° C.

The reaction time is generally about 0.5 to about 20 hr.

In reaction scheme (a), when compound (III) is an oxirane compound (a compound having an oxirane structure), this reaction is performed in the presence of a base, an acid or an additive in a solvent that does not adversely influence the reaction. The amount of the oxirane compound to be used is generally about 1 to about 20 molar equivalents relative to compound (II), and the oxirane compound can also be used as a solvent.

Examples of the "base" include alkali metal salts such as sodium hydrogen carbonate, potassium carbonate and the like; amines such as pyridine, triethylamine, N,N-dimethylaniline, 1,8-diazabicyclo[5.4.0]undec-7-ene and the like, and the like.

The amount of the base to be used is catalytic amount-about 10 molar equivalents, preferably about 1-about 5 molar equivalents, relative to compound (III).

Examples of the "acid" include inorganic acids such as hydrochloric acid, sulfuric acid and the like, organic acids such as acetic acid, trifluoroacetic acid, p-toluenesulfonic acid and the like, Lewis acids such as boron trifluoride ether complex, zinc chloride, zinc iodide and the like, and the like.

The amount of the acid to be used is about 0.05 to about molar equivalents relative to compound (III).

Examples of the "additive" include inorganic salts such as lithium perchlorate, cesium fluoride and the like, ammonium salts such as tetrabutylammonium chloride, tetrabutylammonium bromide, tetrabutylammonium perchlorate and the like, and the like. They may be used together with an acid or base.

The amount of the additive to be used is about 0.05 to about 10 molar equivalents relative to compound (III).

It is advantageous to perform this reaction without a solvent or in a solvent inert to the reaction. The solvent is not particularly limited as long as the reaction proceeds and, for example, solvents such as ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl)benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, nitrogen-containing aromatic hydrocarbons such as pyridine, lutidine, quinoline and the like, a mixed solvent thereof and the like are preferable.

The reaction temperature is generally about −50° C. to about 150° C., preferably about-10° C. to about 100° C.

The reaction time is generally about 0.5 to about 72 hr.

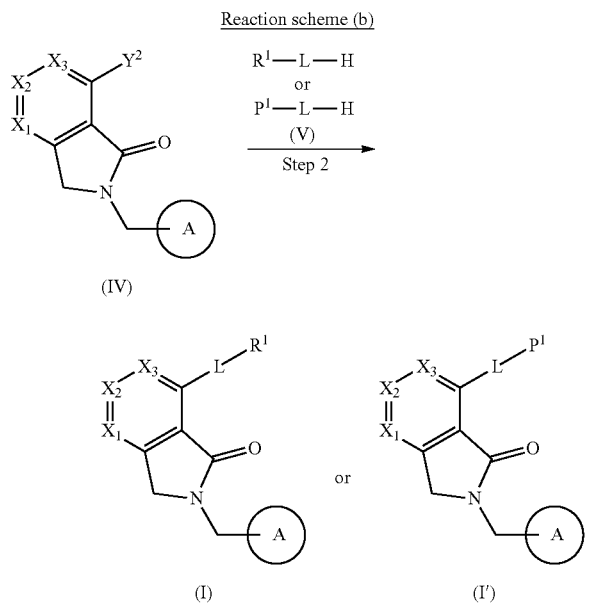

Reaction scheme (b)

wherein Y² is a leaving group, P is a protecting group, H is a hydrogen atom, and other symbols are as defined above.

Reaction scheme (b) shows a production method of compound (I) or (I') from compounds (IV) and (V). The starting compounds (IV) and (V) may be commercially available reagents or can be produced by a method known per se, the method shown in Reference Examples or a method analogous thereto.

The formula (I') can be easily led to compound (II) of reaction scheme (a) by removing the protecting group P¹ in the formula (I') by the aforementioned method or a method known per se.

The amount of compound (V) to be used is generally about 1 to about 10 molar equivalents, preferably about 1 to about 5 molar equivalents, per 1 mol of compound (IV).

The reaction scheme (b) may be performed in the copresence of a base, an additive and a metal catalyst where necessary.

Examples of the "base" include inorganic bases such as sodium hydroxide, barium hydroxide and the like, basic salts such as sodium carbonate, potassium carbonate, cesium carbonate, sodium hydrogen carbonate, potassium fluoride, cesium fluoride, tripotassium phosphate and the like, aromatic amines such as pyridine, lutidine and the like, tertiary amines such as triethylamine, N,N-diisopropylethylamine, tripropylamine, tributylamine, cyclohexyldimethylamine, 4-dimethylaminopyridine, N-methylpiperidine, N-methylpyrrolidine, N-methylmorpholine and the like, alkali metals such as metal sodium and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like.

The amount of such "base" to be used is about 0.1 to about 50 molar equivalents, preferably about 0.8 to about 30 molar equivalents, per 1 mol of compound (IV).

Examples of the "additive" include inorganic salts such as sodium iodide, potassium iodide and the like, ammonium salts such as tetrabutylammonium iodide and the like, and molecular sieves such as molecular sieve 3A, molecular sieve 4A and the like.

The amount of the additive to be used is about 0.05 to about 10 molar equivalents, or about 0.1- to about 500-fold, preferably about 0.1- to about 30-fold, in weight ratio, relative to compound (IV).

Examples of the "metal catalyst" include metals such as nickel, palladium, copper and the like, metal salts thereof, a metal complex thereof with a ligand, and the like. Examples of the reagents include tetrakis(triphenylphosphine)palladium(0), bis(triphenylphosphine)palladium(II)dichloride, [1,1'-bis(diphenylphosphino)ferrocene]palladium(II)dichloride, [1,1'-bis(diphenylphosphino)ferrocene]palladium(II) dichloride-dichloromethane adduct, tris(dibenzylideneacetone)dipalladium(0), bis(di-tert-butyl (4-dimethylaminophenyl)phosphine)dichloropalladium(II), chloro(2-dicyclohexylphosphino-2',4',6'-triisopropyl-1,1'-biphenyl)[2-(2-aminoethyl)phenyl)]palladium(II), chloro-(2-dicyclohexylphosphino-2',6'-diisopropoxy-1,1'-biphenyl) [2-(2-aminoethyl)phenyl]palladium(II)-methyl-tert-butyl ether adduct, chloro[2-(dicyclohexylphosphino)-3,6-dimethoxy-2',4',6'-triisopropyl-1,1'-biphenyl][2-(2-aminoethyl) phenyl]palladium(II)-methyl-tert-butyl ether adduct, chloro [2-(di-tert-butylphosphino)-2',4',6'-triisopropyl-1,1'-biphenyl][2-(2-aminoethyl)phenyl)]palladium(II), trans-dichlorobis(tri-o-tolylphosphine)palladium(II), palladium (II) trifluoroacetate, palladium(II) acetate, nickel(II) acetylacetonate, 1,2-bis(diphenylphosphino)ethane nickel chloride complex, copper iodide, copper bromide, copper chloride, copper acetate, copper oxide and the like.

The amount of the "metal catalyst" to be used is generally about 0.0001 to about 1000 wt %, preferably about 0.01 to about 200 wt %, relative to compound (IV). When such metal catalyst is used, the reaction may be performed under a nitrogen, argon or oxygen atmosphere to perform the reaction smoothly.

Furthermore, a ligand may be added into the reaction system. Examples of the ligand include phosphine ligands [e.g., triphenylphosphine, 2,2'-bis(diphenylphosphino)-1,1'-binaphthyl, 2-dicyclohexylphosphino-2',6'-diisopropoxy-1, 1'-biphenyl, 2-(dicyclohexylphosphino)-3,6-dimethoxy-2', 4',6'-triisopropyl-1,1'-biphenyl, 2-di-tert-butylphosphino-3, 4,5,6-tetramethyl-2',4',6'-triisopropyl-1,1'-biphenyl, 2-(di-tert-butylphosphino)biphenyl, 2-(dicyclohexylphosphino) biphenyl, 2-dicyclohexylphosphino-2',6'-dimethoxy-1,1'-biphenyl, 2-dicyclohexylphosphino-2',4',6'-triisopropyl-1, 1'-biphenyl, 2-(dicyclohexylphosphino)-2'-(N,N-dimethylamino)biphenyl, 1,1'-bis(diphenylphosphino) ferrocene, tri-tert-butylphosphine, tricyclohexylphosphine, 4,5-bis(diphenylphosphino)-9,9-dimethylxanthene and the like], amine ligands (N,N'-dimethylethylenediamine, trans-1,2-diaminocyclohexane, trans-N,N'-dimethyl-1,2-cyclohexanediamine, 1,10-phenanthroline, 4,7-dimethoxy-1,10-phenanthroline, 3,4,7,8-tetramethyl-1,10-phenanthroline etc.), diketone ligands (2-acetylcyclohexanone, 2-isobutyrylhexanone, 2,2,6,6-tetramethyl-3,5-heptanedione etc.), salicylaldoxime, proline and the like.

The amount of the "ligand" to be used is generally about 0.0001 to about 1000 wt %, preferably about 0.01 to about 200 wt %, relative to compound (IV).

It is advantageous to perform this reaction without a solvent or in a solvent inert to the reaction. The solvent is not particularly limited as long as the reaction proceeds and, for example, solvents such as alcohols such as methanol, ethanol, 1-propanol, 2-propanol, 1-butanol, 2-methyl-2-propanol, 2-methyl-2-butanol and the like, ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl) benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, nitrogen-containing aromatic hydrocarbons such as pyridine, lutidine, quinoline and the like, water and the like, a mixed solvent thereof and the like are preferable.

The reaction temperature is about −100° C. to about 300° C., preferably about −78° C. to about 250° C.

The reaction time is generally about 5 min to about 72 hr, preferably about 5 min to about 48 hr.

This reaction may be performed under an atmosphere of oxygen, nitrogen, argon or the like where necessary.

Reaction scheme (c)

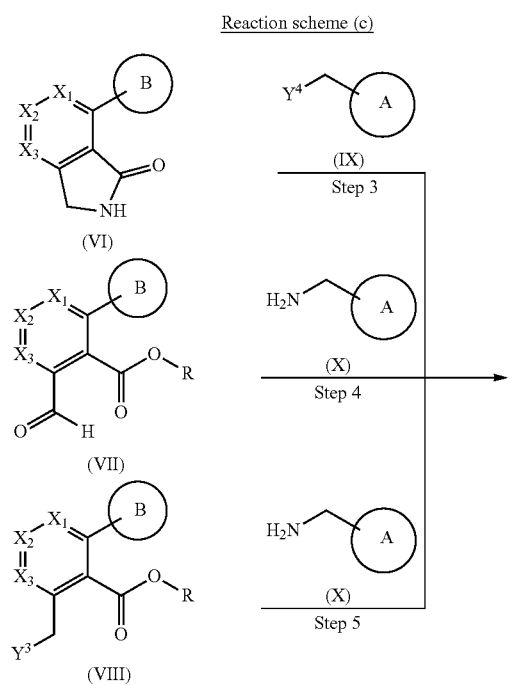

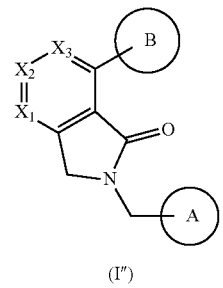

wherein $Y^3$ and $Y^4$ are leaving groups, B is $L-R^1$, $L-P^1$ or $Y^2$, $NH_2$ is an amino group, and other symbols are as defined above.

Reaction scheme (c) shows a production method of compound (I″) from compound (VI), (VII) or (VIII). In the formula, when B is $L-R^1$, compound (I″) is the same as compound (I). When B is $L-P^1$, compound (I″) is the same as compound (I′) shown in reaction scheme (b) and can be easily led to compound (II) of reaction scheme (a) by removing the protecting group $P^1$ by the aforementioned method or a method known per se. When B is $Y^2$, compound (I″) is the same as compound (IV) shown in reaction scheme (b), and can be led to compound (I) by step 2 shown in reaction scheme (b).

In reaction scheme (c), step 3 is a reaction to obtain compound (I″) from the starting compounds (VI) and (IX). The starting compounds (VI) and (IX) may be commercially available reagents or can be produced by a method known per se, the method shown in Reference Examples or a method analogous thereto.

This reaction is performed in the presence of a base in a solvent that does not adversely influence the reaction. The amount of compound (IX) to be used is generally about 1 to about 10 molar equivalents, preferably about 1 to about 5 molar equivalents, relative to compound (VI).

Examples of the "base" include alkali metal salts such as sodium hydrogen carbonate, potassium carbonate, cesium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like, and the like.

The amount of the base to be used is preferably about 1 to about 5 molar equivalents relative to compound (VI).

Step 3 may be performed in the copresence of an additive as necessary.

Examples of the additive include inorganic salts such as sodium iodide, potassium iodide and the like, ammonium salts such as tetrabutylammonium iodide and the like, and the like.

The amount of the additive to be used is about 0.05-about 10 molar equivalents relative to compound (VI).

It is advantageous to perform this reaction without a solvent or in a solvent inert to the reaction. The solvent is not particularly limited as long as the reaction proceeds and, for example, ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as benzene, toluene, xylene, mesitylene, cyclohexane, hexane and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like or a mixed solvent thereof and the like are preferable.

The reaction temperature is generally about −50° C. to about 150° C., preferably about −10° C. to about 100° C.

The reaction time is generally about 0.5 to about 20 hr.

In reaction scheme (c), step 4 is a reaction to obtain compound (I″) from starting compounds (VII) and (X).

The starting compounds (VII) and (X) may be commercially available reagents or can be produced by a method known per se, the method shown in Reference Examples or a method analogous thereto.

This step is performed in the presence of a reducing agent in a solvent that does not adversely influence the reaction. The amount of compound (X) to be used is generally about 1-about 10 molar equivalents, preferably about 1-about 5 molar equivalents, relative to compound (VII).

Examples of the reducing agent include sodium triacetoxyhydroborate, sodium cyanoborohydride, sodium borohydride, picoline borane complex and the like.

The amount of the reducing agent to be used is generally about 1 to about 10 molar equivalents, preferably about 1 to about 5 molar equivalents, relative to compound (VII).

This step may be performed in the copresence of an acid or an additive as necessary.

Examples of the "acid" include inorganic acids such as hydrochloric acid, sulfuric acid and the like, organic acids such as acetic acid, trifluoroacetic acid, p-toluenesulfonic acid and the like, Lewis acids such as boron trifluoride ether complex, zinc chloride, zinc iodide, titanium tetrachloride, tetra(isopropoxy)titanium and the like, and the like.

The amount of the acid to be used is about 0.05 to about molar equivalents, or about 0.1- to about 500-fold, preferably about 0.1- to about 30-fold, in a weight ratio, relative to compound (VII).

Examples of the "additive" include inorganic salts such as anhydrous sodium sulfate, anhydrous magnesium sulfate and the like, molecular sieves such as molecular sieve 3A, molecular sieve 4A and the like.

The amount of the additive to be used is about 0.05 to about 10 molar equivalents, or about 0.1- to about 500-fold, preferably about 0.1- to about 30-fold, at a weight ratio, relative to compound (VII)

This reaction may be performed stepwisely. For example, a reducing agent may be added after stirring for about 0.5-about 20 hr in the presence of an acid or an additive, or a reaction may be performed after removing an acid or an additive or exchanging the solvent before addition of a reducing agent.

This reaction is advantageously performed without solvent or in a solvent inert to the reaction. The solvent is not particularly limited as long as the reaction proceeds, and, for example, solvents such as alcohols such as methanol, ethanol, 1-propanol, 2-propanol, 1-butanol, 2-methyl-2-propanol, 2-methyl-2-butanol and the like, ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl)benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, nitrogen-containing aromatic hydrocarbons such as pyridine, lutidine, quinoline and the like, water and the like or a mixed solvent thereof and the like are preferable.

The reaction temperature is generally about −50° C. to about 150° C., preferably about −10° C. to about 100° C.

The reaction time is generally about 0.5-about 20 hr.

In reaction scheme (c), step 5 is a reaction to obtain compound (I‴) from starting compounds (VIII) and (X). The starting compounds (VIII) and (X) may be commercially available reagents or can be produced by a method known per se, the method shown in Reference Examples or a method analogous thereto.

This step is performed in the presence of a base in a solvent that does not adversely influence the reaction. The amount of compound (X) to be used is generally about 1 to about molar equivalents, preferably about 1 to about 5 molar equivalents, relative to compound (VIII).

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; and alkali metal alkoxides such as sodium methoxide, sodium ethoxide, potassium tert-butoxide and the like.

The amount of the base to be used is preferably about 1 to about 5 molar equivalents relative to compound (VIII).

This step may be performed in the copresence of an additive as necessary.

Examples of the additive include inorganic salts such as sodium iodide, potassium iodide and the like, ammonium salts such as tetrabutylammonium iodide and the like, and the like. These may be used together with an acid or a base.

The amount of the additive to be used is about 0.05 to about 10 molar equivalents relative to compound (VIII).

It is advantageous to perform this reaction without a solvent or in a solvent inert to the reaction. The solvent is not particularly limited as long as the reaction proceeds and, for example, solvents such as alcohols such as methanol, ethanol, 1-propanol, 2-propanol, 1-butanol, 2-methyl-2-propanol, 2-methyl-2-butanol and the like, ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl)benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, nitrogen-containing aromatic hydrocarbons such as pyridine, lutidine, quinoline and the like, water and the like, a mixed solvent thereof and the like are preferable.

The reaction temperature is generally about −50° C. to about 150° C., preferably about −10° C. to about 100° C.

The reaction time is generally about 0.5 to about 20 hr.

The amount of the base to be used is preferably about 1-about 5 molar equivalents relative to compound (XI).

Examples of the additive include inorganic salts such as sodium iodide, potassium iodide and the like, ammonium salts such as tetrabutylammonium iodide and the like, and the like. These may be used together with a base.

The amount of the additive to be used is about 0.05 to about 10 molar equivalents relative to compound (XI).

Reaction scheme (d)

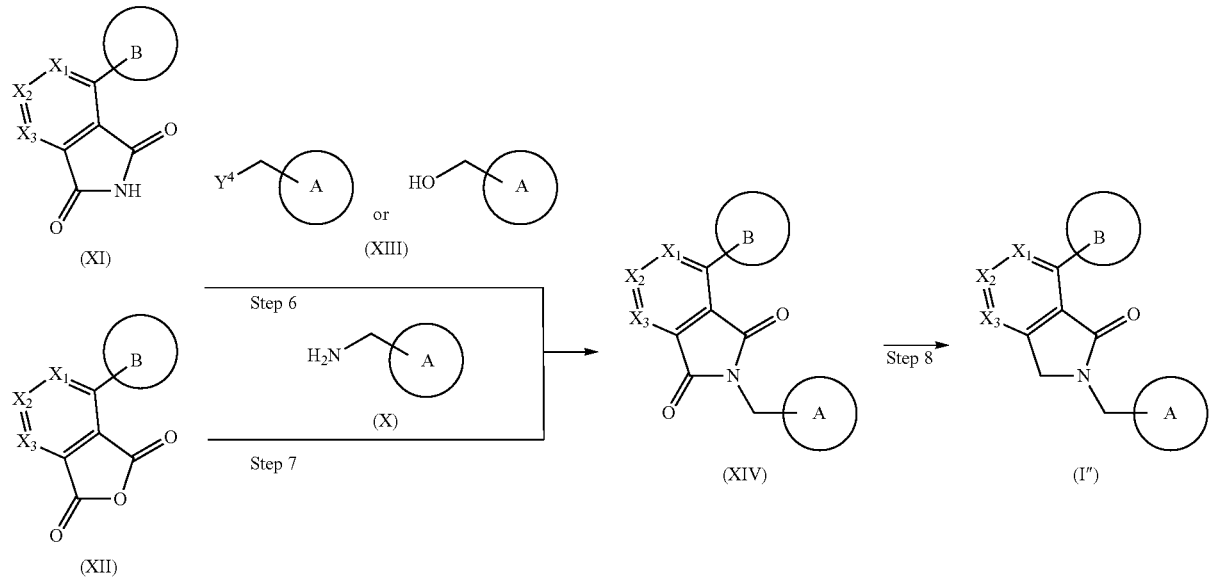

wherein each symbol is as defined above.

Reaction scheme (d) shows a production method of compound (I″) from compound (XI) or (XII) via compound (XIV). In the formula, when B is L-$R^1$, compound (I″) is the same as compound (I). When B is L-$P^1$, compound (I″) is the same as compound (I′) shown in reaction scheme (b) and can be easily led to compound (II) of reaction scheme (a) by removing the protecting group $P^1$ by the aforementioned method or a method known per se. When B is $Y^2$, compound (I″) is the same as compound (IV) shown in reaction scheme (b), and can be led to compound (I) by step 2 shown in reaction scheme (b).

In reaction scheme (d), step 6 is a reaction to obtain compound (XIV) from starting compounds (XI) and (XIII).

The starting compounds (XI) and (XIII) may be commercially available reagents or can be produced by a method known per se, the method shown in Reference Examples or a method analogous thereto.

In reaction scheme (d), when compound (XIII) is represented by $Y^4$—$CH_2$-A having a leaving group $Y^4$, this reaction is performed in the presence of a base and an additive as necessary, in a solvent that does not adversely influence the reaction. The amount of compound (XIII) to be used is generally about 1 to about 10 molar equivalents, preferably about 1 to about 5 molar equivalents, relative to compound (XI).

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; and alkali metal alkoxides such as sodium methoxide, sodium ethoxide, potassium tert-butoxide and the like.

It is advantageous to perform this reaction without a solvent or in a solvent inert to the reaction. The solvent is not particularly limited as long as the reaction proceeds and, for example, solvents such as alcohols such as methanol, ethanol, 1-propanol, 2-propanol, 1-butanol, 2-methyl-2-propanol, 2-methyl-2-butanol and the like, ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl) benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, nitrogen-containing aromatic hydrocarbons such as pyridine, lutidine, quinoline and the like, water and the like, a mixed solvent thereof, and the like are preferable.

The reaction temperature is generally about −50° C. to about 150° C., preferably about −10° C. to about 100° C.

The reaction time is generally about 0.5 to about 48 hr.

In reaction scheme (d), when compound (XIII) is represented by HO—$CH_2$-A, this reaction is performed by a method known per se, for example, the method described in Synthesis, page 1, 1981 and the like, or a method analogous thereto. That is, this reaction is generally performed in the presence of an organic phosphorus compound and an azo reagent in a solvent that does not adversely influence the reaction.

The amount of compound (XIII) to be used is generally about 1-about 10 molar equivalents, preferably about 1-about 5 molar equivalents, relative to compound (XI).

Examples of the "organic phosphorus compound" include triphenylphosphine, tri(n-butyl)phosphine and the like.

Examples of the "azo reagent" include diethyl azodicarboxylate, diisopropyl azodicarboxylate, azodicarbonyldipiperazine and the like.

The amount of the organic phosphorus compound and azo reagent to be used is preferably about 1 to about 5 molar equivalents relative to compound (XI).

It is advantageous to perform this reaction without a solvent or in a solvent inert to the reaction. The solvent is not particularly limited as long as the reaction proceeds and, for example, solvents such as ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl)benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, nitrogen-containing aromatic hydrocarbons such as pyridine, lutidine, quinoline and the like, water and the like, a mixed solvent thereof and the like are preferable.

The reaction temperature is generally about −50° C. to about 150° C., preferably about −10° C. to about 100° C.

The reaction time is generally about 0.5 to about 48 hr.

In reaction scheme (d), step 7 is a reaction to obtain compound (XIV) from starting compounds (XII) and (X).

The starting compounds (XII) and (X) may be commercially available reagents or can be produced by a method known per se, the method shown in Reference Examples or a method analogous thereto.

The amount of compound (X) to be used is generally about 1 to about 10 molar equivalents relative to compound (XII).

This reaction may be performed in the presence of a base or an acid.

Examples of the "base" include alkali metal salts such as potassium hydroxide, sodium hydroxide, sodium hydrogen carbonate, potassium carbonate and the like; amines such as pyridine, N,N-dimethylaminopyridine, triethylamine, N,N-dimethylaniline, 1,8-diazabicyclo[5.4.0]undec-7-ene and the like; metal hydrides such as potassium hydride, sodium hydride and the like; and alkali metal alkoxides such as sodium methoxide, sodium ethoxide, potassium tert-butoxide and the like.

The amount of the base to be used is catalytic amount to about 10 molar equivalents, preferably about 1 to about 5 molar equivalents, relative to compound (XII).

Examples of the "acid" include inorganic acids such as hydrochloric acid, sulfuric acid and the like, organic acids such as acetic acid, trifluoroacetic acid, p-toluenesulfonic acid and the like, Lewis acids such as boron trifluoride ether complex, zinc chloride, zinc iodide and the like, and the like.

It is advantageous to perform this reaction without a solvent or in a solvent inert to the reaction. The solvent is not particularly limited as long as the reaction proceeds and, for example, solvents such as alcohols such as methanol, ethanol, 1-propanol, 2-propanol, 1-butanol, 2-methyl-2-propanol, 2-methyl-2-butanol and the like, ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl) benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, nitrogen-containing aromatic hydrocarbons such as pyridine, lutidine, quinoline and the like, water and the like, a mixed solvent thereof and the like are preferable.

The amount of the acid to be used is about 0.05 to about molar equivalents relative to compound (XII).

The reaction temperature is generally about −50° C. to about 150° C., preferably about −10° C. to about 100° C.

The reaction time is generally about 0.5 to about 48 hr.

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like, and the like. Two or more kinds of these solvents may be used after mixing at an appropriate ratio.

The reaction temperature is generally about −50° C. to about 200° C., preferably about 15° C. to about 150° C.

The reaction time is generally about 0.5 to about 40 hr.

In reaction scheme (d), step 8 is a reaction to obtain compound (I″) from intermediate compound (XIV).

This reaction is performed in the presence of a reducing agent in a solvent that does not adversely influence the reaction. The amount of the reducing agent to be used is generally about 1 to about 10 molar equivalents, preferably about 1 to about 5 molar equivalents, relative to compound (XIV).

Examples of the reducing agent include sodium borohydride, lithium borohydride, zinc powder, iron powder, triethylsilane and the like. Alternatively, palladium or a nickel catalyst may also be used under a hydrogen atmosphere. This reaction may be performed stepwisely. For example, a method including once reducing a carbonyl group to a hydroxy group, and then removing the hydroxy group is used. In this case, the reducing agent, solvent and reaction temperature may be different between the first stage and the second stage. To be specific, sodium borohydride, zinc powder and the like are used as reducing agents in the first stage and palladium, triethylsilane and the like are used in the second stage.

Examples of the solvent that does not adversely influence the reaction include alcohols such as ethanol, methanol and the like, nitriles such as acetonitrile, propionitrile and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like, and the like. Two or more kinds of these solvents may be used after mixing at an appropriate ratio.

The reaction temperature is generally about −50° C. to about 150° C., preferably about −10° C. to about 100° C.

The reaction time is generally about 0.5 to about 20 hr.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se. To be specific, an optically active synthetic intermediate is used, or the final racemate product is subjected to optical resolution according to a conventional method to give an optical isomer.

For example, the method of optical resolution may be a method known per se, such as a fractional recrystallization method, a chiral column method, a diastereomer method etc.

1) Fractional Recrystallization Method

A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series manufactured by Daicel Corporation and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

When compound (I) is obtained as a free compound, the compound can be converted to an objective salt according to a method known per se or a method analogous thereto. Conversely, when it is obtained as a salt, the salt can be converted to a free form or other objective salt by a method known per se or a method analogous thereto.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, t-butylation and the like);

a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like);

a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be a crystal, and a single crystal form and a mixture of crystal forms are both encompassed in compound (I) of the present invention. The crystal can be produced by crystallizing according to a crystallization method known per se.

Compound (I) is useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's syndrome, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, multiple sclerosis], (3) age-related cognition memory disorders [e.g., age-related memory disorders, senile dementia]

(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, peptic ulcer, diarrhea, constipation, postoperative ileus, stress gastrointestinal disorder, (7) pain
and the like.

Compound (I) is particularly preferably effective as a cholinergic muscarinic M1 receptor positive allosteric modulator, a prophylactic or therapeutic drug for Alzheimer's disease, schizophrenia, pain, sleep disorder and the like.

Since compound (I) has an excellent cholinergic muscarinic M1 receptor positive allosteric modulator activity, it is expected to provide an excellent prophylactic or therapeutic effect for the above-mentioned diseases.

Since compound (I) is excellent in in vivo kinetics (e.g., plasma drug half-life, intracerebral migration, metabolic stability), shows low toxicity (e.g., more excellent as a medicament in terms of acute toxicity, chronic toxicity, genetic toxicity, reproductive toxicity, cardiotoxicity, drug interaction, carcinogenicity and the like), and also has excellent properties as a pharmaceutical product such as a few side effects and the like, it can be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

A preparation containing compound (I) may be any of a solid preparation such as powder, granule, tablet, capsule, orally disintegrable film and the like, or a liquid agent such as syrup, emulsion, injection and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation can be produced according to the method described in JP-A-9-263545.

In the preparation of the present invention, the content of compound (I) varies depending on the form of the preparation, but is generally 0.01 to 100% by weight, preferably 0.1 to 50% by weight, more preferably 0.5 to 20% by weight, as the amount of compound (I) relative to the whole preparation.

When compound (I) is used as the above-mentioned pharmaceutical products, it may be used alone or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and safely administered orally or parenterally. When compound (I) is formed as a preparation for topical administration, it can also be directly administered to the affected part of an articular disease. In this case, an injection is preferable. The compound can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound together with vegetable oil such as sesame oil, corn oil and the like or a mixture thereof with a phospholipid such as lecithin and the like, or medium-chain triglyceride (e.g., miglyol 812 etc.) to give an injection to be actually used.

The dose of compound (I) varies depending on the subject of administration, administration route and symptoms and is not particularly limited. For example, for oral administration to adult patients (body weight adult 40 to 80 kg, for example, 60 kg) with schizophrenia, the dose is, for example, 0.001 to 1000 mg/kg body weight/day, preferably 0.01 to 100 mg/kg body weight/day, more preferably 0.1 to 10 mg/kg body weight/day, as compound (I). This amount can be administered in one to three portions per day.

A medicament containing the compound of the present invention can be safely administered solely or by mixing with a pharmaceutically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonic agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrochloride etc.), 5-$HT_3$ antagonist (cyamemazine etc.), heart non-selective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autisma, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anticancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention or a pharmaceutical composition thereof and the concomitant drug or a pharmaceutical composition thereof is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination drug of the present invention is not particularly restricted, and it is sufficient that the compound of the present invention and the concomitant drug are combined in administration. Examples of the administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The combination drug of the present invention exhibits low toxicity. For example, the compound of the present invention or (and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent in the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, general silica gel was used unless particularly indicated, and the indication of NH means use of aminopropylsilane-bonded silica gel. The indication of DIOL means use of 3-(2,3-dihydroxypropoxy) propylsilane-bonded silica gel. In HPLC (high performance liquid chromatography), the indication of C18 means use of octadecyl-bonded silica gel. The ratio of elution solvents is, unless otherwise specified, a volume mixing ratio.

In the Examples, unless particularly indicated, "osmium oxide (immobilized catalyst I)" refers to osmium oxide (about 7% content) immobilized on a polymer with high solvent resistance, which is commercially available from Wako Pure Chemical Industries, Ltd.

In the following Examples, the following abbreviations are used.
THF: tetrahydrofuran
DMF: N,N-dimethylformamide
DMSO: dimethyl sulfoxide
NBS: N-bromosuccinimide
AIBN: 2,2'-azobis(isobutyronitrile)
ADDP: 1,1'-(azodicarbonyl)dipiperidine
DAST: diethylaminosulfur trifluoride
DME: 1,2-dimethoxyethane
$[M+H]^+$: molecular ion peak
DBU: 1,8-diazabicyclo[5.4.0]undec-7-ene
TFA: trifluoroacetic acid
DPPF: 1,1'-bis(diphenylphosphino)ferrocene
DMA: N,N-dimethylacetamide
$Pd_2(dba)_3$: tris(dibenzylideneacetone)dipalladium(0)
TBS: tert-butyldimethylsilyl
Boc: tert-butoxycarbonyl
M: molar concentration
N: normality
HPLC: high performance liquid chromatography
tRn(n=1-4): retention time in high performance liquid chromatography (number shows order of elution)

$^1$H NMR (proton nuclear magnetic resonance spectrum) was measured by Fourier-transform NMR. For the analysis, ACD/SpecManager (trade name) and the like were used. Peaks with very mild protons such as a hydroxy group, an amino group and the like are not sometimes described.

MS (mass spectrum) was measured by LC/MS (liquid chromatography mass spectrometer). As ionization, ESI (Electro Spray Ionization) method, or APCI (Atmospheric Pressure Chemical Ionization) method was used. The data indicates those found. Generally, molecular ion peaks are observed. When a compound having a tert-butoxycarbonyl group (-Boc) is used, a peak free of a tert-butoxycarbonyl group or a tert-butyl group may be observed as a fragment ion. In addition, when a compound having a hydroxyl group (—OH) is used, a peak free of $H_2O$ may be observed as a fragment ion. In a compound containing a bromine atom, a peak of $[M+H+2]^+$ is sometimes observed as a molecular ion peak together with $[M+H]^+$ at a ratio of about 1:1 due to an influence of the isotope of bromine. In this case, both values may be indicated concurrently as molecular ion peaks. In the case of a salt, generally, a molecular ion peak or a fragment ion peak of a free form is observed.

Reference Example 1

Ethyl 2-((tert-butyldimethylsilyl)oxy)-6-methylbenzoate

A solution of ethyl 2-hydroxy-6-methylbenzoate (5.0 g), tert-butyldimethylchlorosilane (4.6 g) and 1H-imidazole (2.08 g) in DMF (20 mL) was stirred at room temperature for 3 days. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (8.17 g).

$^1$H NMR (400 MHz, DMSO-$d_6$) δ 0.23 (6H, s), 0.96 (9H, s), 1.32 (3H, t, J=7.1 Hz), 2.23 (3H, s), 4.29 (2H, q, J=7.1 Hz), 6.79 (1H, d, J=8.1 Hz), 6.89 (1H, d, J=7.8 Hz), 7.20-7.31 (1H, m).

Reference Example 2

Ethyl 2-(bromomethyl)-6-(tert-butyldimethylsilyloxy)benzoate

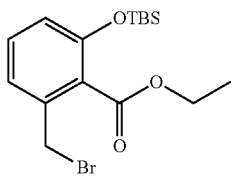 [SMILES: CCOC(=O)c1c(CBr)cccc1O[Si](C)(C)C(C)(C)C]

A solution of ethyl 2-(tert-butyldimethylsilyloxy)-6-methylbenzoate (8.17 g) obtained in Reference Example 1, NBS (5.43 g) and AIBN (0.046 g) in benzortrifluoride (30 mL) was stirred under an argon atmosphere at 90° C. for 5 hr. The reaction mixture was concentrated, and the residue was purified by silica gel chromatography (hexane-ethyl acetate) to give the title compound.

$^1$H NMR (400 MHz, DMSO-$d_6$) δ 0.21 (6H, s), 0.93 (9H, s), 1.29-1.34 (3H, m), 4.29 (2H, q, J=7.1 Hz), 4.60 (2H, s), 6.92 (1H, d, J=8.1 Hz), 7.12 (1H, d, J=7.6 Hz), 7.34 (1H, t, J=7.9 Hz).

Reference Example 3

2-(4-bromobenzyl)-7-((tert-butyldimethylsilyl)oxy)isoindolin-1-one and 2-(4-bromobenzyl)-7-hydroxyisoindolin-1-one

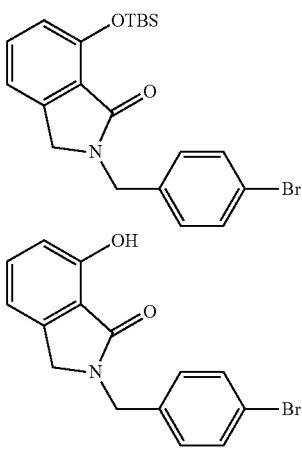

To a solution of ethyl 2-(bromomethyl)-6-((tert-butyldimethylsilyl)oxy)benzoate (3.0 g) obtained in Reference Example 2 in methanol (20 mL) were added (4-bromophenyl)methanamine hydrochloride (1.79 g) and triethylamine (3.36 mL), and the mixture was stirred under an argon atmosphere at room temperature overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give 2-(4-bromobenzyl)-7-((tert-butyldimethylsilyl)oxy)isoindolin-1-one (1.02 g) and 2-(4-bromobenzyl)-7-hydroxyisoindolin-1-one (0.34 g).

2-(4-bromobenzyl)-7-((tert-butyldimethylsilyl)oxy)isoindolin-1-one: $^1$H NMR (300 MHz, DMSO-$d_6$) δ 0.22 (6H, s), 1.01 (9H, s), 4.27 (2H, s), 4.64 (2H, s), 6.86 (1H, dd, J=8.1, 0.6 Hz), 7.06-7.14 (1H, m), 7.18-7.27 (2H, m), 7.40-7.49 (1H, m), 7.50-7.58 (2H, m).

2-(4-bromobenzyl)-7-hydroxyisoindolin-1-one: $^1$H NMR (300 MHz, DMSO-$d_6$) δ 4.29 (2H, s), 4.63 (2H, s), 6.82 (1H, d, J=7.7 Hz), 6.89-6.97 (1H, m), 7.20-7.26 (2H, m), 7.33-7.41 (1H, m), 7.52-7.59 (2H, m), 9.63 (1H, brs).

Reference Example 4

(4-(1-methyl-1H-pyrazol-4-yl)phenyl)methanamine dihydrochloride

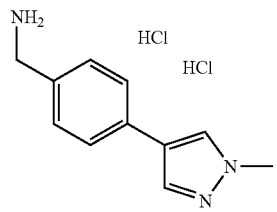

A mixed solution of tert-butyl 4-bromobenzylcarbamate (12.0 g), 1-methyl-4-(4,4,5,5-tetramethyl-1,3,2-dioxaborolan-2-yl)-1H-pyrazole (10.4 g), sodium carbonate (6.64 g) and tetrakis(triphenylphosphine)palladium(0) (2.42 g) in 1,2-dimethoxyethane (120 mL)-water (40 mL) was stirred under an argon atmosphere at 90° C. overnight. The reaction solution was concentrated, and the residue was diluted with ethyl acetate and washed with saturated brine. The organic layer was separated, dried over anhydrous sodium sulfate, and concentrated. The residue was solidified with diisopropyl ether to give a crudely purified product. The crudely purified product was dissolved in ethyl acetate (90 mL), 4N hydrochloric acid (ethyl acetate solution) (50 mL) was added, and the mixture was stirred at room temperature for 3 hr. The precipitate was collected by filtration to give the title compound (9.18 g).

$^1$H NMR (300 MHz, DMSO-$d_6$) δ 3.86 (3H, s), 3.98 (2H, q, J=5.7 Hz), 7.45-7.50 (2H, m), 7.56-7.64 (3H, m), 7.90 (1H, d, J=0.8 Hz), 8.18 (1H, s), 8.46 (3H, brs).

Reference Example 5

7-methoxy-2-(4-(1-methyl-1H-pyrazol-4-yl)benzyl)isoindolin-1-one

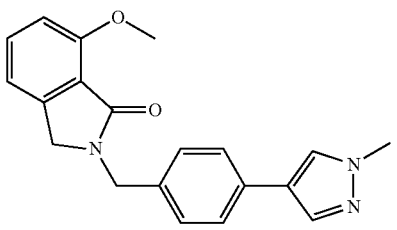 [SMILES: COc1cccc2c1C(=O)N(Cc1ccc(-c3cnn(C)c3)cc1)C2]

A solution of ethyl 2-(bromomethyl)-6-methoxybenzoate (0.95 g), (4-(1-methyl-1H-pyrazol-4-yl)phenyl)methanamine dihydrochloride (0.91 g) obtained in Reference Example 4 and triethylamine (1.94 mL) in ethanol (10 mL) was stirred under a nitrogen atmosphere at room temperature overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (0.44 g).

$^1$H NMR (300 MHz, DMSO-$d_6$) δ 3.80-3.90 (6H, m), 4.28 (2H, s), 4.62 (2H, s), 7.04 (2H, dd, J=11.0, 7.6 Hz), 7.23 (2H, d, J=8.3 Hz), 7.45-7.58 (3H, m), 7.82 (1H, d, J=0.8 Hz), 8.10 (1H, s).

Reference Example 6

7-hydroxy-2-(4-(1-methyl-1H-pyrazol-4-yl)benzyl)isoindolin-1-one

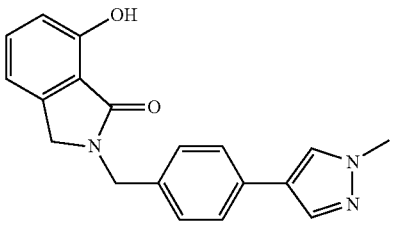 [SMILES: Cn1cc(-c2ccc(CN3Cc4cccc(O)c4C3=O)cc2)cn1]

To 7-methoxy-2-(4-(1-methyl-1H-pyrazol-4-yl)benzyl)isoindolin-1-one (3.14 g) obtained in Reference Example 5 was added 25% hydrobromic acid (acetic acid solution) (30 mL), and the mixture was stirred under a nitrogen atmosphere at 120° C. overnight. The reaction solution was neutralized with saturated aqueous sodium hydrogen carbonate solution, and the resulting precipitate was collected by filtration, and solidified with diisopropyl ether to give the title compound (2.57 g).

$^1$H NMR (300 MHz, DMSO-$d_6$) δ 3.85 (3H, s), 4.29 (2H, s), 4.63 (2H, s), 6.82 (1H, d, J=8.1 Hz), 6.93 (1H, d, J=7.6 Hz), 7.25 (2H, d, J=8.1 Hz), 7.31-7.42 (1H, m), 7.53 (2H, d, J=8.1 Hz), 7.82 (1H, s), 8.10 (1H, s), 9.59 (1H, s).

Reference Example 7

5-(1-methyl-1H-pyrazol-4-yl)thiophene-2-carbaldehyde

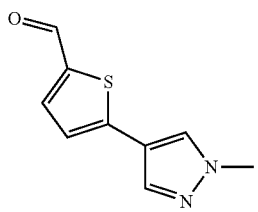

A solution of 1-methyl-4-(4,4,5,5-tetramethyl-1,3,2-dioxaborolan-2-yl)-1H-pyrazole (3.06 g), bis(tri-tert-butylphosphine)palladium(0) (0.19 g), cesium carbonate (7.19 g) and 5-bromothiophene-2-carbaldehyde (1.41 g) in dioxane (20 mL)-water (5 mL) was stirred under an argon atmosphere at 90° C. overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (1.05 g).

$^1$H NMR (300 MHz, DMSO-$d_6$) δ 3.87 (3H, s), 7.41 (1H, d, J=4.0 Hz), 7.86-8.04 (2H, m), 8.28 (1H, s), 9.84 (1H, s).

Reference Example 8

(5-(1-methyl-1H-pyrazol-4-yl)thiophen-2-yl)methanamine

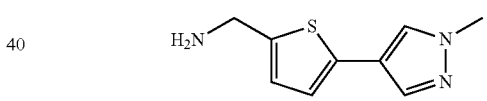

A solution of 5-(1-methyl-1H-pyrazol-4-yl)thiophene-2-carbaldehyde (2.20 g) obtained in Reference Example 7, hydroxylamine hydrochloride (1.19 g) and pyridine (4.62 mL) in ethanol (50 mL) was stirred at 50° C. for 2 hr. The reaction solution was concentrated, and the residue was washed with water, and dried to give a pale-yellow solid. To a solution of the obtained pale-yellow solid (0.17 g) in acetic acid (4 mL) was added zinc powder (0.39 g), and the mixture was stirred at room temperature overnight. The reaction solution was diluted with methanol, and the insoluble material was filtered off through Celite. The filtrate was concentrated, and diluted with ethyl acetate and water, and the insoluble material was filtered off through Celite. To the filtrate was added potassium carbonate, and the mixture was extracted with ethyl acetate. The organic layer was washed with water and saturated brine, dried over anhydrous sodium sulfate, and concentrated.

The residue was solidified with diisopropyl ether to give the title compound (0.06 g).

$^1$H NMR (300 MHz, DMSO-$d_6$) δ 3.83 (3H, s), 3.84 (2H, d, J=0.8 Hz), 6.80 (1H, dt, J=3.5, 1.1 Hz), 6.95 (1H, d, J=3.6 Hz), 7.63 (1H, d, J=0.8 Hz), 7.93 (1H, s). $NH_2$ protons were not detected.

Reference Example 9

7-((tert-butyldimethylsilyl)oxy)-2-((5-(1-methyl-1H-pyrazol-4-yl)thiophen-2-yl)methyl)isoindolin-1-one

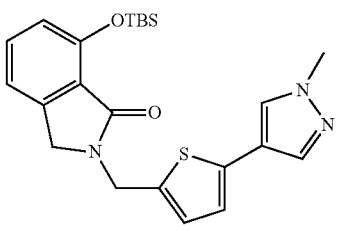 [SMILES: Cn1cc(-c2ccc(CN3Cc4cccc(O[Si](C)(C)C(C)(C)C)c4C3=O)s2)cn1]

A solution of ethyl 2-(bromomethyl)-6-((tert-butyldimethylsilyl)oxy)benzoate (0.96 g) obtained in Reference Example 2, (5-(1-methyl-1H-pyrazol-4-yl)thiophen-2-yl)methanamine (0.39 g) obtained in Reference Example 8 and triethylamine (0.83 mL) in methanol (7 mL) was stirred at room temperature overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (0.19 g).

$^1$H NMR (300 MHz, DMSO-$d_6$) δ 0.22 (6H, s), 1.01 (9H, s), 3.81 (3H, s), 4.33 (2H, s), 4.79 (2H, s), 6.86 (1H, d, J=8.1 Hz), 6.95-7.05 (2H, m), 7.12 (1H, d, J=6.8 Hz), 7.38-7.51 (1H, m), 7.64 (1H, d, J=0.8 Hz), 7.96 (1H, s).

Reference Example 10

7-hydroxy-2-((5-(1-methyl-1H-pyrazol-4-yl)thiophen-2-yl)methyl)isoindolin-1-one

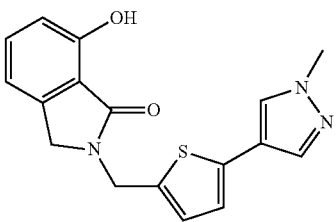 [SMILES: Cn1cc(-c2ccc(CN3Cc4cccc(O)c4C3=O)s2)cn1]

To a solution of 7-((tert-butyldimethylsilyl)oxy)-2-((5-(1-methyl-1H-pyrazol-4-yl)thiophen-2-yl)methyl)isoindolin-1-one (0.19 g) obtained in Reference Example 9 in THF (3 mL) was added 1 mol/L tetrabutylammonium fluoride (THF solution) (0.43 mL), and the mixture was stirred at room temperature for 1 hr. The reaction solution was concentrated, and the residue was purified by silica gel chromatography (hexane-ethyl acetate) to give the title compound (0.11 g).

$^1$H NMR (300 MHz, DMSO-$d_6$) δ 3.81 (3H, s), 4.34 (2H, s), 4.78 (2H, s), 6.81 (1H, d, J=8.1 Hz), 6.89-7.07 (3H, m), 7.37 (1H, dd, J=8.0, 7.5 Hz), 7.65 (1H, d, J=0.8 Hz), 7.96 (1H, s), 9.67 (1H, s).

Reference Example 11

2-(4-bromobenzyl)-7-((tert-butyldimethylsilyl)oxy)isoindolin-1-one

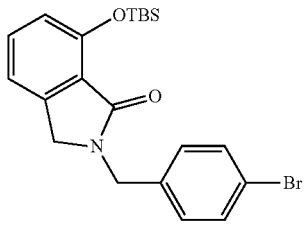 [SMILES: CC(C)(C)[Si](C)(C)Oc1cccc2c1C(=O)N(Cc1ccc(Br)cc1)C2]

A solution of ethyl 2-(bromomethyl)-6-((tert-butyldimethylsilyl)oxy)benzoate (3.0 g) obtained in Reference Example 2, (4-bromophenyl)methanamine hydrochloride (1.79 g) and triethylamine (3.36 mL) in methanol (20 mL) was stirred under an argon atmosphere at room temperature overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (1.02 g).

$^1$H NMR (300 MHz, DMSO-$d_6$) δ 0.22 (6H, s), 1.01 (9H, s), 4.27 (2H, s), 4.64 (2H, s), 6.86 (1H, dd, J=8.1, 0.6 Hz), 7.06-7.14 (1H, m), 7.18-7.27 (2H, m), 7.40-7.49 (1H, m), 7.50-7.58 (2H, m).

Reference Example 12

7-((tert-butyldimethylsilyl)oxy)-2-(4-(1-(tetrahydro-2H-pyran-2-yl)-1H-pyrazol-5-yl)benzyl)isoindolin-1-one

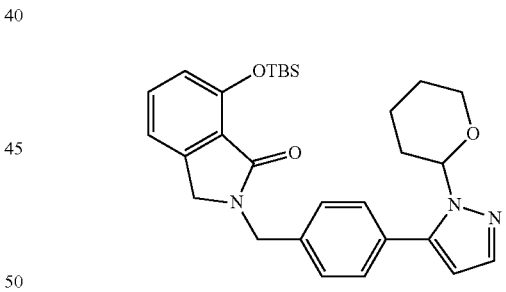

A solution of 2-(4-bromobenzyl)-7-((tert-butyldimethylsilyl)oxy)isoindolin-1-one (0.60 g) obtained in Reference Example 11, 1-(tetrahydro-2H-pyran-2-yl)-5-(4,4,5,5-tetramethyl-1,3,2-dioxaborolan-2-yl)-1H-pyrazole (0.58 g), tetrakis(triphenylphosphine)palladium(0) (0.16 g) and sodium carbonate (0.29 g) in toluene (9 mL)-ethanol (1.5 mL)-water (1.5 mL) was stirred under an argon atmosphere at 90° C. overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (0.32 g).

$^1$H NMR (300 MHz, DMSO-$d_6$) δ 0.23 (6H, s), 1.01 (9H, s), 1.39-1.68 (3H, m), 1.69-1.85 (1H, m), 1.93 (1H, brs), 2.29-2.44 (1H, m), 3.47-3.62 (1H, m), 3.87-3.99 (1H, m), 4.34 (2H, s), 4.74 (2H, s), 5.19 (1H, dd, J=10.2, 2.5 Hz), 6.43 (1H, d, J=1.9 Hz), 6.87 (1H, d, J=7.7 Hz), 7.12 (1H, d, J=7.0 Hz), 7.32-7.60 (6H, m).

Reference Example 13

7-hydroxy-2-(4-(1-(tetrahydro-2H-pyran-2-yl)-1H-pyrazol-5-yl)benzyl)isoindolin-1-one

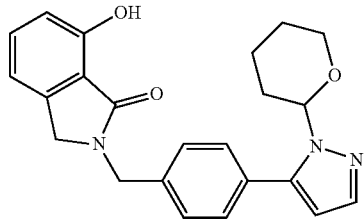 [SMILES: O=C1c2c(O)cccc2CN1Cc1ccc(-c2ccnn2C2CCCCO2)cc1]

To a solution of 7-((tert-butyldimethylsilyl)oxy)-2-(4-(1-(tetrahydro-2H-pyran-2-yl)-1H-pyrazol-5-yl)benzyl)isoindolin-1-one (0.32 g) obtained in Reference Example 12 in THF (3 mL) was added 1 mol/L tetrabutylammonium fluoride (THF solution) (0.64 mL), and the mixture was stirred at room temperature for 30 min. The reaction solution was concentrated, and the residue was purified by silica gel chromatography (hexane-ethyl acetate) to give the title compound (0.19 g).
$^1$H NMR (300 MHz, DMSO-d$_6$) δ 1.44-1.69 (3H, m), 1.70-1.84 (1H, m), 1.92 (1H, brs), 2.30-2.44 (1H, m), 3.45-3.64 (1H, m), 3.89-3.99 (1H, m), 4.36 (2H, s), 4.73 (2H, s), 5.20 (1H, dd, J=10.1, 2.2 Hz), 6.43 (1H, d, J=1.7 Hz), 6.83 (1H, d, J=7.9 Hz), 6.95 (1H, d, J=7.4 Hz), 7.30-7.46 (3H, m), 7.47-7.63 (3H, m), 9.66 (1H, brs).

Reference Example 14

2-(4-(1H-pyrazol-1-yl)benzyl)-7-hydroxyisoindolin-1-one

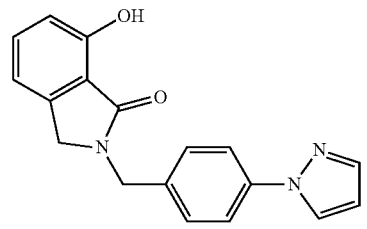 [SMILES: O=C1c2c(O)cccc2CN1Cc1ccc(-n2cccn2)cc1]

A solution of ethyl 2-(bromomethyl)-6-methoxybenzoate (0.50 g), (4-(1H-pyrazol-1-yl)phenyl)methanamine (0.32 g) and potassium carbonate (0.38 g) in ethanol (5 mL) was stirred under a nitrogen atmosphere at room temperature overnight. To the reaction solution was added water, and the resulting precipitate was collected by filtration, and dried. To the obtained white solid was added 25% hydrobromic acid (acetic acid solution) (5 mL), and the mixture was stirred under a nitrogen atmosphere at 120° C. overnight. The reaction solution was neutralized with saturated aqueous sodium hydrogen carbonate solution, and ethyl acetate was added. The organic layer was separated, washed with saturated brine, dried over anhydrous sodium sulfate, and concentrated. The residue was purified by NH silica gel chromatography (hexane-ethyl acetate) to give the title compound (0.31 g).
$^1$H NMR (300 MHz, DMSO-d$_6$) δ 4.31 (2H, s), 4.69 (2H, s), 6.48-6.58 (1H, m), 6.82 (1H, d, J=8.3 Hz), 6.94 (1H, d, J=7.6 Hz), 7.30-7.44 (3H, m), 7.73 (1H, d, J=1.3 Hz), 7.82 (2H, d, J=8.7 Hz), 8.46 (1H, d, J=2.3 Hz), 9.63 (1H, brs).

Reference Example 15

(4-(3-methyl-1H-pyrazol-1-yl)phenyl)methanamine hydrochloride

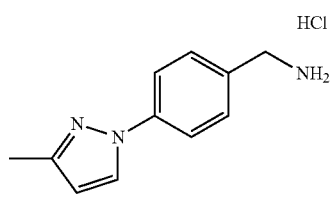

To a solution of (4-(3-methyl-1H-pyrazol-1-yl)phenyl)methanol (0.34 g) in THF (5 mL) were added diphenylphosphoryl azide (0.60 g) and 1,8-diazabicyclo[5.4.0]undec-7-ene (0.33 mL), and the mixture was stirred under an argon atmosphere at 70° C. for 4 hr. The reaction mixture was diluted with ethyl acetate, and washed with saturated brine. The organic layer was separated, dried over anhydrous sodium sulfate, and concentrated. The obtained residue was dissolved in THF (4 mL)-water (0.44 mL), triphenylphosphine (0.57 g) was added, and the mixture was stirred under an argon atmosphere at 70° C. for 4 hr. The reaction mixture was diluted with ethyl acetate, and washed with saturated brine. The organic layer was separated, dried over anhydrous sodium sulfate, and concentrated. The obtained residue was dissolved in ethyl acetate, and 4N hydrochloric acid (ethyl acetate solution) (0.68 mL) was added. The resulting precipitate was collected by filtration to give the title compound (0.32 g).
$^1$H NMR (300 MHz, DMSO-d$_6$) δ 2.27 (3H, s), 4.04 (2H, s), 6.35 (1H, d, J=2.3 Hz), 7.56 (2H, d, J=8.7 Hz), 7.77-7.95 (2H, m), 8.22 (3H, brs), 8.40 (1H, d, J=2.3 Hz).

Reference Example 16

7-hydroxy-2-(4-(3-methyl-1H-pyrazol-1-yl)benzyl)isoindolin-1-one

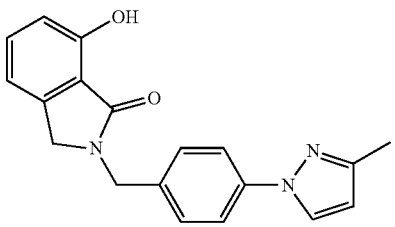 [SMILES: Cc1ccn(-c2ccc(CN3Cc4cccc(O)c4C3=O)cc2)n1]

A solution of ethyl 2-(bromomethyl)-6-((tert-butyldimethylsilyl)oxy)benzoate (0.38 g) obtained in Reference Example 2, (4-(3-methyl-1H-pyrazol-1-yl)phenyl)methanamine hydrochloride (0.32 g) and triethylamine (0.38 g) in methanol (5 mL)

was stirred under an argon atmosphere at room temperature overnight. The reaction mixture was diluted with ethyl acetate, and washed with saturated brine. The organic layer was separated, dried over anhydrous sodium sulfate, and concentrated. The residue was crudely purified by silica gel chromatography (hexane-ethyl acetate). To a solution of the obtained crudely purified product in THF (4 mL) was added 1 mol/L tetrabutylammonium fluoride (THF solution) (0.5 mL), and the mixture was stirred under an argon atmosphere at room temperature for 10 min. The reaction solution was concentrated, and the residue was purified by silica gel chromatography (hexane-ethyl acetate) to give the title compound (0.15 g).

$^1$H NMR (300 MHz, DMSO-$d_6$) δ 2.26 (3H, s), 4.31 (2H, s), 4.68 (2H, s), 6.31 (1H, d, J=2.3 Hz), 6.82 (1H, d, J=8.1 Hz), 6.94 (1H, d, J=7.4 Hz), 7.29-7.46 (3H, m), 7.75 (2H, d, J=8.7 Hz), 8.33 (1H, d, J=2.3 Hz), 9.63 (1H, brs).

Reference Example 17

4-((7-methoxy-1-oxoisoindolin-2-yl)methyl)benzonitrile

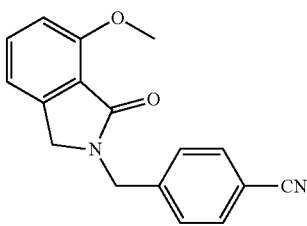 [SMILES: COc1cccc2c1C(=O)N(Cc1ccc(C#N)cc1)C2]

A solution of ethyl 2-(bromomethyl)-6-methoxybenzoate (12.0 g), 4-(aminomethyl)benzonitrile hydrochloride (7.67 g) and triethylamine (10.5 g) in methanol (100 mL) was stirred at 70-80° C. for 18 hr. The reaction solution was concentrated, water was added to the residue, and the mixture was extracted with ethyl acetate. The organic layer was separated, washed with 1N hydrochloric acid and saturated brine, dried over anhydrous sodium sulfate, and concentrated. The residue was purified by silica gel chromatography and HPLC (C18, mobile phase: water/acetonitrile (containing 0.1% TFA)) to give the title compound (2.96 g).

$^1$H NMR (400 MHz, CDCl$_3$) δ 3.96 (3H, s), 4.27 (2H, s), 4.82 (2H, s), 6.91 (1H, d, J=8.4 Hz), 6.97 (1H, d, J=7.6 Hz), 7.42 (2H, d, J=8.0 Hz), 7.50 (1H, t, J=8.0 Hz), 7.62 (2H, d, J=8.4 Hz).

Reference Example 18

4-((7-hydroxy-1-oxoisoindolin-2-yl)methyl)benzonitrile

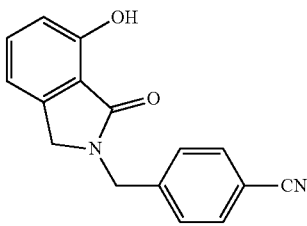 [SMILES: N#Cc1ccc(CN2Cc3cccc(O)c3C2=O)cc1]

To a solution of 4-((7-methoxy-1-oxoisoindolin-2-yl)methyl)benzonitrile (2.96 g) obtained in Reference Example 17 in dichloromethane (50 mL) was added boron tribromide (13.3 g) at 0° C., and the mixture was stirred at 10-15° C. for 18 hr. The reaction solution was poured into ice water, diluted with 1N hydrochloric acid, and extracted with dichloromethane. The organic layer was divided, washed with saturated brine, dried over anhydrous sodium sulfate, and concentrated to give the title compound (2.21 g).

$^1$H NMR (300 MHz, DMSO-$d_6$) δ 4.32 (2H, s), 4.75 (2H, s), 6.83 (1H, d, J=8.1 Hz), 6.94 (1H, d, J=7.5 Hz), 7.38 (1H, t, J=7.8 Hz), 7.44 (2H, d, J=8.4 Hz), 7.82 (2H, d, J=8.4 Hz), 9.72 (1H, brs).

Reference Example 19

(4-(1-methyl-1H-pyrazol-3-yl)phenyl)methanamine hydrochloride

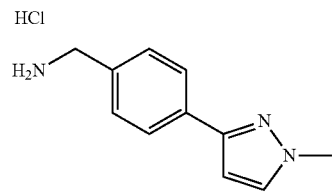

To a solution of (4-(1-methyl-1H-pyrazol-3-yl)phenyl) methanol (4.15 g) in THF (100 mL) were added diphenylphosphoryl azide (11 g) and 1,8-diazabicyclo[5.4.0]undec-7-ene (7.0 g), and the mixture was stirred under a nitrogen atmosphere at 70° C. for 5 hr. The residue was crudely purified by silica gel chromatography (hexane-ethyl acetate). The obtained residue was dissolved in THF (40 mL)-water (4.4 mL), triphenylphosphine (5.86 g) was added, and the mixture was stirred under a nitrogen atmosphere at 70° C. for 3 hr. The reaction mixture was diluted with ethyl acetate, and washed with saturated brine. The organic layer was separated, dried over anhydrous sodium sulfate, and concentrated. The obtained residue was dissolved in ethyl acetate, and 4N hydrochloric acid (ethyl acetate solution) (7 mL) was added. The resulting precipitate was collected by filtration to give the title compound (4.16 g).

$^1$H NMR (300 MHz, DMSO-$d_6$) δ 3.88 (3H, s), 4.02-4.08 (2H, m), 6.72 (1H, d, J=2.3 Hz), 7.49 (2H, d, J=8.3 Hz), 7.74 (1H, d, J=2.3 Hz), 7.78-7.89 (2H, m), 8.32 (3H, brs).

Reference Example 20

7-hydroxy-2-(4-(1-methyl-1H-pyrazol-3-yl)benzyl) isoindolin-1-one

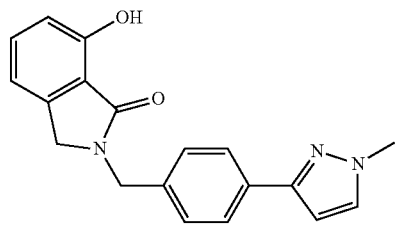 [SMILES: Cn1ccc(-c2ccc(CN3Cc4cccc(O)c4C3=O)cc2)n1]

A solution of ethyl 2-(bromomethyl)-6-((tert-butyldimethylsilyl)oxy)benzoate (2.08 g) obtained in Reference Example 2, (4-(1-methyl-1H-pyrazol-3-yl)phenyl)methanamine hydrochloride (0.83 g) obtained in Reference Example 19 and triethylamine (1.55 mL) in methanol (15 mL) was stirred under an argon atmosphere at room temperature for 3 days. The reaction mixture was concentrated, 1N hydrochloric acid (3 mL) was added, and the resulting precipitate was collected by filtration, and dried to give the title compound (0.60 g).

$^1$H NMR (300 MHz, DMSO-$d_6$) δ 3.87 (3H, s), 4.30 (2H, s), 4.66 (2H, s), 6.65 (1H, d, J=2.3 Hz), 6.82 (1H, d, J=8.3 Hz), 6.94 (1H, d, J=7.2 Hz), 7.28 (2H, d, J=8.3 Hz), 7.37 (1H, t, J=7.7 Hz), 7.63-7.85 (3H, m), 9.55 (1H, brs).

Reference Example 21

2-(3-bromobenzyl)-7-((tert-butyldimethylsilyl)oxy)isoindolin-1-one and 2-(3-bromobenzyl)-7-hydroxy-isoindolin-1-one

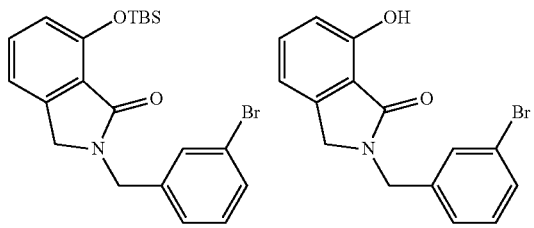

A solution of ethyl 2-(bromomethyl)-6-((tert-butyldimethylsilyl)oxy)benzoate (1.93 g) obtained in Reference Example 2, (3-bromophenyl)methanamine (1.0 g) and triethylamine (2.25 mL) in methanol (20 mL) was stirred at room temperature overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give 2-(3-bromobenzyl)-7-((tert-butyldimethylsilyl)oxy)isoindolin-1-one (0.65 g) and 2-(3-bromobenzyl)-7-hydroxyisoindolin-1-one (0.23 g).

2-(3-bromobenzyl)-7-((tert-butyldimethylsilyl)oxy)isoindolin-1-one: $^1$H NMR (300 MHz, DMSO-$d_6$) δ 0.26 (6H, s), 1.05 (9H, s), 4.34 (2H, s), 4.71 (2H, s), 6.91 (1H, d, J=7.9 Hz), 7.15 (1H, d, J=7.0 Hz), 7.25-7.44 (2H, m), 7.44-7.59 (3H, m).

2-(3-bromobenzyl)-7-hydroxyisoindolin-1-one: $^1$H NMR (300 MHz, DMSO-$d_6$) δ 4.31 (2H, s), 4.66 (2H, s), 6.82 (1H, d, J=8.1 Hz), 6.94 (1H, d, J=7.4 Hz), 7.24-7.41 (3H, m), 7.44-7.54 (2H, m), 9.68 (1H, brs).

Reference Example 22

7-hydroxy-2-(3-(1-methyl-1H-pyrazol-4-yl)benzyl)isoindolin-1-one

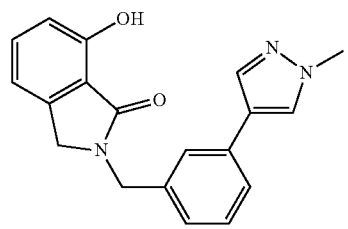 [SMILES: Cn1cc(-c2cccc(CN3Cc4cccc(O)c4C3=O)c2)cn1]

A solution of 2-(3-bromobenzyl)-7-((tert-butyldimethylsilyl)oxy)isoindolin-1-one (0.64 g) obtained in Reference Example 21, 1-methyl-4-(4,4,5,5-tetramethyl-1,3,2-dioxaborolan-2-yl)-1H-pyrazole (0.62 g), tetrakis(triphenylphosphine)palladium(0) (0.17 g) and sodium carbonate (0.47 g) in 1,2-dimethoxyethane (6 mL)-water (1 mL) was stirred under an argon atmosphere at 100° C. overnight. The reaction mixture was diluted with ethyl acetate, and washed with saturated brine. The organic layer was separated, dried over anhydrous sodium sulfate, and concentrated. The residue was crudely purified by silica gel chromatography (hexane-ethyl acetate) and solidified with diisopropyl ether to give the title compound (0.30 g).

$^1$H NMR (300 MHz, DMSO-$d_6$) δ 3.85 (3H, s), 4.31 (2H, s), 4.66 (2H, s), 6.82 (1H, d, J=8.1 Hz), 6.88-7.01 (1H, m), 7.07 (1H, d, J=7.6 Hz), 7.25-7.42 (2H, m), 7.43-7.55 (2H, m), 7.82 (1H, d, J=0.8 Hz), 8.11 (1H, s), 9.61 (1H, s).

Reference Example 23

6-(1-methyl-1H-pyrazol-4-yl)nicotinonitrile

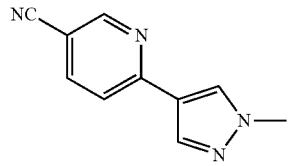

A solution of 6-bromonicotinonitrile (15.0 g), 1-methyl-4-(4,4,5,5-tetramethyl-1,3,2-dioxaborolan-2-yl)-1H-pyrazole (18.9 g), tetrakis(triphenylphosphine)palladium(0) (4.76 g) and sodium carbonate (13.1 g) in 1,2-dimethoxyethane (150 mL)-water (50 mL) was refluxed under a nitrogen atmosphere for 20 hr. The insoluble material was filtered off, and the filtrate was extracted with ethyl acetate. The organic layer was washed with saturated brine, dried over anhydrous sodium sulfate, and concentrated. The residue was purified by silica gel chromatography (petroleum ether-ethyl acetate, 0.1% triethylamine) to give the title compound (6.9 g).

$^1$H NMR (400 MHz, DMSO-$d_6$) δ 3.90 (3H, s), 7.83 (1H, dd, J=8.0, 0.8 Hz), 8.12 (1H, s), 8.23 (1H, dd, J=8.4, 2.0 Hz), 8.44 (1H, s), 8.91 (1H, dd, J=2.0, 0.8 Hz).

Reference Example 24

Tert-butyl ((6-(1-methyl-1H-pyrazol-4-yl)pyridin-3-yl)methyl)carbamate

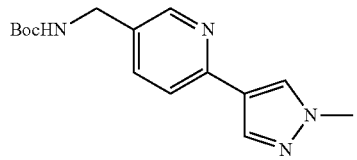 [SMILES: Cn1cc(-c2ccc(CNC(=O)OC(C)(C)C)cn2)cn1]

To a solution of 6-(1-methyl-1H-pyrazol-4-yl)nicotinonitrile (10.0 g) obtained in Reference Example 23 in THF (100 mL) was added 1 mol/L borane-THF complex (THF solution) (160 mL) at 0° C., and the mixture was stirred under a nitrogen atmosphere at 50-60° C. for 16 hr. To the reaction solution was added methanol (100 mL), and the mixture was stirred at 50-60° C. for 1 hr, and concentrated. The residue was dissolved in THF (100 mL), triethylamine (10.8 g) and di-tert-butyl dicarbonate (23.2 g) were added, and the mixture was stirred under a nitrogen atmosphere at 10-15° C. for 72 hr. The reaction mixture was diluted with water and ethyl acetate, and the organic layer was separated, washed with saturated brine, dried over anhydrous sodium sulfate, and concentrated. The residue was purified by silica gel chromatography (ethyl acetate, 1% triethylamine) to give the title compound (5.0 g).

$^1$H NMR (400 MHz, DMSO-d$_6$) δ 1.39 (9H, s), 3.87 (3H, s), 4.11 (2H, d, J=6.0 Hz), 7.44 (1H, t, J=6.0 Hz), 7.55-7.65 (2H, m), 7.96 (1H, s), 8.24 (1H, s), 8.36 (1H, s).

Reference Example 25

(6-(1-methyl-1H-pyrazol-4-yl)pyridin-3-yl)methanamine dihydrochloride

To a solution of tert-butyl ((6-(1-methyl-1H-pyrazol-4-yl)pyridin-3-yl)methyl)carbamate (4.5 g) obtained in Reference Example 24 in methanol (20 mL) was added 4N hydrochloric acid (methanol solution) (40 mL), and the mixture was stirred under a nitrogen atmosphere at 0° C. for 16 hr. The resulting precipitate was collected by filtration to give the title compound (2.85 g).

$^1$H NMR (400 MHz, D2O) δ 4.02 (3H, s), 4.43 (2H, s), 8.24 (1H, d, J=8.8 Hz), 8.26 (1H, s), 8.48 (1H, s), 8.57 (1H, dd, J=8.8, 2.0 Hz), 8.71 (1H, d, J=2.0 Hz), NH$_2$ and 2×HCl protons were not detected.

Reference Example 26

5-(1-methyl-1H-pyrazol-4-yl)picolinonitrile

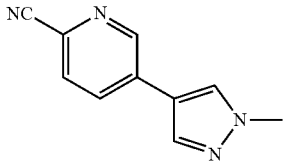

A solution of 5-bromopicolinonitrile (20.0 g), 1-methyl-4-(4,4,5,5-tetramethyl-1,3,2-dioxaborolan-2-yl)-1H-pyrazole (25.2 g), tetrakis(triphenylphosphine)palladium(0) (4.02 g) and sodium carbonate (17.5 g) in dioxane (200 mL)-water (40 mL) was refluxed under a nitrogen atmosphere for 20 hr. The insoluble material was filtered off, and the filtrate was diluted with water and ethyl acetate, and the organic layer was washed with saturated brine, dried over anhydrous sodium sulfate, and concentrated. The residue was purified by silica gel chromatography (petroleum ether-ethyl acetate, 0.5% triethylamine) to give the title compound (12.7 g).

$^1$H NMR (400 MHz, DMSO-d$_6$) δ 3.89 (3H, s), 7.99 (1H, dd, J=8.0, 0.8 Hz), 8.11 (1H, d, J=0.8 Hz), 8.19 (1H, dd, J=8.4, 2.4 Hz), 8.42 (1H, s), 9.01 (1H, dd, J=2.4, 1.2 Hz).

Reference Example 27

Tert-butyl ((5-(1-methyl-1H-pyrazol-4-yl)pyridin-2-yl)methyl)carbamate

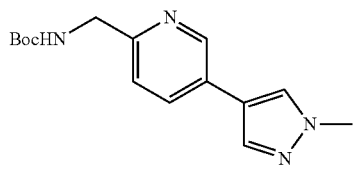 [SMILES: Cn1cc(-c2ccc(CNC(=O)OC(C)(C)C)nc2)cn1]

To a solution of 5-(1-methyl-1H-pyrazol-4-yl)picolinonitrile (18.0 g) obtained in Reference Example 26 in THF (100 mL) was added 1 mol/L borane-THF complex (THF solution) (293 mL) at 0° C., and the mixture was stirred under a nitrogen atmosphere at 50-60° C. for 16 hr. To the reaction solution was added methanol (200 mL), and the mixture was stirred at 50-60° C. for 2 hr, and concentrated. The residue was dissolved in water (400 mL), sodium carbonate (20.8 g) and di-tert-butyl dicarbonate (42.8 g) were added, and the mixture was stirred under a nitrogen atmosphere at 10-15° C. for 48 hr. The reaction mixture was diluted with ethyl acetate, and the organic layer was separated, washed with water and saturated brine, dried over anhydrous sodium sulfate, and concentrated. The residue was purified by silica gel chromatography (ethyl acetate-1% triethylamine and petroleum ether-ethyl acetate-0.5% triethylamine) to give the title compound (3.5 g).

$^1$H NMR (400 MHz, CDCl$_3$) δ 1.46 (9H, s), 3.96 (3H, s), 4.43 (2H, d, J=5.6 Hz), 5.51 (1H, brs), 7.27-7.30 (1H, m), 7.65 (1H, s), 7.71 (1H, dd, J=8.0, 2.4 Hz), 7.76 (1H, s), 8.65 (1H, d, J=2.0 Hz).

Reference Example 28

(5-(1-methyl-1H-pyrazol-4-yl)pyridin-2-yl)methanamine hydrochloride

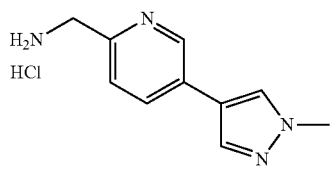

To a solution of tert-butyl ((5-(1-methyl-1H-pyrazol-4-yl)pyridin-2-yl)methyl)carbamate (3.5 g) obtained in Reference Example 27 in methanol (10 mL) was added 4N hydrochloric acid (methanol solution) (50 mL), and the mixture was stirred under a nitrogen atmosphere at room temperature for 16 hr. The reaction solution was concentrated, and the residue was solidified with ethyl acetate-acetone to give the title compound (2.40 g).

$^1$H NMR (400 MHz, DMSO-$d_6$) δ 3.89 (3H, s), 4.25-4.35 (2H, m), 7.86 (1H, d, J=8.0 Hz), 8.11 (1H, s), 8.37 (1H, d, J=8.4 Hz), 8.43 (1H, s), 8.83 (3H, brs), 9.02 (1H, d, J=1.6 Hz).

Reference Example 29

7-((tert-butyldimethylsilyl)oxy)-2-((6-chloropyridin-3-yl)methyl)isoindolin-1-one and 2-((6-chloropyridin-3-yl)methyl)-7-hydroxyisoindolin-1-one

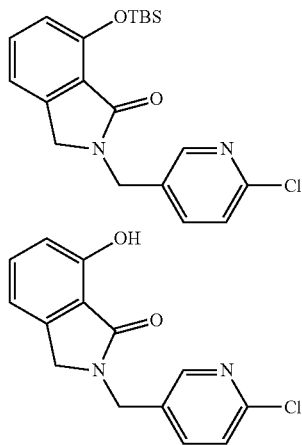

A solution of ethyl 2-(bromomethyl)-6-((tert-butyldimethylsilyl)oxy)benzoate (4.0 g) obtained in Reference Example 2, (6-chloropyridin-3-yl)methanamine (3.1 g) and triethylamine (2.99 mL) in methanol (30 mL) was stirred under an argon atmosphere at room temperature overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give 7-((tert-butyldimethylsilyl)oxy)-2-((6-chloropyridin-3-yl)methyl)isoindolin-1-one (1.67 g) and 2-((6-chloropyridin-3-yl)methyl)-7-hydroxyisoindolin-1-one (0.33 g).

7-((tert-butyldimethylsilyl)oxy)-2-((6-chloropyridin-3-yl)methyl)isoindolin-1-one: $^1$H NMR (300 MHz, DMSO-$d_6$) δ 0.21 (6H, s), 1.00 (9H, s), 4.33 (2H, s), 4.70 (2H, s), 6.86 (1H, d, J=7.6 Hz), 7.10 (1H, d, J=7.6 Hz), 7.40-7.54 (2H, m), 7.74 (1H, dd, J=8.2, 2.5 Hz), 8.36 (1H, d, J=1.9 Hz).

2-((6-chloropyridin-3-yl)methyl)-7-hydroxyisoindolin-1-one: $^1$H NMR (300 MHz, DMSO-$d_6$) δ 4.34 (2H, s), 4.69 (2H, s), 6.81 (1H, d, J=7.4 Hz), 6.93 (1H, d, J=7.4 Hz), 7.30-7.43 (1H, m), 7.44-7.57 (1H, m), 7.71-7.81 (1H, m), 8.31-8.44 (1H, m), 9.68 (1H, brs).

Reference Example 30

(4-(1-methyl-1H-1,2,3-triazol-4-yl)phenyl)methanol

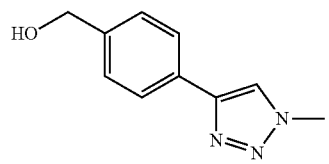

To a solution of triphenylphosphine (1.5 g) in methanol (25 mL) was added copper(I) bromide (0.31 g) at 60° C., and the mixture was stirred at the same temperature for 10 min. The solid was collected by filtration, and washed with ethanol and diethyl ether. To a mixed solution of (4-ethynylphenyl)methanol (0.50 g), sodium azide (0.32 g) and methyl iodide (0.24 mL) in DMSO (8 mL)-water (2 mL) was added the obtained above solid (0.18 g), and the mixture was stirred at room temperature overnight. The reaction mixture was diluted with saturated ammonium chloride solution and ethyl acetate. The organic layer was washed with water and saturated brine, dried over anhydrous magnesium sulfate and concentrated. The residue was purified by silica gel column chromatography (hexane-ethyl acetate) to give the title compound (0.45 g).

$^1$H NMR (300 MHz, CDCl$_3$) δ 1.86 (1H, t, J=5.7 Hz), 4.16 (3H, s), 4.74 (2H, d, J=4.5 Hz), 7.44 (2H, d, J=8.3 Hz), 7.75 (1H, s), 7.82 (2H, d, J=8.3 Hz).

Reference Example 31

Tert-butyl 4-((7-((tert-butyldimethylsilyl)oxy)-1-oxoisoindolin-2-yl)methyl)piperidine-1-carboxylate and tert-butyl 4-((7-hydroxy-1-oxoisoindolin-2-yl)methyl)piperidine-1-carboxylate

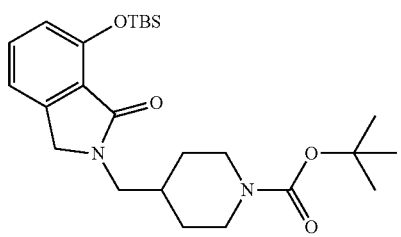

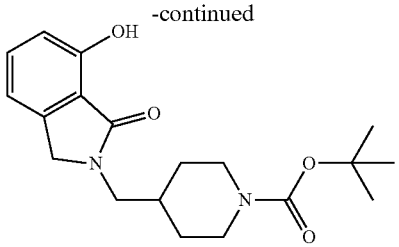

A solution of ethyl 2-(bromomethyl)-6-((tert-butyldimethylsilyl)oxy)benzoate (3.0 g) obtained in Reference Example 2, tert-butyl 4-(aminomethyl)piperidine-1-carboxylate (2.58 g) and triethylamine (2.24 mL) in THF (20 mL) was stirred under an argon atmosphere at 50° C. overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give tert-butyl 4-((7-((tert-butyldimethylsilyl)oxy)-1-oxoisoindolin-2-yl)methyl)piperidine-1-carboxylate (1.55 g) and tert-butyl 4-((7-hydroxy-1-oxoisoindolin-2-yl)methyl)piperidine-1-carboxylate (0.71 g).

tert-butyl 4-((7-((tert-butyldimethylsilyl)oxy)-1-oxoisoindolin-2-yl)methyl)piperidine-1-carboxylate: $^1$H NMR (400 MHz, DMSO-$d_6$) δ 0.19 (6H, s), 0.97-1.10 (11H, m), 1.33-1.44 (10H, m), 1.55 (2H, d, J=10.8 Hz), 1.88 (1H, brs), 2.71 (2H, brs), 3.31-3.32 (1H, m), 3.91 (2H, d, J=14.2 Hz), 4.38 (2H, s), 6.84 (1H, d, J=8.1 Hz), 7.12 (1H, d, J=7.3 Hz), 7.40-7.47 (1H, m).

tert-butyl 4-((7-hydroxy-1-oxoisoindolin-2-yl)methyl)piperidine-1-carboxylate: $^1$H NMR (400 MHz, DMSO-$d_6$) δ0.96-1.09 (2H, m), 1.24-1.47 (10H, m), 1.56 (2H, d, J=13.9 Hz), 1.81-1.95 (1H, m), 2.69 (2H, brs), 3.32 (1H, brs), 3.91 (2H, d, J=10.5 Hz), 4.41 (2H, s), 6.80 (1H, d, J=8.1 Hz), 6.96 (1H, d, J=7.3 Hz), 7.33-7.40 (1H, m), 9.51 (1H, brs).

Reference Example 32

7-bromo-2-(4-(1-methyl-1H-pyrazol-4-yl)benzyl)isoindolin-1-one

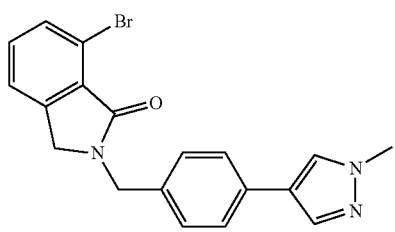 [SMILES: Cn1cc(-c2ccc(CN3Cc4cccc(Br)c4C3=O)cc2)cn1]

To a solution of methyl 2-bromo-6-(bromomethyl)benzoate (0.50 g) in methanol (10 mL) were added (4-(1-methyl-1H-pyrazol-4-yl)phenyl)methanamine (0.31 g) and triethylamine (0.25 g), and the mixture was refluxed for 16 hr. After cooling the reaction solution, the resulting precipitate was collected by filtration to give the title compound (0.23 g).

$^1$H NMR (400 MHz, CDCl$_3$) δ 3.93 (3H, s), 4.22 (2H, s), 4.77 (2H, s), 7.28-7.37 (4H, m), 7.42 (2H, d, J=8.4 Hz), 7.56-7.62 (2H, m), 7.73 (1H, s).

Reference Example 33

7-((tert-butyldimethylsilyl)oxy)-2-(cyclohexylmethyl)isoindolin-1-one

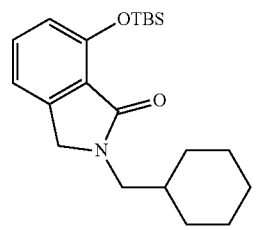 [SMILES: CC(C)(C)[Si](C)(C)Oc1cccc2c1C(=O)N(CC1CCCCC1)C2]

A solution of ethyl 2-(bromomethyl)-6-((tert-butyldimethylsilyl)oxy)benzoate (0.30 g) obtained in Reference Example 2, cyclohexylmethanamine (0.09 g) and triethylamine (0.08 g) in THF (3 mL) was stirred under an argon atmosphere at 50° C. overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (0.09 g).

$^1$H NMR (400 MHz, DMSO-$d_6$) δ 0.19 (6H, s), 0.88-0.96 (2H, m), 0.99 (9H, s), 1.14-1.22 (3H, m), 1.54-1.73 (6H, m), 3.29 (2H, d, J=7.6 Hz), 4.36 (2H, s), 6.84 (1H, d, J=8.1 Hz), 7.11 (1H, d, J=7.1 Hz), 7.38-7.48 (1H, m).

Reference Example 34

2-(cyclohexylmethyl)-7-hydroxyisoindolin-1-one

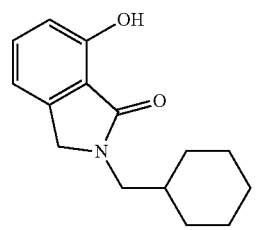 [SMILES: O=C1c2c(O)cccc2CN1CC1CCCCC1]

To a solution of 7-((tert-butyldimethylsilyl)oxy)-2-(cyclohexylmethyl)isoindolin-1-one (0.09 g) obtained in Reference Example 33 in THF (1 mL) was added 1 mol/L tetrabutylammonium fluoride (THF solution) (0.25 mL), and the mixture was stirred at room temperature for 1 hr. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (0.06 g).

$^1$H NMR (400 MHz, DMSO-$d_6$) δ 0.92-0.96 (2H, m), 1.11-1.24 (3H, m), 1.57-1.71 (6H, m), 3.29 (2H, d, J=7.3 Hz), 4.39 (2H, s), 6.79 (1H, d, J=8.1 Hz), 6.96 (1H, d, J=7.3 Hz), 7.34-7.41 (1H, m), 9.48 (1H, brs).

Reference Example 35

4,4-difluorocyclohex-1-ene

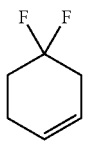

To a solution of 1-methoxycyclohexa-1,4-diene (10.0 g) in dichloromethane (20 mL)-water (50 mL) was added perchloric acid (6 drops), and the mixture was stirred at room temperature for 16 hr. The reaction solution was extracted with dichloromethane, dried over anhydrous sodium sulfate, and the insoluble material was filtered off. To the filtrate was added diethylaminosulfur trifluoride (32.2 g) at 0° C., and the mixture was stirred at room temperature for 16 hr. Water was added to the reaction mixture, and the organic layer was separated, washed with saturated brine, and dried over anhydrous sodium sulfate. The obtained dichloromethane solution was purified by distillation (760 mmHg, 95-100° C.) to give the title compound (4.5 g).

$^1$H NMR (400 MHz, CDCl$_3$) δ 1.92-2.06 (2H, m), 2.25-2.34 (2H, m), 2.45-2.57 (2H, m), 5.52-5.61 (1H, m), 5.71-5.80 (1H, m).

Reference Example 36

3,3-difluoro-7-oxabicyclo[4.1.0]heptane

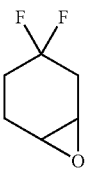

To a solution of 4,4-difluorocyclohex-1-ene (2.0 g) obtained in Reference Example 35 in dichloromethane (50 mL) was added meta-chloroperbenzoic acid (85% purity) (5.14 g) at 0° C., and the mixture was stirred at room temperature for 16 hr. The insoluble material was filtered off, and the filtrate was treated with saturated aqueous sodium sulfite solution. The solution was extracted with dichloromethane, washed with saturated aqueous sodium hydrogen carbonate solution, saturated aqueous sodium carbonate solution and saturated brine, and dried over anhydrous sodium sulfate. The obtained dichloromethane solution was purified by distillation (0.09 MPa, 58-60° C.) to give the title compound (0.70 g).

$^1$H NMR (400 MHz, CDCl$_3$) δ 1.72-1.89 (2H, m), 1.97-2.10 (1H, m), 2.20-2.45 (3H, m), 3.15-3.24 (2H, m).

Reference Example 37

Ethyl 2-cyano-5-(dimethylamino)-3-methoxypenta-2,4-dienoate

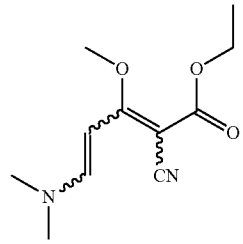 [SMILES: CCOC(=O)C(C#N)=C(C=CN(C)C)OC]

Ethyl 2-cyanoacetate (11 mL) and 1,1,1-trimethoxyethane (15.5 mL) were mixed, and the mixture was stirred at 135° C. for 4 hr. The reaction solution was concentrated, and the residue was solidified with ethyl acetate and hexane. The obtained solid was dissolved in methanol (8 mL), N,N-dimethylformamide dimethyl acetal (8.2 g) was added, and the mixture was stirred under an argon atmosphere at 135° C. for 1 hr. The reaction solution was concentrated, and the residue was purified by silica gel chromatography (hexane-ethyl acetate) to give the title compound (5.95 g).

$^1$H NMR (300 MHz, DMSO-d$_6$) δ 1.19 (3H, t, J=7.1 Hz), 2.94 (3H, s), 3.23 (3H, s), 3.86 (3H, s), 4.07 (2H, q, J=7.0 Hz), 6.05 (1H, d, J=12.3 Hz), 7.76 (1H, d, J=12.3 Hz).

Reference Example 38

Ethyl 2-bromo-4-methoxynicotinate and ethyl 2-bromo-4-hydroxynicotinate

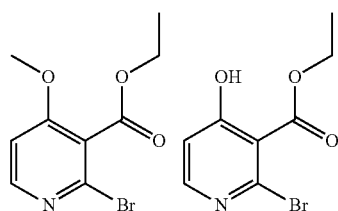

A mixed solution of ethyl 2-cyano-5-(dimethylamino)-3-methoxypenta-2,4-dienoate (5.95 g) obtained in Reference Example 37 and 25% hydrogen bromide (acetic acid solution) (30 mL) was stirred under a nitrogen atmosphere at 75° C. for 1 hr. The reaction solution was neutralized with saturated aqueous sodium hydrogen carbonate solution, and the mixture was extracted with ethyl acetate. The organic layer was divided, washed with saturated brine, dried over anhydrous sodium sulfate, and concentrated. The residue was purified by silica gel chromatography (hexane-ethyl acetate) to give ethyl 2-bromo-4-methoxynicotinate (4.1 g) and ethyl 2-bromo-4-hydroxynicotinate (0.29 g).

Ethyl 2-bromo-4-methoxynicotinate: $^1$H NMR (300 MHz, DMSO-d$_6$) δ 1.30 (3H, t, J=7.2 Hz), 3.91 (3H, s), 4.33

(2H, q, J=7.0 Hz), 7.29 (1H, d, J=5.9 Hz), 8.35 (1H, d, J=5.9 Hz).
Ethyl 2-bromo-4-hydroxynicotinate: MS (ESI+): [M+H]+ 246.0

Reference Example 39

Ethyl 4-((tetrahydrofuran-2-yl)methoxy)-2-vinylnicotinate

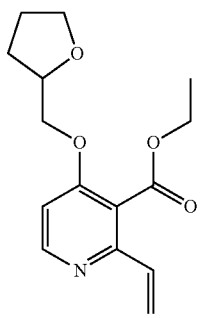 [SMILES: C=Cc1nccc(OCC2CCCO2)c1C(=O)OCC]

A solution of ethyl 2-bromo-4-hydroxynicotinate (0.29 g) obtained in Example 38, (tetrahydrofuran-2-yl)methanol (0.18 g) and triphenylphosphine (0.46 g) in THF (4 mL) was stirred at 60° C. for 20 min, diisopropyl azodicarboxylate (40% toluene solution) (0.36 g) was added, and the mixture was stirred under a nitrogen atmosphere at the same temperature for 1 hr. The reaction mixture was concentrated, and the residue was crudely purified by silica gel chromatography (hexane-ethyl acetate). To a solution of the obtained oil in DMF (4 mL) were added tributyl(vinyl)tin (0.20 g), trans-dichlorobis(triphenylphosphine)palladium(II) (0.015 g) and lithium chloride (0.013 g), and the mixture was stirred under an argon atmosphere at 90° C. for 2 hr. To the reaction solution was added saturated aqueous potassium fluoride solution, and the resulting precipitate was filtered off through Celite. The filtrate was concentrated, and the residue was purified by silica gel chromatography (hexane-ethyl acetate) to give the title compound (0.11 g).
$^1$H NMR (300 MHz, DMSO-$d_6$) δ 1.29 (3H, t, J=7.2 Hz), 1.62-2.03 (4H, m), 3.61-3.79 (2H, m), 4.01-4.19 (3H, m), 4.32 (2H, q, J=7.2 Hz), 5.53 (1H, dd, J=10.5, 2.3 Hz), 6.28-6.44 (1H, m), 6.54-6.73 (1H, m), 7.09 (1H, d, J=5.7 Hz), 8.48 (1H, d, J=6.0 Hz).

Reference Example 40

Methyl 2-fluoro-4-iodonicotinate

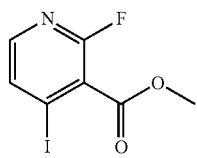

To a solution of 2-fluoro-4-iodonicotinic acid (5.13 g) in diethyl ether (25 mL)-methanol (25 mL) was added 10% trimethylsilyldiazomethane (hexane solution) (32.9 g), and the mixture was stirred under a nitrogen atmosphere at room temperature for 3 hr. The reaction solution was concentrated, and the residue was purified by silica gel chromatography (hexane-ethyl acetate) to give the title compound (5.3 g).
$^1$H NMR (300 MHz, DMSO-$d_6$) δ 3.94 (3H, s), 7.98 (1H, dd, J=5.3, 1.1 Hz), 8.07 (1H, dd, J=5.3, 0.8 Hz).

Reference Example 41

Methyl 4-iodo-2-((tetrahydrofuran-2-yl)methoxy)nicotinate

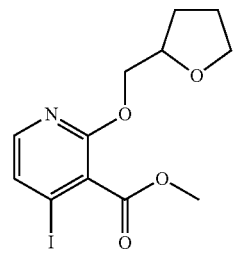 [SMILES: COC(=O)c1c(I)ccnc1OCC1CCCO1]

To a solution of methyl 2-fluoro-4-iodonicotinate (5.03 g) obtained in Reference Example 40 and (tetrahydrofuran-2-yl)methanol (5.48 g) in THF (100 mL) was added 60% sodium hydride (3.22 g) at 0° C., and the mixture was stirred under an argon atmosphere at the same temperature for 1 hr. To the reaction solution was added water at 0° C., and the mixture was diluted with ethyl acetate. The organic layer was separated, washed with saturated brine, dried over anhydrous sodium sulfate, and concentrated. The residue was purified by NH silica gel chromatography (hexane-ethyl acetate) to give the title compound (4.15 g).
$^1$H NMR (300 MHz, DMSO-$d_6$) δ 1.59-1.71 (1H, m), 1.75-1.98 (3H, m), 3.60-3.77 (2H, m), 3.85 (3H, s), 4.08-4.17 (1H, m), 4.21-4.33 (2H, m), 7.52 (1H, d, J=5.5 Hz), 7.92 (1H, d, J=5.5 Hz).

Reference Example 42

Methyl 2-((tetrahydrofuran-2-yl)methoxy)-4-vinylnicotinate

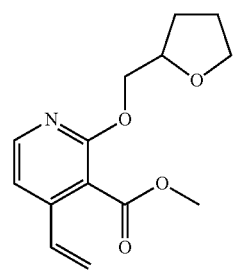 [SMILES: C=Cc1ccnc(OCC2CCCO2)c1C(=O)OC]

To a solution of methyl 4-iodo-2-((tetrahydrofuran-2-yl)methoxy)nicotinate (2.0 g) obtained in Reference Example 41 in DMF (20 mL) were added tributyl(vinyl)tin (2.62 g), trans-dichlorobis(triphenylphosphine)palladium(II) (0.19 g) and lithium chloride (1.73 g), and the mixture was stirred under an argon atmosphere at 90° C. for 2 hr. To the reaction solution was added saturated aqueous potassium fluoride solution, the resulting precipitate was filtered off, and the filtrate was diluted with ethyl acetate. The organic layer was separated, washed with saturated brine, dried over anhydrous sodium sulfate, and concentrated. The residue was purified by NH silica gel chromatography (hexane-ethyl acetate) to give the title compound (1.39 g).
$^1$H NMR (300 MHz, DMSO-$d_6$) δ 1.61-1.98 (4H, m), 3.59-3.79 (2H, m), 3.84 (3H, s), 4.08-4.18 (1H, m), 4.25-

4.31 (2H, m), 5.62 (1H, d, J=11.5 Hz), 6.12 (1H, d, J=17.4 Hz), 6.61 (1H, dd, J=17.4, 11.0 Hz), 7.32 (1H, d, J=5.5 Hz), 8.18 (1H, d, J=5.5 Hz).

Reference Example 43

3-(benzyloxy)-5-chloroisonicotinic acid

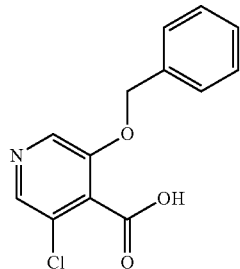 [SMILES: O=C(O)c1c(Cl)cncc1OCc1ccccc1]

To a solution of 3,5-dichloroisonicotinic acid (3.16 g) in 1-methyl-2-pyrrolidone (80 mL) was added 60% sodium hydride (1.38 g) at 0° C., and the mixture was stirred at the same temperature for 10 min. To the reaction solution was added phenylmethanol (1.78 g), and the mixture was stirred under an argon atmosphere at 80° C. for 2 hr. The reaction solution was diluted with water, and the aqueous layer was washed with diethyl ether. The aqueous layer was separated, concentrated hydrochloric acid was added, and the solution was adjusted to about pH 2. To the solution was added saturated brine, and the resulting precipitate was collected by filtration to give the title compound (2.57 g).

$^1$H NMR (300 MHz, DMSO-$d_6$) δ 5.34 (2H, s), 7.30-7.49 (5H, m), 8.36 (1H, s), 8.54 (1H, s), 14.12 (1H, brs).

Reference Example 44

Methyl 3-(benzyloxy)-5-chloroisonicotinate

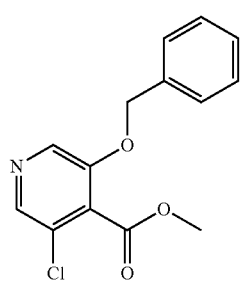 [SMILES: COC(=O)c1c(Cl)cncc1OCc1ccccc1]

To a solution of 3-(benzyloxy)-5-chloroisonicotinic acid (2.57 g) obtained in Reference Example 43 in diethyl ether (15 mL)-methanol (15 mL) was added 10% trimethylsilyldiazomethane (hexane solution) (16.7 g), and the mixture was stirred under a nitrogen atmosphere at room temperature for 3 hr. The reaction solution was concentrated, and the residue was purified by silica gel chromatography (hexane-ethyl acetate) to give the title compound (2.37 g).

$^1$H NMR (300 MHz, DMSO-$d_6$) δ 3.90 (3H, s), 5.37 (2H, s), 7.24-7.50 (5H, m), 8.40 (1H, s), 8.60 (1H, s).

Reference Example 45

Methyl 3-chloro-5-hydroxyisonicotinate

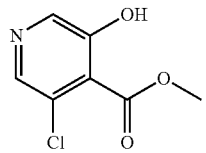

A mixed solution of methyl 3-(benzyloxy)-5-chloroisonicotinate (2.3 g) obtained in Reference Example 44 and 25% hydrogen bromide (acetic acid solution) (5 mL) was stirred at 75° C. for 6 hr. At 0° C., the reaction solution was neutralized with saturated aqueous sodium hydrogen carbonate solution, and the mixture was diluted with ethyl acetate. The organic layer was separated, dried over anhydrous sodium sulfate, and concentrated. The residue was purified by silica gel chromatography (hexane-ethyl acetate) to give the title compound (1.02 g).

$^1$H NMR (300 MHz, DMSO-$d_6$) δ 3.87 (3H, s), 8.19 (1H, s), 8.24 (1H, s), 11.13 (1H, brs).

Reference Example 46

Methyl 3-chloro-5-((tetrahydrofuran-2-yl)methoxy)isonicotinate

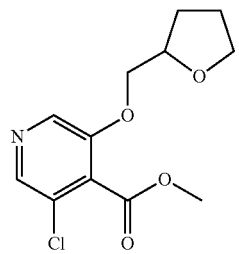 [SMILES: COC(=O)c1c(Cl)cncc1OCC1CCCO1]

A solution of methyl 3-chloro-5-hydroxyisonicotinate (0.50 g) obtained in Reference Example 45, (tetrahydrofuran-2-yl)methanol (0.54 g) and triphenylphosphine (1.40 g) in THF (10 mL) was stirred, 40% diisopropyl azodicarboxylate (toluene solution) (2.70 g) was added, and the mixture was stirred under a nitrogen atmosphere at 60° C. for 2 hr. The reaction mixture was concentrated, and the residue was purified by silica gel chromatography (hexane-ethyl acetate) to give the title compound (0.72 g).

$^1$H NMR (300 MHz, DMSO-$d_6$) δ 1.61-1.75 (1H, m), 1.77-1.89 (2H, m), 1.91-2.01 (1H, m), 3.62-3.78 (2H, m), 3.89 (3H, s), 4.09-4.27 (3H, m), 8.39 (1H, s), 8.54 (1H, s).

Reference Example 47

Methyl 3-((tetrahydrofuran-2-yl)methoxy)-5-vinylisonicotinate

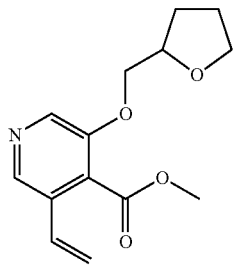 [SMILES: C=Cc1cncc(OCC2CCCO2)c1C(=O)OC]

To a solution of methyl 3-chloro-5-((tetrahydrofuran-2-yl)methoxy)isonicotinate (0.68 g) obtained in Reference Example 46 in 1-propanol (10 mL) were added potassium trifluoro(vinyl)borate (0.67 g), (1,1'-bis(diphenylphosphino)ferrocene)dichloropalladium(II) (0.18 g) and triethylamine (0.51 g), and the mixture was stirred under an argon atmosphere at 90° C. overnight. The reaction solution was concentrated, and the residue was dissolved in ethyl acetate, washed with saturated brine, dried over anhydrous sodium sulfate, and concentrated. The residue was purified by silica gel chromatography (hexane-ethyl acetate) to give the title compound (0.18 g).

$^1$H NMR (300 MHz, DMSO-$d_6$) δ 1.69-1.99 (4H, m), 3.61-3.75 (2H, m), 3.80-3.92 (3H, m), 4.10-4.20 (3H, m), 5.50 (1H, d, J=11.1 Hz), 5.97 (1H, d, J=17.6 Hz), 6.57 (1H, dd, J=17.7, 11.2 Hz), 8.42 (1H, s), 8.56 (1H, s).

Reference Example 48

Ethyl 2-(2-cyano-6-fluorophenoxy)-6-methylbenzoate

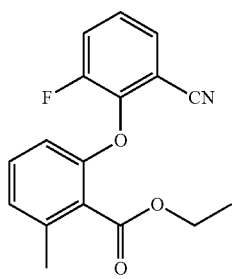 [SMILES: CCOC(=O)c1c(C)cccc1Oc1c(F)cccc1C#N]

To a solution of ethyl 2-hydroxy-6-methylbenzoate (1.00 g) and potassium carbonate (2.30 g) in DMF (10 mL) was added 2,3-difluorobenzonitrile (0.68 mL), and the mixture was stirred at 900° C. overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (1.57 g).

$^1$H NMR (300 MHz, CDCl$_3$) δ 1.37 (3H, t, J=7.2 Hz), 2.40 (3H, s), 4.41 (2H, q, J=7.2 Hz), 6.51 (1H, d, J=8.3 Hz), 6.99 (1H, d, J=7.7 Hz), 7.18 (1H, d, J=8.1 Hz), 7.21-7.31 (1H, m), 7.40 (1H, ddd, J=10.2, 8.5, 1.6 Hz), 7.48 (1H, dt, J=7.7, 1.5 Hz).

Reference Example 49

Ethyl 2-(bromomethyl)-6-(2-cyano-6-fluorophenoxy)benzoate

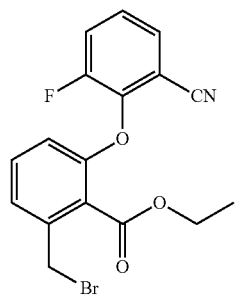 [SMILES: CCOC(=O)c1c(CBr)cccc1Oc1c(F)cccc1C#N]

To a solution of ethyl 2-(2-cyano-6-fluorophenoxy)-6-methylbenzoate (1.57 g) obtained in Reference Example 48 and NBS (1.03 g) in (trifluoromethyl)benzene (30 mL) was added AIBN (0.09 g), and the mixture was stirred at 80° C. for 5 hr. The reaction mixture was diluted with ethyl acetate and 10% aqueous sodium thiosulfate solution. The organic layer was washed with water and saturated brine, dried over anhydrous magnesium sulfate and concentrated. The residue was washed with hexane-ethyl acetate (1:4, 10 mL) to give the title compound (1.29 g).

$^1$H NMR (300 MHz, CDCl$_3$) δ 1.40 (3H, t, J=7.2 Hz), 4.44 (2H, q, J=7.2 Hz), 4.62 (2H, s), 6.68 (1H, dt, J=8.2, 1.2 Hz), 7.19-7.34 (3H, m), 7.41 (1H, ddd, J=10.2, 8.5, 1.7 Hz), 7.50 (1H, dt, J=7.7, 1.5 Hz).

Reference Example 50

4-(1-methyl-1H-pyrazol-4-yl)furan-2-carbaldehyde

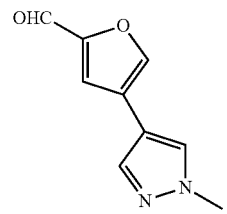

To a solution of 4-bromofuran-2-carbaldehyde (1.00 g), 1-methyl-4-(4,4,5,5-tetramethyl-1,3,2-dioxaborolan-2-yl)-1H-pyrazole (1.31 g) and 2M aqueous sodium carbonate solution (8.57 mL) in DME (5 mL) was added (1,1-bis(diphenylphosphino)ferrocene)dichloropalladium(II) (0.21 g), and the mixture was stirred under an argon atmosphere at 80° C. overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.54 g).

$^1$H NMR (300 MHz, CDCl$_3$) δ 3.95 (3H, s), 7.32 (1H, d, J=0.8 Hz), 7.53 (1H, s), 7.63 (1H, s), 7.78 (1H, s), 9.68 (1H, s).

Reference Example 51

4-(4-methyl-1H-pyrazol-1-yl)benzonitrile

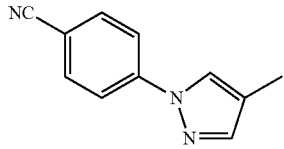

To a solution of 4-methyl-1H-pyrazole (0.75 g) and potassium carbonate (3.42 g) in DMF (10 mL) was added 4-fluorobenzonitrile (1.00 g), and the mixture was stirred at 90° C. overnight. The reaction mixture was diluted with ethyl acetate and water. The organic layer was washed with water and saturated brine, dried over anhydrous magnesium sulfate and concentrated. The residue was washed with hexane-ethyl acetate (1:4, 20 mL) to give the title compound (0.59 g).

$^1$H NMR (300 MHz, CDCl$_3$) δ 2.18 (3H, s), 7.59 (1H, s), 7.69-7.83 (5H, m).

Reference Example 52

Ethyl 2-(2-cyano-4,6-difluorophenoxy)-6-methylbenzoate

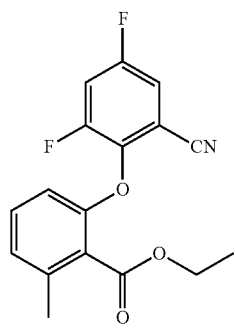 [SMILES: CCOC(=O)c1c(C)cccc1Oc1c(F)cc(F)cc1C#N]

To a solution of ethyl 2-hydroxy-6-methylbenzoate (5.21 g) and potassium carbonate (12.0 g) in DMF (50 mL) was added 2,3,5-trifluorobenzonitrile (5.00 g), and the mixture was stirred at 90° C. overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (5.38 g).

$^1$H NMR (300 MHz, CDCl$_3$) δ 1.38 (3H, t, J=7.2 Hz), 2.40 (3H, s), 4.41 (2H, q, J=6.9 Hz), 6.48 (1H, d, J=8.3 Hz), 6.99 (1H, d, J=7.5 Hz), 7.14-7.28 (3H, m).

Reference Example 53

Ethyl 2-(bromomethyl)-6-(2-cyano-4,6-difluorophenoxy)benzoate

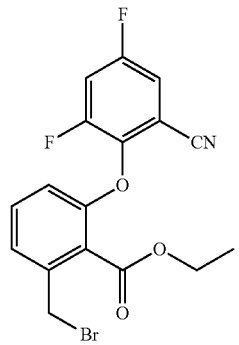 [SMILES: CCOC(=O)c1c(CBr)cccc1Oc1c(F)cc(F)cc1C#N]

To a solution of ethyl 2-(2-cyano-4,6-difluorophenoxy)-6-methylbenzoate (5.38 g) obtained in Reference Example 52 and NBS (3.32 g) in (trifluoromethyl)benzene (100 mL) was added AIBN (0.28 g), and the mixture was stirred at 80° C. for 5 hr. The reaction mixture was diluted with ethyl acetate and 10% aqueous sodium thiosulfate solution. The organic layer was washed with water and saturated brine, dried over anhydrous magnesium sulfate and concentrated. The residue was purified by silica gel column chromatography (hexane-ethyl acetate) to give the title compound (4.05 g).

$^1$H NMR (300 MHz, CDCl$_3$) δ 1.41 (3H, t, J=7.2 Hz), 4.45 (2H, q, J=7.2 Hz), 4.61 (2H, s), 6.64 (1H, d, J=8.3 Hz), 7.16-7.35 (4H, m).

Reference Example 54

4-bromo-7-methoxy-2-(4-(1-methyl-1H-pyrazol-4-yl)benzyl)isoindolin-1-one

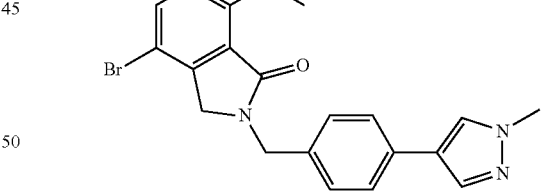

A solution of ethyl 3-bromo-2-(bromomethyl)-6-methoxybenzoate (0.47 g) prepared by referring to a document (Journal of Chemical Research, Synopses (1991), (2), 29.), (4-(1-methyl-1H-pyrazol-4-yl)phenyl)methanamine (0.25 g) and potassium carbonate (0.37 g) in ethanol (20 mL) was stirred under a nitrogen atmosphere at room temperature overnight. Water was added to the reaction mixture, and the precipitate was collected by filtration, washed with water and diisopropyl ether, and dried to give the title compound (0.45 g).

$^1$H NMR (300 MHz, DMSO-d$_6$) δ3.85 (3H, s), 3.88 (3H, s), 4.18 (2H, s), 4.65 (2H, s), 7.06 (1H, d, J=8.9 Hz), 7.26 (2H, d, J=8.3 Hz), 7.50-7.56 (2H, m), 7.70 (1H, d, J=8.9 Hz), 7.82 (1H, d, J=0.8 Hz), 8.10 (1H, s).

Reference Example 55

4-bromo-7-hydroxy-2-(4-(1-methyl-1H-pyrazol-4-yl)benzyl)isoindolin-1-one

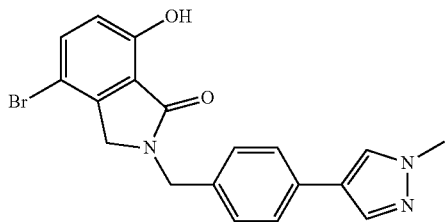 [SMILES: Cn1cc(-c2ccc(CN3Cc4c(Br)ccc(O)c4C3=O)cc2)cn1]

To 4-bromo-7-methoxy-2-(4-(1-methyl-1H-pyrazol-4-yl)benzyl)isoindolin-1-one (0.50 g) obtained in Reference Example 54 was added 25% hydrobromic acid (acetic acid solution) (10 mL), and the mixture was stirred under a nitrogen atmosphere at 120° C. for 3 days. The reaction solution was diluted with water, and neutralized with sodium carbonate. The resulting precipitate was collected by filtration, washed with water, and dried to give the title compound (0.44 g).

$^1$H NMR (300 MHz, DMSO-$d_6$) δ3.84 (3H, brs), 4.17 (2H, s), 4.65 (2H, s), 6.84 (1H, d, J=8.7 Hz), 7.27 (2H, d, J=8.3 Hz), 7.48-7.59 (3H, m), 7.83 (1H, d, J=0.8 Hz), 8.11 (1H, s), OH proton was not detected.

Reference Example 56

6-bromo-7-methoxy-2-(4-(1-methyl-1H-pyrazol-4-yl)benzyl)isoindolin-1-one

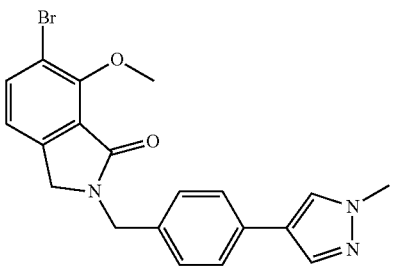 [SMILES: COc1c(Br)ccc2c1C(=O)N(Cc1ccc(-c3cnn(C)c3)cc1)C2]

A solution of ethyl 3-bromo-6-(bromomethyl)-2-methoxybenzoate (0.47 g) prepared by referring to a document (WO2011/044506), (4-(1-methyl-1H-pyrazol-4-yl)phenyl)methanamine (0.25 g) and potassium carbonate (0.37 g) in ethanol (10 mL) was stirred at room temperature overnight. Water was added to the reaction mixture, and the precipitate was collected by filtration, washed with water and diisopropyl ether, and dried to give the title compound (0.32 g).

$^1$H NMR (300 MHz, DMSO-d) δ3.84 (3H, brs), 4.00 (3H, s), 4.32 (2H, s), 4.67 (2H, s), 7.20-7.31 (3H, m), 7.54 (2H, d, J=8.3 Hz), 7.78-7.85 (2H, m), 8.11 (1H, s).

Reference Example 57

6-bromo-7-hydroxy-2-(4-(1-methyl-1H-pyrazol-4-yl)benzyl)isoindolin-1-one

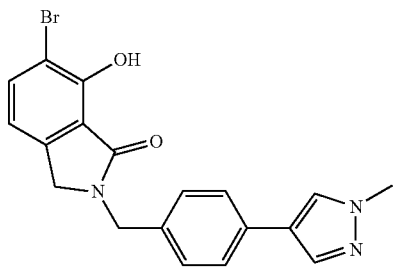 [SMILES: Cn1cc(-c2ccc(CN3Cc4ccc(Br)c(O)c4C3=O)cc2)cn1]

To 6-bromo-7-methoxy-2-(4-(1-methyl-1H-pyrazol-4-yl)benzyl)isoindolin-1-one (0.32 g) obtained in Reference Example 56 was added 25% hydrobromic acid (acetic acid solution) (10 mL), and the mixture was stirred at 120° C. for 6 hr. The reaction solution was diluted with water, and neutralized with sodium carbonate. The resulting precipitate was collected by filtration, washed with water, and dried to give the title compound (0.29 g).

$^1$H NMR (300 MHz, DMSO-$d_6$) δ3.80-3.89 (3H, m), 4.32 (2H, s), 4.66 (2H, s), 6.95 (1H, d, J=7.9 Hz), 7.27 (2H, d, J=8.1 Hz), 7.54 (2H, d, J=8.3 Hz), 7.68 (1H, d, J=7.9 Hz), 7.83 (1H, d, J=0.8 Hz), 8.11 (1H, s), OH proton was not detected.

Reference Example 58

5-bromo-7-methoxy-2-(4-(1-methyl-1H-pyrazol-4-yl)benzyl)isoindolin-1-one

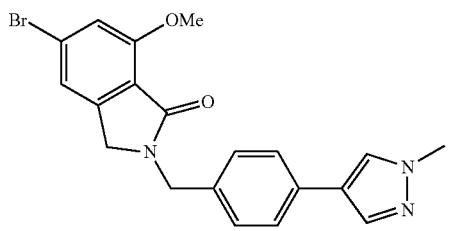 [SMILES: COc1cc(Br)cc2c1C(=O)N(Cc1ccc(-c3cnn(C)c3)cc1)C2]

A solution of methyl 4-bromo-2-(bromomethyl)-6-methoxybenzoate (0.29 g) prepared by referring to a document (WO2006/020879), (4-(1-methyl-1H-pyrazol-4-yl)phenyl)methanamine dihydrochloride (0.33 g) obtained in Reference Example 4 and potassium carbonate (0.35 g) in methanol (15 mL) was stirred at room temperature overnight. The reaction solution was concentrated, and the residue was dissolved in water-THF-ethyl acetate. The organic layer was separated, washed with water and saturated brine, dried over anhydrous sodium carbonate, and concentrated. The residue was solidified with diisopropyl ether to give the title compound (0.23 g).

$^1$H NMR (300 MHz, DMSO-$d_6$) δ3.85 (3H, s), 3.89 (3H, s), 4.27 (2H, s), 4.61 (2H, s), 7.17-7.26 (3H, m), 7.32 (1H, d, J=1.5 Hz), 7.47-7.55 (2H, m), 7.82 (1H, d, J=0.8 Hz), 8.10 (1H, s).

Reference Example 59

5-bromo-7-hydroxy-2-(4-(1-methyl-1H-pyrazol-4-yl)benzyl)isoindolin-1-one

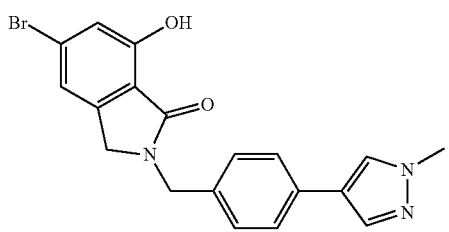 [SMILES: Cn1cc(-c2ccc(CN3Cc4cc(Br)cc(O)c4C3=O)cc2)cn1]

To 5-bromo-7-methoxy-2-(4-(1-methyl-1H-pyrazol-4-yl)benzyl)isoindolin-1-one (0.23 g) obtained in Reference Example 58 was added 25% hydrobromic acid (acetic acid solution) (10 mL), and the mixture was stirred at 120° C. for 6 hr. The reaction solution was diluted with water, and neutralized with sodium carbonate. The resulting precipitate was collected by filtration, washed with water, and dried to give the title compound (0.072 g).

$^1$H NMR (300 MHz, DMSO-$d_6$) δ3.85 (3H, s), 4.27 (2H, s), 4.61 (2H, s), 7.01 (1H, d, J=1.3 Hz), 7.16 (1H, s), 7.23 (2H, d, J=8.1 Hz), 7.53 (2H, d, J=8.1 Hz), 7.82 (1H, s), 8.10 (1H, s), 10.27 (1H, brs).

Reference Example 60

Methyl 2-((trans-2-hydroxycyclopentyl)oxy)-4-iodonicotinate

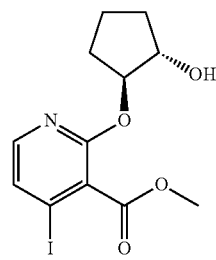 [SMILES: COC(=O)c1c(I)ccnc1O[C@H]1CCC[C@@H]1O]

To a solution of methyl 2-fluoro-4-iodonicotinate (0.55 g) obtained in Reference Example 40 and trans-cyclopentane-1,2-diol (0.80 g) in THF (20 mL) was added 60% sodium hydride (0.39 g) at 0° C., and the mixture was stirred under an argon atmosphere at the same temperature for 30 min. The reaction solution was neutralized with 1N hydrochloric acid at 0° C., and diluted with ethyl acetate. The organic layer was separated, washed with water and saturated brine, dried over anhydrous sodium sulfate, and concentrated. The residue was purified by chromatography (NH silica gel, hexane-ethyl acetate) to give the title compound (0.45 g).

$^1$H NMR (300 MHz, DMSO-$d_6$) δ 1.46-1.85 (5H, m), 1.99-2.11 (1H, m), 3.83 (3H, s), 3.94-4.02 (1H, m), 4.88 (1H, d, J=4.0 Hz), 5.03-5.15 (1H, m), 7.50 (1H, d, J=5.5 Hz), 7.93 (1H, d, J=5.5 Hz).

Reference Example 61

Methyl 2-((trans-2-hydroxycyclopentyl)oxy)-4-vinylnicotinate

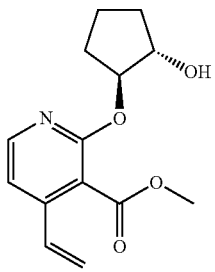 [SMILES: C=Cc1ccnc(O[C@H]2CCC[C@@H]2O)c1C(=O)OC]

To a solution of methyl 2-((trans-2-hydroxycyclopentyl)oxy)-4-iodonicotinate (0.45 g) obtained in Reference Example 60 in DMF (12 mL) were added tributyl(vinyl)tin (0.59 g), trans-dichlorobis(triphenylphosphine)palladium (II) (0.051 g) and lithium chloride (0.39 g), and the mixture was stirred under an argon atmosphere at 90° C. for 2 hr. To the reaction solution was added saturated aqueous potassium fluoride solution, the resulting precipitate was filtered off through Celite, and the filtrate was concentrated. The residue was purified by silica gel chromatography (hexane-ethyl acetate) to give the title compound (0.28 g).

$^1$H NMR (300 MHz, DMSO-$d_6$) δ 1.46-1.88 (5H, m), 1.96-2.12 (1H, m), 3.82 (3H, s), 3.95-4.06 (1H, m), 4.87 (1H, d, J=4.0 Hz), 5.04-5.21 (1H, m), 5.61 (1H, d, J=11.1 Hz), 6.11 (1H, d, J=17.4 Hz), 6.60 (1H, dd, J=17.5, 11.0 Hz), 7.30 (1H, d, J=5.5 Hz), 8.20 (1H, d, J=5.5 Hz).

Reference Example 62

Tert-butyl 4-(2-methylpyridin-4-yl)benzylcarbamate

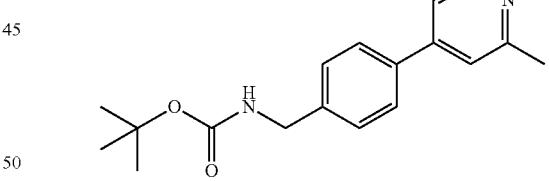

A solution of tert-butyl 4-bromobenzylcarbamate (1.0 g), (2-methylpyridin-4-yl)boronic acid (0.72 g), 2 mol/L aqueous sodium carbonate solution (3.49 mL) and (1,1-bis(diphenylphosphino)ferrocene)dichloropalladium(II) (0.26 g) in 1,2-dimethoxyethane (7 mL) was stirred under an argon atmosphere at 90° C. overnight. The reaction solution was diluted with water and ethyl acetate, and the organic layer was separated, washed with saturated brine, dried over anhydrous sodium sulfate, and concentrated. The residue was purified by chromatography (NH silica gel, hexane-ethyl acetate) to give the title compound (0.80 g).

$^1$H NMR (300 MHz, DMSO-$d_6$) δ 1.40 (9H, s), 2.52 (3H, s), 4.18 (2H, d, J=6.2 Hz), 7.36 (2H, d, J=8.3 Hz), 7.41-7.51 (2H, m), 7.57 (1H, s), 7.74 (2H, d, J=8.1 Hz), 8.48 (1H, d, J=5.3 Hz).

Reference Example 63

(4-(2-methylpyridin-4-yl)phenyl)methanamine

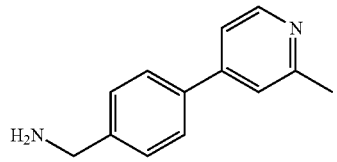

To a solution of tert-butyl 4-(2-methylpyridin-4-yl)benzylcarbamate (0.80 g) obtained in Reference Example 62 in methanol (15 mL) was added 4N hydrochloric acid (ethyl acetate solution) (15 mL), and the mixture was stirred at room temperature for 1 hr. The reaction solution was concentrated, the residue was suspended in ethyl acetate, and the precipitate was collected by filtration. The obtained white solid was dissolved in water, and neutralized with saturated aqueous sodium hydrogen carbonate solution. The aqueous layer was extracted with ethyl acetate, dried over anhydrous sodium sulfate, and concentrated to give the title compound (0.21 g).

$^1$H NMR (300 MHz, DMSO-$d_6$) δ 2.52 (3H, s), 3.76 (2H, s), 7.42-7.52 (3H, m), 7.57 (1H, s), 7.72 (2H, d, J=8.3 Hz), 8.47 (1H, d, J=5.3 Hz), NH$_2$ protons were not detected.

Reference Example 64

Ethyl 2-(2-fluoro-6-nitrophenoxy)-6-methylbenzoate

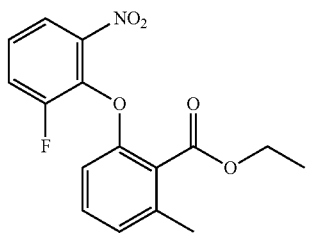 [SMILES: CCOC(=O)c1c(C)cccc1Oc1c(F)cccc1[N+](=O)[O-]]

A solution of 1,2-difluoro-3-nitrobenzene (4.86 g), ethyl 2-hydroxy-6-methylbenzoate (5.0 g) and potassium carbonate (11.50 g) in DMF (50 mL) was stirred at 80° C. overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (7.96 g).

$^1$H NMR (300 MHz, CDCl$_3$) δ 1.38 (3H, t, J=7.0 Hz), 2.40 (3H, s), 4.41 (2H, q, J=7.2 Hz), 6.49 (1H, d, J=8.3 Hz), 6.97 (1H, d, J=7.9 Hz), 7.13-7.22 (1H, m), 7.29-7.38 (1H, m), 7.41-7.49 (1H, m), 7.79 (1H, dt, J=8.3, 1.7 Hz).

Reference Example 65

Ethyl 2-(2-chloro-6-fluorophenoxy)-6-methylbenzoate

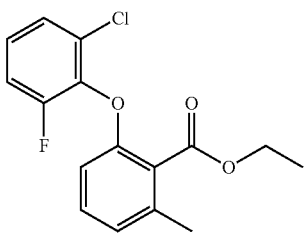

To a solution of ethyl 2-(2-fluoro-6-nitrophenoxy)-6-methylbenzoate (7.96 g) obtained in Reference Example 64 in THF (80 mL) was added 5% Pd—C (0.80 g), and the mixture was stirred under a hydrogen atmosphere at room temperature for 2 days. The insoluble material was filtered off, and the filtrate was concentrated. To a solution of the obtained residue in concentrated hydrochloric acid (25 mL) was added aqueous solution (5 mL) of sodium nitrite (1.192 g) at 0° C., and the mixture was stirred for 20 min. Sequentially, the reaction mixture was added to a solution of copper(I) chloride (1.711 g) in concentrated hydrochloric acid (25 mL), and the mixture was stirred at 80° C. for 2 hr. The reaction mixture was adjusted to around pH 6-7 with 8N aqueous sodium hydroxide solution, saturated aqueous ammonium chloride solution was added, and the mixture was extracted with ethyl acetate. The organic layer was washed with water and saturated brine, dried over anhydrous magnesium sulfate and concentrated. The residue was purified by silica gel column chromatography (hexane-ethyl acetate) to give the title compound (3.08 g).

$^1$H NMR (300 MHz, CDCl$_3$) δ 1.40 (3H, t, J=7.2 Hz), 2.40 (3H, s), 4.45 (2H, q, J=7.2 Hz), 6.39 (1H, d, J=8.3 Hz), 6.92 (1H, d, J=7.5 Hz), 7.07-7.20 (3H, m), 7.24-7.30 (1H, m).

Reference Example 66

Ethyl 2-(bromomethyl)-6-(2-chloro-6-fluorophenoxy)benzoate

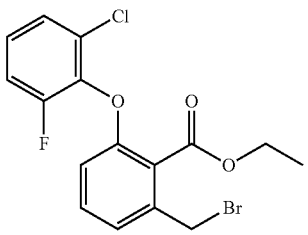 [SMILES: CCOC(=O)c1c(CBr)cccc1Oc1c(F)cccc1Cl]

To a solution of ethyl 2-(2-chloro-6-fluorophenoxy)-6-methylbenzoate (0.5 g) obtained in Reference Example 65 and NBS (0.32 g) in (trifluoromethyl)benzene (10 mL) was added AIBN (0.027 g), and the mixture was stirred under an argon atmosphere at 80° C. for 5 hr. The reaction mixture was diluted with ethyl acetate and aqueous sodium thiosulfate solution. The organic layer was washed with water and saturated brine, dried over anhydrous magnesium sulfate and concentrated. The residue was purified by silica gel column chromatography (hexane-ethyl acetate) to give the title compound (0.48 g).

$^1$H NMR (300 MHz, CDCl$_3$) δ 1.43 (3H, t, J=7.2 Hz), 4.49 (2H, q, J=7.2 Hz), 4.62 (2H, s), 6.53 (1H, d, J=8.3 Hz), 7.07-7.31 (5H, m).

Reference Example 67

Ethyl 2-(bromomethyl)-6-(2-fluoro-6-nitrophenoxy)benzoate

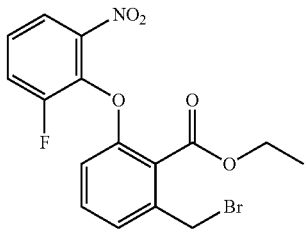 [SMILES: CCOC(=O)c1c(CBr)cccc1Oc1c(F)cccc1[N+](=O)[O-]]

To a solution of ethyl 2-(2-fluoro-6-nitrophenoxy)-6-methylbenzoate (8.34 g) obtained in Reference Example 64 and NBS (5.11 g) in (trifluoromethyl)benzene (150 mL) was added AIBN (0.43 g), and the mixture was stirred under an argon atmosphere at 80° C. for 5 hr. The reaction mixture was diluted with ethyl acetate and aqueous sodium thiosulfate solution. The organic layer was washed with water and saturated brine, dried over anhydrous magnesium sulfate and concentrated. The residue was washed with hexane-ethyl acetate (1:4, 50 mL) to give the title compound (6.40 g).

$^1$H NMR (300 MHz, CDCl$_3$) δ 1.40 (3H, t, J=7.0 Hz), 4.45 (2H, q, J=7.2 Hz), 4.62 (2H, s), 6.65 (1H, d, J=8.3 Hz), 7.16-7.21 (1H, m), 7.27 (1H, t, J=4.1 Hz), 7.30-7.40 (1H, m), 7.42-7.50 (1H, m), 7.80 (1H, dt, J=8.2, 1.6 Hz).

Reference Example 68

3-fluoro-6-methoxy-2-methylbenzoic acid

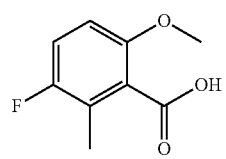

To a solution of 5-fluoro-2-methoxybenzoic acid (20.0 g) in THF (200 mL) were added tetramethylethylenediamine (30.0 g) and sec-butyllithium (200 mL, 1.3M, hexane solution) under a nitrogen atmosphere at −78° C., and the mixture was stirred for 2 hr. Methyl iodide (50.3 g) was added dropwise at −78° C., and the mixture was stirred for 1 hr and at room temperature for 18 hr, adjusted to pH=2 with 2N hydrochloric acid, and extracted with ethyl acetate. The organic layer was washed with water and saturated brine, dried over anhydrous sodium sulfate and concentrated. The residue was purified by HPLC (C18, mobile phase: water/acetonitrile (containing 0.1% TFA)) to give the title compound (8.0 g).

$^1$H NMR (400 MHz, CDCl$_3$) δ 2.36 (3H, d, J=2.0 Hz), 3.88 (3H, s), 6.77 (1H, dd, J=9.2, 3.6 Hz), 7.08 (1H, t, J=8.8 Hz).

Reference Example 69

Ethyl 3-fluoro-6-methoxy-2-methylbenzoate

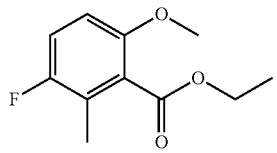

To a solution of 3-fluoro-6-methoxy-2-methylbenzoic acid (7.4 g) obtained in Reference Example 68 and potassium carbonate (6.1 g) in DMF (70 mL) was added ethyl iodide (6.9 g), and the mixture was stirred at 25-30° C. for 18 hr. The reaction solution was concentrated, and ethyl acetate and water were added. The organic layer was washed with water and saturated brine, dried over anhydrous sodium sulfate and concentrated to give the title compound (7.92 g).

$^1$H NMR (400 MHz, CDCl$_3$) δ 1.38 (3H, t, J=7.2 Hz), 2.20 (3H, d, J=2.0 Hz), 3.79 (3H, s), 4.40 (2H, q, J=7.2 Hz), 6.70 (1H, dd, J=8.8, 3.6 Hz), 6.99 (1H, t, J=8.8 Hz).

Reference Example 70

Ethyl 2-(bromomethyl)-3-fluoro-6-methoxybenzoate

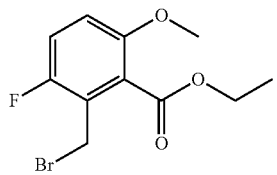

To a solution of ethyl 3-fluoro-6-methoxy-2-methylbenzoate (7 g) obtained in Reference Example 69 in carbon tetrachloride (120 mL) were added NBS (6.46 g) and AIBN (1.08 g), and the mixture was heated under reflux for 18 hr. The reaction solution was concentrated, and the residue was purified by silica gel column chromatography (petroleum ether-ethyl acetate) to give the title compound (8.6 g).

$^1$H NMR (400 MHz, CDCl$_3$) δ 1.42 (3H, t, J=7.2 Hz), 3.82 (3H, s), 4.46 (2H, q, J=7.2 Hz), 4.51 (2H, d, J=1.2 Hz), 6.87 (1H, dd, J=9.2, 4.0 Hz), 7.09 (1H, t, J=9.2 Hz).

Reference Example 71

2-(4-(1H-pyrazol-1-yl)benzyl)-4-fluoro-7-methoxy-isoindolin-1-one

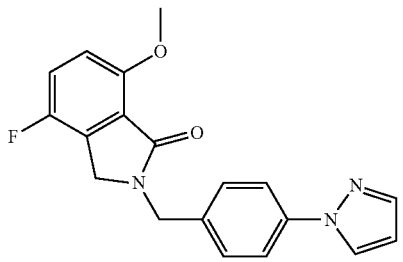 [SMILES: COc1ccc(F)c2c1C(=O)N(Cc1ccc(-n3cccn3)cc1)C2]

To a solution of ethyl 2-(bromomethyl)-3-fluoro-6-methoxybenzoate (4.21 g) obtained in Reference Example 70 in methanol (50 mL) were added (4-(1H-pyrazol-1-yl)phenyl)methanamine (2.5 g) and potassium carbonate (5.0 g), and the mixture was heated under reflux for 1 hr. The reaction solution was concentrated, dichloromethane, isopropanol and water were added, and the organic layer was separated, washed with water and saturated brine, dried over anhydrous sodium sulfate and concentrated. The residue was washed with methyl tert-butyl ether to give the title compound (2.7 g).
$^1$H NMR (400 MHz, CDCl$_3$) δ 3.97 (3H, s), 4.27 (2H, s), 4.78 (2H, s), 6.46 (1H, t, J=2.0 Hz), 6.86 (1H, dd, J=8.8, 3.2 Hz), 7.14 (1H, t, J=8.8 Hz), 7.41 (2H, d, J=8.4 Hz), 7.66 (2H, d, J=7.6 Hz), 7.71 (1H, d, J=1.6 Hz), 7.90 (1H, d, J=2.4 Hz).

Reference Example 72

2-(4-(1H-pyrazol-1-yl)benzyl)-4-fluoro-7-hydroxy-isoindolin-1-one

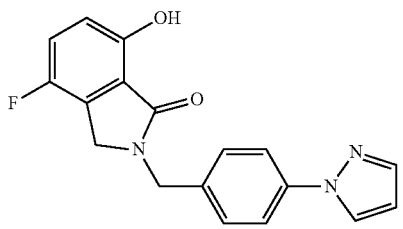 [SMILES: O=C1c2c(O)ccc(F)c2CN1Cc1ccc(-n2cccn2)cc1]

To a solution of 2-(4-(1H-pyrazol-1-yl)benzyl)-4-fluoro-7-methoxyisoindolin-1-one (3.3 g) obtained in Reference Example 71 in dichloromethane (50 mL) was added boron tribromide (12.3 g) at 0° C., and the mixture was stirred at 25-30° C. for 18 hr. To the reaction solution was added methanol, and the mixture was concentrated. To the residue were added dichloromethane, methanol and water, and the organic layer was separated, washed with water and saturated brine, dried over anhydrous sodium sulfate and concentrated. The residue was washed with methyl tert-butyl ether to give the title compound (2.6 g).
$^1$H NMR (400 MHz, CDCl$_3$) δ 4.40 (2H, s), 4.70 (2H, s), 6.54 (1H, t, J=2.0 Hz), 6.86 (1H, dd, J=8.8, 3.6 Hz), 7.24 (1H, t, J=8.8 Hz), 7.42 (2H, d, J=8.4 Hz), 7.74 (1H, d, J=2.0 Hz), 7.83 (2H, d, J=8.8 Hz), 8.48 (1H, d, J=2.4 Hz), 9.78 (1H, brs).

Reference Example 73

Methyl 2-(2-(1H-pyrazol-1-yl)ethoxy)-4-iodonicotinate

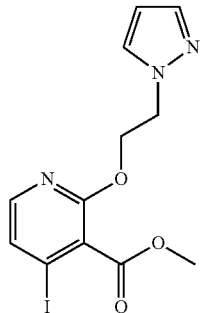 [SMILES: COC(=O)c1c(I)ccnc1OCCn1cccn1]

To a solution of methyl 2-fluoro-4-iodonicotinate (0.50 g) obtained in Reference Example 40 and 2-(1H-pyrazol-1-yl)ethanol (0.98 g) in THF (10 mL) was added 60% sodium hydride (0.32 g) at 0° C., and the mixture was stirred under an argon atmosphere at the same temperature for 20 min. To the reaction solution was added water, and the mixture was diluted with ethyl acetate. The organic layer was separated, washed with water and saturated brine, dried over anhydrous sodium sulfate, and concentrated. The residue was purified by NH silica gel chromatography (hexane-ethyl acetate) to give the title compound (0.46 g).
$^1$H NMR (300 MHz, DMSO-d$_6$) δ 3.80 (3H, s), 4.39-4.49 (2H, m), 4.54-4.64 (2H, m), 6.23 (1H, t, J=2.1 Hz), 7.43 (1H, d, J=1.9 Hz), 7.53 (1H, d, J=5.7 Hz), 7.63 (1H, d, J=2.3 Hz), 7.92 (1H, d, J=5.3 Hz).

Reference Example 74

Methyl 2-(2-(1H-pyrazol-1-yl)ethoxy)-4-vinylnicotinate

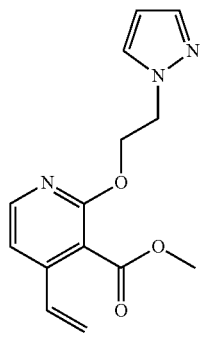 [SMILES: C=Cc1ccnc(OCCn2cccn2)c1C(=O)OC]

To a solution of methyl 2-(2-(1H-pyrazol-1-yl)ethoxy)-4-iodonicotinate (0.46 g) obtained in Reference Example 73 in DMF (12 mL) were added tributyl(vinyl)tin (0.59 g), trans-dichlorobis(triphenylphosphine)palladium(II) (0.043 g) and lithium chloride (0.39 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was purified by silica gel chromatography (hexane-ethyl acetate) to give the title compound (0.32 g).

$^1$H NMR (300 MHz, DMSO-$d_6$) δ 3.79 (3H, s), 4.39-4.52 (2H, m), 4.53-4.65 (2H, m), 5.61 (1H, d, J=11.3 Hz), 6.12 (1H, d, J=17.2 Hz), 6.23 (1H, t, J=2.1 Hz), 6.60 (1H, dd, J=17.4, 11.0 Hz), 7.33 (1H, d, J=5.7 Hz), 7.44 (1H, d, J=1.5 Hz), 7.65 (1H, d, J=1.9 Hz), 8.19 (1H, d, J=5.5 Hz).

Reference Example 75

3-fluoro-2-iodo-6-methylbenzoic acid

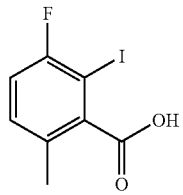

A solution of 5-fluoro-2-methylbenzoic acid (50 g), iodobenzene diacetate (210 g), palladium(II) acetate (3.64 g) and iodine (165 g) in DMF (700 mL) was stirred at 100° C. for 16 hr. The reaction solution was diluted with saturated aqueous sodium sulfite solution and ethyl acetate, and the organic layer was separated, washed with saturated aqueous sodium sulfite solution, water and saturated brine, dried over anhydrous sodium sulfate, and concentrated. The residue was purified by silica gel chromatography (petroleum ether-ethyl acetate) to give the title compound (80 g).

$^1$H NMR (400 MHz, DMSO-$d_6$) δ 2.28 (3H, s), 7.20 (1H, t, J=8.0 Hz), 7.25-7.35 (1H, m).

Reference Example 76

Ethyl 3-fluoro-2-iodo-6-methylbenzoate

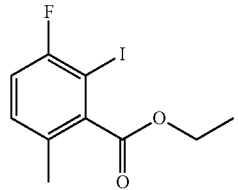

A solution of 3-fluoro-2-iodo-6-methylbenzoic acid (40 g) obtained in Reference Example 75, ethyl iodide (24.5 g) and potassium carbonate (21.7 g) in DMF (300 mL) was stirred at room temperature for 16 hr. The reaction solution was diluted with water and ethyl acetate, and the organic layer was separated, washed with water, dried over anhydrous sodium sulfate, and concentrated. The residue was purified by silica gel chromatography (petroleum ether-ethyl acetate) to give the title compound (35 g).

$^1$H NMR (400 MHz, DMSO-$d_6$) δ 1.34 (3H, t, J=7.2 Hz), 2.25 (3H, s), 4.38 (2H, q, J=7.2 Hz), 7.24 (1H, t, J=8.0 Hz), 7.29-7.38 (1H, m).

Reference Example 77

Ethyl 6-(bromomethyl)-3-fluoro-2-iodobenzoate

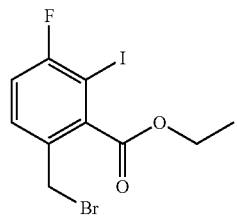

To a solution of ethyl 3-fluoro-2-iodo-6-methylbenzoate (10 g) obtained in Reference Example 76 in carbon tetrachloride (150 mL) were added NBS (6.36 g) and AIBN (1.07 g), and the mixture was heated under reflux for 18 hr. The insoluble material was filtered off, and the filtrate was concentrated. The residue was purified by silica gel chromatography (petroleum ether-ethyl acetate) to give the title compound (5.65 g).

$^1$H NMR (400 MHz, CDCl$_3$) δ 1.46 (3H, t, J=7.2 Hz), 4.43-4.55 (4H, m), 7.08 (1H, dd, J=8.4, 7.2 Hz), 7.40 (1H, d, J=8.4, 4.8 Hz).

Reference Example 78

2-(4-(1H-pyrazol-1-yl)benzyl)-6-fluoro-7-iodoisoindolin-1-one

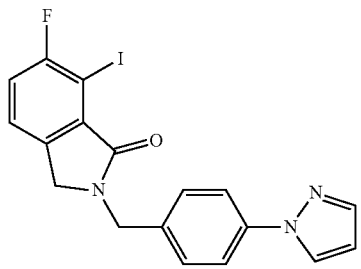 [SMILES: O=C1c2c(ccc(F)c2I)CN1Cc1ccc(-n2cccn2)cc1]

To a solution of ethyl 6-(bromomethyl)-3-fluoro-2-iodobenzoate (5.59 g) obtained in Reference Example 77 in methanol (50 mL) were added (4-(1H-pyrazol-1-yl)phenyl)methanamine (2.5 g) and potassium carbonate (5.0 g), and the mixture was heated under reflux for 1 hr. The reaction solution was concentrated, and dichloromethane and water were added. The organic layer was washed with water and saturated brine, dried over anhydrous sodium sulfate and concentrated. The residue was washed by solid-liquid washing with methyl tert-butyl ether to give the title compound (3.35 g).

$^1$H NMR (400 MHz, DMSO-$d_6$) δ 4.31 (2H, s), 4.76 (2H, s), 6.54 (1H, t, J=2.0 Hz), 7.38-7.51 (3H, m), 7.52-7.60 (1H, m), 7.73 (1H, d, J=1.6 Hz), 7.83 (2H, d, J=8.4 Hz), 8.47 (1H, d, J=2.4 Hz).

Reference Example 79

2-(4-(1H-pyrazol-1-yl)benzyl)-6-fluoro-7-hydroxy-isoindolin-1-one

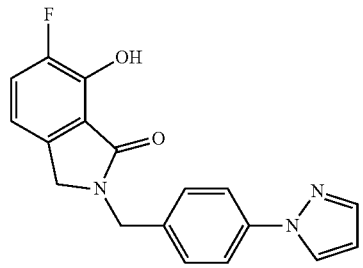 [SMILES: O=C1c2c(ccc(F)c2O)CN1Cc1ccc(-n2cccn2)cc1]

A mixed solution of 2-(4-(1H-pyrazol-1-yl)benzyl)-6-fluoro-7-iodoisoindolin-1-one (1.5 g) obtained in Reference Example 78, tris(dibenzylideneacetone)dipalladium(0) (0.063 g), 2-di-tert-butylphosphino-2',4',6'-triisopropylbiphenyl (0.12 g) and potassium hydroxide (0.78 g) in dioxane (15 mL)-water (15 mL) was stirred under a nitrogen atmosphere at 110° C. for 18 hr. The reaction solution was diluted with water and methyl tert-butyl ether, the aqueous layer was adjusted to pH=3 with 1N hydrochloric acid, and the resulting precipitate was collected by filtration. The obtained solid was washed by solid-liquid washing with methyl tert-butyl ether to give the title compound (1.0 g).

$^1$H NMR (400 MHz, DMSO-$d_6$) δ 4.29 (2H, s), 4.70 (2H, s), 6.53 (1H, t, J=2.0 Hz), 6.94 (1H, dd, J=8.0, 3.6 Hz), 7.31-7.48 (3H, m), 7.73 (1H, d, J=1.2 Hz), 7.82 (2H, d, J=8.4 Hz), 8.46 (1H, d, J=2.4 Hz).

Reference Example 80

Tert-butyl 2-fluoro-4-(1-methyl-1H-pyrazol-3-yl)benzylcarbamate

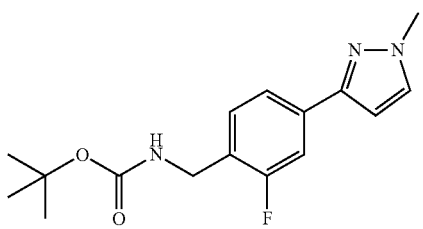 [SMILES: Cn1ccc(-c2ccc(CNC(=O)OC(C)(C)C)c(F)c2)n1]

A solution of tert-butyl 4-bromo-2-fluorobenzylcarbamate (1.46 g), 1-methyl-3-(4,4,5,5-tetramethyl-1,3,2-dioxaborolan-2-yl)-1H-pyrazole (1.0 g), sodium carbonate (1.02 g) and (1,1-bis(diphenylphosphino)ferrocene)dichloropalladium(II) (0.35 g) in 1,2-dimethoxyethane (13 mL)-water (4 mL) was stirred under an argon atmosphere at 90° C. overnight. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.64 g).

$^1$H NMR (300 MHz, DMSO-$d_6$) δ 1.39 (9H, s), 3.88 (3H, s), 4.17 (2H, d, J=5.7 Hz), 6.72 (1H, d, J=2.3 Hz), 7.26-7.34 (1H, m), 7.38 (1H, brs), 7.51 (1H, dd, J=11.7, 1.5 Hz), 7.58 (1H, d, J=7.9 Hz), 7.73 (1H, d, J=2.1 Hz).

Reference Example 81

(2-fluoro-4-(1-methyl-1H-pyrazol-3-yl)phenyl)methanamine

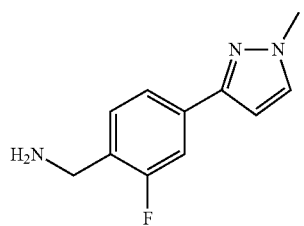

To tert-butyl 2-fluoro-4-(1-methyl-1H-pyrazol-3-yl)benzylcarbamate (0.64 g) obtained in Reference Example 80 was added 2N hydrochloric acid (methanol solution) (7 mL), and the mixture was stirred under a nitrogen atmosphere at room temperature overnight. The reaction solution was concentrated, the residue was suspended in ethyl acetate, and the precipitate was collected by filtration. The obtained white solid was dissolved in water, and neutralized with saturated aqueous sodium hydrogen carbonate solution. The aqueous layer was extracted with THF, dried over anhydrous sodium sulfate, and concentrated to give the title compound (0.39 g).

$^1$H NMR (300 MHz, DMSO-$d_6$) δ 2.41 (2H, brs), 3.76 (2H, s), 3.87 (3H, s), 6.72 (1H, d, J=2.3 Hz), 7.43-7.53 (2H, m), 7.54-7.63 (1H, m), 7.73 (1H, d, J=2.1 Hz).

Reference Example 82

Methyl 2-(2-chloro-6-fluorophenoxy)-4-iodonicotinate

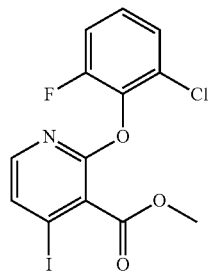 [SMILES: COC(=O)c1c(I)ccnc1Oc1c(F)cccc1Cl]

To a solution of methyl 2-fluoro-4-iodonicotinate (0.52 g) obtained in Reference Example 40 and 2-chloro-6-fluorophenol (0.82 g) in DMF (5 mL) was added 60% sodium hydride (0.30 g) at 0° C., and the mixture was stirred under an argon atmosphere at 90° C. overnight. The reaction solution was diluted with water and ethyl acetate, and the organic layer was separated, washed with saturated brine, dried over anhydrous sodium sulfate, and concentrated. The residue was purified by NH silica gel chromatography (hexane-ethyl acetate) to give the title compound (0.11 g).

MS: [M+H]$^+$ 407.9

Reference Example 83

Methyl 2-(2-chloro-6-fluorophenoxy)-4-vinylnicotinate

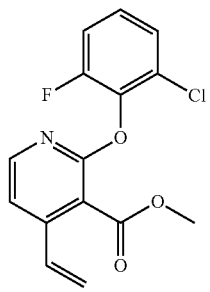 [SMILES: C=Cc1ccnc(Oc2c(F)cccc2Cl)c1C(=O)OC]

To a solution of methyl 2-(2-chloro-6-fluorophenoxy)-4-iodonicotinate (0.11 g) obtained in Reference Example 82 in DMF (3 mL) were added tributyl(vinyl)tin (0.12 g), trans-dichlorobis(triphenylphosphine)palladium(II) (0.018 g) and lithium chloride (0.081 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was purified by silica gel chromatography (hexane-ethyl acetate) to give the title compound (0.066 g).

MS: [M+H]$^+$ 308.1

Reference Example 84

5-(azidomethyl)-5,6,7,8-tetrahydroimidazo[1,2-a]pyridine

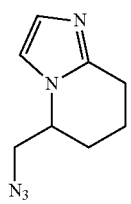

To a solution of (5,6,7,8-tetrahydroimidazo[1,2-a]pyridin-5-yl)methanol (3.0 g) and triethylamine (5.97 g) in dichloromethane (60 mL) was added mesyl chloride (3.39 g) at 0° C., and the mixture was stirred at room temperature for 4 hr. The reaction solution was diluted with water and dichloromethane, and the organic layer was separated, washed with water, dried over anhydrous sodium sulfate, and concentrated. To a solution of the residue (3.0 g) in DMF (100 mL) was added sodium azide (8.45 g), and the mixture was stirred at 90° C. for 3 hr. The insoluble material was filtered off, the filtrate was concentrated, and the residue was purified by silica gel chromatography (dichloromethane-methanol) to give the title compound (2.2 g).

$^1$H NMR (400 MHz, DMSO-d$_6$) δ 1.62-1.86 (2H, m), 1.88-2.16 (2H, m), 2.60-2.73 (2H, m), 3.70 (1H, dd, J=12.8, 4.4 Hz), 3.89 (1H, dd, J=12.8, 5.6 Hz), 4.17-4.28 (1H, m), 6.82 (1H, d, J=1.6 Hz), 7.20 (1H, d, J=1.6 Hz).

Reference Example 85

(5,6,7,8-tetrahydroimidazo[1,2-a]pyridin-5-yl)methanamine

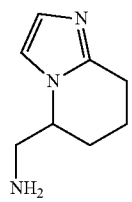 [SMILES: NCC1CCCc2nccn21]

A solution of 5-(azidomethyl)-5,6,7,8-tetrahydroimidazo[1,2-a]pyridine (2.9 g) obtained in Reference Example 84 and 10% palladium carbon (0.30 g) in methanol (50 mL) was stirred under a hydrogen atmosphere at room temperature for 3 hr, and the catalyst was filtered off. The filtrate was concentrated, and the residue was purified by HPLC (C18, mobile phase: water/acetonitrile (containing 0.1% NH4OH)) to give the title compound (1.12 g).

$^1$H NMR (400 MHz, DMSO-d$_6$) δ 1.58-1.72 (1H, m), 1.75-1.98 (3H, m), 2.56-2.70 (2H, m), 2.71-2.80 (1H, m), 2.82-2.90 (1H, m), 3.85-3.95 (1H, m), 6.76 (1H, d, J=1.2 Hz), 7.12 (1H, d, J=1.2 Hz).

Reference Example 86

(5,6,7,8-tetrahydroimidazo[1,2-a]pyridin-7-yl)methyl methanesulfonate

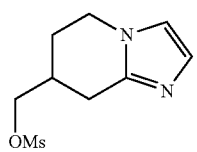 [SMILES: CS(=O)(=O)OCC1CCn2ccnc2C1]

To a solution of (5,6,7,8-tetrahydroimidazo[1,2-A]pyridin-7-yl)methanol (2.25 g) and triethylamine (4.48 g) in dichloromethane (40 mL) was added mesyl chloride (2.54 g) at 0° C., and the mixture was stirred at room temperature for 4 hr. The reaction solution was diluted with water and dichloromethane, and the organic layer was separated, washed with water, dried over anhydrous sodium sulfate, and concentrated to give the title compound (3.3 g).

$^1$H NMR (400 MHz, DMSO-d$_6$) δ 1.62-1.77 (1H, m), 2.01-2.10 (1H, m), 2.25-2.40 (1H, m), 2.41-2.50 (1H, m, overlap with the signal of DMSO-d$_6$), 2.85-2.95 (1H, m), 3.22 (3H, s), 3.87 (1H, td, J=11.6, 4.8 Hz), 4.05-4.12 (1H, m), 4.20-4.30 (2H, m), 6.82 (1H, d, J=1.2 Hz), 7.00 (1H, d, J=1.2 Hz).

Reference Example 87

7-(azidomethyl)-5,6,7,8-tetrahydroimidazo[1,2-a]pyridine

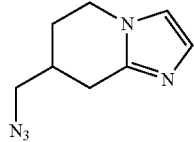

To a solution of (5,6,7,8-tetrahydroimidazo[1,2-a]pyridin-7-yl)methyl methanesulfonate (3.1 g) obtained in Reference Example 86 in DMF (100 mL) was added sodium azide (8.78 g), and the mixture was stirred at 90° C. for 3 hr. The insoluble material was filtered off, the filtrate was concentrated, and the residue was purified by silica gel chromatography (dichloromethane-methanol) and HPLC (C18, mobile phase: water/acetonitrile (containing 0.1% NH4OH)) to give the title compound (1.5 g).

$^1$H NMR (400 MHz, DMSO-$d_6$) δ 1.58-1.72 (1H, m), 1.96-2.06 (1H, m), 2.06-2.21 (1H, m), 2.40 (1H, dd, J=16.4, 10.8 Hz), 2.82-2.89 (1H, m), 3.42-3.50 (2H, s), 3.85 (1H, td, J=11.6, 4.8 Hz), 4.02-4.12 (1H, m), 6.80 (1H, d, J=1.2 Hz), 6.98 (1H, d, J=1.2 Hz).

Reference Example 88

(5,6,7,8-tetrahydroimidazo[1,2-a]pyridin-7-yl)methanamine

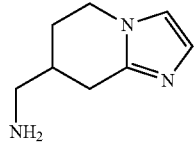

A solution of 7-(azidomethyl)-5,6,7,8-tetrahydroimidazo[1,2-a]pyridine (1.7 g) obtained in Reference Example 87 and 10% palladium carbon (0.20 g) in methanol (50 mL) was stirred under a hydrogen atmosphere at room temperature for 3 hr. The catalyst was filtered off, the filtrate was concentrated, and the residue was purified by HPLC (C18, mobile phase: water/acetonitrile (containing 0.1% NH4OH)) to give the title compound (0.62 g).

$^1$H NMR (400 MHz, DMSO-$d_6$) δ 1.42-1.60 (1H, m), 1.70-1.90 (1H, m), 1.96-2.10 (1H, m), 2.21-2.35 (1H, m), 2.52-2.60 (2H, m, overlap with the signal of DMSO-$d_6$), 2.85 (1H, dd, J=16.4, 8.0 Hz), 3.79 (1H, td, J=11.6, 4.8 Hz), 3.95-4.10 (1H, m), 6.77 (1H, d, J=0.8 Hz), 6.96 (1H, s).

Reference Example 89

(4-(4-fluoro-1H-pyrazol-1-yl)phenyl)methanol

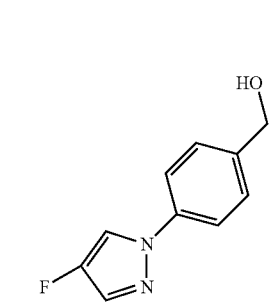 [SMILES: [N-]=[N+]=NCc1ccc(-n2cc(F)cn2)cc1]

To a suspension of (4-(1H-pyrazol-1-yl)phenyl)methanol (22.5 g) in acetonitrile (500 mL) was added N-fluoro-N'-(chloromethyl)triethylenediamine bis(tetrafluoroborate) (108 g) at room temperature, and the mixture was stirred at 80° C. for 16 hr. The reaction solution was diluted with ethyl acetate, washed with saturated brine, dried over anhydrous sodium sulfate, and concentrated. The residue was purified by silica gel chromatography (petroleum ether-ethyl acetate) to give the title compound (4.5 g).

$^1$H NMR (400 MHz, CDCl$_3$) δ 4.73 (2H, s), 7.45 (2H, d, J=8.0 Hz), 7.57 (1H, d, J=4.0 Hz), 7.61 (2H, d, J=8.0 Hz), 7.80 (1H, d, J=4.8 Hz).

Reference Example 90

1-(4-(azidomethyl)phenyl)-4-fluoro-1H-pyrazole

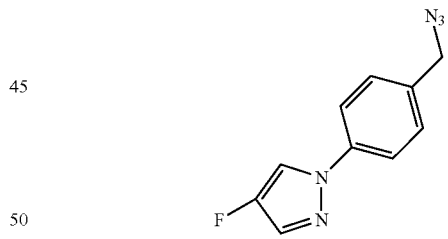

To a solution of (4-(4-fluoro-1H-pyrazol-1-yl)phenyl)methanol (3.7 g) obtained in Reference Example 89 in toluene (50 mL)-dichloromethane (50 mL) were added diphenylphosphoryl azide (9.01 g) and 1,8-diazabicyclo[5.4.0]undec-7-ene (5.57 g) at 0° C., and the mixture was stirred under a nitrogen atmosphere at room temperature for 16 hr. The reaction solution was diluted with dichloromethane, and the organic layer was separated, washed with water, dried over anhydrous sodium sulfate, and concentrated. The residue was purified by silica gel chromatography (petroleum ether-ethyl acetate) to give the title compound (2.96 g).

$^1$H NMR (400 MHz, CDCl$_3$) δ 4.40 (2H, s), 7.43 (2H, d, J=8.8 Hz), 7.61 (1H, d, J=4.4 Hz), 7.67 (2H, dd, J=8.4, 1.6 Hz), 7.84 (1H, d, J=4.8 Hz).

Reference Example 91

Tert-butyl 4-(4-fluoro-1H-pyrazol-1-yl)benzylcarbamate

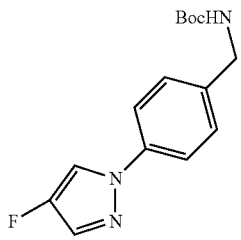 [SMILES: CC(C)(C)OC(=O)NCc1ccc(-n2cc(F)cn2)cc1]

A solution of 1-(4-(azidomethyl)phenyl)-4-fluoro-1H-pyrazole (3.25 g) obtained in Reference Example 90, 10% palladium carbon (0.40 g) and di-tert-butyl dicarbonate (6.53 g) in methanol (50 mL) was stirred under a hydrogen atmosphere at room temperature for 4 hr. The insoluble material was filtered off, the filtrate was concentrated, and the residue was purified by HPLC (C18, mobile phase: water/acetonitrile (containing 0.1% NH4OH)) to give the title compound (1.4 g).

$^1$H NMR (400 MHz, CDCl$_3$) δ 1.49 (9H, s), 4.36 (2H, d, J=6.0 Hz), 4.92 (1H, brs), 7.39 (2H, d, J=8.8 Hz), 7.58-7.62 (3H, m), 7.81 (1H, d, J=4.8 Hz).

Reference Example 92

(4-(4-fluoro-1H-pyrazol-1-yl)phenyl)methanamine hydrochloride

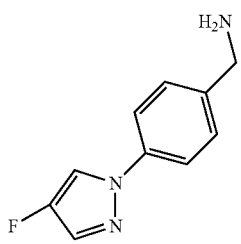

To tert-butyl 4-(4-fluoro-1H-pyrazol-1-yl)benzylcarbamate (1.4 g) obtained in Reference Example 91 was added 4N hydrochloric acid (ethyl acetate solution) (20 mL), and the mixture was stirred at room temperature for 2 hr. The reaction solution was concentrated, dissolved in water, and lyophilized to give the title compound (1.09 g).

$^1$H NMR (400 MHz, DMSO-d$_6$) δ 4.04 (2H, s), 7.64 (2H, d, J=8.8 Hz), 7.81-7.86 (3H, m), 8.58 (3H, brs), 8.74 (1H, d, J=4.4 Hz).

Reference Example 93

(tetrahydrofuran-2-yl)methyl 4-iodo-2-((tetrahydrofuran-2-yl)methoxy)nicotinate

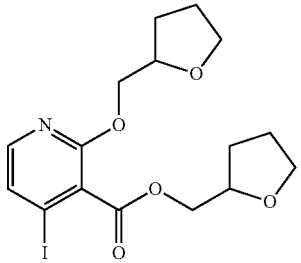 [SMILES: O=C(OCC1CCCO1)c1c(I)ccnc1OCC1CCCO1]

To a solution of methyl 2-fluoro-4-iodonicotinate (5.03 g) obtained in Reference Example 40 and (tetrahydrofuran-2-yl)methanol (5.48 g) in THF (100 mL) was added 60% sodium hydride (3.22 g) at 0° C., and the mixture was stirred under an argon atmosphere at the same temperature for 1 hr. To the reaction solution was added water at 0° C., and the mixture was diluted with ethyl acetate. The organic layer was separated, washed with saturated brine, dried over anhydrous sodium sulfate, and concentrated. The residue was purified by NH silica gel chromatography (hexane-ethyl acetate) to give the title compound (1.43 g).

$^1$H NMR (300 MHz, DMSO-d$_6$) δ 1.63-1.99 (8H, m), 3.59-3.82 (4H, m), 4.07-4.31 (6H, m), 7.52 (1H, d, J=5.5 Hz), 7.92 (1H, d, J=5.3 Hz).

Reference Example 94

(tetrahydrofuran-2-yl)methyl 2-((tetrahydrofuran-2-yl)methoxy)-4-vinylnicotinate

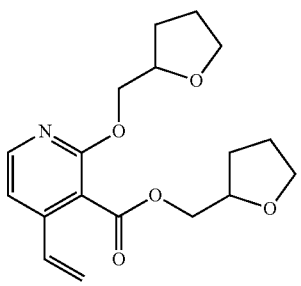 [SMILES: C=Cc1ccnc(OCC2CCCO2)c1C(=O)OCC1CCCO1]

To a solution of (tetrahydrofuran-2-yl)methyl 4-iodo-2-((tetrahydrofuran-2-yl)methoxy)nicotinate (1.4 g) obtained in Reference Example 93 in DMF (20 mL) were added tributyl(vinyl)tin (1.54 g), trans-dichlorobis(triphenylphosphine)palladium(II) (0.11 g) and lithium chloride (1.01 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (1.06 g).

¹H NMR (300 MHz, DMSO-d₆) δ1.58-2.01 (8H, m), 3.59-3.81 (4H, m), 4.03-4.32 (6H, m), 5.62 (1H, d, J=11.3 Hz), 6.13 (1H, d, J=17.2 Hz), 6.66 (1H, dd, J=17.4, 11.0 Hz), 7.33 (1H, d, J=5.7 Hz), 8.18 (1H, d, J=5.5 Hz).

Reference Example 95

7-methoxy-2-(4-(1-methyl-1H-1,2,3-triazol-4-yl)benzyl)isoindolin-1-one

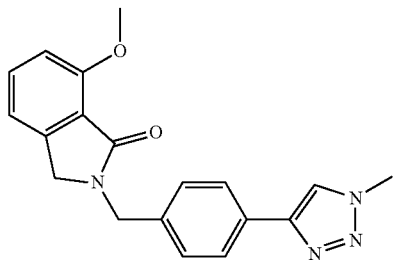 [SMILES: COc1cccc2c1C(=O)N(Cc1ccc(-c3cn(C)nn3)cc1)C2]

A solution of ethyl 2-(bromomethyl)-6-methoxybenzoate (0.15 g), (4-(1-methyl-1H-1,2,3-triazol-4-yl)phenyl)methanamine (0.10 g) obtained in Reference Example 162 and potassium carbonate (0.11 g) in ethanol (3 mL) was stirred under a nitrogen atmosphere at room temperature overnight. Water was added to the reaction mixture, the resulting precipitate was collected by filtration, and dried to give the title compound (0.14 g).

¹H NMR (300 MHz, DMSO-d₆) δ 3.87 (3H, s), 4.08 (3H, s), 4.30 (2H, s), 4.67 (2H, s), 7.05 (2H, dd, J=11.7, 7.9 Hz), 7.32 (2H, d, J=8.3 Hz), 7.47-7.57 (1H, m), 7.80 (2H, d, J=8.1 Hz), 8.48 (1H, s).

Reference Example 96

7-hydroxy-2-(4-(1-methyl-1H-1,2,3-triazol-4-yl)benzyl)isoindolin-1-one

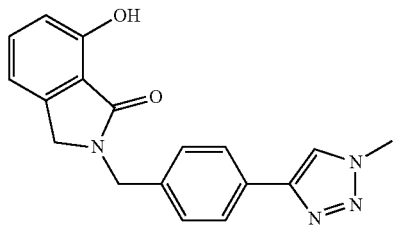 [SMILES: Cn1cc(-c2ccc(CN3Cc4cccc(O)c4C3=O)cc2)nn1]

To 7-methoxy-2-(4-(1-methyl-1H-1,2,3-triazol-4-yl)benzyl)isoindolin-1-one (0.14 g) obtained in Reference Example 95 was added 25% hydrobromic acid (acetic acid solution) (3 mL), and the mixture was stirred under a nitrogen atmosphere at 120° C. overnight. The reaction solution was diluted with water, and neutralized with sodium carbonate. Ethyl acetate was added, and the organic layer was separated, washed with water and saturated brine, dried over anhydrous sodium sulfate, and concentrated. The residue was purified by NH silica gel chromatography (hexane-ethyl acetate) to give the title compound (0.094 g).

¹H NMR (300 MHz, DMSO-d₆) δ 4.08 (3H, s), 4.32 (2H, s), 4.68 (2H, s), 6.78-6.88 (1H, m), 6.94 (1H, d, J=7.4 Hz), 7.28-7.44 (3H, m), 7.81 (2H, d, J=8.1 Hz), 8.49 (1H, s), 9.61 (1H, s).

Reference Example 97

4-fluoro-2-iodo-6-methylbenzoic acid

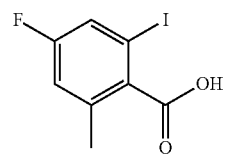

A solution of 4-fluoro-2-methylbenzoic acid (80 g), iodobenzene diacetate (234 g), palladium(II) acetate (5.82 g) and iodine (264 g) in DMF (1000 mL) was stirred at 100° C. for 2 days. The reaction solution was diluted with saturated aqueous sodium sulfite solution and methyl tert-butyl ether, and the organic layer was separated, washed with 2N sodium hydroxide, and adjusted to pH=3-4 with 1N hydrochloric acid. The organic layer was separated, dried over anhydrous sodium sulfate, and concentrated. The residue was purified by silica gel chromatography (petroleum ether-ethyl acetate) to give the title compound (130 g).

¹H NMR (400 MHz, DMSO-d₆) δ 2.31 (3H, s), 7.20 (1H, dd, J=10.0, 2.0 Hz), 7.59 (1H, dd, J=8.0, 2.4 Hz).

Reference Example 98

Methyl 4-fluoro-2-iodo-6-methylbenzoate

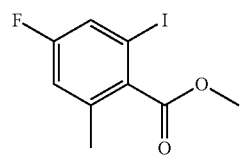

A solution of 4-fluoro-2-iodo-6-methylbenzoic acid (130 g) obtained in Reference Example 97, methyl iodide (72.4 g) and potassium carbonate (70.4 g) in DMF (1000 mL) was stirred at room temperature for 16 hr. The reaction solution was diluted with water and ethyl acetate, and the organic layer was separated, washed with water, dried over anhydrous sodium sulfate, and concentrated. The residue was purified by silica gel chromatography (petroleum ether-ethyl acetate) to give the title compound (90 g).

¹H NMR (400 MHz, CDCl₃) δ 2.34 (3H, s), 3.94 (3H, s), 6.85-7.00 (1H, m), 7.33-7.45 (1H, m).

Reference Example 99

Methyl 2-(bromomethyl)-4-fluoro-6-iodobenzoate

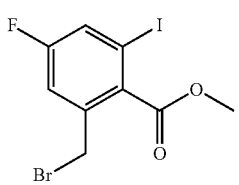

To a solution of methyl 4-fluoro-2-iodo-6-methylbenzoate (10 g) obtained in Reference Example 98 in carbon tetrachloride (150 mL) were added NBS (6.66 g) and AIBN (0.56 g), and the mixture was heated under reflux for 16 hr. The reaction solution was diluted with dichloromethane, washed with water and saturated brine, dried over anhydrous sodium sulfate, and concentrated. The residue was purified by silica gel chromatography (petroleum ether-ethyl acetate) to give the title compound (4.5 g).

$^1$H NMR (400 MHz, DMSO-$d_6$) δ 3.99 (3H, s), 4.45 (2H, s), 7.16 (1H, dd, J=8.8, 2.4 Hz), 7.54 (1H, dd, J=8.0, 2.4 Hz).

Reference Example 100

2-(4-(1H-pyrazol-1-yl)benzyl)-5-fluoro-7-iodoisoindolin-1-one

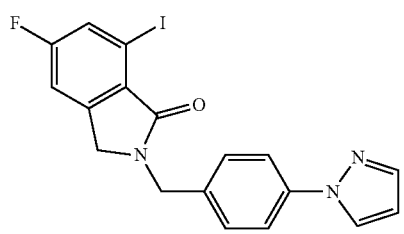 [SMILES: O=C1c2c(I)cc(F)cc2CN1Cc1ccc(-n2cccn2)cc1]

To a solution of methyl 2-(bromomethyl)-4-fluoro-6-iodobenzoate (2.54 g) obtained in Reference Example 99 in THF (30 mL) were added (4-(1H-pyrazol-1-yl)phenyl)methanamine (4.5 g), triethylamine (2.44 g) and potassium carbonate (1.67 g), and the mixture was heated under reflux under a nitrogen atmosphere for 12 hr. The reaction solution was diluted with water and ethyl acetate, and the organic layer was separated, washed with water and saturated brine, dried over anhydrous sodium sulfate, and concentrated. The residue was solidified with petroleum ether-ethyl acetate to give the title compound (2.85 g).

$^1$H NMR (400 MHz, CDCl$_3$) δ 4.18 (2H, s), 4.81 (2H, s), 6.47 (1H, t, J=2.0 Hz), 7.10 (1H, dd, J=7.6, 2.0 Hz), 7.41 (2H, d, J=8.8 Hz), 7.60-7.80 (4H, m), 7.91 (1H, d, J=2.4 Hz).

Reference Example 101

2-(4-(1H-pyrazol-1-yl)benzyl)-5-fluoro-7-hydroxy-isoindolin-1-one

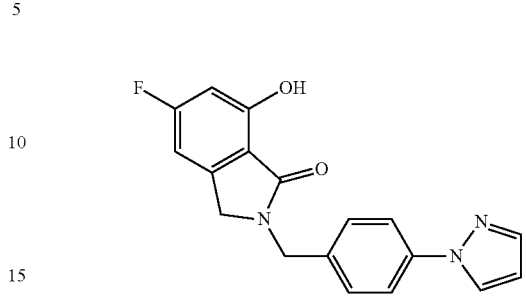

A mixed solution of 2-(4-(1H-pyrazol-1-yl)benzyl)-5-fluoro-7-iodoisoindolin-1-one (1.8 g) obtained in Reference Example 100, tris(dibenzylideneacetone)dipalladium(0) (0.076 g), 2-di-tert-butylphosphino-2',4',6'-triisopropylbiphenyl (0.14 g) and potassium hydroxide (0.93 g) in dioxane (12 mL)-water (12 mL) was stirred under a nitrogen atmosphere at 110° C. for 12 hr. To the reaction solution was added 1.5N hydrochloric acid to give an acidic solution, and ethyl acetate was added. The organic layer was separated, washed with saturated brine, dried over anhydrous sodium sulfate, and concentrated. The residue was purified by silica gel chromatography (petroleum ether-ethyl acetate) to give the title compound (0.68 g).

$^1$H NMR (400 MHz, CDCl$_3$) δ 4.26 (2H, s), 4.74 (2H, s), 6.47 (1H, t, J=2.0 Hz), 6.55-6.70 (2H, m), 7.38 (2H, d, J=8.4 Hz), 7.62-7.75 (3H, m), 7.91 (1H, d, J=2.4 Hz), 8.71 (1H, brs).

Reference Example 102

Methyl 2-fluoro-4-vinylnicotinate

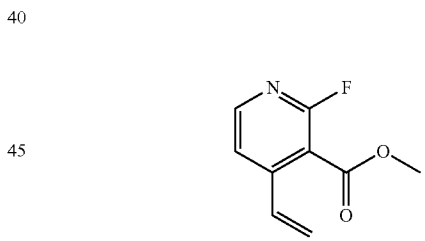

To a solution of methyl 2-fluoro-4-iodonicotinate (0.70 g) obtained in Reference Example 40 in DMF (12 mL) were added tributyl(vinyl)tin (1.19 g), trans-dichlorobis(triphenylphosphine)palladium(II) (0.087 g) and lithium chloride (0.78 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was purified by silica gel chromatography (hexane-ethyl acetate) to give the title compound (0.39 g).

$^1$H NMR (300 MHz, DMSO-$d_6$) δ 3.91 (3H, s), 5.73 (1H, d, J=11.0 Hz), 6.22 (1H, d, J=17.4 Hz), 6.85 (1H, dd, J=17.4, 11.0 Hz), 7.74 (1H, dd, J=5.4, 1.2 Hz), 8.33 (1H, d, J=5.5 Hz).

Reference Example 103

Methyl 2-(2,6-difluorophenoxy)-4-vinylnicotinate

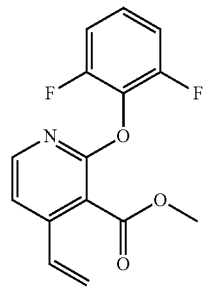 [SMILES: C=Cc1ccnc(Oc2c(F)cccc2F)c1C(=O)OC]

A solution of methyl 2-fluoro-4-vinylnicotinate (0.39 g) obtained in Reference Example 102, 2,6-difluorophenol (0.56 g) and potassium carbonate (0.89 g) in DMF (5 mL) was stirred under a nitrogen atmosphere at 110° C. overnight. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.10 g).

$^1$H NMR (300 MHz, DMSO-$d_6$) δ 3.92 (3H, s), 5.72 (1H, d, J=11.1 Hz), 6.21 (1H, d, J=17.4 Hz), 6.75 (1H, dd, J=17.4, 11.0 Hz), 7.20-7.45 (3H, m), 7.55 (1H, d, J=5.3 Hz), 8.15 (1H, d, J=5.5 Hz).

Reference Example 104

Ethyl 4-iodo-2-((tetrahydro-2H-pyran-2-yl)methoxy)nicotinate

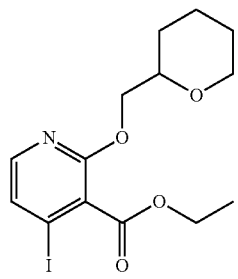 [SMILES: CCOC(=O)c1c(I)ccnc1OCC1CCCCO1]

To a solution of ethyl 2-fluoro-4-iodonicotinate (0.50 g) obtained by a known method (Organic Letters, 7(10), 1943-1946; 2005) and (tetrahydro-2H-pyran-2-yl)methanol (0.79 g) in THF (20 mL) was added 60% sodium hydride (0.34 g) at 0° C., and the mixture was stirred under an argon atmosphere at the same temperature for 1 hr. The reaction solution was diluted with water and ethyl acetate. The organic layer was separated, washed with water and saturated brine, dried over anhydrous sodium sulfate, and concentrated. The residue was purified by silica gel chromatography (hexane-ethyl acetate) to give the title compound (0.57 g).

$^1$H NMR (300 MHz, DMSO-$d_6$) δ 1.23-1.37 (4H, m), 1.39-1.51 (3H, m), 1.52-1.62 (1H, m), 1.74-1.85 (1H, m), 3.32-3.39 (1H, m), 3.47-3.62 (1H, m), 3.79-3.91 (1H, m), 4.13-4.40 (4H, m), 7.50 (1H, d, J=5.3 Hz), 7.90 (1H, d, J=5.3 Hz).

Reference Example 105

Ethyl 2-((tetrahydro-2H-pyran-2-yl)methoxy)-4-vinylnicotinate

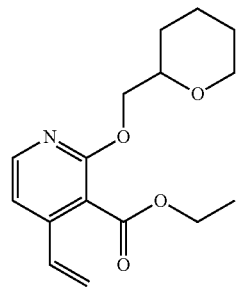 [SMILES: C=Cc1ccnc(OCC2CCCCO2)c1C(=O)OCC]

To a solution of ethyl 4-iodo-2-((tetrahydro-2H-pyran-2-yl)methoxy)nicotinate (0.57 g) obtained in Reference Example 104 in DMF (10 mL) were added tributyl(vinyl)tin (0.69 g), trans-dichlorobis(triphenylphosphine)palladium (II) (0.051 g) and lithium chloride (0.46 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.42 g).

$^1$H NMR (300 MHz, DMSO-$d_6$) δ 1.23-1.37 (4H, m), 1.39-1.53 (3H, m), 1.55-1.66 (1H, m), 1.73-1.86 (1H, m), 3.33-3.41 (1H, m), 3.50-3.62 (1H, m), 3.80-3.92 (1H, m), 4.13-4.38 (4H, m), 5.62 (1H, d, J=11.3 Hz), 6.12 (1H, d, J=17.2 Hz), 6.62 (1H, dd, J=17.4, 11.0 Hz), 7.31 (1H, d, J=5.5 Hz), 8.17 (1H, d, J=5.5 Hz).

Reference Example 106

Ethyl 4-(4-bromo-1H-pyrazol-1-yl)benzoate

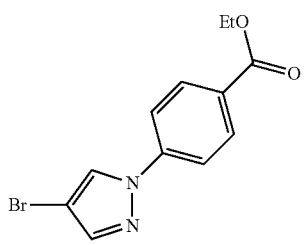 [SMILES: CCOC(=O)c1ccc(-n2cc(Br)cn2)cc1]

A solution of ethyl 4-fluorobenzoate (71.4 g), 4-bromo-1H-pyrazole (50 g) and potassium carbonate (93.8 g) in DMSO (150 mL) was stirred at 130° C. for 16 hr. The reaction solution was diluted with water and ethyl acetate. The organic layer was separated, washed with water and saturated brine, dried over anhydrous sodium sulfate, and concentrated. The residue was solidified with methyl tert-butyl ether to give the title compound (76 g).

$^1$H NMR ((400 MHz, CDCl$_3$) δ 1.41 (3H, t, J=7.2 Hz), 4.40 (2H, q, J=7.2 Hz), 7.71 (1H, s), 7.73 (2H, d, J=8.8 Hz), 8.02 (1H, s), 8.14 (2H, d, J=8.8 Hz).

Reference Example 107

Ethyl 4-(4-bromo-5-fluoro-1H-pyrazol-1-yl)benzoate

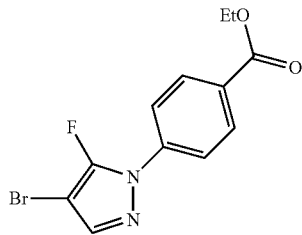 [SMILES: CCOC(=O)c1ccc(-n2ncc(Br)c2F)cc1]

To a solution of ethyl 4-(4-bromo-1H-pyrazol-1-yl)benzoate (20 g) obtained in Reference Example 106 in acetonitrile (400 mL) was added N-fluoro-N'-(chloromethyl)triethylenediamine bis(tetrafluoroborate) (47.8 g) at room temperature, and the mixture was stirred at 80° C. for 16 hr. The reaction solution was concentrated, and to the residue were added ethyl acetate and water. The organic layer was separated, washed with saturated brine, dried over anhydrous sodium sulfate, and concentrated. The residue was purified by silica gel chromatography (petroleum ether-ethyl acetate) to give the title compound (3.22 g).

$^1$H NMR (400 MHz, CDCl$_3$) δ 1.42 (3H, t, J=7.2 Hz), 4.40 (2H, q, J=7.2 Hz), 7.58 (1H, d, J=2.4 Hz), 7.73 (2H, dd, J=8.8, 2.0 Hz), 8.16 (2H, d, J=8.8 Hz).

Reference Example 108

Ethyl 4-(5-fluoro-1H-pyrazol-1-yl)benzoate

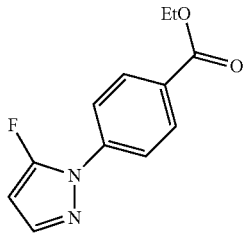 [SMILES: CCOC(=O)c1ccc(-n2nccc2F)cc1]

A solution of ethyl 4-(4-bromo-5-fluoro-1H-pyrazol-1-yl)benzoate (3.22 g) obtained in Reference Example 107 and 10% palladium carbon (3.0 g) in ethanol (100 mL) was stirred under a hydrogen atmosphere at room temperature for 16 hr. The catalyst was filtered off, and the filtrate was concentrated to give the title compound (2.4 g).

$^1$H NMR (400 MHz, CDCl$_3$) δ 1.42 (3H, t, J=7.2 Hz), 4.41 (2H, q, J=7.2 Hz), 5.98 (1H, d, J=4.4 Hz), 7.61 (1H, s), 7.77 (2H, d, J=8.0 Hz), 8.16 (2H, d, J=8.4 Hz).

Reference Example 109

4-(5-fluoro-1H-pyrazol-1-yl)benzoic acid

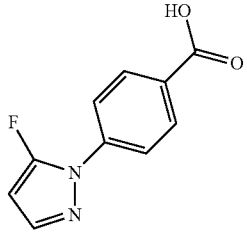 [SMILES: O=C(O)c1ccc(-n2nccc2F)cc1]

A solution of ethyl 4-(5-fluoro-1H-pyrazol-1-yl)benzoate (3.14 g) obtained in Reference Example 108 and lithium hydroxide monohydrate (2.82 g) in THF (40 mL)-methanol (40 mL)-water (20 mL) was stirred at room temperature for 16 hr. The organic layer was evaporated, and the aqueous layer was washed with methyl tert-butyl ether. The aqueous layer was separated, and adjusted to pH=3-4 with citric acid. The resulting precipitate was collected by filtration, and dissolved in ethyl acetate. The organic layer was washed with saturated brine, dried over anhydrous sodium sulfate, and concentrated to give the title compound (2.25 g).

$^1$H NMR (400 MHz, DMSO-d$_6$) δ 6.29 (1H, dd, J=5.2, 2.0 Hz), 7.73 (1H, dd, J=2.8, 2.0 Hz), 7.79 (2H, dd, J=8.8, 2.0 Hz), 8.09 (2H, d, J=8.8 Hz), 13.10 (1H, brs).

Reference Example 110

(4-(5-fluoro-1H-pyrazol-1-yl)phenyl)methanol

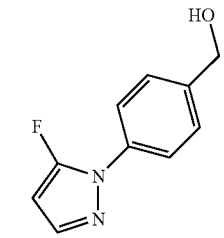 [SMILES: OCc1ccc(-n2nccc2F)cc1]

To a suspension of 4-(5-fluoro-1H-pyrazol-1-yl)benzoic acid (1.83 g) obtained in Reference Example 109 in THF (50 mL) were added triethylamine (1.35 g) and isobutyl carbonochloridate (1.34 g) at 0° C., and the mixture was stirred at the same temperature for 1 hr. To the reaction solution was added dropwise a solution of sodium tetrahydroborate (1.01 g) in water (5 mL) at 0° C., and the mixture was stirred at the same temperature for 1 hr and at room temperature for 2 hr. The reaction solution was neutralized with 1N hydrochloric acid, and ethyl acetate was added. The organic layer was separated, washed with saturated brine, dried over anhydrous sodium sulfate, and concentrated. The residue was purified by silica gel chromatography (petroleum ether-ethyl acetate) to give the title compound (1.21 g).

$^1$H NMR (400 MHz, CDCl$_3$) δ 1.97 (1H, brs), 4.74 (2H, s), 5.91 (1H, dd, J=5.2, 2.0 Hz), 7.46 (2H, d, J=8.4 Hz), 7.50-7.56 (1H, m), 7.62 (2H, dd, J=8.4, 1.6 Hz).

Reference Example 111

1-(4-(azidomethyl)phenyl)-5-fluoro-1H-pyrazole

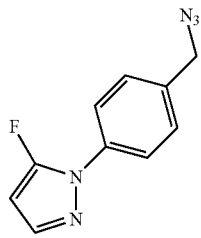 [SMILES: [N-]=[N+]=NCc1ccc(-n2nccc2F)cc1]

To a solution of (4-(5-fluoro-1H-pyrazol-1-yl)phenyl)methanol (1.15 g) obtained in Reference Example 110 in dichloromethane (60 mL)-toluene (60 mL) were added diphenylphosphoryl azide (2.8 g) and 1,8-diazabicyclo[5.4.0]undec-7-ene (1.73 g) at 0° C., and the mixture was stirred under a nitrogen atmosphere at the same temperature for 1 hr and at room temperature for 22 hr. The reaction solution was diluted with dichloromethane, and the organic layer was separated, washed with water and saturated brine, dried over anhydrous sodium sulfate, and concentrated. The residue was purified by silica gel chromatography (petroleum ether-ethyl acetate) to give the title compound (1.27 g).

$^1$H NMR (400 MHz, CDCl$_3$) δ 4.39 (2H, s), 5.92 (1H, dd, J=5.2, 2.0 Hz), 7.42 (2H, d, J=8.8 Hz), 7.54 (1H, dd, J=2.8, 2.0 Hz), 7.68 (2H, dd, J=8.4, 1.6 Hz).

Reference Example 112

(4-(5-fluoro-1H-pyrazol-1-yl)phenyl)methanamine hydrochloride

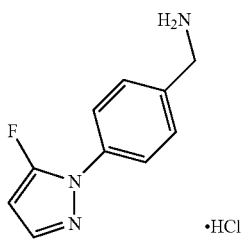 [SMILES: NCc1ccc(-n2nccc2F)cc1 ; Cl]

A solution of 1-(4-(azidomethyl)phenyl)-5-fluoro-1H-pyrazole (1.27 g) obtained in Reference Example 111 and triphenylphosphine (3.07 g) in THF (20 mL)-water (2 mL) was stirred at room temperature for 16 hr. The reaction solution was diluted with ethyl acetate, and the organic layer was separated, washed with saturated brine, dried over anhydrous sodium sulfate, and concentrated. The residue was purified by alumina chromatography (dichloromethane-methanol) and HPLC (C18, mobile phase: water/acetonitrile (containing 0.04% HCl)) to give the title compound (0.44 g).

$^1$H NMR (400 MHz, DMSO-d$_6$) δ 4.10 (2H, q, J=4.8 Hz), 6.26 (1H, dd, J=5.2, 2.0 Hz), 7.63 (2H, d, J=8.4 Hz), 7.66-7.72 (3H, m), 8.29 (3H, brs).

Reference Example 113

Ethyl 4-iodo-2-((tetrahydro-2H-pyran-4-yl)methoxy)nicotinate

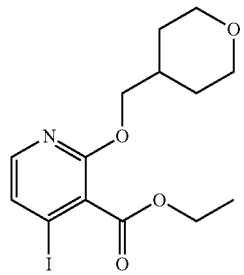 [SMILES: CCOC(=O)c1c(I)ccnc1OCC1CCOCC1]

To a solution of ethyl 2-fluoro-4-iodonicotinate (0.50 g) obtained by a known method (Organic Letters, 7(10), 1943-1946; 2005) and (tetrahydro-2H-pyran-4-yl)methanol (0.59 g) in THF (10 mL) was added 60% sodium hydride (0.27 g) at 0° C., and the mixture was stirred under an argon atmosphere at the same temperature for 1 hr. The reaction solution was neutralized with 1N hydrochloric acid, and ethyl acetate was added. The organic layer was separated, washed with water and saturated brine, dried over anhydrous sodium sulfate, and concentrated. The residue was purified by silica gel chromatography (hexane-ethyl acetate) to give the title compound (0.35 g).

MS: [M+H]$^+$ 392.0

Reference Example 114

5-fluoro-2'-methyl-(3,4'-bipyridine)-6-carbonitrile

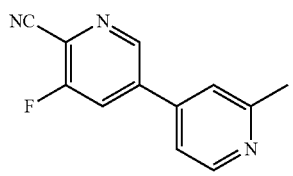 [SMILES: Cc1cc(-c2cnc(C#N)c(F)c2)ccn1]

A solution of 5-bromo-3-fluoropicolinonitrile (0.46 g), 2-methyl-4-(4,4,5,5-tetramethyl-1,3,2-dioxaborolan-2-yl)pyridine (0.60 g), sodium carbonate (0.49 g) and (1,1-bis(diphenylphosphino)ferrocene)dichloropalladium(II) (0.17 g) in 1,2-dimethoxyethane (10 mL)-water (3 mL) was stirred under an argon atmosphere at 90° C. overnight. The reaction solution was diluted with water and ethyl acetate, and the organic layer was separated, washed with saturated brine, dried over anhydrous sodium sulfate, and concentrated. The residue was purified by NH silica gel chromatography (hexane-ethyl acetate) to give the title compound (0.33 g).

$^1$H NMR (300 MHz, DMSO-d$_6$) δ 2.57 (3H, s), 7.72 (1H, dd, J=5.4, 1.4 Hz), 7.82 (1H, s), 8.58-8.66 (2H, m), 9.12 (1H, t, J=1.6 Hz).

Reference Example 115

Ethyl 2-(bromomethyl)-6-(2,6-difluorophenoxyl)benzoate

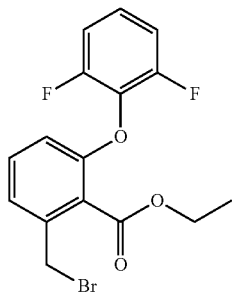 [SMILES: CCOC(=O)c1c(CBr)cccc1Oc1c(F)cccc1F]

A solution of ethyl 2-hydroxy-6-methylbenzoate (3.55 g), 1,2,3-trifluoro-5-nitrobenzene (3.84 g) and potassium carbonate (4.08 g) in DMF (30 mL) was stirred at 70° C. overnight. The reaction solution was diluted with water and ethyl acetate, and the organic layer was separated, washed with saturated brine, dried over anhydrous sodium sulfate, and concentrated. The residue was crudely purified by silica gel chromatography (hexane-ethyl acetate). A solution of the crudely purified product (6.64 g) and 10% palladium carbon (0.63 g) in ethanol (50 mL) was stirred under a hydrogen atmosphere at room temperature overnight. The catalyst was filtered off, and the filtrate was concentrated. A solution of the residue (1 g) and pentyl nitrite (0.76 g) in THF (15 mL) was stirred under an argon atmosphere at 60° C. The reaction solution was concentrated, and the residue was crudely purified by silica gel chromatography (hexane-ethyl acetate). To a solution of the crudely purified product (0.64 g) in benzotrifluoride (13 mL) were added NBS (0.43 g) and AIBN (0.036 g), and the mixture was stirred under an argon atmosphere at 90° C. for 4 hr. The resulting precipitate was filtered off, and the filtrate was concentrated. The residue was purified by silica gel chromatography (hexane-ethyl acetate) to give the title compound (0.14 g).

$^1$H NMR (300 MHz, DMSO-$d_6$) δ 1.31 (3H, t, J=7.2 Hz), 4.36 (2H, q, J=7.0 Hz), 4.71 (2H, s), 6.75 (1H, dd, J=8.4, 0.8 Hz), 7.26-7.45 (5H, m).

Reference Example 116

Ethyl 2-((trans-2-hydroxycyclohexyl)oxy)-4-vinylnicotinate

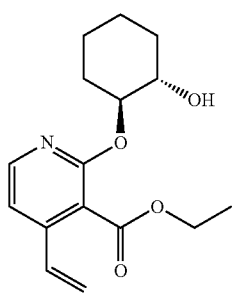 [SMILES: C=Cc1ccnc(O[C@H]2CCCC[C@@H]2O)c1C(=O)OCC]

To a solution of ethyl 2-fluoro-4-iodonicotinate (3.0 g) obtained by a known method (Organic Letters, 7(10), 1943-1946; 2005) and trans-cyclohexane-1,2-diol (4.72 g) in THF (100 mL) was added 60% sodium hydride (2.03 g) at 0° C., and the mixture was stirred under an argon atmosphere at the same temperature for 1 hr. The reaction solution was neutralized with 1N hydrochloric acid, and ethyl acetate was added. The organic layer was separated, washed with water and saturated brine, dried over anhydrous sodium sulfate, and concentrated. The residue was crudely purified by silica gel chromatography (hexane-ethyl acetate). To a solution of the crudely purified product (1.12 g) in DMF (20 mL) were added tributyl(vinyl)tin (1.36 g), trans-dichlorobis(triphenylphosphine)palladium(II) (0.10 g) and lithium chloride (0.90 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was purified by silica gel chromatography (hexane-ethyl acetate) to give the title compound (0.82 g).

$^1$H NMR (300 MHz, DMSO-$d_6$) δ 1.23-1.45 (7H, m), 1.47-1.71 (2H, m), 1.72-1.85 (1H, m), 1.88-1.98 (1H, m), 3.48-3.63 (1H, m), 4.23-4.42 (2H, m), 4.69 (1H, d, J=4.5 Hz), 4.87-5.02 (1H, m), 5.61 (1H, d, J=11.5 Hz), 6.10 (1H, d, J=17.0 Hz), 6.62 (1H, dd, J=17.5, 11.0 Hz), 7.26 (1H, d, J=5.7 Hz), 8.16 (1H, d, J=5.5 Hz).

Reference Example 118

Ethyl 2-fluoro-4-vinylnicotinate

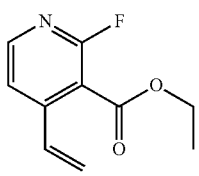

To a solution of ethyl 2-fluoro-4-iodonicotinate (20 g) obtained by a known method (Organic Letters, 7(10), 1943-1946; 2005) in DME (270 mL) were added 4,4,5,5-tetramethyl-2-vinyl-1,3,2-dioxaborolane (11.48 g), [1,1'-bis(diphenylphosphino)ferrocene]dichloropalladium(II) dichloromethane adduct (1.66 g) and 2 mol/L aqueous sodium carbonate solution (68 mL), and the mixture was stirred under an argon atmosphere at 90° C. overnight. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (12.57 g).

$^1$H NMR (300 MHz, DMSO-$d_6$) δ 1.31 (3H, t, J=7.1 Hz), 4.39 (2H, q, J=7.1 Hz), 5.74 (1H, d, J=11.0 Hz), 6.23 (1H, d, J=17.4 Hz), 6.85 (1H, dd, J=17.5, 11.0 Hz), 7.73 (1H, dd, J=5.5, 1.3 Hz), 8.33 (1H, d, J=5.3 Hz).

Reference Example 119

Ethyl 2-(2-chloro-6-fluorophenoxy)-4-vinylnicotinate

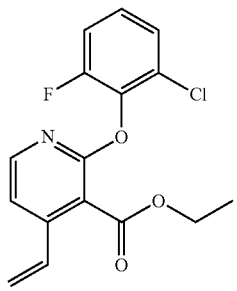 [SMILES: C=Cc1ccnc(Oc2c(F)cccc2Cl)c1C(=O)OCC]

A solution of ethyl 2-fluoro-4-vinylnicotinate (1.0 g) obtained in Reference Example 118, 2-chloro-6-fluorophenol (3.0 g) and potassium carbonate (4.25 g) in DMF (10 mL) was stirred under a nitrogen atmosphere at 100° C. overnight. The reaction solution was diluted with water and ethyl acetate, and the organic layer was separated, washed with saturated brine, dried over anhydrous sodium sulfate, and concentrated. The residue was purified by NH silica gel chromatography (hexane-ethyl acetate) to give the title compound (0.55 g).

$^1$H NMR (300 MHz, DMSO-$d_6$) δ 1.31 (3H, t, J=7.1 Hz), 4.41 (2H, q, J=7.1 Hz), 5.72 (1H, d, J=11.1 Hz), 6.21 (1H, d, J=17.4 Hz), 6.75 (1H, dd, J=17.3, 11.0 Hz), 7.31-7.47 (3H, m), 7.53 (1H, d, J=5.5 Hz), 8.13 (1H, d, J=5.5 Hz).

Reference Example 120

Ethyl 2-(2,6-difluoro-3-methoxyphenoxy)-4-vinylnicotinate

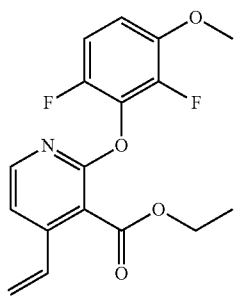 [SMILES: C=Cc1ccnc(Oc2c(F)ccc(OC)c2F)c1C(=O)OCC]

A solution of ethyl 2-fluoro-4-vinylnicotinate (0.45 g) obtained in Reference Example 118, 2,6-difluoro-3-methoxyphenol (1.1 g) and potassium carbonate (1.58 g) in DMF (10 mL) was stirred under an argon atmosphere at 100° C. overnight. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.31 g).

MS: [M+H]$^+$ 336.1

Reference Example 121 isopropyl 2-fluoro-4-iodonicotinate

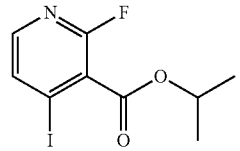

To a solution of 2-fluoro-4-iodopyridine (50.0 g) in THF (150 mL) was added dropwise 2 mol/L lithium diisopropylamide (THF solution) (112 mL) at −78° C., and the mixture was stirred under a nitrogen atmosphere at the same temperature for 3 hr. The reaction solution was added to a solution of isopropyl chlorocarbonate (30.3 g) in THF (50 mL) at −78° C., and the mixture was stirred at the same temperature for 1 hr and at room temperature for 12 hr. To the reaction solution were added saturated aqueous ammonium chloride solution and ethyl acetate. The organic layer was separated, washed with saturated brine, dried over anhydrous sodium sulfate, and concentrated. The residue was purified by silica gel chromatography (petroleum ether-ethyl acetate) to give the title compound (25 g).

$^1$H NMR (400 MHz, CDCl$_3$) δ 1.41 (6H, d, J=6.0 Hz), 5.20-5.40 (1H, m), 7.68 (1H, dd, J=5.2, 0.8 Hz), 7.89 (1H, dd, J=5.2, 0.8 Hz)

Reference Example 122 isopropyl 4-iodo-2-((tetrahydrofuran-2-yl)methoxy)nicotinate

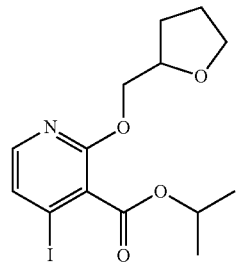 [SMILES: CC(C)OC(=O)c1c(I)ccnc1OCC1CCCO1]

To a suspension of 60% sodium hydride (4.84 g) in THF (100 mL) was added dropwise (tetrahydrofuran-2-yl)methanol (12.3 g) under a nitrogen atmosphere at 0° C., and the mixture was stirred at the same temperature for 30 min. To the reaction solution was added a solution of isopropyl 2-fluoro-4-iodonicotinate (25 g) obtained in Reference Example 121 in THF (50 mL), and the mixture was stirred at 0-5° C. for 2 hr. To the reaction solution were added ice water and ethyl acetate, and the organic layer was separated, washed with saturated brine, dried over anhydrous sodium sulfate, and concentrated. The residue was purified by silica gel chromatography (petroleum ether-ethyl acetate) to give the title compound (21 g).

$^1$H NMR (400 MHz, CDCl$_3$) δ 1.40 (6H, d, J=6.4 Hz), 1.72-2.05 (4H, m), 3.71-3.81 (1H, m), 3.83-3.93 (1H, m), 4.19-4.28 (1H, m), 4.39-4.41 (2H, m), 5.20-5.40 (1H, m), 7.31 (1H, d, J=5.2 Hz), 7.78 (1H, d, J=5.2 Hz).

Reference Example 123 isopropyl 4-formyl-2-((tetrahydrofuran-2-yl)methoxy)nicotinate

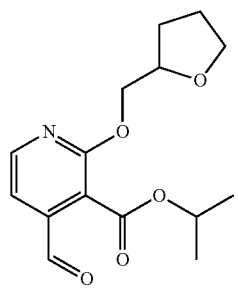 [SMILES: CC(C)OC(=O)c1c(C=O)ccnc1OCC1CCCO1]

To a solution of isopropyl 4-iodo-2-((tetrahydrofuran-2-yl)methoxy)nicotinate (5 g) obtained in Reference Example 122 in THF (50 mL) was added dropwise 2 mol/L isopropylmagnesium chloride (THF solution) (7.5 mL) under a nitrogen atmosphere at −40° C., and the mixture was stirred at the same temperature for 1 hr. To the reaction solution was added ethyl formate (4.74 g), and the mixture was stirred at −40° C. for 1 hr and at room temperature for 3 hr. To the reaction solution were added saturated aqueous ammonium chloride solution and ethyl acetate.

The organic layer was separated, washed with saturated brine, dried over anhydrous sodium sulfate, and concentrated. The residue was purified by silica gel chromatography (petroleum ether-ethyl acetate) to give the title compound (1.7 g).

$^1$H NMR (400 MHz, CDCl$_3$) δ 1.40 (6H, d, J=6.4 Hz), 1.75-2.05 (4H, m), 3.71-3.82 (1H, m), 3.85-3.95 (1H, m), 4.21-4.32 (1H, m), 4.35-4.50 (2H, m), 5.30-5.42 (1H, m), 7.29 (1H, d, J=4.8 Hz), 8.38 (1H, d, J=4.4 Hz), 10.09 (1H, s)

Reference Example 124

Ethyl 2-(2-fluoro-5-(methoxymethyl)phenoxy)-4-vinylnicotinate

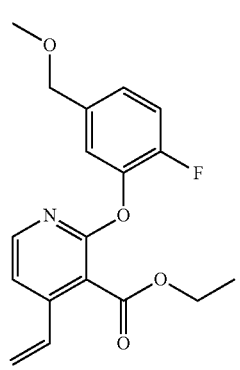 [SMILES: C=Cc1ccnc(Oc2cc(COC)ccc2F)c1C(=O)OCC]

To a solution of ethyl 2-(2-fluoro-5-(hydroxymethyl)phenoxy)-4-vinylnicotinate (0.43 g) obtained in Reference Example 261 and methyl iodide (0.23 g) in THF (5 mL) was added potassium tert-butoxide (0.18 g) at 0° C., and the mixture was stirred under an argon atmosphere at the same temperature for 30 min. The reaction mixture was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.28 g).

$^1$H NMR (300 MHz, DMSO-d$_6$) δ 1.30 (3H, t, J=7.1 Hz), 3.29 (3H, s), 4.33-4.46 (4H, m), 5.71 (1H, d, J=11.3 Hz), 6.20 (1H, d, J=17.4 Hz), 6.73 (1H, dd, J=17.4, 11.1 Hz), 7.19-7.27 (2H, m), 7.29-7.38 (1H, m), 7.50 (1H, d, J=5.5 Hz), 8.14 (1H, d, J=5.3 Hz).

Reference Example 125

2-(4-chlorobenzyl)-7-methoxyisoindolin-1-one

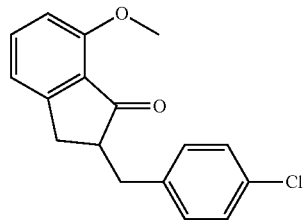 [SMILES: COc1cccc2c1C(=O)C(Cc1ccc(Cl)cc1)C2]

A solution of ethyl 2-(bromomethyl)-6-methoxybenzoate (0.90 g), (4-chlorophenyl)methanamine (0.47 g) and potassium carbonate (0.91 g) in ethanol (20 mL) was stirred at room temperature overnight. The reaction mixture was diluted with water and ethyl acetate, and the organic layer was separated, washed with saturated brine, dried over anhydrous sodium sulfate, and concentrated. The residue was purified by NH silica gel chromatography (hexane-ethyl acetate) to give the title compound (0.56 g).

$^1$H NMR (300 MHz, DMSO-d$_6$) δ 3.86 (3H, s), 4.28 (2H, s), 4.64 (2H, s), 7.05 (2H, dd, J=11.8, 7.8 Hz), 7.24-7.31 (2H, m), 7.36-7.44 (2H, m), 7.47-7.56 (1H, m).

Reference Example 126

2-(4-chlorobenzyl)-7-hydroxyisoindolin-1-one

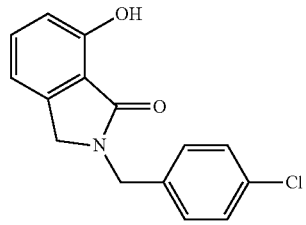 [SMILES: O=C1c2c(O)cccc2CN1Cc1ccc(Cl)cc1]

To 2-(4-chlorobenzyl)-7-methoxyisoindolin-1-one (0.56 g) obtained in Reference Example 125 was added 25% hydrobromic acid (acetic acid solution) (20 mL), and the mixture was stirred under a nitrogen atmosphere at 120° C. overnight. The reaction solution was neutralized with saturated aqueous sodium hydrogen carbonate solution, and ethyl acetate was added. The organic layer was separated, washed with saturated brine, dried over anhydrous sodium sulfate, and concentrated. The residue was purified by NH silica gel chromatography (hexane-ethyl acetate) to give the title compound (0.47 g).

$^1$H NMR (300 MHz, DMSO-d$_6$) δ 4.29 (2H, s), 4.65 (2H, s), 6.82 (1H, d, J=8.1 Hz), 6.94 (1H, d, J=7.4 Hz), 7.24-7.45 (5H, m), 9.62 (1H, brs), Reference Example 127

Ethyl 2-(5-cyano-2-fluorophenoxy)-4-vinylnicotinate

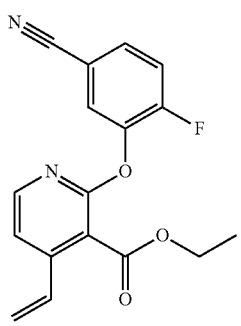 [SMILES: C=Cc1ccnc(Oc2cc(C#N)ccc2F)c1C(=O)OCC]

A solution of ethyl 2-fluoro-4-vinylnicotinate (0.95 g) obtained in Reference Example 118, 4-fluoro-3-hydroxybenzonitrile (1.0 g) and potassium carbonate (2.02 g) in DMF (10 mL) was stirred under an argon atmosphere at 100° C. overnight. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.90 g).
MS: [M+H]$^+$ 313.1

Reference Example 128

3-((2-(4-bromobenzyl)-3-oxo-2,3-dihydro-1H-pyrrolo[3,4-c]pyridin-4-yl)oxy)-4-fluorobenzonitrile

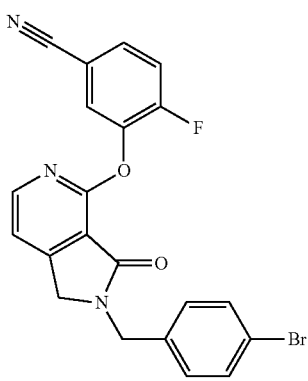 [SMILES: N#Cc1ccc(F)c(Oc2nccc3c2C(=O)N(Cc2ccc(Br)cc2)C3)c1]

A mixed solution of ethyl 2-(5-cyano-2-fluorophenoxy)-4-vinylnicotinate (0.90 g) obtained in Reference Example 127, sodium periodate (3.1 g) and osmium oxide (immobilized catalyst I) (0.37 g) in acetonitrile (12 mL)-acetone (12 mL)-water (12 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.50 g) was dissolved in THF (5 mL), (4-bromophenyl)methanamine (0.30 g) and anhydrous magnesium sulfate (0.38 g) were added, and the mixture was stirred under an argon atmosphere at room temperature for 20 min. The insoluble material was filtered off, and the filtrate was concentrated. To a solution of the residue in acetic acid (5 mL) was added sodium triacetoxyhydroborate (0.51 g), and the mixture was stirred under an argon atmosphere at room temperature overnight. To the reaction solution was added water, the resulting precipitate was collected by filtration, and dried to give the title compound (0.57 g).
MS: [M+H]$^+$ 438.0

Reference Example 129

2-(2,4-difluorobenzyl)-7-methoxyisoindolin-1-one

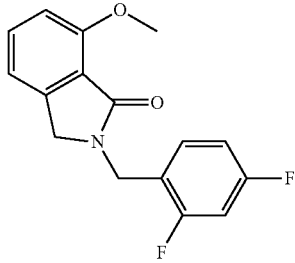 [SMILES: COc1cccc2c1C(=O)N(Cc1ccc(F)cc1F)C2]

A solution of ethyl 2-(bromomethyl)-6-methoxybenzoate (0.90 g), (2,4-difluorophenyl)methanamine (0.47 g) and potassium carbonate (0.91 g) in ethanol (20 mL) was stirred at room temperature overnight. The reaction mixture was diluted with water and ethyl acetate, and the organic layer was separated, washed with saturated brine, dried over anhydrous sodium sulfate, and concentrated. The residue was purified by NH silica gel chromatography (hexane-ethyl acetate) to give the title compound (0.54 g).
$^1$H NMR (300 MHz, DMSO-d$_6$) δ 3.85 (3H, s), 4.31 (2H, s), 4.67 (2H, s), 6.98-7.12 (3H, m), 7.19-7.40 (2H, m), 7.52 (1H, t, J=7.8 Hz).

Reference Example 130

2-(2,4-difluorobenzyl)-7-hydroxyisoindolin-1-one

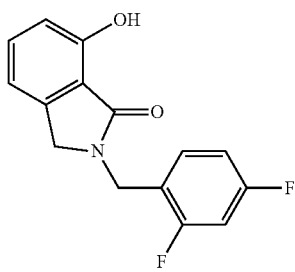 [SMILES: O=C1c2c(O)cccc2CN1Cc1ccc(F)cc1F]

To 2-(2,4-difluorobenzyl)-7-methoxyisoindolin-1-one (0.54 g) obtained in Reference Example 129 was added 25% hydrobromic acid (acetic acid solution) (20 mL), and the mixture was stirred under a nitrogen atmosphere at 120° C. overnight. The reaction solution was neutralized with saturated aqueous sodium hydrogen carbonate solution, and ethyl acetate was added. The organic layer was separated, washed with saturated brine, dried over anhydrous sodium sulfate, and concentrated. The residue was purified by NH silica gel chromatography (hexane-ethyl acetate) to give the title compound (0.41 g).

$^1$H NMR (300 MHz, DMSO-d$_6$) δ 4.31 (2H, s), 4.68 (2H, s), 6.81 (1H, d, J=8.3 Hz), 6.94 (1H, d, J=7.2 Hz), 7.08 (1H, td, J=8.6, 2.4 Hz), 7.21-7.45 (3H, m), 9.65 (1H, s).

Reference Example 131

2-(4-bromobenzyl)-4-(2-fluoro-5-(methoxymethyl) phenoxy)-1H-pyrrolo[3,4-c]pyridin-3(2H)-one

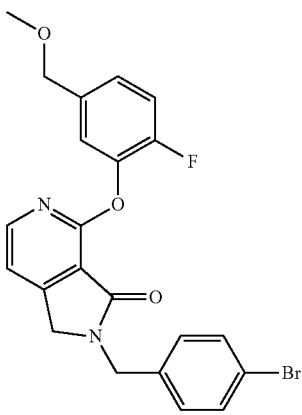 [SMILES: COCc1ccc(F)c(Oc2nccc3c2C(=O)N(Cc2ccc(Br)cc2)C3)c1]

A mixed solution of ethyl 2-(2-fluoro-5-(methoxymethyl) phenoxy)-4-vinylnicotinate (0.28 g) obtained in Reference Example 124, sodium periodate (0.90 g) and osmium oxide (immobilized catalyst I) (0.11 g) in acetonitrile (4 mL)-acetone (4 mL)-water (4 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.19 g) was dissolved in THF (3 mL), (4-bromophenyl) methanamine (0.10 g) and anhydrous magnesium sulfate (0.13 g) were added, and the mixture was stirred under an argon atmosphere at room temperature 20 min. The insoluble material was filtered off, and the filtrate was concentrated. To a solution of the residue in acetic acid (3 mL) was added sodium triacetoxyhydroborate (0.18 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.20 g).

MS: [M+H]$^+$ 457.1

Reference Example 132

2-(4-bromobenzyl)-4-(2-fluoro-4-(trifluoromethyl) phenoxy)-1H-pyrrolo[3,4-c]pyridin-3 (2H)-one

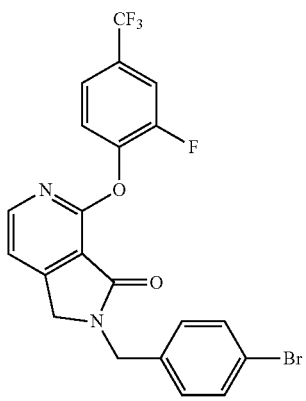 [SMILES: O=C1c2c(ccnc2Oc2ccc(C(F)(F)F)cc2F)CN1Cc1ccc(Br)cc1]

Ethyl 2-(2-fluoro-4-(trifluoromethyl)phenoxy)-4-formyl-nicotinate (0.34 g) obtained in Reference Example 282 was dissolved in THF (3 mL), (4-bromophenyl)methanamine (0.18 g) and anhydrous magnesium sulfate (0.23 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.30 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) and solidified with ethyl acetate-hexane to give the title compound (0.37 g).

$^1$H NMR (300 MHz, DMSO-d$_6$) δ 4.51 (2H, s), 4.70 (2H, s), 7.29 (2H, d, J=8.3 Hz), 7.42 (1H, d, J=5.3 Hz), 7.53-7.74 (4H, m), 7.88-7.99 (1H, m), 8.23 (1H, d, J=5.1 Hz).

Reference Example 133

Methyl 4-chloro-6-(2-fluoro-4-(trifluoromethyl)phenoxy)pyrimidine-5-carboxylate

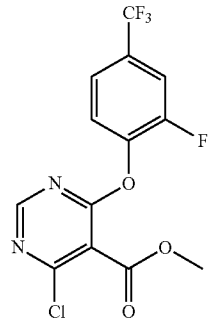 [SMILES: COC(=O)c1c(Cl)ncnc1Oc1ccc(C(F)(F)F)cc1F]

A solution of methyl 4,6-dichloropyrimidine-5-carboxylate (0.53 g), 2-fluoro-4-(trifluoromethyl)phenol (0.46 g) and potassium carbonate (1.1 g) in DMF (5 mL) was stirred under an argon atmosphere at 0° C. for 1 hr. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.63 g).

¹H NMR (300 MHz, DMSO-d₆) δ 3.99 (3H, s), 7.66-7.81 (2H, m), 8.00 (1H, d, J=11.1 Hz), 8.79 (1H, s).

Reference Example 134

Methyl 4-(2-fluoro-4-(trifluoromethyl)phenoxy)-6-vinylpyrimidine-5-carboxylate

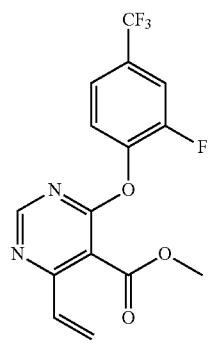 [SMILES: C=Cc1ncnc(Oc2ccc(C(F)(F)F)cc2F)c1C(=O)OC]

To a solution of methyl 4-chloro-6-(2-fluoro-4-(trifluoromethyl)phenoxy)pyrimidine-5-carboxylate (0.63 g) obtained in Reference Example 133 in DME (5 mL)-water (1.7 mL) were added 4,4,5,5-tetramethyl-2-vinyl-1,3,2-dioxaborolane (0.36 g), [1,1'-bis(diphenylphosphino)ferrocene]dichloropalladium(II) dichloromethane adduct (0.15 g) and sodium carbonate (0.57 g), and the mixture was stirred under an argon atmosphere at 90° C. for 4 hr. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.22 g).

¹H NMR (300 MHz, DMSO-d₆) δ 3.97 (3H, s), 5.82-5.96 (1H, m), 6.60-6.76 (1H, m), 6.84-6.99 (1H, m), 7.63-7.77 (2H, m), 7.97 (1H, d, J=11.3 Hz), 8.81 (1H, s).

Reference Example 135

Methyl 4-chloro-6-(4-(difluoromethyl)-2-fluorophenoxy) pyrimidine-5-carboxylate

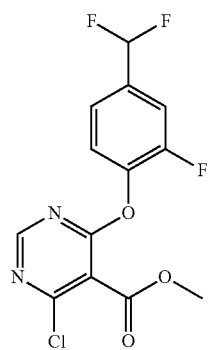 [SMILES: COC(=O)c1c(Cl)ncnc1Oc1ccc(C(F)F)cc1F]

A solution of methyl 4,6-dichloropyrimidine-5-carboxylate (0.79 g), 4-(difluoromethyl)-2-fluorophenol (0.62 g) and potassium carbonate (1.6 g) in DMF (10 mL) was stirred under an argon atmosphere at 0° C. for 1 hr. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (1.23 g).

¹H NMR (300 MHz, DMSO-d₆) δ 3.99 (3H, s), 6.89-7.29 (1H, m), 7.49-7.76 (3H, m), 8.78 (1H, s).

Reference Example 136

Methyl 4-(4-(difluoromethyl)-2-fluorophenoxy)-6-vinylpyrimidine-5-carboxylate

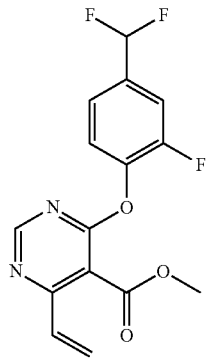 [SMILES: C=Cc1ncnc(Oc2ccc(C(F)F)cc2F)c1C(=O)OC]

To a solution of methyl 4-chloro-6-(4-(difluoromethyl)-2-fluorophenoxy)pyrimidine-5-carboxylate (1.23 g) obtained in Reference Example 135 in DME (12 mL)-water (4 mL) were added 4,4,5,5-tetramethyl-2-vinyl-1,3,2-dioxaborolane (0.74 g), [1,1'-bis(diphenylphosphino)ferrocene] dichloropalladium(II) dichloromethane adduct (0.30 g) and sodium carbonate (1.18 g), and the mixture was stirred under an argon atmosphere at 90° C. overnight. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.29 g).

¹H NMR (300 MHz, DMSO-d₆) δ 3.97 (3H, s), 5.80-5.99 (1H, m), 6.57-6.78 (1H, m), 6.82-7.31 (2H, m), 7.42-7.77 (3H, m), 8.79 (1H, s).

Reference Example 137

2-fluoro-5-(2-hydroxypropan-2-yl)phenol

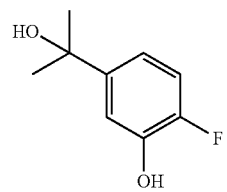

To a solution of 1-(4-fluoro-3-hydroxyphenyl)ethanone (0.92 g) in THF (10 mL) was added 1 mol/L methylmagnesium bromide (THF solution) (18 mL) at 0° C., and the mixture was stirred under a nitrogen atmosphere at room temperature for 1 hr. The reaction solution was neutralized with 1N hydrochloric acid, and ethyl acetate was added. The organic layer was separated, washed with saturated brine, dried over anhydrous sodium sulfate, and concentrated. The residue was purified by silica gel chromatography (hexane-ethyl acetate) to give the title compound (0.88 g).

$^1$H NMR (300 MHz, DMSO-d$_6$) δ 1.37 (6H, s), 4.93 (1H, s), 6.73-6.88 (1H, m), 6.94-7.17 (2H, m), 9.59 (1H, s).

Reference Example 138

Ethyl 2-(2-fluoro-5-(2-hydroxypropan-2-yl)phenoxy)-4-vinylnicotinate

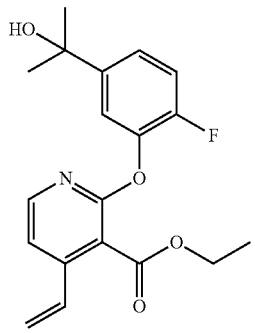 [SMILES: C=Cc1ccnc(Oc2cc(C(C)(C)O)ccc2F)c1C(=O)OCC]

A solution of ethyl 2-fluoro-4-vinylnicotinate (0.67 g) obtained in Reference Example 118, 2-fluoro-5-(2-hydroxypropan-2-yl)phenol (0.88 g) obtained in Reference Example 137 and potassium carbonate (1.43 g) in DMF (10 mL) was stirred under an argon atmosphere at 100° C. overnight. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (1.19 g).

$^1$H NMR (300 MHz, DMSO-d$_6$) δ 1.31 (3H, t, J=7.2 Hz), 1.42 (6H, s), 4.39 (2H, q, J=7.2 Hz), 5.12 (1H, s), 5.70 (1H, d, J=11.3 Hz), 6.20 (1H, d, J=17.4 Hz), 6.66-6.79 (1H, m), 7.17-7.39 (3H, m), 7.48 (1H, d, J=5.5 Hz), 8.14 (1H, d, J=5.5 Hz).

Reference Example 139

7-hydroxy-2-(2,4,6-trifluorobenzyl)isoindolin-1-one

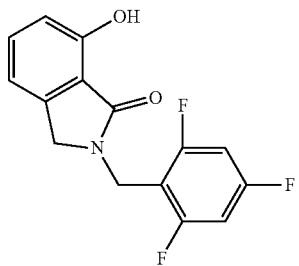 [SMILES: O=C1c2c(O)cccc2CN1Cc1c(F)cc(F)cc1F]

A solution of ethyl 2-(bromomethyl)-6-methoxybenzoate (2.0 g), (2,4,6-trifluorophenyl)methanamine (1.2 g) and potassium carbonate (2.0 g) in ethanol (20 mL) was stirred at room temperature overnight. The reaction mixture was diluted with water and ethyl acetate, and the organic layer was separated, washed with saturated brine, dried over anhydrous sodium sulfate, and concentrated. The residue was crudely purified by NH silica gel chromatography (hexane-ethyl acetate). To the crudely purified product was added 25% hydrobromic acid (acetic acid solution) (44 mL), and the mixture was stirred under a nitrogen atmosphere at 120° C. overnight. The reaction solution was neutralized with saturated aqueous sodium hydrogen carbonate solution, and ethyl acetate was added. The organic layer was separated, washed with saturated brine, dried over anhydrous sodium sulfate, and concentrated. The residue was purified by NH silica gel chromatography (hexane-ethyl acetate) to give the title compound (0.51 g).

$^1$H NMR (300 MHz, DMSO-d$_6$) δ 4.28 (2H, s), 4.70 (2H, s), 6.79 (1H, d, J=8.1 Hz), 6.93 (1H, d, J=7.4 Hz), 7.13-7.28 (2H, m), 7.32-7.43 (1H, m), 9.34 (1H, brs).

Reference Example 140

Methyl 4-chloro-6-cyclobutoxypyrimidine-5-carboxylate

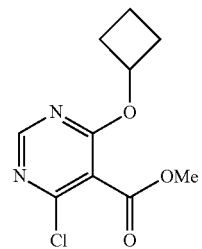 [SMILES: COC(=O)c1c(Cl)ncnc1OC1CCC1]

To a solution of cyclobutanol (1.0 g) in THF (25 mL) was added 60% sodium hydride (0.68 g) at 0° C., and the mixture was stirred at the same temperature for 20 min. To the reaction solution was added methyl 4,6-dichloropyrimidine-5-carboxylate (2.69 g), and the mixture was stirred under an argon atmosphere at room temperature for 1 hr. To the reaction solution were added water and ethyl acetate, and the organic layer was separated, washed with saturated brine, dried over anhydrous sodium sulfate, and concentrated. The residue was purified by silica gel chromatography (hexane-ethyl acetate) to give the title compound (2.94 g).

MS: [M+H]$^+$ 243.1

Reference Example 141

Methyl 4-cyclobutoxy-6-vinylpyrimidine-5-carboxylate

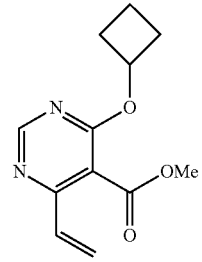 [SMILES: C=Cc1ncnc(OC2CCC2)c1C(=O)OC]

To a solution of methyl 4-chloro-6-cyclobutoxypyrimidine-5-carboxylate (2.94 g) obtained in Reference Example 140 in DME (30 mL) were added 4,4,5,5-tetramethyl-2-vinyl-1,3,2-dioxaborolane (3.73 g), [1,1'-bis(diphenylphosphino)ferrocene]dichloropalladium(II) dichloromethane adduct (0.50 g) and 2 mol/L aqueous sodium carbonate solution (12 mL), and the mixture was stirred under an argon atmosphere at 90° C. for 2 hr. The reaction solution was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (1.69 g).

MS: [M+H]+ 235.1

Reference Example 142

Methyl 4-formyl-2-((tetrahydrofuran-2-yl)methoxy)nicotinate

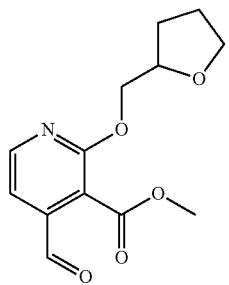 [SMILES: COC(=O)c1c(C=O)ccnc1OCC1CCCO1]

A mixed solution of methyl 2-((tetrahydrofuran-2-yl)methoxy)-4-vinylnicotinate (3.20 g) obtained in Reference Example 42, sodium periodate (13.0 g) and osmium oxide (immobilized catalyst I) (1.55 g) in acetonitrile (20 mL)-acetone (20 mL)-water (20 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (2.71 g).

MS: [M+H]+ 266.1
1H NMR (300 MHz, CDCl3) δ 1.94 (4H, d, J=7.0 Hz), 3.77-3.93 (2H, m), 3.97 (3H, s), 4.22-4.39 (1H, m), 4.43 (2H, d, J=4.7 Hz), 7.29 (1H, d, J=5.1 Hz), 8.40 (1H, d, J=5.1 Hz), 10.07 (1H, s).

Reference Example 143

(4-(2-(trifluoromethyl)pyridin-4-yl)phenyl)methanamine

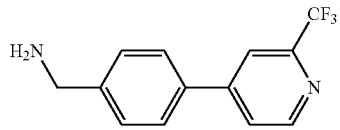 [SMILES: NCc1ccc(-c2ccnc(C(F)(F)F)c2)cc1]

To a solution of (4-(aminomethyl)phenyl)boronic acid hydrochloride (2.40 g) in DME (20 mL)-water (20 mL) were added 4-iodo-2-trifluoromethylpyridine (4.20 g), sodium carbonate (6.79 g), (1,1-bis(diphenylphosphino)ferrocene)dichloropalladium(II) methylene chloride adduct (1.05 g), and the mixture was stirred under a nitrogen atmosphere at 80° C. overnight. The reaction mixture was diluted with water and ethyl acetate, and the organic layer was separated, washed with saturated brine, dried over anhydrous sodium sulfate, and concentrated. The residue was purified by NH silica gel chromatography (hexane-ethyl acetate) to give the title compound (2.06 g).

MS: [M+H]+ 253.1
1H NMR (300 MHz, CDCl3) δ 1.52 (2H, brs), 3.97 (2H, s), 7.49 (2H, d, J=8.3 Hz), 7.59-7.74 (3H, m), 7.89 (1H, d, J=1.1 Hz), 8.76 (1H, d, J=5.1 Hz).

Reference Example 144

5-(4-bromophenyl)pyridazin-3-ol

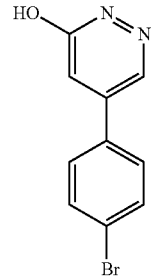

To a solution of 2-(4-bromophenyl)acetaldehyde (11.8 g) in THF (100 mL) was added dropwise 6N hydrochloric acid (14.1 mL) at room temperature. Thereafter, to the reaction mixture were added morpholine (5.41 g) and 2-oxoacetic acid (50% aqueous solution, 6.27 mL) at room temperature, and the mixture was stirred at 90° C. for 26 hr. The reaction mixture was concentrated, and diluted with water and ethyl acetate, and the organic layer was separated, washed with saturated brine, dried over anhydrous sodium sulfate, and concentrated. To a solution of the residue in ethanol (100 mL) was added hydrazine monohydrate (2.71 mL), and the mixture was stirred at 80° C. overnight. The reaction mixture was concentrated, and the residue was washed with ethanol to give the title compound (3.78 g).
1H NMR (300 MHz, DMSO-d6) δ 7.17 (1H, d, J=2.3 Hz), 7.61-7.87 (4H, m), 8.29 (1H, d, J=2.1 Hz), 11.39 (1H, brs).

Reference Example 145

5-(4-bromophenyl)pyridazin-3-yl trifluoromethanesulfonate

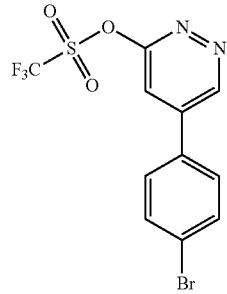 [SMILES: O=S(=O)(Oc1cc(-c2ccc(Br)cc2)cnn1)C(F)(F)F]

To a solution of 5-(4-bromophenyl)pyridazin-3-ol (3.70 g) obtained in Reference Example 144 in pyridine (50 mL) was added trifluoromethanesulfonic anhydride (2.99 mL) under ice-cooling, and the mixture was stirred at room temperature for 1 hr. The reaction mixture was diluted with saturated aqueous sodium hydrogen carbonate solution and ethyl acetate, and the organic layer was separated, washed with saturated brine, dried over anhydrous sodium sulfate, and concentrated. The residue was purified by silica gel chromatography (hexane-ethyl acetate) to give the title compound (5.17 g).

MS: [M+H]$^+$ 382.9

$^1$H NMR (300 MHz, CDCl$_3$) δ 7.51-7.61 (3H, m), 7.70-7.78 (2H, m), 9.49 (1H, d, J=1.9 Hz).

Reference Example 146

4-(6-methylpyridazin-4-yl)benzonitrile

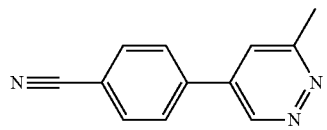

To a solution of 5-(4-bromophenyl)pyridazin-3-yl trifluoromethanesulfonate (4.70 g) obtained in Reference Example 145 and (1,1-bis(diphenylphosphino)ferrocene)dichloronickel(II) (3.32 g) in THF (80 mL) was added methylmagnesium bromide (1M THF solution, 24.5 mL) under ice-cooling, and the mixture was stirred under a nitrogen atmosphere at room temperature for 5 hr. The reaction mixture was diluted with saturated aqueous ammonium chloride solution and ethyl acetate, and the organic layer was separated, washed with saturated brine, dried over anhydrous sodium sulfate, and concentrated. The residue was crudely purified by silica gel chromatography (hexane-ethyl acetate). A mixture of the obtained crudely purified product (0.18 g), zinc cyanide (0.27 g) and (1,1-bis(diphenylphosphino)ferrocene)dichloropalladium(II) methylene chloride adduct (0.31 g) in DMA (4 mL) was stirred under microwave irradiation at 150° C. for 20 min. The reaction mixture was diluted with saturated aqueous sodium hydrogen carbonate solution and ethyl acetate, and the organic layer was separated, washed with saturated brine, dried over anhydrous sodium sulfate, and concentrated. The residue was purified by NH silica gel chromatography (hexane-ethyl acetate) to give the title compound (0.19 g).

MS: [M+H]$^+$ 196.1

Reference Example 147

(4-(6-methylpyridazin-4-yl)phenyl)methanamine

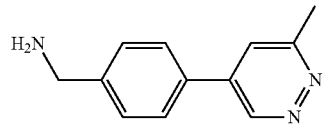

A mixture of 4-(6-methylpyridazin-4-yl)benzonitrile (0.18 g) obtained in Reference Example 146, ammonia (8M methanol solution 2.3 mL) and Raney-nickel (3 mL volume) in ethanol (10 mL) was stirred under a hydrogen atmosphere at room temperature overnight. The insoluble material was filtered off, and the filtrate was concentrated to give the title compound (2.7 g).

MS: [M+H]$^+$ 200.1

Reference Example 148

Methyl 2-((2-fluorobenzyl)oxy)-4-iodonicotinate

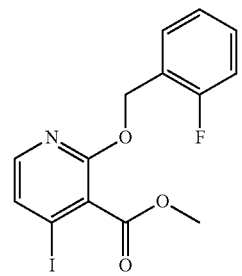 [SMILES: COC(=O)c1c(I)ccnc1OCc1ccccc1F]

To a solution of methyl 2-fluoro-4-iodonicotinate (0.70 g) obtained in Reference Example 40 and (2-fluorophenyl)methanol (0.63 g) in THF (7 mL) was added 60% sodium hydride (0.20 g) at 0° C., and the mixture was stirred at the same temperature for 1 hr. To the reaction solution was added water at 0° C., and the mixture was diluted with ethyl acetate. The organic layer was separated, washed with saturated brine, dried over anhydrous sodium sulfate, and concentrated. The residue was purified by silica gel chromatography (hexane-ethyl acetate) to give the title compound (0.88 g).

MS: [M+H]$^+$ 388.0

Reference Example 149

Methyl 2-((2-fluorobenzyl)oxy)-4-vinylnicotinate

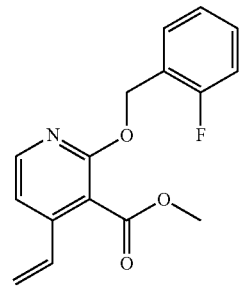 [SMILES: C=Cc1ccnc(OCc2ccccc2F)c1C(=O)OC]

To a solution of methyl 2-((2-fluorobenzyl)oxy)-4-iodonicotinate (0.88 g) obtained in Reference Example 148 in DMF (10 mL) were added tributyl(vinyl)tin (0.94 g), (1,1-bis(diphenylphosphino)ferrocene)dichloropalladium(II) methylene chloride adduct (0.19 g) and lithium chloride (0.72 g), and the mixture was stirred under a nitrogen atmosphere at 90° C. for 3 hr. To the reaction solution was added saturated aqueous potassium fluoride solution, and the mixture was diluted with ethyl acetate. The organic layer was separated, washed with saturated brine, dried over anhydrous sodium sulfate, and concentrated. The residue was purified by silica gel chromatography (hexane-ethyl acetate) to give the title compound (0.50 g).

MS: [M+H]+ 288.1

1H NMR (300 MHz, CDCl3) δ 3.91 (3H, s), 5.36-5.59 (4H, m), 5.82-5.99 (1H, m), 6.73 (1H, dd, J=17.4, 11.0 Hz), 7.04-7.16 (3H, m), 7.40 (1H, s), 8.00-8.21 (1H, m).

Reference Example 150

Methyl 2-((2-fluorobenzyl)oxy)-4-formylnicotinate

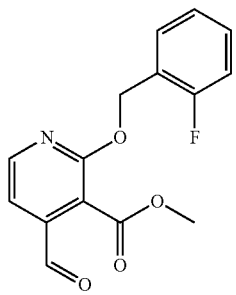 [SMILES: COC(=O)c1c(C=O)ccnc1OCc1ccccc1F]

A mixed solution of methyl 2-((2-fluorobenzyl)oxy)-4-vinylnicotinate (0.49 g) obtained in Reference Example 149, sodium periodate (1.8 g) and osmium oxide (immobilized catalyst I) (0.22 g) in acetonitrile (3 mL)-acetone (3 mL)-water (3 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous sodium sulfate, and concentrated to give the title compound (0.43 g).

1H NMR (300 MHz, CDCl3) δ 3.97 (3H, s), 5.57 (2H, s), 6.99-7.19 (3H, m), 7.30-7.35 (2H, m), 8.35-8.49 (1H, m), 10.01-10.13 (1H, m).

Reference Example 151

Tert-butyl 2-fluoro-4-((trimethylsilyl)ethynyl)benzylcarbamate

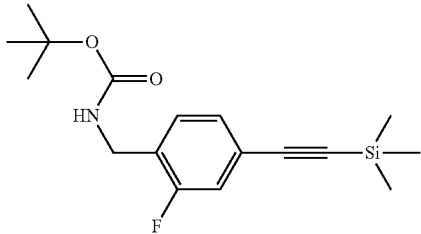 [SMILES: CC(C)(C)OC(=O)NCc1ccc(C#C[Si](C)(C)C)cc1F]

To a solution of tert-butyl 4-bromo-2-fluorobenzylcarbamate (10.0 g) in acetonitrile (100 mL) were added ethynyltrimethylsilane (4.8 g), copper iodide (0.31 g), and (1,1-bis(diphenylphosphino)ferrocene)dichloropalladium(II) methylene chloride adduct (1.34 g) at room temperature, and the mixture was stirred under a nitrogen atmosphere at 70° C. for 3 hr. The reaction mixture was concentrated, the residue was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (10.3 g).

1H NMR (300 MHz, CDCl3) δ 0.24 (9H, s), 1.44 (9H, s), 4.34 (2H, d, J=5.9 Hz), 4.87 (1H, brs), 7.13 (1H, d, J=10.8 Hz), 7.18-7.30 (2H, m).

Reference Example 152

Tert-butyl 4-ethynyl-2-fluorobenzylcarbamate

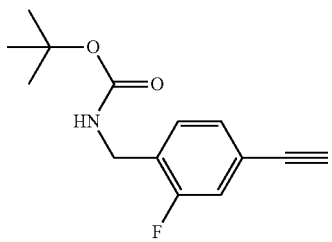 [SMILES: C#Cc1ccc(CNC(=O)OC(C)(C)C)c(F)c1]

To a solution of tert-butyl 2-fluoro-4-((trimethylsilyl)ethynyl)benzylcarbamate (10.3 g) obtained in Reference Example 151 in methanol (200 mL) was added potassium carbonate (4.87 g) at room temperature, and the mixture was stirred at room temperature for 2 hr. The insoluble material was filtered off, and the filtrate was concentrated. The residue was diluted with water and ethyl acetate, and the organic layer was separated, washed with saturated brine, dried over anhydrous sodium sulfate, and concentrated to give the title compound (7.88 g).

1H NMR (300 MHz, CDCl3) δ 1.44 (9H, s), 3.09 (1H, s), 4.35 (2H, d, J=6.0 Hz), 4.89 (1H, brs), 7.12-7.19 (1H, m), 7.21-7.34 (2H, m).

Reference Example 153

Tert-butyl 2-fluoro-4-(1-methyl-1H-1,2,3-triazol-4-yl)benzylcarbamate

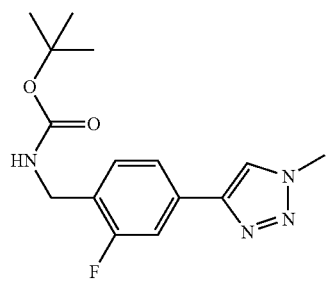 [SMILES: Cn1cc(-c2ccc(CNC(=O)OC(C)(C)C)c(F)c2)nn1]

To a solution of tert-butyl 4-ethynyl-2-fluorobenzylcarbamate (7.80 g) obtained in Reference Example 152, iodomethane (2.14 mL), and tris(triphenylphosphine)copper bromide (2.91 g) in DMSO (80 mL) was added aqueous solution (20 mL) of sodium azide (3.05 g) at room temperature, and the mixture was stirred under a nitrogen atmosphere at room temperature overnight. The reaction mixture was diluted with water and ethyl acetate, and the organic layer was separated, washed with saturated brine, dried over anhydrous sodium sulfate, and concentrated. The residue was washed with ethyl acetate to give the title compound (2.55 g).

MS: [M+H]+ 307.1

$^1$H NMR (300 MHz, CDCl$_3$) δ 1.45 (9H, s), 4.15 (3H, s), 4.38 (2H, d, J=6.0 Hz), 4.92 (1H, brs), 7.33-7.44 (1H, m), 7.49-7.61 (2H, m), 7.74 (1H, s).

Reference Example 154

(2-fluoro-4-(1-methyl-1H-1,2,3-triazol-4-yl)phenyl)methanamine

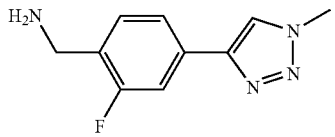

To a solution of tert-butyl 2-fluoro-4-(1-methyl-1H-1,2,3-triazol-4-yl)benzylcarbamate (2.55 g) obtained in Reference Example 153 in ethanol (50 mL)-THF (25 mL) was added 4N hydrochloric acid (ethyl acetate solution, 10.4 mL) at room temperature, and the mixture was stirred at room temperature overnight. The reaction mixture was concentrated, and a solution of the residue in methanol was neutralized with triethylamine, and concentrated. The residue was purified by NH silica gel chromatography (hexane-ethyl acetate), and the obtained solid was washed with diisopropyl ether to give the title compound (1.70 g).

MS: [M+H]$^+$ 207.1

Reference Example 155

2,6-difluoro-4-(1-methyl-1H-pyrazol-3-yl)benzonitrile

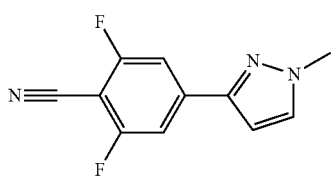 [SMILES: Cn1ccc(-c2cc(F)c(C#N)c(F)c2)n1]

To a solution of 4-bromo-2,6-difluorobenzonitrile (0.50 g) in DME (3 mL)-water (3 mL) were added 1-methyl-3-(4,4,5,5-tetramethyl-1,3,2-dioxaborolan-2-yl)-1H-pyrazole (0.62 g), sodium carbonate (0.73 g), and (1,1-bis(diphenylphosphino)ferrocene)dichloropalladium(II) methylene chloride adduct (0.19 g), and the mixture was stirred under a nitrogen atmosphere at 90° C. overnight. The reaction mixture was diluted with water and ethyl acetate, and the organic layer was separated, washed with saturated brine, dried over anhydrous sodium sulfate, and concentrated. The residue was purified by NH silica gel chromatography (hexane-ethyl acetate) to give the title compound (0.14 g).

MS: [M+H]$^+$ 220.1

$^1$H NMR (300 MHz, CDCl$_3$) δ 3.97 (3H, s), 6.58 (1H, d, J=2.6 Hz), 7.41-7.50 (3H, m).

Reference Example 156

(2,6-difluoro-4-(1-methyl-1H-pyrazol-3-yl)phenyl)methanamine

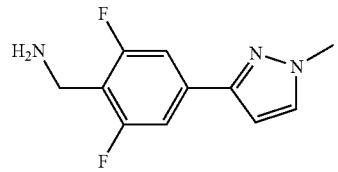 [SMILES: Cn1ccc(-c2cc(F)c(CN)c(F)c2)n1]

A mixture of 2,6-difluoro-4-(1-methyl-1H-pyrazol-3-yl)benzonitrile (0.14 g) obtained in Reference Example 155, ammonia (8 M methanol solution 0.77 mL) and Raney-nickel (3 mL volume) in ethanol (4 mL) was stirred under a hydrogen atmosphere at room temperature overnight. The insoluble material was filtered off, and the filtrate was concentrated to give the title compound (0.12 g).

$^1$H NMR (300 MHz, CDCl$_3$) δ 1.43 (2H, s), 3.92 (2H, s), 3.95 (3H, s), 6.49 (1H, d, J=2.3 Hz), 7.31 (2H, d, J=8.9 Hz), 7.38 (1H, d, J=2.3 Hz).

Reference Example 157

Methyl 2-((3-fluoropyridin-2-yl)methoxy)-4-iodonicotinate

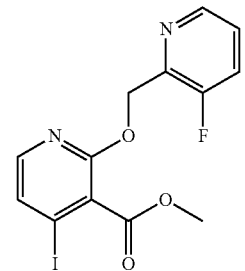 [SMILES: COC(=O)c1c(I)ccnc1OCc1ncccc1F]

To a solution of methyl 2-fluoro-4-iodonicotinate (0.70 g) obtained in Reference Example 40 and (3-fluoropyridin-2-yl)methanol (0.48 g) in THF (7 mL) was added 60% sodium hydride (0.20 g) at 0° C., and the mixture was stirred at the same temperature for 1 hr. To the reaction solution was added water at 0° C., and the mixture was diluted with ethyl acetate. The organic layer was separated, washed with saturated brine, dried over anhydrous sodium sulfate, and concentrated. The residue was purified by silica gel chromatography (hexane-ethyl acetate) to give the title compound (0.87 g).

MS: [M+H]$^+$ 389.0

$^1$H NMR (300 MHz, CDCl$_3$) δ 3.89 (3H, s), 5.59 (2H, d, J=1.9 Hz), 7.24-7.32 (1H, m), 7.35 (1H, d, J=5.5 Hz), 7.37-7.45 (1H, m), 7.81 (1H, d, J=5.5 Hz), 8.40 (1H, dt, J=4.7, 1.3 Hz).

Reference Example 158

Methyl 2-((3-fluoropyridin-2-yl)methoxy)-4-vinylnicotinate

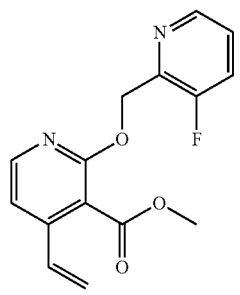 [SMILES: C=Cc1ccnc(OCc2ncccc2F)c1C(=O)OC]

To a solution of methyl 2-((3-fluoropyridin-2-yl)methoxy)-4-iodonicotinate (0.87 g) obtained in Reference Example 157 in DMF (7 mL) were added tributyl(vinyl)tin (0.92 g), (1,1-bis(diphenylphosphino)ferrocene)dichloropalladium(II) methylene chloride adduct (0.18 g) and lithium chloride (0.71 g), and the mixture was stirred under a nitrogen atmosphere at 90° C. for 4 hr. To the reaction solution was added saturated aqueous potassium fluoride solution, the insoluble material was filtered off, and the filtrate was diluted with ethyl acetate. The organic layer of the filtrate was separated, washed with saturated brine, dried over anhydrous sodium sulfate, and concentrated. The residue was purified by silica gel chromatography (hexane-ethyl acetate) to give the title compound (0.36 g).

MS: [M+H]+ 289.1

$^1$H NMR (300 MHz, CDCl$_3$) δ 3.86 (3H, s), 5.51 (1H, dd, J=11.0, 0.6 Hz), 5.61 (2H, d, J=1.7 Hz), 5.90 (1H, d, J=17.4 Hz), 6.72 (1H, dd, J=17.4, 11.0 Hz), 7.06 (1H, d, J=5.5 Hz), 7.19-7.33 (1H, m), 7.41 (1H, td, J=9.0, 1.3 Hz), 8.14 (1H, d, J=5.5 Hz), 8.36-8.48 (1H, m).

Reference Example 159

Methyl 2-((3-fluoropyridin-2-yl)methoxy)-4-formylnicotinate

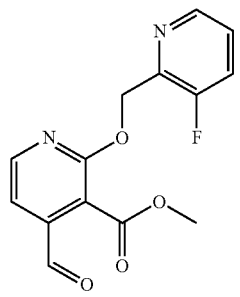 [SMILES: COC(=O)c1c(C=O)ccnc1OCc1ncccc1F]

A mixed solution of methyl 2-((3-fluoropyridin-2-yl)methoxy)-4-vinylnicotinate (0.35 g) obtained in Reference Example 158, sodium periodate (1.30 g) and osmium oxide (immobilized catalyst I) (0.15 g) in acetonitrile (3 mL)-acetone (3 mL)-water (3 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous sodium sulfate, and concentrated to give the title compound (0.25 g).

$^1$H NMR (300 MHz, CDCl$_3$) δ 3.93 (3H, s), 5.67 (2H, d, J=1.7 Hz), 7.27-7.35 (2H, m), 7.38-7.47 (1H, m), 8.30-8.50 (2H, m), 10.08 (1H, s).

Reference Example 160

Methyl 2-(cyclopropylmethoxy)-4-formylnicotinate

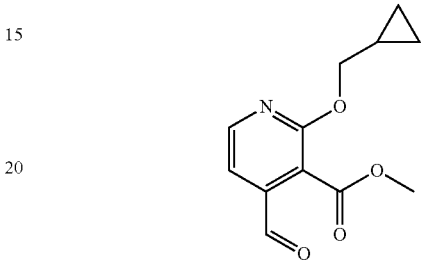

To a solution of methyl 2-fluoro-4-iodonicotinate (0.70 g) obtained in Reference Example 40 and cyclopropylmethanol (0.36 g) in THF (7 mL) was added 60% sodium hydride (0.20 g) at 0° C., and the mixture was stirred at the same temperature for 1 hr. To the reaction solution was added water at 0° C., and the mixture was diluted with ethyl acetate. The organic layer was separated, washed with saturated brine, dried over anhydrous sodium sulfate, and concentrated. The residue was crudely purified by silica gel chromatography (hexane-ethyl acetate). To a solution of the obtained crudely purified product in DMF (6 mL) were added tributyl(vinyl)tin (0.82 g), (1,1-bis(diphenylphosphino)ferrocene)dichloropalladium(II) methylene chloride adduct (0.16 g) and lithium chloride (0.64 g), and the mixture was stirred under a nitrogen atmosphere at 90° C. for 3 hr. To the reaction solution was added saturated aqueous potassium fluoride solution, the insoluble material was filtered off, and the filtrate was diluted with ethyl acetate. The organic layer was separated, washed with saturated brine, dried over anhydrous sodium sulfate, and concentrated. The residue was crudely purified by silica gel chromatography (hexane-ethyl acetate). A mixed solution of the obtained crudely purified product, sodium periodate (1.28 g) and osmium oxide (immobilized catalyst I) (0.25 g) in acetonitrile (6 mL)-acetone (3 mL)-water (3 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous sodium sulfate, and concentrated to give the title compound (0.33 g).

MS: [M+H]+ 236.1

Reference Example 161

4-(1-methyl-1H-1,2,3-triazol-4-yl)benzonitrile

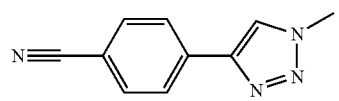

To a solution of 4-ethynylbenzonitrile (5.00 g), iodomethane (2.69 mL), and tris(triphenylphosphine)copper bromide (3.66 g) in DMSO (60 mL) was added aqueous solution (15 mL) of sodium azide (3.83 g) at room temperature, and the mixture was stirred under a nitrogen atmosphere at room temperature for 3 days. The reaction mixture was diluted with water and ethyl acetate, and the insoluble material was filtered off. The filtrate was extracted with ethyl acetate, and the organic layer was divided, washed with saturated brine, dried over anhydrous sodium sulfate, and concentrated. The residue was washed with ethyl acetate to give the title compound (4.11 g).

MS: [M+H]$^+$ 185.1

$^1$H NMR (300 MHz, DMSO-d$_6$) δ 4.12 (3H, s), 7.85-7.96 (2H, m), 7.98-8.08 (2H, m), 8.72 (1H, s).

Reference Example 162

(4-(1-methyl-1H-1,2,3-triazol-4-yl)phenyl)methanamine

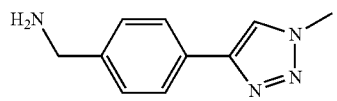

A mixture of 4-(1-methyl-1H-1,2,3-triazol-4-yl)benzonitrile (4.10 g) obtained in Reference Example 161, ammonia (8M methanol solution 27.8 mL) and Raney-nickel (10 mL volume) in ethanol (300 mL)-THF (150 mL) was stirred under a hydrogen atmosphere at room temperature overnight. The insoluble material was filtered off, and the filtrate was concentrated. The residue was washed with ethyl acetate to give the title compound (3.38 g).

MS: [M+H]$^+$ 189.1

Reference Example 163

Ethyl 2-(1-(2-fluorophenyl)ethoxy)-4-iodonicotinate

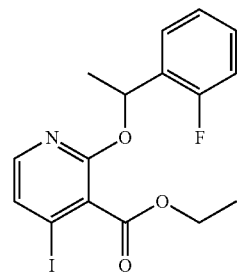 [SMILES: CCOC(=O)c1c(I)ccnc1OC(C)c1ccccc1F]

To a solution of ethyl 2-fluoro-4-iodonicotinate (0.70 g) obtained by a known method (Organic Letters, 7(10), 1943-1946; 2005) and 1-(2-fluorophenyl)ethanol (0.50 g) in THF (7 mL) was added 60% sodium hydride (0.14 g) at 0° C., and the mixture was stirred at the same temperature for 1 hr. To the reaction solution was added water at 0° C., and the mixture was diluted with ethyl acetate. The organic layer was separated, washed with saturated brine, dried over anhydrous sodium sulfate, and concentrated. The residue was purified by silica gel chromatography (hexane-ethyl acetate) to give the title compound (0.77 g).

$^1$H NMR (300 MHz, CDCl$_3$) δ 1.42 (3H, t, J=7.1 Hz), 1.61 (3H, d, J=6.6 Hz), 4.47 (2H, q, J=7.2 Hz), 6.48 (1H, q, J=6.5 Hz), 6.94-7.14 (2H, m), 7.17-7.24 (1H, m), 7.25-7.30 (1H, m), 7.41 (1H, td, J=7.5, 1.6 Hz), 7.73 (1H, d, J=5.5 Hz).

Reference Example 164

Ethyl 2-(1-(2-fluorophenyl)ethoxy)-4-vinylnicotinate

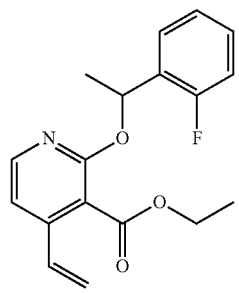 [SMILES: C=Cc1ccnc(OC(C)c2ccccc2F)c1C(=O)OCC]

To a solution of ethyl 2-(1-(2-fluorophenyl)ethoxy)-4-iodonicotinate (0.76 g) obtained in Reference Example 163 in DMF (7 mL) were added tributyl(vinyl)tin (0.76 g), (1,1-bis(diphenylphosphino)ferrocene)dichloropalladium (II) methylene chloride adduct (0.15 g) and lithium chloride (0.58 g), and the mixture was stirred under a nitrogen atmosphere at 90° C. for 3 hr. To the reaction solution was added saturated aqueous potassium fluoride solution, the insoluble material was filtered off, and the filtrate was diluted with ethyl acetate. The organic layer was separated, washed with saturated brine, dried over anhydrous sodium sulfate, and concentrated. The residue was purified by silica gel chromatography (hexane-ethyl acetate) to give the title compound (0.55 g).

$^1$H NMR (300 MHz, CDCl$_3$) δ 1.40 (3H, t, J=7.2 Hz), 1.62 (3H, d, J=6.6 Hz), 4.45 (2H, q, J=7.1 Hz), 5.51 (1H, dd, J=11.1, 0.6 Hz), 5.80-5.98 (1H, m), 6.52 (1H, q, J=6.5 Hz), 6.73 (1H, dd, J=17.6, 11.0 Hz), 6.96-7.12 (3H, m), 7.16-7.25 (1H, m), 7.46 (1H, td, J=7.6, 1.7 Hz), 8.05 (1H, d, J=5.3 Hz).

Reference Example 165

Ethyl 2-(1-(2-fluorophenyl)ethoxy)-4-formylnicotinate

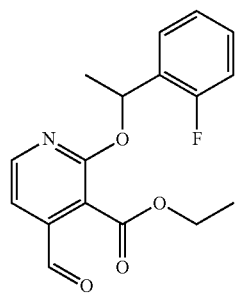 [SMILES: CCOC(=O)c1c(C=O)ccnc1OC(C)c1ccccc1F]

A mixed solution of ethyl 2-(1-(2-fluorophenyl)ethoxy)-4-vinylnicotinate (0.55 g) obtained in Reference Example 164, sodium periodate (1.87 g) and osmium oxide (immobilized catalyst I) (0.22 g) in acetonitrile (4 mL)-acetone (4 mL)-water (4 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous sodium sulfate, and concentrated to give the title compound (0.52 g).

¹H NMR (300 MHz, CDCl₃) δ 1.43 (3H, t, J=7.2 Hz), 1.66 (3H, d, J=6.6 Hz), 4.51 (2H, q, J=7.1 Hz), 6.55 (1H, q, J=6.4 Hz), 6.97-7.14 (2H, m), 7.17-7.29 (2H, m), 7.46 (1H, td, J=7.6, 1.7 Hz), 8.34 (1H, d, J=5.1 Hz), 10.08 (1H, s).

Reference Example 166

Ethyl 2-fluoro-4-formylnicotinate

A mixed solution of ethyl 2-fluoro-4-vinylnicotinate (4.80 g) obtained in Reference Example 118, sodium periodate (26.3 g) and osmium oxide (immobilized catalyst I) (1.25 g) in acetonitrile (50 mL)-acetone (50 mL)-water (50 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous sodium sulfate, and concentrated to give the title compound (4.03 g).

¹H NMR (300 MHz, CDCl₃) δ 1.44 (3H, t, J=7.2 Hz), 4.51 (2H, q, J=7.2 Hz), 7.64 (1H, dd, J=4.9, 1.1 Hz), 8.52 (1H, d, J=5.1 Hz), 10.27 (1H, s).

Reference Example 167

4-fluoro-2-(4-(1-methyl-1H-1,2,3-triazol-4-yl)benzyl)-1H-pyrrolo[3,4-c]pyridin-3 (2H)-one

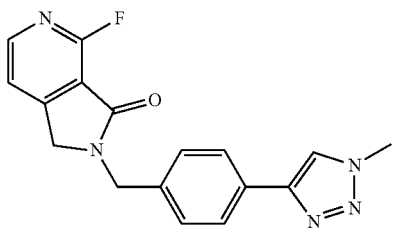 [SMILES: Cn1cc(-c2ccc(CN3Cc4ccnc(F)c4C3=O)cc2)nn1]

To a solution of ethyl 2-fluoro-4-formylnicotinate (2.60 g) obtained in Reference Example 166 and (4-(1-methyl-1H-1,2,3-triazol-4-yl)phenyl)methanamine (2.98 g) obtained in Reference Example 162 in methanol (40 mL)-THF (20 mL) was added tetra(isopropoxy)titanium (4.87 g) at room temperature, and the mixture was stirred under a nitrogen atmosphere at room temperature for 1 hr. Sodium tetrahydroborate (1.25 g) was added to the reaction mixture under ice-cooling, and the mixture was stirred under a nitrogen atmosphere at room temperature for 4 hr. The reaction mixture was diluted with water and ethyl acetate, and the organic layer was separated, washed with saturated brine, dried over anhydrous magnesium sulfate and concentrated. The residue was washed with ethyl acetate to give the title compound (1.44 g).

MS: [M+H]⁺ 324.1

¹H NMR (300 MHz, DMSO-d₆) δ 4.08 (3H, s), 4.54 (2H, s), 4.74 (2H, s), 7.38 (2H, d, J=8.1 Hz), 7.60 (1H, dd, J=5.0, 2.5 Hz), 7.82 (2H, d, J=8.1 Hz), 8.39 (1H, d, J=5.1 Hz), 8.50 (1H, s).

Reference Example 168

Ethyl 2-(cyclopropylmethoxy)-4-iodonicotinate

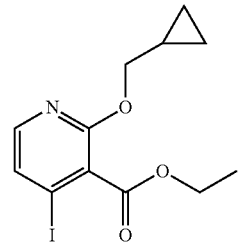 [SMILES: CCOC(=O)c1c(I)ccnc1OCC1CC1]

To a solution of ethyl 2-fluoro-4-iodonicotinate (3.00 g) obtained by a known method (Organic Letters, 7(10), 1943-1946; 2005) and cyclopropylmethanol (1.47 g) in THF (30 mL) was added 60% sodium hydride (0.61 g) at 0° C., and the mixture was stirred at the same temperature for 2 hr. To the reaction solution was added water at 0° C., and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (3.38 g).

MS: [M+H]⁺ 348.0

Reference Example 169

Ethyl 2-(cyclopropylmethoxy)-4-vinylnicotinate

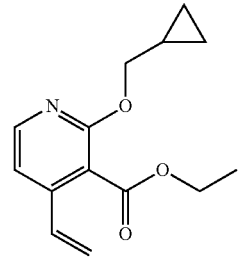 [SMILES: C=Cc1ccnc(OCC2CC2)c1C(=O)OCC]

To a solution of ethyl 2-(cyclopropylmethoxy)-4-iodonicotinate (3.37 g) obtained in Reference Example 168 in DMF (35 mL) were added tributyl(vinyl)tin (4.00 g), (1,1-bis(diphenylphosphino)ferrocene)dichloropalladium(II) methylene chloride adduct (0.79 g) and lithium chloride (3.09 g), and the mixture was stirred under a nitrogen atmosphere at 90° C. for 4 hr. To the reaction solution was added saturated aqueous potassium fluoride solution, the insoluble material was filtered off, and the filtrate was diluted with ethyl acetate. The organic layer was separated, washed with saturated brine, dried over anhydrous magnesium sulfate and concentrated. The residue was purified by silica gel chromatography (hexane-ethyl acetate) to give the title compound (2.06 g).

MS: [M+H]$^+$ 248.1

Reference Example 170

Ethyl 2-(cyclopropylmethoxy)-4-formylnicotinate

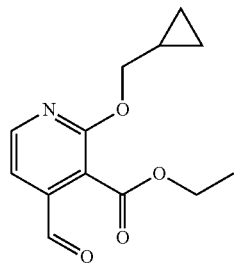 [SMILES: CCOC(=O)c1c(C=O)ccnc1OCC1CC1]

A mixed solution of ethyl 2-(cyclopropylmethoxy)-4-vinylnicotinate (2.05 g) obtained in Reference Example 169, sodium periodate (8.87 g) and osmium oxide (immobilized catalyst I) (0.63 g) in acetonitrile (15 mL)-acetone (15 mL)-water (15 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous magnesium sulfate and concentrated to give the title compound (1.82 g).

MS: [M+H]$^+$ 250.1

Reference Example 171

Ethyl 2-cyclobutoxy-4-iodonicotinate

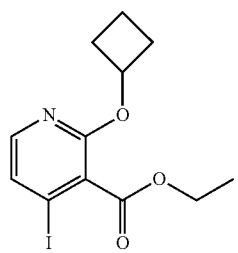 [SMILES: CCOC(=O)c1c(I)ccnc1OC1CCC1]

To a solution of ethyl 2-fluoro-4-iodonicotinate (1.80 g) obtained by a known method (Organic Letters, 7(10), 1943-1946; 2005) and cyclobutanol (0.88 g) in THF (30 mL) was added 60% sodium hydride (0.37 g) at 0° C., and the mixture was stirred at the same temperature for 2 hr. To the reaction solution was added water at 0° C., and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (2.03 g).

MS: [M+H]$^+$ 348.0

$^1$H NMR (300 MHz, CDCl$_3$) δ 1.42 (3H, t, J=7.2 Hz), 1.58-1.89 (2H, m), 2.06-2.19 (2H, m), 2.35-2.51 (2H, m), 4.44 (2H, q, J=7.1 Hz), 5.12-5.27 (1H, m), 7.29 (1H, d, J=5.5 Hz), 7.76 (1H, d, J=5.3 Hz).

Reference Example 172

Ethyl 2-cyclobutoxy-4-vinylnicotinate

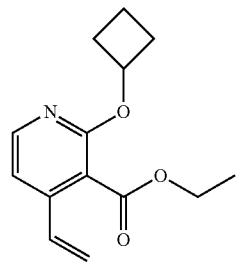 [SMILES: C=Cc1ccnc(OC2CCC2)c1C(=O)OCC]

To a solution of ethyl 2-cyclobutoxy-4-iodonicotinate (1.50 g) obtained in Reference Example 171 in DMF (15 mL) were added tributyl(vinyl)tin (1.78 g), (1,1-bis(diphenylphosphino)ferrocene)dichloropalladium(II) methylene chloride adduct (0.35 g) and lithium chloride (1.37 g), and the mixture was stirred under a nitrogen atmosphere at 90° C. for 4 hr. To the reaction solution was added saturated aqueous potassium fluoride solution, and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (0.84 g).

MS: [M+H]$^+$ 248.1

$^1$H NMR (300 MHz, CDCl$_3$) δ 1.40 (3H, t, J=7.2 Hz), 1.58-1.89 (2H, m), 2.05-2.20 (2H, m), 2.35-2.54 (2H, m), 4.42 (2H, q, J=7.1 Hz), 5.13-5.32 (1H, m), 5.44-5.58 (1H, m), 5.89 (1H, d, J 17.4 Hz), 6.71 (1H, dd, J=17.4, 11.0 Hz), 7.01 (1H, d, J 5.5 Hz), 8.08 (1H, d, J=5.5 Hz).

Reference Example 173

Ethyl 2-cyclobutoxy-4-formylnicotinate

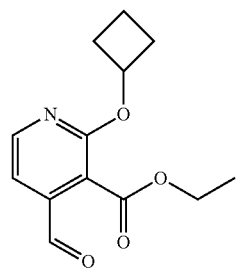 [SMILES: CCOC(=O)c1c(C=O)ccnc1OC1CCC1]

A mixed solution of ethyl 2-cyclobutoxy-4-vinylnicotinate (0.83 g) obtained in Reference Example 172, sodium periodate (3.59 g) and osmium oxide (immobilized catalyst I) (0.26 g) in acetonitrile (7 mL)-acetone (7 mL)-water (7 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous magnesium sulfate and concentrated to give the title compound (0.81 g).

MS: [M+H]$^+$ 250.1

$^1$H NMR (300 MHz, CDCl$_3$) δ 1.42 (3H, t, J=7.2 Hz), 1.60-1.93 (2H, m), 2.06-2.24 (2H, m), 2.37-2.55 (2H, m), 4.48 (2H, q, J=7.1 Hz), 5.26 (1H, quin, J=7.4 Hz), 7.20-7.31 (1H, m), 8.37 (1H, d, J=5.1 Hz), 10.07 (1H, s).

Reference Example 174

Methyl 4-chloro-6-((2,4-difluorobenzyl)oxy)pyrimidine-5-carboxylate

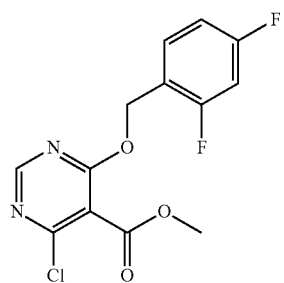 [SMILES: COC(=O)c1c(Cl)ncnc1OCc1ccc(F)cc1F]

To a solution of methyl 4,6-dichloropyrimidine-5-carboxylate (1.00 g) and (2,4-difluorophenyl)methanol (0.73 g) in THF (15 mL) was added 60% sodium hydride (0.20 g) at 0° C., and the mixture was stirred at the same temperature for 2 hr. To the reaction solution was added water at 0° C., and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (1.37 g).

MS: [M+H]$^+$ 315.0

Reference Example 175

Methyl 4-((2,4-difluorobenzyl)oxy)-6-vinylpyrimidine-5-carboxylate

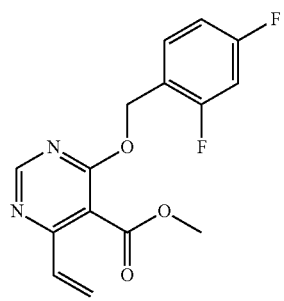 [SMILES: C=Cc1ncnc(OCc2ccc(F)cc2F)c1C(=O)OC]

To a solution of methyl 4-chloro-6-((2,4-difluorobenzyl)oxy)pyrimidine-5-carboxylate (1.35 g) obtained in Reference Example 174 in DME (7 mL)-water (7 mL) were added 4,4,5,5-tetramethyl-2-vinyl-1,3,2-dioxaborolane (0.99 g), (1,1-bis(diphenylphosphino)ferrocene)dichloropalladium (II) methylene chloride adduct (0.35 g) and sodium carbonate (1.36 g), and the mixture was stirred under a nitrogen atmosphere at 90° C. for 4 hr. To the reaction solution was added water, and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (0.87 g).

MS: [M+H]$^+$ 307.0

$^1$H NMR (300 MHz, CDCl$_3$) δ 3.92 (3H, s), 5.51 (2H, s), 5.71 (1H, dd, J=10.2, 2.3 Hz), 6.61-6.71 (1H, m), 6.73-6.94 (3H, m), 7.36-7.52 (1H, m), 8.74 (1H, s).

Reference Example 176

Methyl 4-((2,4-difluorobenzyl)oxy)-6-formylpyrimidine-5-carboxylate

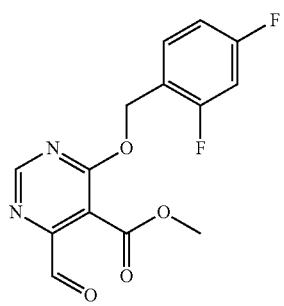 [SMILES: COC(=O)c1c(C=O)ncnc1OCc1ccc(F)cc1F]

A mixed solution of methyl 4-((2,4-difluorobenzyl)oxy)-6-vinylpyrimidine-5-carboxylate (0.86 g) obtained in Reference Example 175, sodium periodate (3.00 g) and osmium oxide (immobilized catalyst I) (0.36 g) in acetonitrile (6 mL)-acetone (6 mL)-water (6 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous magnesium sulfate and concentrated to give the title compound (0.83 g).

$^1$H NMR (300 MHz, CDCl$_3$) δ 3.96 (3H, s), 5.57 (2H, s), 6.77-6.96 (2H, m), 7.37-7.50 (1H, m), 8.99 (1H, s), 9.97 (1H, s).

Reference Example 177

Ethyl 4-iodo-2-((1-methylcyclopropyl)methoxy)nicotinate

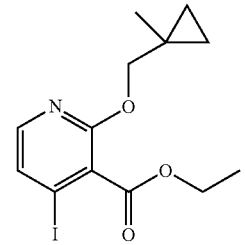 [SMILES: CCOC(=O)c1c(I)ccnc1OCC1(C)CC1]

To a solution of ethyl 2-fluoro-4-iodonicotinate (1.00 g) obtained by a known method (Organic Letters, 7(10), 1943-1946; 2005) and (1-methylcyclopropyl)methanol (0.58 g) in THF (10 mL) was added 60% sodium hydride (0.20 g) at 0°

C., and the mixture was stirred at the same temperature for 2 hr. To the reaction solution was added water at 0° C., and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (1.21 g).

MS: [M+H]⁺ 362.0

Reference Example 178

Ethyl 2-((1-methylcyclopropyl)methoxy)-4-vinylnicotinate

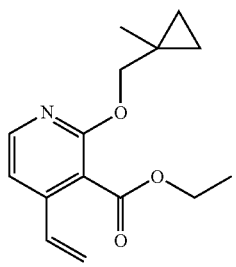 [SMILES: C=Cc1ccnc(OCC2(C)CC2)c1C(=O)OCC]

To a solution of ethyl 4-iodo-2-((1-methylcyclopropyl)methoxy)nicotinate (1.21 g) obtained in Reference Example 177 in DMF (12 mL) were added tributyl(vinyl)tin (1.28 g), (1,1-bis(diphenylphosphino)ferrocene)dichloropalladium (II) methylene chloride adduct (0.27 g) and lithium chloride (1.07 g), and the mixture was stirred under a nitrogen atmosphere at 90° C. for 3 hr. To the reaction solution was added saturated aqueous potassium fluoride solution, and the insoluble material was filtered off. The filtrate was extracted with ethyl acetate, and the organic layer was divided, washed with saturated brine, dried over anhydrous magnesium sulfate and concentrated. The residue was purified by silica gel chromatography (hexane-ethyl acetate) to give the title compound (0.57 g).

MS: [M+H]⁺ 262.1

Reference Example 179

Ethyl 4-formyl-2-((1-methylcyclopropyl)methoxy)nicotinate

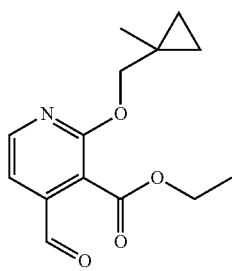 [SMILES: CCOC(=O)c1c(C=O)ccnc1OCC1(C)CC1]

A mixed solution of ethyl 2-((1-methylcyclopropyl)methoxy)-4-vinylnicotinate (0.33 g) obtained in Reference Example 178, sodium periodate (1.35 g) and osmium oxide (immobilized catalyst I) (0.096 g) in acetonitrile (4 mL)-acetone (4 mL)-water (4 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous magnesium sulfate and concentrated to give the title compound (0.28 g).

¹H NMR (300 MHz, CDCl₃) δ 0.34-0.43 (2H, m), 0.53-0.58 (2H, m), 1.20 (3H, s), 1.40-1.45 (3H, m), 4.16-4.24 (2H, m), 4.43-4.54 (2H, m), 7.21-7.31 (1H, m), 8.31-8.45 (1H, m), 10.09 (1H, s).

Reference Example 180

2-(4-bromo-2-fluorobenzyl)-4-((1-methylcyclopropyl)methoxy)-1H-pyrrolo[3,4-c]pyridin-3 (2H)-one

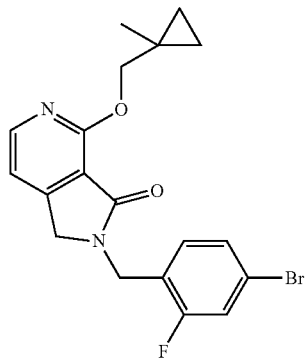 [SMILES: CC1(COc2nccc3c2C(=O)N(Cc2ccc(Br)cc2F)C3)CC1]

To a solution of ethyl 4-formyl-2-((1-methylcyclopropyl)methoxy)nicotinate (0.28 g) obtained in Reference Example 179 and (4-bromo-2-fluorophenyl)methanamine (0.23 g) in methanol (4 mL)-THF (2 mL) was added titanium tetraisopropoxide (0.33 g) at room temperature, and the mixture was stirred under a nitrogen atmosphere at room temperature for 1 hr. Sodium tetrahydroborate (0.079 g) was added to the reaction mixture under ice-cooling, and the mixture was stirred under a nitrogen atmosphere at room temperature for 3 hr. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) and recrystallization (ethyl acetate-diisopropyl ether) to give the title compound (0.15 g).

MS: [M+H]⁺ 405.0

Reference Example 181

Ethyl 2-((2-fluorobenzyl)oxy)-4-iodonicotinate

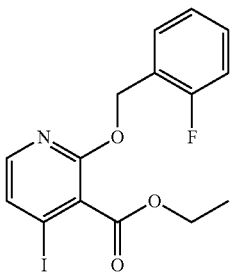 [SMILES: CCOC(=O)c1c(I)ccnc1OCc1ccccc1F]

To a solution of ethyl 2-fluoro-4-iodonicotinate (5.00 g) obtained by a known method (Organic Letters, 7(10), 1943-1946; 2005) and (2-fluorophenyl)methanol (4.27 g) in THF (50 mL) was added 60% sodium hydride (1.02 g) at 0° C., and the mixture was stirred at the same temperature for 1 hr. To the reaction solution was added water at 0° C., and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (6.70 g).

MS: [M+H]+ 402.0

¹H NMR (300 MHz, CDCl₃) δ 1.34 (3H, t, J=7.1 Hz), 4.41 (2H, q, J=7.2 Hz), 5.49 (2H, s), 6.99-7.18 (2H, m), 7.23-7.38 (2H, m), 7.44 (1H, td, J=7.5, 1.5 Hz), 7.82 (1H, d, J=5.3 Hz).

Reference Example 182

Ethyl 2-((2-fluorobenzyl)oxy)-4-vinylnicotinate

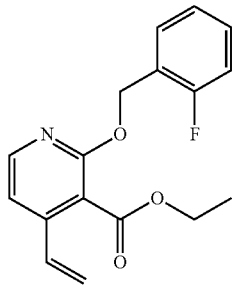 [SMILES: C=Cc1ccnc(OCc2ccccc2F)c1C(=O)OCC]

To a solution of ethyl 2-((2-fluorobenzyl)oxy)-4-iodonicotinate (3.00 g) obtained in Reference Example 181 in DMF (20 mL) were added tributyl(vinyl)tin (2.85 g), (1,1-bis(diphenylphosphino)ferrocene)dichloropalladium(II) methylene chloride adduct (0.61 g) and lithium chloride (2.06 g), and the mixture was stirred under a nitrogen atmosphere at 90° C. for 2 hr. To the reaction solution was added saturated aqueous potassium fluoride solution, and the mixture was diluted with ethyl acetate. The organic layer was separated, washed with saturated brine, dried over anhydrous sodium sulfate, and concentrated. The residue was purified by silica gel chromatography (hexane-ethyl acetate) to give the title compound (2.14 g).

MS: [M+H]+ 302.1

¹H NMR (300 MHz, CDCl₃) δ 1.31 (3H, t, J=7.2 Hz), 4.38 (2H, q, J=7.1 Hz), 5.45-5.60 (3H, m), 5.92 (1H, d, J=17.4 Hz), 6.75 (1H, dd, J=17.4, 11.0 Hz), 6.99-7.16 (3H, m), 7.19-7.35 (1H, m), 7.48 (1H, td, J=7.4, 1.6 Hz), 8.14 (1H, d, J=5.5 Hz).

Reference Example 183

Ethyl 2-((2-fluorobenzyl)oxy)-4-formylnicotinate

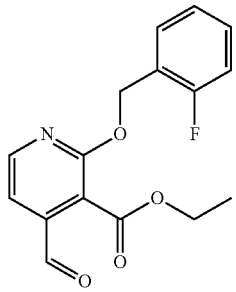 [SMILES: CCOC(=O)c1c(C=O)ccnc1OCc1ccccc1F]

A mixed solution of ethyl 2-((2-fluorobenzyl)oxy)-4-vinylnicotinate (2.10 g) obtained in Reference Example 182, sodium periodate (7.45 g) and osmium oxide (immobilized catalyst I) (0.53 g) in acetonitrile (15 mL)-acetone (15 mL)-water (15 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous magnesium sulfate and concentrated to give the title compound (2.10 g).

¹H NMR (300 MHz, CDCl₃) δ 1.34 (3H, t, J=7.2 Hz), 4.45 (2H, q, J=7.1 Hz), 5.56 (2H, s), 7.00-7.18 (3H, m), 7.23-7.35 (1H, m), 7.45-7.54 (1H, m), 8.43 (1H, d, J=5.1 Hz), 10.10 (1H, s).

Reference Example 184

2-(4-bromo-2-fluorobenzyl)-4-((2-fluorobenzyl)oxy)-1H-pyrrolo[3,4-c]pyridin-3(2H)-one

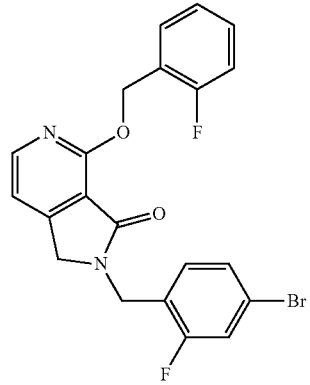 [SMILES: O=C1c2c(ccnc2OCc2ccccc2F)CN1Cc1ccc(Br)cc1F]

To a solution of ethyl 2-((2-fluorobenzyl)oxy)-4-formylnicotinate (2.10 g) obtained in Reference Example 183 and (4-bromo-2-fluorophenyl)methanamine (1.48 g) in methanol (13 mL)-THF (13 mL) was added magnesium sulfate (1.67 g) at room temperature, and the mixture was stirred under a nitrogen atmosphere at room temperature for 1 hr. The insoluble material was filtered off, and the filtrate was concentrated. To a solution of the residue in acetic acid (13 mL) was added sodium triacetoxyhydroborate (2.20 g) at room temperature, and the mixture was stirred under a nitrogen atmosphere at room temperature for 3 hr. The reaction mixture was diluted with saturated aqueous sodium hydrogen carbonate solution and ethyl acetate, and the organic layer was separated, washed with saturated brine, dried over anhydrous magnesium sulfate and concentrated. The residue was purified by silica gel chromatography (hexane-ethyl acetate) to give the title compound (1.06 g).

MS: [M+H]+ 445.0

¹H NMR (300 MHz, CDCl₃) δ 4.32 (2H, s), 4.76 (2H, s), 5.67 (2H, s), 6.93-7.20 (3H, m), 7.22-7.38 (4H, m), 7.71 (1H, t, J=7.4 Hz), 8.27 (1H, d, J=5.1 Hz).

Reference Example 186

Ethyl 2-((6,7-dihydro-5H-cyclopenta[b]pyridin-7-yl)oxy)-4-iodonicotinate

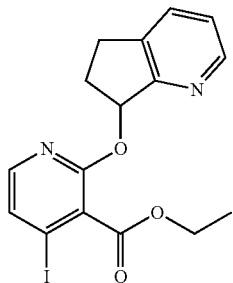 [SMILES: CCOC(=O)c1c(I)ccnc1OC1CCc2cccnc21]

To a solution of ethyl 2-fluoro-4-iodonicotinate (1.50 g) obtained by a known method (Organic Letters, 7(10), 1943-1946; 2005) and 6,7-dihydro-5H-cyclopenta[b]pyridin-7-ol (1.03 g) in THF (15 mL) was added 60% sodium hydride (0.31 g) at 0° C., and the mixture was stirred at the same temperature for 1 hr. To the reaction solution was added water at 0° C., and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (1.84 g).

MS: [M+H]$^+$ 411.0

$^1$H NMR (300 MHz, CDCl$_3$) δ 1.21 (3H, t, J=7.1 Hz), 2.13-2.29 (1H, m), 2.52-2.71 (1H, m), 2.82-2.98 (1H, m), 3.02-3.21 (1H, m), 4.21-4.37 (2H, m), 6.53 (1H, dd, J=7.2, 4.0 Hz), 7.17 (1H, dd, J=7.6, 4.9 Hz), 7.35 (1H, d, J=5.3 Hz), 7.59 (1H, dd, J=7.6, 1.0 Hz), 7.87 (1H, d, J=5.3 Hz), 8.48 (1H, dd, J=4.8, 0.7 Hz).

Reference Example 187

Ethyl 2-((6,7-dihydro-5H-cyclopenta[b]pyridin-7-yl)oxy)-4-vinylnicotinate

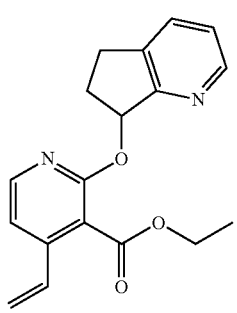 [SMILES: C=Cc1ccnc(OC2CCc3cccnc32)c1C(=O)OCC]

To a solution of ethyl 2-((6,7-dihydro-5H-cyclopenta[b]pyridin-7-yl)oxy)-4-iodonicotinate (1.80 g) obtained in Reference Example 186 in DMF (15 mL) were added tributyl(vinyl)tin (1.81 g), (1,1-bis(diphenylphosphino)ferrocene)dichloropalladium(II) methylene chloride adduct (0.36 g) and lithium chloride (1.40 g), and the mixture was stirred under a nitrogen atmosphere at 90° C. for 2 hr. To the reaction solution was added saturated aqueous potassium fluoride solution, and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (1.31 g).

MS: [M+H]$^+$ 311.1

$^1$H NMR (300 MHz, CDCl$_3$) δ 1.16 (3H, t, J=7.1 Hz), 2.23 (1H, qd, J=9.0, 4.8 Hz), 2.55-2.73 (1H, m), 2.82-2.98 (1H, m), 3.02-3.21 (1H, m), 4.26 (2H, qq, J=7.1, 3.5 Hz), 5.50 (1H, d, J=11.0 Hz), 5.90 (1H, d, J=17.4 Hz), 6.55 (1H, dd, J=7.1, 4.1 Hz), 6.74 (1H, dd, J=17.4, 11.0 Hz), 7.06 (1H, d, J=5.5 Hz), 7.17 (1H, dd, J=7.6, 4.8 Hz), 7.59 (1H, d, J=7.7 Hz), 8.19 (1H, d, J=5.5 Hz), 8.48 (1H, d, J=4.2 Hz).

Reference Example 188

Ethyl 2-((6,7-dihydro-5H-cyclopenta[b]pyridin-7-yl)oxy)-4-formylnicotinate

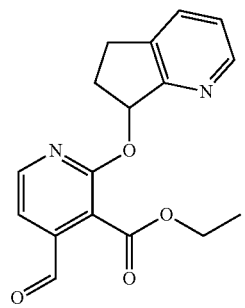 [SMILES: CCOC(=O)c1c(C=O)ccnc1OC1CCc2cccnc21]

A mixed solution of ethyl 2-((6,7-dihydro-5H-cyclopenta[b]pyridin-7-yl)oxy)-4-vinylnicotinate (1.30 g) obtained in Reference Example 187, sodium periodate (3.58 g) and osmium oxide (immobilized catalyst I) (0.32 g) in acetonitrile (10 mL)-acetone (10 mL)-water (10 mL) was stirred at room temperature for 7 hr. The insoluble material was filtered off, and the filtrate was diluted with saturated aqueous sodium thiosulfate solution and ethyl acetate. The organic layer was separated, washed with saturated brine, dried over anhydrous magnesium sulfate and concentrated to give the title compound (1.11 g).

$^1$H NMR (300 MHz, CDCl$_3$) δ 1.20 (3H, t, J=7.2 Hz), 2.25 (1H, ddt, J=13.7, 9.2, 4.6 Hz), 2.58-2.77 (1H, m), 2.85-3.02 (1H, m), 3.05-3.24 (1H, m), 4.24-4.42 (2H, m), 6.61 (1H, dd, J=7.0, 4.2 Hz), 7.19 (1H, dd, J=7.6, 4.9 Hz), 7.32 (1H, d, J=5.1 Hz), 7.62 (1H, d, J=7.7 Hz), 8.40-8.56 (2H, m), 10.10 (1H, s).

Reference Example 189

2-(4-bromo-2-fluorobenzyl)-4-((6,7-dihydro-5H-cyclopenta[b]pyridin-7-yl)oxy)-1H-pyrrolo[3,4-c]pyridin-3(2H)-one

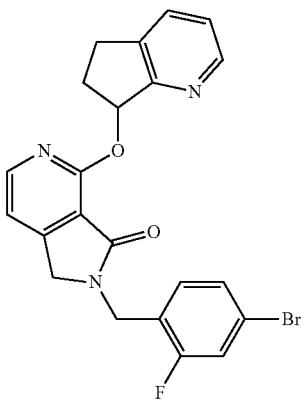 [SMILES: O=C1c2c(ccnc2OC2CCc3cccnc32)CN1Cc1ccc(Br)cc1F]

To a solution of ethyl 2-((6,7-dihydro-5H-cyclopenta[b]pyridin-7-yl)oxy)-4-formylnicotinate (1.10 g) obtained in Reference Example 188 and (4-bromo-2-fluorophenyl)methanamine (0.76 g) in methanol (10 mL) was added magnesium sulfate (0.85 g) at room temperature, and the mixture was stirred under a nitrogen atmosphere at room temperature for 1 hr. The insoluble material was filtered off, to the filtrate were added acetic acid (1 mL) solution and sodium triacetoxyhydroborate (1.12 g) at room temperature, and the mixture was stirred under a nitrogen atmosphere at room temperature for 4 hr. The reaction mixture was diluted with saturated aqueous sodium hydrogen carbonate solution and ethyl acetate, and the organic layer was separated, washed with saturated brine, dried over anhydrous magnesium sulfate and concentrated. The residue was purified by silica gel chromatography (hexane-ethyl acetate), and the obtained solid was washed with diisopropyl ether to give the title compound (0.58 g).

MS: [M+H]$^+$ 454.0

Reference Example 190

Ethyl 2-(2,2-difluoro-2-(pyridin-2-yl)ethoxy)-4-iodonicotinate

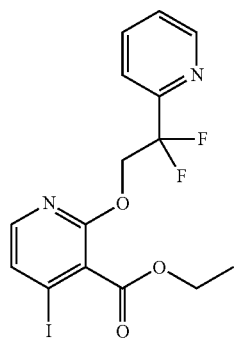 [SMILES: CCOC(=O)c1c(I)ccnc1OCC(F)(F)c1ccccn1]

To a solution of ethyl 2-fluoro-4-iodonicotinate (1.20 g) obtained by a known method (Organic Letters, 7(10), 1943-1946; 2005) and 2,2-difluoro-2-(pyridin-2-yl)ethanol (0.97 g) in THF (12 mL) was added 60% sodium hydride (0.21 g) at 0° C., and the mixture was stirred at the same temperature for 1 hr. To the reaction solution was added water at 0° C., and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (1.75 g).

MS: [M+H]$^+$ 435.0

$^1$H NMR (300 MHz, CDCl$_3$) δ 1.25-1.32 (3H, m), 4.27 (2H, q, J=7.2 Hz), 5.04 (2H, t, J=12.6 Hz), 7.31-7.45 (2H, m), 7.63-7.73 (1H, m), 7.75-7.89 (2H, m), 8.66 (1H, dd, J=4.7, 0.8 Hz).

Reference Example 191

Ethyl 2-(2,2-difluoro-2-(pyridin-2-yl)ethoxy)-4-vinylnicotinate

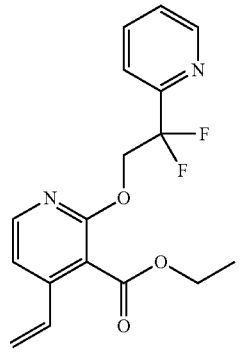 [SMILES: C=Cc1ccnc(OCC(F)(F)c2ccccn2)c1C(=O)OCC]

To a solution of ethyl 2-(2,2-difluoro-2-(pyridin-2-yl)ethoxy)-4-iodonicotinate (1.75 g) obtained in Reference Example 190 in DMF (15 mL) were added tributyl(vinyl)tin (1.66 g), (1,1-bis(diphenylphosphino)ferrocene)dichloropalladium(II) methylene chloride adduct (0.33 g) and lithium chloride (1.28 g), and the mixture was stirred under a nitrogen atmosphere at 90° C. for 2 hr. To the reaction solution was added saturated aqueous potassium fluoride solution, and the insoluble material was filtered off. The filtrate was extracted with ethyl acetate, and the organic layer was divided, washed with saturated brine, dried over anhydrous magnesium sulfate and concentrated. The residue was purified by silica gel chromatography (hexane-ethyl acetate) to give the title compound (1.24 g).

MS: [M+H]$^+$ 335.1

$^1$H NMR (300 MHz, CDCl$_3$) δ 1.26 (3H, t, J=7.2 Hz), 4.24 (2H, q, J=7.2 Hz), 5.05 (2H, t, J=12.7 Hz), 5.43-5.57 (1H, m), 5.89 (1H, d, J=17.4 Hz), 6.70 (1H, dd, J=17.5, 11.0 Hz), 7.07 (1H, d, J=5.5 Hz), 7.37 (1H, dd, J=7.1, 5.4 Hz), 7.62-7.73 (1H, m), 7.75-7.88 (1H, m), 8.10 (1H, d, J=5.5 Hz), 8.66 (1H, dd, J=4.9, 0.8 Hz).

Reference Example 192

Ethyl 2-(2,2-difluoro-2-(pyridin-2-yl)ethoxy)-4-formylnicotinate

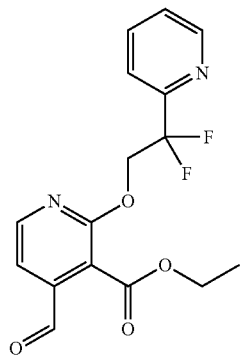 [SMILES: CCOC(=O)c1c(C=O)ccnc1OCC(F)(F)c1ccccn1]

A mixed solution of ethyl 2-(2,2-difluoro-2-(pyridin-2-yl)ethoxy)-4-vinylnicotinate (1.24 g) obtained in Reference Example 191, sodium periodate (3.17 g) and osmium oxide (immobilized catalyst I) (0.28 g) in acetonitrile (10 mL)-acetone (10 mL)-water (10 mL) was stirred at room temperature for 3 hr. The insoluble material was filtered off, and the filtrate was diluted with saturated aqueous thiosulfate solution and ethyl acetate. The organic layer was separated, washed with saturated brine, dried over anhydrous magnesium sulfate and concentrated to give the title compound (1.19 g).

$^1$H NMR (300 MHz, CDCl$_3$) δ 1.28 (3H, t, J=7.3 Hz), 4.32 (2H, q, J=7.2 Hz), 5.13 (2H, t, J=12.7 Hz), 7.33 (1H, d, J=5.3 Hz), 7.39 (1H, dd, J=7.0, 4.9 Hz), 7.72 (1H, d, J=7.9 Hz), 7.78-7.91 (1H, m), 8.40 (1H, d, J=5.3 Hz), 8.66 (1H, d, J=4.7 Hz), 10.07 (1H, s).

Reference Example 193

2-(4-bromo-2-fluorobenzyl)-4-(2,2-difluoro-2-(pyridin-2-yl)ethoxy)-1H-pyrrolo[3,4-c]pyridin-3(2H)-one

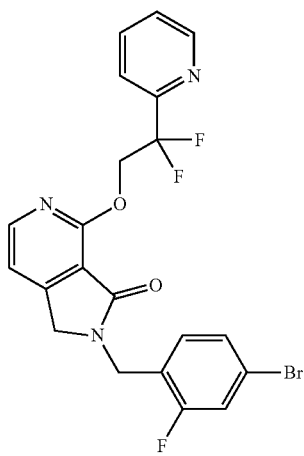 [SMILES: O=C1c2c(ccnc2OCC(F)(F)c2ccccn2)CN1Cc1ccc(Br)cc1F]

To a solution of ethyl 2-(2,2-difluoro-2-(pyridin-2-yl)ethoxy)-4-formylnicotinate (1.19 g) obtained in Reference Example 192 and (4-bromo-2-fluorophenyl)methanamine (0.76 g) in methanol (20 mL) was added magnesium sulfate (0.85 g) at room temperature, and the mixture was stirred under a nitrogen atmosphere at room temperature for 1 hr. The insoluble material was filtered off, to the filtrate were added acetic acid (2 mL) solution and sodium triacetoxyhydroborate (1.13 g) at room temperature, and the mixture was stirred under a nitrogen atmosphere at room temperature overnight. The reaction mixture was concentrated, the residue was diluted with saturated aqueous sodium hydrogen carbonate solution and ethyl acetate, and the organic layer was separated, washed with saturated brine, dried over anhydrous magnesium sulfate and concentrated. The residue was purified by silica gel chromatography (hexane-ethyl acetate), and the obtained solid was washed with diisopropyl ether to give the title compound (0.42 g).

MS: [M+H]$^+$ 478.0

Reference Example 194

4-cyclobutoxy-2-(4-iodobenzyl)-1H-pyrrolo[3,4-c]pyridin-3(2H)-one

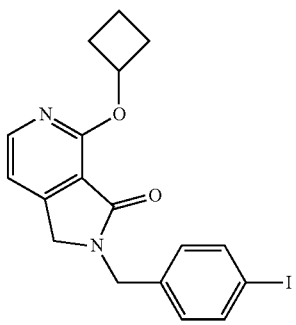 [SMILES: O=C1c2c(ccnc2OC2CCC2)CN1Cc1ccc(I)cc1]

To a solution of ethyl 2-cyclobutoxy-4-formylnicotinate (0.70 g) obtained in Reference Example 173 and (4-iodophenyl)methanamine (0.69 g) in methanol (10 mL) was added magnesium sulfate (0.68 g) at room temperature, and the mixture was stirred under a nitrogen atmosphere at room temperature for 1 hr. The insoluble material was filtered off, to the filtrate were added acetic acid (1 mL) solution and sodium triacetoxyhydroborate (0.89 g) at room temperature, and the mixture was stirred under a nitrogen atmosphere at room temperature overnight. The reaction mixture was concentrated, the residue was diluted with saturated aqueous sodium hydrogen carbonate solution and ethyl acetate, and the organic layer was separated, washed with saturated brine, dried over anhydrous magnesium sulfate and concentrated. The residue was purified by silica gel chromatography (hexane-ethyl acetate), and the obtained solid was washed with diisopropyl ether to give the title compound (0.24 g).

MS: [M+H]$^+$ 421.0

Reference Example 195

6,6-dimethyl-5H-cyclopenta[b]pyridin-7(6H)-one

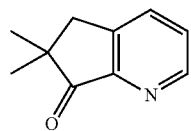

To a solution of 5H-cyclopenta[b]pyridin-7(6H)-one (4.90 g) and iodomethane (6.90 mL) in THF (100 mL) was added dropwise potassium tert-butoxide (9.09 g) in THF (100 mL) under ice-cooling, and the mixture was stirred under a nitrogen atmosphere at the same temperature overnight. The reaction mixture was directly purified by silica gel chromatography (hexane-ethyl acetate) to give the title compound (3.91 g).

MS: [M+H]$^+$ 162.1

$^1$H NMR (300 MHz, CDCl$_3$) δ 1.29 (6H, s), 3.01 (2H, s), 7.46 (1H, dd, J=7.8, 4.6 Hz), 7.84 (1H, dt, J=7.9, 0.6 Hz), 8.79 (1H, d, J=4.5 Hz).

Reference Example 196

6,6-dimethyl-6,7-dihydro-5H-cyclopenta[b]pyridin-7-ol

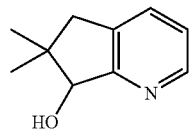

To a solution of 6,6-dimethyl-5H-cyclopenta[b]pyridin-7(6H)-one (3.90 g) obtained in Reference Example 195 in THF (100 mL)-ethanol (10 mL) was added sodium tetrahydroborate (0.33 g) at room temperature, and the mixture was stirred at the same temperature for 2 hr. The reaction mixture was diluted with saturated aqueous ammonium chloride solution and ethyl acetate at 0° C., and the organic layer was separated, washed with saturated brine, dried over anhydrous magnesium sulfate and concentrated. The residue was washed with IPE to give the title compound (1.87 g).

$^1$H NMR (300 MHz, CDCl$_3$) δ 1.04 (3H, s), 1.27 (3H, s), 2.56-2.83 (2H, m), 3.46 (1H, brs), 4.71 (1H, d, J=4.2 Hz), 7.11 (1H, dd, J=7.6, 5.1 Hz), 7.50 (1H, dd, J=7.6, 0.9 Hz), 8.39 (1H, d, J=4.9 Hz).

Reference Example 197

Ethyl 2-((6,6-dimethyl-6,7-dihydro-5H-cyclopenta[b]pyridin-7-yl)oxy)-4-iodonicotinate

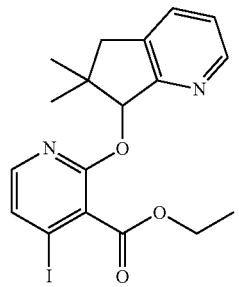 [SMILES: CCOC(=O)c1c(I)ccnc1OC1c2ncccc2CC1(C)C]

To a solution of ethyl 2-fluoro-4-iodonicotinate (2.00 g) obtained by a known method (Organic Letters, 7(10), 1943-1946; 2005) and 6,6-dimethyl-6,7-dihydro-5H-cyclopenta[b]pyridin-7-ol (1.33 g) obtained in Reference Example 196 in THF (20 mL) was added 60% sodium hydride (0.33 g) at 0° C., and the mixture was stirred at the same temperature for 1 hr. To the reaction solution was added water at 0° C., and the mixture was diluted with ethyl acetate. The organic layer was separated, washed with saturated brine, dried over anhydrous magnesium sulfate and concentrated. The residue was purified by silica gel chromatography (hexane-ethyl acetate) to give the title compound (2.16 g).

MS: [M+H]$^+$ 439.0

$^1$H NMR (300 MHz, CDCl$_3$) δ 1.13 (3H, s), 1.19-1.27 (6H, m), 2.59-2.97 (2H, m), 4.18-4.41 (2H, m), 6.37 (1H, s), 7.13 (1H, dd, J=7.6, 4.9 Hz), 7.34 (1H, d, J=5.5 Hz), 7.52 (1H, d, J=7.7 Hz), 7.87 (1H, d, J=5.3 Hz), 8.43 (1H, dd, J=4.9, 0.8 Hz).

Reference Example 198

Ethyl 2-((6,6-dimethyl-6,7-dihydro-5H-cyclopenta[b]pyridin-7-yl)oxy)-4-vinylnicotinate

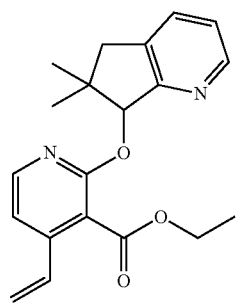 [SMILES: C=Cc1ccnc(OC2c3ncccc3CC2(C)C)c1C(=O)OCC]

To a solution of ethyl 2-((6,6-dimethyl-6,7-dihydro-5H-cyclopenta[b]pyridin-7-yl)oxy)-4-iodonicotinate (2.15 g) obtained in Reference Example 197 in DMF (15 mL) were added tributyl(vinyl)tin (2.02 g), (1,1-bis(diphenylphosphino)ferrocene)dichloropalladium(II) methylene chloride adduct (0.40 g) and lithium chloride (1.56 g), and the mixture was stirred under a nitrogen atmosphere at 90° C. for 2 hr. To the reaction solution was added saturated aqueous potassium fluoride solution, and the insoluble material was filtered off. The filtrate was extracted with ethyl acetate, and the organic layer was divided, washed with saturated brine, dried over anhydrous magnesium sulfate and concentrated. The residue was purified by silica gel chromatography (hexane-ethyl acetate) to give the title compound (1.30 g).

MS: [M+H]+ 339.2

Reference Example 199

Ethyl 2-((6,6-dimethyl-6,7-dihydro-5H-cyclopenta[b]pyridin-7-yl)oxy)-4-formylnicotinate

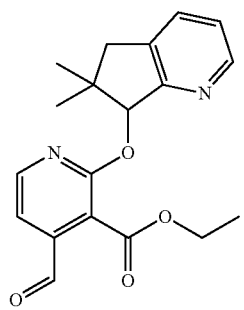 [SMILES: CCOC(=O)c1c(C=O)ccnc1OC1c2ncccc2CC1(C)C]

A mixed solution of ethyl 2-((6,6-dimethyl-6,7-dihydro-5H-cyclopenta[b]pyridin-7-yl)oxy)-4-vinylnicotinate (1.29 g) obtained in Reference Example 198, sodium periodate (2.85 g) and osmium oxide (immobilized catalyst I) (0.24 g) in acetonitrile (10 mL)-acetone (10 mL)-water (10 mL) was stirred at room temperature overnight. The insoluble material was filtered off, and the filtrate was diluted with saturated aqueous sodium thiosulfate solution and ethyl acetate. The organic layer was separated, washed with saturated brine, dried over anhydrous magnesium sulfate and concentrated to give the title compound (1.16 g).

$^1$H NMR (300 MHz, CDCl$_3$) δ 1.17 (3H, s), 1.20-1.26 (6H, m), 2.62-2.80 (1H, m), 2.86-3.02 (1H, m), 4.26-4.42 (2H, m), 6.46 (1H, s), 7.15 (1H, dd, J=7.6, 5.0 Hz), 7.31 (1H, d, J=5.1 Hz), 7.54 (1H, dd, J=7.6, 1.0 Hz), 8.43 (1H, d, J=4.3 Hz), 8.48 (1H, d, J=5.1 Hz), 10.09 (1H, s).

Reference Example 200

2-(4-bromobenzyl)-4-((6,6-dimethyl-6,7-dihydro-5H-cyclopenta[b]pyridin-7-yl)oxy)-1H-pyrrolo[3,4-c]pyridin-3 (2H)-one

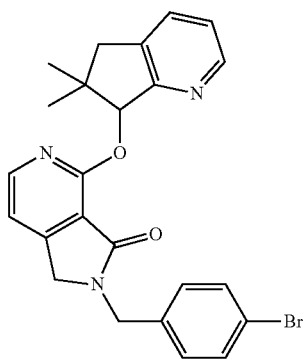 [SMILES: CC1(C)Cc2cccnc2C1Oc1nccc2c1C(=O)N(Cc1ccc(Br)cc1)C2]

To a solution of ethyl 2-((6,6-dimethyl-6,7-dihydro-5H-cyclopenta[b]pyridin-7-yl)oxy)-4-formylnicotinate (1.15 g) obtained in Reference Example 199 and (4-bromophenyl)methanamine (0.66 g) in methanol (20 mL) was added magnesium sulfate (0.81 g) at room temperature, and the mixture was stirred under a nitrogen atmosphere at room temperature for 1 hr. The insoluble material was filtered off, to the filtrate were added acetic acid (2 mL) solution and sodium triacetoxyhydroborate (1.07 g) at room temperature, and the mixture was stirred under a nitrogen atmosphere at room temperature for 5 hr. The reaction mixture was concentrated, the residue was diluted with saturated aqueous sodium hydrogen carbonate solution and ethyl acetate, and the organic layer was separated, washed with saturated brine, dried over anhydrous magnesium sulfate and concentrated. The residue was purified by silica gel chromatography (hexane-ethyl acetate), and the obtained solid was washed with diisopropyl ether to give the title compound (0.21 g).

MS: [M+H]+ 464.1

Reference Example 201

Methyl 2-(dimethoxymethyl)-6-hydroxybenzoate

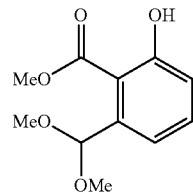 [SMILES: COC(=O)c1c(O)cccc1C(OC)OC]

To a solution of methyl 2-formyl-6-hydroxybenzoate (12.7 g) obtained by a known method (Eur. Pat. Appl. (1991) EP455170) and trimethyl orthoformate (72 mL) in methanol (360 mL) was added 4M hydrochloric acid-methanol solution (12.7 mL), and the mixture was heated under reflux for 24 hr. The solvent was evaporated to give the title compound (15.8 g).

$^1$H NMR (400 MHz, CDCl$_3$) δ 3.35 (6H, s), 3.99 (3H, s), 5.91 (1H, s), 6.99 (1H, dd, J=8.0, 1.2 Hz), 7.28 (1H, d, J=7.6 Hz), 7.41 (1H, t, J=8.0 Hz), 10.54 (1H, brs).

Reference Example 202

Methyl 2-(dimethoxymethyl)-6-((trans-2-hydroxycyclohexyl)oxy)benzoate

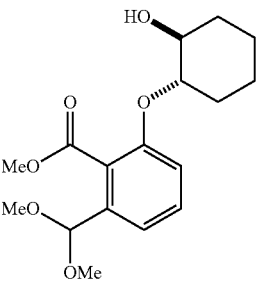

A solution of methyl 2-(dimethoxymethyl)-6-hydroxybenzoate (5.13 g) obtained in Reference Example 201, 7-oxabicyclo[4.1.0]heptane (11.1 g) and pyridine (8.93 g) in methanol (160 mL) was stirred at 55° C. for 16 hr. The solvent was evaporated, and the residue was purified by silica gel chromatography (petroleum ether-ethyl acetate) to give the title compound (4.66 g).

$^1$H NMR (400 MHz, DMSO-$d_6$) δ 1.20-1.43 (4H, m), 1.48-1.66 (2H, m), 1.72-1.83 (1H, m), 1.83-1.96 (1H, m), 3.13-3.27 (6H, m), 3.47-3.57 (1H, m), 3.76 (3H, s), 4.06-4.14 (1H, m), 4.81 (1H, d, J=4.0 Hz), 5.38 (1H, s), 7.06 (1H, d, J=7.6 Hz), 7.20 (1H, d, J=8.0 Hz), 7.38 (1H, t, J=8.0 Hz).

Reference Example 203

Methyl 2-formyl-6-((trans-2-hydroxycyclohexyl)oxy)benzoate

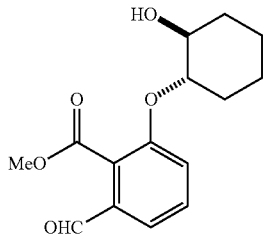

To a solution of methyl 2-(dimethoxymethyl)-6-((trans-2-hydroxycyclohexyl)oxy)benzoate (4.66 g) obtained in Reference Example 202 in dichloromethane-water (66 mL, 10:1) was added p-toluenesulfonic acid monohydrate (2.73 g), and the mixture was stirred at room temperature for 16 hr. The reaction mixture was neutralized with saturated aqueous sodium hydrogen carbonate solution, and the mixture was extracted with dichloromethane (3×20 mL), washed with saturated brine, dried over anhydrous sodium sulfate, and concentrated. The residue was purified by silica gel chromatography (petroleum ether-ethyl acetate) to give the title compound (2.63 g).

$^1$H NMR (400 MHz, DMSO-$d_6$) δ 1.20-1.42 (4H, m), 1.48-1.68 (2H, m), 1.72-1.85 (1H, m), 1.85-1.93 (1H, m), 3.48-3.59 (1H, m), 3.81 (3H, s), 4.11-4.22 (1H, m), 4.90 (1H, d, J=4.4 Hz), 7.50-7.71 (3H, m), 9.92 (1H, s).

Reference Example 204

Methyl 2-(dimethoxymethyl)-6-((tetrahydrofuran-2-yl)methoxy)benzoate

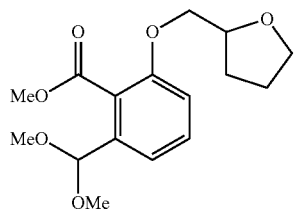 [SMILES: COC(=O)c1c(OCC2CCCO2)cccc1C(OC)OC]

To a suspension of sodium hydride (0.80 g, 60% in mineral oil) in anhydrous DMF (25 mL) was added a solution of methyl 2-(dimethoxymethyl)-6-hydroxybenzoate (3.00 g) obtained in Reference Example 201 in anhydrous DMF (5 mL), and the mixture was stirred at room temperature for 30 min. Tetrahydrofurfuryl bromide (3.31 g) was added to the reaction mixture, and the mixture was stirred under a nitrogen atmosphere at 90° C. for 24 hr. The reaction mixture was diluted with water, extracted with ethyl acetate, washed with saturated brine, dried over anhydrous sodium sulfate, and concentrated. The residue was purified by silica gel chromatography (petroleum ether-ethyl acetate) to give the title compound (1.77 g).

$^1$H NMR (400 MHz, CDCl$_3$) δ 1.80-2.09 (4H, m), 3.29 (6H, s), 3.76-3.84 (1H, m), 3.85-3.92 (4H, m), 3.92-4.00 (1H, m), 4.01-4.08 (1H, m), 4.20-4.29 (1H, m), 5.54 (1H, s), 6.92 (1H, d, J=8.4 Hz), 7.18 (1H, d, J=7.6 Hz), 7.33 (1H, t, J=8.0 Hz).

Reference Example 205

Methyl 2-formyl-6-((tetrahydrofuran-2-yl)methoxy)benzoate

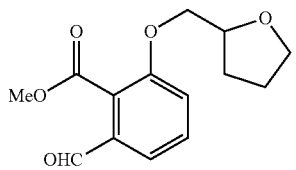 [SMILES: COC(=O)c1c(C=O)cccc1OCC1CCCO1]

To a solution of methyl 2-(dimethoxymethyl)-6-((tetrahydrofuran-2-yl)methoxy)benzoate (1.77 g) obtained in Reference Example 204 in dichloromethane-water (33 mL, 10:1) was added p-toluenesulfonic acid monohydrate (0.22 g), and the mixture was stirred at room temperature for 16 hr. To the reaction mixture was added saturated aqueous sodium hydrogen carbonate solution, and the mixture was extracted with dichloromethane (10 mL×3), washed with saturated brine, dried over anhydrous sodium sulfate, and concentrated. The residue was purified by silica gel column chromatography (petroleum ether-ethyl acetate) to give the title compound (1.12 g).

$^1$H NMR (400 MHz, CDCl$_3$) δ 1.80-2.11 (4H, m), 3.75-3.84 (1H, m), 3.85-3.93 (1H, m), 3.95 (3H, s), 4.00-4.12 (2H, m), 4.20-4.30 (1H, m), 7.24 (1H, d, J=8.0 Hz), 7.46 (1H, dt, J=7.6, 0.8 Hz), 7.49-7.55 (1H, m), 9.96 (1H, s).

Reference Example 206

Ethyl 2-(2-fluoro-6-methoxyphenoxy)-4-vinylnicotinate

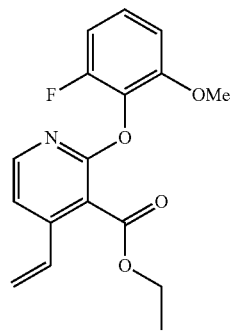 [SMILES: C=Cc1ccnc(Oc2c(F)cccc2OC)c1C(=O)OCC]

A solution of ethyl 2-fluoro-4-vinylnicotinate (0.30 g) obtained in Reference Example 118, 2-fluoro-6-methoxyphenol (0.66 g) and potassium carbonate (1.06 g) in DMF (6 mL) was stirred at 100° C. overnight. The reaction mixture was diluted with ethyl acetate, washed with water and saturated brine, dried over anhydrous sodium sulfate, and concentrated. The residue was purified by NH silica gel chromatography (hexane-ethyl acetate) to give the title compound (0.32 g).

$^1$H NMR (300 MHz, CDCl$_3$) δ 1.40 (3H, t, J=7.1 Hz), 3.79 (3H, s), 4.46 (2H, q, J=7.1 Hz), 5.56 (1H, d, J=11.1 Hz), 5.94 (1H, d, J=17.4 Hz), 6.73-6.87 (3H, m), 7.08-7.20 (2H, m), 8.05 (1H, d, J=5.5 Hz).

Reference Example 207

Ethyl 2-(2,4-difluoro-6-methylphenoxy)-4-vinylnicotinate

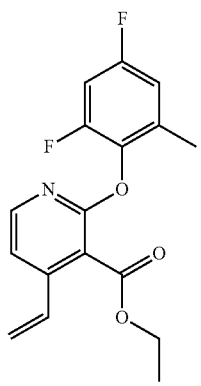 [SMILES: C=Cc1ccnc(Oc2c(C)cc(F)cc2F)c1C(=O)OCC]

A solution of ethyl 2-fluoro-4-vinylnicotinate (0.35 g) obtained in Reference Example 118, 2,4-difluoro-6-methylphenol (0.78 g) and potassium carbonate (1.24 g) in DMF (6 mL) was stirred at 100° C. overnight. The reaction mixture was diluted with ethyl acetate, washed with water and saturated brine, dried over anhydrous sodium sulfate, and concentrated. The residue was purified by NH silica gel chromatography (hexane-ethyl acetate) to give the title compound (0.47 g).

$^1$H NMR (300 MHz, CDCl$_3$) δ 1.40 (3H, t, J=7.1 Hz), 2.21 (3H, s), 4.46 (2H, q, J=7.2 Hz), 5.59 (1H, d, J=11.0 Hz), 5.96 (1H, d, J=17.4 Hz), 6.72-6.89 (3H, m), 7.16 (1H, d, J=5.5 Hz), 8.05 (1H, d, J=5.3 Hz).

Reference Example 208

(2-bromo-4,6-difluorophenoxy)(tert-butyl)dimethylsilane

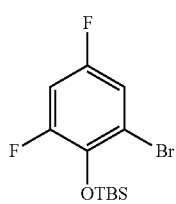

To a solution of 2-bromo-4,6-difluorophenol (16.1 g) and imidazole (7.85 g) in DMF was added tert-butylchlorodimethylsilane (11.6 g), and the mixture was stirred at room temperature for 2 hr. The reaction mixture was diluted with ethyl acetate, washed with 1N hydrochloric acid, saturated sodium hydrogen carbonate, and saturated brine, dried over anhydrous sodium sulfate, and concentrated to give the title compound (17.0 g).

$^1$H NMR (300 MHz, CDCl$_3$) δ 0.21-0.25 (6H, m), 1.02-1.07 (9H, m), 6.82 (1H, ddd, J=10.7, 8.1, 3.1 Hz), 7.04-7.11 (1H, m).

Reference Example 209

2-cyclopropyl-4,6-difluorophenol

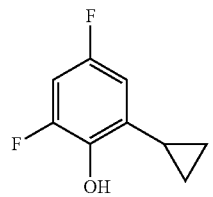 [SMILES: Oc1c(F)cc(F)cc1C1CC1]

To a suspension of (2-bromo-4,6-difluorophenoxy)(tert-butyl)dimethylsilane (3.00 g) obtained in Reference Example 208, cyclopropylboronic acid (1.20 g), potassium phosphate (5.91 g) and tricyclohexylphosphine (1.04 g) in toluene-water (20.5 mL, 40:1) was added palladium acetate (0.21 g), and the mixture was stirred under an argon atmosphere at 100° C. overnight. The reaction mixture was diluted with ethyl acetate, and the insoluble material was filtered off. The filtrate was washed with 1N hydrochloric acid, saturated aqueous sodium hydrogen carbonate solution, and saturated brine, and dried over anhydrous sodium sulfate. The residue was purified by silica gel chromatography (hexane-ethyl acetate) to give the title compound (0.27 g).

$^1$H NMR (300 MHz, CDCl$_3$) δ 0.61-0.72 (2H, m), 0.95-1.07 (2H, m), 2.06-2.16 (1H, m), 5.10 (1H, d, J=3.8 Hz), 6.39 (1H, dt, J=9.5, 2.4 Hz), 6.67 (1H, ddd, J=10.5, 8.0, 3.0 Hz).

Reference Example 210

Ethyl 2-(2-cyclopropyl-4,6-difluorophenoxy)-4-vinylnicotinate

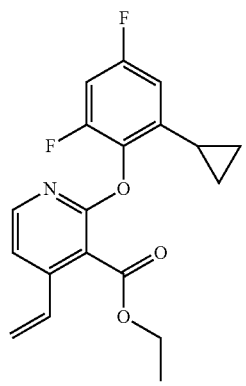 [SMILES: C=Cc1ccnc(Oc2c(F)cc(F)cc2C2CC2)c1C(=O)OCC]

A solution of ethyl 2-fluoro-4-vinylnicotinate (0.21 g) obtained in Reference Example 118, 2-cyclopropyl-4,6-difluorophenol (0.27 g) obtained in Reference Example 209 and potassium carbonate (0.74 g) in DMF (8 mL) was stirred at 100° C. overnight. The reaction mixture was diluted with ethyl acetate, washed with water and saturated brine, dried over anhydrous sodium sulfate, and concentrated. The residue was purified by NH silica gel chromatography (hexane-ethyl acetate) to give the title compound (0.19 g).

¹H NMR (300 MHz, CDCl₃) δ 0.59-0.68 (2H, m), 0.83-0.94 (2H, m), 1.35-1.45 (3H, m), 1.94-2.07 (1H, m), 4.41-4.52 (2H, m), 5.59 (1H, d, J=11.0 Hz), 5.96 (1H, d, J=17.6 Hz), 6.42 (1H, dt, J=9.6, 2.4 Hz), 6.67-6.89 (2H, m), 7.16 (1H, d, J=5.5 Hz), 8.07 (1H, d, J=5.5 Hz).

Reference Example 211

Ethyl 2-(2-fluoro-4-(trifluoromethoxy)phenoxy)-4-vinylnicotinate

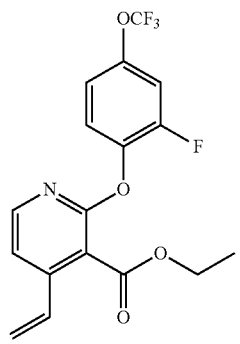 [SMILES: C=Cc1ccnc(Oc2ccc(OC(F)(F)F)cc2F)c1C(=O)OCC]

A solution of ethyl 2-fluoro-4-vinylnicotinate (0.30 g) obtained in Reference Example 118, 2-fluoro-4-(trifluoromethoxy)phenol (0.60 g) obtained by a known method (WO2008/130581) and potassium carbonate (0.64 g) in DMF (10 mL) was stirred at 100° C. overnight. The reaction mixture was diluted with ethyl acetate, washed with water and saturated brine, dried over anhydrous sodium sulfate, and concentrated. The residue was purified by NH silica gel chromatography (hexane-ethyl acetate) to give the title compound (0.47 g).

¹H NMR (300 MHz, DMSO-d₆) δ 1.25-1.36 (3H, m), 4.40 (2H, q, J=7.2 Hz), 5.66-5.76 (1H, m), 6.16-6.26 (1H, m), 6.75 (1H, dd, J=17.4, 11.0 Hz), 7.27-7.34 (1H, m), 7.44-7.50 (1H, m), 7.53 (1H, d, J=5.5 Hz), 7.61 (1H, dd, J=10.8, 2.5 Hz), 8.16 (1H, d, J=5.5 Hz).

Reference Example 212

Ethyl 2-(2-cyano-4-(trifluoromethoxy)phenoxy)-4-vinylnicotinate

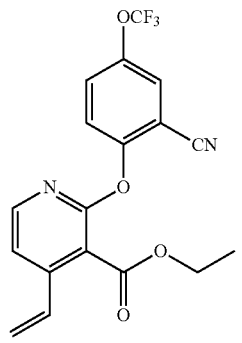 [SMILES: C=Cc1ccnc(Oc2ccc(OC(F)(F)F)cc2C#N)c1C(=O)OCC]

A solution of ethyl 2-fluoro-4-vinylnicotinate (0.30 g) obtained in Reference Example 118, 2-hydroxy-5-(trifluoromethoxy)benzonitrile (0.62 g) and potassium carbonate (0.64 g) in DMF (10 mL) was stirred at 100° C. overnight. The reaction mixture was diluted with ethyl acetate, washed with water and saturated brine, dried over anhydrous sodium sulfate, and concentrated. The residue was purified by NH silica gel chromatography (hexane-ethyl acetate) to give the title compound (0.096 g).

¹H NMR (300 MHz, CDCl₃) δ 1.41 (3H, t, J=7.1 Hz), 4.47 (2H, q, J=7.1 Hz), 5.63 (1H, d, J=11.1 Hz), 5.99 (1H, d, J=17.4 Hz), 6.85 (1H, dd, J=17.4, 11.0 Hz), 7.28 (1H, d, J=5.5 Hz), 7.36-7.56 (3H, m), 8.12 (1H, d, J=5.5 Hz).

Reference Example 213

2-(4-bromobenzyl)-4-(2,4-difluoro-6-methylphenoxy)-1H-pyrrolo[3,4-c]pyridin-3 (2H)-one

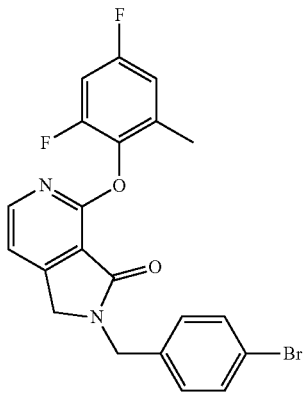 [SMILES: Cc1cc(F)cc(F)c1Oc1nccc2c1C(=O)N(Cc1ccc(Br)cc1)C2]

To a solution of ethyl 2-(2,4-difluoro-6-methylphenoxy)-4-vinylnicotinate (0.47 g) obtained in Reference Example 207 in acetone-acetonitrile-water (1:1:1, 12 mL) were added sodium periodate (1.57 g) and osmium oxide (immobilized catalyst I) (0.19 g), and the mixture was stirred at room temperature overnight. The insoluble material was filtered off, and the filtrate was concentrated. The residue was dissolved in THF (10 mL), (4-bromophenyl)methanamine (0.27 g) and anhydrous magnesium sulfate (1.77 g) were added, and the mixture was stirred for 20 min. The insoluble material was filtered off, and the filtrate was concentrated. The residue was dissolved in acetic acid (10 mL), sodium triacetoxyborohydride (0.62 g) was added, and the mixture was stirred overnight. The reaction mixture was diluted with ethyl acetate and saturated aqueous sodium hydrogen carbonate solution, and the organic layer was separated, washed with saturated brine, dried over anhydrous sodium sulfate, and concentrated. The concentrate was purified by NH silica gel chromatography (hexane-ethyl acetate) to give the title compound (0.23 g).

¹H NMR (300 MHz, CDCl₃) δ 2.23-2.30 (3H, m), 4.29 (2H, s), 4.75 (2H, s), 6.80 (2H, d, J=8.9 Hz), 7.06 (1H, d, J=5.1 Hz), 7.24 (2H, d, J=8.3 Hz), 7.45-7.54 (2H, m), 8.18 (1H, d, J=5.1 Hz).

Reference Example 214

2-(4-bromobenzyl)-4-(2-cyclopropyl-4,6-difluorophenoxy)-1H-pyrrolo[3,4-c]pyridin-3 (2H)-one

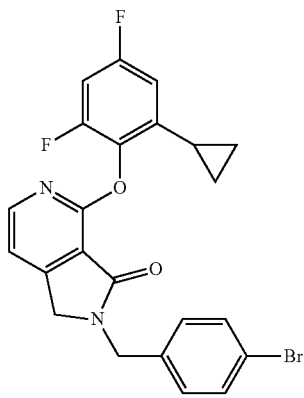 [SMILES: O=C1c2c(ccnc2Oc2c(F)cc(F)cc2C2CC2)CN1Cc1ccc(Br)cc1]

To a solution of ethyl 2-(2-cyclopropyl-4,6-difluorophenoxy)-4-vinylnicotinate (0.19 g) obtained in Reference Example 210 in acetone-acetonitrile-water (1:1:1, 9 mL) were added sodium periodate (0.59 g) and osmium oxide (immobilized catalyst I) (0.070 g), and the mixture was stirred at room temperature overnight. The insoluble material was filtered off, and the filtrate was concentrated. The residue was diluted with ethyl acetate and water, and the organic layer was separated, washed with saturated brine, dried over anhydrous sodium sulfate, and concentrated. The residue was dissolved in THF (5 mL), (4-bromophenyl)methanamine (0.10 g) and anhydrous magnesium sulfate (0.23 g) were added, and the mixture was stirred for 20 min. The insoluble material was filtered off, and the filtrate was concentrated. The residue was dissolved in acetic acid (5 mL), sodium triacetoxyborohydride (0.23 g) was added, and the mixture was stirred overnight. The reaction mixture was diluted with ethyl acetate and saturated aqueous sodium hydrogen carbonate solution, and the organic layer was separated, washed with saturated brine, dried over anhydrous sodium sulfate, and concentrated. The concentrate was purified by NH silica gel chromatography (hexane-ethyl acetate) to give the title compound (0.072 g).

$^1$H NMR (300 MHz, DMSO-d$_6$) δ 0.73 (2H, d, J=3.4 Hz), 0.79-0.92 (2H, m), 1.84-1.97 (1H, m), 4.49 (2H, s), 4.70 (2H, s), 6.71 (1H, dt, J=9.9, 2.3 Hz), 7.19 (1H, ddd, J=10.4, 8.6, 2.9 Hz), 7.30 (2H, d, J=8.5 Hz), 7.36 (1H, d, J=5.1 Hz), 7.53-7.61 (2H, m), 8.21 (1H, d, J=5.1 Hz).

Reference Example 215

Methyl 2-(2,4,6-trifluorophenoxy)-4-vinylnicotinate

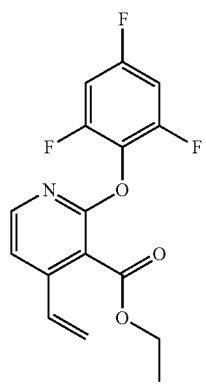 [SMILES: C=Cc1ccnc(Oc2c(F)cc(F)cc2F)c1C(=O)OCC]

To a solution of 2,4,6-trifluorophenol (0.40 g) in DMF (10 mL) was added potassium carbonate (1.01 g), and the mixture was stirred under an argon atmosphere at room temperature for 10 min. To the reaction solution was added methyl 2-fluoro-4-vinylnicotinate (0.44 g) obtained in Reference Example 102, and the mixture was stirred at 90° C. overnight. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.19 g).

MS: [M+H]$^+$ 310.0

$^1$H NMR (300 MHz, CDCl$_3$) δ 4.00 (3H, s), 5.61 (1H, d, J=11.3 Hz), 5.97 (1H, d, J=17.7 Hz), 6.74-6.89 (3H, m), 7.22 (1H, d, J=5.3 Hz), 8.07 (1H, d, J=5.3 Hz).

Reference Example 216

Methyl 4-chloro-6-(2,4,6-trifluorophenoxyl)pyrimidine-5-carboxylate

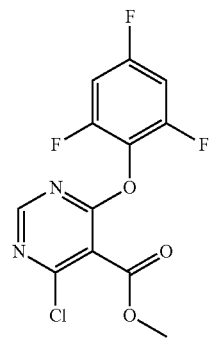 [SMILES: COC(=O)c1c(Cl)ncnc1Oc1c(F)cc(F)cc1F]

To a solution of methyl 4,6-dichloropyrimidine-5-carboxylate (0.90 g) and triethylamine (1.33 mL) in DMF (20 mL) was added 2,4,6-trifluorophenol (0.71 g) under an argon atmosphere at 0° C., and the mixture was stirred at the same temperature for 3 hr. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (1.15 g).

MS: [M+H]$^+$ 319.0

$^1$H NMR (300 MHz, CDCl$_3$) δ 4.04 (3H, s), 6.77-6.88 (2H, m), 8.56 (1H, s)

Reference Example 217

Methyl 4-(2,4,6-trifluorophenoxy)-6-vinylpyrimidine-5-carboxylate

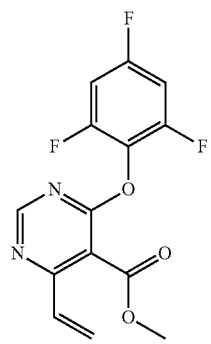 [SMILES: C=Cc1ncnc(Oc2c(F)cc(F)cc2F)c1C(=O)OC]

To a solution of methyl 4-chloro-6-(2,4,6-trifluorophenoxyl)pyrimidine-5-carboxylate (1.15 g) obtained in Reference Example 216, 4,4,5,5-tetramethyl-2-vinyl-1,3,2-dioxaborolane (0.673 mL) and 2M aqueous sodium carbonate solution (3.61 mL) in DME (20 mL) was added [1,1-bis(diphenylphosphino)ferrocene]dichloropalladium(II) (0.13 g), and the mixture was stirred under an argon atmosphere at 80° C. for 6 hr. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.56 g).

$^1$H NMR (300 MHz, CDCl$_3$) δ 3.98 (3H, s), 5.72 (1H, d, J=2.6 Hz), 5.75 (1H, d, J=2.6 Hz), 6.66-6.85 (3H, m), 9.11 (1H, s).

Reference Example 218

Methyl 4-formyl-6-(2,4,6-trifluorophenoxyl)pyrimidine-5-carboxylate

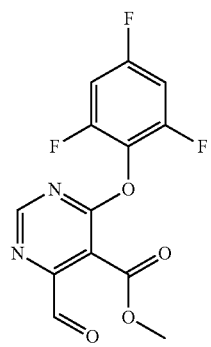 [SMILES: COC(=O)c1c(C=O)ncnc1Oc1c(F)cc(F)cc1F]

A mixed solution of methyl 4-(2,4,6-trifluorophenoxy)-6-vinylpyrimidine-5-carboxylate (0.61 g) obtained in Reference Example 217, sodium periodate (2.10 g) and osmium oxide (immobilized catalyst I) (0.25 g) in acetonitrile (12 mL)-acetone (12 mL)-water (12 mL) was stirred at room temperature overnight. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (0.23 g).

MS: [M+H]$^+$ 313.0

$^1$H NMR (300 MHz, CDCl$_3$) δ 4.06 (3H, s), 6.79-6.89 (2H, m), 8.94 (1H, s), 10.04 (1H, s).

Reference Example 219

Ethyl 2-(4-cyano-2-fluorophenoxy)-4-vinylnicotinate

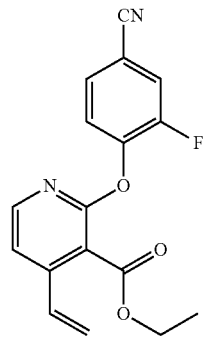 [SMILES: C=Cc1ccnc(Oc2ccc(C#N)cc2F)c1C(=O)OCC]

To a solution of 3-fluoro-4-hydroxybenzonitrile (0.46 g) in DMF (12 mL) was added potassium carbonate (1.25 g), and the mixture was stirred under an argon atmosphere at room temperature for 10 min. To the reaction mixture was added ethyl 2-fluoro-4-vinylnicotinate (0.59 g) obtained in Reference Example 118, and the mixture was stirred at 90° C. overnight. To the reaction mixture was added 3-fluoro-4-hydroxybenzonitrile (0.46 g) at room temperature, and the mixture was stirred under an argon atmosphere at 120° C. for 6 hr. Furthermore, 3-fluoro-4-hydroxybenzonitrile (0.46 g) was added at room temperature, and the mixture was stirred under an argon atmosphere at 120° C. overnight. The reaction mixture was diluted with saturated aqueous sodium hydrogen carbonate solution and ethyl acetate, and the organic layer was separated, washed with saturated brine, dried over anhydrous magnesium sulfate and concentrated. The residue was purified by silica gel chromatography (hexane-ethyl acetate) to give the title compound (0.29 g).

MS: [M+H]$^+$ 313.1

$^1$H NMR (300 MHz, CDCl$_3$) δ 1.40 (3H, t, J=7.2 Hz), 4.46 (2H, q, J=7.2 Hz), 5.63 (1H, d, J=10.9 Hz), 5.99 (1H, d, J=17.3 Hz), 6.84 (1H, dd, J=17.3, 10.9 Hz), 7.25 (1H, d, J=5.3 Hz), 7.35-7.42 (1H, m), 7.47-7.54 (2H, m), 8.08 (1H, d, J=5.3 Hz).

Reference Example 220

Ethyl 2-(4-cyano-2-fluorophenoxy)-4-formylnicotinate

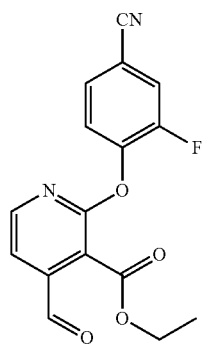 [SMILES: CCOC(=O)c1c(C=O)ccnc1Oc1ccc(C#N)cc1F]

A mixed solution of ethyl 2-(4-cyano-2-fluorophenoxy)-4-vinylnicotinate (0.29 g) obtained in Reference Example 219, sodium periodate (0.99 g) and osmium oxide (immobilized catalyst I) (0.12 g) in acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (0.22 g).

$^1$H NMR (300 MHz, CDCl$_3$) δ 1.43 (3H, t, J=7.2 Hz), 4.53 (2H, q, J=7.2 Hz), 7.41 (1H, t, J=8.1 Hz), 7.49-7.58 (3H, m), 8.37 (1H, d, J=5.3 Hz), 10.19 (1H, s).

Reference Example 221

Methyl 4-chloro-6-(4-cyano-2-fluorophenoxy)pyrimidine-5-carboxylate

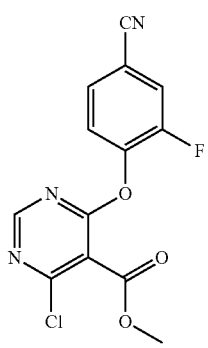 [SMILES: COC(=O)c1c(Cl)ncnc1Oc1ccc(C#N)cc1F]

To a solution of methyl 4,6-dichloropyrimidine-5-carboxylate (0.90 g) and triethylamine (1.33 mL) in THF (20 mL) was added 3-fluoro-4-hydroxybenzonitrile (0.63 g) under an argon atmosphere at 0° C., and the mixture was stirred at the same temperature for 1 hr. After stirring at room temperature for 1 hr, the mixture was stirred at 60° C. for 5 hr. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.38 g)

MS: [M+H]$^+$ 308.0

$^1$H NMR (300 MHz, CDCl$_3$) δ 4.04 (3H, s), 7.40 (1H, dd, J=8.6, 7.3 Hz), 7.51-7.60 (2H, m), 8.56 (1H, s).

Reference Example 222

Methyl 4-(4-cyano-2-fluorophenoxy)-6-vinylpyrimidine-5-carboxylate

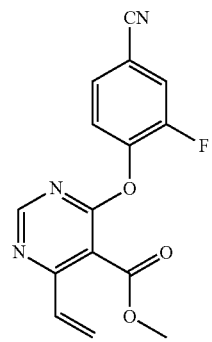 [SMILES: C=Cc1ncnc(Oc2ccc(C#N)cc2F)c1C(=O)OC]

To a solution of methyl 4-chloro-6-(4-cyano-2-fluorophenoxy)pyrimidine-5-carboxylate (0.38 g) obtained in Reference Example 221, 4,4,5,5-tetramethyl-2-vinyl-1,3,2-dioxaborolane (0.23 mL) and 2M aqueous sodium carbonate solution (1.24 mL) in DME (8 mL) was added [1,1-bis(diphenylphosphino)ferrocene]dichloropalladium(II) (0.090 g), and the mixture was stirred under an argon atmosphere at 80° C. overnight and at room temperature for 2 days. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.14 g).

MS: [M+H]$^+$ 300.0

$^1$H NMR (300 MHz, CDCl$_3$) δ 4.02 (3H, s), 5.82 (1H, dd, J=10.4, 1.9 Hz), 6.72-6.81 (1H, m), 6.86-6.98 (1H, m), 7.36-7.44 (1H, m), 7.50-7.59 (2H, m), 8.67 (1H, s).

Reference Example 223

Methyl 4-(4-cyano-2-fluorophenoxy)-6-formylpyrimidine-5-carboxylate

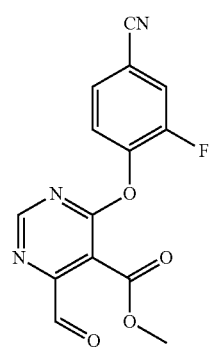 [SMILES: COC(=O)c1c(C=O)ncnc1Oc1ccc(C#N)cc1F]

A mixed solution of methyl 4-(4-cyano-2-fluorophenoxy)-6-vinylpyrimidine-5-carboxylate (0.14 g) obtained in Reference Example 222, sodium periodate (0.50 g) and osmium oxide (immobilized catalyst I) (0.059 g) in acetonitrile (3 mL)-acetone (3 mL)-water (3 mL) was stirred at room temperature overnight. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (0.072 g).

MS: [M+H]+ 302.0

1H NMR (300 MHz, CDCl3) δ 4.05 (3H, s), 7.41 (1H, dd, J=8.7, 7.4 Hz), 7.51-7.60 (2H, m), 8.92 (1H, s), 10.03 (1H, s).

Reference Example 224

Methyl 4-chloro-6-(2,6-difluorophenoxyl)pyrimidine-5-carboxylate

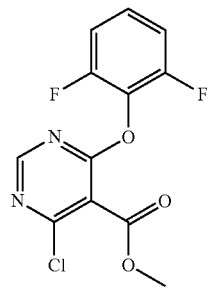 [SMILES: COC(=O)c1c(Cl)ncnc1Oc1c(F)cccc1F]

To a solution of methyl 4,6-dichloropyrimidine-5-carboxylate (1.90 g) and triethylamine (2.81 mL) in THF (40 mL) was added 2,6-difluorophenol (1.25 g) under an argon atmosphere at 0° C., and the mixture was stirred at the same temperature for 1 hr. After stirring at room temperature for 2 hr, the mixture was stirred at 60° C. for 1 hr. The reaction mixture was diluted with water and ethyl acetate, and the organic layer was separated, washed with saturated brine, dried over anhydrous magnesium sulfate and concentrated. The residue of other lot was combined, and the mixture was purified by silica gel chromatography (hexane-ethyl acetate) to give the title compound (0.95 g).

MS: [M+H]+ 300.9

1H NMR (300 MHz, CDCl3) δ 4.04 (3H, s), 7.00-7.09 (2H, m), 7.20-7.30 (1H, m), 8.56 (1H, s).

Reference Example 225

Methyl 4-(2,6-difluorophenoxy)-6-vinylpyrimidine-5-carboxylate

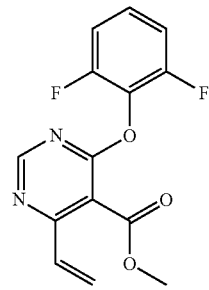 [SMILES: C=Cc1ncnc(Oc2c(F)cccc2F)c1C(=O)OC]

To a solution of methyl 4-chloro-6-(2,6-difluorophenoxyl)pyrimidine-5-carboxylate (0.95 g) obtained in Reference Example 224, 4,4,5,5-tetramethyl-2-vinyl-1,3,2-dioxaborolane (0.58 mL) and 2M aqueous sodium carbonate solution (3.16 mL) in DME (20 mL) was added [1,1-bis(diphenylphosphino)ferrocene]dichloropalladium(II) (0.12 g), and the mixture was stirred under an argon atmosphere at 80° C. overnight. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.22 g).

MS: [M+H]+ 293.1

1H NMR (300 MHz, CDCl3) δ 4.02 (3H, s), 5.80 (1H, dd, J=10.4, 1.7 Hz), 6.70-6.78 (1H, m), 6.88-6.99 (1H, m), 7.00-7.08 (2H, m), 7.20-7.27 (1H, m), 8.69 (1H, s).

Reference Example 226

Methyl 4-(2,6-difluorophenoxy)-6-formylpyrimidine-5-carboxylate

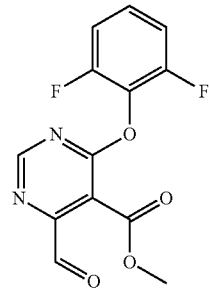

A mixed solution of methyl 4-(2,6-difluorophenoxy)-6-vinylpyrimidine-5-carboxylate (0.21 g) obtained in Reference Example 225, sodium periodate (0.77 g) and osmium oxide (immobilized catalyst I) (0.091 g) in acetonitrile (4 mL)-acetone (4 mL)-water (4 mL) was stirred at room temperature overnight. The insoluble material was filtered off, and the filtrate was diluted with ethyl acetate. The organic layer was separated, washed with saturated brine, dried over anhydrous magnesium sulfate, and concentrated.

The residue was purified by silica gel chromatography (hexane-ethyl acetate) to give the title compound (0.14 g).

MS: [M+H]+ 295.0

¹H NMR (300 MHz, CDCl₃) δ 4.06 (3H, s), 7.01-7.11 (2H, m), 7.24-7.30 (1H, m), 8.94 (1H, s), 10.05 (1H, s).

Reference Example 227

Ethyl 2-(4-bromo-2,6-difluorophenoxy)-4-vinylnicotinate

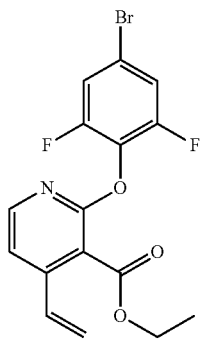 [SMILES: C=Cc1ccnc(Oc2c(F)cc(Br)cc2F)c1C(=O)OCC]

To a solution of 4-bromo-2,6-difluorophenol (2.54 g) and potassium carbonate (2.29 g) in DMF (20 mL) was added ethyl 2-fluoro-4-vinylnicotinate (1.08 g) obtained in Reference Example 118, and the mixture was stirred under an argon atmosphere at 120° C. overnight. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.63 g).

MS: [M+H]+ 384.0

¹H NMR (300 MHz, CDCl₃) δ 1.41 (3H, t, J=7.1 Hz), 4.47 (2H, q, J=7.2 Hz), 5.61 (1H, d, J=11.0 Hz), 5.97 (1H, d, J=17.4 Hz), 6.85 (1H, dd, J=17.4, 11.0 Hz), 7.17-7.24 (3H, m), 8.06 (1H, d, J=5.5 Hz).

Reference Example 228

Ethyl 2-(4-cyano-2,6-difluorophenoxy)-4-vinylnicotinate

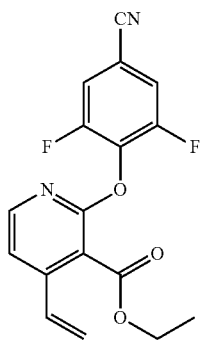 [SMILES: C=Cc1ccnc(Oc2c(F)cc(C#N)cc2F)c1C(=O)OCC]

To a solution of ethyl 2-(4-bromo-2,6-difluorophenoxy)-4-vinylnicotinate (0.30 g) obtained in Reference Example 227, zinc cyanide (0.12 g) and DPPF (0.087 g) in DMA (6 mL) was added Pd₂(dba)₃ (0.072 g) under an argon atmosphere at room temperature, and the mixture was stirred at 120° C. for 1 hr. The reaction mixture was diluted with 14% aqueous ammonia and ethyl acetate, and the organic layer was separated, washed with saturated brine, dried over anhydrous magnesium sulfate and concentrated. The residue was purified by silica gel chromatography (hexane-ethyl acetate) to give the title compound (0.19 g).

MS: [M+H]+ 331.0

¹H NMR (300 MHz, CDCl₃) δ 1.41 (3H, t, J=7.2 Hz), 4.47 (2H, q, J=7.2 Hz), 5.63 (1H, d, J=11.1 Hz), 5.99 (1H, d, J=17.4 Hz), 6.86 (1H, dd, J=17.5, 11.0 Hz), 7.25 (1H, m), 7.35 (2H, d, J=6.6 Hz), 8.04 (1H, d, J=5.5 Hz).

Reference Example 229

Ethyl 2-(4-cyano-2,6-difluorophenoxy)-4-formylnicotinate

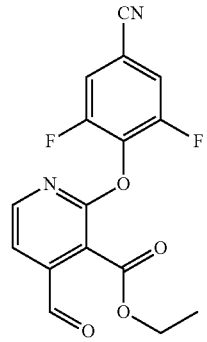 [SMILES: CCOC(=O)c1c(C=O)ccnc1Oc1c(F)cc(C#N)cc1F]

A mixed solution of ethyl 2-(4-cyano-2,6-difluorophenoxy)-4-vinylnicotinate (0.41 g) obtained in Reference Example 228, sodium periodate (1.33 g) and osmium oxide (immobilized catalyst I) (0.16 g) in acetonitrile (8 mL)-acetone (8 mL)-water (8 mL) was stirred under an argon atmosphere at room temperature overnight. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (0.29 g).

MS: [M+H]+ 332.8

¹H NMR (300 MHz, CDCl₃) δ 1.43 (3H, t, J=7.2 Hz), 4.53 (2H, q, J=7.1 Hz), 7.36 (2H, d, J=6.6 Hz), 7.53 (1H, d, J=5.1 Hz), 8.33 (1H, d, J=5.1 Hz), 10.20 (1H, s).

Reference Example 230

Ethyl 2-(4-cyano-2,6-difluorophenoxy)-6-methylbenzoate

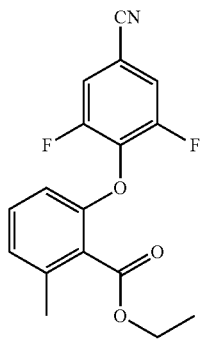 [SMILES: CCOC(=O)c1c(C)cccc1Oc1c(F)cc(C#N)cc1F]

To a solution of ethyl 2-hydroxy-6-methylbenzoate (5.00 g) and potassium carbonate (11.50 g) in DMF (100 mL) was added 3,4,5-trifluorobenzonitrile (5.13 g), and the mixture was stirred at 120° C. overnight. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (6.30 g).
MS: [M+H]$^+$ 318.1
$^1$H NMR (300 MHz, CDCl$_3$) δ 1.35 (3H, t, J=7.1 Hz), 2.39 (3H, s), 4.39 (2H, q, J=7.1 Hz), 6.54 (1H, d, J=8.3 Hz), 7.00 (1H, d, J=7.6 Hz), 7.17-7.24 (1H, m), 7.33 (2H, d, J=7.0 Hz).

Reference Example 231

Ethyl 2-(bromomethyl)-6-(4-cyano-2,6-difluorophenoxy)benzoate

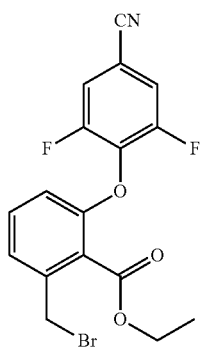 [SMILES: CCOC(=O)c1c(CBr)cccc1Oc1c(F)cc(C#N)cc1F]

A solution of ethyl 2-(4-cyano-2,6-difluorophenoxy)-6-methylbenzoate (6.30 g) obtained in Reference Example 230, N-bromosuccinimide (3.89 g) and 2,2'-azobis(isobutyronitrile) (0.33 g) in benzortrifluoride (120 mL) was stirred at 80° C. for hr. The reaction mixture was diluted with 10% aqueous sodium thiosulfate solution and ethyl acetate, and the organic layer was separated, washed with saturated brine, dried over anhydrous magnesium sulfate and concentrated. The residue was purified by silica gel chromatography (hexane-ethyl acetate) to give the title compound (5.09 g).

$^1$H NMR (300 MHz, CDCl$_3$) δ 1.39 (3H, t, J=7.2 Hz), 4.44 (2H, q, J=7.2 Hz), 4.61 (2H, s), 6.70 (1H, dd, J=8.2, 0.8 Hz), 7.20-7.25 (1H, m), 7.29-7.40 (3H, m).

Reference Example 232

Ethyl 2-(2-fluoro-4-formylphenoxy)-4-vinylnicotinate

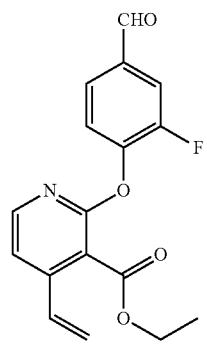 [SMILES: C=Cc1ccnc(Oc2ccc(C=O)cc2F)c1C(=O)OCC]

To a solution of 3-fluoro-4-hydroxybenzaldehyde (5.00 g) and potassium carbonate (6.73 g) in DMF (60 mL) was added ethyl 2-fluoro-4-vinylnicotinate (3.17 g) obtained in Reference Example 118, and the mixture was stirred under an argon atmosphere at 120° C. overnight. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (1.94 g).
MS: [M+H]$^+$ 316.1
$^1$H NMR (300 MHz, CDCl$_3$) δ 1.39 (3H, t, J=7.2 Hz), 4.46 (2H, q, J=7.2 Hz), 5.61 (1H, d, J=11.0 Hz), 5.98 (1H, d, J=17.4 Hz), 6.84 (1H, dd, J=17.6, 11.0 Hz), 7.24 (1H, d, J=5.5 Hz), 7.43 (1H, dd, J=8.3, 7.4 Hz), 7.68-7.75 (2H, m), 8.09 (1H, d, J=5.5 Hz), 9.96 (1H, d, J=1.9 Hz).

Reference Example 233

Ethyl 2-(4-(difluoromethyl)-2-fluorophenoxy)-4-vinylnicotinate

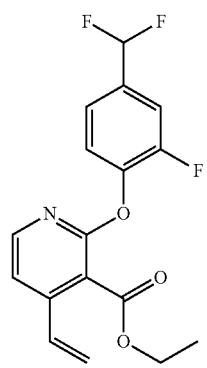 [SMILES: C=Cc1ccnc(Oc2ccc(C(F)F)cc2F)c1C(=O)OCC]

To a solution of ethyl 2-(2-fluoro-4-formylphenoxy)-4-vinylnicotinate (0.91 g) obtained in Reference Example 232 in benzortrifluoride (18 mL) was added DAST (0.84 mL) at 0° C., and the mixture was stirred at room temperature overnight. The mixture was diluted with saturated aqueous sodium hydrogen carbonate solution and ethyl acetate, and the organic layer was separated, washed with saturated brine, dried over anhydrous magnesium sulfate, and concentrated. The residue was combined with a residue separately obtained from a solution of ethyl 2-(2-fluoro-4-formylphenoxy)-4-vinylnicotinate (0.50 g) and DAST (0.46 mL) in benzortrifluoride (10 mL) by a similar operation, and the mixture was purified by silica gel chromatography (hexane-ethyl acetate) to give the title compound (1.10 g).

MS: [M+H]$^+$ 338.0

$^1$H NMR (300 MHz, CDCl$_3$) δ 1.40 (3H, t, J=7.1 Hz), 4.47 (2H, q, J=7.2 Hz), 5.61 (1H, d, J=11.0 Hz), 5.98 (1H, d, J=17.6 Hz), 6.44-6.90 (2H, m), 7.21 (1H, d, J=5.5 Hz), 7.32-7.40 (3H, m), 8.09 (1H, d, J=5.5 Hz).

Reference Example 234

Ethyl 2-(4-(difluoromethyl)-2-fluorophenoxy)-4-formylnicotinate

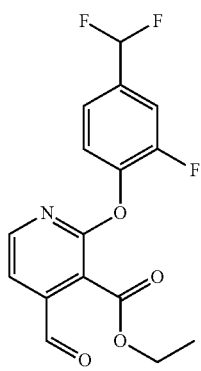 [SMILES: CCOC(=O)c1c(C=O)ccnc1Oc1ccc(C(F)F)cc1F]

A mixed solution of ethyl 2-(4-(difluoromethyl)-2-fluorophenoxy)-4-vinylnicotinate (1.10 g) obtained in Reference Example 233, sodium periodate (3.49 g) and osmium oxide (immobilized catalyst I) (0.42 g) in acetonitrile (22 mL)-acetone (22 mL)-water (22 mL) was stirred under an argon atmosphere at room temperature overnight. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (0.92 g).

MS: [M+H]$^+$ 340.0

$^1$H NMR (300 MHz, CDCl$_3$) δ 1.44 (3H, t, J=7.2 Hz), 4.54 (2H, q, J=7.2 Hz), 6.46-6.87 (1H, m), 7.34-7.41 (3H, m), 7.48 (1H, d, J=5.1 Hz), 8.37 (1H, d, J=5.1 Hz), 10.18 (1H, s).

Reference Example 235

Ethyl 2-(4-chloro-2-fluorophenoxy)-4-vinylnicotinate

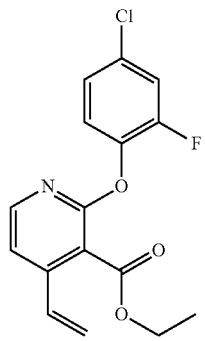 [SMILES: C=Cc1ccnc(Oc2ccc(Cl)cc2F)c1C(=O)OCC]

To a solution of 4-chloro-2-fluorophenol (4.36 mL) and potassium carbonate (7.08 g) in DMF (40 mL) was added ethyl 2-fluoro-4-vinylnicotinate (2.00 g) obtained in Reference Example 118, and the mixture was stirred under an argon atmosphere at 120° C. overnight and at room temperature for 2 days. The reaction mixture was diluted with water and ethyl acetate, and the organic layer was separated, washed with saturated brine, dried over anhydrous magnesium sulfate and concentrated. The residue was purified by NH silica gel chromatography (hexane-ethyl acetate) to give the title compound (1.91 g).

MS: [M+H]$^+$ 322.0

$^1$H NMR (300 MHz, CDCl$_3$) δ 1.40 (3H, t, J=7.2 Hz), 4.46 (2H, q, J=7.1 Hz), 5.60 (1H, J=11.0 Hz), 5.97 (1H, d, J=17.6 Hz), 6.82 (1H, dd, J=17.6, 11.0 Hz), 7.13-7.24 (4H, m), 8.08 (1H, d, J=5.3 Hz).

Reference Example 236

Ethyl 2-(4-chloro-2-fluorophenoxy)-4-formylnicotinate

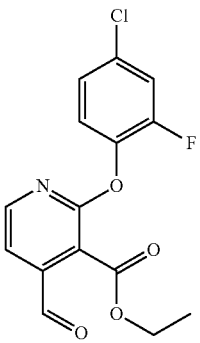 [SMILES: CCOC(=O)c1c(C=O)ccnc1Oc1ccc(Cl)cc1F]

A mixed solution of ethyl 2-(4-chloro-2-fluorophenoxy)-4-vinylnicotinate (1.91 g) obtained in Reference Example 235, sodium periodate (6.35 g) and osmium oxide (immobilized catalyst I) (0.76 g) in acetonitrile (40 mL)-acetone (40 mL)-water (40 mL) was stirred under an argon atmosphere at room temperature overnight. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (1.69 g).

$^1$H NMR (300 MHz, CDCl$_3$) δ 1.43 (3H, t, J=7.2 Hz), 4.53 (2H, q, J=7.2 Hz), 7.18-7.26 (3H, m), 7.47 (1H, d, J=5.1 Hz), 8.36 (1H, d, J=5.1 Hz), 10.17 (1H, s).

Reference Example 237

Ethyl 2-(2-fluoro-4-formylphenoxy)-6-methylbenzoate

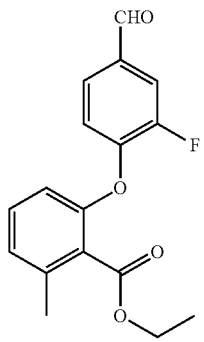 [SMILES: CCOC(=O)c1c(C)cccc1Oc1ccc(C=O)cc1F]

To a solution of ethyl 2-hydroxy-6-methylbenzoate (5.00 g) and potassium carbonate (11.50 g) in DMF (100 mL) was added 3,4-difluorobenzaldehyde (3.37 mL), and the mixture was stirred under an argon atmosphere at 90° C. for 30 min. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (6.98 g).

MS: [M+H]$^+$ 303.1

$^1$H NMR (300 MHz, CDCl$_3$) δ 1.20 (3H, t, J=7.1 Hz), 2.43 (3H, s), 4.28 (2H, q, J=7.2 Hz), 6.88 (1H, d, J=8.3 Hz), 6.98 (1H, t, J=8.0 Hz), 7.12 (1H, d, J=7.7 Hz), 7.30-7.37 (1H, m), 7.54-7.60 (1H, m), 7.70 (1H, dd, J=10.4, 1.9 Hz), 9.90 (1H, d, J=1.9 Hz).

Reference Example 238

Ethyl 2-(2-fluoro-4-(2,2,2-trifluoro-1-hydroxyethyl)phenoxy)-6-methylbenzoate

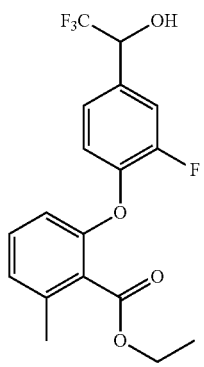 [SMILES: CCOC(=O)c1c(C)cccc1Oc1ccc(C(O)C(F)(F)F)cc1F]

To a solution of ethyl 2-(2-fluoro-4-formylphenoxy)-6-methylbenzoate (4.89 g) obtained in Reference Example 237 and (trifluoromethyl)trimethylsilane (5.06 mL) in THF (50 mL) was added 1M tetrabutylammonium fluoride THF solution (1.62 mL) at 0° C., and the mixture was stirred under an argon atmosphere at 0° C. for 2 hr. To the reaction mixture was added 1N hydrochloric acid (32 mL) at 0° C., and the mixture was stirred under an argon atmosphere at 0° C. for 2 hr. The reaction mixture was diluted with saturated aqueous sodium hydrogen carbonate solution and ethyl acetate, and the organic layer was separated, washed with saturated brine, dried over anhydrous magnesium sulfate and concentrated. The residue was purified by silica gel chromatography (hexane-ethyl acetate) to give the title compound (4.43 g).

MS: [M+H]$^+$ 373.1

$^1$H NMR (300 MHz, CDCl$_3$) δ 1.26 (3H, t, J=7.2 Hz), 2.40 (3H, s), 2.60 (1H, d, J=4.3 Hz), 4.32 (2H, q, J=7.1 Hz), 4.96-5.07 (1H, m), 6.76 (1H, d, J=8.1 Hz), 6.96-7.05 (2H, m), 7.17 (1H, d, J=8.1 Hz), 7.22-7.29 (1H, m), 7.34 (1H, dd, J=11.3, 1.7 Hz).

Reference Example 239

Ethyl 2-(2-fluoro-4-(2,2,2-trifluoroacetyl)phenoxy)-6-methylbenzoate

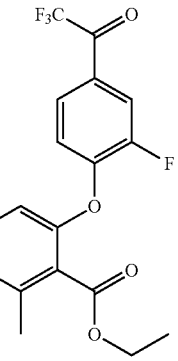

To a solution of sodium 2-iodobenzenesulfonate (0.14 g) and potassium monopersulfate (5.66 g) in acetonitrile (60 mL) was added ethyl 2-(2-fluoro-4-(2,2,2-trifluoro-1-hydroxyethyl)phenoxy)-6-methylbenzoate (3.43 g) obtained in Reference Example 238 at room temperature, and the mixture was stirred at 80° C. overnight. The insoluble material in the reaction mixture was filtered off, and the filtrate was concentrated. The residue was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (2.43 g).

MS: [M+H]$^+$ 371.1

$^1$H NMR (300 MHz, CDCl$_3$) δ 1.20 (3H, t, J=7.1 Hz), 2.44 (3H, s), 4.28 (2H, q, J=7.2 Hz), 6.88-6.98 (2H, m), 7.16 (1H, d, J=7.7 Hz), 7.33-7.41 (1H, m), 7.75-7.82 (1H, m), 7.89 (1H, dd, J=11.0, 1.3 Hz).

Reference Example 240

Ethyl 2-(bromomethyl)-6-(2-fluoro-4-(2,2,2-trifluoroacetyl)phenoxy)benzoate

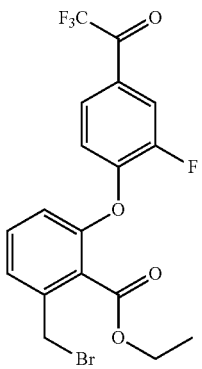 [SMILES: CCOC(=O)c1c(CBr)cccc1Oc1ccc(C(=O)C(F)(F)F)cc1F]

A solution of ethyl 2-(2-fluoro-4-(2,2,2-trifluoroacetyl)phenoxy)-6-methylbenzoate (2.43 g) obtained in Reference Example 239, N-bromosuccinimide (1.29 g) and 2,2'-azobis(isobutyronitrile) (0.11 g) in benzortrifluoride (50 mL) was stirred at 80° C. for 2 hr. The reaction mixture was diluted with 10% aqueous sodium thiosulfate solution and ethyl acetate, and the organic layer was separated, washed with saturated brine, dried over anhydrous magnesium sulfate and concentrated. The residue was purified by silica gel chromatography (hexane-ethyl acetate) to give the title compound (2.64 g).

MS: [M+H]$^+$ 450.1

$^1$H NMR (300 MHz, CDCl$_3$) δ 1.22 (3H, t, J=7.2 Hz), 4.32 (2H, q, J=7.2 Hz), 4.66 (2H, s), 6.92-6.99 (1H, m), 7.05 (1H, dd, J=8.1, 0.9 Hz), 7.34-7.39 (1H, m), 7.43-7.50 (1H, m), 7.78-7.85 (1H, m), 7.91 (1H, dd, J=11.0, 1.1 Hz).

Reference Example 241

Ethyl 2-(bromomethyl)-6-(2-fluoro-4-(2,2,2-trifluoro-1-hydroxyethyl)phenoxy)benzoate

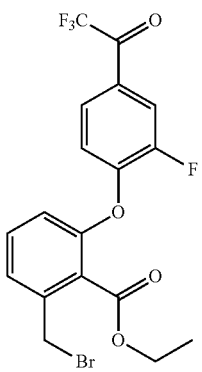 [SMILES: CCOC(=O)c1c(CBr)cccc1Oc1ccc(C(=O)C(F)(F)F)cc1F]

To a solution of ethyl 2-(bromomethyl)-6-(2-fluoro-4-(2,2,2-trifluoroacetyl)phenoxy)benzoate (0.20 g) obtained in Reference Example 240 in THF (2 mL) was added sodium tetrahydroborate (0.020 g) under an argon atmosphere at 0° C., and the mixture was stirred at 0° C. for 2 hr. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.19 g).

MS: [M+H]$^+$ 451.0

$^1$H NMR (300 MHz, CDCl$_3$) δ 1.29 (3H, t, J=7.2 Hz), 2.58-2.65 (1H, m), 4.37 (2H, q, J=7.1 Hz), 4.62 (2H, s), 6.87 (1H, d, J=8.3 Hz), 6.97-7.05 (1H, m), 7.15-7.25 (2H, m), 7.31-7.38 (2H, m).

Reference Example 242

Ethyl 2-(2-fluoro-4-(2,2,2-trifluoro-1-hydroxyethyl)phenoxy)-4-vinylnicotinate

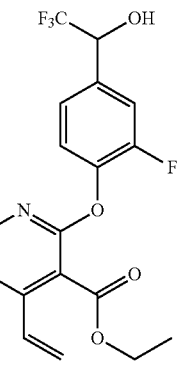

To a solution of ethyl 2-(2-fluoro-4-formylphenoxy)-4-vinylnicotinate (1.50 g) obtained in Reference Example 232 and (trifluoromethyl)trimethylsilane (1.49 mL) in THF (15 mL) was added 1M tetrabutylammonium fluoride THF solution (0.48 mL) at 0° C., and the mixture was stirred under an argon atmosphere at 0° C. for 2 hr. To the reaction mixture was added 1N hydrochloric acid (9.51 mL) at 0° C., and the mixture was stirred under an argon atmosphere at 0° C. for 2 hr. The reaction mixture was diluted with saturated aqueous sodium hydrogen carbonate solution and ethyl acetate, and the organic layer was separated, washed with saturated brine, dried over anhydrous magnesium sulfate and concentrated. The residue was purified by NH silica gel chromatography (hexane-ethyl acetate) to give the title compound (0.31 g).

MS: [M+H]$^+$ 386.1

$^1$H NMR (300 MHz, CDCl$_3$) δ 1.40 (3H, t, J=7.2 Hz), 3.66 (1H, d, J=5.3 Hz), 4.46 (2H, q, J=7.2 Hz), 4.86 (1H, quin, J=6.1 Hz), 5.62 (1H, d, J=11.3 Hz), 5.99 (1H, d, J=17.7 Hz), 6.83 (1H, dd, J=17.5, 11.1 Hz), 7.18-7.34 (4H, m), 8.09 (1H, d, J=5.7 Hz).

Reference Example 243

Ethyl 2-(4-acetyl-2-fluorophenoxy)-4-vinylnicotinate

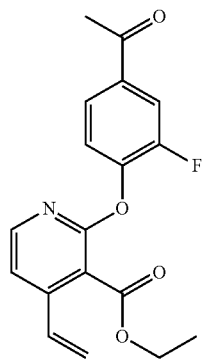 [SMILES: C=Cc1ccnc(Oc2ccc(C(C)=O)cc2F)c1C(=O)OCC]

To a solution of ethyl 2-fluoro-4-vinylnicotinate (2.11 g) obtained in Reference Example 118 and 1-(3-fluoro-4-hydroxyphenyl)ethanone (5.00 g) in DMF (40 mL) was added potassium carbonate (5.98 g), and the mixture was stirred under an argon atmosphere at 100° C. overnight. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (1.71 g).

MS: [M+H]$^+$ 330.0

$^1$H NMR (300 MHz, CDCl$_3$) δ 1.40 (3H, t, J=7.2 Hz), 2.61 (3H, s), 4.47 (2H, q, J=7.2 Hz), 5.62 (1H, d, J=11.1 Hz), 5.98 (1H, d, J=17.4 Hz), 6.84 (1H, dd, J=17.6, 11.0 Hz), 7.23 (1H, d, J=5.5 Hz), 7.35 (1H, t, J=7.9 Hz), 7.76-7.84 (2H, m), 8.09 (1H, d, J=5.5 Hz).

Reference Example 244

Ethyl 2-(2-fluoro-4-(1-hydroxyethyl)phenoxy)-4-vinylnicotinate

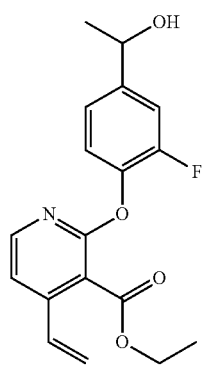 [SMILES: C=Cc1ccnc(Oc2ccc(C(C)O)cc2F)c1C(=O)OCC]

To a solution of ethyl 2-(4-acetyl-2-fluorophenoxy)-4-vinylnicotinate (0.80 g) obtained in Reference Example 243 in THF (16 mL) was added sodium tetrahydroborate (0.10 g) under an argon atmosphere at 0° C., and the mixture was stirred at room temperature overnight. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.62 g).

MS: [M+H]$^+$ 331.9

$^1$H NMR (300 MHz, CDCl$_3$) δ 1.40 (3H, t, J=7.1 Hz), 1.51 (3H, d, J=6.6 Hz), 1.83 (1H, d, J=3.8 Hz), 4.46 (2H, q, J=7.2 Hz), 4.92 (1H, dd, J=6.4, 3.8 Hz), 5.59 (1H, d, J=11.3 Hz), 5.97 (1H, d, J=17.6 Hz), 6.83 (1H, dd, J=17.6, 11.0 Hz), 7.13-7.26 (4H, m), 8.09 (1H, d, J=5.3 Hz).

Reference Example 245

Ethyl 2-(2-fluoro-4-(1-hydroxyethyl)phenoxy)-4-formylnicotinate

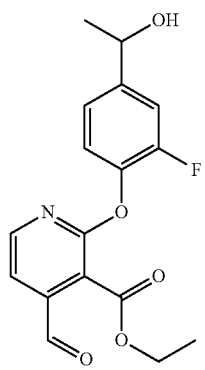 [SMILES: CCOC(=O)c1c(C=O)ccnc1Oc1ccc(C(C)O)cc1F]

A mixed solution of ethyl 2-(2-fluoro-4-(1-hydroxyethyl)phenoxy)-4-vinylnicotinate (0.62 g) obtained in Reference Example 244, sodium periodate (2.00 g) and osmium oxide (immobilized catalyst I) (0.24 g) in acetonitrile (12 mL)-acetone (12 mL)-water (12 mL) was stirred under an argon atmosphere at room temperature overnight. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (0.46 g).

MS: [M+H]$^+$ 334.0

$^1$H NMR (300 MHz, CDCl$_3$) δ 1.44 (3H, t, J=7.1 Hz), 1.52 (3H, dd, J=6.4, 1.7 Hz), 1.84 (1H, d, J=3.8 Hz), 4.53 (2H, q, J=7.1 Hz), 7.17-7.25 (3H, m), 7.43-7.47 (1H, m), 8.37 (1H, d, J=4.9 Hz), 10.18 (1H, s).

Reference Example 246

Methyl 4-chloro-6-(2-chloro-6-fluorophenoxy)pyrimidine-5-carboxylate

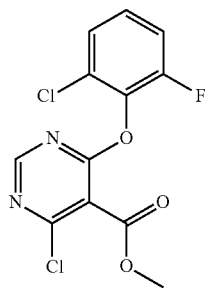 [SMILES: COC(=O)c1c(Cl)ncnc1Oc1c(F)cccc1Cl]

To a solution of methyl 4,6-dichloropyrimidine-5-carboxylate (0.50 g) and 2-chloro-6-fluorophenol (0.37 g) in DMF (10 mL) was added potassium carbonate (1.00 g) at 0° C., and the mixture was stirred at the same temperature for 5 hr. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.61 g).

MS: [M+H]$^+$ 317.0

$^1$H NMR (300 MHz, CDCl$_3$) δ 4.05 (3H, s), 7.11-7.34 (3H, m), 8.55 (1H, s).

Reference Example 247

Methyl 4-(2-chloro-6-fluorophenoxy)-6-vinylpyrimidine-5-carboxylate

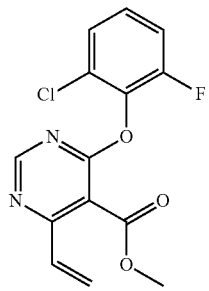 [SMILES: C=Cc1ncnc(Oc2c(F)cccc2Cl)c1C(=O)OC]

To a solution of methyl 4-chloro-6-(2-chloro-6-fluorophenoxy)pyrimidine-5-carboxylate (0.61 g) obtained in Reference Example 246, 4,4,5,5-tetramethyl-2-vinyl-1,3,2-dioxaborolane (0.33 g) and 2M aqueous sodium carbonate solution (1.92 mL) in DME (12 mL) was added [1,1-bis(diphenylphosphino)ferrocene]dichloropalladium(II) (0.14 g), and the mixture was stirred under an argon atmosphere at 80° C. for 5 hr. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.27 g).

MS: [M+H]$^+$ 309.1

$^1$H NMR (300 MHz, CDCl$_3$) δ 4.03 (3H, s), 5.80 (1H, dd, J=10.4, 1.7 Hz), 6.71-6.79 (1H, m), 6.89-7.00 (1H, m), 7.11-7.26 (2H, m), 7.28-7.32 (1H, m), 8.67 (1H, s).

Reference Example 248

Methyl 4-(2-chloro-6-fluorophenoxy)-6-formylpyrimidine-5-carboxylate

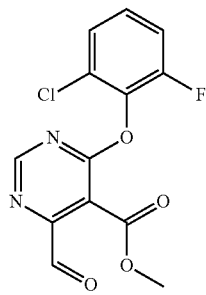 [SMILES: COC(=O)c1c(C=O)ncnc1Oc1c(F)cccc1Cl]

A mixed solution of methyl 4-(2-chloro-6-fluorophenoxy)-6-vinylpyrimidine-5-carboxylate (0.27 g) obtained in Reference Example 247, sodium periodate (0.94 g) and osmium oxide (immobilized catalyst I) (0.11 g) in acetonitrile (5 mL)-acetone (5 mL)-water (5 mL) was stirred under an argon atmosphere at room temperature for 9 hr. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (0.19 g).

MS: [M+H]$^+$ 311.0

$^1$H NMR (300 MHz, CDCl$_3$) δ 4.07 (3H, s), 7.13-7.21 (1H, m), 7.22-7.34 (2H, m), 8.93 (1H, s), 10.05 (1H, s).

Reference Example 249

Ethyl 2-(2-chloro-6-fluorophenoxy)-4-formylnicotinate

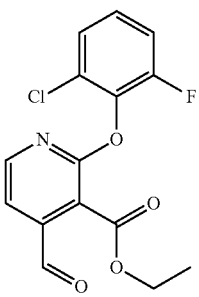 [SMILES: CCOC(=O)c1c(C=O)ccnc1Oc1c(F)cccc1Cl]

To a solution of ethyl 2-fluoro-4-vinylnicotinate (0.89 g) obtained in Reference Example 118 and 2-chloro-6-fluorophenol (2.00 g) in DMF (20 mL) was added potassium carbonate (2.51 g), and the mixture was stirred under an argon atmosphere at 120° C. overnight. The reaction mixture was diluted with water and ethyl acetate, and the organic layer was separated, washed with saturated brine, dried over anhydrous magnesium sulfate and concentrated. The residue was crudely purified by silica gel chromatography (hexane-ethyl acetate). A mixed solution of the obtained ethyl 2-(2-chloro-6-fluorophenoxy)-4-vinylnicotinate (0.77 g), sodium periodate (2.56 g) and osmium oxide (immobilized catalyst I) (0.30 g) in acetonitrile (15 mL)-acetone (15 mL)-water (15 mL) was stirred under an argon atmosphere at room temperature for 5 hr. The insoluble material was filtered off, and the filtrate was diluted with ethyl acetate. The organic layer was separated, washed with saturated brine, dried over anhydrous magnesium sulfate, and concentrated. The residue was purified by silica gel chromatography (hexane-ethyl acetate) to give the title compound (0.32 g).

MS: [M+H]$^+$ 324.0

$^1$H NMR (300 MHz, CDCl$_3$) δ 1.44 (3H, t, J=7.2 Hz), 4.54 (2H, q, J=7.2 Hz), 7.09-7.24 (2H, m), 7.27-7.31 (1H, m), 7.46 (1H, d, J=4.9 Hz), 8.33 (1H, d, J=5.3 Hz), 10.19 (1H, s).

Reference Example 251

2-(4-ethynylbenzyl)isoindoline-1,3-dione

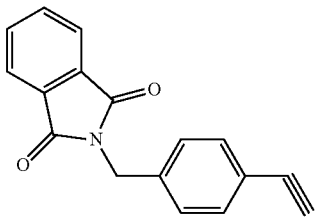 [SMILES: C#Cc1ccc(CN2C(=O)c3ccccc3C2=O)cc1]

To a solution of (4-ethynylphenyl)methanol (1.00 g), isoindoline-1,3-dione (1.11 g) and triphenylphosphine (2.08 g) in THF (15 mL) was added a solution of (E)-di-tert-butyl diazene-1,2-dicarboxylate (1.83 g) in toluene (15 mL) at room temperature, and the mixture was stirred at room temperature overnight. The reaction mixture was diluted with water and ethyl acetate, and the organic layer was separated, washed with saturated brine, dried over anhydrous magnesium sulfate and concentrated. The residue was washed with ethyl acetate-hexane (1:1) (40 mL) to give the title compound (1.05 g).

MS: [M+H]$^+$ 262.0

$^1$H NMR (300 MHz, CDCl$_3$) δ 3.05 (1H, s), 4.84 (2H, s), 7.36-7.47 (4H, m), 7.72 (2H, dd, J=5.5, 3.2 Hz), 7.85 (2H, dd, J=5.5, 3.0 Hz).

Reference Example 252

Ethyl 2-(2-methoxy-2-oxoethoxy)-4-vinylnicotinate

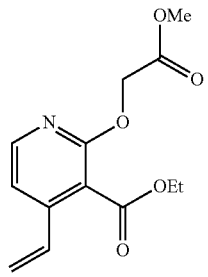 [SMILES: C=Cc1ccnc(OCC(=O)OC)c1C(=O)OCC]

To a solution of methyl 2-hydroxyacetate (1.27 g), sodium hydride (0.56 g) in THF (10 mL) was added ethyl 2-fluoro-4-vinylnicotinate (2.50 g) obtained in Reference Example 118 at 0° C., and the mixture was stirred at the same temperature for 1 hr. Water was added to the reaction mixture, and the mixture was diluted with ethyl acetate. The organic layer was separated, washed with water and saturated brine, dried over anhydrous sodium sulfate, and concentrated. The residue was purified by silica gel chromatography (hexane-ethyl acetate) to give the title compound (2.82 g).

$^1$H NMR (300 MHz, CDCl$_3$) δ 1.39 (3H, t, J=7.1 Hz), 3.75 (3H, s), 4.43 (2H, q, J=7.2 Hz), 4.92 (2H, s), 5.53 (1H, d, J 11.0 Hz), 5.91 (1H, d, J=17.4 Hz), 6.75 (1H, dd, J=17.5, 11.0 Hz), 7.08 (1H, d, J=5.3 Hz), 8.07 (1H, d, J=5.5 Hz).

Reference Example 253

Ethyl 4-formyl-2-(2-methoxy-2-oxoethoxy)nicotinate

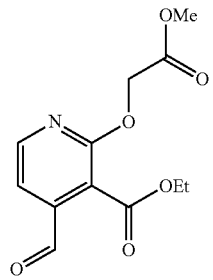 [SMILES: CCOC(=O)c1c(C=O)ccnc1OCC(=O)OC]

A mixed solution of ethyl 2-(2-methoxy-2-oxoethoxy)-4-vinylnicotinate (2.82 g) obtained in Reference Example 252, sodium periodate (9.10 g) and osmium oxide (immobilized catalyst I) (0.58 g) in acetonitrile (10 mL)-acetone (10 mL)-water (10 mL) was stirred at room temperature overnight. The insoluble material was filtered off, and the filtrate was diluted with ethyl acetate. The organic layer was separated, washed with saturated brine, dried over anhydrous magnesium sulfate, and concentrated to give the title compound (2.44 g).

$^1$H NMR (300 MHz, CDCl$_3$) δ 1.41 (3H, t, J=7.2 Hz), 3.76 (3H, s), 4.49 (2H, q, J=7.1 Hz), 4.98 (2H, s), 7.35 (1H, d, J=5.1 Hz), 8.37 (1H, d, J=5.3 Hz), 10.12 (1H, s).

Reference Example 254

Methyl ((2-(4-bromobenzyl)-3-oxo-2,3-dihydro-1H-pyrrolo[3,4-c]pyridin-4-yl)oxy)acetate

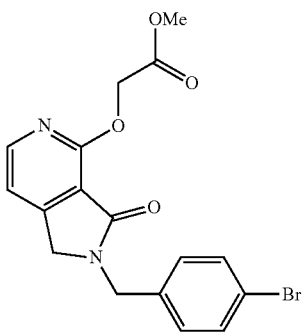 [SMILES: COC(=O)COc1nccc2c1C(=O)N(Cc1ccc(Br)cc1)C2]

To a solution of ethyl 4-formyl-2-(2-methoxy-2-oxoethoxy)nicotinate (2.44 g) obtained in Reference Example 253 in THF (10 mL) was added (4-bromophenyl)methanamine (1.78 g), and the mixture was stirred at room temperature for 1 hr. To the reaction mixture were added methanol (1 mL) and sodium triacetoxyhydroborate (9.70 g), and the mixture was stirred at room temperature overnight. The reaction mixture was neutralized with saturated aqueous sodium hydrogen carbonate solution, and diluted with water and ethyl acetate. The organic layer was separated, washed with saturated aqueous sodium hydrogen carbonate solution and saturated brine, dried over anhydrous sodium sulfate, and concentrated. The residue was purified by silica gel chromatography (hexane-ethyl acetate) to give the title compound (1.72 g).

$^1$H NMR (300 MHz, CDCl$_3$) δ 3.75 (3H, s), 4.23 (2H, s), 4.71 (2H, s), 5.09 (2H, s), 6.95-7.02 (1H, m), 7.19 (2H, d, J=8.5 Hz), 7.46 (2H, d, J=8.3 Hz), 8.20 (1H, d, J=5.3 Hz).

Reference Example 255

((2-(4-(1-ethyl-1H-pyrazol-4-yl)benzyl)-3-oxo-2,3-dihydro-1H-pyrrolo[3,4-c]pyridin-4-yl)oxy)acetic acid

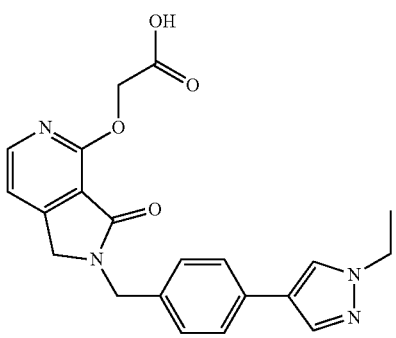 [SMILES: CCn1cc(-c2ccc(CN3Cc4ccnc(OCC(=O)O)c4C3=O)cc2)cn1]

To a mixed solution of methyl ((2-(4-bromobenzyl)-3-oxo-2,3-dihydro-1H-pyrrolo[3,4-c]pyridin-4-yl)oxy)acetate (1.70 g) obtained in Reference Example 254, 1-ethyl-4-(4,4,5,5-tetramethyl-1,3,2-dioxaborolan-2-yl)-1H-pyrazole (1.26 g) and 2M aqueous sodium carbonate solution (4.35 mL) in 1,2-dimethoxyethane (10 mL)-water (1 mL) was added (1,1-bis(diphenylphosphino)ferrocene)dichloropalladium(II) (0.11 g), and the mixture was stirred under an argon atmosphere at 90° C. overnight. The reaction mixture was diluted with ethyl acetate and water, and the organic layer was washed with water and saturated brine, dried over anhydrous magnesium sulfate and concentrated to give the title compound (1.50 g).

MS: [M+H]$^+$ 393.1

Reference Example 256

2-(4-bromobenzyl)-4-(2-fluoro-4-(trifluoromethoxy)phenoxy)-1H-pyrrolo[3,4-c]pyridin-3(2H)-one

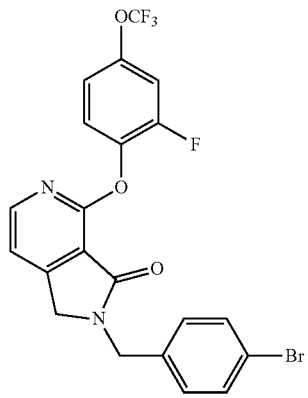 [SMILES: O=C1c2c(ccnc2Oc2ccc(OC(F)(F)F)cc2F)CN1Cc1ccc(Br)cc1]

To a solution of ethyl 2-(2-fluoro-4-(trifluoromethoxy)phenoxy)-4-vinylnicotinate (0.47 g) obtained in Reference Example 211 in acetone-acetonitrile-water (1:1:1, 12 mL) were added sodium periodate (1.34 g) and osmium oxide (immobilized catalyst I) (0.16 g), and the mixture was stirred at room temperature overnight. The insoluble material was filtered off, and the filtrate was concentrated. The residue was dissolved in THF (10 mL), (4-bromophenyl)methanamine (0.23 g) and anhydrous magnesium sulfate (1.52 g) were added, and the mixture was stirred for 20 min. The insoluble material was filtered off, and the filtrate was concentrated. The residue was dissolved in acetic acid (10 mL), sodium triacetoxyborohydride (0.53 g) was added, and the mixture was stirred overnight. The reaction mixture was diluted with ethyl acetate and saturated aqueous sodium hydrogen carbonate solution, and the organic layer was separated, washed with saturated brine, dried over anhydrous sodium sulfate, and concentrated. The residue was purified by column chromatography (NH silica gel, hexane/ethyl acetate) to give the title compound (0.26 g).

$^1$H NMR (300 MHz, DMSO-d$_6$) δ 4.49 (2H, s), 4.70 (2H, s), 7.24-7.43 (4H, m), 7.49-7.67 (4H, m), 8.23 (1H, d, J=5.1 Hz).

Reference Example 257

Ethyl 2-(2-fluoro-4-(hydroxymethyl)phenoxy)-4-vinylnicotinate

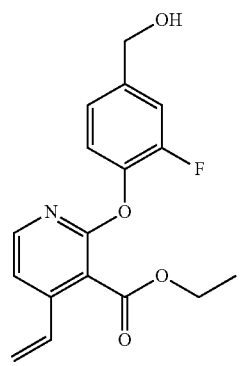 [SMILES: C=Cc1ccnc(Oc2ccc(CO)cc2F)c1C(=O)OCC]

To a solution of ethyl 2-(2-fluoro-4-formylphenoxy)-4-vinylnicotinate (0.92 g) obtained in Reference Example 232 in methanol (10 mL) was added sodium borohydride (0.18 g) under ice-cooling, and the mixture was stirred for 2 hr. The reaction mixture was concentrated and diluted with water. The organic layer was washed with water and saturated brine, dried over anhydrous magnesium sulfate and concentrated. The residue was purified by silica gel column chromatography (hexane-ethyl acetate) to give the title compound (0.45 g).

$^1$H NMR (300 MHz, DMSO-d$_6$) δ 1.30 (3H, t, J=7.1 Hz), 4.39 (2H, q, J=7.2 Hz), 4.51 (2H, d, J=5.9 Hz), 5.32 (1H, t, J=5.8 Hz), 5.70 (1H, d, J=11.1 Hz), 6.19 (1H, d, J=17.4 Hz), 6.73 (1H, dd, J=17.4, 11.0 Hz), 7.13-7.20 (1H, m), 7.20-7.31 (2H, m), 7.48 (1H, d, J=5.5 Hz), 8.12 (1H, d, J=5.3 Hz).

Reference Example 258

Ethyl 2-(4-(cyanomethyl)-2-fluorophenoxy)-4-vinylnicotinate

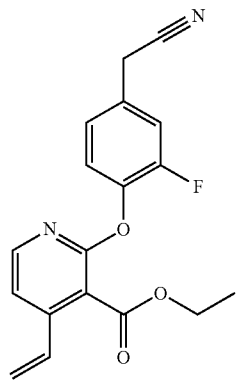 [SMILES: C=Cc1ccnc(Oc2ccc(CC#N)cc2F)c1C(=O)OCC]

To a solution of ethyl 2-(2-fluoro-4-(hydroxymethyl)phenoxy)-4-vinylnicotinate (0.45 g) obtained in Reference Example 257, 2-hydroxy-2-methylpropanenitrile (0.494 g) and tri-n-butylphosphine (0.43 g) in THF (7 mL) was added diazene-1,2-diylbis(piperidin-1-ylmethanone) (0.54 g), and the mixture was stirred at room temperature for 3 hr. The reaction mixture was diluted with water and ethyl acetate, and the organic layer was separated, washed with saturated brine, dried over anhydrous magnesium sulfate and concentrated. The residue was purified by silica gel chromatography (hexane-ethyl acetate) to give the title compound (0.30 g).

$^1$H NMR (300 MHz, DMSO-d$_6$) δ 1.30 (3H, t, J=7.2 Hz), 4.09 (2H, s), 4.39 (2H, q, J=7.0 Hz), 5.71 (1H, d, J=11.3 Hz), 6.20 (1H, d, J=17.2 Hz), 6.74 (1H, dd, J=17.4, 11.0 Hz), 7.20-7.27 (1H, m), 7.30-7.41 (2H, m), 7.51 (1H, d, J=5.5 Hz), 8.13 (1H, d, J=5.3 Hz).

Reference Example 259

Ethyl 2-(4-(cyanomethyl)-2-fluorophenoxy)-4-formylnicotinate

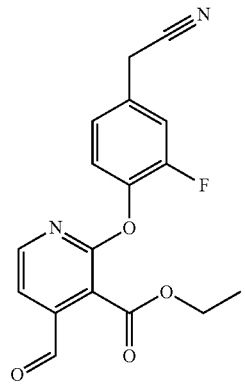 [SMILES: CCOC(=O)c1c(C=O)ccnc1Oc1ccc(CC#N)cc1F]

A solution of ethyl 2-(4-(cyanomethyl)-2-fluorophenoxy)-4-vinylnicotinate (0.30 g) obtained in Reference Example 258, sodium periodate (0.99 g) and osmium oxide (immobilized catalyst I) (0.12 g) in acetonitrile (5 mL)-acetone (5 mL)-water (5 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.32 g).

$^1$H NMR (300 MHz, DMSO-d$_6$) δ 1.31 (3H, t, J=7.1 Hz), 4.10 (2H, s), 4.41 (2H, q, J=7.1 Hz), 7.27 (1H, dd, J=8.3, 1.1 Hz), 7.35-7.46 (2H, m), 7.70 (1H, d, J=5.1 Hz), 8.49 (1H, d, J=4.9 Hz), 10.11 (1H, s).

Reference Example 260

Ethyl 2-(2-fluoro-5-formylphenoxy)-4-vinylnicotinate

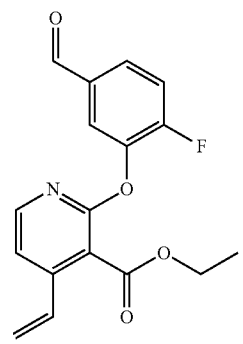 [SMILES: C=Cc1ccnc(Oc2cc(C=O)ccc2F)c1C(=O)OCC]

A solution of ethyl 2-fluoro-4-vinylnicotinate (1.13 g) obtained in Reference Example 118, 4-fluoro-3-hydroxybenzaldehyde (0.97 g) and potassium carbonate (1.20 g) in DMF (6 mL) was stirred at 110° C. overnight. The reaction mixture was diluted with ethyl acetate and water. The organic layer was washed with water and saturated brine, dried over anhydrous magnesium sulfate and concentrated.

The residue was purified by silica gel column chromatography (hexane-ethyl acetate) to give the title compound (0.76 g).

$^1$H NMR (300 MHz, DMSO-$d_6$) δ 1.31 (3H, t, J=7.1 Hz), 4.41 (2H, q, J=7.0 Hz), 5.72 (1H, d, J=11.1 Hz), 6.22 (1H, d, J=17.4 Hz), 6.76 (1H, dd, J=17.5, 11.0 Hz), 7.55 (1H, d, J=5.5 Hz), 7.63 (1H, dd, J=10.3, 8.4 Hz), 7.83-7.95 (2H, m), 8.16 (1H, d, J=5.5 Hz), 9.97 (1H, s).

Reference Example 261

Ethyl 2-(2-fluoro-5-(hydroxymethyl)phenoxy)-4-vinylnicotinate

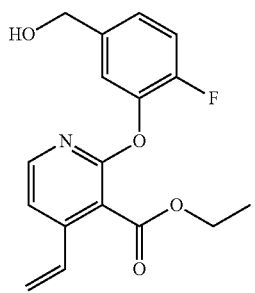 [SMILES: C=Cc1ccnc(Oc2cc(CO)ccc2F)c1C(=O)OCC]

To a solution of ethyl 2-(2-fluoro-5-formylphenoxy)-4-vinylnicotinate (0.76 g) obtained in Reference Example 260 in methanol (10 mL) was added sodium borohydride (0.14 g) under ice-cooling, and the mixture was stirred for 2 hr. The reaction mixture was concentrated and diluted with water, and the organic layer was washed with water and saturated brine, dried over anhydrous magnesium sulfate and concentrated to give the title compound (0.41 g).

$^1$H NMR (300 MHz, DMSO-$d_6$) δ 1.30 (3H, t, J=7.1 Hz), 4.39 (2H, q, J=7.2 Hz), 4.51 (2H, d, J=5.9 Hz), 5.32 (1H, t, J=5.8 Hz), 5.70 (1H, d, J=11.1 Hz), 6.19 (1H, d, J=17.4 Hz), 6.73 (1H, dd, J=17.4, 11.0 Hz), 7.13-7.20 (1H, m), 7.20-7.31 (2H, m), 7.48 (1H, d, J=5.5 Hz), 8.12 (1H, d, J=5.3 Hz).

Reference Example 262

Ethyl 2-(5-(cyanomethyl)-2-fluorophenoxy)-4-vinylnicotinate

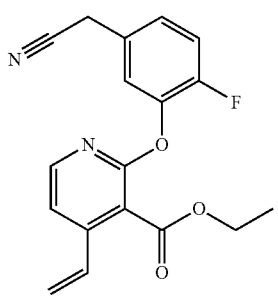 [SMILES: C=Cc1ccnc(Oc2cc(CC#N)ccc2F)c1C(=O)OCC]

To a solution of ethyl 2-(2-fluoro-5-(hydroxymethyl)phenoxy)-4-vinylnicotinate (0.41 g) obtained in Reference Example 261, 2-hydroxy-2-methylpropanenitrile (0.44 g) and tri-n-butylphosphine (0.39 g) in THF (7 mL) was added diazene-1,2-diylbis(piperidin-1-ylmethanone) (0.49 g), and the mixture was stirred at room temperature for 3 hr. The reaction mixture was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.40 g).

$^1$H NMR (300 MHz, DMSO-$d_6$) δ 1.30 (3H, t, J=7.2 Hz), 4.05 (2H, s), 4.40 (2H, q, J=7.0 Hz), 5.73 (1H, s), 6.21 (1H, d, J=17.2 Hz), 6.74 (1H, dd, J=17.5, 11.0 Hz), 7.27-7.34 (2H, m), 7.36-7.46 (1H, m), 7.52 (1H, d, J=5.5 Hz), 8.15 (1H, d, J=5.5 Hz).

Reference Example 263

Ethyl 2-(5-(cyanomethyl)-2-fluorophenoxy)-4-formylnicotinate

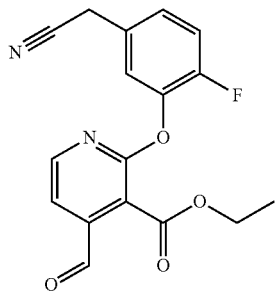 [SMILES: CCOC(=O)c1c(C=O)ccnc1Oc1cc(CC#N)ccc1F]

A solution of ethyl 2-(5-(cyanomethyl)-2-fluorophenoxy)-4-vinylnicotinate (0.40 g) obtained in Reference Example 262, sodium periodate (1.32 g) and osmium oxide (immobilized catalyst I) (0.16 g) in acetonitrile (5 mL)-acetone (5 mL)-water (5 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.36 g).

$^1$H NMR (300 MHz, DMSO-$d_6$) δ 1.31 (3H, t, J=7.2 Hz), 4.06 (2H, s), 4.41 (2H, q, J=7.2 Hz), 7.31 (1H, d, J=7.9 Hz), 7.34-7.38 (1H, m), 7.39-7.47 (1H, m), 7.71 (1H, d, J=5.1 Hz), 8.50 (1H, d, J=5.1 Hz), 10.11 (1H, s).

Reference Example 264

Ethyl 2-(2-methyl-4-(trifluoromethyl)phenoxy)-4-vinylnicotinate

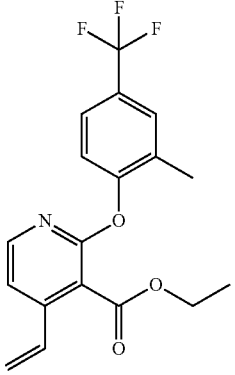 [SMILES: C=Cc1ccnc(Oc2ccc(C(F)(F)F)cc2C)c1C(=O)OCC]

A solution of ethyl 2-fluoro-4-vinylnicotinate (0.37 g) obtained in Reference Example 118, 2-methyl-4-(trifluoromethyl)phenol (0.44 g) and potassium carbonate (0.40 g) in DMF (8 mL) was stirred at 100° C. overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.53 g).

¹H NMR (300 MHz, DMSO-d₆) δ 1.26-1.31 (3H, m), 2.16 (3H, s), 4.39 (2H, q, J=7.1 Hz), 5.71 (1H, d, J=11.3 Hz), 6.21 (1H, d, J=17.2 Hz), 6.68-6.79 (1H, m), 7.29 (1H, d, J=8.5 Hz), 7.51 (1H, d, J=5.5 Hz), 7.56-7.65 (1H, m), 7.70-7.72 (1H, m), 8.15 (1H, d, J=5.3 Hz).

Reference Example 265

Ethyl 4-formyl-2-(2-methyl-4-(trifluoromethyl)phenoxy)nicotinate

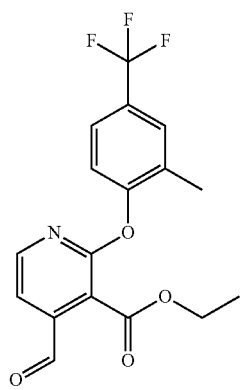 [SMILES: CCOC(=O)c1c(C=O)ccnc1Oc1ccc(C(F)(F)F)cc1C]

A solution of ethyl 2-(2-methyl-4-(trifluoromethyl)phenoxy)-4-vinylnicotinate (0.53 g) obtained in Reference Example 264, sodium periodate (1.60 g) and osmium oxide (immobilized catalyst I) (0.19 g) in acetonitrile (7 mL)-acetone (7 mL)-water (7 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.095 g).

¹H NMR (300 MHz, DMSO-d₆) δ 1.27-1.34 (3H, m), 2.16 (3H, s), 4.41 (2H, q, J=7.1 Hz), 7.33 (1H, d, J=8.5 Hz), 7.60-7.67 (1H, m), 7.70 (1H, d, J=5.1 Hz), 7.74 (1H, s), 8.50 (1H, d, J=5.1 Hz), 10.11 (1H, s).

Reference Example 266

2-(4-bromobenzyl)-4-(2-methyl-4-(trifluoromethyl)phenoxy)-1H-pyrrolo[3,4-c]pyridin-3 (2H)-one

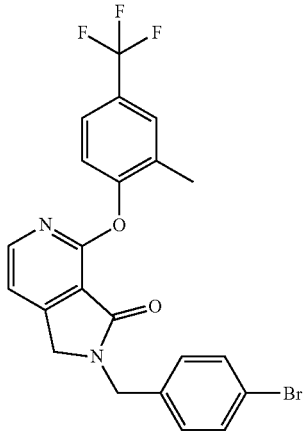 [SMILES: Cc1cc(C(F)(F)F)ccc1Oc1nccc2c1C(=O)N(Cc1ccc(Br)cc1)C2]

To a solution of ethyl 4-formyl-2-(2-methyl-4-(trifluoromethyl)phenoxy)nicotinate (0.095 g) obtained in Reference Example 265, (4-bromophenyl)methanamine hydrochloride (0.36 g), acetic acid (0.081 g) and triethylamine (0.34 g) in methanol (5 mL) was added sodium triacetoxyhydroborate (1.43 g), and the mixture was stirred at room temperature for 1 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate) to give the title compound (0.13 g).

MS: [M+H]⁺ 477.1

Reference Example 267

Ethyl 2-(2-fluoro-4-(2-hydroxypropan-2-yl)phenoxy)-4-vinylnicotinate

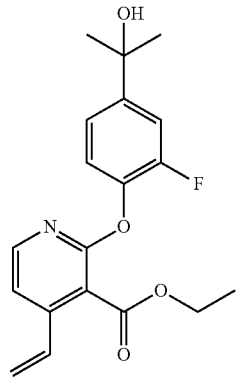 [SMILES: C=Cc1ccnc(Oc2ccc(C(C)(C)O)cc2F)c1C(=O)OCC]

A solution of ethyl 2-fluoro-4-vinylnicotinate (0.75 g) obtained in Reference Example 118, 2-fluoro-4-(2-hydroxypropan-2-yl)phenol (0.85 g) and potassium carbonate (0.80 g) in DMF (15 mL) was stirred at 100° C. for 2 days. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.96 g).

$^1$H NMR (300 MHz, DMSO-d$_6$) δ 1.30 (3H, t, J=7.1 Hz), 1.44 (6H, s), 4.39 (2H, q, J=7.0 Hz), 5.16 (1H, s), 5.70 (1H, d, J=11.1 Hz), 6.19 (1H, d, J=17.4 Hz), 6.73 (1H, dd, J=17.4, 11.0 Hz), 7.14-7.26 (1H, m), 7.26-7.33 (1H, m), 7.38 (1H, dd, J=12.4, 2.0 Hz), 7.48 (1H, d, J=5.3 Hz), 8.13 (1H, d, J=5.3 Hz).

Reference Example 268

Ethyl 2-(2-fluoro-4-(2-hydroxypropan-2-yl)phenoxy)-4-formylnicotinate

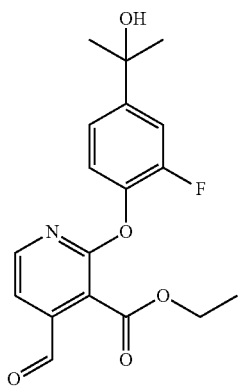 [SMILES: CCOC(=O)c1c(C=O)ccnc1Oc1ccc(C(C)(C)O)cc1F]

A solution of ethyl 2-(2-fluoro-4-(2-hydroxypropan-2-yl)phenoxy)-4-vinylnicotinate (0.76 g) obtained in Reference Example 267, sodium periodate (2.06 g) and osmium oxide (immobilized catalyst I) (0.25 g) in acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.72 g).

$^1$H NMR (300 MHz, DMSO-d$_6$) δ 1.31 (3H, t, J=7.1 Hz), 1.44 (6H, s), 4.40 (2H, q, J=7.1 Hz), 5.18 (1H, s), 7.20-7.34 (2H, m), 7.41 (1H, dd, J=12.4, 2.0 Hz), 7.68 (1H, d, J=5.1 Hz), 8.49 (1H, d, J=4.9 Hz), 10.10 (1H, s).

Reference Example 269

Ethyl 2-(4-(2-cyanopropan-2-yl)-2-fluorophenoxy)-4-vinylnicotinate

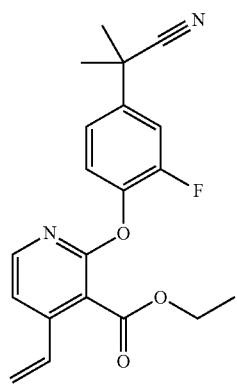 [SMILES: C=Cc1ccnc(Oc2ccc(C(C)(C)C#N)cc2F)c1C(=O)OCC]

To a solution of ethyl 2-(4-(cyanomethyl)-2-fluorophenoxy)-4-vinylnicotinate (0.20 g) obtained in Reference Example 258 and iodomethane (0.26 g) in DMF (3 mL) was added 60% sodium hydride (0.059 g) under ice-cooling, and the mixture was stirred at room temperature overnight. To the reaction solution was added saturated aqueous ammonium chloride solution, and the mixture was extracted twice with ethyl acetate. The organic layer was divided, washed with saturated brine, dried over anhydrous sodium sulfate, and concentrated. The residue was purified by silica gel chromatography (hexane-ethyl acetate) to give the title compound (0.028 g).

$^1$H NMR (300 MHz, CDCl$_3$) δ 1.39 (3H, t, J=7.2 Hz), 1.74 (6H, s), 4.45 (2H, q, J=7.2 Hz), 5.59 (1H, d, J=11.0 Hz), 5.96 (1H, d, J=17.4 Hz), 6.82 (1H, dd, J=17.5, 11.0 Hz), 7.19 (1H, d, J=5.5 Hz), 7.23-7.34 (3H, m), 8.08 (1H, d, J=5.5 Hz).

Reference Example 270 ethyl 2-(4-(2-cyanopropan-2-yl)-2-fluorophenoxy)-4-formylnicotinate

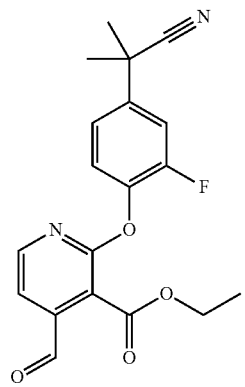 [SMILES: CCOC(=O)c1c(C=O)ccnc1Oc1ccc(C(C)(C)C#N)cc1F]

A solution of ethyl 2-(4-(2-cyanopropan-2-yl)-2-fluorophenoxy)-4-vinylnicotinate (0.028 g) obtained in Reference Example 269, sodium periodate (0.085 g) and osmium oxide (immobilized catalyst I) (0.010 g) in acetonitrile (1.5 mL)-acetone (1.5 mL)-water (1.5 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.029 g).

$^1$H NMR (300 MHz, DMSO-d$_6$) δ 1.44 (3H, t, J=7.2 Hz), 1.76 (6H, s), 4.53 (2H, q, J=7.2 Hz), 7.28-7.37 (3H, m), 7.47 (1H, d, J=5.1 Hz), 8.38 (1H, d, J=5.1 Hz), 10.18 (1H, s).

Reference Example 271

2-(4-bromobenzyl)-4-(2-fluoro-4-(2-hydroxypropan-2-yl)phenoxy)-1H-pyrrolo[3,4-c]pyridin-3(2H)-one

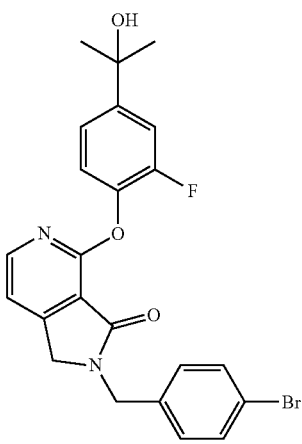 [SMILES: CC(C)(O)c1ccc(Oc2nccc3c2C(=O)N(Cc2ccc(Br)cc2)C3)c(F)c1]

A solution of ethyl 2-(2-fluoro-4-(2-hydroxypropan-2-yl)phenoxy)-4-formylnicotinate (0.53 g) obtained in Reference Example 268 and (4-bromophenyl)methanamine (0.28 g) in THF (7.5 mL) was stirred at room temperature for 30 min. After evaporation of the solvent, to the residue were added acetic acid (7.5 mL) and sodium triacetoxyhydroborate (0.48 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and the obtained solid was washed with a mixed solvent of hexane-ethyl acetate to give the title compound (0.32 g).

$^1$H NMR (300 MHz, DMSO-$d_6$) δ 1.46 (6H, s), 4.48 (2H, s), 4.69 (2H, s), 5.17 (1H, s), 7.22-7.38 (5H, m), 7.41 (1H, dd, J=12.4, 2.0 Hz), 7.52-7.60 (2H, m), 8.20 (1H, d, J=5.1 Hz).

Reference Example 272

2-(benzyloxy)-1,5-dibromo-3-fluorobenzene

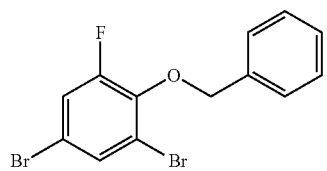 [SMILES: Fc1cc(Br)cc(Br)c1OCc1ccccc1]

To a solution of 2,4-dibromo-6-fluorophenol (6.60 g) in DMF (25 mL) were added potassium carbonate (5.07 g) and benzyl bromide (6.27 g) at room temperature, and the mixture was stirred at 50° C. overnight. After evaporation of the solvent, the residue was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (7.22 g).

$^1$H NMR (300 MHz, DMSO-$d_6$) δ 5.12 (2H, s), 7.32-7.44 (3H, m), 7.44-7.53 (2H, m), 7.64-7.80 (2H, m).

Reference Example 273

2-(benzyloxy)-1-fluoro-3,5-dimethylbenzene

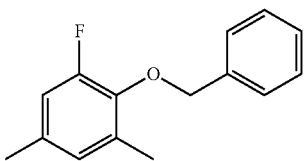 [SMILES: Cc1cc(C)c(OCc2ccccc2)c(F)c1]

A solution of 2-(benzyloxy)-1,5-dibromo-3-fluorobenzene (2.52 g) obtained in Reference Example 272, 1,1'-bis(diphenylphosphino)ferrocene-palladium(II)dichloride dichloromethane complex (0.57 g), trimethylboroxine (8.79 g) and tripotassium phosphate (4.46 g) in DME (20 mL)-water (5 mL) was stirred under an argon atmosphere at 90° C. overnight. After evaporation of the solvent, the residue was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (1.21 g).

$^1$H NMR (300 MHz, DMSO-$d_6$) δ 2.13 (3H, s), 2.22 (3H, s), 4.96 (2H, s), 6.81 (1H, s), 6.90 (1H, dd, J=12.3, 1.9 Hz), 7.29-7.50 (5H, m).

Reference Example 274

2-fluoro-4,6-dimethylphenol

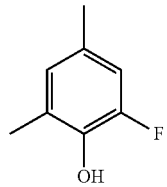

A solution of 2-(benzyloxy)-1-fluoro-3,5-dimethylbenzene (1.20 g) obtained in Reference Example 273 and 10% palladium carbon (0.12 g) in ethanol (25 mL) was stirred under a hydrogen atmosphere at room temperature for 2 hr. The insoluble material was filtered off, and the filtrate was concentrated to give the title compound (0.72 g).

$^1$H NMR (300 MHz, DMSO-$d_6$) δ 2.13 (3H, s), 2.16 (3H, s), 6.70 (1H, s), 6.73-6.82 (1H, m), 9.01 (1H, brs).

Reference Example 275

Ethyl 2-(2-fluoro-4,6-dimethylphenoxy)-4-vinylnicotinate

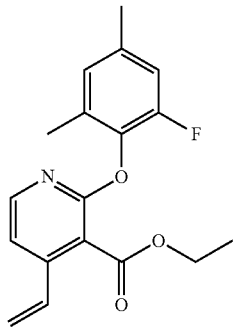 [SMILES: C=Cc1ccnc(Oc2c(C)cc(C)cc2F)c1C(=O)OCC]

A solution of ethyl 2-fluoro-4-vinylnicotinate (0.92 g) obtained in Reference Example 118, 2-fluoro-4,6-dimethylphenol (0.72 g) obtained in Reference Example 274 and potassium carbonate (0.79 g) in DMF (15 mL) was stirred at 100° C. for 2 days. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (1.07 g).

$^1$H NMR (300 MHz, DMSO-$d_6$) δ 1.31 (3H, t, J=7.1 Hz), 2.06 (3H, s), 2.29 (3H, s), 4.34-4.45 (2H, m), 5.70 (1H, d, J=11.3 Hz), 6.19 (1H, d, J=17.4 Hz), 6.73 (1H, dd, J=17.4, 11.0 Hz), 6.94 (1H, s), 6.98 (1H, d, J=11.1 Hz), 7.45 (1H, d, J=5.5 Hz), 8.09 (1H, d, J=5.3 Hz).

Reference Example 276

Ethyl 2-(2-fluoro-4,6-dimethylphenoxy)-4-formylnicotinate

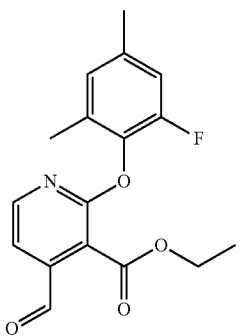 [SMILES: CCOC(=O)c1c(C=O)ccnc1Oc1c(C)cc(C)cc1F]

A solution of ethyl 2-(2-fluoro-4,6-dimethylphenoxy)-4-vinylnicotinate (1.26 g) obtained in Reference Example 275, sodium periodate (4.27 g) and osmium oxide (immobilized catalyst I) (0.51 g) in acetonitrile (15 mL)-acetone (15 mL)-water (15 mL) was stirred at room temperature, and the mixture was stirred overnight. The insoluble material was filtered off, and the filtrate was diluted with ethyl acetate. The organic layer was separated, washed with saturated brine, dried over anhydrous sodium sulfate, and concentrated to give the title compound (1.29 g).

$^1$H NMR (300 MHz, DMSO-$d_6$) δ 1.32 (3H, t, J=7.1 Hz), 2.07 (3H, s), 2.30 (3H, s), 4.42 (2H, q, J=7.1 Hz), 6.96 (1H, s), 7.01 (1H, d, J=11.0 Hz), 7.66 (1H, d, J=4.9 Hz), 8.45 (1H, d, J=5.1 Hz), 10.09 (1H, s).

Reference Example 277

Ethyl 2-(2-cyano-4-(trifluoromethyl)phenoxy)-4-vinylnicotinate

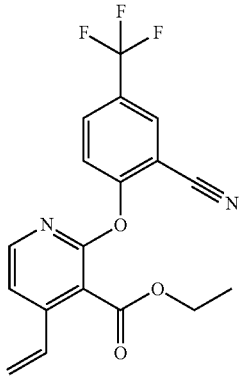 [SMILES: C=Cc1ccnc(Oc2ccc(C(F)(F)F)cc2C#N)c1C(=O)OCC]

A solution of ethyl 2-fluoro-4-vinylnicotinate (1.0 g) obtained in Reference Example 118, 2-hydroxy-5-(trifluoromethyl)benzonitrile (1.06 g) and potassium carbonate (0.85 g) in DMF (20 mL) was stirred at 100° C. for 5 days. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.089 g).

$^1$H NMR (300 MHz, DMSO-$d_6$) δ 1.28 (3H, t, J=7.1 Hz), 4.39 (2H, q, J=7.2 Hz), 5.75 (1H, d, J=11.3 Hz), 6.25 (1H, d, J=17.4 Hz), 6.80 (1H, dd, J=17.4, 11.0 Hz), 7.63 (1H, d, J=8.7 Hz), 7.67 (1H, d, J=5.5 Hz), 8.12 (1H, dd, J=9.1, 2.3 Hz), 8.27 (1H, d, J=5.3 Hz), 8.48 (1H, d, J=2.1 Hz).

Reference Example 278

Ethyl 2-(2-cyano-4-(trifluoromethyl)phenoxy)-4-formylnicotinate

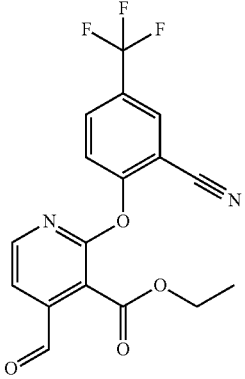 [SMILES: CCOC(=O)c1c(C=O)ccnc1Oc1ccc(C(F)(F)F)cc1C#N]

A solution of ethyl 2-(2-cyano-4-(trifluoromethyl)phenoxy)-4-vinylnicotinate (0.087 g) obtained in Reference Example 277, sodium periodate (0.26 g) and osmium oxide (immobilized catalyst I) (0.031 g) in acetonitrile (2 mL)-acetone (2 mL)-water (2 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.091 g).

$^{1}$H NMR (300 MHz, DMSO-d$_{6}$) δ 1.30 (3H, t, J=7.2 Hz), 4.41 (2H, q, J=7.1 Hz), 7.68 (1H, d, J=8.9 Hz), 7.83 (1H, d, J=5.1 Hz), 8.16 (1H, dd, J=9.0, 2.4 Hz), 8.51 (1H, d, J=2.1 Hz), 8.61 (1H, d, J=5.1 Hz), 10.15 (1H, s).

Reference Example 279

Ethyl 2-(4-cyano-2-fluoro-6-methylphenoxy)-4-vinylnicotinate

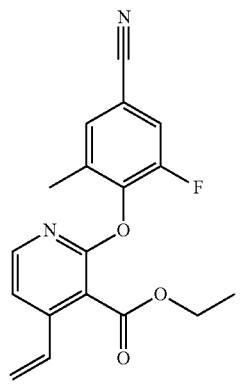 [SMILES: C=Cc1ccnc(Oc2c(C)cc(C#N)cc2F)c1C(=O)OCC]

A solution of ethyl 2-fluoro-4-vinylnicotinate (0.68 g) obtained in Reference Example 118, 3-fluoro-4-hydroxy-5-methylbenzonitrile (0.58 g) and potassium carbonate (0.58 g) in DMF (15 mL) was stirred at 100° C. for 2 days. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.060 g).

$^{1}$H NMR (300 MHz, DMSO-d$_{6}$) δ 1.31 (3H, t, J=7.2 Hz), 2.17 (3H, s), 4.41 (2H, q, J=7.2 Hz), 5.73 (1H, d, J=10.9 Hz), 6.22 (1H, d, J=17.3 Hz), 6.76 (1H, dd, J=17.5, 11.1 Hz), 7.54 (1H, d, J=5.7 Hz), 7.75 (1H, s), 7.88 (1H, dd, J=10.0, 1.7 Hz), 8.12 (1H, d, J=5.3 Hz).

Reference Example 280

Ethyl 2-(4-cyano-2-fluoro-6-methylphenoxy)-4-formylnicotinate

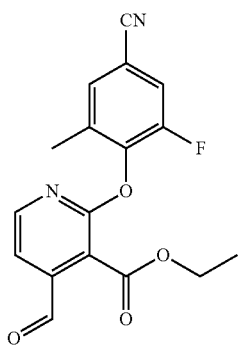 [SMILES: CCOC(=O)c1c(C=O)ccnc1Oc1c(C)cc(C#N)cc1F]

A solution of ethyl 2-(4-cyano-2-fluoro-6-methylphenoxy)-4-vinylnicotinate (0.060 g) obtained in Reference Example 279, sodium periodate (0.20 g) and osmium oxide (immobilized catalyst I) (0.023 g) in acetonitrile (1.5 mL)-acetone (1.5 mL)-water (1.5 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.057 g).

$^{1}$H NMR (300 MHz, DMSO-d$_{6}$) δ 1.17 (3H, t, J=7.1 Hz), 2.18 (3H, s), 4.42 (2H, q, J=7.1 Hz), 7.73 (1H, d, J=5.1 Hz), 7.75-7.82 (2H, m), 8.48 (1H, d, J=4.9 Hz), 10.11 (1H, s).

Reference Example 281

Ethyl 2-(2-fluoro-4-(trifluoromethyl)phenoxy)-4-vinylnicotinate

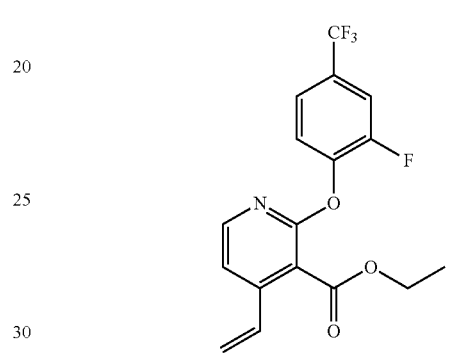

A solution of ethyl 2-fluoro-4-vinylnicotinate (2.93 g) obtained in Reference Example 118, 2-fluoro-4-(trifluoromethyl)phenol (4.05 g) and potassium carbonate (4.15 g) in DMF (75 mL) was stirred at 120° C. for 3 days. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (1.70 g).

$^{1}$H NMR (300 MHz, DMSO-d$_{6}$) δ 1.30 (3H, t, J=7.1 Hz), 4.40 (2H, q, J=7.0 Hz), 5.73 (1H, d, J=11.1 Hz), 6.22 (1H, d, J=17.4 Hz), 6.76 (1H, dd, J=17.4, 11.0 Hz), 7.53-7.62 (2H, m), 7.62-7.70 (1H, m), 7.89 (1H, dd, J=10.7, 2.0 Hz), 8.17 (1H, d, J=5.3 Hz).

Reference Example 282

Ethyl 2-(2-fluoro-4-(trifluoromethyl)phenoxy)-4-formylnicotinate

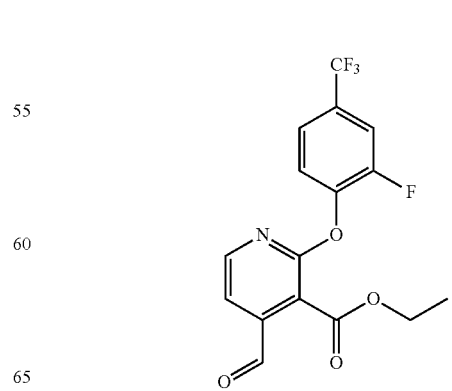

A solution of ethyl 2-(2-fluoro-4-(trifluoromethyl)phenoxy)-4-vinylnicotinate (1.70 g) obtained in Reference Example 281, sodium periodate (5.12 g) and osmium oxide (immobilized catalyst I) (0.61 g) in acetonitrile (20 mL)-acetone (20 mL)-water (20 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (1.74 g).

$^1$H NMR (300 MHz, DMSO-d$_6$) δ 1.31 (3H, t, J=7.2 Hz), 4.41 (2H, q, J=7.2 Hz), 7.57-7.72 (2H, m), 7.75 (1H, d, J=5.1 Hz), 7.93 (1H, dd, J=10.7, 1.8 Hz), 8.52 (1H, d, J=5.1 Hz), 10.12 (1H, s).

Reference Example 283

(4-(4-methyl-1H-imidazol-1-yl)phenyl)methanol

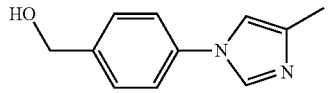

A solution of methyl 4-iodobenzoate (5.24 g), 4-methyl-1H-imidazole (1.81 g), copper(I) iodide (0.19 g), 8-quinolinol (0.15 g) and potassium carbonate (3.32 g) in dimethyl sulfoxide (20 mL) was stirred under an argon atmosphere at 140° C. overnight. The reaction mixture was diluted with saturated brine and ethyl acetate, and the organic layer was separated, washed twice with saturated brine, dried over anhydrous sodium sulfate, and concentrated. The residue was crudely purified by NH silica gel chromatography (hexane-ethyl acetate). A solution of the obtained crudely purified product in THF (10 mL) was added to a suspension of lithium aluminum hydride (0.45 g) in THF (30 mL) at 0° C., and the reaction mixture was stirred at room temperature for 2 hr. Water (0.45 mL), 15% aqueous sodium hydroxide solution (0.45 mL) and water (1.35 mL) were added in this order, and the mixture was further stirred for 2 hr. The insoluble material was filtered off, and the filtrate was concentrated. The obtained residue was recrystallized from ethyl acetate to give the title compound (0.90 g).

$^1$H NMR (300 MHz, DMSO-d$_6$) δ 2.16 (3H, d, J=0.8 Hz), 4.52 (2H, d, J=5.5 Hz), 5.24 (1H, t, J=5.7 Hz), 7.37-7.46 (3H, m), 7.49-7.58 (2H, m), 8.09 (1H, d, J=1.3 Hz).

Reference Example 284

1-(4-(azidomethyl)phenyl)-4-methyl-1H-imidazole

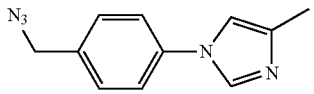 [SMILES: Cc1cn(-c2ccc(CN=[N+]=[N-])cc2)cn1]

To a solution of (4-(4-methyl-1H-imidazol-1-yl)phenyl)methanol (0.90 g) obtained in Reference Example 283 and 1,8-diazabicyclo[5.4.0]undec-7-ene (1.46 g) in THF (20 mL) was added at room temperature diphenylphosphoryl azide (1.99 g), and the mixture was stirred at the same temperature for 1 hr. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.99 g).

$^1$H NMR (300 MHz, DMSO-d$_6$) δ 2.16 (3H, d, J=0.8 Hz), 4.49 (2H, s), 7.43-7.54 (3H, m), 7.59-7.68 (2H, m), 8.15 (1H, d, J=1.5 Hz).

Reference Example 285

(4-(4-methyl-1H-imidazol-1-yl)phenyl)methanamine dihydrochloride

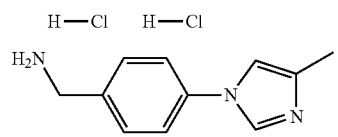

To a solution of 1-(4-(azidomethyl)phenyl)-4-methyl-1H-imidazole (0.99 g) obtained in Reference Example 284 in THF (15 mL)-water (3 mL) was added triphenylphosphine (1.33 g), and the mixture was stirred at room temperature for 2 hr. After evaporation of the solvent, the residue was diluted with ethyl acetate, and 4N hydrogen chloride ethyl acetate solution (3.5 mL) was added. The precipitate was collected by filtration, and the obtained white solid was washed with ethyl acetate and dried to give the title compound (1.13 g).

$^1$H NMR (300 MHz, DMSO-d$_6$) δ 2.36 (3H, d, J=0.8 Hz), 4.11 (2H, q, J=5.5 Hz), 7.71-7.78 (2H, m), 7.79-7.87 (2H, m), 8.02 (1H, s), 8.59 (3H, brs), 9.61 (1H, d, J=1.1 Hz), 1H not detected.

Reference Example 286

(4-(1-methyl-1H-imidazol-4-yl)phenyl)methanamine dihydrochloride

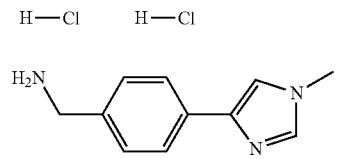

A solution of (4-(aminomethyl)phenyl)boronic acid hydrochloride (0.85 g), 1,1'-bis(diphenylphosphino)ferrocene-palladium(II) dichloride dichloromethane complex (0.37 g), 4-bromo-1-methyl-1H-imidazole (0.80 g) and sodium carbonate (1.20 g) in DME (12 mL)-water (3 mL) was stirred under an argon atmosphere at 120° C. for 6 hr under microwave irradiation. To the reaction mixture was added 6N hydrochloric acid, and the mixture was washed with ethyl acetate. The aqueous layer was separated, neutralized with 8N aqueous sodium hydroxide solution, and concentrated under reduced pressure. The residue was washed with THF, and the obtained organic layer was concentrated. The residue was crudely purified by NH silica gel chromatography (hexane-ethyl acetate). The obtained crudely purified product was diluted with ethyl acetate, 4N hydrogen chloride ethyl acetate solution (1 mL) was added, and the resulting precipitate was collected by filtration, and dried to give the title compound (0.12 g).

¹H NMR (300 MHz, DMSO-d₆) δ 3.90 (3H, s), 4.05-4.10 (2H, m), 7.63 (2H, d, J=8.3 Hz), 7.90 (2H, d, J=8.3 Hz), 8.20 (1H, d, J=1.1 Hz), 8.42 (3H, brs), 9.19 (1H, s), 1H not detected.

Reference Example 287

Ethyl 2-(2-fluoro-4-methylphenoxy)-4-vinylnicotinate

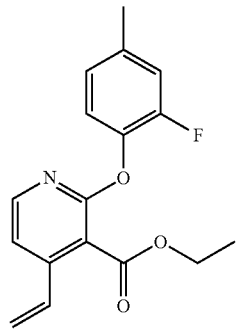 [SMILES: C=Cc1ccnc(Oc2ccc(C)cc2F)c1C(=O)OCC]

A solution of ethyl 2-fluoro-4-vinylnicotinate (1.95 g) obtained in Reference Example 118, 2-fluoro-4-methylphenol (1.51 g) and potassium carbonate (2.07 g) in DMF (40 mL) was stirred at 100° C. for 2 days. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (2.72 g).

¹H NMR (300 MHz, DMSO-d₆) δ 1.30 (3H, t, J=7.1 Hz), 2.33 (3H, s), 4.39 (2H, q, J=7.2 Hz), 5.70 (1H, d, J=11.1 Hz), 6.19 (1H, d, J=17.4 Hz), 6.73 (1H, dd, J=17.5, 11.0 Hz), 7.03 (1H, dd, J=8.2, 0.8 Hz), 7.10-7.21 (2H, m), 7.47 (1H, d, J=5.5 Hz), 8.12 (1H, d, J=5.5 Hz).

Reference Example 288

Ethyl 2-(2-fluoro-4-methylphenoxy)-4-formylnicotinate

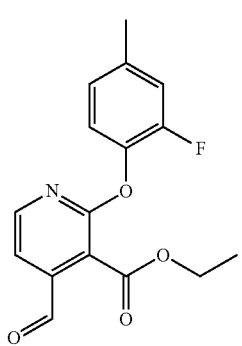 [SMILES: CCOC(=O)c1c(C=O)ccnc1Oc1ccc(C)cc1F]

A solution of ethyl 2-(2-fluoro-4-methylphenoxy)-4-vinylnicotinate (2.72 g) obtained in Reference Example 287, sodium periodate (9.65 g) and osmium oxide (immobilized catalyst I) (1.15 g) in acetonitrile (30 mL)-acetone (30 mL)-water (30 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (2.59 g).

¹H NMR (300 MHz, DMSO-d₆) δ 1.31 (3H, t, J=7.1 Hz), 2.34 (3H, s), 4.40 (2H, q, J=7.2 Hz), 6.99-7.10 (1H, m), 7.15-7.24 (2H, m), 7.67 (1H, d, J=4.9 Hz), 8.48 (1H, d, J=5.1 Hz), 10.10 (1H, s).

Reference Example 289

2-bromo-6-fluoro-4-(trifluoromethyl)phenol

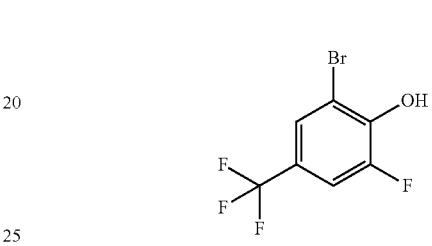

To a solution of 2-fluoro-4-(trifluoromethyl)phenol (2.0 g) in acetic acid (6 mL) was added bromine (2.31 g), and the mixture was stirred at room temperature for 2 days. To the reaction solution was added saturated aqueous sodium thiosulfate solution, and the solvent was evaporated under reduced pressure. The residue was diluted with ethyl acetate and water, and the organic layer was washed with water and saturated brine, dried over anhydrous magnesium sulfate and concentrated to give the title compound (2.62 g).

¹H NMR (300 MHz, DMSO-d₆) δ 7.70 (1H, dd, J=10.6, 2.3 Hz), 7.75 (1H, d, J=0.6 Hz), 11.50 (1H, brs).

Reference Example 290

2-(benzyloxy)-1-bromo-3-fluoro-5-(trifluoromethyl)benzene

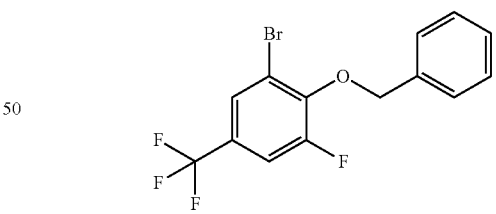

A solution of 2-bromo-6-fluoro-4-(trifluoromethyl)phenol (2.62 g) obtained in Reference Example 289, benzyl bromide (2.60 g) and potassium carbonate (2.80 g) in DMF (20 mL) was stirred at 60° C. overnight. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (2.71 g).

¹H NMR (300 MHz, DMSO-d₆) δ 5.26 (2H, d, J=0.9 Hz), 7.33-7.46 (3H, m), 7.47-7.55 (2H, m), 7.82-7.94 (2H, m).

Reference Example 291

2-(benzyloxy)-1-fluoro-3-methyl-5-(trifluoromethyl)benzene

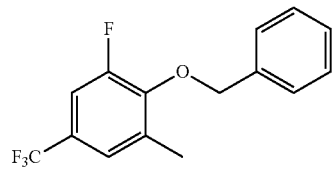 [SMILES: Cc1cc(C(F)(F)F)cc(F)c1OCc1ccccc1]

A solution of 2-(benzyloxy)-1-bromo-3-fluoro-5-(trifluoromethyl)benzene (2.71 g) obtained in Reference Example 290, 1,1'-bis(diphenylphosphino)ferrocene-palladium(II) dichloride dichloromethane complex (0.32 g), trimethylboroxine (1.95 g) and tripotassium phosphate (4.94 g) in DME (25 mL)-water (5 mL) was stirred under an argon atmosphere at 90° C. overnight. After evaporation of the solvent, the residue was diluted with water and ethyl acetate. The organic layer was separated, washed with saturated brine, dried over anhydrous sodium sulfate, and concentrated. The residue was purified by silica gel chromatography (hexane-ethyl acetate) to give the title compound (1.89 g).

$^1$H NMR (300 MHz, DMSO-$d_6$) δ 2.24 (3H, s), 5.16 (2H, d, J=1.1 Hz), 7.32-7.51 (6H, m), 7.57 (1H, dd, J=11.4, 2.2 Hz).

Reference Example 292

2-fluoro-6-methyl-4-(trifluoromethyl)phenol

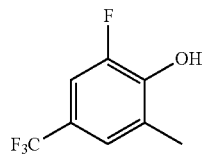

A solution of 2-(benzyloxy)-1-fluoro-3-methyl-5-(trifluoromethyl)benzene (1.89 g) obtained in Reference Example 291 and 10% palladium carbon (0.19 g) in ethanol (30 mL) was stirred under a hydrogen atmosphere at room temperature overnight. The insoluble material was filtered off, and the filtrate was concentrated to give the title compound (1.27 g).

$^1$H NMR (300 MHz, DMSO-$d_6$) δ 2.24 (3H, s), 7.32 (1H, s), 7.41 (1H, dd, J=10.8, 2.1 Hz), 10.37 (1H, brs).

Reference Example 293

Ethyl 2-(2-fluoro-6-methyl-4-(trifluoromethyl)phenoxy)-4-vinylnicotinate

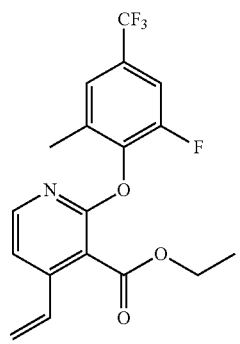 [SMILES: C=Cc1ccnc(Oc2c(C)cc(C(F)(F)F)cc2F)c1C(=O)OCC]

A solution of ethyl 2-fluoro-4-vinylnicotinate (1.05 g) obtained in Reference Example 118, 2-fluoro-6-methyl-4-(trifluoromethyl)phenol (1.25 g) obtained in Reference Example 292 and potassium carbonate (1.12 g) in DMF (20 mL) was stirred at 100° C. for 2 days. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.036 g).

$^1$H NMR (300 MHz, DMSO-$d_6$) δ 1.31 (3H, t, J=7.1 Hz), 2.21 (3H, s), 4.42 (2H, q, J=7.0 Hz), 5.72 (1H, d, J=11.1 Hz), 6.21 (1H, d, J=17.2 Hz), 6.76 (1H, dd, J=17.5, 11.0 Hz), 7.53 (1H, d, J=5.5 Hz), 7.62 (1H, s), 7.69 (1H, d, J=10.0 Hz), 8.12 (1H, d, J=5.5 Hz).

Reference Example 294

Ethyl 2-(2-fluoro-6-methyl-4-(trifluoromethyl)phenoxy)-4-formylnicotinate

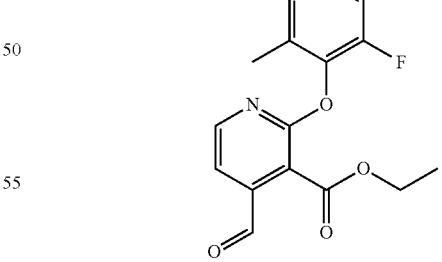

A solution of ethyl 2-(2-fluoro-6-methyl-4-(trifluoromethyl)phenoxy)-4-vinylnicotinate (0.037 g) obtained in Reference Example 293, sodium periodate (0.11 g) and osmium oxide (immobilized catalyst I)(0.013 g) in acetonitrile (1 mL)-acetone (1 mL)-water (1 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.037 g).

$^1$H NMR (300 MHz, DMSO-d$_6$) δ 1.32 (3H, t, J=7.1 Hz), 2.22 (3H, s), 4.43 (2H, q, J=7.2 Hz), 7.65 (1H, s), 7.69-7.77 (2H, m), 8.48 (1H, d, J=5.1 Hz), 10.11 (1H, s).

Reference Example 295

Methyl 4-((4-(2-fluoro-4-(trifluoromethyl)phenoxy)-3-oxo-1H-pyrrolo[3,4-c]pyridin-2(3H)-yl)methyl) benzoate

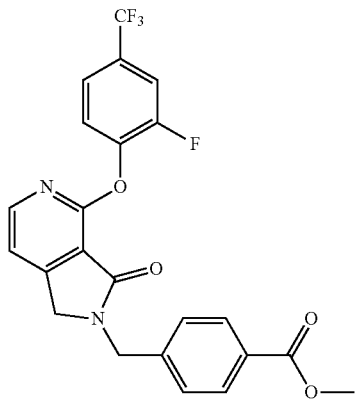 [SMILES: COC(=O)c1ccc(CN2Cc3ccnc(Oc4ccc(C(F)(F)F)cc4F)c3C2=O)cc1]

A solution of ethyl 2-(2-fluoro-4-(trifluoromethyl)phenoxy)-4-formylnicotinate (0.70 g) obtained in Reference Example 282, methyl 4-(aminomethyl)benzoate hydrochloride (0.44 g), triethylamine (0.22 g) and acetic acid (0.024 g) in methanol (15 mL) was stirred at room temperature for 1 hr, sodium triacetoxyhydroborate (2.09 g) was added, and the mixture was stirred at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and the obtained crystals were recrystallized from a mixed solvent of hexane-ethyl acetate to give the title compound (0.42 g).

$^1$H NMR (300 MHz, DMSO-d$_6$) δ 3.85 (3H, s), 4.54 (2H, s), 4.81 (2H, s), 7.39-7.50 (3H, m), 7.57-7.74 (2H, m), 7.88-8.01 (3H, m), 8.24 (1H, d, J=5.1 Hz).

Reference Example 296

Ethyl 2-(((2R,3R)-3-hydroxybutan-2-yl)oxy)-4-vinylnicotinate

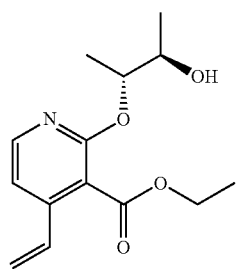 [SMILES: C=Cc1ccnc(O[C@H](C)[C@@H](C)O)c1C(=O)OCC]

To a solution of 60% sodium hydride (0.44 g) in THF (20 mL) was added a solution of (2R,3R)-(−)-2,3-butanediol in THF (5 mL) at 0° C., and the mixture was stirred at the same temperature for 30 min. To the reaction solution was added a solution of ethyl 2-fluoro-4-vinylnicotinate (1.81 g) obtained in Reference Example 118 in THF (5 mL), and the mixture was stirred at room temperature for 2 hr. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.97 g).

$^1$H NMR (300 MHz, DMSO-d$_6$) δ 1.04 (3H, d, J=6.4 Hz), 1.17 (3H, d, J=6.4 Hz), 1.28 (3H, t, J=7.1 Hz), 3.72-3.84 (1H, m), 4.31 (2H, q, J=7.1 Hz), 4.69 (1H, d, J=4.7 Hz), 5.11 (1H, qd, J=6.3, 4.6 Hz), 5.61 (1H, d, J=11.5 Hz), 6.10 (1H, d, J=17.0 Hz), 6.61 (1H, dd, J=17.4, 11.0 Hz), 7.27 (1H, d, J 5.5 Hz), 8.16 (1H, d, J=5.5 Hz).

Reference Example 297

Ethyl 4-formyl-2-(((2R,3R)-3-hydroxybutan-2-yl)oxy)nicotinate

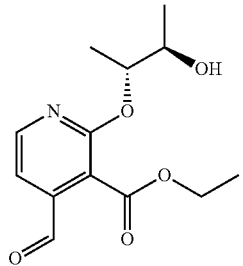 [SMILES: CCOC(=O)c1c(C=O)ccnc1O[C@H](C)[C@@H](C)O]

A solution of ethyl 2-(((2R,3R)-3-hydroxybutan-2-yl)oxy)-4-vinylnicotinate (0.97 g) obtained in Reference Example 296, sodium periodate (3.89 g) and osmium oxide (immobilized catalyst I) (0.46 g) in acetonitrile (15 mL)-acetone (15 mL)-water (15 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.80 g).

$^1$H NMR (300 MHz, DMSO-d$_6$) δ 1.05 (3H, d, J=6.4 Hz), 1.20 (3H, d, J=6.2 Hz), 1.29 (3H, t, J=7.2 Hz), 3.74-3.84 (1H, m), 4.33 (2H, q, J=7.2 Hz), 4.73 (1H, d, J=4.7 Hz), 5.16 (1H, qd, J=6.2, 4.9 Hz), 7.46 (1H, d, J=5.1 Hz), 8.52 (1H, d, J=5.1 Hz), 10.02 (1H, s).

Reference Example 298

Ethyl 2-(2,6-difluoro-4-methylphenoxy)-4-vinylnicotinate

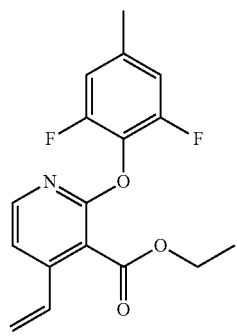 [SMILES: C=Cc1ccnc(Oc2c(F)cc(C)cc2F)c1C(=O)OCC]

A solution of ethyl 2-fluoro-4-vinylnicotinate (0.49 g) obtained in Reference Example 118, 2,6-difluoro-4-methylphenol (0.44 g) and potassium carbonate (0.53 g) in DMF (15 mL) was stirred at 100° C. for 2 days. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.094 g).

$^1$H NMR (300 MHz, DMSO-d$_6$) δ 1.30 (3H, t, J=7.1 Hz), 2.34 (3H, s), 4.40 (2H, q, J=7.1 Hz), 5.71 (1H, d, J=11.3 Hz), 6.21 (1H, d, J=17.4 Hz), 6.74 (1H, dd, J=17.5, 11.0 Hz), 7.00-7.16 (2H, m), 7.53 (1H, d, J=5.5 Hz), 8.13 (1H, d, J=5.3 Hz).

Reference Example 299

Ethyl 2-(2,6-difluoro-4-methylphenoxy)-4-formylnicotinate

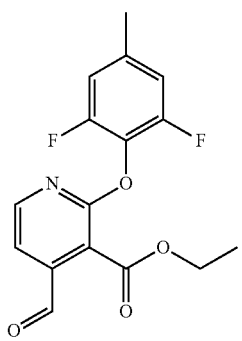 [SMILES: CCOC(=O)c1c(C=O)ccnc1Oc1c(F)cc(C)cc1F]

A solution of ethyl 2-(2,6-difluoro-4-methylphenoxy)-4-vinylnicotinate (0.094 g) obtained in Reference Example 298, sodium periodate (0.32 g) and osmium oxide (immobilized catalyst I) (0.037 g) in acetonitrile (2 mL)-acetone (2 mL)-water (2 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.094 g).

$^1$H NMR (300 MHz, DMSO-d$_6$) δ 1.31 (3H, t, J=7.1 Hz), 2.35 (3H, s), 4.41 (2H, q, J=7.1 Hz), 7.13 (2H, d, J=9.4 Hz), 7.73 (1H, d, J=5.1 Hz), 8.50 (1H, d, J=4.9 Hz), 10.10 (1H, s).

Reference Example 300

Ethyl 2-(4-ethyl-2,6-difluorophenoxy)-4-vinylnicotinate

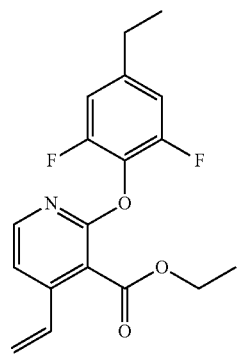 [SMILES: C=Cc1ccnc(Oc2c(F)cc(CC)cc2F)c1C(=O)OCC]

A solution of ethyl 2-fluoro-4-vinylnicotinate (0.64 g) obtained in Reference Example 118, 4-ethyl-2,6-difluorophenol (0.63 g) prepared by referring to a document (Journal of Vacuum Science & Technology, B: Microelectronics and Nanometer Structures (2000), 18(6), 3328-3331.) and potassium carbonate (0.68 g) in DMF (10 mL) was stirred at 100° C. for 2 days. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.29 g).

$^1$H NMR (300 MHz, DMSO-d$_6$) δ 1.20 (3H, t, J=7.6 Hz), 1.30 (3H, t, J=7.1 Hz), 2.64 (2H, q, J=7.6 Hz), 4.40 (2H, q, J=7.2 Hz), 5.72 (1H, d, J=11.1 Hz), 6.21 (1H, d, J=17.4 Hz), 6.74 (1H, dd, J=17.5, 11.0 Hz), 7.08-7.18 (2H, m), 7.53 (1H, d, J=5.5 Hz), 8.14 (1H, d, J=5.3 Hz).

Reference Example 301

Ethyl 2-(4-ethyl-2,6-difluorophenoxy)-4-formylnicotinate

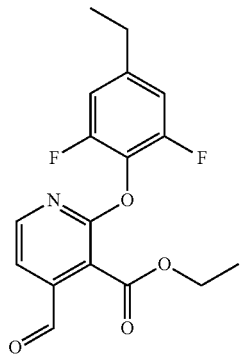 [SMILES: CCOC(=O)c1c(C=O)ccnc1Oc1c(F)cc(CC)cc1F]

A solution of ethyl 2-(4-ethyl-2,6-difluorophenoxy)-4-vinylnicotinate (0.29 g) obtained in Reference Example 300, sodium periodate (0.94 g) and osmium oxide (immobilized catalyst I) (0.11 g) in acetonitrile (4 mL)-acetone (4 mL)-water (4 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.30 g).

$^1$H NMR (300 MHz, DMSO-$d_6$) δ 1.20 (3H, t, J=7.6 Hz), 1.31 (3H, t, J=7.1 Hz), 2.65 (2H, q, J=7.6 Hz), 4.41 (2H, q, J=7.2 Hz), 7.11-7.21 (2H, m), 7.73 (1H, d, J=5.1 Hz), 8.50 (1H, d, J=5.1 Hz), 10.10 (1H, s).

Reference Example 302

Tert-butyl 3-fluoro-4-(methylcarbamoyl)benzylcarbamate

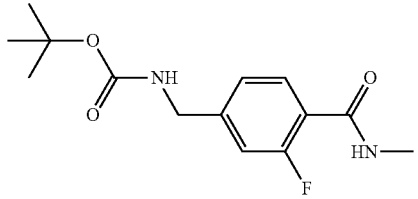 [SMILES: CNC(=O)c1ccc(CNC(=O)OC(C)(C)C)cc1F]

To a solution of 4-(((tert-butoxycarbonyl)amino)methyl)-2-fluorobenzoic acid (1.08 g), methanamine hydrochloride (0.540 g), triethylamine (1.62 g) and 1-hydroxybenzotriazole (0.811 g) in DMF (6 mL) was added 1-(3-dimethylaminopropyl)-3-ethylcarbodiimide hydrochloride (1.15 g), and the mixture was stirred at room temperature overnight. After evaporation of the solvent, the residue was diluted with ethyl acetate and water. The organic layer was washed with saturated aqueous sodium hydrogen carbonate solution and saturated brine, dried over anhydrous magnesium sulfate and concentrated to give the title compound (1.15 g).

$^1$H NMR (300 MHz, CDCl$_3$) δ 1.25-1.44 (9H, m), 2.76 (3H, d, J 4.5 Hz), 4.15 (2H, d, J=6.2 Hz), 7.03-7.16 (2H, m), 7.47 (1H, t, J=5.9 Hz), 7.57 (1H, t, J=7.7 Hz), 8.15 (1H, brs).

Reference Example 303

4-(aminomethyl)-2-fluoro-N-methylbenzamide hydrochloride

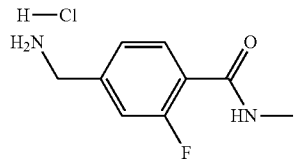

To a solution of tert-butyl 3-fluoro-4-(methylcarbamoyl)benzylcarbamate (1.13 g) obtained in Reference Example 302 in ethanol (15 mL) was added 4N hydrogen chloride ethyl acetate solution (5 mL), and the mixture was stirred at room temperature for 2 hr. The precipitate was collected by filtration, washed with ethyl acetate and dried to give the title compound (0.643 g).

$^1$H NMR (300 MHz, DMSO-$d_6$) δ 2.77 (3H, d, J=4.5 Hz), 4.08 (2H, s), 7.37 (1H, dd, J=7.9, 1.5 Hz), 7.45 (1H, dd, J=11.5, 1.3 Hz), 7.66 (1H, t, J=7.7 Hz), 8.27 (1H, brs), 8.46 (3H, brs).

Reference Example 304

Tert-butyl 4-(ethylcarbamoyl)-3-fluorobenzylcarbamate

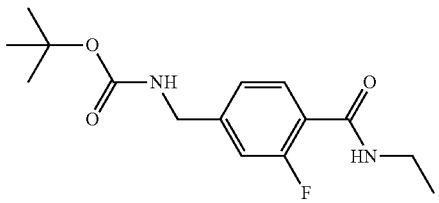 [SMILES: CCNC(=O)c1ccc(CNC(=O)OC(C)(C)C)cc1F]

To a solution of 4-(((tert-butoxycarbonyl)amino)methyl)-2-fluorobenzoic acid (1.08 g), 2M ethanamine THF solution (4 mL), triethylamine (0.809 g) and 1-hydroxybenzotriazole (0.811 g) in DMF (6 mL) was added 1-(3-dimethylaminopropyl)-3-ethylcarbodiimide hydrochloride (1.15 g), and the mixture was stirred at room temperature overnight. After evaporation of the solvent, the residue was diluted with ethyl acetate and water. The organic layer was washed with saturated aqueous sodium hydrogen carbonate solution and saturated brine, dried over anhydrous magnesium sulfate and concentrated to give the title compound (1.18 g).

$^1$H NMR (300 MHz, CDCl$_3$) δ 1.10 (3H, t, J=7.2 Hz), 1.24-1.45 (9H, m), 3.20-3.28 (2H, m), 4.15 (2H, d, J=6.0 Hz), 7.03-7.16 (2H, m), 7.47 (1H, t, J=5.9 Hz), 7.51-7.59 (1H, m), 8.21 (1H, t, J=6.1 Hz).

Reference Example 305

4-(aminomethyl)-N-ethyl-2-fluorobenzamide hydrochloride

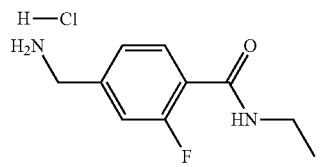

To a solution of tert-butyl 4-(ethylcarbamoyl)-3-fluorobenzylcarbamate (1.15 g) obtained in Reference Example 304 in ethanol (15 mL) was added 4N hydrogen chloride ethyl acetate solution (5 mL), and the mixture was stirred at room temperature for 2 hr. The precipitate was collected by filtration, washed with ethyl acetate and dried to give the title compound (0.638 g).

$^1$H NMR (300 MHz, DMSO-$d_6$) δ 1.11 (3H, t, J=7.2 Hz), 3.21-3.30 (2H, m), 4.08 (2H, s), 7.36 (1H, dd, J=7.9, 1.5 Hz), 7.43 (1H, dd, J=11.5, 1.3 Hz), 7.63 (1H, t, J=7.7 Hz), 8.33 (1H, t, J=4.5 Hz), 8.41 (3H, s).

Reference Example 306

Tert-butyl 4-carbamoyl-3-fluorobenzylcarbamate

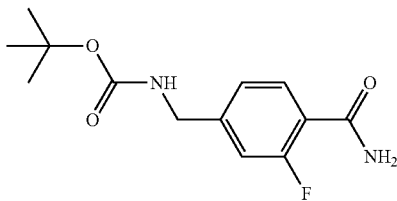 [SMILES: CC(C)(C)OC(=O)NCc1ccc(C(N)=O)c(F)c1]

To a solution of 4-(((tert-butoxycarbonyl)amino)methyl)-2-fluorobenzoic acid (1.84 g) in THF (8 mL)-methanol (8 mL) were added ammonium chloride (1.28 g), triethylamine (5.46 g) and 4-(4,6-dimethoxy[1,3,5]triazin-2-yl)-4-methylmorpholinium chloride hydrate (1.25 g), and the mixture was stirred at room temperature overnight. After evaporation of the solvent, the residue was diluted with ethyl acetate and water. The organic layer was washed with water and saturated brine, dried over anhydrous magnesium sulfate and concentrated. The residue was purified by NH silica gel column chromatography (hexane-ethyl acetate) to give the title compound (0.592 g).

$^1$H NMR (300 MHz, DMSO-$d_6$) δ 1.22-1.46 (9H, m), 4.15 (2H, d, J=6.0 Hz), 7.01-7.18 (2H, m), 7.27-7.79 (4H, m).

Reference Example 307

4-(aminomethyl)-2-fluorobenzamide hydrochloride

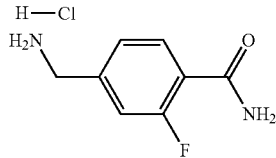

To a solution of tert-butyl 4-carbamoyl-3-fluorobenzylcarbamate (0.592 g) obtained in Reference Example 306 in ethanol (15 mL) was added 4N hydrogen chloride ethyl acetate solution (5 mL), and the mixture was stirred at room temperature for 2 hr. The precipitate was collected by filtration, washed with ethyl acetate and dried to give the title compound (0.304 g).

$^1$H NMR (300 MHz, DMSO-$d_6$) δ 4.09 (2H, q, J=6.0 Hz), 7.30-7.45 (2H, m), 7.64-7.77 (3H, m), 8.35 (3H, brs).

Reference Example 308

Tert-butyl 4-(ethylcarbamoyl)-2-fluorobenzylcarbamate

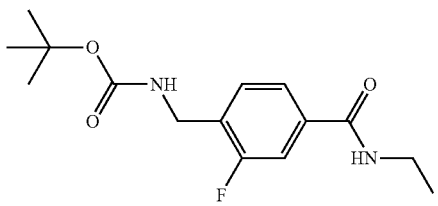 [SMILES: CCNC(=O)c1ccc(CNC(=O)OC(C)(C)C)c(F)c1]

To a solution of 4-(((tert-butoxycarbonyl)amino)methyl)-3-fluorobenzoic acid (0.208 g), 2M ethanamine THF solution (0.772 mL), triethylamine (0.156 g) and 1-hydroxybenzotriazole (0.157 g) in DMF (4 mL) was added 1-(3-dimethylaminopropyl)-3-ethylcarbodiimide hydrochloride (0.222 g), and the mixture was stirred at room temperature overnight. After evaporation of the solvent, the residue was diluted with ethyl acetate and water. The organic layer was washed with water and saturated brine, dried over anhydrous magnesium sulfate and concentrated. The residue was purified by NH silica gel column chromatography (hexane-ethyl acetate) to give the title compound (0.169 g).

$^1$H NMR (300 MHz, CDCl$_3$) δ 1.12 (3H, t, J=7.2 Hz), 1.28-1.42 (9H, m), 3.19-3.30 (2H, m), 4.19 (2H, d, J=5.9 Hz), 7.36 (1H, t, J=7.8 Hz), 7.43 (1H, t, J=5.9 Hz), 7.59 (1H, dd, J=11.1, 1.5 Hz), 7.65 (1H, dd, J=8.0, 1.0 Hz), 8.48 (1H, t, J=5.2 Hz).

Reference Example 309

4-(aminomethyl)-N-ethyl-3-fluorobenzamide hydrochloride

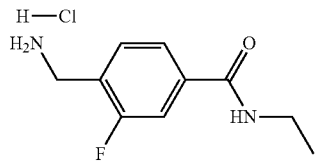

To a solution of tert-butyl 4-(ethylcarbamoyl)-2-fluorobenzylcarbamate (0.169 g) obtained in Reference Example 308 in ethyl acetate (2 mL)-ethanol (1 mL) was added 4N hydrogen chloride ethyl acetate solution (1 mL), and the mixture was stirred at room temperature for 30 min. The precipitate was collected by filtration, washed with ethyl acetate and dried to give the title compound (0.127 g).

$^1$H NMR (300 MHz, DMSO-$d_6$) δ 1.13 (3H, t, J=7.2 Hz), 3.23-3.28 (2H, m), 4.11 (2H, s), 7.56-7.66 (1H, m), 7.66-7.79 (2H, m), 8.02 (3H, brs), 8.58 (1H, t, J=5.6 Hz).

Reference Example 310

Ethyl 2-(4-bromo-2-fluorophenoxy)-4-vinylnicotinate

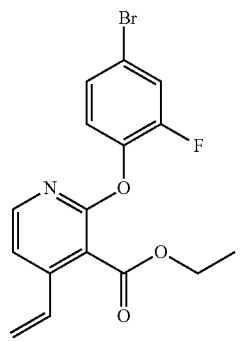 [SMILES: C=Cc1ccnc(Oc2ccc(Br)cc2F)c1C(=O)OCC]

A solution of ethyl 2-fluoro-4-vinylnicotinate (0.976 g) obtained in Reference Example 118, 4-bromo-2-fluorophenol (1.91 g) and potassium carbonate (1.38 g) in DMF (25 mL) was stirred at 100° C. overnight. After evaporation of the solvent, the residue was diluted with ethyl acetate and water. The organic layer was washed with water and saturated brine, dried over anhydrous magnesium sulfate and concentrated. The residue was purified by NH silica gel column chromatography (hexane-ethyl acetate) to give the title compound (1.52 g).

$^1$H NMR (300 MHz, DMSO-$d_6$) δ 1.30 (3H, t, J=7.1 Hz), 4.39 (2H, q, J=7.1 Hz), 5.71 (1H, d, J=11.3 Hz), 6.20 (1H, d, J=17.4 Hz), 6.74 (1H, dd, J=17.4, 11.0 Hz), 7.24-7.36 (1H, m), 7.41-7.48 (1H, m), 7.52 (1H, d, J=5.5 Hz), 7.72 (1H, dd, J=10.2, 2.3 Hz), 8.14 (1H, d, J=5.3 Hz).

Reference Example 311

Ethyl 2-(4-bromo-2-fluorophenoxy)-4-formylnicotinate

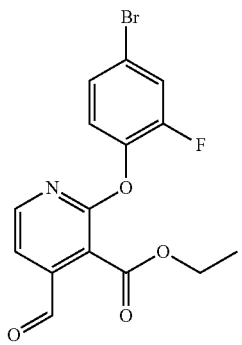 [SMILES: CCOC(=O)c1c(C=O)ccnc1Oc1ccc(Br)cc1F]

A solution of ethyl 2-(4-bromo-2-fluorophenoxy)-4-vinylnicotinate (1.52 g) obtained in Reference Example 310, sodium periodate (4.44 g) and osmium oxide (immobilized catalyst I) (0.528 g) in acetonitrile (15 mL)-acetone (15 mL)-water (15 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (1.52 g).

$^1$H NMR (300 MHz, DMSO-$d_6$) δ 1.31 (3H, t, J=7.2 Hz), 4.40 (2H, q, J=7.1 Hz), 7.30-7.40 (1H, m), 7.46-7.51 (1H, m), 7.71 (1H, d, J=5.1 Hz), 7.75 (1H, dd, J=10.2, 2.3 Hz), 8.50 (1H, d, J=5.1 Hz), 10.11 (1H, s).

Reference Example 312

Ethyl 2-(4-ethyl-2-fluorophenoxy)-4-vinylnicotinate

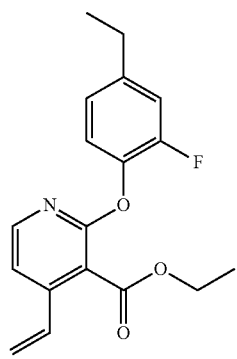 [SMILES: C=Cc1ccnc(Oc2ccc(CC)cc2F)c1C(=O)OCC]

A solution of ethyl 2-fluoro-4-vinylnicotinate (1.46 g) obtained in Reference Example 118, 4-ethyl-2-fluorophenol (1.26 g) and potassium carbonate (1.45 g) in DMF (30 mL) was stirred at 100° C. overnight. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (1.78 g).

$^1$H NMR (300 MHz, DMSO-$d_6$) δ 1.20 (3H, t, J=7.6 Hz), 1.26-1.33 (3H, m), 2.63 (2H, q, J=7.6 Hz), 4.39 (2H, q, J=7.2 Hz), 5.70 (1H, d, J=11.3 Hz), 6.19 (1H, d, J=17.4 Hz), 6.73 (1H, dd, J=17.5, 11.0 Hz), 7.01-7.13 (1H, m), 7.13-7.25 (2H, m), 7.48 (1H, d, J=5.5 Hz), 8.12 (1H, d, J=5.3 Hz).

Reference Example 313

Ethyl 2-(4-ethyl-2-fluorophenoxy)-4-formylnicotinate

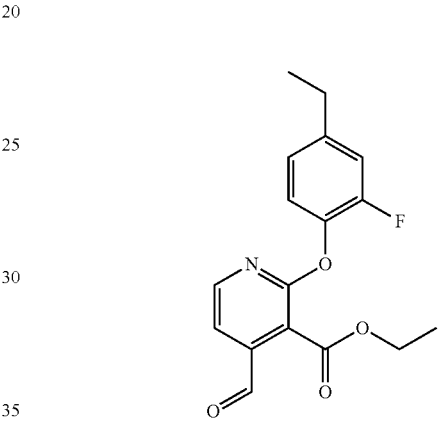

A solution of ethyl 2-(4-ethyl-2-fluorophenoxy)-4-vinylnicotinate (1.78 g) obtained in Reference Example 312, sodium periodate (6.04 g) and osmium oxide (immobilized catalyst I) (0.718 g) in acetonitrile (20 mL)-acetone (20 mL)-water (20 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (1.84 g).

$^1$H NMR (300 MHz, DMSO-$d_6$) δ 1.20 (3H, t, J=7.9 Hz), 1.31 (3H, t, J=7.1 Hz), 2.64 (2H, q, J=7.6 Hz), 4.40 (2H, q, J=7.2 Hz), 7.09 (1H, dd, J=8.3, 1.3 Hz), 7.19-7.22 (1H, m), 7.23-7.27 (1H, m), 7.68 (1H, d, J=5.1 Hz), 8.48 (1H, d, J=5.1 Hz), 10.10 (1H, s).

Reference Example 314

4-cyclopropyl-2-fluorophenyl acetate

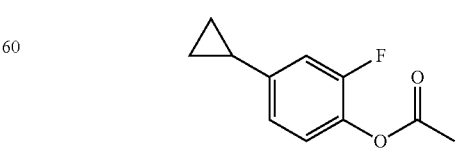

A solution of 4-bromo-2-fluorophenyl acetate (2.32 g), tris(dibenzylideneacetone)dipalladium(0) (0.638 g), 2-dicyclohexylphosphino-2',6'-dimethoxy-1,1'-biphenyl (0.613 g), cyclopropylboronic acid (1.71 g) and sodium carbonate (3.16 g) in toluene (50 mL) was stirred under an argon atmosphere at 100° C. for 2 days. The mixture was diluted with ethyl acetate and neutralized with 1N hydrochloric acid. The insoluble material was filtered off, and the organic layer was separated, washed with saturated brine, dried over anhydrous magnesium sulfate and concentrated. The residue was purified by silica gel chromatography (hexane-ethyl acetate) to give the title compound (0.402 g).

$^1$H NMR (300 MHz, DMSO-d$_6$) δ 0.64-0.74 (2H, m), 0.91-1.01 (2H, m), 1.88-1.99 (1H, m), 2.29 (3H, s), 6.92-6.99 (1H, m), 7.04 (1H, dd, J=11.9, 2.1 Hz), 7.08-7.16 (1H, m).

Reference Example 315

4-cyclopropyl-2-fluorophenol

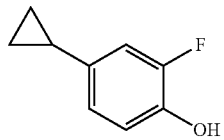 [SMILES: Oc1ccc(C2CC2)cc1F]

A solution of 4-cyclopropyl-2-fluorophenyl acetate (0.402 g) obtained in Reference Example 314 and potassium carbonate (1.43 g) in methanol (15 mL) was stirred at room temperature for 1 hr. After evaporation of the solvent, the residue was neutralized with 1N hydrochloric acid, and extracted twice with ethyl acetate. The combined organic layer was washed with water and saturated brine, dried over anhydrous magnesium sulfate and concentrated. The residue was purified by NH silica gel column chromatography (hexane-ethyl acetate) to give the title compound (0.293 g).

$^1$H NMR (300 MHz, DMSO-d$_6$) δ 0.51-0.59 (2H, m), 0.80-0.89 (2H, m), 1.74-1.87 (1H, m), 6.67-6.75 (1H, m), 6.75-6.85 (2H, m), 9.46 (1H, s).

Reference Example 316

Ethyl 2-(4-cyclopropyl-2-fluorophenoxy)-4-vinylnicotinate

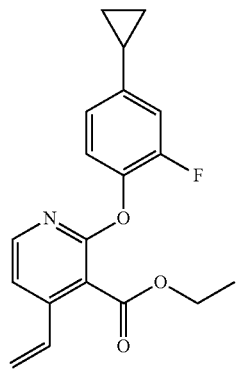 [SMILES: C=Cc1ccnc(Oc2ccc(C3CC3)cc2F)c1C(=O)OCC]

A solution of ethyl 2-fluoro-4-vinylnicotinate (0.565 g) obtained in Reference Example 118, 4-cyclopropyl-2-fluorophenol (0.293 g) obtained in Reference Example 315 and potassium carbonate (0.373 g) in DMF (10 mL) was stirred at 100° C. overnight. After evaporation of the solvent, the residue was diluted with ethyl acetate and water. The organic layer was washed with water and saturated brine, dried over anhydrous magnesium sulfate and concentrated. The residue was purified by NH silica gel column chromatography (hexane-ethyl acetate) to give the title compound (0.578 g).

$^1$H NMR (300 MHz, DMSO-d$_6$) δ 0.66-0.75 (2H, m), 0.92-1.02 (2H, m), 1.29 (3H, t, J=7.2 Hz), 1.89-2.01 (1H, m), 4.38 (2H, q, J=7.2 Hz), 5.69 (1H, d, J=11.3 Hz), 6.19 (1H, d, J=17.3 Hz), 6.72 (1H, dd, J=17.3, 10.9 Hz), 6.96 (1H, dd, J=8.3, 1.9 Hz), 7.03 (1H, dd, J=12.2, 2.1 Hz), 7.14 (1H, t, J=8.5 Hz), 7.47 (1H, d, J=5.3 Hz), 8.11 (1H, d, J=5.3 Hz).

Reference Example 317

Ethyl 2-(4-cyclopropyl-2-fluorophenoxy)-4-formylnicotinate

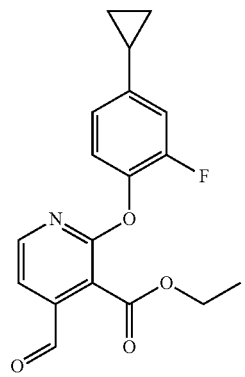 [SMILES: CCOC(=O)c1c(C=O)ccnc1Oc1ccc(C2CC2)cc1F]

A solution of ethyl 2-(4-cyclopropyl-2-fluorophenoxy)-4-vinylnicotinate (0.578 g) obtained in Reference Example 316, sodium periodate (1.89 g) and osmium oxide (immobilized catalyst I) (0.224 g) in acetonitrile (8 mL)-acetone (8 mL)-water (8 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.573 g).

$^1$H NMR (300 MHz, DMSO-d$_6$) δ 0.68-0.75 (2H, m), 0.94-1.02 (2H, m), 1.30 (3H, t, J=7.2 Hz), 1.89-2.03 (1H, m), 4.40 (2H, q, J=7.2 Hz), 6.98 (1H, dd, J=8.3, 1.9 Hz), 7.06 (1H, dd, J=12.2, 2.1 Hz), 7.18 (1H, t, J=8.5 Hz), 7.67 (1H, d, J=4.9 Hz), 8.48 (1H, d, J=4.9 Hz), 10.09 (1H, s).

Reference Example 318

Ethyl 2-(2-fluoro-4-propylphenoxy)-4-vinylnicotinate

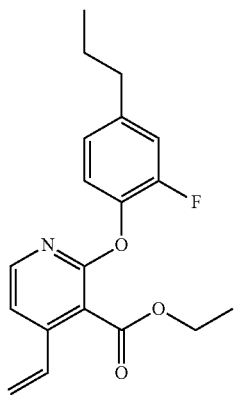 [SMILES: C=Cc1ccnc(Oc2ccc(CCC)cc2F)c1C(=O)OCC]

A solution of ethyl 2-fluoro-4-vinylnicotinate (1.00 g) obtained in Reference Example 118, 2-fluoro-4-propylphenol (1.03 g) and potassium carbonate (0.991 g) in DMF (25 mL) was stirred at 100° C. overnight. After evaporation of the solvent, the residue was diluted with ethyl acetate and water. The organic layer was washed with water and saturated brine, dried over anhydrous magnesium sulfate and concentrated. The residue was purified by NH silica gel column chromatography (hexane-ethyl acetate) to give the title compound (1.41 g).

$^1$H NMR (300 MHz, DMSO-$d_6$) δ 0.91 (3H, t, J=7.4 Hz), 1.30 (3H, t, J=7.2 Hz), 1.61 (2H, sxt, J=7.4 Hz), 2.53-2.64 (2H, m), 4.32-4.46 (2H, m), 5.70 (1H, d, J=11.5 Hz), 6.19 (1H, d, J=17.4 Hz), 6.73 (1H, dd, J=17.4, 11.1 Hz), 7.04 (1H, dd, J=8.3, 1.3 Hz), 7.11-7.24 (2H, m), 7.48 (1H, d, J=5.5 Hz), 8.13 (1H, d, J=5.5 Hz).

Reference Example 319

Ethyl 2-(2-fluoro-4-propylphenoxy)-4-formylnicotinate

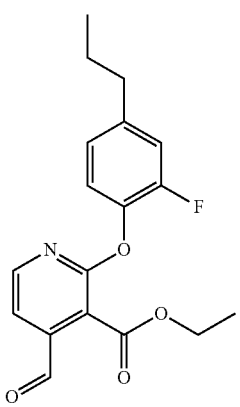 [SMILES: CCCc1ccc(Oc2nccc(C=O)c2C(=O)OCC)c(F)c1]

A solution of ethyl 2-(2-fluoro-4-propylphenoxy)-4-vinylnicotinate (1.41 g) obtained in Reference Example 318, sodium periodate (4.58 g) and osmium oxide (immobilized catalyst I) (0.544 g) in acetonitrile (15 mL)-acetone (15 mL)-water (15 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (1.49 g).

$^1$H NMR (300 MHz, DMSO-$d_6$) δ 0.91 (3H, t, J=7.4 Hz), 1.31 (3H, t, J=7.1 Hz), 1.61 (2H, sxt, J=7.4 Hz), 2.53-2.65 (2H, m), 4.40 (2H, q, J=7.2 Hz), 7.07 (1H, dd, J=8.3, 1.3 Hz), 7.16-7.27 (2H, m), 7.68 (1H, d, J=5.1 Hz), 8.49 (1H, d, J=4.9 Hz), 10.10 (1H, s).

Reference Example 320

Tert-butyl ((6-(methylcarbamoyl)pyridin-3-yl)methyl)carbamate

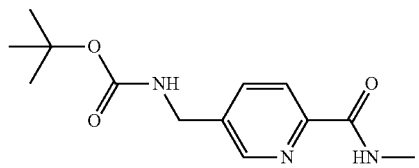 [SMILES: CNC(=O)c1ccc(CNC(=O)OC(C)(C)C)cn1]

To a solution of 5-((((tert-butoxycarbonyl)amino)methyl)picolinic acid (1.16 g), methanamine hydrochloride (0.621 g), triethylamine (1.86 g) and 1-hydroxybenzotriazole (0.932 g) in DMF (25 mL) was added 1-(3-dimethylaminopropyl)-3-ethylcarbodiimide hydrochloride (1.32 g), and the mixture was stirred at room temperature overnight. The solvent was evaporated, and the residue was diluted with water, saturated with potassium carbonate, and extracted three times with ethyl acetate. The combined organic layer was washed with saturated brine, dried over anhydrous magnesium sulfate and concentrated. The residue was purified by NH silica gel column chromatography (hexane-ethyl acetate) to give the title compound (1.14 g).

$^1$H NMR (300 MHz, CDCl$_3$) δ 1.28-1.44 (9H, m), 2.81 (3H, d, J=4.9 Hz), 4.22 (2H, d, J=6.0 Hz), 7.50 (1H, t, J=6.0 Hz), 7.80 (1H, dd, J=8.1, 2.1 Hz), 7.98 (1H, d, J=7.9 Hz), 8.49 (1H, d, J=1.5 Hz), 8.72 (1H, q, J=4.7 Hz).

Reference Example 321

5-(aminomethyl)-N-methylpicolinamide hydrochloride

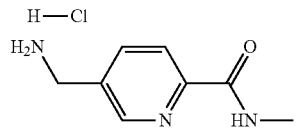

To a solution of tert-butyl ((6-(methylcarbamoyl)pyridin-3-yl)methyl)carbamate (1.14 g) obtained in Reference Example 320 in ethyl acetate (20 mL)-methanol (10 mL) was added 4N hydrogen chloride ethyl acetate solution (5 mL), and the mixture was stirred at room temperature for 2 hr. The precipitate was collected by filtration, washed with ethyl acetate and dried to give the title compound (0.726 g).

$^1$H NMR (300 MHz, DMSO-d$_6$) δ 2.82 (3H, d, J=4.9 Hz), 4.16 (2H, q, J=5.9 Hz), 8.02-8.14 (2H, m), 8.49 (3H, brs), 8.74 (1H, d, J=1.1 Hz), 8.80 (1H, q, J=4.5 Hz).

Reference Example 322

1-(4-(benzyloxy)-3-fluorophenyl)-2,2,2-trifluoroethanol

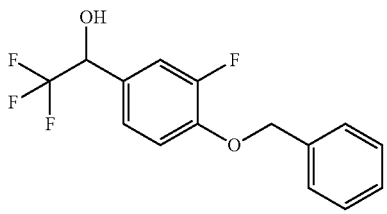

To a solution of 4-(benzyloxy)-3-fluorobenzaldehyde (4.56 g) and (trifluoromethyl)trimethylsilane (3.10 g) in THF (100 mL) was added 1M tetrabutylammonium fluoride THF solution (3.96 mL), and the mixture was stirred at room temperature overnight. The solvent was evaporated, and the residue was purified by NH silica gel column chromatography (hexane-ethyl acetate) to give the title compound (4.61 g).

$^1$H NMR (300 MHz, CDCl$_3$) δ 5.05-5.18 (1H, m), 5.20 (2H, s), 6.85 (1H, d, J=5.7 Hz), 7.18-7.53 (8H, m).

Reference Example 323

1-(benzyloxy)-4-(1-chloro-2,2,2-trifluoroethyl)-2-fluorobenzene

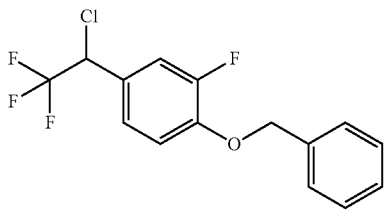 [SMILES: Fc1cc(C(Cl)C(F)(F)F)ccc1OCc1ccccc1]

A mixture of 1-(4-(benzyloxy)-3-fluorophenyl)-2,2,2-trifluoroethanol (4.61 g) obtained in Reference Example 322 and thionyl chloride (13.0 g) was stirred at 70° C. for 3 hr. The reaction mixture was concentrated under reduced pressure, and the residue was purified by silica gel column chromatography (hexane-ethyl acetate) to give the title compound (5.04 g).

$^1$H NMR (300 MHz, CDCl$_3$) δ 5.23 (2H, s), 6.17 (1H, q, J=7.4 Hz), 7.31-7.51 (8H, m).

Reference Example 324

2-fluoro-4-(2,2,2-trifluoroethyl)phenol

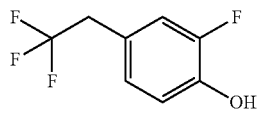 [SMILES: Oc1ccc(CC(F)(F)F)cc1F]

To a solution of lithium aluminum hydride (0.60 g) in THF (75 mL) was added a solution of 1-(benzyloxy)-4-(1-chloro-2,2,2-trifluoroethyl)-2-fluorobenzene (5.04 g) obtained in Reference Example 323 in THF (15 mL) at 0° C., and the reaction mixture was stirred at 50° C. overnight. To the reaction mixture were added water (0.6 mL), 15% aqueous sodium hydroxide solution (0.6 mL) and water (1.8 mL) in this order under ice-cooling, and the mixture was stirred at room temperature for 2 hr. The insoluble material was filtered off, and the filtrate was concentrated. A solution of the obtained residue and 10% palladium carbon (1.0 g) in acetic acid (50 mL) was stirred under a hydrogen atmosphere at room temperature for 2 hr. The insoluble material was filtered off, and the filtrate was concentrated, and the residue was purified by NH silica gel column chromatography (hexane-ethyl acetate) to give the title compound (0.88 g).

$^1$H NMR (300 MHz, DMSO-d$_6$) δ 3.52 (2H, q, J=11.5 Hz), 6.88-7.02 (2H, m), 7.07-7.20 (1H, m), 9.92 (1H, s).

Reference Example 325

Ethyl 2-(2-fluoro-4-(2,2,2-trifluoroethyl)phenoxy)-4-vinylnicotinate

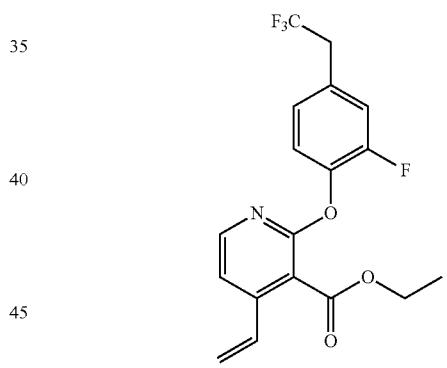

A solution of ethyl 2-fluoro-4-vinylnicotinate (1.59 g) obtained in Reference Example 118, 2-fluoro-4-(2,2,2-trifluoroethyl)phenol (0.88 g) obtained in Reference Example 324 and potassium carbonate (0.94 g) in DMF (25 mL) was stirred at 100° C. for 4 hr. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (0.89 g).

$^1$H NMR (300 MHz, DMSO-d$_6$) δ 1.30 (3H, t, J=7.1 Hz), 3.72 (2H, q, J=11.5 Hz), 4.39 (2H, q, J=7.0 Hz), 5.71 (1H, d, J=11.3 Hz), 6.20 (1H, d, J=17.4 Hz), 6.74 (1H, dd, J=17.5, 11.0 Hz), 7.19-7.29 (1H, m), 7.29-7.44 (2H, m), 7.51 (1H, d, J 5.3 Hz), 8.15 (1H, d, J=5.5 Hz).

Reference Example 326

Ethyl 2-(2-fluoro-4-(2,2,2-trifluoroethyl)phenoxy)-4-formylnicotinate

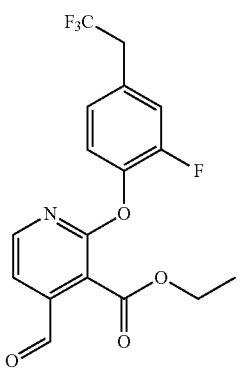 [SMILES: CCOC(=O)c1c(C=O)ccnc1Oc1ccc(CC(F)(F)F)cc1F]

A solution of ethyl 2-(2-fluoro-4-(2,2,2-trifluoroethyl)phenoxy)-4-vinylnicotinate (0.88 g) obtained in Reference Example 325, sodium periodate (2.55 g) and osmium oxide (immobilized catalyst I) (0.30 g) in acetonitrile (8 mL)-acetone (8 mL)-water (8 mL) was stirred at room temperature overnight. The insoluble material was filtered off, and the filtrate was diluted with ethyl acetate. The organic layer was separated, washed with saturated brine, dried over anhydrous sodium sulfate, and concentrated to give the title compound (0.87 g).

$^1$H NMR (300 MHz, DMSO-$d_6$) δ 1.31 (3H, t, J=7.1 Hz), 3.73 (2H, q, J=11.5 Hz), 4.41 (2H, q, J=7.1 Hz), 7.22-7.32 (1H, m), 7.33-7.48 (2H, m), 7.70 (1H, d, J=5.1 Hz), 8.50 (1H, d, J=4.9 Hz), 10.11 (1H, s).

Reference Example 327

Ethyl 2-(2-fluoro-4-(trifluoromethyl)phenoxy)-6-methylbenzoate

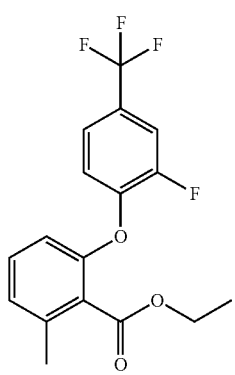 [SMILES: CCOC(=O)c1c(C)cccc1Oc1ccc(C(F)(F)F)cc1F]

To a solution of ethyl 2-hydroxy-6-methylbenzoate (1.80 g) and potassium carbonate (2.07 g) in DMF (50 mL) was added 1,2-difluoro-4-(trifluoromethyl)benzene (2.37 g), and the mixture was stirred at 100° C. for 3 days. After evaporation of the solvent, the residue was diluted with ethyl acetate and water. The organic layer was washed with water and saturated brine, dried over anhydrous magnesium sulfate and concentrated. The residue was purified by NH silica gel column chromatography (hexane-ethyl acetate) to give the title compound (2.45 g).

$^1$H NMR (300 MHz, DMSO-$d_6$) δ 1.10 (3H, t, J=7.1 Hz), 2.33 (3H, s), 4.20 (2H, q, J=7.2 Hz), 7.00-7.09 (2H, m), 7.22 (1H, d, J=7.6 Hz), 7.40-7.49 (1H, m), 7.55 (1H, d, J=8.7 Hz), 7.87 (1H, dd, J=11.1, 2.1 Hz)

Reference Example 328

Ethyl 2-(bromomethyl)-6-(2-fluoro-4-(trifluoromethyl)phenoxy)benzoate

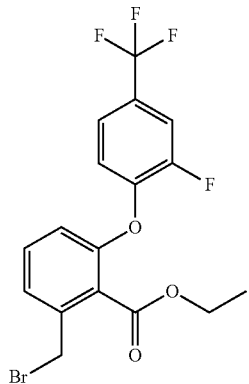 [SMILES: CCOC(=O)c1c(CBr)cccc1Oc1ccc(C(F)(F)F)cc1F]

To a solution of ethyl 2-(2-fluoro-4-(trifluoromethyl)phenoxy)-6-methylbenzoate (2.45 g) obtained in Reference Example 327 and NBS (1.40 g) in (trifluoromethyl)benzene (30 mL) was added AIBN (0.12 g), and the mixture was stirred at 100° C. for 2 hr. Furthermore, NBS (1.40 g) and AIBN (0.12 g) were added, and the mixture was stirred for 1 hr. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate) to give the title compound (2.54 g).

$^1$H NMR (300 MHz, DMSO-$d_6$) δ 1.13 (3H, t, J=7.1 Hz), 4.24 (2H, q, J=7.2 Hz), 4.76 (2H, s), 7.06-7.13 (1H, m), 7.18-7.23 (1H, m), 7.46-7.51 (1H, m), 7.56 (2H, t, J=7.9 Hz), 7.89 (1H, dd, J=10.9, 2.4 Hz).

Reference Example 329

7-((7-oxabicyclo[2.2.2.]hept-1-yl)methoxy)-2-(4-bromobenzyl)isoindolin-1-one

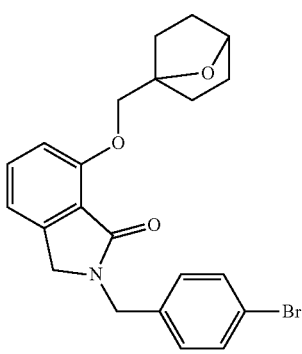 [SMILES: O=C1c2c(cccc2OCC23CCC(CC2)O3)CN1Cc1ccc(Br)cc1]

A solution of 2-(4-bromobenzyl)-7-hydroxyisoindolin-1-one (0.20 g) obtained in Reference Example 3, (1-(iodomethyl)-7-oxabicyclo[2.2.1]heptane (0.22 g) prepared by referring a document (WO2007/091703) and potassium carbonate (0.17 g) in DMF (5 mL) was stirred at 70° C. overnight. The reaction mixture was diluted with water, extracted with ethyl acetate, washed with 1N hydrochloric acid, saturated aqueous sodium hydrogen carbonate solution, and saturated brine, dried over anhydrous sodium sulfate, and concentrated. The residue was purified by NH silica gel column chromatography (hexane-ethyl acetate) to give the title compound (0.073 g).

MS: [M+H]$^+$ 318.0, 320.0

$^1$H NMR (300 MHz, DMSO-$d_6$) δ 1.49-1.85 (8H, m), 4.29 (2H, s), 4.38 (2H, s), 4.50 (1H, t, J=4.5 Hz), 4.62 (2H, s), 7.08 (2H, t, J=7.2 Hz), 7.23 (2H, d, J=8.5 Hz), 7.45-7.56 (3H, m).

Reference Example 330

2-(4-bromobenzyl)-4-(2-fluoro-6-methoxyphenoxy)-1H-pyrrolo[3,4-c]pyridin-3 (2H)-one

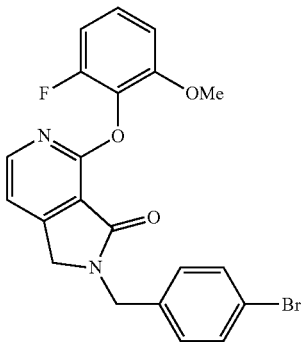 [SMILES: COc1cccc(F)c1Oc1nccc2c1C(=O)N(Cc1ccc(Br)cc1)C2]

To a solution of ethyl 2-(2-fluoro-6-methoxyphenoxy)-4-vinylnicotinate (0.31 g) obtained in Reference Example 206 in acetone-acetonitrile-water (1:1:1, 12 mL) were added sodium periodate (1.05 g) and osmium oxide (immobilized catalyst I) (0.12 g), and the mixture was stirred at room temperature overnight. The insoluble material was filtered off, and the filtrate was concentrated. The residue was dissolved in THF (15 mL), (4-bromophenyl)methanamine (0.18 g) and anhydrous magnesium sulfate (1.18 g) were added, and the mixture was stirred for 1 hr. The insoluble material was filtered off, and the filtrate was concentrated. The residue was dissolved in acetic acid (15 mL), sodium triacetoxyborohydride (0.41 g) was added, and the mixture was stirred for 1 hr. The reaction mixture was diluted with ethyl acetate and saturated aqueous sodium hydrogen carbonate solution, and the organic layer was separated, washed with saturated brine, dried over anhydrous sodium sulfate, and concentrated. The residue was solidified with diisopropyl ether-ethyl acetate to give the title compound (0.21 g).

MS: [M+H]$^+$ 443.1

$^1$H NMR (300 MHz, CDCl$_3$) δ 3.76-3.81 (3H, m), 4.28 (2H, s), 4.75 (2H, s), 6.77-6.86 (2H, m), 7.03 (1H, d, J=5.3 Hz), 7.12-7.25 (3H, m), 7.45-7.52 (2H, m), 8.17 (1H, d, J=5.3 Hz).

Reference Example 331

2-(4-bromobenzyl)-7-((tetrahydrofuran-2-yl)methoxy)isoindolin-1-one

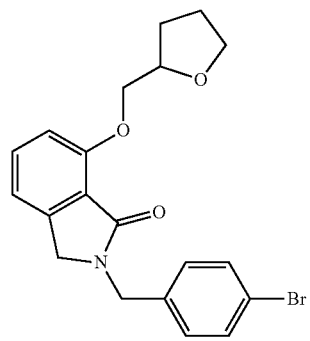

A solution of methyl 2-formyl-6-((tetrahydrofuran-2-yl)methoxy)benzoate (0.94 g) obtained in Reference Example 205, (4-bromophenyl)methanamine (0.73 g) and anhydrous magnesium sulfate (0.86 g) in THF (20 mL) was stirred under an argon atmosphere at room temperature for 1 hr. The insoluble material was filtered off, and the filtrate was concentrated. The residue was dissolved in acetic acid (20 mL), sodium triacetoxyborohydride (0.62 g) was added, and the mixture was stirred under an argon atmosphere at room temperature for 1 hr. The reaction mixture was diluted with saturated aqueous sodium hydrogen carbonate solution and ethyl acetate, and the organic layer was separated, washed with saturated brine, dried over anhydrous sodium sulfate, and concentrated. The residue was purified by NH silica gel chromatography (hexane-ethyl acetate) to give the title compound (0.72 g).

$^1$H NMR (300 MHz, CDCl$_3$) 51.91-2.22 (4H, m), 3.78-3.90 (1H, m), 3.93-4.07 (1H, m), 4.08-4.24 (4H, m), 4.32-4.45 (1H, m), 4.65-4.74 (2H, m), 6.86-6.98 (2H, m), 7.12-7.22 (2H, m), 7.37-7.50 (3H, m).

Reference Example 332

7-((tetrahydrofuran-2-yl)methoxy)-2-((5,6,7,8-tetrahydroimidazo[1,2-a]pyridin-5-yl)methyl)isoindolin-1-one

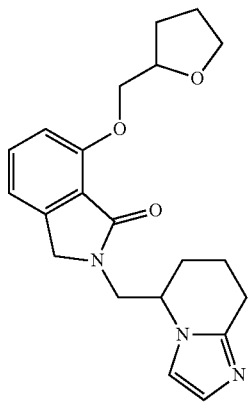 [SMILES: O=C1c2c(cccc2OCC2CCCO2)CN1CC1CCCc2nccn21]

To a solution of methyl 2-formyl-6-((tetrahydrofuran-2-yl)methoxy)benzoate (0.10 g) obtained in Reference Example 205 and (5,6,7,8-tetrahydroimidazo[1,2-a]pyridin-5-yl)methanamine (0.057 g) obtained in Reference Example 85 in acetic acid (3 mL) was added sodium triacetoxyhydroborate (0.16 g), and the mixture was stirred under a nitrogen atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.058 g).

MS: [M+H]$^+$ 368.2

$^1$H NMR (300 MHz, DMSO-$d_6$) δ 1.67-1.87 (4H, m), 1.90-2.02 (4H, m), 2.62-2.77 (2H, m), 3.60-3.89 (4H, m), 4.03-4.08 (2H, m), 4.13-4.24 (2H, m), 4.32-4.48 (2H, m), 6.84 (1H, d, J=1.3 Hz), 6.98-7.14 (3H, m), 7.49 (1H, t, J=7.9 Hz).

Reference Example 333

7-((tetrahydrofuran-2-yl)methoxy)-2-((5,6,7,8-tetrahydroimidazo[1,2-a]pyridin-7-yl)methyl)isoindolin-1-one

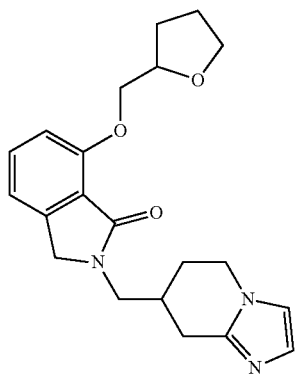 [SMILES: O=C1c2c(cccc2OCC2CCCO2)CN1CC1CCn2ccnc2C1]

To a solution of methyl 2-formyl-6-((tetrahydrofuran-2-yl)methoxy)benzoate (0.10 g) obtained in Reference Example 205 and (5,6,7,8-tetrahydroimidazo[1,2-a]pyridin-7-yl)methanamine (0.057 g) obtained in Reference Example 88 in acetic acid (3 mL) was added sodium triacetoxyhydroborate (0.16 g), and the mixture was stirred under a nitrogen atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.011 g).

MS: [M+H]$^+$ 368.2

$^1$H NMR (300 MHz, CDCl$_3$) δ 1.72-1.83 (1H, m), 1.93-2.01 (2H, m), 2.04-2.17 (3H, m), 2.33-2.46 (1H, m), 2.52-2.66 (1H, m), 3.06 (1H, dd, J=16.4, 3.8 Hz), 3.31-3.49 (1H, m), 3.74-3.90 (3H, m), 3.93-4.05 (1H, m), 4.08-4.22 (3H, m), 4.25-4.49 (3H, m), 6.78 (1H, d, J=1.1 Hz), 6.88-7.04 (3H, m), 7.45 (1H, t, J=7.8 Hz).

Example 1

7-((trans-2-hydroxycyclohexyl)oxy)-2-(4-(1-methyl-1H-pyrazol-4-yl)benzyl)isoindolin-1-one

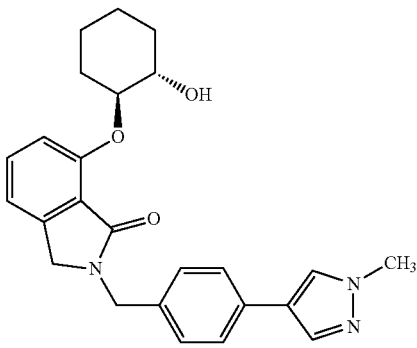 [SMILES: Cn1cc(-c2ccc(CN3Cc4cccc(O[C@H]5CCCC[C@@H]5O)c4C3=O)cc2)cn1]

To a solution of 7-hydroxy-2-(4-(1-methyl-1H-pyrazol-4-yl)benzyl)isoindolin-1-one (0.20 g) obtained in Reference Example 6 in ethanol (4 mL) were added 7-oxabicyclo[4.1.0]heptane (0.62 g) and pyridine (0.64 g), and the mixture was stirred under an argon atmosphere at 90° C. for 5 hr. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) and recrystallization (hexane-ethyl acetate) to give the title compound (0.19 g).

MS: [M+H]$^+$ 418.3

$^1$H NMR (300 MHz, DMSO-$d_6$) δ 1.23-1.36 (3H, m), 1.42-1.54 (1H, m), 1.57-1.73 (2H, m), 1.91 (1H, brs), 2.04-2.13 (1H, m), 3.58-3.66 (1H, m), 3.85 (3H, s), 4.00-4.09 (1H, m), 4.30 (2H, s), 4.64 (2H, s), 5.19 (1H, d, J=3.4 Hz), 7.09-7.14 (2H, m), 7.25 (2H, d, J=8.1 Hz), 7.45-7.50 (1H, m), 7.53 (2H, d, J=8.1 Hz), 7.83 (1H, s), 8.11 (1H, s).

Example 2

7-((trans-4,4-difluoro-2-hydroxycyclohexyl)oxy)-2-(4-(1-methyl-1H-pyrazol-4-yl)benzyl)isoindolin-1-one

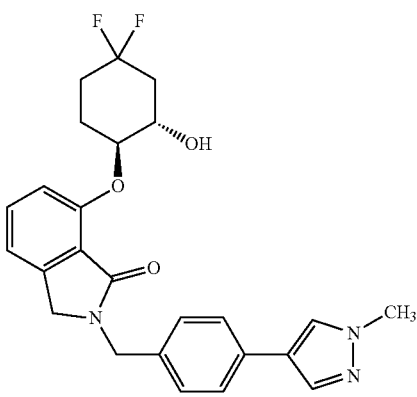 [SMILES: Cn1cc(-c2ccc(CN3Cc4cccc(O[C@H]5CCC(F)(F)C[C@@H]5O)c4C3=O)cc2)cn1]

To a solution of 3,3-difluoro-7-oxabicyclo[4.1.0]heptane (0.49 g) obtained in Reference Example 36 in ethanol (5 mL) were added 7-hydroxy-2-(4-(1-methyl-1H-pyrazol-4- yl)benzyl)isoindolin-1-one (0.12 g) obtained in Reference Example 6, and pyridine (0.29 g), and the mixture was heated under reflux for 16 hr. The reaction mixture was concentrated, and the residue was purified by silica gel chromatography (petroleum ether-ethyl acetate) to give the title compound (0.078 g).

MS: [M+H]+ 454.3

$^1$H NMR (400 MHz, CDCl$_3$) δ 1.75-2.03 (3H, m), 2.18-32 (2H, m), 2.57-2.69 (1H, m), 3.90-4.00 (4H, m), 4.09-4.18 (1H, m), 4.26 (2H, d, J=2.4 Hz), 4.66 (1H, d, J=14.8 Hz), 4.85 (1H, d, J=15.2 Hz), 5.93 (1H, brs), 7.04 (1H, dd, J=8.0, 0.8 Hz), 7.09 (1H, dd, J=7.6, 0.8 Hz), 7.27-7.33 (2H, m), 7.40-7.49 (3H, m), 7.59 (1H, d, J=0.4 Hz), 7.73 (1H, d, J=0.8 Hz).

Example 3

7-((trans-2-hydroxycycloheptyl)oxy)-2-(4-(1-methyl-1H-pyrazol-4-yl)benzyl)isoindolin-1-one

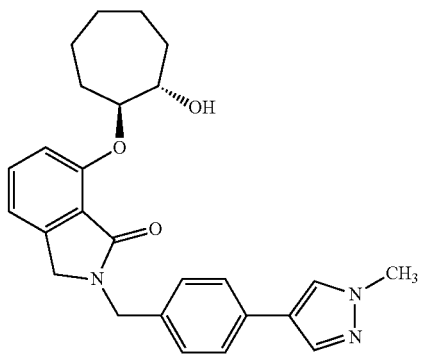 [SMILES: Cn1cc(-c2ccc(CN3Cc4cccc(O[C@H]5CCCCC[C@@H]5O)c4C3=O)cc2)cn1]

To a solution of 7-hydroxy-2-(4-(1-methyl-1H-pyrazol-4-yl)benzyl)isoindolin-1-one (0.10 g) obtained in Reference Example 6 in ethanol (5 mL) were added 8-oxabicyclo[5.1.0]octane (0.35 g) and pyridine (0.38 g), and the mixture was stirred under an argon atmosphere at 90° C. for 3 days. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.051 g).

MS: [M+H]+ 432.2

$^1$H NMR (300 MHz, DMSO-d$_6$) δ 1.37-1.62 (6H, m), 1.69-1.94 (4H, m), 3.71-3.93 (4H, m), 4.08-4.42 (3H, m), 4.64 (2H, s), 5.05 (1H, d, J=3.4 Hz), 6.90-7.16 (2H, m), 7.25 (2H, d, J=8.3 Hz), 7.40-7.59 (3H, m), 7.82 (1H, d, J=0.8 Hz), 8.10 (1H, s).

Example 4

7-((trans-2-hydroxycyclopentyl)oxy)-2-(4-(1-methyl-1H-pyrazol-4-yl)benzyl)isoindolin-1-one

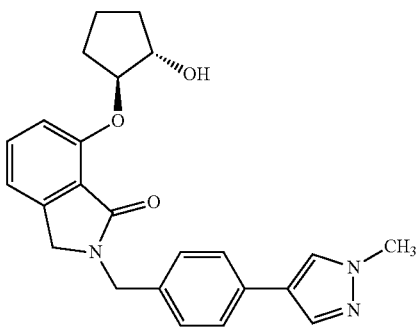 [SMILES: Cn1cc(-c2ccc(CN3Cc4cccc(O[C@H]5CCC[C@@H]5O)c4C3=O)cc2)cn1]

To a solution of 7-hydroxy-2-(4-(1-methyl-1H-pyrazol-4-yl)benzyl)isoindolin-1-one (0.05 g) obtained in Reference Example 6 in ethanol (3 mL) were added 6-oxabicyclo[3.1.0]hexane (0.13 g) and pyridine (0.16 g), and the mixture was stirred under an argon atmosphere at 90° C. for 5 hr. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) and recrystallization (hexane-ethyl acetate) to give the title compound (0.03 g).

MS: [M+H]+ 404.3

$^1$H NMR (400 MHz, DMSO-d$_6$) δ 1.56 (1H, brs), 1.73 (3H, brs), 1.94 (1H, brs), 2.11 (1H, brs), 3.85 (3H, s), 4.09 (1H, brs), 4.27 (2H, brs), 4.61 (3H, brs), 4.97 (1H, brs), 7.00-7.11 (2H, m), 7.24 (2H, d, J=7.8 Hz), 7.44-7.59 (3H, m), 7.82 (1H, s), 8.10 (1H, s).

Example 5

2-(4-(1-methyl-1H-pyrazol-4-yl)benzyl)-7-((tetrahydrofuran-2-yl)methoxy)isoindolin-1-one

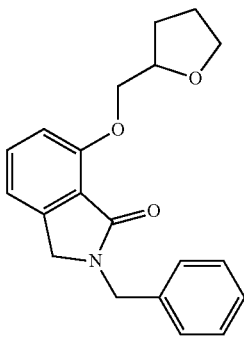

A solution of 7-hydroxy-2-(4-(1-methyl-1H-pyrazol-4-yl)benzyl)isoindolin-1-one (0.10 g) obtained in Reference Example 6, (tetrahydrofuran-2-yl)methanol (0.064 g) and triphenylphosphine (0.16 g) in THF (4 mL) was stirred at 60° C. for 20 min, diisopropyl azodicarboxylate (40% toluene solution) (0.33 mL) was added, and the mixture was stirred under a nitrogen atmosphere at the same temperature for 3 hr. The reaction mixture was diluted with ethyl acetate, and washed with saturated brine. The organic layer was separated, dried over anhydrous sodium sulfate, and concentrated. The residue was crudely purified by NH silica gel chromatography (hexane-ethyl acetate), and solidified with diisopropyl ether to give the title compound (0.095 g).

MS: [M+H]+ 404.3

$^1$H NMR (300 MHz, DMSO-d$_6$) δ 1.61-1.91 (2H, m), 1.94-2.13 (2H, m), 3.61-3.75 (1H, m), 3.78-3.93 (4H, m), 4.00-4.13 (2H, m), 4.13-4.23 (1H, m), 4.28 (2H, s), 4.63 (2H, s), 6.92-7.13 (2H, m), 7.24 (2H, d, J=8.3 Hz), 7.39-7.59 (3H, m), 7.82 (1H, d, J=0.8 Hz), 8.10 (1H, s).

Example 6

3-fluoro-2-((2-(4-(1-methyl-1H-pyrazol-4-yl)benzyl)-3-oxo-2,3-dihydro-1H-isoindol-4-yl)oxy)benzonitrile

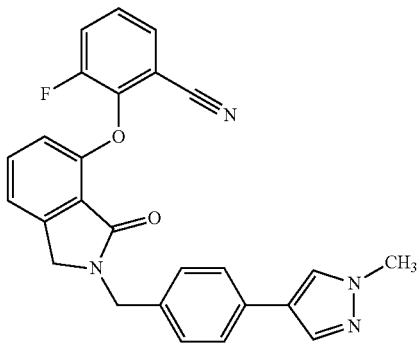

To a solution of 7-hydroxy-2-(4-(1-methyl-1H-pyrazol-4-yl)benzyl)isoindolin-1-one (0.050 g) obtained in Reference Example 6 in DMF (2 mL) was added potassium tert-butoxide (0.018 g), and the mixture was stirred under an argon atmosphere at room temperature for 30 min. To the reaction solution was added 2,3-difluorobenzonitrile (0.024 g), and the mixture was stirred at 50° C. for 6 hr. The reaction mixture was diluted with ethyl acetate, and washed with saturated brine. The organic layer was separated, dried over anhydrous sodium sulfate, and concentrated. The residue was crudely purified by NH silica gel chromatography (hexane-ethyl acetate), and solidified with hexane-ethyl acetate to give the title compound (0.035 g).

MS: [M+H]+ 439.2

$^1$H NMR (400 MHz, DMSO-d$_6$) δ 3.85 (3H, s), 4.41 (2H, s), 4.66 (2H, s), 6.84 (1H, d, J=8.3 Hz), 7.27 (2H, d, J=8.1 Hz), 7.33 (1H, d, J=7.3 Hz), 7.46-7.58 (4H, m), 7.77-7.86 (3H, m), 8.12 (1H, s).

Example 7

7-((trans-3,3-difluoro-2-hydroxycyclohexyl)oxy)-2-(4-(1-methyl-1H-pyrazol-4-yl)benzyl)isoindolin-1-one

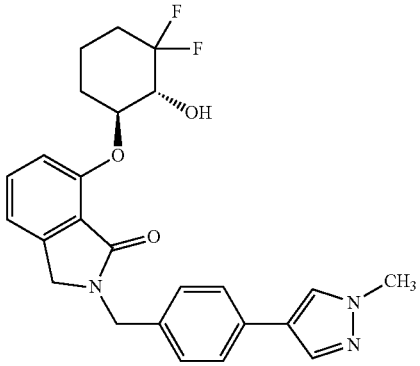 [SMILES: Cn1cc(-c2ccc(CN3Cc4cccc(O[C@H]5CCCC(F)(F)[C@@H]5O)c4C3=O)cc2)cn1]

A solution of 7-oxa-bicyclo[4.1.0]heptan-2-one (2.0 g) in dichloromethane (10 mL) was cooled to 0° C., and diethylaminosulfur trifluoride (6.32 g) was added dropwise. The reaction solution was warmed to room temperature, and the mixture was stirred at room temperature for 16 hr. To the reaction solution was added water at 0° C., and the organic layer was separated, and dried over anhydrous sodium sulfate to give a dichloromethane solution. To a suspension of 7-hydroxy-2-(4-(1-methyl-1H-pyrazol-4-yl)benzyl)isoindolin-1-one (0.20 g) obtained in Reference Example 6 in ethanol (8 mL) were added 80% amount of dichloromethane solution prepared earlier and pyridine (1.36 g), and the mixture was refluxed for 16 hr. The reaction solution was concentrated, and the residue was purified by silica gel chromatography (petroleum ether-ethyl acetate) and HPLC (C18, mobile phase: water/acetonitrile (containing 0.1% TFA)) to give the title compound (0.10 g).

MS: [M+H]+ 454.3

$^1$H NMR (400 MHz, CDCl$_3$) δ 1.45-1.55 (1H, m), 1.69-1.85 (3H, m), 2.15-2.35 (2H, m), 3.94 (3H, s), 3.95-4.20 (2H, m), 4.26 (2H, s), 4.66 (1H, d, J=14.4 Hz), 4.84 (1H, d, J=14.8 Hz), 6.43 (1H, brs), 7.04 (1H, d, J=8.0 Hz), 7.10 (1H, d, J=7.6 Hz), 7.30 (2H, d, J=8.0 Hz), 7.38-7.49 (3H, m), 7.60 (1H, s), 7.74 (1H, s).

Example 8

2-(4-(1-methyl-1H-pyrazol-4-yl)benzyl)-7-(2-(pyrrolidin-1-yl)ethoxy)isoindolin-1-one

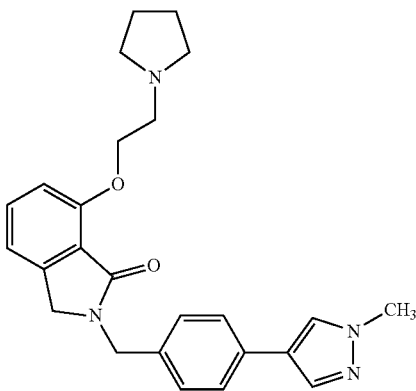 [SMILES: Cn1cc(-c2ccc(CN3Cc4cccc(OCCN5CCCC5)c4C3=O)cc2)cn1]

To a solution of 7-hydroxy-2-(4-(1-methyl-1H-pyrazol-4-yl)benzyl)isoindolin-1-one (0.20 g) obtained in Reference Example 6 in DMF (5 mL) were added 1-(2-chloroethyl)pyrrolidine hydrochloride (0.21 g) and potassium carbonate (0.35 g), and the mixture was stirred at 70° C. for 4 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.091 g).

MS: [M+H]$^+$ 417.3

$^1$H NMR (300 MHz, DMSO-d$_6$) δ 1.61-1.74 (4H, m), 2.54-2.63 (4H, m), 2.83 (2H, t, J=5.8 Hz), 3.85 (3H, s), 4.19 (2H, t, J=5.8 Hz), 4.27 (2H, s), 4.62 (2H, s), 6.93-7.13 (2H, m), 7.23 (2H, d, J=8.3 Hz), 7.40-7.58 (3H, m), 7.82 (1H, d, J=0.8 Hz), 8.09 (1H, s).

Example 9

3-chloro-2-((2-(4-(1-methyl-1H-pyrazol-4-yl)benzyl)-3-oxo-2,3-dihydro-1H-isoindol-4-yl)oxy)benzonitrile

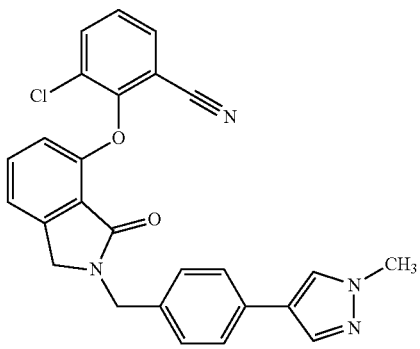

To a solution of 7-hydroxy-2-(4-(1-methyl-1H-pyrazol-4-yl)benzyl)isoindolin-1-one (0.10 g) obtained in Reference Example 6 in DMF (5 mL) were added 3-chloro-2-fluorobenzonitrile (0.20 g) and potassium carbonate (0.17 g), and the mixture was stirred at 90° C. for 5 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.10 g).

MS: [M+H]$^+$ 455.1

$^1$H NMR (300 MHz, DMSO-d$_6$) δ 3.85 (3H, s), 4.41 (2H, s), 4.69 (2H, s), 6.56 (1H, d, J=8.3 Hz), 7.20-7.37 (3H, m), 7.41-7.63 (4H, m), 7.84 (1H, s), 7.95-8.08 (2H, m), 8.12 (1H, s).

Example 10

7-(2-chloro-6-fluoro-4-nitrophenoxy)-2-(4-(1-methyl-1H-pyrazol-4-yl)benzyl)isoindolin-1-one

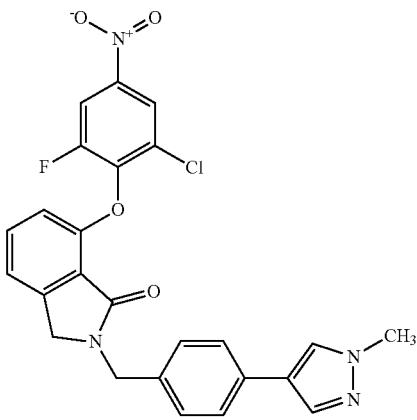

To a solution of 7-hydroxy-2-(4-(1-methyl-1H-pyrazol-4-yl)benzyl)isoindolin-1-one (0.10 g) obtained in Reference Example 6 in DMF (3 mL) were added 1-chloro-2,3-difluoro-5-nitrobenzene (0.18 g) and potassium carbonate (0.13 g), and the mixture was stirred under an argon atmosphere at 80° C. for 1 hr. The reaction mixture was diluted with ethyl acetate, and washed with saturated brine. The organic layer was separated, dried over anhydrous sodium sulfate, and concentrated. The residue was crudely purified by NH silica gel chromatography (hexane-ethyl acetate), and solidified with diisopropyl ether to give the title compound (0.11 g).

MS: [M+H]$^+$ 493.2

$^1$H NMR (300 MHz, DMSO-d$_6$) δ 3.85 (3H, s), 4.41 (2H, s), 4.66 (2H, s), 6.85 (1H, d, J=8.3 Hz), 7.17-7.39 (3H, m), 7.44-7.60 (3H, m), 7.83 (1H, d, J=0.8 Hz), 8.11 (1H, s), 8.32-8.54 (2H, m).

Example 11

7-(4-amino-2-chloro-6-fluorophenoxy)-2-(4-(1-methyl-1H-pyrazol-4-yl)benzyl)isoindolin-1-one

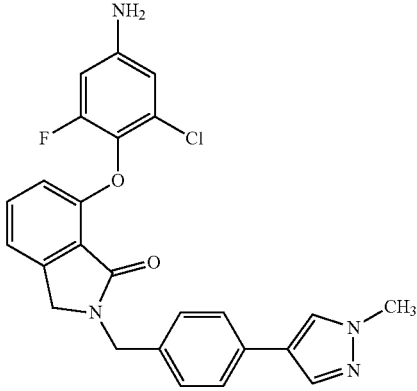 [SMILES: Cn1cc(-c2ccc(CN3Cc4cccc(Oc5c(F)cc(N)cc5Cl)c4C3=O)cc2)cn1]

A solution of 7-(2-chloro-6-fluoro-4-nitrophenoxy)-2-(4-(1-methyl-1H-pyrazol-4-yl)benzyl)isoindolin-1-one (0.10 g) obtained in Example 10, iron(III) chloride hexahydrate (0.001 g) and activated carbon (0.01 g) in THF (4 mL)- methanol (2 mL) was stirred under a nitrogen atmosphere at 60° C. for 10 min. To the reaction solution was added hydrazine monohydrate (0.10 g), and the mixture was stirred at 70° C. overnight. The insoluble material was filtered off, and the filtrate was concentrated. The residue was purified by NH silica gel chromatography (hexane-ethyl acetate) to give the title compound (0.04 g).

MS: [M+H]$^+$ 463.2

$^1$H NMR (300 MHz, DMSO-d$_6$) δ 3.85 (3H, s), 4.36 (2H, s), 4.67 (2H, s), 5.71 (2H, s), 6.41-6.65 (3H, m), 7.16 (1H, d, J=7.2 Hz), 7.29 (2H, d, J=8.3 Hz), 7.43 (1H, dd, J=8.2, 7.5 Hz), 7.55 (2H, d, J=8.3 Hz), 7.83 (1H, d, J=0.8 Hz), 8.11 (1H, s).

Example 12

7-(2-chloro-6-fluorophenoxy)-2-(4-(1-methyl-1H-pyrazol-4-yl)benzyl)isoindolin-1-one

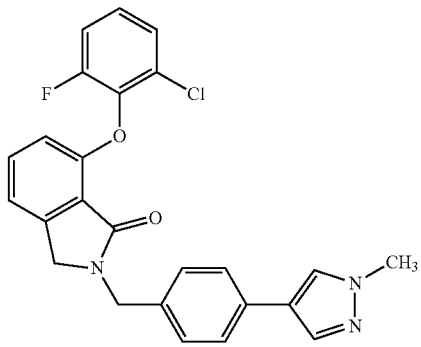

To a solution of 7-(4-amino-2-chloro-6-fluorophenoxy)-2-(4-(1-methyl-1H-pyrazol-4-yl)benzyl)isoindolin-1-one (0.03 g) obtained in Example 11 in THF (2 mL) was added isopentyl nitrite (0.017 g), and the mixture was stirred under an argon atmosphere at 70° C. overnight. The reaction solution was concentrated, and the residue was purified by NH silica gel chromatography (hexane-ethyl acetate) to give the title compound (0.017 g).

MS: [M+H]$^+$ 448.2

$^1$H NMR (300 MHz, DMSO-d$_6$) δ 3.85 (3H, s), 4.40 (2H, s), 4.68 (2H, s), 6.51 (1H, d, J=8.3 Hz), 7.19-7.35 (3H, m), 7.36-7.63 (6H, m), 7.83 (1H, s), 8.12 (1H, s).

Example 13

2-(4-(1-methyl-1H-pyrazol-4-yl)benzyl)-7-((2R)-(tetrahydrofuran-2-yl)methoxy)isoindolin-1-one

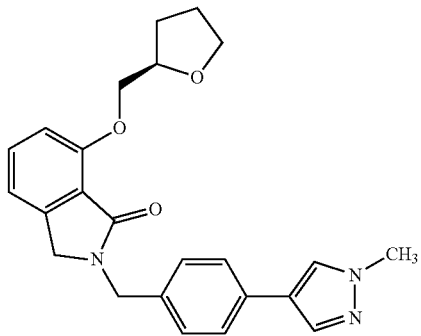 [SMILES: Cn1cc(-c2ccc(CN3Cc4cccc(OC[C@H]5CCCO5)c4C3=O)cc2)cn1]

A solution of 7-hydroxy-2-(4-(1-methyl-1H-pyrazol-4-yl)benzyl)isoindolin-1-one (0.10 g) obtained in Reference Example 6, (R)-(tetrahydrofuran-2-yl)methanol (0.064 g) and tributylphosphine (0.13 g) in THF (4 mL) was added diazene-1,2-diylbis(piperidin-1-ylmethanone) (0.16 g) at 60° C., and the mixture was stirred under a nitrogen atmosphere at 70° C. for 1 hr. The reaction mixture was diluted with ethyl acetate, and washed with saturated brine. The organic layer was separated, dried over anhydrous sodium sulfate, and concentrated. The residue was crudely purified by NH silica gel chromatography (hexane-ethyl acetate), and purified by HPLC (L-column2 ODS, mobile phase: water/acetonitrile (containing 0.1% NH4HCO3)) to give the title compound (0.035 g).

MS: [M+H]$^+$ 404.2

$^1$H NMR (300 MHz, DMSO-d$_6$) δ 1.73-1.91 (2H, m), 1.92-2.13 (2H, m), 3.62-3.74 (1H, m), 3.79-3.92 (4H, m), 3.99-4.14 (2H, m), 4.15-4.31 (3H, m), 4.63 (2H, s), 6.97-7.11 (2H, m), 7.24 (2H, d, J=8.1 Hz), 7.42-7.58 (3H, m), 7.82 (1H, d, J=0.8 Hz), 8.10 (1H, s).

Example 14

Methyl ((2-(4-(1-methyl-1H-pyrazol-4-yl)benzyl)-3-oxo-2,3-dihydro-1H-isoindol-4-yl)oxy)acetate

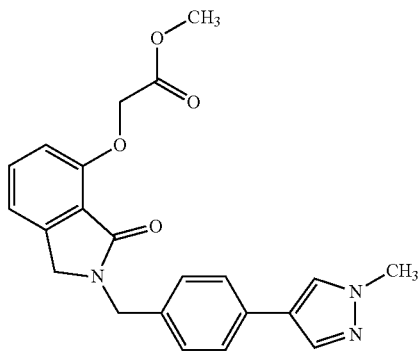 [SMILES: COC(=O)COc1cccc2c1C(=O)N(Cc1ccc(-c3cnn(C)c3)cc1)C2]

To a solution of 7-hydroxy-2-(4-(1-methyl-1H-pyrazol-4-yl)benzyl)isoindolin-1-one (0.30 g) obtained in Reference Example 6 in DMF (5 mL) were added methyl 2-bromoacetate (0.29 g) and potassium carbonate (0.26 g), and the mixture was stirred at 70° C. for 5 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.16 g).

MS: [M+H]$^+$ 392.1

$^1$H NMR (300 MHz, DMSO-d$_6$) δ 3.70 (3H, s), 3.85 (3H, s), 4.30 (2H, s), 4.64 (2H, s), 4.98 (2H, s), 6.91 (1H, d, J=8.1 Hz), 7.11 (1H, d, J=7.4 Hz), 7.25 (2H, d, J=8.3 Hz), 7.40-7.61 (3H, m), 7.82 (1H, d, J=0.8 Hz), 8.09 (1H, s).

Example 15

((2-(4-(1-methyl-1H-pyrazol-4-yl)benzyl)-3-oxo-2,3-dihydro-1H-isoindol-4-yl)oxy)acetic acid

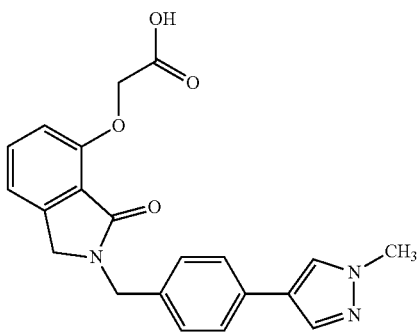 [SMILES: Cn1cc(-c2ccc(CN3Cc4cccc(OCC(=O)O)c4C3=O)cc2)cn1]

To a solution of methyl ((2-(4-(1-methyl-1H-pyrazol-4-yl)benzyl)-3-oxo-2,3-dihydro-1H-isoindol-4-yl)oxy)acetate (0.15 g) obtained in Example 14 in methanol (3 mL) was added 1N aqueous sodium hydroxide solution (3 mL), and the mixture was stirred at room temperature for 3 hr. The reaction mixture was neutralized with 1N hydrochloric acid, and the resulting precipitate was collected by filtration, and dried to give the title compound (0.14 g).

MS: [M+H]$^+$ 378.2

$^1$H NMR (300 MHz, DMSO-$d_6$) δ 3.85 (3H, s), 4.30 (2H, s), 4.64 (2H, s), 4.79 (2H, s), 6.89 (1H, d, J=8.1 Hz), 7.08 (1H, d, J=7.2 Hz), 7.25 (2H, d, J=8.3 Hz), 7.39-7.60 (3H, m), 7.81 (1H, d, J=0.8 Hz), 8.09 (1H, s). (COOH proton was not observed)

Example 16

2-(4-(1-methyl-1H-pyrazol-4-yl)benzyl)-7-(2-oxo-2-(piperidin-1-yl)ethoxy)isoindolin-1-one

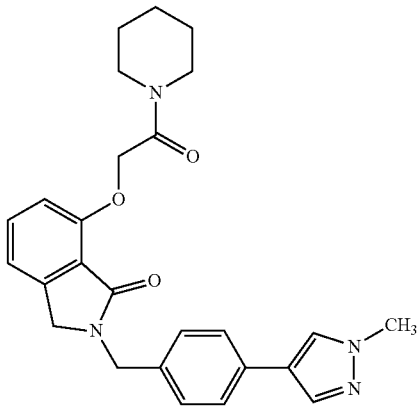 [SMILES: Cn1cc(-c2ccc(CN3Cc4cccc(OCC(=O)N5CCCCC5)c4C3=O)cc2)cn1]

To a solution of ((2-(4-(1-methyl-1H-pyrazol-4-yl)benzyl)-3-oxo-2,3-dihydro-1H-isoindol-4-yl)oxy)acetic acid (0.14 g) obtained in Example 15 in DMF (3 mL) were added piperidine (37 mg), 2-(3H-[1,2,3]triazolo[4,5-b]pyridin-3-yl)-1,1,3,3-tetramethylisouronium hexafluorophosphate (0.27 g) and triethylamine (0.1 mL), and the mixture was stirred at room temperature overnight. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.13 g).

MS: [M+H]$^+$ 445.3

$^1$H NMR (300 MHz, DMSO-$d_6$) δ 1.43 (2H, brs), 1.57 (4H, brs), 3.44 (4H, brs), 3.85 (3H, s), 4.29 (2H, s), 4.64 (2H, s), 4.96 (2H, s), 6.87 (1H, d, J=8.1 Hz), 7.07 (1H, d, J=7.4 Hz), 7.24 (2H, d, J=8.1 Hz), 7.40-7.59 (3H, m), 7.82 (1H, d, J=0.6 Hz), 8.09 (1H, s).

Example 17

7-(2-hydroxyethoxy)-2-(4-(1-methyl-1H-pyrazol-4-yl)benzyl)isoindolin-1-one

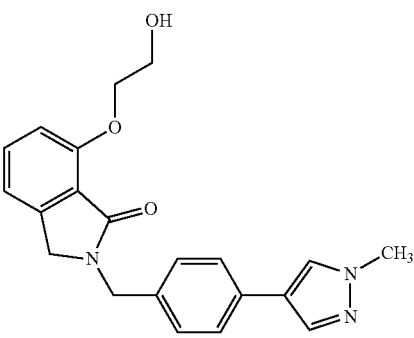 [SMILES: Cn1cc(-c2ccc(CN3Cc4cccc(OCCO)c4C3=O)cc2)cn1]

To a solution of 7-hydroxy-2-(4-(1-methyl-1H-pyrazol-4-yl)benzyl)isoindolin-1-one (0.60 g) obtained in Reference Example 6 in DMF (5 mL) were added 2-bromoethanol (2.35 g) and potassium carbonate (1.56 g), and the mixture was stirred at 70° C. for 6 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.32 g).

MS: [M+H]$^+$ 364.2

$^1$H NMR (300 MHz, DMSO-$d_6$) δ 3.74 (2H, q, J=5.4 Hz), 3.85 (3H, s), 4.14 (2H, t, J=5.3 Hz), 4.29 (2H, s), 4.63 (2H, s), 4.86 (1H, t, J=5.5 Hz), 6.99-7.13 (2H, m), 7.24 (2H, d, J=8.3 Hz), 7.42-7.57 (3H, m), 7.81 (1H, d, J=0.8 Hz), 8.09 (1H, s).

Example 18

7-(2-(4,4-difluoropiperidin-1-yl)ethoxy)-2-(4-(1-methyl-1H-pyrazol-4-yl)benzyl)isoindolin-1-one

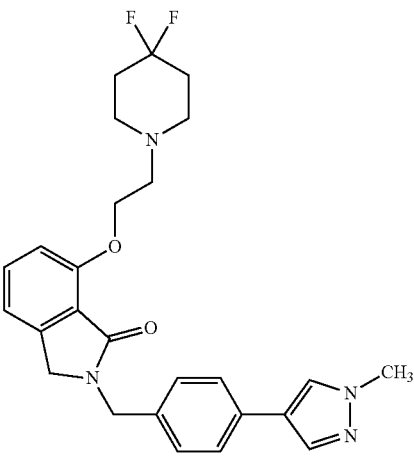 [SMILES: Cn1cc(-c2ccc(CN3Cc4cccc(OCCN5CCC(F)(F)CC5)c4C3=O)cc2)cn1]

To a solution of 7-(2-hydroxyethoxy)-2-(4-(1-methyl-1H-pyrazol-4-yl)benzyl)isoindolin-1-one (0.30 g) obtained in Example 17 in toluene (5 mL)-THF (5 mL) were added thionyl chloride (0.12 mL) and pyridine (0.07 mL), and the mixture was stirred under an argon atmosphere at room temperature for 3 hr. The reaction mixture was diluted with ethyl acetate, and washed with saturated brine. The organic layer was separated, dried over anhydrous sodium sulfate, and concentrated. To a solution of 50% amount of the residue in DMF (3 mL) were added 4,4-difluoropiperidine hydrochloride (0.20 g) and potassium carbonate (0.34 g), and the mixture was stirred at 70° C. overnight. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) and silica gel chromatography (hexane-ethyl acetate) to give the title compound (0.023 g).

MS: [M+H]$^+$ 467.2

$^1$H NMR (300 MHz, DMSO-$d_6$) δ 1.81-2.07 (4H, m), 2.64-2.77 (4H, m), 2.83 (2H, t, J=5.7 Hz), 3.85 (3H, s), 4.22 (2H, t, J=5.7 Hz), 4.27 (2H, s), 4.62 (2H, s), 6.93-7.13 (2H, m), 7.23 (2H, d, J=8.1 Hz), 7.42-7.57 (3H, m), 7.81 (1H, d, J=0.8 Hz), 8.09 (1H, s).

Example 19

2-(4-(1-methyl-1H-pyrazol-4-yl)benzyl)-7-(2-(H-pyrazol-1-yl)ethoxy)isoindolin-1-one

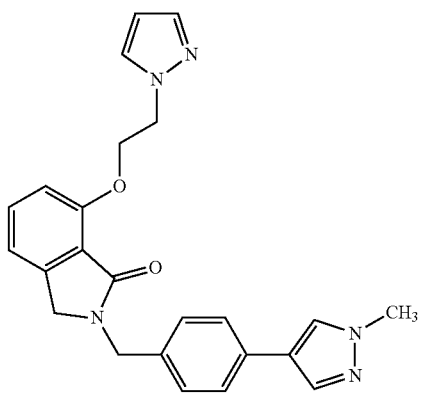 [SMILES: Cn1cc(-c2ccc(CN3Cc4cccc(OCCn5cccn5)c4C3=O)cc2)cn1]

To a solution of 7-hydroxy-2-(4-(1-methyl-1H-pyrazol-4-yl)benzyl)isoindolin-1-one (0.10 g) obtained in Reference Example 6 in DMF (3 mL) were added 1-(2-bromoethyl)-1H-pyrazole (0.16 g) and potassium carbonate (0.13 g), and the mixture was stirred at 80° C. for 1 hr. The reaction mixture was diluted with ethyl acetate, and washed with saturated brine. The organic layer was separated, dried over anhydrous sodium sulfate, and concentrated. The residue was crudely purified by NH silica gel chromatography (hexane-ethyl acetate), and solidified with ethyl acetate-hexane to give the title compound (0.086 g).

MS: [M+H]$^+$ 414.2

$^1$H NMR (300 MHz, DMSO-$d_6$) δ 3.85 (3H, s), 4.29 (2H, s), 4.34-4.44 (2H, m), 4.50-4.60 (2H, m), 4.65 (2H, s), 6.18-6.30 (1H, m), 6.97 (1H, d, J=8.1 Hz), 7.08 (1H, d, J=7.4 Hz), 7.25 (2H, d, J=8.1 Hz), 7.37-7.62 (4H, m), 7.82 (1H, d, J=0.8 Hz), 8.04-8.19 (2H, m).

Example 20

3-((2-(4-(1-methyl-1H-pyrazol-4-yl)benzyl)-3-oxo-2,3-dihydro-1H-isoindol-4-yl)oxy)pyridine-2-carbonitrile

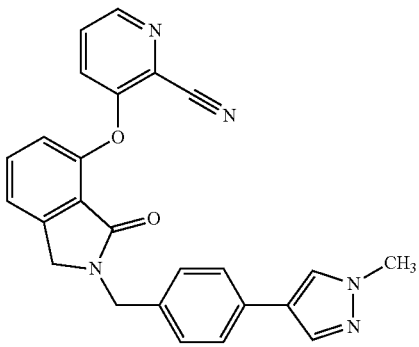 [SMILES: Cn1cc(-c2ccc(CN3Cc4cccc(Oc5cccnc5C#N)c4C3=O)cc2)cn1]

To a solution of 7-hydroxy-2-(4-(1-methyl-1H-pyrazol-4-yl)benzyl)isoindolin-1-one (0.10 g) obtained in Reference Example 6 in DMF (5 mL) were added 3-fluoropicolinonitrile (0.15 g) and potassium carbonate (0.17 g), and the mixture was stirred at 90° C. for 5 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.022 g).

MS: [M+H]$^+$ 422.2

$^1$H NMR (300 MHz, DMSO-$d_6$) δ 3.85 (3H, s), 4.41 (2H, s), 4.58 (2H, s), 7.21 (2H, d, J=8.3 Hz), 7.26-7.41 (2H, m), 7.47-7.57 (3H, m), 7.59-7.66 (1H, m), 7.68-7.76 (1H, m), 7.82 (1H, s), 8.10 (1H, s), 8.44 (1H, dd, J=4.5, 1.1 Hz).

Example 21

2-(4-(1-methyl-1H-pyrazol-4-yl)benzyl)-7-(2-(piperidin-1-yl)ethoxy)isoindolin-1-one

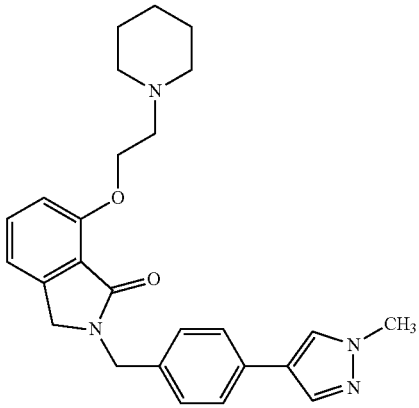 [SMILES: Cn1cc(-c2ccc(CN3Cc4cccc(OCCN5CCCCC5)c4C3=O)cc2)cn1]

To a solution of 7-hydroxy-2-(4-(1-methyl-1H-pyrazol-4-yl)benzyl)isoindolin-1-one (0.05 g) obtained in Reference Example 6 in DMF (2 mL) were added 1-(2-chloroethyl)piperidine hydrochloride (0.29 g) and potassium carbonate (0.43 g), and the mixture was stirred under an argon atmosphere at 80° C. for 3 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.038 g).

MS: [M+H]⁺ 431.2

¹H NMR (400 MHz, DMSO-d₆) δ 1.34-1.41 (2H, m), 1.45-1.54 (4H, m), 2.41-2.49 (4H, m), 2.69 (2H, t, J=6.1 Hz), 3.85 (3H, s), 4.19 (2H, t, J=6.1 Hz), 4.27 (2H, s), 4.62 (2H, s), 7.04 (2H, t, J=8.3 Hz), 7.23 (2H, d, J=8.1 Hz), 7.45-7.55 (3H, m), 7.82 (1H, s), 8.10 (1H, s).

Example 22

7-((3,5-dimethyl-1H-pyrazol-4-yl)oxy)-2-(4-(1-methyl-1H-pyrazol-4-yl)benzyl)isoindolin-1-one

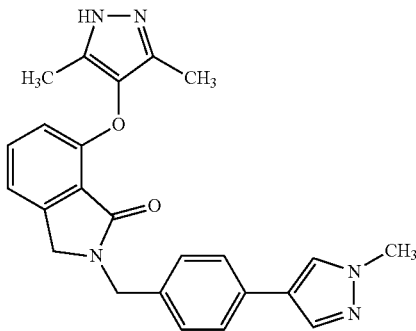 [SMILES: Cc1n[nH]c(C)c1Oc1cccc2c1C(=O)N(Cc1ccc(-c3cnn(C)c3)cc1)C2]

To a solution of 7-hydroxy-2-(4-(1-methyl-1H-pyrazol-4-yl)benzyl)isoindolin-1-one (0.05 g) obtained in Reference Example 6 in acetone (3 mL) were added 3-chloropentane-2,4-dione (0.025 g) and cesium carbonate (0.077 g), and the mixture was stirred under a nitrogen atmosphere at 50° C. for 8 hr. The reaction solution was neutralized with ammonium chloride, ethyl acetate was added, and the organic layer was separated, washed with saturated brine, dried over anhydrous sodium sulfate, and concentrated. The residue was crudely purified by silica gel chromatography (hexane-ethyl acetate). To a solution of the obtained crudely purified product in 2-propanol (3 mL) was added hydrazine monohydrate (0.0060 g), and the mixture was stirred under a nitrogen atmosphere at 60° C. for 1 hr. The reaction solution was concentrated, and the residue was crudely purified by silica gel chromatography (hexane-ethyl acetate, ethyl acetate-methanol), and solidified with diisopropyl ether to give the title compound (0.018 g).

MS: [M+H]⁺ 414.2

¹H NMR (300 MHz, DMSO-d₆) δ 1.91-2.09 (6H, m), 3.85 (3H, s), 4.35 (2H, s), 4.67 (2H, s), 6.56 (1H, d, J=8.1 Hz), 7.12 (1H, d, J=7.2 Hz), 7.29 (2H, d, J=8.3 Hz), 7.37-7.47 (1H, m), 7.55 (2H, d, J=8.3 Hz), 7.83 (1H, d, J=0.8 Hz), 8.11 (1H, s), 12.28 (1H, s).

Example 23

Tert-butyl 3-((2-(4-(1-methyl-1H-pyrazol-4-yl)benzyl)-3-oxo-2,3-dihydro-1H-isoindol-4-yl)oxy)methyl)-1H-pyrazole-1-carboxylate

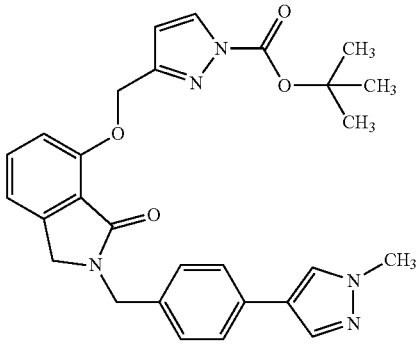 [SMILES: Cn1cc(-c2ccc(CN3Cc4cccc(OCc5ccn(C(=O)OC(C)(C)C)n5)c4C3=O)cc2)cn1]

To a solution of 7-hydroxy-2-(4-(1-methyl-1H-pyrazol-4-yl)benzyl)isoindolin-1-one (0.10 g) obtained in Reference Example 6 in DMF (3 mL) were added tert-butyl 3-(bromomethyl)-1H-pyrazole-1-carboxylate (0.25 g) and potassium carbonate (0.065 g), and the mixture was stirred at 90° C. for 2 hr. To the reaction solution was added ethyl acetate, the mixture was washed with saturated brine, and the organic layer was separated, dried over anhydrous sodium sulfate, and concentrated. The residue was purified by NH silica gel chromatography (hexane-ethyl acetate) to give the title compound (0.054 g).

MS: [M+H-Boc]⁺ 400.2

¹H NMR (300 MHz, DMSO-d₆) δ 1.59 (9H, s), 3.85 (3H, s), 4.30 (2H, s), 4.63 (2H, s), 5.27 (2H, s), 6.69 (1H, d, J=2.6 Hz), 7.13 (2H, t, J=8.9 Hz), 7.24 (2H, d, J=8.3 Hz), 7.45-7.58 (3H, m), 7.82 (1H, s), 8.10 (1H, s), 8.28 (1H, d, J=2.6 Hz).

Example 24

2-(4-(1-methyl-1H-pyrazol-4-yl)benzyl)-7-((1H-pyrazol-3-yl)methoxy)isoindolin-1-one hydrochloride

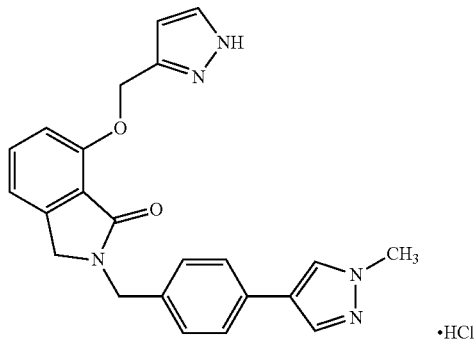 [SMILES: Cn1cc(-c2ccc(CN3Cc4cccc(OCc5cc[nH]n5)c4C3=O)cc2)cn1 ; Cl]

To a solution of tert-butyl 3-(((2-(4-(1-methyl-1H-pyrazol-4-yl)benzyl)-3-oxo-2,3-dihydro-1H-isoindol-4-yl)oxy)methyl)-1H-pyrazole-1-carboxylate (0.051 g) obtained in Example 23 in THF (2 mL) was added 4N hydrochloric acid (ethyl acetate solution) (3 mL), and the mixture was stirred under a nitrogen atmosphere at room temperature for 3 days. The resulting precipitate was collected by filtration to give the title compound (0.045 g).

MS: [M+H]⁺ 400.2

$^1$H NMR (300 MHz, DMSO-d$_6$) δ 3.84 (3H, s), 4.28 (2H, s), 4.62 (2H, s), 5.22 (2H, s), 6.40 (1H, d, J=2.3 Hz), 7.07 (1H, d, J=7.5 Hz), 7.15-7.28 (3H, m), 7.45-7.55 (3H, m), 7.69 (1H, d, J=2.3 Hz), 7.82 (1H, s), 8.10 (1H, s). (NH and HCl protons were not observed.)

Example 25

2-(4-bromobenzyl)-7-((trans-2-hydroxycyclohexyl)oxy)isoindolin-1-one

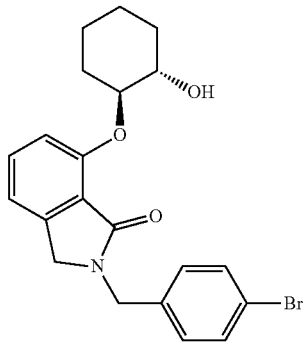 [SMILES: O=C1c2c(cccc2O[C@H]2CCCC[C@@H]2O)CN1Cc1ccc(Br)cc1]

To a solution of 2-(4-bromobenzyl)-7-hydroxyisoindolin-1-one (0.33 g) obtained in Reference Example 3 in ethanol (3 mL) were added 7-oxabicyclo[4.1.0]heptane (1.02 g) and pyridine (1.23 g), and the mixture was stirred under an argon atmosphere at 90° C. for 4 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.29 g).

$^1$H NMR (300 MHz, DMSO-d$_6$) δ 1.22-1.37 (3H, m), 1.41-1.53 (1H, m), 1.57-1.73 (2H, m), 1.84-1.96 (1H, m), 2.01-2.14 (1H, m), 3.53-3.70 (1H, m), 3.97-4.14 (1H, m), 4.30 (2H, s), 4.64 (2H, s), 5.12 (1H, d, J=3.6 Hz), 7.04-7.14 (2H, m), 7.23 (2H, d, J=8.1 Hz), 7.44-7.59 (3H, m).

Example 26

7-((trans-2-hydroxycyclohexyl)oxy)-2-(4-(1H-pyrazol-4-yl)benzyl)isoindolin-1-one

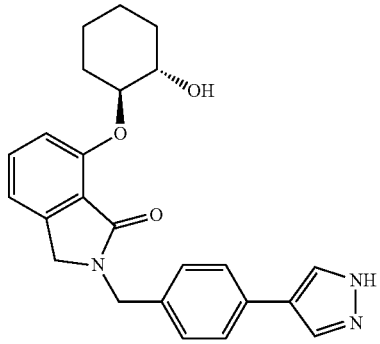 [SMILES: O=C1c2c(cccc2O[C@H]2CCCC[C@@H]2O)CN1Cc1ccc(-c2cn[nH]c2)cc1]

A mixed solution of 2-(4-bromobenzyl)-7-((trans-2-hydroxycyclohexyl)oxy)isoindolin-1-one (0.10 g) obtained in Example 25, tert-butyl 4-(4,4,5,5-tetramethyl-1,3,2-dioxaborolan-2-yl)-1H-pyrazole-1-carboxylate (0.11 g), tetrakis(triphenylphosphine)palladium(0) (0.028 g) and sodium carbonate (0.076 g) in DME (4 mL)-water (0.4 mL) was stirred under an argon atmosphere at 100° C. overnight. The reaction mixture was diluted with ethyl acetate, and washed with saturated brine. The organic layer was separated, dried over anhydrous sodium sulfate, and concentrated. The residue was purified by silica gel chromatography (hexane-ethyl acetate) to give the title compound (0.066 g).

MS: [M+H]$^+$ 404.3

$^1$H NMR (300 MHz, DMSO-d$_6$) δ 1.22-1.38 (3H, m), 1.40-1.56 (1H, m), 1.57-1.75 (2H, m), 1.86-1.97 (1H, m), 2.03-2.15 (1H, m), 3.61 (1H, brs), 4.04-4.10 (1H, m), 4.30 (2H, s), 4.65 (2H, s), 5.18 (1H, d, J=3.6 Hz), 7.05-7.17 (2H, m), 7.25 (2H, d, J=8.3 Hz), 7.42-7.52 (1H, m), 7.58 (2H, d, J=8.3 Hz), 7.89 (1H, s), 8.15 (1H, s), 12.91 (1H, brs).

Example 27

7-((trans-2-hydroxycyclohexyl)oxy)-2-(6-(1-methyl-1H-pyrazol-4-yl)pyridin-3-yl)methyl)isoindolin-1-one

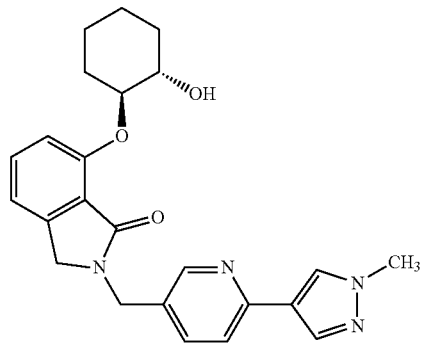

To a solution of ethyl 2-(bromomethyl)-6-(tert-butyldimethylsilyloxy)benzoate (1.0 g) obtained in Reference Example 2 in methanol (30 mL) were added (6-(1-methyl-1H-pyrazol-4-yl)pyridin-3-yl)methanamine dihydrochloride (0.63 g) obtained in Reference Example 25 and potassium carbonate (1.15 g), and the mixture was stirred under a nitrogen atmosphere at room temperature overnight. The reaction mixture was diluted with ethyl acetate, and washed with saturated brine. The organic layer was separated, dried over anhydrous sodium sulfate, and concentrated. The residue was crudely purified by silica gel chromatography (methanol-ethyl acetate). To a solution of the obtained crudely purified product in ethanol (8 mL) were added 7-oxabicyclo[4.1.0]heptane (1.45 g) and pyridine (1.76 g), and the mixture was stirred under a nitrogen atmosphere at 90° C. for 4 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) and HPLC (L-column2 ODS, mobile phase: water/acetonitrile (containing 5 mM AcONH4)) to give the title compound (0.13 g).

MS: [M+H]$^+$ 419.2

$^1$H NMR (300 MHz, DMSO-d$_6$) δ 1.22-1.37 (3H, m), 1.41-1.55 (1H, m), 1.57-1.72 (2H, m), 1.88-1.96 (1H, m), 2.03-2.13 (1H, m), 3.61 (1H, brs), 3.87 (3H, s), 4.04-4.12 (1H, m), 4.35 (2H, s), 4.67 (2H, s), 5.14 (1H, brs), 7.05-7.16

(2H, m), 7.43-7.53 (1H, m), 7.58-7.69 (2H, m), 7.96 (1H, d, J=0.8 Hz), 8.25 (1H, s), 8.46 (1H, d, J=1.3 Hz).

Example 28

7-((trans-2-hydroxycyclohexyl)oxy)-2-((5-(1-methyl-1H-pyrazol-4-yl)-2-thienyl)methyl)isoindolin-1-one

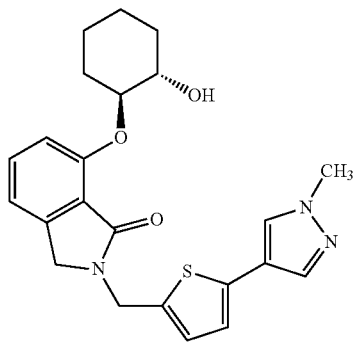 [SMILES: Cn1cc(-c2ccc(CN3Cc4cccc(O[C@H]5CCCC[C@@H]5O)c4C3=O)s2)cn1]

To a solution of 7-hydroxy-2-((5-(1-methyl-1H-pyrazol-4-yl)thiophen-2-yl)methyl)isoindolin-1-one (0.08 g) obtained in Reference Example 10 in ethanol (3 mL) were added 7-oxabicyclo[4.1.0]heptane (0.24 g) and pyridine (0.29 g), and the mixture was stirred at 90° C. for 6 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.07 g).

MS: [M+H]$^+$ 424.2

$^1$H NMR (300 MHz, DMSO-d$_6$) δ 1.22-1.33 (3H, m), 1.40-1.54 (1H, m), 1.56-1.72 (2H, m), 1.92 (1H, d, J=9.3 Hz), 2.05 (1H, d, J 8.7 Hz), 3.53-3.69 (1H, m), 3.75-3.87 (3H, m), 3.97-4.14 (1H, m), 4.36 (2H, s), 4.79 (2H, s), 5.11 (1H, d, J=3.6 Hz), 6.94-7.04 (2H, m), 7.07-7.17 (2H, m), 7.41-7.53 (1H, m), 7.65 (1H, d, J=0.6 Hz), 7.97 (1H, s).

Example 29

7-((trans-2-hydroxycyclohexyl)oxy)-2-(4-(1H-pyrazol-1-yl)benzyl)isoindolin-1-one

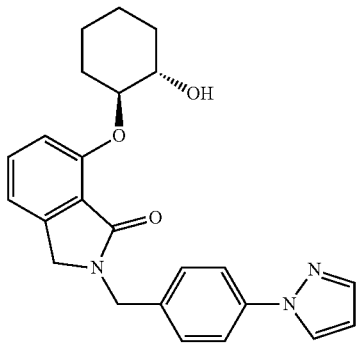 [SMILES: O=C1c2c(cccc2O[C@H]2CCCC[C@@H]2O)CN1Cc1ccc(-n2cccn2)cc1]

To a solution of 2-(4-(1H-pyrazol-1-yl)benzyl)-7-hydroxyisoindolin-1-one (0.06 g) obtained in Reference Example 14 in ethanol (3 mL) were added 7-oxabicyclo[4.1.0]heptane (0.19 g) and pyridine (0.23 g), and the mixture was stirred under an argon atmosphere at 90° C. for 3 hr. The reaction solution was concentrated, and the residue was purified by NH silica gel chromatography (hexane-ethyl acetate) to give the title compound (0.032 g).

MS: [M+H]$^+$ 404.3

$^1$H NMR (400 MHz, DMSO-d$_6$) δ 1.21-1.37 (3H, m), 1.40-1.55 (1H, m), 1.56-1.72 (2H, m), 1.92 (1H, brs), 2.04-2.14 (1H, m), 3.57-3.67 (1H, m), 4.03-4.11 (1H, m), 4.33 (2H, s), 4.70 (2H, s), 5.18 (1H, d, J=3.7 Hz), 6.52-6.55 (1H, m), 7.12 (2H, dd, J=7.8, 4.9 Hz), 7.39 (2H, d, J=8.6 Hz), 7.46-7.51 (1H, m), 7.73 (1H, d, J=1.5 Hz), 7.82 (2H, d, J=8, 6 Hz), 8.48 (1H, d, J=2.4 Hz).

Example 30

7-((trans-2-hydroxycyclohexyl)oxy)-2-(4-(1-(tetrahydro-2H-pyran-2-yl)-1H-pyrazol-5-yl)benzyl)isoindolin-1-one

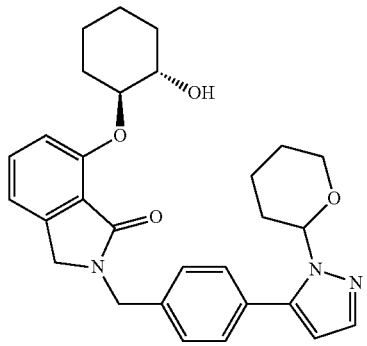 [SMILES: O=C1c2c(cccc2O[C@H]2CCCC[C@@H]2O)CN1Cc1ccc(-c2ccnn2C2CCCCO2)cc1]

To a solution of 7-hydroxy-2-(4-(1-(tetrahydro-2H-pyran-2-yl)-1H-pyrazol-5-yl)benzyl)isoindolin-1-one (0.09 g) obtained in Reference Example 13 in ethanol (3 mL) were added 7-oxabicyclo[4.1.0]heptane (0.23 g) and pyridine (0.27 g), and the mixture was stirred under a nitrogen atmosphere at 80° C. for 3 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.075 g).

MS: [M+H]$^+$ 488.3

$^1$H NMR (300 MHz, DMSO-d$_6$) δ 1.24-1.35 (3H, m), 1.41-1.54 (3H, m), 1.57-1.69 (3H, m), 1.73-1.81 (1H, m), 1.87-1.96 (2H, m), 2.11 (1H, brs), 2.31-2.43 (1H, m), 3.48-3.67 (2H, m), 3.92-3.99 (1H, m), 4.06-4.12 (1H, m), 4.38 (2H, s), 4.74 (2H, s), 5.09-5.26 (2H, m), 6.43 (1H, d, J=1.7 Hz), 7.13 (2H, d, J=7.9 Hz), 7.36-7.44 (2H, m), 7.46-7.58 (4H, m).

Example 31

7-((trans-2-hydroxycyclohexyl)oxy)-2-(4-(1H-pyrazol-5-yl)benzyl)isoindolin-1-one

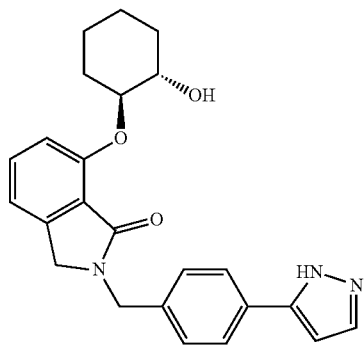 [SMILES: O=C1c2c(cccc2O[C@H]2CCCC[C@@H]2O)CN1Cc1ccc(-c2ccn[nH]2)cc1]

A mixed solution of 7-((trans-2-hydroxycyclohexyl)oxy)-2-(4-(1-(tetrahydro-2H-pyran-2-yl)-1H-pyrazol-5-yl)benzyl)isoindolin-1-one (0.07 g) obtained in Example 30 and 2N hydrochloric acid (ethanol solution, 3 mL) was stirred at room temperature for 3 hr. The reaction solution was neutralized with saturated aqueous sodium hydrogen carbonate solution, and the mixture was diluted with ethyl acetate. The organic layer was separated, washed with water and saturated brine, dried over anhydrous sodium sulfate, and concentrated. The residue was purified by silica gel chromatography (hexane-ethyl acetate) to give the title compound (0.052 g).

MS: [M+H]$^+$ 404.2

$^1$H NMR (300 MHz, DMSO-d$_6$) δ 1.23-1.38 (3H, m), 1.50 (1H, brs), 1.65 (2H, brs), 1.92 (1H, brs), 2.03-2.13 (1H, m), 3.56-3.70 (1H, m), 4.03-4.13 (1H, m), 4.32 (2H, s), 4.68 (2H, s), 5.18 (1H, d, J=3.6 Hz), 6.68 (1H, d, J=1.9 Hz), 7.12 (2H, dd, J=7.9, 2.6 Hz), 7.25-7.39 (2H, m), 7.48 (1H, dd, J=8.2, 7.5 Hz), 7.77 (3H, brs), 12.85 (1H, brs).

Example 32

7-((trans-2-hydroxycyclohexyl)oxy)-2-(4-(3-methyl-1H-pyrazol-1-yl)benzyl)isoindolin-1-one

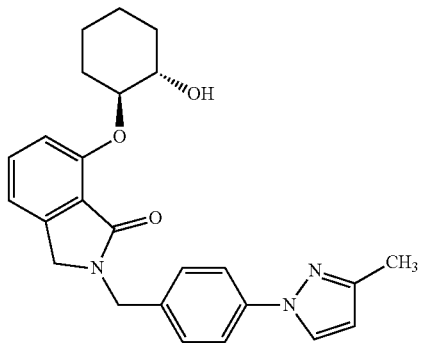 [SMILES: Cc1ccn(-c2ccc(CN3Cc4cccc(O[C@H]5CCCC[C@@H]5O)c4C3=O)cc2)n1]

To a solution of 7-hydroxy-2-(4-(3-methyl-1H-pyrazol-1-yl)benzyl)isoindolin-1-one (0.07 g) obtained in Reference Example 16 in ethanol (3 mL) were added 7-oxabicyclo[4.1.0]heptane (0.22 g) and pyridine (0.26 g), and the mixture was stirred under an argon atmosphere at 90° C. for 5 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.071 g).

MS: [M+H]$^+$ 418.3

$^1$H NMR (300 MHz, DMSO-d$_6$) δ 1.24-1.37 (3H, m), 1.42-1.54 (1H, m), 1.58-1.71 (2H, m), 1.85-1.96 (1H, m), 2.02-2.14 (1H, m), 2.26 (3H, s), 3.62 (1H, brs), 4.05-4.12 (1H, m), 4.32 (2H, s), 4.68 (2H, s), 5.16 (1H, d, J=3.6 Hz), 6.31 (1H, d, J=2.3 Hz), 7.12 (2H, dd, J=7.5, 2.3 Hz), 7.36 (2H, d, J=8.5 Hz), 7.48 (1H, dd, J=8.5, 7.5 Hz), 7.76 (2H, d, J=8.7 Hz), 8.33 (1H, d, J=2.5 Hz).

Example 33

4-((7-((trans-2-hydroxycyclohexyl)oxy)-1-oxo-1,3-dihydro-2H-isoindol-2-yl)methyl)benzonitrile

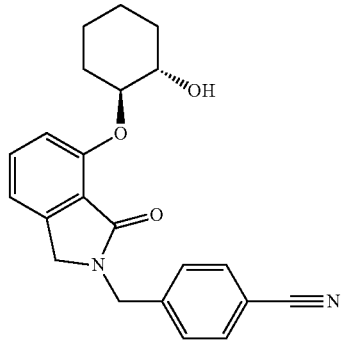 [SMILES: N#Cc1ccc(CN2Cc3cccc(O[C@H]4CCCC[C@@H]4O)c3C2=O)cc1]

To a solution of 4-((7-hydroxy-1-oxoisoindolin-2-yl)methyl)benzonitrile (1.16 g) obtained in Reference Example 18 in ethanol (20 mL) were added 7-oxabicyclo[4.1.0]heptane (4.31 g) and pyridine (4.16 g), and the mixture was refluxed for 18 hr. The reaction solution was concentrated, and the residue was purified by HPLC (C18, mobile phase: water/acetonitrile (containing 0.1% TFA)) to give the title compound (0.40 g).

MS: [M+H]$^+$ 362.7

$^1$H NMR (400 MHz, CDCl$_3$) δ 1.20-1.40 (3H, m), 1.55-1.69 (1H, m), 1.70-1.85 (2H, m), 2.05-2.19 (1H, m), 2.25-2.35 (1H, m), 3.75-3.88 (2H, m), 4.18-4.30 (2H, m), 4.72 (1H, d, J=15.2 Hz), 4.88 (1H, d, J=15.2 Hz), 7.06 (2H, d, J=8.4 Hz), 7.41 (2H, d, J=8.0 Hz), 7.46 (1H, d, J=8.0 Hz), 7.62 (2H, d, J=8.4 Hz). (OH proton was not observed.)

Example 34

4-((7-((trans-2-hydroxycyclohexyl)oxy)-1-oxo-1,3-dihydro-2H-isoindol-2-yl)methyl)benzamide

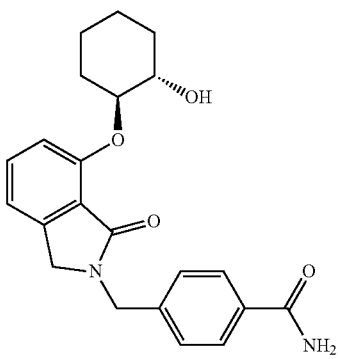 [SMILES: NC(=O)c1ccc(CN2Cc3cccc(O[C@H]4CCCC[C@@H]4O)c3C2=O)cc1]

To a solution of 4-((7-((trans-2-hydroxycyclohexyl)oxy)-1-oxo-1,3-dihydro-2H-isoindol-2-yl)methyl)benzonitrile (0.20 g) obtained in Example 33 in DMSO (5 mL) were added potassium carbonate (0.15 g) and hydrogen peroxide (0.33 g), and the mixture was stirred at 5° C. for 7 hr. The reaction mixture was diluted with water and ethyl acetate. The organic layer was separated, washed with saturated brine, dried over anhydrous sodium sulfate, and concentrated. The residue was suspended in ethyl acetate (10 mL)-petroleum ether (10 mL), and the mixture was stirred at 5° C. for 18 hr. The precipitate was collected by filtration, and washed with ethyl acetate to give the title compound (0.081 g).

MS: [M+H]$^+$ 381.1

$^1$H NMR (300 MHz, DMSO-$d_6$) δ 1.15-1.35 (3H, m), 1.37-1.53 (1H, m), 1.55-1.78 (2H, m), 1.82-1.98 (1H, m), 2.01-2.14 (1H, m), 3.52-3.70 (1H, m), 3.98-4.13 (1H, m), 4.32 (2H, s), 4.71 (2H, s), 5.16 (1H, d, J=3.9 Hz), 7.01-7.20 (2H, m), 7.25-7.40 (3H, m), 7.48 (1H, t, J=7.5 Hz), 7.85 (2H, d, J=7.8 Hz), 7.95 (1H, brs).

Example 35

7-((trans-2-hydroxycyclohexyl)oxy)-2-(4-(1-methyl-1H-pyrazol-3-yl)benzyl)isoindolin-1-one

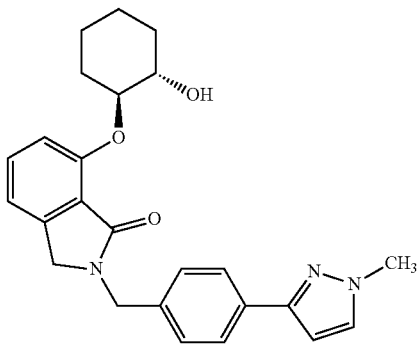 [SMILES: Cn1ccc(-c2ccc(CN3Cc4cccc(O[C@H]5CCCC[C@@H]5O)c4C3=O)cc2)n1]

To a solution of 7-hydroxy-2-(4-(1-methyl-1H-pyrazol-3-yl)benzyl)isoindolin-1-one (0.10 g) obtained in Reference Example 20 in ethanol (5 mL) were added 7-oxabicyclo[4.1.0]heptane (0.31 g) and pyridine (0.37 g), and the mixture was stirred at 90° C. for 6 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.09 g).

MS: [M+H]$^+$ 418.2

$^1$H NMR (300 MHz, DMSO-$d_6$) δ 1.22-1.38 (3H, m), 1.40-1.73 (3H, m), 1.83-1.96 (1H, m), 2.01-2.17 (1H, m), 3.52-3.71 (1H, m), 3.87 (3H, s), 4.05-4.12 (1H, m), 4.32 (2H, s), 4.67 (2H, s), 5.17 (1H, d, J=3.6 Hz), 6.65 (1H, d, J=2.5 Hz), 7.12 (2H, dd, J=7.5, 2.5 Hz), 7.28 (2H, d, J=8.1 Hz), 7.48 (1H, dd, J=8.2, 7.5 Hz), 7.65-7.82 (3H, m).

Example 36

Methyl 4-((1-oxo-7-((tetrahydrofuran-2-yl)methoxy)-1,3-dihydro-2H-isoindol-2-yl)methyl)benzoate

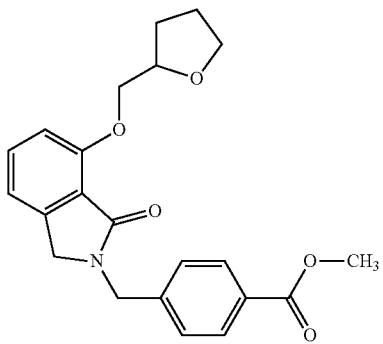 [SMILES: COC(=O)c1ccc(CN2Cc3cccc(OCC4CCCO4)c3C2=O)cc1]

A solution of ethyl 2-(bromomethyl)-6-((tert-butyldimethylsilyl)oxy)benzoate (7.36 g) obtained in Reference Example 2, methyl 4-(aminomethyl)benzoate hydrochloride (3.98 g) and potassium carbonate (8.17 g) in methanol (30 mL) was stirred under a nitrogen atmosphere at room temperature overnight. The reaction mixture was diluted with ethyl acetate, and washed with saturated brine. The organic layer was separated, dried over anhydrous sodium sulfate, and concentrated. To a solution of the residue in THF (100 mL) were added (tetrahydrofuran-2-yl)methanol (2.38 g), triphenylphosphine (6.10 g), and 40% diisopropyldiazene-1,2-dicarboxylate (toluene solution) (11.8 g), and the mixture was stirred at 60° C. The reaction mixture was concentrated, and the residue was crudely purified by NH silica gel chromatography (hexane-ethyl acetate), and HPLC (L-column2 ODS, mobile phase: water/acetonitrile (containing 0.1% TFA)) to give the title compound (1.03 g).

MS: [M+H]$^+$ 382.2

$^1$H NMR (300 MHz, DMSO-$d_6$) δ 1.74-1.90 (2H, m), 1.99-2.09 (2H, m), 3.60-3.74 (1H, m), 3.77-3.94 (4H, m), 4.05-4.11 (2H, m), 4.15-4.26 (1H, m), 4.31 (2H, s), 4.74 (2H, s), 7.05 (2H, dd, J=12.8, 7.7 Hz), 7.39 (2H, d, J=8.5 Hz), 7.49 (1H, dd, J=8.1, 7.6 Hz), 7.86-8.03 (2H, m).

Example 37

4-((1-oxo-7-((tetrahydrofuran-2-yl)methoxy)isoindolin-2-yl)methyl)benzoic acid

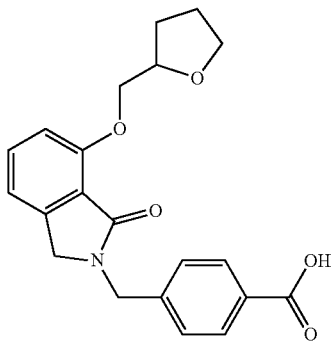 [SMILES: O=C(O)c1ccc(CN2Cc3cccc(OCC4CCCO4)c3C2=O)cc1]

To a solution of methyl 4-((1-oxo-7-((tetrahydrofuran-2-yl)methoxy)-1,3-dihydro-2H-isoindol-2-yl)methyl)benzoate (1.0 g) obtained in Example 36 in methanol (10 mL) was added 8N aqueous sodium hydroxide solution (0.66 mL), and the mixture was stirred under a nitrogen atmosphere at room temperature overnight. The reaction solution was neutralized with 1N hydrochloric acid, and ethyl acetate was added. The organic layer was separated, washed with water and saturated brine, dried over anhydrous sodium sulfate, and concentrated to give the title compound (0.94 g).

MS: [M+H]$^+$ 368.2

$^1$H NMR (300 MHz, DMSO-d$_6$) δ 1.70-1.91 (2H, m), 1.93-2.14 (2H, m), 3.59-3.73 (1H, m), 3.79-3.92 (1H, m), 4.01-4.14 (2H, m), 4.14-4.26 (1H, in), 4.31 (2H, s), 4.72 (2H, s), 7.05 (2H, dd, J20=13.0, 7.7 Hz), 7.28-7.43 (2H, m), 7.45-7.55 (1H, m), 7.83-7.99 (2H, m), 12.28-13.58 (1H, m).

Example 38

4-((1-oxo-7-((tetrahydrofuran-2-yl)methoxy)-1,3-dihydro-2H-isoindol-2-yl)methyl)-N-((tetrahydrofuran-2-yl)methyl)benzamide

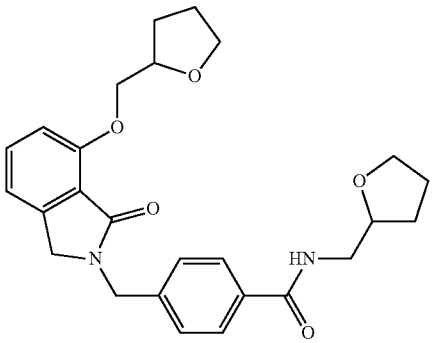 [SMILES: O=C(NCC1CCCO1)c1ccc(CN2Cc3cccc(OCC4CCCO4)c3C2=O)cc1]

A solution of 4-((1-oxo-7-((tetrahydrofuran-2-yl)methoxy)isoindolin-2-yl)methyl)benzoic acid (0.10 g) obtained in Example 37, (tetrahydrofuran-2-yl)methanamine (41 mg), 2-(3H-[1,2,3]triazolo[4,5-b]pyridin-3-yl)-1,1,3,3-tetramethylisouronium hexafluorophosphate (0.16 g) and triethylamine (0.041 g) in DMF (4 mL) was stirred at room temperature overnight. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.084 g).

MS: [M+H]$^+$ 451.3

$^1$H NMR (300 MHz, DMSO-d$_6$) δ 1.48-1.65 (1H, m), 1.72-1.94 (5H, m), 1.97-2.08 (2H, m), 3.21-3.31 (2H, m), 3.56-3.89 (4H, m), 3.91-4.02 (1H, m), 4.03-4.13 (2H, m), 4.15-4.25 (1H, m), 4.29 (2H, s), 4.70 (2H, s), 7.05 (2H, dd, J=11.9, 7.7 Hz), 7.33 (2H, d, J=8.3 Hz), 7.49 (1H, dd, J=8.1, 7.6 Hz), 7.83 (2H, d, J=8.3 Hz), 8.49 (1H, t, J=5.9 Hz).

Example 39

7-((trans-2-hydroxycyclohexyl)oxy)-2-(3-(1-methyl-1H-pyrazol-4-yl)benzyl)isoindolin-1-one

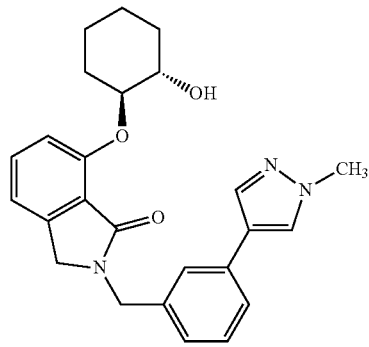 [SMILES: Cn1cc(-c2cccc(CN3Cc4cccc(O[C@H]5CCCC[C@@H]5O)c4C3=O)c2)cn1]

To a solution of 7-hydroxy-2-(3-(1-methyl-1H-pyrazol-4-yl)benzyl)isoindolin-1-one (0.15 g) obtained in Reference Example 22 in ethanol (3 mL) were added 7-oxabicyclo[4.1.0]heptane (0.46 g) and pyridine (0.56 g), and the mixture was stirred at 90° C. for 3 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.13 g).

MS: [M+H]$^+$ 418.3

$^1$H NMR (300 MHz, DMSO-d$_6$) δ 1.27 (3H, brs), 1.40-1.54 (1H, m), 1.57-1.71 (2H, m), 1.94 (1H, brs), 2.02-2.15 (1H, m), 3.51-3.69 (1H, m), 3.85 (3H, s), 3.99-4.09 (1H, m), 4.33 (2H, s), 4.67 (2H, s), 5.19 (1H, d, J=3.6 Hz), 6.99-7.19 (3H, m), 7.24-7.40 (1H, m), 7.41-7.56 (3H, m), 7.83 (1H, d, J=0.6 Hz), 8.11 (1H, s).

Example 40

7-((trans-2-hydroxycyclopentyl)oxy)-2-(4-(3-methyl-1H-pyrazol-1-yl)benzyl)isoindolin-1-one

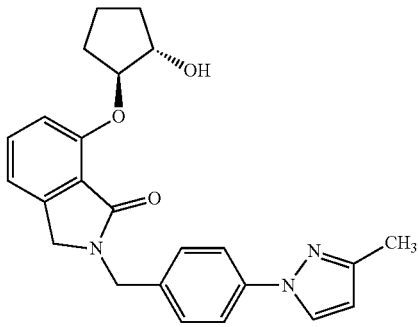 [SMILES: Cc1ccn(-c2ccc(CN3Cc4cccc(O[C@H]5CCC[C@@H]5O)c4C3=O)cc2)n1]

To a solution of 7-hydroxy-2-(4-(3-methyl-1H-pyrazol-1-yl)benzyl)isoindolin-1-one (0.07 g) obtained in Reference Example 16 in ethanol (3 mL) were added 6-oxabicyclo[3.1.0]hexane (0.18 g) and pyridine (0.26 g), and the mixture was stirred under an argon atmosphere at 90° C. for 5 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.049 g).

MS: [M+H]$^+$ 404.2

$^1$H NMR (300 MHz, DMSO-d$_6$) δ 1.49-1.58 (1H, m), 1.64-1.78 (3H, m), 1.87-1.97 (1H, m), 2.04-2.15 (1H, m), 2.25 (3H, s), 4.10 (1H, brs), 4.29 (2H, s), 4.55-4.70 (3H, m), 4.95 (1H, d, J=4.0 Hz), 6.31 (1H, d, J=2.5 Hz), 6.97-7.14 (2H, m), 7.35 (2H, d, J=8.7 Hz), 7.43-7.54 (1H, m), 7.75 (2H, d, J=8.7 Hz), 8.32 (1H, d, J=2.5 Hz).

Example 41

3-fluoro-2-((3-oxo-2-(4-(1-(tetrahydro-2H-pyran-2-yl)-1H-pyrazol-5-yl)benzyl)-2,3-dihydro-1H-isoindol-4-yl)oxy)benzonitrile

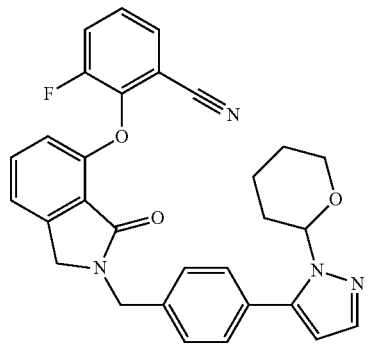 [SMILES: N#Cc1cccc(F)c1Oc1cccc2c1C(=O)N(Cc1ccc(-c3ccnn3C3CCCCO3)cc1)C2]

To a solution of 7-hydroxy-2-(4-(1-(tetrahydro-2H-pyran-2-yl)-1H-pyrazol-5-yl)benzyl)isoindolin-1-one (0.23 g) obtained in Reference Example 13 in DMF (4 mL) were added 2,3-difluorobenzonitrile (0.24 g) and potassium carbonate (0.16 g), and the mixture was stirred under a nitrogen atmosphere at 80° C. for 3 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.088 g).

MS: [M+H–(THP)]$^+$ 425.1

$^1$H NMR (300 MHz, DMSO-d$_6$) δ 1.44-1.66 (3H, m), 1.70-1.82 (1H, m), 1.86-1.97 (1H, m), 2.33-2.43 (1H, m), 3.50-3.61 (1H, m), 3.91-4.01 (1H, m), 4.49 (2H, s), 4.76 (2H, s), 5.21 (1H, dd, J=9.9, 2.2 Hz), 6.44 (1H, d, J=1.7 Hz), 6.85 (1H, d, J=8.1 Hz), 7.33-7.59 (8H, m), 7.73-7.87 (2H, m).

Example 42

3-fluoro-2-((3-oxo-2-(4-(1H-pyrazol-5-yl)benzyl)-2,3-dihydro-1H-isoindol-4-yl)oxy)benzonitrile hydrochloride

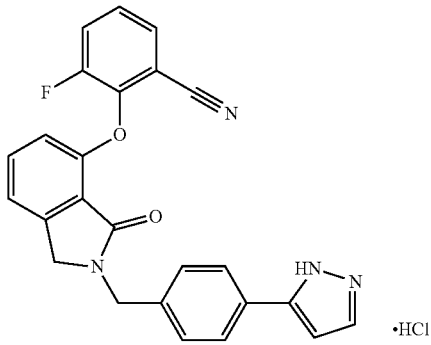 [SMILES: N#Cc1cccc(F)c1Oc1cccc2c1C(=O)N(Cc1ccc(-c3ccn[nH]3)cc1)C2 ; Cl]

A mixed solution of 3-fluoro-2-((3-oxo-2-(4-(1-(tetrahydro-2H-pyran-2-yl)-1H-pyrazol-5-yl)benzyl)-2,3-dihydro-1H-isoindol-4-yl)oxy)benzonitrile (0.08 g) obtained in Example 41 and 2N hydrochloric acid (ethanol solution, 5 mL) was stirred at room temperature for 30 min. The resulting precipitate was collected by filtration to give the title compound (0.066 g).

MS: [M+H]$^+$ 425.1

$^1$H NMR (300 MHz, DMSO-d$_6$) δ 4.43 (2H, s), 4.70 (2H, s), 6.69 (1H, d, J=2.1 Hz), 6.84 (1H, d, J=8.3 Hz), 7.26-7.40 (3H, m), 7.44-7.57 (2H, m), 7.71 (1H, d, J=2.1 Hz), 7.76-7.88 (4H, m), NH and HCl protons were not observed.

Example 43

2-((6-chloropyridin-3-yl)methyl)-7-((trans-2-hydroxycyclohexyl)oxy)isoindolin-1-one

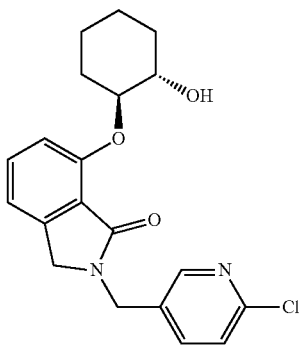 [SMILES: O=C1c2c(cccc2O[C@H]2CCCC[C@@H]2O)CN1Cc1ccc(Cl)nc1]

To a solution of 2-((6-chloropyridin-3-yl)methyl)-7-hydroxyisoindolin-1-one (0.80 g) obtained in Reference Example 29 in ethanol (5 mL) were added 7-oxabicyclo[4.1.0]heptane (2.85 g) and pyridine (3.45 g), and the mixture was stirred under an argon atmosphere at 90° C. for 3 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.68 g).

MS: [M+H]$^+$ 373.2

$^1$H NMR (300 MHz, DMSO-d$_6$) δ 1.23-1.38 (3H, m), 1.39-1.53 (1H, m), 1.56-1.74 (2H, m), 1.87 (1H, brs), 2.01-2.13 (1H, m), 3.52-3.69 (1H, m), 4.02-4.16 (1H, m), 4.36 (2H, s), 4.70 (2H, s), 5.01-5.14 (1H, m), 7.04-7.18 (2H, m), 7.40-7.57 (2H, m), 7.76 (1H, dd, J=7.9, 2.5 Hz), 8.38 (1H, d, J=2.5 Hz).

Example 44

2-((6-cyclopropylpyridin-3-yl)methyl)-7-((trans-2-hydroxycyclohexyl)oxy)isoindolin-1-one

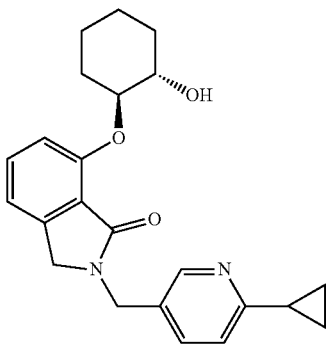 [SMILES: O=C1c2c(cccc2O[C@H]2CCCC[C@@H]2O)CN1Cc1ccc(C2CC2)nc1]

A solution of 2-((6-chloropyridin-3-yl)methyl)-7-((trans-2-hydroxycyclohexyl)oxy)isoindolin-1-one (0.47 g) obtained in Example 43, cyclopropylboronic acid (0.16 g), palladium acetate (0.014 g), tripotassium phosphate (0.94 g) and tricyclohexylphosphine (20% toluene solution) (0.18 g) in toluene (8 mL)-water (0.4 mL) was stirred under an argon atmosphere at 100° C. overnight. The reaction mixture was diluted with ethyl acetate, and washed with saturated brine. The organic layer was separated, dried over anhydrous sodium sulfate, and concentrated. The residue was crudely purified by NH silica gel chromatography (hexane-ethyl acetate) and silica gel chromatography (hexane-ethyl acetate), and solidified with ethyl acetate and hexane to give the title compound (0.078 g).

MS: [M+H]$^+$ 379.2

$^1$H NMR (300 MHz, DMSO-d$_6$) δ 0.85-0.95 (4H, m), 1.23-1.33 (3H, m), 1.40-1.54 (1H, m), 1.58-1.72 (2H, m), 1.91 (1H, brs), 2.01-2.12 (2H, m), 3.55-3.67 (1H, m), 4.03-4.09 (1H, m), 4.31 (2H, s), 4.62 (2H, s), 5.13 (1H, d, J=3.8 Hz), 7.07-7.14 (2H, m), 7.25 (1H, d, J=7.9 Hz), 7.42-7.58 (2H, m), 8.34 (1H, d, J=1.9 Hz).

Example 45

7-((trans-2-hydroxycyclohexyl)oxy)-2-((6-(piperidin-1-yl)pyridin-3-yl)methyl)isoindolin-1-one

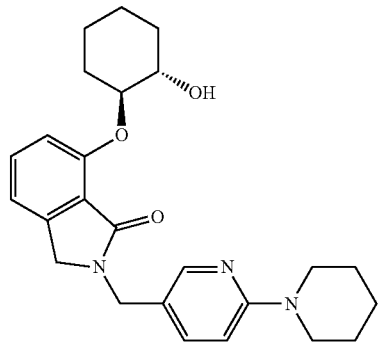 [SMILES: O=C1c2c(cccc2O[C@H]2CCCC[C@@H]2O)CN1Cc1ccc(N2CCCCC2)nc1]

A solution of 7-((tert-butyldimethylsilyl)oxy)-2-((6-chloropyridin-3-yl)methyl)isoindolin-1-one (0.20 g) obtained in Reference Example 29, piperidine (0.13 g), palladium acetate (0.012 g), sodium tert-butoxide (0.015 g) and 2,2'-bis(diphenylphosphino)-1,1'-binaphthalene (0.096 g) in toluene (5 mL) was stirred under an argon atmosphere at 100° C. overnight. The reaction mixture was concentrated, and the residue was crudely purified by silica gel chromatography (hexane-ethyl acetate). To a solution of the obtained crudely purified product in ethanol (2 mL) were added 7-oxabicyclo[4.1.0]heptane (0.068 g) and pyridine (0.055 g), and the mixture was stirred under an argon atmosphere at 90° C. for 4 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.012 g).

MS: [M+H]$^+$ 422.3

$^1$H NMR (300 MHz, DMSO-d$_6$) δ 1.25-1.35 (3H, m), 1.44-1.67 (9H, m), 1.91 (1H, brs), 2.02-2.15 (1H, m), 3.42-3.53 (4H, m), 3.60 (1H, brs), 3.93-4.09 (1H, m), 4.27 (2H, s), 4.51 (2H, s), 5.18 (1H, d, J=3.6 Hz), 6.70-6.85 (1H, m), 7.10 (2H, d, J=8.1 Hz), 7.33-7.58 (2H, m), 8.00-8.13 (1H, m).

Example 46

4-((1-oxo-7-phenoxy-1,3-dihydro-2H-isoindol-2-yl)methyl)benzonitrile

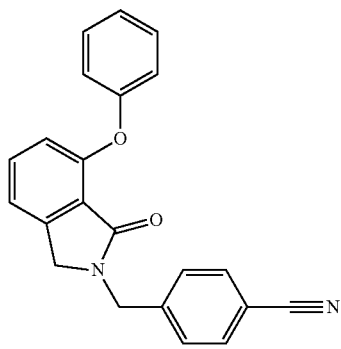 [SMILES: N#Cc1ccc(CN2Cc3cccc(Oc4ccccc4)c3C2=O)cc1]

To a solution of 4-((7-hydroxy-1-oxoisoindolin-2-yl)methyl)benzonitrile (1.0 g) obtained in Reference Example 18 in dichloromethane (30 mL) were added phenylboronic acid (0.69 g), copper(II) acetate (1.03 g) and triethylamine (0.58 g), and the mixture was stirred at room temperature for 68 hr. The insoluble material was filtered off, and the filtrate was concentrated. The residue was purified by HPLC (C18, mobile phase: water/acetonitrile (containing 0.1% TFA)) to give the title compound (0.45 g).

MS: [M+H]$^+$ 340.9

$^1$H NMR (400 MHz, CDCl$_3$) δ 4.32 (2H, s), 4.82 (2H, s), 6.82 (1H, d, J=8.0 Hz), 7.08 (1H, d, J=7.6 Hz), 7.15-7.21 (3H, m), 7.35-7.50 (5H, m), 7.64 (2H, d, J=8.0 Hz).

Example 47

4-((1-oxo-7-phenoxy-1,3-dihydro-2H-isoindol-2-yl)methyl)benzamide

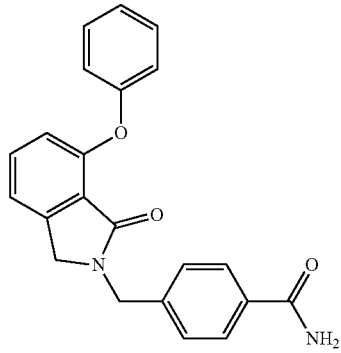 [SMILES: NC(=O)c1ccc(CN2Cc3cccc(Oc4ccccc4)c3C2=O)cc1]

To a solution of 4-((1-oxo-7-phenoxy-1,3-dihydro-2H-isoindol-2-yl)methyl)benzonitrile (0.25 g) obtained in Example 46 in DMSO (5 mL) were added potassium carbonate (0.20 g) and hydrogen peroxide (0.44 g), and the mixture was stirred at 5° C. for 3 hr. Water was added to the reaction mixture, and the resulting precipitate was collected by filtration to give the title compound (0.24 g).

MS: [M+H]$^+$ 359.0

$^1$H NMR (300 MHz, DMSO-d$_6$) δ 4.39 (2H, s), 4.71 (2H, s), 6.86 (1H, d, J=7.8 Hz), 6.95-7.05 (2H, m), 7.16 (1H, t, J=7.5 Hz), 7.26-7.47 (6H, m), 7.54 (1H, t, J=7.8 Hz), 7.85 (2H, d, J=8.1 Hz), 7.96 (1H, brs).

Example 48

2-(3-bromobenzyl)-7-((trans-2-hydroxycyclohexyl)oxy)isoindolin-1-one

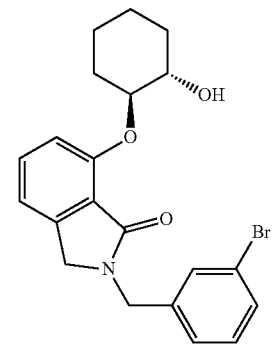 [SMILES: O=C1c2c(cccc2O[C@H]2CCCC[C@@H]2O)CN1Cc1cccc(Br)c1]

To a solution of 2-(3-bromobenzyl)-7-hydroxyisoindolin-1-one (0.11 g) obtained in Reference Example 21 in ethanol (3 mL) were added 7-oxabicyclo[4.1.0]heptane (0.34 g) and pyridine (0.41 g), and the mixture was stirred at 90° C. for 3 hr. The reaction mixture was diluted with ethyl acetate, and washed with saturated brine. The organic layer was separated, dried over anhydrous sodium sulfate, and concentrated. The residue was purified by NH silica gel chromatography (hexane-ethyl acetate) to give the title compound (0.083 g).

$^1$H NMR (300 MHz, DMSO-d$_6$) δ 1.22-1.37 (3H, m), 1.39-1.54 (1H, m), 1.58-1.73 (2H, m), 1.84-1.96 (1H, m), 2.02-2.13 (1H, m), 3.54-3.68 (1H, m), 4.06-4.16 (1H, m), 4.33 (2H, s), 4.67 (2H, s), 5.12 (1H, d, J=3.6 Hz), 7.07-7.17 (2H, m), 7.22-7.38 (2H, m), 7.43-7.54 (3H, m).

Example 49

Tert-butyl 4-((7-((trans-2-hydroxycyclohexyl)oxy)-1-oxo-1,3-dihydro-2H-isoindol-2-yl)methyl)piperidine-1-carboxylate

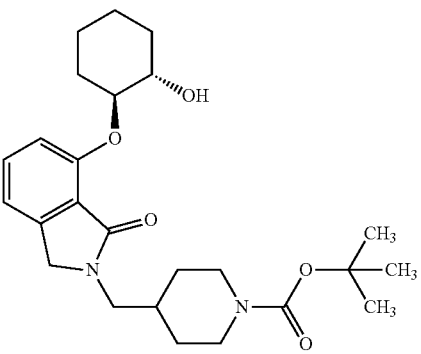 [SMILES: CC(C)(C)OC(=O)N1CCC(CN2Cc3cccc(O[C@H]4CCCC[C@@H]4O)c3C2=O)CC1]

To a solution of tert-butyl 4-((7-hydroxy-1-oxoisoindolin-2-yl)methyl)piperidine-1-carboxylate (1.05 g) obtained in Reference Example 31 in ethanol (10 mL) were added 7-oxabicyclo[4.1.0]heptane (2.97 g) and pyridine (3.6 g), and the mixture was stirred under an argon atmosphere at 90° C. for 3 hr. The reaction mixture was concentrated, and the residue was purified by NH silica gel chromatography (hexane-ethyl acetate) to give the title compound (0.67 g).

MS: [M+H]$^+$ 445.4

$^1$H NMR (400 MHz, DMSO-d$_6$) δ 0.97-1.08 (2H, m), 1.23-1.30 (3H, m), 1.39 (9H, s), 1.41-1.72 (6H, m), 1.82-1.95 (2H, m), 2.03-2.13 (1H, m), 2.67 (2H, brs), 3.35-3.39 (1H, m), 3.58 (1H, brs), 3.87-4.00 (3H, m), 4.42 (2H, s), 5.23 (1H, d, J=3.4 Hz), 7.07-7.19 (2H, m), 7.44-7.53 (1H, m).

Example 50

7-((trans-2-hydroxycyclohexyl)oxy)-2-((piperidin-4-yl)methyl)isoindolin-1-one

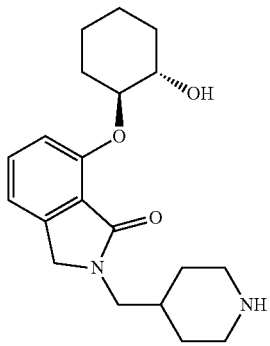 [SMILES: O=C1c2c(cccc2O[C@H]2CCCC[C@@H]2O)CN1CC1CCNCC1]

To a solution of tert-butyl 4-((7-((trans-2-hydroxycyclohexyl)oxy)-1-oxo-1,3-dihydro-2H-isoindol-2-yl)methyl)piperidine-1-carboxylate (0.67 g) obtained in Example 49 in ethyl acetate (5 mL) was added 4N hydrochloric acid (ethyl acetate solution) (0.75 mL), the mixture was stirred at room temperature overnight, and the reaction solution was concentrated. To a solution of the obtained residue (0.25 g) in ethyl acetate (3 mL) was added sodium hydrogen carbonate (0.055 g), and the mixture was stirred at room temperature for 30 min. The reaction mixture was diluted with ethyl acetate, and washed with saturated brine. The organic layer was separated, dried over anhydrous sodium sulfate, and concentrated. The residue was solidified with ethyl acetate and hexane to give the title compound (0.19 g).

MS: [M+H]$^+$ 345.3

$^1$H NMR (400 MHz, DMSO-d$_6$) δ 0.99-1.10 (2H, m), 1.26 (3H, brs), 1.41-1.54 (3H, m), 1.57-1.69 (2H, m), 1.73-1.82 (1H, m), 1.87-1.94 (1H, m), 2.08 (1H, d, J=15.2 Hz), 2.36-2.46 (2H, m), 2.91 (2H, d, J=12.0 Hz), 3.22-3.31 (3H, m), 3.58 (1H, brs), 3.92-4.02 (1H, m), 4.40 (2H, s), 5.26 (1H, brs), 7.07-7.18 (2H, m), 7.48 (1H, t, J=7.8 Hz).

Example 51

7-((trans-2-hydroxycyclohexyl)oxy)-2-((1-(pyridin-2-yl) piperidin-4-yl)methyl)isoindolin-1-one

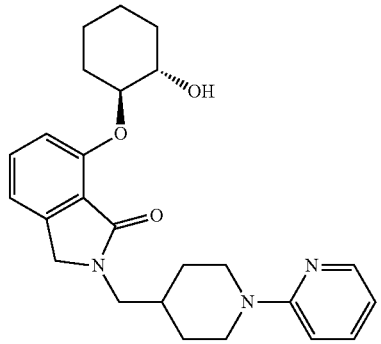 [SMILES: O=C1c2c(cccc2O[C@H]2CCCC[C@@H]2O)CN1CC1CCN(c2ccccn2)CC1]

A solution of 7-((trans-2-hydroxycyclohexyl)oxy)-2-((piperidin-4-yl)methyl)isoindolin-1-one (0.10 g) obtained in Example 50, 2-bromopyridine (0.092 g), palladium acetate (0.007 g), sodium tert-butoxide (0.042 g) and (±)-2,2'-bis(diphenylphosphino)-1,1'-binaphthyl (0.018 g) in toluene (3 mL) was stirred under an argon atmosphere at 110° C. overnight. The reaction mixture was diluted with ethyl acetate, and washed with saturated brine. The organic layer was separated, dried over anhydrous sodium sulfate, and concentrated. The residue was crudely purified by NH silica gel chromatography (hexane-ethyl acetate), and solidified with ethyl acetate and hexane to give the title compound (0.010 g).

MS: [M+H]$^+$ 422.3

$^1$H NMR (400 MHz, DMSO-d$_6$) δ 1.11-1.29 (5H, m), 1.41-1.51 (1H, m), 1.59-1.68 (4H, m), 1.87-2.10 (3H, m), 2.72-2.82 (2H, m), 3.35-3.40 (2H, m), 3.58 (1H, brs), 3.94-4.02 (1H, m), 4.27 (2H, d, J=13.0 Hz), 4.44 (2H, s), 5.24 (1H, d, J=3.2 Hz), 6.55-6.61 (1H, m), 6.78-6.83 (1H, m), 7.08-7.18 (2H, m), 7.45-7.52 (2H, m), 8.06-8.11 (1H, m).

Example 52

2-((1-(4-fluorobenzyl)piperidin-4-yl)methyl)-7-(trans-2-hydroxycyclohexyl)oxy)isoindolin-1-one

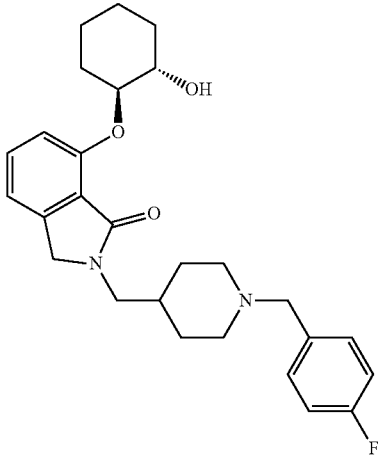 [SMILES: O=C1c2c(cccc2O[C@H]2CCCC[C@@H]2O)CN1CC1CCN(Cc2ccc(F)cc2)CC1]

To a solution of tert-butyl 4-((7-((trans-2-hydroxycyclo-hexyl)oxy)-1-oxo-1,3-dihydro-2H-isoindol-2-yl)methyl)piperidine-1-carboxylate (0.67 g) obtained in Example 49 in ethyl acetate (5 mL) was added 4N hydrochloric acid (ethyl acetate solution) (0.75 mL), the mixture was stirred at room temperature overnight, and the reaction solution was concentrated. To a solution of the residue (0.10 g) in DMF (3 mL) were added 1-(bromomethyl)-4-fluorobenzene (0.099 g) and cesium carbonate (0.26 g), and the mixture was stirred under an argon atmosphere at room temperature for 1 hr. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.067 g).

MS: [M+H]$^+$ 453.4

$^1$H NMR (400 MHz, DMSO-d$_6$) δ 1.17-1.31 (5H, m), 1.43-1.73 (6H, m), 1.84-1.94 (3H, m), 2.03-2.12 (1H, m), 2.71-2.80 (2H, m), 3.35 (2H, brs), 3.42 (2H, s), 3.58 (1H, brs), 3.91-4.00 (1H, m), 4.40 (2H, s), 5.24 (1H, d, J=3.4 Hz), 7.07-7.16 (4H, m), 7.27-7.35 (2H, m), 7.47 (1H, t, J=7.8 Hz).

Example 53

2-(4-(1H-pyrazol-1-yl)benzyl)-7-((tetrahydrofuran-2-yl)methoxy)isoindolin-1-one

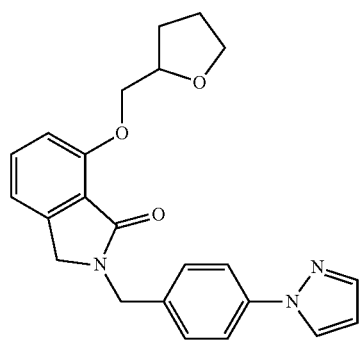 [SMILES: O=C1c2c(cccc2OCC2CCCO2)CN1Cc1ccc(-n2cccn2)cc1]

A solution of 2-(4-(1H-pyrazol-1-yl)benzyl)-7-hydroxyisoindolin-1-one (0.10 g) obtained in Reference Example 14, (tetrahydrofuran-2-yl)methanol (0.067 g) and tributylphosphine (0.13 g) in THF (3 mL) was stirred at 60° C. for 20 min, diisopropyl azodicarboxylate (40% toluene solution) (0.33 g) was added, and the mixture was stirred under a nitrogen atmosphere at 60° C. overnight. The reaction mixture was concentrated, and the residue was crudely purified by NH silica gel chromatography (hexane-ethyl acetate), and solidified with ethyl acetate and hexane to give the title compound (0.03 g).

MS: [M+H]$^+$ 390.2

$^1$H NMR (300 MHz, DMSO-d$_6$) δ 1.75-1.91 (2H, m), 1.93-2.12 (2H, m), 3.63-3.73 (1H, m), 3.80-3.92 (1H, m), 4.03-4.14 (2H, m), 4.16-4.25 (1H, m), 4.30 (2H, s), 4.69 (2H, s), 6.49-6.56 (1H, m), 7.05 (2H, dd, J=13.6, 7.9 Hz), 7.38 (2H, d, J=8.7 Hz), 7.48 (1H, t, J=7.7 Hz), 7.72 (1H, d, J=1.5 Hz), 7.81 (2H, d, J=8.7 Hz), 8.46 (1H, d, J=2.6 Hz).

Example 54

2-(4-(1H-pyrazol-1-yl)benzyl)-7-((trans-2-hydroxycyclopentyl)oxy)isoindolin-1-one

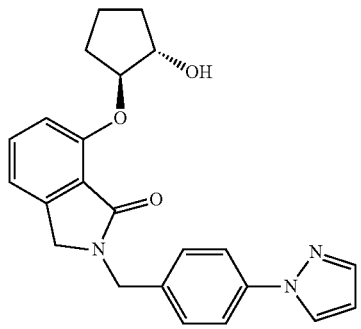 [SMILES: O=C1c2c(cccc2O[C@H]2CCC[C@@H]2O)CN1Cc1ccc(-n2cccn2)cc1]

To a solution of 2-(4-(1H-pyrazol-1-yl)benzyl)-7-hydroxyisoindolin-1-one (0.095 g) obtained in Reference Example 14 in ethanol (5 mL) were added 6-oxabicyclo[3.1.0]hexane (0.39 g) and pyridine (0.37 g), and the mixture was stirred under a nitrogen atmosphere at 90° C. overnight. The reaction mixture was concentrated, and the residue was crudely purified by NH silica gel chromatography (hexane-ethyl acetate), and solidified with ethyl acetate and hexane to give the title compound (0.057 g).

MS: [M+H]$^+$ 390.2

$^1$H NMR (300 MHz, DMSO-d$_6$) δ 1.49-1.60 (1H, m), 1.63-1.79 (3H, m), 1.87-2.00 (1H, m), 2.04-2.17 (1H, m), 4.06-4.15 (1H, m), 4.30 (2H, s), 4.57-4.64 (1H, m), 4.67 (2H, s), 4.95 (1H, d, J=3.8 Hz), 6.48-6.56 (1H, m), 7.01-7.12 (2H, m), 7.38 (2H, d, J=8.7 Hz), 7.44-7.53 (1H, m), 7.72 (1H, d, J=1.3 Hz), 7.81 (2H, d, J=8.5 Hz), 8.46 (1H, d, J=2.1 Hz).

Example 55

7-((2-fluorophenyl)sulfanyl)-2-(4-(1-methyl-1H-pyrazol-4-yl)benzyl)isoindolin-1-one

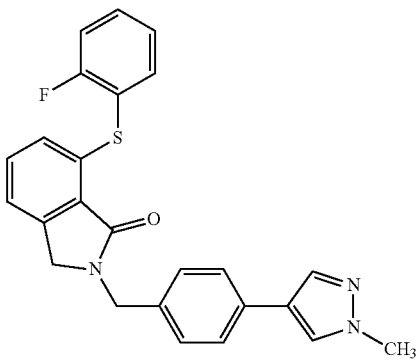 [SMILES: Cn1cc(-c2ccc(CN3Cc4cccc(Sc5ccccc5F)c4C3=O)cc2)cn1]

To a suspension of 7-bromo-2-(4-(1-methyl-1H-pyrazol-4-yl)benzyl)isoindolin-1-one (0.50 g) obtained in Reference Example 32, 2-fluorobenzenethiol (0.18 g) and sodium tert-butoxide (0.50 g) in toluene (5 mL) was added tetrakis(triphenylphosphine)palladium(0) (0.15 g), and the mixture was refluxed under a nitrogen atmosphere for 16 hr. After cooling the reaction solution, methanol (20 mL) was added, and the insoluble material was filtered off. The filtrate was concentrated, and the residue was purified by HPLC (C18, mobile phase: water/acetonitrile (containing 0.1% TFA)) to give the title compound (0.06 g).

MS: [M+H]⁺ 429.7

$^1$H NMR (400 MHz, CDCl$_3$) δ 3.95 (3H, s), 4.27 (2H, s), 4.78 (2H, s), 6.64 (1H, d, J=7.6 Hz), 7.07 (1H, d, J=7.6 Hz), 7.20-7.28 (3H, m), 7.34 (2H, d, J=8.4 Hz), 7.42-7.51 (3H, m), 7.61 (1H, s), 7.62-7.68 (1H, m), 7.75 (1H, s).

Example 56

7-((2-fluorophenyl)sulfinyl)-2-(4-(1-methyl-1H-pyrazol-4-yl)benzyl)isoindolin-1-one

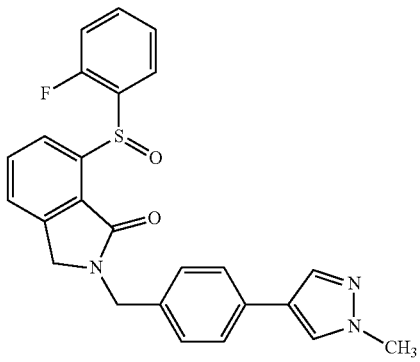 [SMILES: Cn1cc(-c2ccc(CN3Cc4cccc(S(=O)c5ccccc5F)c4C3=O)cc2)cn1]

To a solution of 7-((2-fluorophenyl)sulfanyl)-2-(4-(1-methyl-1H-pyrazol-4-yl)benzyl)isoindolin-1-one (0.30 g) obtained in Example 55 in methanol (10 mL) was added an aqueous solution (5 mL) of Oxone (registered trademark) (0.22 g) at 0° C. The mixed solution was stirred at 0° C. for 2 hr and at 30° C. for 16 hr. The reaction solution was filtered and washed with dichloromethane (20 mL). The filtrate was concentrated, and the residue was purified by silica gel chromatography (dichloromethane-ethyl acetate) to give the title compound (0.096 g).

MS: [M+H]⁺ 445.9

$^1$H NMR (300 MHz, CDCl$_3$) δ 3.93 (3H, s), 4.25-4.33 (2H, m), 4.49 (1H, d, J=15.0 Hz), 4.84 (1H, d, J=15.0 Hz), 7.10 (1H, t, J=8.7 Hz), 7.15-7.28 (3H, m), 7.36-7.46 (3H, m), 7.49 (1H, d, J=7.8 Hz), 7.58 (1H, s), 7.61-7.69 (1H, m), 7.70-7.80 (2H, m), 8.26 (1H, d, J=7.5 Hz).

Example 57

7-((2-fluorophenyl)sulfonyl)-2-(4-(1-methyl-1H-pyrazol-4-yl)benzyl)isoindolin-1-one

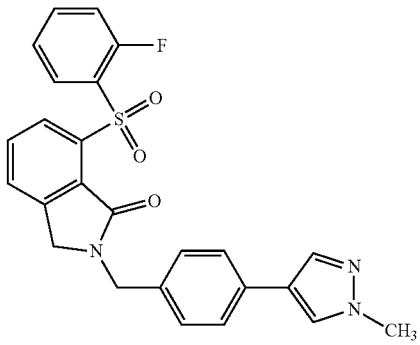 [SMILES: Cn1cc(-c2ccc(CN3Cc4cccc(S(=O)(=O)c5ccccc5F)c4C3=O)cc2)cn1]

To a solution of 7-((2-fluorophenyl)sulfanyl)-2-(4-(1-methyl-1H-pyrazol-4-yl)benzyl)isoindolin-1-one (0.30 g) obtained in Example 55 in methanol (10 mL) was added an aqueous solution (10 mL) of Oxone (registered trademark) (0.86 g), and the mixture was stirred at 30° C. for 16 hr. Methanol was evaporated under reduced pressure, and dichloromethane (30 mL) was added. The organic layer was separated, and concentrated. The residue was purified by silica gel chromatography (dichloromethane-ethyl acetate) to give the title compound (0.15 g).

MS: [M+H]⁺ 461.7

$^1$H NMR (300 MHz, CDCl$_3$) δ 3.92 (3H, s), 4.22 (2H, s), 4.64 (2H, s), 7.03 (1H, t, J=9.3 Hz), 7.18 (2H, d, J=8.1 Hz), 7.34-7.44 (3H, m), 7.52-7.67 (3H, m), 7.67-7.76 (2H, m), 8.45 (1H, d, J=7.8 Hz), 8.48-8.57 (1H, m).

Example 58

2-(cyclohexylmethyl)-7-((trans-2-hydroxycyclohexyl)oxy)isoindolin-1-one

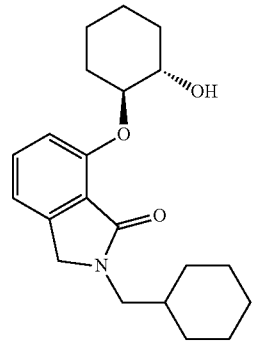 [SMILES: O=C1c2c(cccc2O[C@H]2CCCC[C@@H]2O)CN1CC1CCCCC1]

To a solution of 2-(cyclohexylmethyl)-7-hydroxyisoindolin-1-one (0.061 g) obtained in Reference Example 34 in ethanol (3 mL) were added 7-oxabicyclo[4.1.0]heptane (0.24 g) and pyridine (0.30 g), and the mixture was stirred under an argon atmosphere at 90° C. for 5 hr. The reaction mixture was concentrated, and the residue was crudely purified by NH silica gel chromatography (hexane-ethyl acetate), and solidified with ethyl acetate and hexane to give the title compound (0.065 g).

MS: [M+H]⁺ 344.3

$^1$H NMR (400 MHz, DMSO-d$_6$) δ 0.89-0.99 (2H, m), 1.17-1.70 (15H, m), 1.85-1.94 (1H, m), 2.08 (1H, d, J=12.0 Hz), 3.25-3.32 (2H, m), 3.54-3.63 (1H, m), 3.93-4.00 (1H, m), 4.40 (2H, s), 5.27 (1H, d, J=3.4 Hz), 7.12 (2H, dd, J=16.9, 7.8 Hz), 7.48 (1H, t, J=7.8 Hz).

Example 59

6-(4-(1-methyl-1H-pyrazol-4-yl)benzyl)-4-((tetrahydrofuran-2-yl)methoxy)-6,7-dihydro-5H-pyrrolo[3,4-b]pyridin-5-one

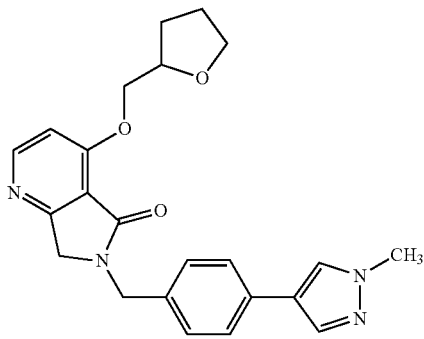 [SMILES: Cn1cc(-c2ccc(CN3Cc4nccc(OCC5CCCO5)c4C3=O)cc2)cn1]

A mixture of ethyl 4-((tetrahydrofuran-2-yl)methoxy)-2-vinylnicotinate (0.11 g) obtained in Reference Example 39, sodium periodate (0.41 g) and osmium oxide (immobilized catalyst I) (0.048 g) and acetonitrile (1 mL)-acetone (1 mL)-water (1 mL) was stirred at room temperature overnight. The insoluble material was filtered off, and the filtrate was concentrated. The residue was dissolved in DMF (3 mL), (4-(1-methyl-1H-pyrazol-4-yl)phenyl)methanamine (0.068 g) and sodium triacetoxyhydroborate (0.21 g) were added, and the mixture was stirred under a nitrogen atmosphere at room temperature overnight. The reaction mixture was diluted with water and ethyl acetate. The organic layer was separated, washed with saturated brine, dried over anhydrous sodium sulfate, and concentrated. The residue was crudely purified by NH silica gel chromatography (hexane-ethyl acetate) and silica gel chromatography (methanol-ethyl acetate), and solidified with ethyl acetate and hexane to give the title compound (0.018 g).

MS: [M+H]+ 405.2
1H NMR (300 MHz, DMSO-$d_6$) δ 1.73-1.88 (2H, m), 1.94-2.10 (2H, m), 3.62-3.73 (1H, m), 3.79-3.89 (4H, m), 4.13-4.27 (3H, m), 4.31 (2H, s), 4.65 (2H, s), 7.11 (1H, d, J=5.9 Hz), 7.26 (2H, d, J=8.1 Hz), 7.53 (2H, d, J=8.1 Hz), 7.82 (1H, s), 8.10 (1H, s), 8.51 (1H, d, J=5.9 Hz).

Example 60

6-(4-(1H-pyrazol-1-yl)benzyl)-4-((tetrahydrofuran-2-yl)methoxy)-6,7-dihydro-5H-pyrrolo[3,4-b]pyridin-5-one

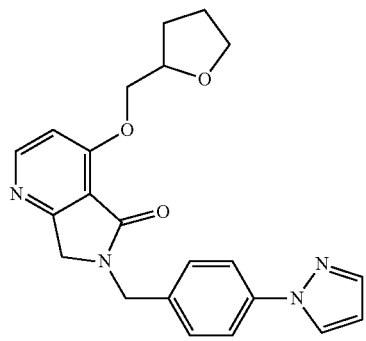 [SMILES: O=C1c2c(OCC3CCCO3)ccnc2CN1Cc1ccc(-n2cccn2)cc1]

A mixture of ethyl 4-((tetrahydrofuran-2-yl)methoxy)-2-vinylnicotinate (0.20 g) obtained in Reference Example 39, sodium periodate (0.77 g) and osmium oxide (immobilized catalyst I) (0.092 g) and acetonitrile (3 mL)-acetone (3 mL)-water (3 mL) was stirred under a nitrogen atmosphere at room temperature overnight. The insoluble material was filtered off, and the filtrate was diluted with ethyl acetate and water. The organic layer was separated, washed with saturated brine, dried over anhydrous sodium sulfate, and concentrated. The residue was dissolved in diethyl ether (5 mL), (4-(1H-pyrazol-1-yl)phenyl)methanamine (0.13 g) and anhydrous magnesium sulfate (0.20 g) were added, and the mixture was stirred under a nitrogen atmosphere at room temperature for 1 hr. The insoluble material was filtered off, and the filtrate was concentrated. To a solution of the residue in methanol (5 mL)-THF (5 mL) was added sodium triacetoxyhydroborate (0.31 g), and the mixture was stirred under a nitrogen atmosphere at room temperature overnight. The reaction mixture was diluted with water and ethyl acetate. The organic layer was separated, washed with saturated brine, dried over anhydrous sodium sulfate, and concentrated. The residue was purified by HPLC (L-column2 ODS, mobile phase: water/acetonitrile (containing 5 mM AcONH4)) to give the title compound (0.035 g).

MS: [M–H]+ 391.2
1H NMR (300 MHz, DMSO-$d_6$) δ 1.74-1.90 (2H, m), 1.95-2.10 (2H, m), 3.63-3.74 (1H, m), 3.78-3.90 (1H, m), 4.14-4.28 (3H, m), 4.34 (2H, s), 4.71 (2H, s), 6.48-6.57 (1H, m), 7.11 (1H, d, J=6.0 Hz), 7.41 (2H, d, J=8.5 Hz), 7.73 (1H, d, J=1.5 Hz), 7.81 (2H, d, J=8.7 Hz), 8.47 (1H, d, J=2.3 Hz), 8.52 (1H, d, J=5.9 Hz).

Example 61

2-(4-(1H-pyrazol-1-yl)benzyl)-4-((tetrahydrofuran-2-yl)methoxy)-1H-pyrrolo[3,4-c]pyridin-3(2H)-one

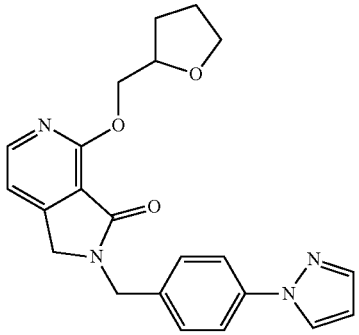 [SMILES: O=C1c2c(ccnc2OCC2CCCO2)CN1Cc1ccc(-n2cccn2)cc1]

A mixture of methyl 2-((tetrahydrofuran-2-yl)methoxy)-4-vinylnicotinate (0.25 g) obtained in Reference Example 42, sodium periodate (1.02 g) and osmium oxide (immobilized catalyst I) (0.12 g) and acetonitrile (4 mL)-acetone (4 mL)-water (4 mL) was stirred under a nitrogen atmosphere at room temperature overnight. The insoluble material was filtered off, and the filtrate was diluted with ethyl acetate and water. The organic layer was separated, washed with saturated brine, dried over anhydrous sodium sulfate, and concentrated. The residue was dissolved in DMF (4 mL), (4-(1H-pyrazol-1-yl)phenyl)methanamine (0.17 g) and sodium triacetoxyhydroborate (0.40 g) were added, and the mixture was stirred under a nitrogen atmosphere at room temperature overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) and HPLC (L-column2 ODS, mobile phase: water/acetonitrile (containing 5 mM AcONH4)) to give the title compound (0.026 g).

MS: [M+H]+ 391.2

$^1$H NMR (300 MHz, DMSO-$d_6$) δ 1.70-1.88 (2H, m), 1.93-2.06 (2H, m), 3.63-3.72 (1H, m), 3.79-3.89 (1H, m), 4.18-4.28 (1H, m), 4.33-4.43 (4H, m), 4.70 (2H, s), 6.51-6.54 (1H, m), 7.19 (1H, d, J=5.3 Hz), 7.39 (2H, d, J=8.7 Hz), 7.73 (1H, d, J=1.5 Hz), 7.81 (2H, d, J=8.5 Hz), 8.27 (1H, d, J=5.3 Hz), 8.46 (1H, d, J=2.3 Hz).

Example 62

2-(4-(1H-pyrazol-1-yl)benzyl)-7-((tetrahydrofuran-2-yl)methoxy)-2,3-dihydro-1H-pyrrolo[3,4-c]pyridin-1-one

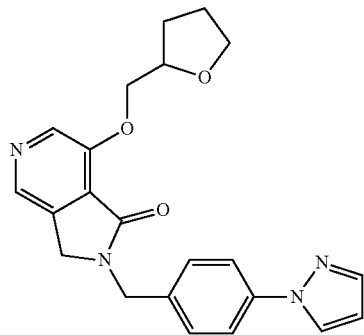 [SMILES: O=C1c2c(cncc2OCC2CCCO2)CN1Cc1ccc(-n2cccn2)cc1]

A mixture of methyl 3-((tetrahydrofuran-2-yl)methoxy)-5-vinylisonicotinate (0.18 g) obtained in Reference Example 47, sodium periodate (0.71 g) and osmium oxide (immobilized catalyst I) (0.084 g) and acetonitrile (4 mL)-acetone (4 mL)-water (4 mL) was stirred at room temperature overnight. The insoluble material was filtered off, the filtrate was ethyl acetate and water, and the organic layer was separated, washed with saturated brine, dried over anhydrous sodium sulfate, and concentrated. The residue was dissolved in diethyl ether (5 mL)-THF (5 mL), (4-(1H-pyrazol-1-yl)phenyl)methanamine (0.10 g) and anhydrous magnesium sulfate (0.15 g) were added, and the mixture was stirred under a nitrogen atmosphere at room temperature for 1 hr. The insoluble material was filtered off, and the filtrate was concentrated. To a solution of the residue in acetic acid (5 mL) was added sodium triacetoxyhydroborate (0.28 g), and the mixture was stirred at room temperature for 3 hr. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.095 g).

MS: [M+H]+ 391.2

$^1$H NMR (300 MHz, DMSO-$d_6$) δ 1.73-1.90 (2H, m), 1.97-2.07 (2H, m), 3.62-3.75 (1H, m), 3.82 (1H, t, J=7.1 Hz), 4.20-4.33 (3H, m), 4.44 (2H, s), 4.72 (2H, s), 6.46-6.59 (1H, m), 7.41 (2H, d, J=8.5 Hz), 7.73 (1H, d, J=1.7 Hz), 7.82 (2H, d, J=8.5 Hz), 8.40-8.51 (3H, m).

Example 63

2-((2-(4-bromo-2-fluorobenzyl)-3-oxo-2,3-dihydro-1H-isoindol-4-yl)oxy)-3-fluorobenzonitrile

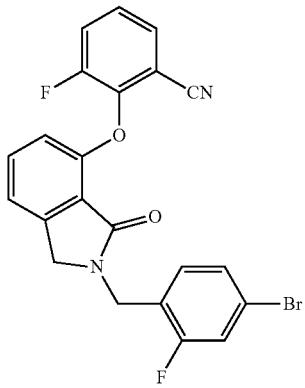 [SMILES: N#Cc1cccc(F)c1Oc1cccc2c1C(=O)N(Cc1ccc(Br)cc1F)C2]

To a solution of (4-bromo-2-fluorophenyl)methanamine (0.30 g) and potassium carbonate (0.55 g) in ethanol (10 mL) was added ethyl 2-(bromomethyl)-6-(2-cyano-6-fluorophenoxy)benzoate (0.50 g) obtained in Reference Example 49, and the mixture was stirred at room temperature overnight. The reaction mixture was diluted with ethyl acetate and water. The organic layer was washed with water and saturated brine, dried over anhydrous magnesium sulfate and concentrated. The residue was solidified with hexane-ethyl acetate to give the title compound (0.21 g).

$^1$H NMR (300 MHz, CDCl$_3$) δ 4.36 (2H, s), 4.78 (2H, d, J=0.9 Hz), 6.74 (1H, d, J=8.3 Hz), 7.17 (1H, dd, J=7.6, 0.6 Hz), 7.24-7.34 (4H, m), 7.37-7.47 (2H, m), 7.50 (1H, dt, J=7.7, 1.4 Hz).

Example 64

3-fluoro-2-((2-(2-fluoro-4-(1-methyl-1H-pyrazol-4-yl)benzyl)-3-oxo-2,3-dihydro-1H-isoindol-4-yl)oxy)benzonitrile

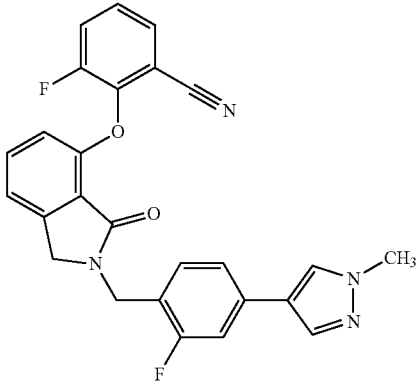 [SMILES: Cn1cc(-c2ccc(CN3Cc4cccc(Oc5c(F)cccc5C#N)c4C3=O)c(F)c2)cn1]

To a solution of 2-((2-(4-bromo-2-fluorobenzyl)-3-oxo-2,3-dihydro-1H-isoindol-4-yl)oxy)-3-fluorobenzonitrile (0.21 g) obtained in Example 63, 1-methyl-4-(4,4,5,5-tetramethyl-1,3,2-dioxaborolan-2-yl)-1H-pyrazole (0.11 g) and 2M aqueous sodium carbonate solution (0.69 mL) in DME (4 mL) was added tetrakis(triphenylphosphine)palladium(0) (0.053 g), and the mixture was stirred at 80° C. overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate), and solidified with ethanol to give the title compound (0.023 g).

MS: [M+H]+ 457.1

$^1$H NMR (300 MHz, CDCl$_3$) δ 3.95 (3H, s), 4.37 (2H, s), 4.81 (2H, s), 6.75 (1H, d, J=8.3 Hz), 7.13-7.25 (3H, m), 7.25-7.31 (3H, m), 7.35-7.46 (1H, m), 7.50 (1H, dt, J=7.7, 1.4 Hz), 7.61 (1H, s), 7.74 (1H, d, J=0.6 Hz).

Example 65

3-fluoro-2-((2-((6-(1-methyl-1H-pyrazol-4-yl)pyridin-3-yl)methyl)-3-oxo-2,3-dihydro-1H-isoindol-4-yl)oxy)benzonitrile

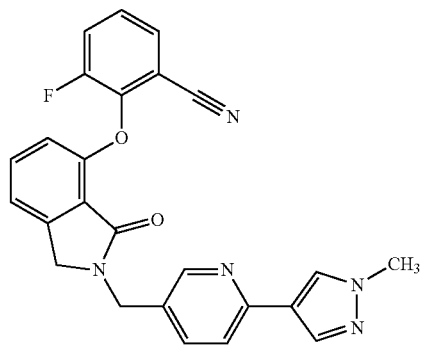 [SMILES: Cn1cc(-c2ccc(CN3Cc4cccc(Oc5c(F)cccc5C#N)c4C3=O)cn2)cn1]

To a solution of (6-(1-methyl-1H-pyrazol-4-yl)pyridin-3-yl)methanamine dihydrochloride (0.13 g) obtained in Reference Example 25 and potassium carbonate (0.22 g) in ethanol (4 mL) was added ethyl 2-(bromomethyl)-6-(2-cyano-6-fluorophenoxy)benzoate (0.20 g) obtained in Reference Example 49, and the mixture was stirred at room temperature overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate-methanol), and solidified with ethyl acetate and ethanol to give the title compound (0.019 g).

MS: [M+H]+ 440.2

$^1$H NMR (300 MHz, CDCl$_3$) δ 3.96 (3H, s), 4.31 (2H, s), 4.77 (2H, s), 6.76 (1H, d, J=8.3 Hz), 7.16 (1H, dd, J=7.6, 0.8 Hz), 7.24-7.32 (1H, m), 7.38-7.47 (3H, m), 7.51 (1H, dt, J=7.7, 1.4 Hz), 7.68 (1H, dd, J=8.2, 2.4 Hz), 7.91-7.96 (2H, m), 8.51 (1H, d, J=1.7 Hz).

Example 66

3-fluoro-2-((3-oxo-2-(4-(1H-pyrazol-1-yl)benzyl)-2,3-dihydro-1H-isoindol-4-yl)oxy)benzonitrile

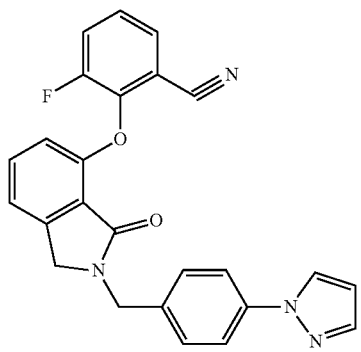 [SMILES: N#Cc1cccc(F)c1Oc1cccc2c1C(=O)N(Cc1ccc(-n3cccn3)cc1)C2]

Under an argon atmosphere, to a solution of (4-(1H-pyrazol-1-yl)phenyl)methanamine (0.20 g) and potassium carbonate (0.44 g) in DMF (8 mL) was added ethyl 2-(bromomethyl)-6-(2-cyano-6-fluorophenoxy)benzoate (0.20 g) obtained in Reference Example 49, and the mixture was stirred at room temperature overnight and further at 60° C. for 3 hr. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate-methanol), fractionated by HPLC (C18, mobile phase: water/acetonitrile (containing 0.1% TFA)). To the obtained fraction was added saturated aqueous sodium hydrogen carbonate solution, and the mixture was extracted with ethyl acetate, dried over anhydrous magnesium sulfate, and concentrated under reduced pressure. The residue was solidified with ethyl acetate to give the title compound (0.01 g).

MS: [M+H]+ 425.2

$^1$H NMR (300 MHz, CDCl$_3$) δ 4.30 (2H, s), 4.80 (2H, s), 6.46-6.49 (1H, m), 6.77 (1H, d, J=8.3 Hz), 7.16 (1H, d, J=7.5 Hz), 7.24-7.32 (1H, m), 7.38-7.47 (4H, m), 7.51 (1H, dt, J=7.9, 1.5 Hz), 7.66-7.71 (2H, m), 7.73 (1H, d, J=1.5 Hz), 7.92 (1H, d, J=2.3 Hz).

Example 67

2-((2-(4-bromo-2-chlorobenzyl)-3-oxo-2,3-dihydro-1H-isoindol-4-yl)oxy)-3-fluorobenzonitrile

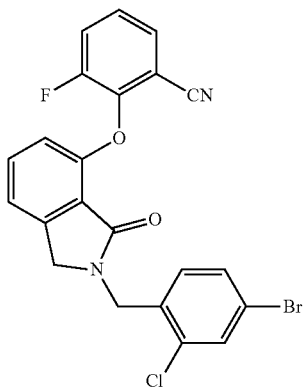 [SMILES: N#Cc1cccc(F)c1Oc1cccc2c1C(=O)N(Cc1ccc(Br)cc1Cl)C2]

To a solution of (4-bromo-2-chlorophenyl)methanamine (0.63 g) and potassium carbonate (0.59 g) in ethanol (5 mL) was added ethyl 2-(bromomethyl)-6-(2-cyano-6-fluorophenoxy)benzoate (0.54 g) obtained in Reference Example 49, and the mixture was stirred at room temperature overnight. The reaction mixture was diluted with ethyl acetate and water, and the organic layer was washed with water and saturated brine, dried over anhydrous magnesium sulfate and concentrated to give the title compound (0.27 g).

$^1$H NMR (300 MHz, CDCl$_3$) δ 4.36 (2H, s), 4.85 (2H, s), 6.76 (1H, d, J=7.9 Hz), 7.18 (1H, d, J=7.5 Hz), 7.24-7.31 (1H, m), 7.36-7.46 (3H, m), 7.46-7.52 (2H, m), 7.57 (1H, d, J=1.9 Hz).

Example 68

2-((2-(2-chloro-4-(1-methyl-1H-pyrazol-4-yl)benzyl)-3-oxo-2,3-dihydro-1H-isoindol-4-yl)oxy)-3-fluorobenzonitrile

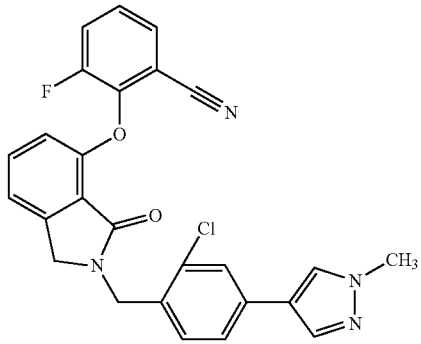 [SMILES: Cn1cc(-c2ccc(CN3Cc4cccc(Oc5c(F)cccc5C#N)c4C3=O)c(Cl)c2)cn1]

le;3qTo a solution of 2-((2-(4-bromo-2-chlorobenzyl)-3-oxo-2,3-dihydro-1H-isoindol-4-yl)oxy)-3-fluorobenzonitrile (0.20 g) obtained in Example 67, 1-methyl-4-(4,4,5,5-tetramethyl-1,3,2-dioxaborolan-2-yl)-1H-pyrazole (0.088 g) and 2M aqueous sodium carbonate solution (0.85 mL) in DME (4 mL) was added (1,1-bis(diphenylphosphino)ferrocene)dichloropalladium(II) (0.016 g), and the mixture was stirred under an argon atmosphere at 80° C. for 5 hr. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate), and solidified with ethanol to give the title compound (0.075 g).

MS: [M+H]$^+$ 473.1

$^1$H NMR (300 MHz, CDCl$_3$) δ 3.95 (3H, s), 4.38 (2H, s), 4.90 (2H, s), 6.77 (1H, d, J=8.3 Hz), 7.17 (1H, d, J=7.5 Hz), 7.23-7.32 (1H, m), 7.33-7.47 (4H, m), 7.48-7.53 (2H, m), 7.61 (1H, s), 7.74 (1H, s).

Example 69

3-fluoro-2-((2-((4-(1-methyl-1H-pyrazol-4-yl)-2-furyl)methyl)-3-oxo-2,3-dihydro-1H-isoindol-4-yl)oxy)benzonitrile

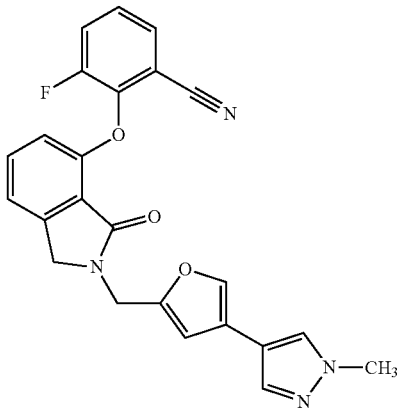 [SMILES: Cn1cc(-c2coc(CN3Cc4cccc(Oc5c(F)cccc5C#N)c4C3=O)c2)cn1]

To a solution of 4-(1-methyl-1H-pyrazol-4-yl)furan-2-carbaldehyde (0.54 g) obtained in Reference Example 50 in THF (5 mL) was added sodium tetrahydroborate (0.13 g) at 0° C., and the mixture was stirred under an argon atmosphere at the same temperature for 30 min and further at room temperature overnight. The reaction mixture was diluted with ethyl acetate and water. The organic layer was washed with water and saturated brine, dried over anhydrous magnesium sulfate and concentrated. To a solution of the obtained residue and diphenylphosphoryl azide (0.66 mL) in THF (5 mL) was added 1,8-diazabicyclo[5.4.0]undec-7-ene (0.46 mL), and the mixture was stirred under an argon atmosphere at 60° C. for 4 hr. The reaction mixture was diluted with ethyl acetate and water. The organic layer was washed with water and saturated brine, dried over anhydrous magnesium sulfate and concentrated. To a mixed solution of the obtained residue in THF-water (4:1, 5 mL) was added triphenylphosphine (0.80 g), and the mixture was stirred under an argon atmosphere at 60° C. for 2 hr. The reaction mixture was diluted with ethyl acetate and water. The organic layer was washed with water and saturated brine, dried over anhydrous magnesium sulfate and concentrated. To a solution of the obtained residue and potassium carbonate (0.64 g) in ethanol (10 mL) was added ethyl 2-(bromomethyl)-6-(2-cyano-6-fluorophenoxy)benzoate (0.58 g) obtained in Reference Example 49, and the mixture was stirred at room temperature for 2 days. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate), and solidified with ethanol to give the title compound (0.11 g).

MS: [M+H]$^+$ 429.2

$^1$H NMR (300 MHz, CDCl$_3$) δ 3.91 (3H, s), 4.43 (2H, s), 4.75 (2H, s), 6.44 (1H, s), 6.76 (1H, d, J=8.3 Hz), 7.19 (1H, d, J=7.5 Hz), 7.23-7.31 (1H, m), 7.37-7.52 (5H, m), 7.56 (1H, s).

Example 70

3-fluoro-2-((2-(4-(4-methyl-1H-pyrazol-1-yl)benzyl)-3-oxo-2,3-dihydro-1H-isoindol-4-yl)oxy)benzonitrile

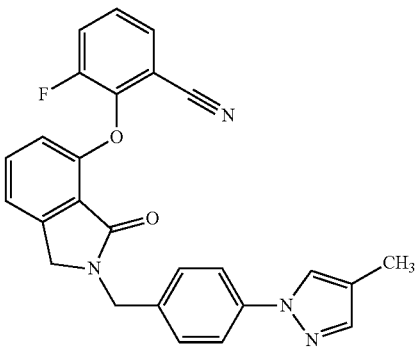 [SMILES: Cc1cnn(-c2ccc(CN3Cc4cccc(Oc5c(F)cccc5C#N)c4C3=O)cc2)c1]

To a solution of 4-(4-methyl-1H-pyrazol-1-yl)benzonitrile (0.29 g) obtained in Reference Example 51 in THF (6 mL) was added a solution of 1M lithium aluminum hydride in THF (2.38 mL), and the mixture was stirred under an argon atmosphere at 0° C. for 3 hr. The reaction mixture was diluted with ethyl acetate and 10% aqueous potassium sodium (+)-tartrate solution. The organic layer was washed with water and saturated brine, dried over anhydrous magnesium sulfate and concentrated. To a solution of the residue and potassium carbonate (0.22 g) in ethanol (4 mL) was added ethyl 2-(bromomethyl)-6-(2-cyano-6-fluorophenoxy)benzoate (0.20 g) obtained in Reference Example 49, and the mixture was stirred at room temperature overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate), and solidified with ethanol to give the title compound (0.042 g).

MS: [M+H]$^+$ 439.2

$^1$H NMR (300 MHz, CDCl$_3$) δ 2.16 (3H, s), 4.29 (2H, s), 4.78 (2H, s), 6.77 (1H, d, J=8.3 Hz), 7.16 (1H, dd, J=7.5, 0.8 Hz), 7.23-7.32 (1H, m), 7.36-7.54 (6H, m), 7.60-7.66 (2H, m), 7.69 (1H, s).

Example 71

2-((2-(4-bromobenzyl)-3-oxo-2,3-dihydro-1H-isoindol-4-yl)oxy)-3-fluorobenzonitrile

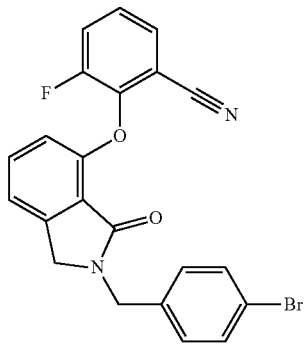 [SMILES: N#Cc1cccc(F)c1Oc1cccc2c1C(=O)N(Cc1ccc(Br)cc1)C2]

To a solution of (4-bromophenyl)methanamine hydrochloride (0.32 g) and potassium carbonate (0.55 g) in ethanol (10 mL) was added ethyl 2-(bromomethyl)-6-(2-cyano-6-fluorophenoxy)benzoate (0.50 g) obtained in Reference Example 49, and the mixture was stirred at room temperature overnight. The reaction mixture was diluted with ethyl acetate and water, and the organic layer was washed with water and saturated brine, dried over anhydrous magnesium sulfate and concentrated to give the title compound (0.44 g).

$^1$H NMR (300 MHz, CDCl$_3$) δ 4.27 (2H, s), 4.71 (2H, s), 6.76 (1H, d, J=7.9 Hz), 7.13-7.24 (3H, m), 7.24-7.33 (1H, m), 7.37-7.53 (5H, m).

Example 72

3-fluoro-2-((2-(4-(2-methylpyridin-4-yl)benzyl)-3-oxo-2,3-dihydro-1H-isoindol-4-yl)oxy)benzonitrile

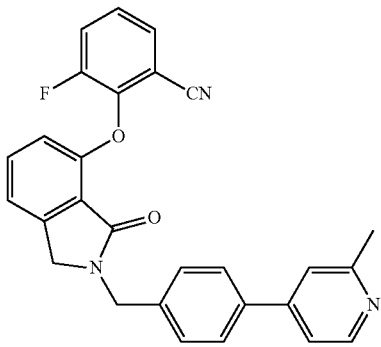 [SMILES: Cc1cc(-c2ccc(CN3Cc4cccc(Oc5c(F)cccc5C#N)c4C3=O)cc2)ccn1]

To a solution of 2-((2-(4-bromobenzyl)-3-oxo-2,3-dihydro-1H-isoindol-4-yl)oxy)-3-fluorobenzonitrile (0.15 g) obtained in Example 71, 2-methyl-4-(4,4,5,5-tetramethyl-1,3,2-dioxaborolan-2-yl)pyridine (0.083 g) and 2M aqueous sodium carbonate solution (0.69 mL) in DME (3 mL) was added (1,1-bis(diphenylphosphino)ferrocene)dichloropalladium(II) (0.025 g), and the mixture was stirred under an argon atmosphere at 80° C. overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate), and solidified with ethyl acetate to give the title compound (0.071 g).

MS: [M+H]$^+$ 450.2

$^1$H NMR (300 MHz, CDCl$_3$) 52.63 (3H, s), 4.32 (2H, s), 4.82 (2H, s), 6.77 (1H, d, J=8.3 Hz), 7.16 (1H, d, J=7.5 Hz), 7.24-7.33 (2H, m), 7.36 (1H, s), 7.39-7.48 (4H, m), 7.51 (1H, dt, J=7.6, 1.5 Hz), 7.61 (2H, d, J=8.3 Hz), 8.54 (1H, d, J=5.3 Hz).

Example 73

3,5-difluoro-2-((2-((4-(1-methyl-1H-pyrazol-4-yl)benzyl)-3-oxo-2,3-dihydro-1H-isoindol-4-yl)oxy)benzonitrile

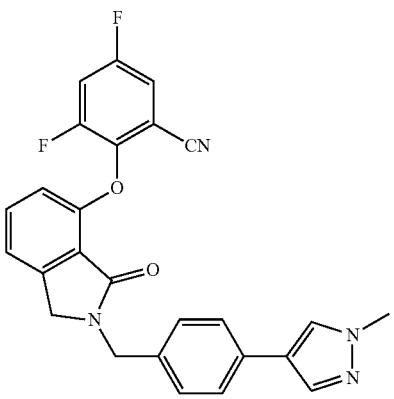 [SMILES: Cn1cc(-c2ccc(CN3Cc4cccc(Oc5c(F)cc(F)cc5C#N)c4C3=O)cc2)cn1]

To a solution of (4-(1-methyl-1H-pyrazol-4-yl)phenyl)methanamine dihydrochloride (0.14 g) obtained in Reference Example 4 and potassium carbonate (0.35 g) in ethanol (4 mL) was added ethyl 2-(bromomethyl)-6-(2-cyano-4,6-difluorophenoxy)benzoate (0.20 g) obtained in Reference Example 53, and the mixture was stirred at room temperature overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate), and solidified with ethanol to give the title compound (0.081 g).

MS: [M+H]$^+$ 457.2

$^1$H NMR (300 MHz, CDCl$_3$) 53.95 (3H, s), 4.29 (2H, s), 4.75 (2H, s), 6.78 (1H, d, J=8.3 Hz), 7.13-7.28 (3H, m), 7.31 (2H, d, J=7.9 Hz), 7.40-7.47 (3H, m), 7.60 (1H, s), 7.75 (1H, d, J=0.8 Hz).

Example 74

4-bromo-2-(4-(1-methyl-1H-pyrazol-4-yl)benzyl)-7-((tetrahydrofuran-2-yl)methoxy)isoindolin-1-one

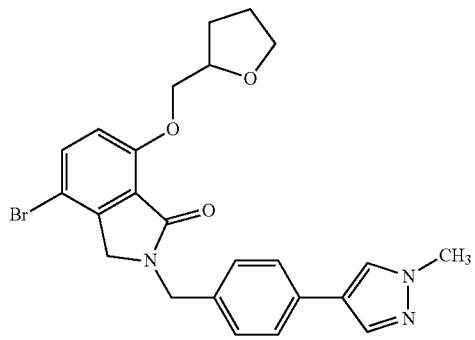 [SMILES: Cn1cc(-c2ccc(CN3Cc4c(Br)ccc(OCC5CCCO5)c4C3=O)cc2)cn1]

To a solution of 4-bromo-7-hydroxy-2-(4-(1-methyl-1H-pyrazol-4-yl)benzyl)isoindolin-1-one (0.44 g) obtained in Reference Example 55, (tetrahydrofuran-2-yl)methanol (0.56 g) and tributylphosphine (1.12 g) in THF (10 mL) was added diisopropyl azodicarboxylate (1.9M toluene solution) (2.9 mL), and the mixture was stirred under a nitrogen atmosphere at room temperature overnight. The reaction mixture was concentrated, the residue was diluted with ethyl acetate and water, and the organic layer was separated. The organic layer was washed with water, saturated aqueous sodium hydrogen carbonate solution, and saturated brine, dried over anhydrous sodium sulfate, and concentrated. The residue was purified by NH silica gel chromatography (hexane-ethyl acetate) to give the title compound (0.095 g).

$^1$H NMR (300 MHz, DMSO-d$_6$) δ1.76-1.90 (2H, m), 1.92-2.09 (2H, m), 3.62-3.73 (1H, m), 3.80-3.91 (4H, m), 4.05-4.25 (5H, m), 4.65 (2H, s), 7.06 (1H, d, J=8.7 Hz), 7.27 (2H, d, J=8.1 Hz), 7.53 (2H, d, J=8.1 Hz), 7.67 (1H, d, J=8.9 Hz), 7.82 (1H, s), 8.10 (1H, s).

Example 75

2-(4-(1-methyl-1H-pyrazol-4-yl)benzyl)-7-((tetrahydrofuran-2-yl)methoxy)-4-vinylisoindolin-1-one

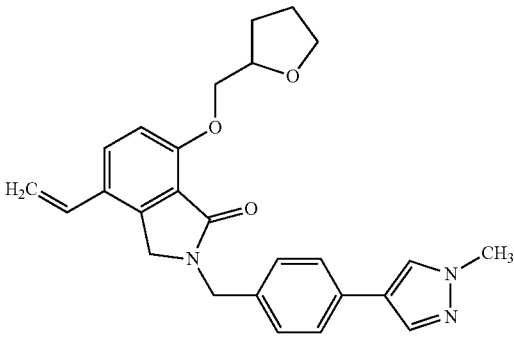 [SMILES: C=Cc1ccc(OCC2CCCO2)c2c1CN(Cc1ccc(-c3cnn(C)c3)cc1)C2=O]

To a solution of 4-bromo-2-(4-(1-methyl-1H-pyrazol-4-yl)benzyl)-7-((tetrahydrofuran-2-yl)methoxy)isoindolin-1-one (0.09 g) obtained in Example 74, potassium trifluoro(vinyl)borate (0.038 g), and triethylamine (0.052 mL) in ethanol (5 mL) was added (1,1'-bis(diphenylphosphino)ferrocene)dichloropalladium(II) (0.014 g), and the mixture was stirred under an argon atmosphere at 100° C. overnight. The reaction solution was diluted with ethyl acetate, and the insoluble material was filtered off. The filtrate was washed with saturated aqueous sodium hydrogen carbonate solution and saturated brine, dried over anhydrous sodium sulfate, and concentrated. The residue was purified by NH silica gel chromatography (hexane-ethyl acetate) to give the title compound (0.044 g).

MS: [M+H]$^+$ 430.2

$^1$H NMR (300 MHz, DMSO-d$_6$) δ1.75-2.09 (4H, m), 3.62-3.73 (1H, m), 3.79-3.90 (4H, m), 4.10 (2H, dd, J=4.3, 2.3 Hz), 4.20 (1H, d, J=4.2 Hz), 4.37 (2H, s), 4.65 (2H, s), 5.27 (1H, d, J=11.3 Hz), 5.66 (1H, d, J=17.8 Hz), 6.68 (1H, dd, J=17.8, 11.1 Hz), 7.07 (1H, d, J=8.7 Hz), 7.25 (2H, d, J=8.1 Hz), 7.52 (2H, d, J=8.3 Hz), 7.67 (1H, d, J=8.7 Hz), 7.81 (1H, s), 8.09 (1H, s).

Example 76

4-((trans-2-hydroxycyclopentyl)oxy)-2-(4-(2-methylpyridin-4-yl)benzyl)-1,2-dihydro-3H-pyrrolo[3,4-c]pyridin-3-one

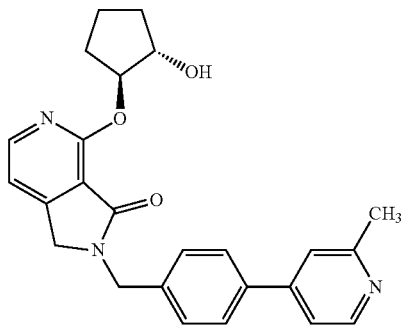 [SMILES: Cc1cc(-c2ccc(CN3Cc4ccnc(O[C@H]5CCC[C@@H]5O)c4C3=O)cc2)ccn1]

A mixture of methyl 2-((trans-2-hydroxycyclopentyl)oxy)-4-vinylnicotinate (0.16 g) obtained in Reference Example 61, sodium periodate (0.65 g) and osmium oxide (immobilized catalyst I) (0.077 g) and acetonitrile (3 mL)-acetone (3 mL)-water (3 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), (4-(2-methylpyridin-4-yl)phenyl)methanamine (0.12 g) and anhydrous magnesium sulfate (0.15 g) obtained in Reference Example 63 were added, and the mixture was stirred under an argon atmosphere at room temperature for 30 min. The insoluble material was filtered off, and the filtrate was concentrated. To a solution of the residue in acetic acid (3 mL) was added sodium triacetoxyhydroborate (0.19 g), and the mixture was stirred under an argon atmosphere at room temperature for 1 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) and DIOL silica gel chromatography (hexane-ethyl acetate), and solidified with diisopropyl ether to give the title compound (0.078 g).

MS: [M+H]$^+$ 416.5

$^1$H NMR (300 MHz, DMSO-$d_6$) δ1.51-1.78 (4H, m), 1.87-1.98 (1H, m), 2.08-2.21 (1H, m), 2.52 (3H, brs), 4.09-4.19 (1H, m), 4.39 (2H, s), 4.70 (2H, s), 4.91 (1H, d, J=4.0 Hz), 5.20-5.30 (1H, m), 7.17 (1H, d, J=5.1 Hz), 7.41 (2H, d, J=8.1 Hz), 7.47 (1H, dd, J=5.2, 1.2 Hz), 7.55 (1H, s), 7.76 (2H, d, J=8.1 Hz), 8.29 (1H, d, J=5.1 Hz), 8.48 (1H, d, J=5.3 Hz).

Example 77

4-((trans-2-hydroxycyclopentyl)oxy)-2-(4-(1H-pyrazol-1-yl)benzyl)-1,2-dihydro-3H-pyrrolo[3,4-c]pyridin-3-one

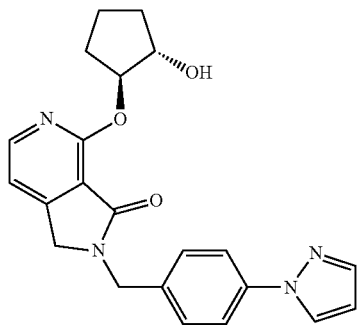 [SMILES: O=C1c2c(ccnc2O[C@H]2CCC[C@@H]2O)CN1Cc1ccc(-n2cccn2)cc1]

A mixture of methyl 2-((trans-2-hydroxycyclopentyl)oxy)-4-vinylnicotinate (0.12 g) obtained in Reference Example 61, sodium periodate (0.50 g) and osmium oxide (immobilized catalyst I) (0.06 g) and acetonitrile (3 mL)-acetone (3 mL)-water (3 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), (4-(1H-pyrazol-1-yl)phenyl)methanamine (0.081 g) and anhydrous magnesium sulfate (0.11 g) were added, and the mixture was stirred under an argon atmosphere at room temperature for 30 min. The insoluble material was filtered off, and the filtrate was concentrated. To a solution of the residue in acetic acid (3 mL) was added sodium triacetoxyhydroborate (0.15 g), and the mixture was stirred under an argon atmosphere at room temperature for 1 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with THF-ethyl acetate-hexane to give the title compound (0.059 g).

MS: [M+H]$^+$ 391.2

$^1$H NMR (300 MHz, DMSO-$d_6$) δ1.51-1.78 (4H, m), 1.86-2.00 (1H, m), 2.07-2.21 (1H, m), 4.07-4.18 (1H, m), 4.38 (2H, s), 4.68 (2H, s), 4.92 (1H, d, J=3.8 Hz), 5.18-5.30 (1H, m), 6.51-6.55 (1H, m), 7.17 (1H, d, J=5.3 Hz), 7.39 (2H, d, J=8.3 Hz), 7.73 (1H, d, J=1.9 Hz), 7.81 (2H, d, J=8.3 Hz), 8.28 (1H, d, J=4.9 Hz), 8.47 (1H, d, J=2.6 Hz).

Example 78

2-(4-(1,3-dimethyl-1H-pyrazol-4-yl)benzyl)-4-((tetrahydrofuran-2-yl)methoxy)-1,2-dihydro-3H-pyrrolo[3,4-c]pyridin-3-one

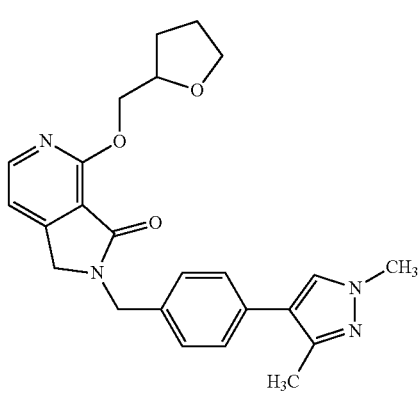 [SMILES: Cc1nn(C)cc1-c1ccc(CN2Cc3ccnc(OCC4CCCO4)c3C2=O)cc1]

A mixture of methyl 2-((tetrahydrofuran-2-yl)methoxy)-4-vinylnicotinate (0.30 g) obtained in Reference Example 42, sodium periodate (1.21 g) and osmium oxide (immobilized catalyst I) (0.14 g) and acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (9 mL), (4-(1,3-dimethyl-1H-pyrazol-4-yl)phenyl)methanamine (0.23 g) and anhydrous magnesium sulfate (0.27 g) were added, and the mixture was stirred under an argon atmosphere at room temperature for 1 hr. The insoluble material was filtered off, and the filtrate was concentrated. To a solution of the residue in acetic acid (5 mL) was added sodium triacetoxyhydroborate (0.36 g), and the mixture was stirred under an argon atmosphere at room temperature for 1 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diethyl ether to give the title compound (0.13 g).

MS: [M+H]$^+$ 419.2

$^1$H NMR (300 MHz, DMSO-d$_6$) δ1.70-1.91 (2H, m), 1.91-2.09 (2H, m), 2.27 (3H, s), 3.62-3.72 (1H, m), 3.77 (3H, s), 3.79-3.89 (1H, m), 4.17-4.29 (1H, m), 4.30-4.44 (4H, m), 4.65 (2H, s), 7.18 (1H, d, J=5.3 Hz), 7.24-7.32 (2H, m), 7.35-7.44 (2H, m), 7.85 (1H, s), 8.26 (1H, d, J=5.1 Hz).

Example 79

2-(4-(1-methyl-1H-pyrazol-3-yl)benzyl)-4-((tetrahydrofuran-2-yl)methoxy)-1,2-dihydro-3H-pyrrolo[3,4-c]pyridin-3-one

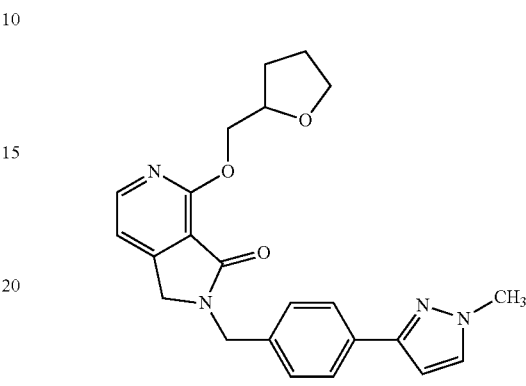

A mixture of methyl 2-((tetrahydrofuran-2-yl)methoxy)-4-vinylnicotinate (405 mg) obtained in Reference Example 42, sodium periodate (1.65 g) and osmium oxide (immobilized catalyst I) (0.20 g) and acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (9 mL), (4-(1-methyl-1H-pyrazol-3-yl)phenyl)methanamine (0.29 g) and anhydrous magnesium sulfate (0.37 g) were added, and the mixture was stirred under an argon atmosphere at room temperature for 1 hr. The insoluble material was filtered off, and the filtrate was concentrated. To a solution of the residue in acetic acid (5 mL) was added sodium triacetoxyhydroborate (0.49 g), and the mixture was stirred under an argon atmosphere at room temperature for 1 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether to give the title compound (0.27 g).

MS: [M+H]$^+$ 405.2

$^1$H NMR (300 MHz, DMSO-d$_6$) δ1.68-1.89 (2H, m), 1.93-2.07 (2H, m), 3.62-3.72 (1H, m), 3.78-3.89 (4H, m), 4.18-4.29 (1H, m), 4.32-4.45 (4H, m), 4.66 (2H, s), 6.65 (1H, d, J=2.3 Hz), 7.19 (1H, d, J=5.3 Hz), 7.28 (2H, d, J=8.3 Hz), 7.68-7.80 (3H, m), 8.27 (1H, d, J=5.1 Hz).

Example 80

2-(4-(2-methylpyridin-4-yl)benzyl)-4-((tetrahydrofuran-2-yl)methoxy)-1,2-dihydro-3H-pyrrolo[3,4-c]pyridin-3-one

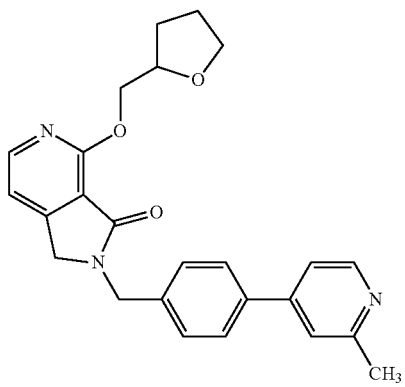 [SMILES: Cc1cc(-c2ccc(CN3Cc4ccnc(OCC5CCCO5)c4C3=O)cc2)ccn1]

A mixture of methyl 2-((tetrahydrofuran-2-yl)methoxy)-4-vinylnicotinate (0.27 g) obtained in Reference Example 42, sodium periodate (1.08 g) and osmium oxide (immobilized catalyst I) (0.13 g) and acetonitrile (6 mL)-acetone (6 mL)-water (6 mL) was stirred under a nitrogen atmosphere at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (5 mL), (4-(2-methylpyridin-4-yl)phenyl)methanamine (0.20 g) obtained in Reference Example 63 and anhydrous magnesium sulfate (0.23 g) were added, and the mixture was stirred under an argon atmosphere at room temperature for 2 hr. The insoluble material was filtered off, and the filtrate was concentrated. To a solution of the residue in acetic acid (5 mL) was added sodium triacetoxyhydroborate (0.32 g), and the mixture was stirred under an argon atmosphere at room temperature for 2 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether to give the title compound (0.17 g).

MS: [M+H]$^+$ 416.2

$^1$H NMR (300 MHz, DMSO-$d_6$) δ 1.69-1.89 (2H, m), 1.92-2.08 (2H, m), 2.52 (3H, s), 3.60-3.73 (1H, m), 3.76-3.90 (1H, m), 4.16-4.28 (1H, m), 4.34-4.45 (4H, m), 4.72 (2H, s), 7.19 (1H, d, J=5.3 Hz), 7.41 (2H, d, J=8.1 Hz), 7.48 (1H, dd, J=5.2, 1.4 Hz), 7.56 (1H, s), 7.77 (2H, d, J=8.3 Hz), 8.27 (1H, d, J=5.1 Hz), 8.48 (1H, d, J=5.3 Hz).

Example 81

7-(2-chloro-6-fluorophenoxy)-2-(4-(pyridazin-4-yl)benzyl)isoindolin-1-one

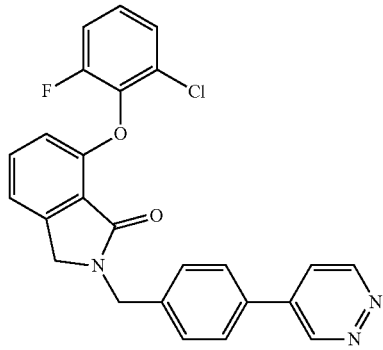 [SMILES: O=C1c2c(cccc2Oc2c(F)cccc2Cl)CN1Cc1ccc(-c2ccnnc2)cc1]

A solution of ethyl 2-(bromomethyl)-6-(2-chloro-6-fluorophenoxy)benzoate (0.50 g) obtained in Reference Example 66, (4-(4,4,5,5-tetramethyl-1,3,2-dioxaborolan-2-yl)phenyl)methanamine (0.33 g) and potassium carbonate (0.54 g) in ethanol (10 mL) was stirred at room temperature overnight. The reaction mixture was diluted with water, and the mixture was extracted with ethyl acetate. The organic layer was washed with water and saturated brine, dried over anhydrous magnesium sulfate and concentrated. A solution of the obtained residue (0.20 g), 4-bromopyridazine hydrobromide (0.11 g) and 2M aqueous sodium carbonate solution (0.81 mL) in DME (4 mL) was added (1,1-bis(diphenylphosphino)ferrocene)dichloropalladium(II) (0.030 g), and the mixture was stirred under an argon atmosphere at 80° C. overnight. The reaction mixture was diluted with ethyl acetate, washed with saturated brine, dried over anhydrous sodium sulfate, and concentrated. The residue was recrystallized from ethanol to give the title compound (0.037 g).

MS: [M+H]$^+$ 446.1

$^1$H NMR (300 MHz, CDCl$_3$) δ 4.33 (2H, s), 4.88 (2H, s), 6.54 (1H, d, J=8.3 Hz), 7.07 (1H, d, J=6.8 Hz), 7.10-7.23 (2H, m), 7.27-7.32 (1H, m), 7.33-7.39 (1H, m), 7.52-7.57 (2H, m), 7.61-7.70 (3H, m), 9.23 (1H, dd, J=5.3, 1.1 Hz), 9.46 (1H, dd, J=2.3, 1.1 Hz).

Example 82

3-fluoro-2-((2-(4-iodobenzyl)-3-oxoisoindolin-4-yl)oxy)benzonitrile

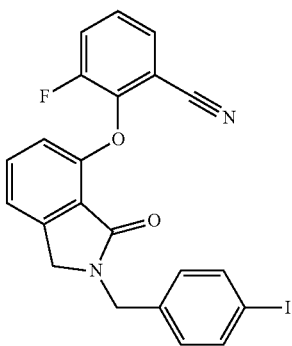 [SMILES: N#Cc1cccc(F)c1Oc1cccc2c1C(=O)N(Cc1ccc(I)cc1)C2]

To a solution of (4-iodophenyl)methanamine (0.31 g) and potassium carbonate (0.55 g) in ethanol (10 mL) was added ethyl 2-(bromomethyl)-6-(2-cyano-6-fluorophenoxy)benzoate (0.50 g) obtained in Reference Example 49, and the mixture was stirred at room temperature overnight. The reaction mixture was diluted with ethyl acetate and water. The organic layer was washed with water and saturated brine, dried over anhydrous magnesium sulfate and concentrated. The residue was collected by filtration, and washed with a mixed solution of hexane-ethyl acetate (1:4, 10 mL) to give the title compound (0.19 g).

MS: [M+H]$^+$ 485.0

$^1$H NMR (300 MHz, CDCl$_3$) δ 4.26 (2H, s), 4.69 (2H, s), 6.75 (1H, d, J=7.9 Hz), 7.07 (2H, d, J=8.3 Hz), 7.14 (1H, d, J=7.5 Hz), 7.24-7.31 (1H, m), 7.37-7.46 (2H, m), 7.49 (1H, dt, J=7.8, 1.4 Hz), 7.65-7.70 (2H, m).

Example 83

3-fluoro-2-((2-(4-(4-methyl-1H-1,2,3-triazol-1-yl)benzyl)-3-oxoisoindolin-4-yl)oxy)benzonitrile

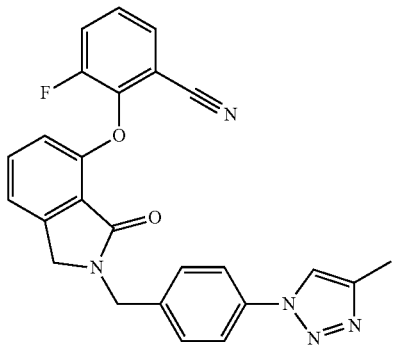 [SMILES: Cc1cn(-c2ccc(CN3Cc4cccc(Oc5c(F)cccc5C#N)c4C3=O)cc2)nn1]

To a solution of 3-fluoro-2-((2-(4-iodobenzyl)-3-oxoisoindolin-4-yl)oxy)benzonitrile (0.19 g) obtained in Example 82, 2-butynoic acid (0.052 g), copper(II) sulfate pentahydrate (0.016 g), L-proline (0.014 g), sodium L-ascorbate salt (0.025 g) and potassium carbonate (0.10 g) in DMSO (2.3 mL)-water (0.25 mL) was added sodium azide (0.06 g), and the mixture was stirred at 65° C. overnight. The reaction mixture was diluted with ethyl acetate and saturated aqueous ammonium chloride solution. The organic layer was washed with water and saturated brine, dried over anhydrous magnesium sulfate and concentrated. The residue was purified by silica gel column chromatography (hexane-ethyl acetate), and solidified with ethanol to give the title compound (0.016 g).

MS: [M+H]$^+$ 440.2

$^1$H NMR (300 MHz, CDCl$_3$) δ 2.44 (3H, s), 4.33 (2H, s), 4.83 (2H, s), 6.77 (1H, d, J=8.3 Hz), 7.17 (1H, d, J=7.5 Hz), 7.24-7.34 (1H, m), 7.38-7.54 (5H, m), 7.70 (3H, d, J=8.3 Hz).

Example 84

3-fluoro-2-((2-(4-(1-methyl-1H-1,2,3-triazol-4-yl)benzyl)-3-oxoisoindolin-4-yl)oxy)benzonitrile

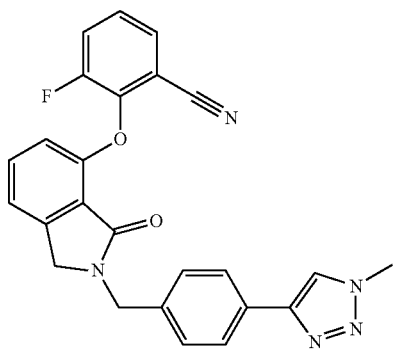 [SMILES: Cn1cc(-c2ccc(CN3Cc4cccc(Oc5c(F)cccc5C#N)c4C3=O)cc2)nn1]

Under an argon atmosphere, to a solution of (4-(1-methyl-1H-1,2,3-triazol-4-yl)phenyl)methanol (0.45 g) obtained in Reference Example 30 and diphenylphosphoryl azide (0.57 mL) in THF (5 mL) was added DBU (0.40 mL), and the mixture was stirred under an argon atmosphere at 60° C. overnight. The reaction mixture was diluted with ethyl acetate and water. The organic layer was washed with water and saturated brine, dried over anhydrous magnesium sulfate and concentrated. Under an argon atmosphere, to a mixed solution of the residue in THF (5 mL)-water (1 mL) was added triphenylphosphine (0.63 g), and the mixture was stirred at 60° C. for 2 hr. The reaction mixture was diluted with ethyl acetate and water. The organic layer was washed with water and saturated brine, dried over anhydrous magnesium sulfate and concentrated. The residue was crudely purified by silica gel column chromatography (ethyl acetate-methanol). To a solution of this crudely purified product and potassium carbonate (0.33 g) in ethanol (5 mL) was added ethyl 2-(bromomethyl)-6-(2-cyano-6-fluorophenoxy)benzoate (0.27 g) obtained in Reference Example 49, and the mixture was stirred at room temperature overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate), and solidified with ethanol to give the title compound (0.012 g).

MS: [M+H]$^+$ 440.2

$^1$H NMR (300 MHz, CDCl$_3$) δ 4.15 (3H, s), 4.29 (2H, s), 4.78 (2H, s), 6.76 (1H, d, J=7.9 Hz), 7.15 (1H, d, J=6.8 Hz), 7.24-7.33 (2H, m), 7.35-7.53 (4H, m), 7.73 (1H, s), 7.80 (2H, d, J=8.3 Hz).

Example 85

7-(2-fluoro-6-nitrophenoxy)-2-(4-(1-methyl-1H-pyrazol-4-yl)benzyl)isoindolin-1-one

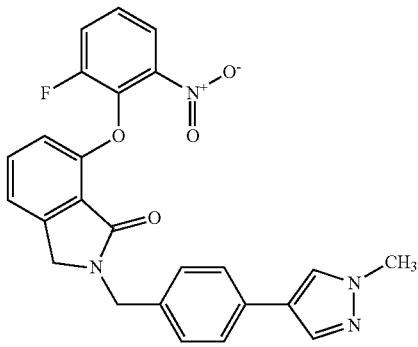 [SMILES: Cn1cc(-c2ccc(CN3Cc4cccc(Oc5c(F)cccc5[N+](=O)[O-])c4C3=O)cc2)cn1]

A solution of ethyl 2-(bromomethyl)-6-(2-fluoro-6-nitrophenoxy)benzoate (0.20 g) obtained in Reference Example 67, (4-(1-methyl-1H-pyrazol-4-yl)phenyl)methanamine dihydrochloride (0.14 g) obtained in Reference Example 4 and potassium carbonate (0.35 g) in ethanol (4 mL) was stirred at room temperature overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate), and solidified with ethanol to give the title compound (0.074 g).

MS: $[M+H]^+$ 459.2

$^1$H NMR (300 MHz, CDCl$_3$) δ 3.95 (3H, s), 4.29 (2H, s), 4.77 (2H, s), 6.70 (1H, d, J=8.3 Hz), 7.11 (1H, d, J=7.6 Hz), 7.31-7.52 (7H, m), 7.61 (1H, s), 7.75 (1H, d, J=0.6 Hz), 7.86 (1H, dt, J=8.3, 1.7 Hz).

Example 86

2-(2-fluoro-4-(1H-pyrazol-1-yl)benzyl)-4-((tetrahydrofuran-2-yl)methoxy)-1,2-dihydro-3H-pyrrolo[3,4-c]pyridin-3-one

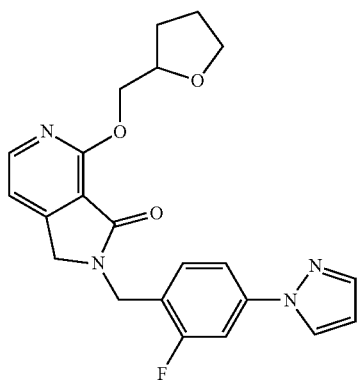 [SMILES: O=C1c2c(ccnc2OCC2CCCO2)CN1Cc1ccc(-n2cccn2)cc1F]

A mixture of methyl 2-((tetrahydrofuran-2-yl)methoxy)-4-vinylnicotinate (0.89 g) obtained in Reference Example 42, sodium periodate (3.62 g) and osmium oxide (immobilized catalyst I) (0.43 g), and acetonitrile (12 mL)-acetone (12 mL)-water (12 mL) was stirred under a nitrogen atmosphere at room temperature overnight. The insoluble material was filtered off, and the filtrate was diluted with ethyl acetate. The organic layer was separated, washed with saturated brine, dried over anhydrous sodium sulfate and concentrated to give a crude product of methyl 4-formyl-2-((tetrahydrofuran-2-yl)methoxy)nicotinate. Separately, to a solution of 2-fluoro-4-(1H-pyrazol-1-yl)benzonitrile (1.33 g) prepared by referring to a document (WO2003/050132) in THF (13 mL) was added lithium aluminum hydride (0.30 g) at 0° C., and the mixture was stirred at the same temperature for 30 min. To the reaction solution was added sodium sulfate decahydrate, and the insoluble material was filtered off. The filtrate was concentrated, and the residue was crudely purified by NH silica gel chromatography (hexane-ethyl acetate). The obtained crudely purified product (0.31 g) and the crude product of methyl 4-formyl-2-((tetrahydrofuran-2-yl)methoxy)nicotinate obtained earlier were dissolved in THF (8 mL), anhydrous magnesium sulfate (0.80 g) was added, and the mixture was stirred under a nitrogen atmosphere at room temperature for 1 hr. The insoluble material was filtered off, and the filtrate was concentrated. The residue was dissolved in acetic acid (8 mL), sodium triacetoxyhydroborate (0.72 g) was added, and the mixture was stirred at room temperature for 3 hr. The reaction mixture was diluted with water and ethyl acetate. The organic layer was separated, washed with saturated brine, dried over anhydrous sodium sulfate, and concentrated. The residue was crudely purified by NH silica gel chromatography (hexane-ethyl acetate), and solidified with ethyl acetate-hexane to give the title compound (0.064 g).

MS: $[M+H]^+$ 409.2

$^1$H NMR (300 MHz, DMSO-d$_6$) δ 1.69-1.89 (2H, m), 1.93-2.07 (2H, m), 3.61-3.71 (1H, m), 3.78-3.88 (1H, m), 4.17-4.27 (1H, m), 4.35-4.39 (2H, m), 4.41-4.47 (2H, m), 4.73 (2H, s), 6.51-6.60 (1H, m), 7.20 (1H, d, J=5.1 Hz), 7.44 (1H, t, J=8.4 Hz), 7.66-7.80 (3H, m), 8.27 (1H, d, J=5.1 Hz), 8.55 (1H, d, J=2.5 Hz).

Example 223

4-fluoro-7-((trans-2-hydroxycyclohexyl)oxy)-2-(4-(1H-pyrazol-1-yl)benzyl)isoindolin-1-one

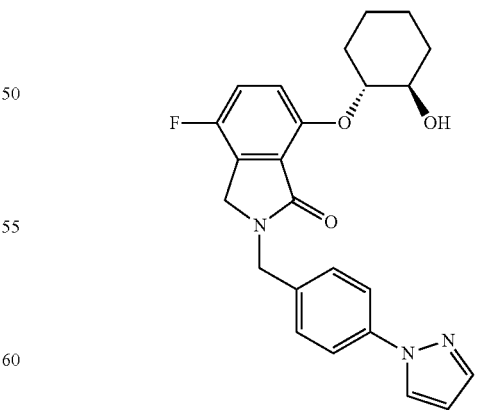

To a solution of 2-(4-(1H-pyrazol-1-yl)benzyl)-4-fluoro-7-hydroxyisoindolin-1-one (0.20 g) obtained in Reference Example 72 in ethanol (3 mL) was added 7-oxabicyclo[4.1.0]heptane (0.067 g), pyridine (0.073 g) was added, and the mixture was heated under reflux for 48 hr. The reaction mixture was diluted with water and ethyl acetate. The organic layer was separated, washed with saturated brine, dried over anhydrous sodium sulfate, and concentrated. The residue was purified by preparative TLC (petroleum ether-ethyl acetate), and washed with methyl tert-butyl ether to give the title compound (0.16 g).

MS: [M+H]$^+$ 422.1

$^1$H NMR (400 MHz, CDCl$_3$) δ 1.15-1.44 (3H, m), 1.50-1.88 (3H, m, overlap with water signal), 2.05-2.20 (1H, m), 2.21-2.35 (1H, m), 3.70-3.89 (2H, m), 4.28 (2H, s), 4.70 (1H, d, J=14.8 Hz), 4.86 (1H, d, J=14.8 Hz), 5.53 (1H, brs), 6.40-6.51 (1H, m), 7.03 (1H, dd, J=8.8, 3.2 Hz), 7.12 (1H, t, J=8.8 Hz), 7.40 (2H, d, J=8.4 Hz), 7.67 (2H, d, J=8.4 Hz), 7.70-7.78 (1H, m), 7.90 (1H, d, J=2.0 Hz).

Example 224

7-((trans-2-hydroxycyclopentyl)oxy)-2-(4-(2-methylpyridin-4-yl)benzyl)isoindolin-1-one

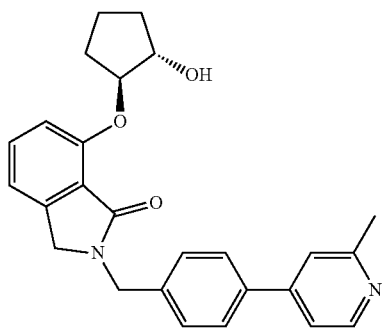 [SMILES: Cc1cc(-c2ccc(CN3Cc4cccc(O[C@H]5CCC[C@@H]5O)c4C3=O)cc2)ccn1]

To a solution of 2-(4-bromobenzyl)-7-hydroxyisoindolin-1-one (0.20 g) obtained in Reference Example 3 in ethanol (5 mL) were added 7-oxabicyclo[3.1.0]hexane (0.79 g) and pyridine (0.75 g), and the mixture was heated under reflux overnight. The reaction mixture was diluted with water and ethyl acetate. The organic layer was separated, washed with saturated brine, dried over anhydrous sodium sulfate, and concentrated. The residue was crudely purified by NH silica gel chromatography (hexane-ethyl acetate). To a solution of the obtained crudely purified product in DME (4 mL) was added (2-methylpyridin-4-yl)boronic acid (0.079 g), 2 mol/L aqueous sodium carbonate solution (0.39 mL) and (1,1-bis(diphenylphosphino)ferrocene)dichloropalladium (II) (0.028 g) were added, and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was crudely purified by NH silica gel chromatography (hexane-ethyl acetate), and solidified with diisopropyl ether to give the title compound (0.037 g).

MS: [M+H]$^+$ 415.2

$^1$H NMR (300 MHz, DMSO-d$_6$) δ 1.48-1.59 (1H, m), 1.62-1.80 (3H, m), 1.86-1.99 (1H, m), 2.03-2.17 (1H, m), 2.52 (3H, brs), 4.04-4.16 (1H, m), 4.31 (2H, s), 4.57-4.64 (1H, m), 4.70 (2H, s), 4.95 (1H, d, J=4.0 Hz), 7.07 (2H, dd, J=7.8, 3.9 Hz), 7.40 (2H, d, J=8.1 Hz), 7.44-7.52 (2H, m), 7.55 (1H, s), 7.76 (2H, d, J=8.3 Hz), 8.48 (1H, d, J=5.3 Hz).

Example 225

2-(4-(1,3-dimethyl-1H-pyrazol-4-yl)benzyl)-4-(2-(1H-pyrazol-1-yl)ethoxy)-1,2-dihydro-3H-pyrrolo[3,4-c]pyridin-3-one

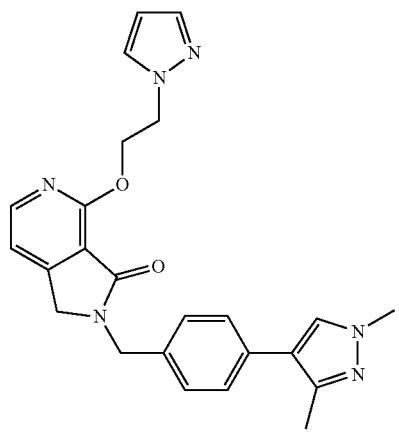 [SMILES: Cc1nn(C)cc1-c1ccc(CN2Cc3ccnc(OCCn4cccn4)c3C2=O)cc1]

A mixture of methyl 2-(2-(1H-pyrazol-1-yl)ethoxy)-4-vinylnicotinate (0.15 g) obtained in Reference Example 74, sodium periodate (0.59 g) and osmium oxide (immobilized catalyst I) (0.070 g), and acetonitrile (3 mL)-acetone (3 mL)-water (3 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), anhydrous magnesium sulfate (0.13 g) was added, and the mixture was stirred under an argon atmosphere at room temperature for 20 min. The insoluble material was filtered off, and the filtrate was concentrated. The residue was dissolved in acetic acid (3 mL), sodium triacetoxyhydroborate (0.18 g) was added, and the mixture was stirred under an argon atmosphere at room temperature for 3 hr. The reaction mixture was neutralized with saturated aqueous sodium hydrogen carbonate solution, and the mixture was diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.11 g).

MS: [M+H]$^+$ 429.2

$^1$H NMR (300 MHz, DMSO-d$_6$) δ 2.27 (3H, s), 3.77 (3H, s), 4.39 (2H, s), 4.52-4.60 (2H, m), 4.63-4.72 (4H, m), 6.21-6.29 (1H, m), 7.21 (1H, d, J=5.1 Hz), 7.24-7.31 (2H, m), 7.36-7.46 (3H, m), 7.85 (1H, s), 7.97 (1H, d, J=2.3 Hz), 8.28 (1H, d, J=5.3 Hz).

Example 226

2-(4-(1,3-dimethyl-1H-pyrazol-4-yl)benzyl)-7-((trans-2-hydroxycyclopentyl)oxy)isoindolin-1-one

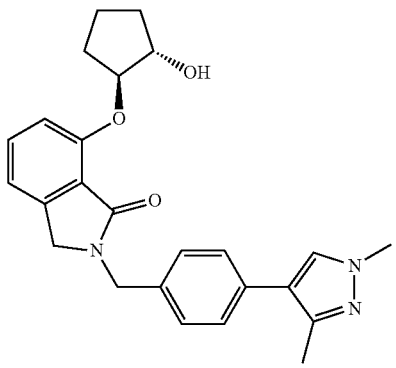 [SMILES: Cc1nn(C)cc1-c1ccc(CN2Cc3cccc(O[C@H]4CCC[C@@H]4O)c3C2=O)cc1]

To a solution of 2-(4-bromobenzyl)-7-hydroxyisoindolin-1-one (0.20 g) obtained in Reference Example 3 in ethanol (5 mL) were added 6-oxabicyclo[3.1.0]hexane (0.79 g) and pyridine (0.75 g), and the mixture was heated under reflux overnight. The reaction mixture was diluted with water and ethyl acetate. The organic layer was separated, washed with saturated brine, dried over anhydrous sodium sulfate, and concentrated. The residue was crudely purified by NH silica gel chromatography (hexane-ethyl acetate). To a solution of the obtained crudely purified product in DME (6 mL) were added 1,3-dimethyl-4-(4,4,5,5-tetramethyl-1,3,2-dioxaborolan-2-yl)-1H-pyrazole (0.18 g), sodium carbonate (0.12 g) and (1,1-bis(diphenylphosphino)ferrocene)dichloropalladium(II) (0.040 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.061 g).

MS: [M+H]$^+$ 418.2

$^1$H NMR (300 MHz, DMSO-d$_6$) δ 1.47-1.60 (1H, m), 1.63-1.79 (3H, m), 1.87-2.00 (1H, m), 2.04-2.15 (1H, m), 2.26 (3H, s), 3.77 (3H, s), 4.07-4.14 (1H, m), 4.29 (2H, s), 4.57-4.66 (3H, m), 4.95 (1H, d, J=4.0 Hz), 7.03-7.09 (2H, m), 7.23-7.29 (2H, m), 7.35-7.42 (2H, m), 7.44-7.52 (1H, m), 7.84 (1H, s).

Example 227

2-(4-(1,3-dimethyl-1H-pyrazol-4-yl)benzyl)-4-((trans-2-hydroxycyclopentyl)oxy)-1,2-dihydro-3H-pyrrolo[3,4-c]pyridin-3-one

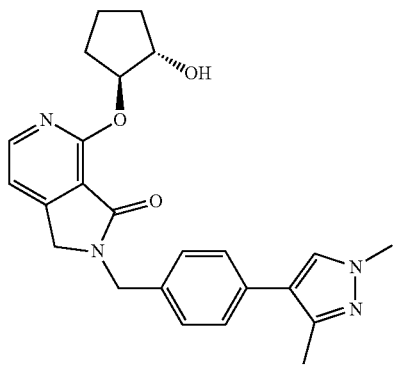 [SMILES: Cc1nn(C)cc1-c1ccc(CN2Cc3ccnc(O[C@H]4CCC[C@@H]4O)c3C2=O)cc1]

A mixture of methyl 2-((trans-2-hydroxycyclopentyl)oxy)-4-vinylnicotinate (0.19 g) obtained in Reference Example 61, sodium periodate (0.75 g) and osmium oxide (immobilized catalyst I) (0.090 g), and acetonitrile (3 mL)-acetone (3 mL)-water (3 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), (4-(1,3-dimethyl-1H-pyrazol-4-yl)phenyl)methanamine (0.14 g) and anhydrous magnesium sulfate (0.17 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.22 g), and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diethyl ether to give the title compound (0.095 g).

MS: [M+H]$^+$ 419.2

$^1$H NMR (300 MHz, DMSO-d$_6$) δ 1.48-1.79 (4H, m), 1.86-2.00 (1H, m), 2.07-2.21 (1H, m), 2.26 (3H, s), 3.77 (3H, s), 4.08-4.19 (1H, m), 4.37 (2H, s), 4.63 (2H, s), 4.91 (1H, d, J=4.0 Hz), 5.20-5.29 (1H, m), 7.16 (1H, d, J=5.1 Hz), 7.23-7.31 (2H, m), 7.34-7.42 (2H, m), 7.84 (1H, s), 8.28 (1H, d, J=5.1 Hz).

Example 228

6-fluoro-7-((trans-2-hydroxycyclohexyl)oxy)-2-(4-(1H-pyrazol-1-yl)benzyl)isoindolin-1-one

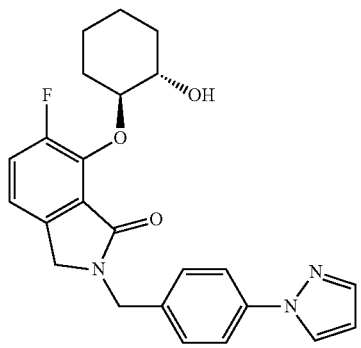 [SMILES: O=C1c2c(ccc(F)c2O[C@H]2CCCC[C@@H]2O)CN1Cc1ccc(-n2cccn2)cc1]

To a solution of 2-(4-(1H-pyrazol-1-yl)benzyl)-6-fluoro-7-hydroxyisoindolin-1-one (0.20 g) obtained in Reference Example 79 in ethanol (5 mL) were added 7-oxabicyclo[4.1.0]heptane (0.067 g) and pyridine (0.059 g), and the mixture was heated under reflux for 48 hr. The reaction mixture was diluted with water and dichloromethane, and the organic layer was separated, washed with water and saturated brine, dried over anhydrous sodium sulfate, and concentrated. The residue was crudely purified by preparative TLC (petroleum ether-ethyl acetate), and washed by solid-liquid washing with methyl tert-butyl ether to give the title compound (0.069 g).

MS: [M+H]$^+$ 422.3

¹H NMR (400 MHz, CDCl₃) δ 1.18-1.41 (3H, m), 1.62-1.84 (3H, m, overlap with water signal), 2.07-2.18 (1H, m), 2.31-2.48 (1H, m), 3.73-3.92 (2H, m), 4.21 (2H, s), 4.70 (1H, d, J=14.8 Hz), 4.86 (1H, d, J=14.8 Hz), 5.82 (1H, d, J=2.8 Hz), 6.46 (1H, t, J=2.0 Hz), 7.01 (1H, dd, J=8.4, 3.6 Hz), 7.20-7.32 (1H, m, overlap with CDCl₃ signal), 7.39 (2H, d, J=8.4 Hz), 7.66 (2H, d, J=8.4 Hz), 7.72 (1H, d, J=1.2 Hz), 7.90 (1H, d, J=2.4 Hz).

Example 229

2-(4-(1,3-dimethyl-1H-pyrazol-4-yl)-2-fluorobenzyl)-4-((tetrahydrofuran-2-yl)methoxy)-1,2-dihydro-3H-pyrrolo[3,4-c]pyridin-3-one

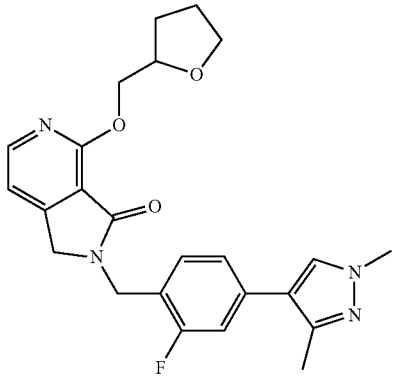 [SMILES: Cc1nn(C)cc1-c1ccc(CN2Cc3ccnc(OCC4CCCO4)c3C2=O)c(F)c1]

A mixture of methyl 2-((tetrahydrofuran-2-yl)methoxy)-4-vinylnicotinate (0.19 g) obtained in Reference Example 42, sodium periodate (0.76 g) and osmium oxide (immobilized catalyst I) (0.090 g), and acetonitrile (4 mL)-acetone (4 mL)-water (4 mL) was stirred under a nitrogen atmosphere at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), (4-(1,3-dimethyl-1H-pyrazol-4-yl)-2-fluorophenyl)methanamine (0.16 g) and anhydrous magnesium sulfate (0.17 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.23 g), and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diethyl ether to give the title compound (0.065 g).

MS: [M+H]⁺ 437.2

¹H NMR (300 MHz, DMSO-d₆) δ 1.69-1.88 (2H, m), 1.93-2.08 (2H, m), 2.29 (3H, s), 3.62-3.71 (1H, m), 3.77 (3H, s), 3.79-3.87 (1H, m), 4.17-4.26 (1H, m), 4.34-4.39 (2H, m), 4.42 (2H, s), 4.70 (2H, s), 7.18-7.34 (4H, m), 7.95 (1H, s), 8.27 (1H, d, J=5.3 Hz).

Example 230

2-(2-fluoro-4-(1-methyl-1H-pyrazol-3-yl)benzyl)-4-((tetrahydrofuran-2-yl)methoxy)-1,2-dihydro-3H-pyrrolo[3,4-c]pyridin-3-one

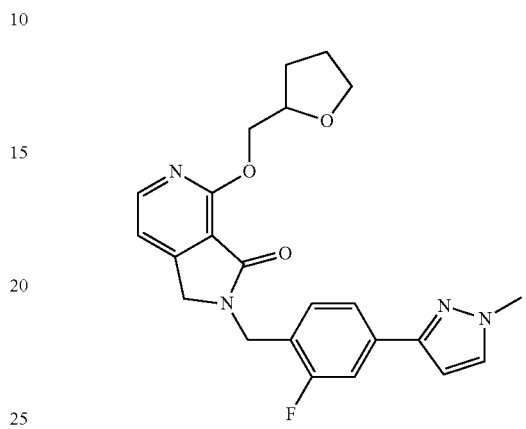

A mixture of methyl 2-((tetrahydrofuran-2-yl)methoxy)-4-vinylnicotinate (0.19 g) obtained in Reference Example 42, sodium periodate (0.76 g) and osmium oxide (immobilized catalyst I) (0.090 g), and acetonitrile (4 mL)-acetone (4 mL)-water (4 mL) was stirred under a nitrogen atmosphere at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), (2-fluoro-4-(1-methyl-1H-pyrazol-3-yl)phenyl)methanamine (0.15 g) obtained in Reference Example 81 and anhydrous magnesium sulfate (0.17 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.23 g), and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diethyl ether-hexane-ethyl acetate to give the title compound (0.11 g).

MS: [M+H]⁺ 423.1

¹H NMR (300 MHz, DMSO-d₆) δ 1.69-1.88 (2H, m), 1.91-2.06 (2H, m), 3.61-3.71 (1H, m), 3.79-3.85 (1H, m), 3.87 (3H, s), 4.19-4.27 (1H, m), 4.34-4.40 (2H, m), 4.42 (2H, s), 4.71 (2H, s), 6.74 (1H, d, J=2.3 Hz), 7.20 (1H, d, J=5.3 Hz), 7.27-7.36 (1H, m), 7.54-7.63 (2H, m), 7.74 (1H, d, J=2.3 Hz), 8.27 (1H, d, J=5.3 Hz).

Example 231

4-(2-chloro-6-fluorophenoxy)-2-(4-(1-methyl-1H-1,2,3-triazol-4-yl)benzyl)-1,2-dihydro-3H-pyrrolo[3,4-c]pyridin-3-one

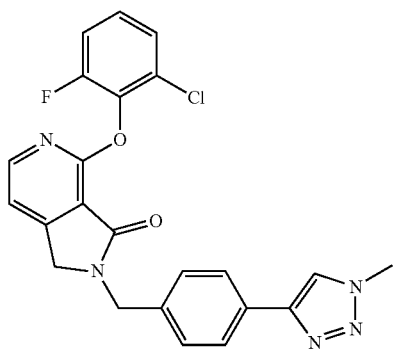 [SMILES: Cn1cc(-c2ccc(CN3Cc4ccnc(Oc5c(F)cccc5Cl)c4C3=O)cc2)nn1]

A mixture of methyl 2-(2-chloro-6-fluorophenoxy)-4-vinylnicotinate (0.066 g) obtained in Reference Example 83, sodium periodate (0.23 g) and osmium oxide (immobilized catalyst I) (0.027 g), and acetonitrile (3 mL)-acetone (3 mL)-water (3 mL) was stirred under a nitrogen atmosphere at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), (4-(1-methyl-1H-1,2,3-triazol-4-yl)phenyl)methanamine (0.040 g) obtained in Reference Example 162 and anhydrous magnesium sulfate (0.051 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.067 g), and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.018 g).

MS: [M+H]$^+$ 450.1

$^1$H NMR (300 MHz, DMSO-d$_6$) δ 4.09 (3H, s), 4.53 (2H, s), 4.75 (2H, s), 7.37-7.51 (6H, m), 7.84 (2H, d, J=8.3 Hz), 8.20 (1H, d, J=5.3 Hz), 8.51 (1H, s).

Example 234

2-(4-(4-fluoro-1H-pyrazol-1-yl)benzyl)-4-((tetrahydrofuran-2-yl)methoxy)-1,2-dihydro-3H-pyrrolo[3,4-c]pyridin-3-one

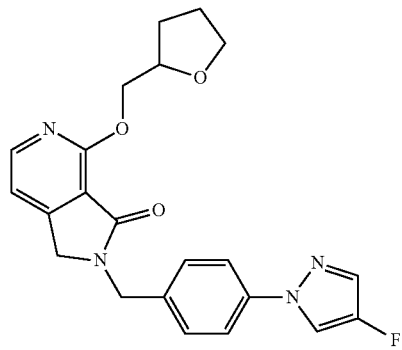 [SMILES: O=C1c2c(ccnc2OCC2CCCO2)CN1Cc1ccc(-n2cc(F)cn2)cc1]

A mixture of (tetrahydrofuran-2-yl)methyl 2-((tetrahydrofuran-2-yl)methoxy)-4-vinylnicotinate (0.20 g) obtained in Reference Example 94, sodium periodate (0.64 g) and osmium oxide (immobilized catalyst I) (0.076 g), and acetonitrile (4 mL)-acetone (4 mL)-water (4 mL) was stirred under a nitrogen atmosphere at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), (4-(4-fluoro-1H-pyrazol-1-yl)phenyl)methanamine hydrochloride (0.14 g) obtained in Reference Example 92, triethylamine (0.067 g) and sodium triacetoxyhydroborate (0.19 g) were added, and the mixture was stirred under a nitrogen atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.028 g).

MS: [M+H]$^+$ 409.2

$^1$H NMR (300 MHz, DMSO-d$_6$) δ 1.69-1.89 (2H, m), 1.92-2.10 (2H, m), 3.61-3.73 (1H, m), 3.78-3.89 (1H, m), 4.17-4.28 (1H, m), 4.32-4.44 (4H, m), 4.69 (2H, s), 7.19 (1H, d, J=5.1 Hz), 7.40 (2H, d, J=8.7 Hz), 7.76 (2H, d, J=8.7 Hz), 7.82 (1H, d, J=4.3 Hz), 8.27 (1H, d, J=5.3 Hz), 8.67 (1H, d, J=4.5 Hz).

Example 235

7-((trans-2-hydroxycyclopentyl)oxy)-2-(4-(1-methyl-1H-1,2,3-triazol-4-yl)benzyl)isoindolin-1-one

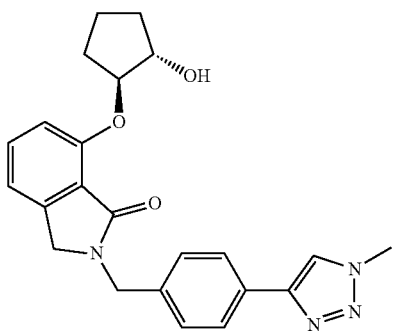 [SMILES: Cn1cc(-c2ccc(CN3Cc4cccc(O[C@H]5CCC[C@@H]5O)c4C3=O)cc2)nn1]

To a solution of 7-hydroxy-2-(4-(1-methyl-1H-1,2,3-triazol-4-yl)benzyl)isoindolin-1-one (0.090 g) obtained in Reference Example 96 in ethanol (4 mL) were added 6-oxabicyclo[3.1.0]hexane (0.35 g) and pyridine (0.33 g), and the mixture was stirred under a nitrogen atmosphere at 90° C. overnight. The reaction mixture was concentrated, and the residue was purified by NH silica gel chromatography (hexane-ethyl acetate) to give the title compound (0.063 g).

MS: [M+H]$^+$ 405.2

$^1$H NMR (300 MHz, DMSO-d$_6$) δ 1.47-1.60 (1H, m), 1.62-1.80 (3H, m), 1.86-2.01 (1H, m), 2.04-2.17 (1H, m), 4.03-4.14 (4H, m), 4.29 (2H, s), 4.57-4.63 (1H, m), 4.66 (2H, s), 4.95 (1H, brs), 7.06 (2H, dd, J=7.8, 4.0 Hz), 7.33 (2H, d, J=8.3 Hz), 7.43-7.54 (1H, m), 7.77-7.85 (2H, m), 8.49 (1H, s).

Example 236

2-(2-fluoro-4-(1-methyl-1H-pyrazol-3-yl)benzyl)-4-((trans-2-hydroxycyclopentyl)oxy)-1,2-dihydro-3H-pyrrolo[3,4-c]pyridin-3-one

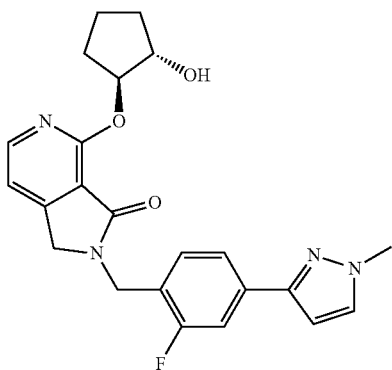 [SMILES: Cn1ccc(-c2ccc(CN3Cc4ccnc(O[C@H]5CCC[C@@H]5O)c4C3=O)c(F)c2)n1]

A mixture of methyl 2-((trans-2-hydroxycyclopentyl)oxy)-4-vinylnicotinate (0.18 g) obtained in Reference Example 61, sodium periodate (0.73 g) and osmium oxide (immobilized catalyst I) (0.087 g), and acetonitrile (5 mL)-acetone (5 mL)-water (5 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (3 mL), (2-fluoro-4-(1-methyl-1H-pyrazol-3-yl)phenyl)methanamine (0.14 g) obtained in Reference Example 81 and anhydrous magnesium sulfate (0.16 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.22 g), and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with hexane-ethyl acetate to give the title compound (0.11 g).

MS: [M+H]$^+$ 423.2

$^1$H NMR (300 MHz, DMSO-d$_6$) δ 1.48-1.78 (4H, m), 1.87-2.00 (1H, m), 2.06-2.20 (1H, m), 3.87 (3H, s), 4.07-4.18 (1H, m), 4.41 (2H, s), 4.69 (2H, s), 4.90 (1H, d, J=4.0 Hz), 5.19-5.29 (1H, m), 6.74 (1H, d, J=2.3 Hz), 7.17 (1H, d, J=5.1 Hz), 7.32 (1H, t, J=8.0 Hz), 7.52-7.64 (2H, m), 7.74 (1H, d, J=2.1 Hz), 8.28 (1H, d, J=5.1 Hz).

Example 237

4-((trans-2-hydroxycyclopentyl)oxy)-2-(4-(1-methyl-1H-pyrazol-3-yl)benzyl)-1,2-dihydro-3H-pyrrolo[3,4-c]pyridin-3-one

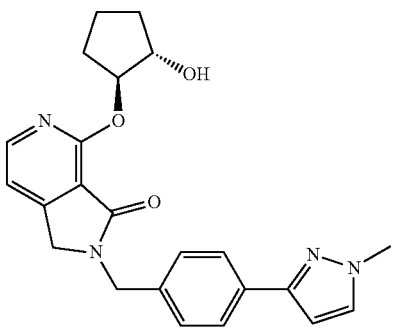 [SMILES: Cn1ccc(-c2ccc(CN3Cc4ccnc(O[C@H]5CCC[C@@H]5O)c4C3=O)cc2)n1]

A mixture of methyl 2-((trans-2-hydroxycyclopentyl)oxy)-4-vinylnicotinate (0.25 g) obtained in Reference Example 61, sodium periodate (1.0 g) and osmium oxide (immobilized catalyst I) (0.12 g), and acetonitrile (5 mL)-acetone (5 mL)-water (5 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in methanol (4 mL), (4-(1-methyl-1H-pyrazol-3-yl)phenyl)methanamine (0.17 g) and anhydrous magnesium sulfate (0.22 g) were added, and the mixture was stirred under an argon atmosphere at room temperature for 30 min. Sodium triacetoxyhydroborate (0.59 g) was added, and the mixture was stirred under an argon atmosphere at room temperature for 3 hr. The reaction mixture was diluted with ethyl acetate, and the organic layer was separated, washed with water and saturated brine, dried over anhydrous sodium sulfate, and concentrated. The residue was purified by NH silica gel chromatography (hexane-ethyl acetate), and solidified with hexane-ethyl acetate to give the title compound (0.052 g).

MS: [M+H]$^+$ 405.2

$^1$H NMR (300 MHz, DMSO-d$_6$) δ 1.48-1.81 (4H, m), 1.85-2.02 (1H, m), 2.05-2.23 (1H, m), 3.87 (3H, s), 4.13 (1H, brs), 4.36 (2H, s), 4.65 (2H, s), 4.91 (1H, d, J=3.6 Hz), 5.18-5.31 (1H, m), 6.65 (1H, d, J=2.3 Hz), 7.16 (1H, d, J=5.1 Hz), 7.28 (2H, d, J=8.3 Hz), 7.66-7.81 (3H, m), 8.28 (1H, d, J=5.3 Hz).

Example 238, Example 239

Optically active 1,5-anhydro-2-deoxy-3-O-(3-oxo-2-(4-(1H-pyrazol-1-yl)benzyl)-2,3-dihydro-1H-isoindol-4-yl)-threo-pentitol and Example 240, Example 241

Optically active 1,5-anhydro-2-deoxy-4-O-(3-oxo-2-(4-(1H-pyrazol-1-yl)benzyl)-2,3-dihydro-1H-isoindol-4-yl)-threo-pentitol

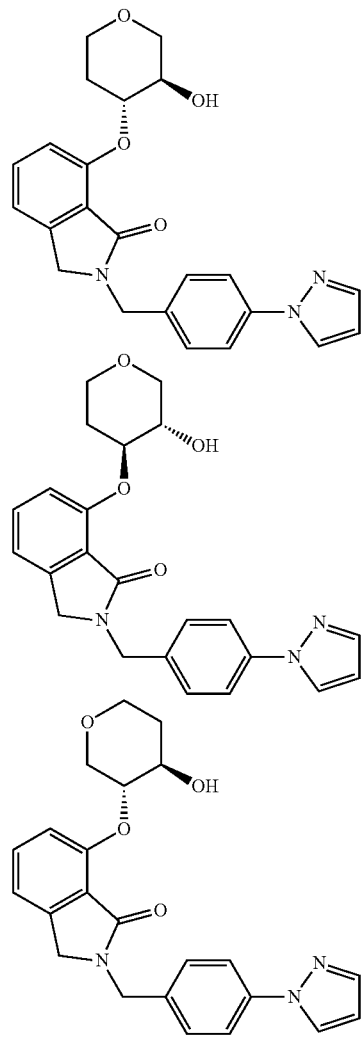

-continued

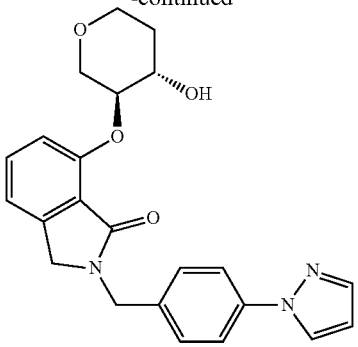

To a solution of 2-(4-(1H-pyrazol-1-yl)benzyl)-7-hydroxyisoindolin-1-one (0.20 g) obtained in Reference Example 14 in ethanol (4 mL) were added 3,7-dioxabicyclo[4.1.0]heptane (0.66 g) and pyridine (0.78 g), and the mixture was stirred under a nitrogen atmosphere at 100° C. for 3 hr. The reaction mixture was concentrated, and the residue was purified by NH silica gel chromatography (hexane-ethyl acetate) and chiral HPLC (column: CHIRALPAK AD (trade name), 50 mmID×500 mmL, manufactured by Dicel Corporation, mobile phase: hexane/2-propanol=300/700) to give the title compound.

retention time: tR2 (Example 238, yield 0.047 g)

MS: [M+H]$^+$ 406.2

$^1$H NMR (300 MHz, DMSO-d$_6$) δ 1.55-1.71 (1H, m), 2.04-2.21 (1H, m), 3.14-3.25 (1H, m), 3.36-3.47 (1H, m), 3.54-3.67 (1H, m), 3.75-3.93 (2H, m), 4.28-4.43 (3H, m), 4.70 (2H, s), 5.39 (1H, d, J=4.5 Hz), 6.46-6.56 (1H, m), 7.14 (2H, t, J=7.6 Hz), 7.40 (2H, d, J=8.7 Hz), 7.46-7.55 (1H, m), 7.73 (1H, d, J=1.7 Hz), 7.82 (2H, d, J=8.7 Hz), 8.46 (1H, d, J=2.3 Hz).

retention time: tR3 (Example 239, yield 0.050 g)

MS: [M+H]$^+$ 406.2

$^1$H NMR (300 MHz, DMSO-d$_6$) δ 1.51-1.71 (1H, m), 2.03-2.20 (1H, m), 3.20 (1H, dd, J=11.2, 7.8 Hz), 3.36-3.49 (1H, m), 3.52-3.67 (1H, m), 3.73-3.93 (2H, m), 4.26-4.43 (3H, m), 4.70 (2H, s), 5.39 (1H, brs), 6.50-6.56 (1H, m), 7.14 (2H, t, J=7.6 Hz), 7.40 (2H, d, J=8.5 Hz), 7.45-7.55 (1H, m), 7.73 (1H, d, J=1.5 Hz), 7.82 (2H, d, J=8.7 Hz), 8.46 (1H, d, J=2.5 Hz).

retention time: tR1 (Example 240, yield 0.013 g)

MS: [M+H]$^+$ 406.2

$^1$H NMR (300 MHz, DMSO-d$_6$) δ 1.40-1.58 (1H, m), 1.95-2.10 (1H, m), 3.36-3.51 (2H, m), 3.71-3.87 (2H, m), 4.01 (1H, dd, J=11.4, 3.7 Hz), 4.06-4.16 (1H, m), 4.33 (2H, s), 4.70 (2H, s), 5.35 (1H, brs), 6.48-6.56 (1H, m), 7.10-7.19 (2H, m), 7.40 (2H, d, J=8.5 Hz), 7.44-7.53 (1H, m), 7.73 (1H, d, J=1.7 Hz), 7.82 (2H, d, J=8.7 Hz), 8.46 (1H, d, J=2.5 Hz).

retention time: tR4 (Example 241, yield 0.047 g)

MS: [M+H]$^+$ 406.2

$^1$H NMR (300 MHz, DMSO-d$_6$) δ 1.41-1.57 (1H, m), 1.97-2.09 (1H, m), 3.42-3.48 (2H, m), 3.73-3.86 (2H, m), 4.01 (1H, dd, J=11.4, 4.1 Hz), 4.06-4.16 (1H, m), 4.33 (2H, s), 4.70 (2H, s), 6.49-6.56 (1H, m), 7.10-7.18 (2H, m), 7.40 (2H, d, J=8.5 Hz), 7.45-7.53 (1H, m), 7.73 (1H, d, J=1.7 Hz), 7.79-7.87 (2H, m), 8.46 (1H, d, J=2.5 Hz), OH proton was merged with H$_2$O signal.

Example 242 and Example 243

Optically active 4-((trans-2-hydroxycyclopentyl)oxy)-2-(4-(2-methylpyridin-4-yl)benzyl)-1,2-dihydro-3H-pyrrolo[3,4-c]pyridin-3-one

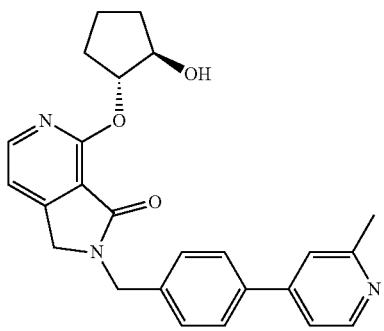

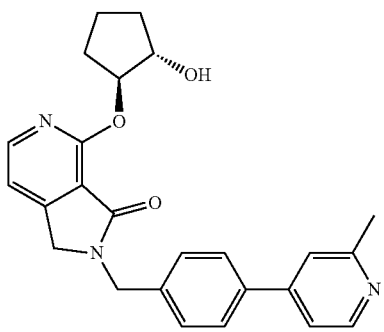

4-((trans-2-Hydroxycyclopentyl)oxy)-2-(4-(2-methylpyridin-4-yl)benzyl)-1,2-dihydro-3H-pyrrolo[3,4-c]pyridin-3-one (0.061 g) obtained in Example 76 was fractionated by chiral HPLC (column: CHIRALPAK AD (trade name), 50 mmID×500 mmL, manufactured by Dicel Corporation, mobile phase: methanol) to give the title compound.

retention time: tR1 (Example 242, yield 0.036 g)

MS: [M+H]$^+$ 416.2

$^1$H NMR (300 MHz, DMSO-d$_6$) δ 1.48-1.78 (4H, m), 1.87-1.98 (1H, m), 2.04-2.22 (1H, m), 2.52 (3H, brs), 4.13 (1H, brs), 4.39 (2H, s), 4.71 (2H, s), 4.91 (1H, d, J=3.8 Hz), 5.19-5.31 (1H, m), 7.17 (1H, d, J=5.3 Hz), 7.41 (2H, d, J=8.3 Hz), 7.47 (1H, d, J=5.1 Hz), 7.55 (1H, s), 7.76 (2H, d, J=8.3 Hz), 8.29 (1H, d, J=5.1 Hz), 8.48 (1H, d, J=5.3 Hz).

retention time: tR2 (Example 243, yield 0.031 g)

MS: [M+H]$^+$ 416.2

$^1$H NMR (300 MHz, DMSO-d$_6$) δ 1.51-1.78 (4H, m), 1.87-1.98 (1H, m), 2.08-2.21 (1H, m), 2.52 (3H, brs), 4.09-4.18 (1H, m), 4.39 (2H, s), 4.70 (2H, s), 4.91 (1H, d, J=4.0 Hz), 5.22-5.29 (1H, m), 7.17 (1H, d, J=5.1 Hz), 7.41 (2H, d, J=8.3 Hz), 7.47 (1H, d, J=5.3 Hz), 7.55 (1H, s), 7.76 (2H, d, J=8.1 Hz), 8.29 (1H, d, J=5.3 Hz), 8.48 (1H, d, J=5.3 Hz).

Example 244

5-fluoro-7-((trans-2-hydroxycyclohexyl)oxy)-2-(4-(1H-pyrazol-1-yl)benzyl)isoindolin-1-one

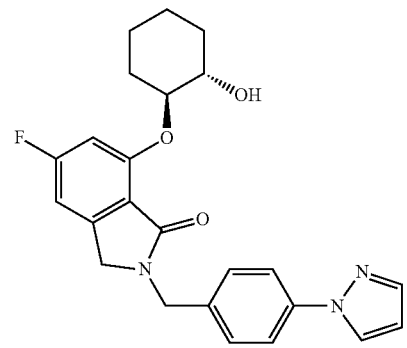 [SMILES: O=C1c2c(cc(F)cc2O[C@H]2CCCC[C@@H]2O)CN1Cc1ccc(-n2cccn2)cc1]

To a solution of 2-(4-(1H-pyrazol-1-yl)benzyl)-5-fluoro-7-hydroxyisoindolin-1-one (0.20 g) obtained in Reference Example 101 in ethanol (20 mL) were added 7-oxabicyclo[4.1.0]heptane (0.30 g) and pyridine (0.25 g), and the mixture was stirred under a nitrogen atmosphere at 78° C. for 48 hr. The reaction mixture was concentrated, and the residue was crudely purified by preparative TLC (petroleum ether-ethyl acetate), and the crudely purified product was dissolved in acetonitrile (2 mL)-water (15 mL). The solution was lyophilized to give the title compound (0.15 g).

MS: [M+H]$^+$ 422.4

$^1$H NMR (400 MHz, DMSO-d$_6$) δ 1.21-1.37 (3H, m), 1.38-1.52 (1H, m), 1.55-1.77 (2H, m), 1.85-1.96 (1H, m), 1.98-2.10 (1H, m), 3.54-3.65 (1H, m), 4.12-4.23 (1H, m), 4.31 (2H, s), 4.59-4.76 (2H, m), 5.02 (1H, d, J=4.4 Hz), 6.53 (1H, t, J=2.0 Hz), 6.94 (1H, d, J=8.0 Hz), 7.04 (1H, dd, J=12.0, 2.0 Hz), 7.38 (2H, d, J=8.4 Hz), 7.73 (1H, d, J=1.6 Hz), 7.81 (1H, d, J=8.8 Hz), 8.46 (1H, d, J=2.4 Hz).

Example 245 and Example 246

Optically active 2-(4-(1-methyl-1H-pyrazol-3-yl)benzyl)-4-((tetrahydrofuran-2-yl)methoxy)-1,2-dihydro-3H-pyrrolo[3,4-c]pyridin-3-one

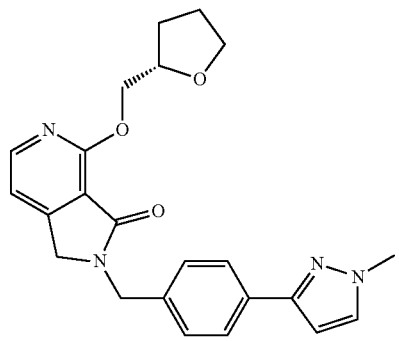

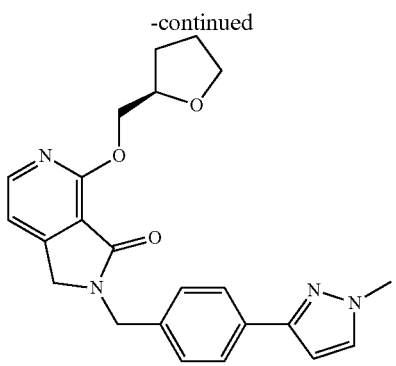

2-(4-(1-Methyl-1H-pyrazol-3-yl)benzyl)-4-((tetrahydrofuran-2-yl)methoxy)-1,2-dihydro-3H-pyrrolo[3,4-c]pyridin-3-one (0.25 g) obtained in Example 79 was purified by chiral HPLC (column: CHIRALPAK AD (trade name), 50 mmID× 500 mmL, manufactured by Dicel Corporation, mobile phase: hexane/ethanol=500/500) to give the title compound.

retention time: tR1 (Example 245, yield 0.11 g)
MS: [M+H]$^+$ 405.2
$^1$H NMR (300 MHz, DMSO-d$_6$) δ1.69-1.90 (2H, m), 1.93-2.08 (2H, m), 3.62-3.71 (1H, m), 3.80-3.91 (4H, m), 4.18-4.29 (1H, m), 4.32-4.45 (4H, m), 4.66 (2H, s), 6.65 (1H, d, J=2.3 Hz), 7.18 (1H, d, J=5.3 Hz), 7.28 (2H, d, J=8.3 Hz), 7.68-7.78 (3H, m), 8.27 (1H, d, J=5.1 Hz).

retention time: tR2 (Example 246, yield 0.11 g)
MS: [M+H]$^+$ 405.2
$^1$H NMR (300 MHz, DMSO-d$_6$) δ1.68-1.89 (2H, m), 1.93-2.09 (2H, m), 3.61-3.73 (1H, m), 3.79-3.91 (4H, m), 4.18-4.30 (1H, m), 4.31-4.47 (4H, m), 4.66 (2H, s), 6.65 (1H, d, J=2.3 Hz), 7.18 (1H, d, J=5.3 Hz), 7.28 (2H, d, J=8.3 Hz), 7.67-7.79 (3H, m), 8.27 (1H, d, J=5.1 Hz).

Example 247

4-(2,6-difluorophenoxy)-2-(4-(1,3-dimethyl-1H-pyrazol-4-yl)-2-fluorobenzyl)-1,2-dihydro-3H-pyrrolo[3,4-c]pyridin-3-one

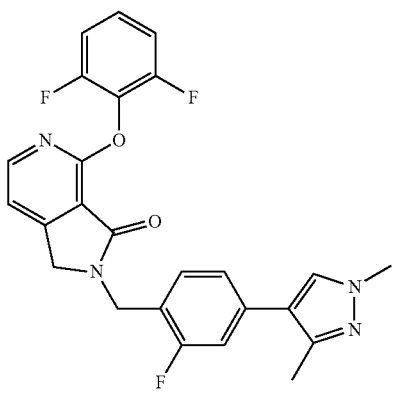 [SMILES: Cc1nn(C)cc1-c1ccc(CN2Cc3ccnc(Oc4c(F)cccc4F)c3C2=O)c(F)c1]

A mixture of methyl 2-(2,6-difluorophenoxy)-4-vinylnicotinate (0.10 g) obtained in Reference Example 103, sodium periodate (0.37 g) and osmium oxide (immobilized catalyst I) (0.044 g), and acetonitrile (4 mL)-acetone (4 mL)-water (4 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (4 mL), (4-(1,3-dimethyl-1H-pyrazol-4-yl)-2-fluorophenyl)methanamine (0.075 g) and anhydrous magnesium sulfate (0.082 g) were added, and the mixture was stirred under an argon atmosphere at room temperature for 30 min. The insoluble material was filtered off, and the filtrate was concentrated. To a solution of the residue in acetic acid (4 mL) was added sodium triacetoxyhydroborate (0.11 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.069 g).

MS: [M+H]$^+$ 465.1
$^1$H NMR (300 MHz, DMSO-d$_6$) δ 2.30 (3H, s), 3.78 (3H, s), 4.55 (2H, s), 4.77 (2H, s), 7.23-7.45 (7H, m), 7.96 (1H, s), 8.22 (1H, d, J=5.3 Hz).

Example 248, Example 249

Optically active 1,5-anhydro-2-deoxy-3-O-(2-(4-(1,3-dimethyl-1H-pyrazol-4-yl)benzyl)-3-oxo-2,3-dihydro-1H-isoindol-4-yl)-threo-pentitol and Example 250, Example 251

Optically active 1,5-anhydro-2-deoxy-4-O-(2-(4-(1,3-dimethyl-1H-pyrazol-4-yl)benzyl)-3-oxo-2,3-dihydro-1H-isoindol-4-yl)-threo-pentitol

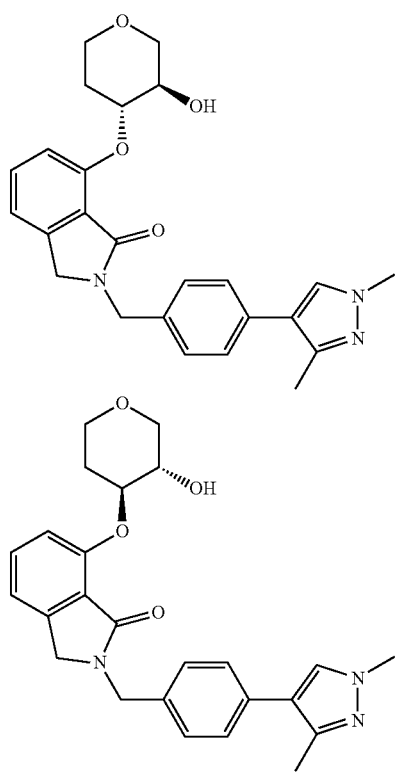

-continued

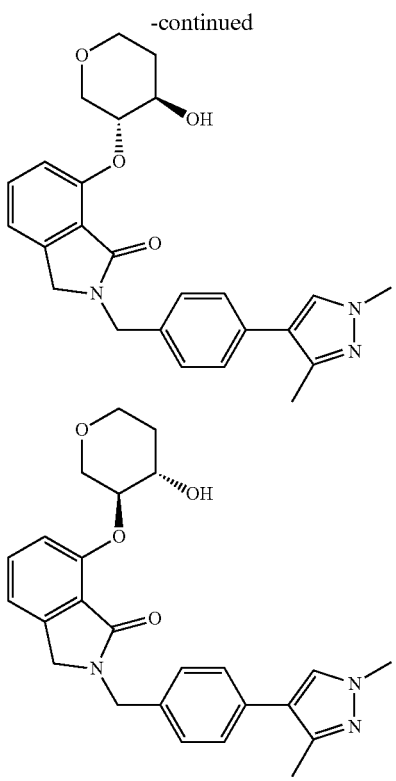

To a solution of 2-(4-bromobenzyl)-7-hydroxyisoindolin-1-one (0.18 g) obtained in Reference Example 3 in ethanol (4 mL) were added 3,7-dioxabicyclo[4.1.0]heptane (0.29 g) and pyridine (0.45 g), and the mixture was stirred at 90° C. overnight. The reaction mixture was concentrated, and the residue was crudely purified by NH silica gel chromatography (hexane-ethyl acetate). To a solution of the obtained crudely purified product in DME (6 mL)-water (1 mL) were added 1,3-dimethyl-4-(4,4,5,5-tetramethyl-1,3,2-dioxaborolan-2-yl)-1H-pyrazole (0.11 g), sodium carbonate (0.10 g) and (1,1-bis(diphenylphosphino)ferrocene)dichloropalladium(II) (0.035 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK AD (trade name), 50 mmID×500 mmL, manufactured by Dicel Corporation, mobile phase: hexane/2-propanol=400/600) to give the title compound (0.053 g).

retention time: tR2 (Example 248, yield 0.053 g)
MS: [M+H]$^+$ 434.2
$^1$H NMR (300 MHz, DMSO-d$_6$) δ1.92-2.07 (1H, m), 2.14-2.26 (1H, m), 2.38 (3H, s), 3.24 (1H, dd, J=11.2, 9.5 Hz), 3.39 (1H, td, J=11.8, 2.3 Hz), 3.88 (3H, s), 3.92-4.11 (3H, m), 4.17 (1H, dd, J=11.2, 5.0 Hz), 4:29 (2H, s), 4.62-4.73 (1H, m), 4.81-4.93 (1H, m), 5.92 (1H, brs), 7.05 (1H, d, J=7.9 Hz), 7.12 (1H, d, J=7.6 Hz), 7.29-7.38 (4H, m), 7.40-7.50 (2H, m).

retention time: tR3 (Example 249, yield 0.054 g)
MS: [M+H]$^+$ 434.2
$^1$H NMR (300 MHz, DMSO-d$_6$) δ 1.92-2.10 (1H, m), 2.14-2.26 (1H, m), 2.39 (3H, s), 3.18-3.30 (1H, m), 3.32-3.45 (1H, m), 3.88 (3H, s), 3.92-4.12 (3H, m), 4.18 (1H, dd, J=10.9, 4.6 Hz), 4.29 (2H, s), 4.64-4.73 (1H, m), 4.83-4.93 (1H, m), 5.90 (1H, brs), 7.05 (1H, d, J=8.1 Hz), 7.12 (1H, d, J=7.4 Hz), 7.30-7.39 (4H, m), 7.40-7.51 (2H, m).

retention time: tR1 (Example 250, yield 0.0073 g)
MS: [M+H]$^+$ 434.2
$^1$H NMR (300 MHz, CDCl$_3$) δ 1.65-1.83 (1H, m), 2.06-2.17 (1H, m), 2.37 (3H, s), 3.38-3.54 (2H, m), 3.87 (3H, s), 3.88-4.07 (3H, m), 4.25-4.33 (3H, m), 4.64-4.74 (1H, m), 4.79-4.89 (1H, m), 5.81-6.00 (1H, m), 5.92 (1H, brs), 6.99 (1H, d, J=7.9 Hz), 7.10 (1H, d, J=7.4 Hz), 7.28-7.37 (4H, m), 7.37-7.50 (2H, m).

retention time: tR4 (Example 251, yield 0.0022 g)
MS: [M+H]$^+$ 434.2
$^1$H NMR (300 MHz, CDCl$_3$) δ 1.65-1.82 (1H, m), 2.05-2.17 (1H, m), 2.37 (3H, s), 3.40-3.54 (2H, m), 3.87 (3H, s), 3.89-4.05 (3H, m), 4.23-4.34 (3H, m), 4.64-4.74 (1H, m), 4.79-4.90 (1H, m), 5.92 (1H, s), 6.99 (1H, d, J=7.9 Hz), 7.10 (1H, d, J=7.6 Hz), 7.29-7.36 (4H, m), 7.39-7.49 (2H, m).

Example 252

2-(4-(1,3-dimethyl-1H-pyrazol-4-yl)benzyl)-4-((tetrahydro-2H-pyran-2-yl)methoxy)-1,2-dihydro-3H-pyrrolo[3,4-c]pyridin-3-one

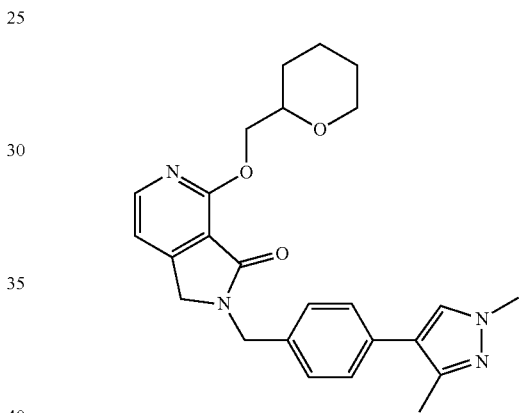

A mixture of ethyl 2-((tetrahydro-2H-pyran-2-yl)methoxy)-4-vinylnicotinate (0.42 g) obtained in Reference Example 105, sodium periodate (1.56 g) and osmium oxide (immobilized catalyst I) (0.185 g), and acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.19 g) was dissolved in THF (3 mL), (4-(1,3-dimethyl-1H-pyrazol-4-yl)phenyl)methanamine (0.13 g) and anhydrous magnesium sulfate (0.156 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.21 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was crudely purified by NH silica gel chromatography (hexane-ethyl acetate), and solidified with diisopropyl ether to give the title compound (0.11 g).

MS: [M+H]$^+$ 433.1

$^1$H NMR (300 MHz, DMSO-d$_6$) δ 1.29-1.58 (4H, m), 1.70 (1H, d, J=14.2 Hz), 1.81 (1H, brs), 2.26 (3H, s), 3.34-3.48 (1H, m), 3.61-3.73 (1H, m), 3.77 (3H, s), 3.84-3.94 (1H, m), 4.24-4.45 (4H, m), 4.65 (2H, s), 7.18 (1H, d, J=5.1 Hz), 7.23-7.33 (2H, m), 7.34-7.44 (2H, m), 7.84 (1H, s), 8.27 (1H, d, J=5.3 Hz).

Example 253

2-(4-(1-methyl-1H-pyrazol-3-yl)benzyl)-4-((tetrahydro-2H-pyran-2-yl)methoxy)-1,2-dihydro-3H-pyrrolo[3,4-c]pyridin-3-one

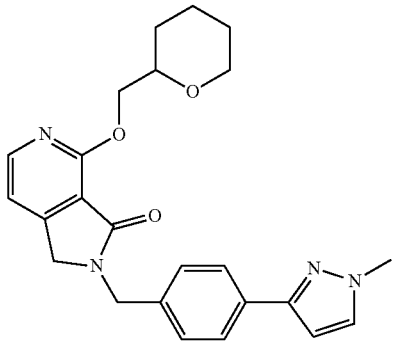 [SMILES: Cn1ccc(-c2ccc(CN3Cc4ccnc(OCC5CCCCO5)c4C3=O)cc2)n1]

A mixture of ethyl 2-((tetrahydro-2H-pyran-2-yl)methoxy)-4-vinylnicotinate (0.42 g) obtained in Reference Example 105, sodium periodate (1.56 g) and osmium oxide (immobilized catalyst I) (0.185 g), and acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.19 g) was dissolved in THF (3 mL), (4-(1-methyl-1H-pyrazol-3-yl)phenyl)methanamine (0.12 g) and anhydrous magnesium sulfate (0.156 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.21 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.011 g).

MS: [M+H]$^+$ 419.2

$^1$H NMR (300 MHz, DMSO-d$_6$) δ 1.27-1.59 (4H, m), 1.70 (1H, d, J=11.5 Hz), 1.83 (1H, brs), 3.34-3.47 (1H, m), 3.63-3.74 (1H, m), 3.81-3.94 (4H, m), 4.25-4.44 (4H, m), 4.66 (2H, s), 6.65 (1H, d, J=2.3 Hz), 7.18 (1H, d, J=5.1 Hz), 7.28 (2H, d, J=8.3 Hz), 7.67-7.79 (3H, m), 8.27 (1H, d, J=5.3 Hz).

Example 254

4-(2-cyclopropylethoxy)-2-(4-(1-methyl-1H-1,2,3-triazol-4-yl)benzyl)-1,2-dihydro-3H-pyrrolo[3,4-c]pyridin-3-one

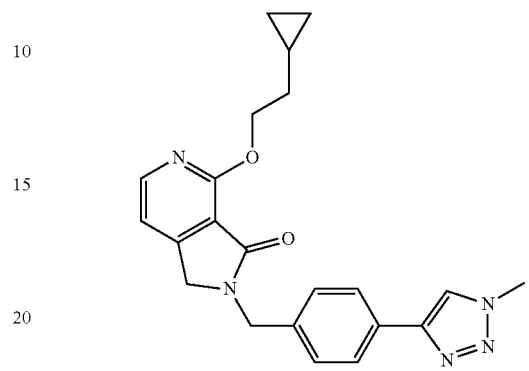

To a solution of ethyl 2-fluoro-4-iodonicotinate (0.50 g) obtained by a known method (Organic Letters, 7(10), 1943-1946; 2005) and 2-cyclopropylethanol (0.58 g) in THF (20 mL) was added 60% sodium hydride (0.34 g) at 0° C., and the mixture was stirred under an argon atmosphere at the same temperature for 1 hr. To the reaction solution was added 1N hydrochloric acid, the mixture was neutralized and diluted with ethyl acetate. The organic layer was separated, washed with water and saturated brine, dried over anhydrous sodium sulfate, and concentrated. The residue was crudely purified by silica gel chromatography (hexane-ethyl acetate). To a solution of the crudely purified product (0.54 g) in DMF (10 mL) was added tributyl(vinyl)tin (0.71 g), trans-dichlorobis(triphenylphosphine)palladium(II) (0.053 g) and lithium chloride (0.47 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was crudely purified by silica gel chromatography (hexane-ethyl acetate). A mixture of the obtained crudely purified product (0.41 g), sodium periodate (1.69 g) and osmium oxide (immobilized catalyst I) (0.20 g), and acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.069 g) was dissolved in THF (2 mL), (4-(1-methyl-1H-1,2,3-triazol-4-yl)phenyl)methanamine (0.045 g) and anhydrous magnesium sulfate (0.058 g) were added, and the mixture was stirred under an argon atmosphere at room temperature for 20 min. The insoluble material was filtered off, and the filtrate was concentrated. To a solution of the residue in acetic acid (2 mL) was added sodium triacetoxyhydroborate (0.076 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.026 g).

MS: [M+H]$^+$ 390.2

$^1$H NMR (300 MHz, DMSO-d$_6$) δ 0.11-0.21 (2H, m), 0.38-0.47 (2H, m), 0.80-0.93 (1H, m), 1.66 (2H, q, J=6.8 Hz), 4.08 (3H, s), 4.38 (2H, s), 4.45 (2H, t, J=6.7 Hz), 4.68 (2H, s), 7.17 (1H, d, J=5.1 Hz), 7.34 (2H, d, J=8.1 Hz), 7.80 (2H, d, J=8.1 Hz), 8.28 (1H, d, J=5.3 Hz), 8.49 (1H, s).

Example 255 and Example 256

Optically active 2-(4-(1,3-dimethyl-1H-pyrazol-4-yl)benzyl)-4-((trans-2-hydroxycyclopentyl)oxy)-1,2-dihydro-3H-pyrrolo[3,4-c]pyridin-3-one

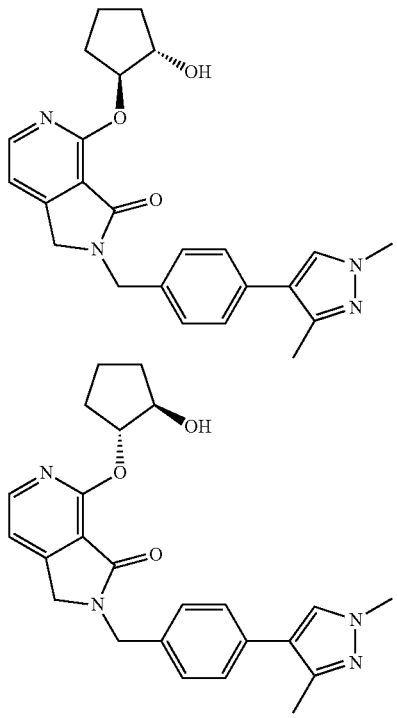

2-(4-(1,3-Dimethyl-1H-pyrazol-4-yl)benzyl)-4-((trans-2-hydroxycyclopentyl)oxy)-1,2-dihydro-3H-pyrrolo[3,4-c]pyridin-3-one (0.088 g) obtained in Example 227 was purified by chiral HPLC (column: CHIRALPAK IC (trade name), 50 mmID×500 mmL, manufactured by Dicel Corporation, mobile phase: hexane/ethanol=400/600) to give the title compound.

retention time: tR1 (Example 255, yield 0.026 g)

MS: [M+H]$^+$ 419.2

$^1$H NMR (300 MHz, DMSO-d$_6$) δ 1.50-1.79 (4H, m), 1.86-1.99 (1H, m), 2.07-2.20 (1H, m), 2.27 (3H, s), 3.77 (3H, s), 4.13 (1H, brs), 4.37 (2H, s), 4.63 (2H, s), 4.92 (1H, brs), 5.19-5.30 (1H, m), 7.16 (1H, d, J=5.1 Hz), 7.23-7.31 (2H, m), 7.35-7.42 (2H, m), 7.85 (1H, s), 8.28 (1H, d, J=5.3 Hz).

retention time: tR2 (Example 256, yield 0.026 g)

MS: [M+H]$^+$ 419.2

$^1$H NMR (300 MHz, DMSO-d$_6$) δ 1.51-1.78 (4H, m), 1.88-2.00 (1H, m), 2.07-2.19 (1H, m), 2.26 (3H, s), 3.77 (3H, s), 4.10-4.17 (1H, m), 4.37 (2H, s), 4.63 (2H, s), 4.92 (1H, d, J=4.0 Hz), 5.20-5.29 (1H, m), 7.16 (1H, d, J=5.3 Hz), 7.24-7.31 (2H, m), 7.34-7.42 (2H, m), 7.85 (1H, s), 8.28 (1H, d, J=5.1 Hz).

Example 257

2-(4-(5-fluoro-1H-pyrazol-1-yl)benzyl)-4-((tetrahydrofuran-2-yl)methoxy)-1,2-dihydro-3H-pyrrolo[3,4-c]pyridin-3-one

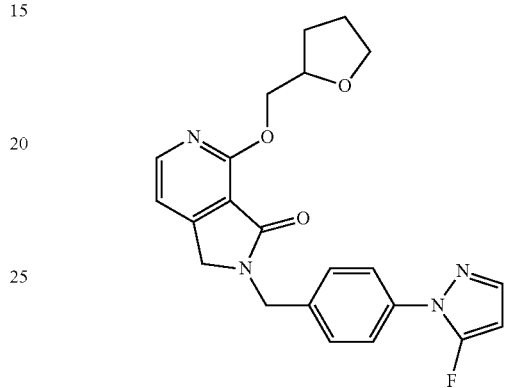

A mixture of methyl 2-((tetrahydrofuran-2-yl)methoxy)-4-vinylnicotinate (0.19 g) obtained in Reference Example 42, sodium periodate (0.76 g) and osmium oxide (immobilized catalyst I) (0.090 g), and acetonitrile (4 mL)-acetone (4 mL)-water (4 mL) was stirred under a nitrogen atmosphere at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (10 mL), (4-(5-fluoro-1H-pyrazol-1-yl)phenyl)methanamine hydrochloride (0.16 g) obtained in Reference Example 112 and anhydrous magnesium sulfate (0.20 g) were added, and the mixture was stirred under an argon atmosphere at room temperature for 20 min. The insoluble material was filtered off, and the filtrate was concentrated. To a solution of the residue in acetic acid (30 mL) was added sodium triacetoxyhydroborate (0.26 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was crudely purified by NH silica gel chromatography (hexane-ethyl acetate), solidified with diisopropyl ether to give the title compound (0.031 g).

MS: [M+H]$^+$ 409.1

$^1$H NMR (300 MHz, DMSO-d$_6$) δ 1.70-1.89 (2H, m), 1.93-2.08 (2H, m), 3.62-3.73 (1H, m), 3.79-3.89 (1H, m), 4.17-4.28 (1H, m), 4.32-4.47 (4H, m), 4.72 (2H, s), 6.23 (1H, dd, J=5.4, 2.0 Hz), 7.20 (1H, d, J=5.1 Hz), 7.44 (2H, d, J=8.5 Hz), 7.57-7.68 (3H, m), 8.28 (1H, d, J=5.3 Hz).

Example 258 and Example 259

Optically active 4-((trans-2-hydroxycyclopentyl)oxy)-2-(4-(2-methylpyridin-4-yl)benzyl)-1,2-dihydro-3H-pyrrolo[3,4-c]pyridin-3-one hydrochloride

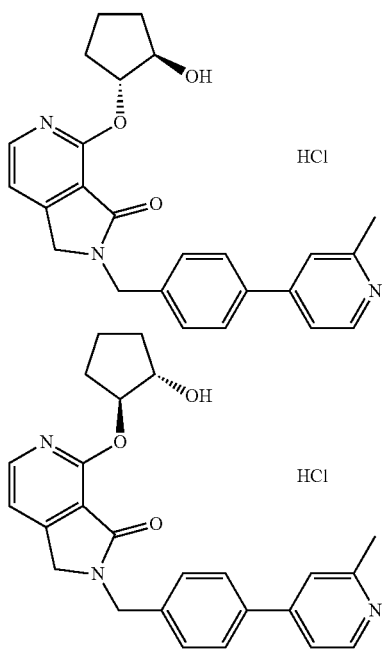

A mixture of methyl 2-((trans-2-hydroxycyclopentyl)oxy)-4-vinylnicotinate (1.93 g) obtained in Reference Example 61, sodium periodate (7.44 g) and osmium oxide (immobilized catalyst I) (0.89 g), and acetonitrile (20 mL)-acetone (20 mL)-water (20 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue was dissolved in THF (20 mL), (4-(2-methylpyridin-4-yl)phenyl)methanamine (1.38 g) obtained in Reference Example 63 and anhydrous magnesium sulfate (1.68 g) were added, and the mixture was stirred under an argon atmosphere at room temperature for 20 min. The insoluble material was filtered off, and the filtrate was concentrated. To a solution of the residue in acetic acid (30 mL) was added sodium triacetoxyhydroborate (2.21 g), and the mixture was stirred under an argon atmosphere at room temperature for 4 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK AD (trade name), 50 mmID×500 mmL, manufactured by Dicel Corporation, mobile phase: methanol/diethylamine=1000/1). tR1 and tR2 of the obtained optically active 4-((trans-2-hydroxycyclopentyl)oxy)-2-(4-(2-methylpyridin-4-yl)benzyl)-1H-pyrrolo[3,4-c]pyridin-3(2H)-one were each dissolved in ethyl acetate, and solidified with 4N hydrochloric acid (ethyl acetate solution) and diethyl ether to give the title compound.

retention time: hydrochloride derived from tR1 (Example 258, yield 0.37 g)

MS: [M+H]$^+$ 416.1

$^1$H NMR (300 MHz, DMSO-d$_6$) δ 1.51-1.79 (4H, m), 1.87-2.00 (1H, m), 2.08-2.21 (1H, m), 2.72 (3H, s), 4.08-4.16 (1H, m), 4.42 (2H, s), 4.75 (2H, s), 5.21-5.30 (1H, m), 7.18 (1H, d, J=5.1 Hz), 7.50 (2H, d, J=8.3 Hz), 7.97 (2H, d, J=8.1 Hz), 8.08 (1H, d, J=5.9 Hz), 8.18 (1H, s), 8.30 (1H, d, J=5.3 Hz), 8.76 (1H, d, J=6.2 Hz), OH and HCl protons were merged with H$_2$O signal.

retention time: hydrochloride derived from tR2 (Example 259, yield 0.74 g)

MS: [M+H]$^+$ 416.2

$^1$H NMR (300 MHz, DMSO-d$_6$) δ 1.49-1.79 (4H, m), 1.86-1.98 (1H, m), 2.08-2.21 (1H, m), 2.75 (3H, s), 4.09-4.18 (1H, m), 4.42 (2H, s), 4.75 (2H, s), 5.22-5.31 (1H, m), 7.19 (1H, d, J=5.3 Hz), 7.51 (2H, d, J=8.3 Hz), 7.99 (2H, d, J=8.3 Hz), 8.14 (1H, d, J=6.2 Hz), 8.24 (1H, s), 8.30 (1H, d, J=5.3 Hz), 8.78 (1H, d, J=6.2 Hz), OH and HCl protons were merged with H$_2$O signal.

Example 260

4-(2-cyclopropylethoxy)-2-(2-fluoro-4-(1-methyl-1H-1,2,3-triazol-4-yl)benzyl)-1,2-dihydro-3H-pyrrolo[3,4-c]pyridin-3-one

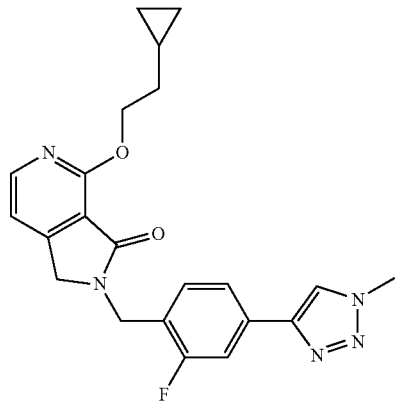 [SMILES: Cn1cc(-c2ccc(CN3Cc4ccnc(OCCC5CC5)c4C3=O)c(F)c2)nn1]

To a solution of ethyl 2-fluoro-4-iodonicotinate (0.50 g) obtained by a known method (Organic Letters, 7(10), 1943-1946; 2005) and 2-cyclopropylethanol (0.58 g) in THF (20 mL) was added 60% sodium hydride (0.34 g) at 0° C., and the mixture was stirred under an argon atmosphere at the same temperature for 1 hr. The reaction solution was neutralized with 1N hydrochloric acid, and diluted with ethyl acetate. The organic layer was separated, washed with water and saturated brine, dried over anhydrous sodium sulfate, and concentrated. The residue was crudely purified by silica gel chromatography (hexane-ethyl acetate). To a solution of the crudely purified product (0.54 g) in DMF (10 mL) were added tributyl(vinyl)tin (0.71 g), trans-dichlorobis(triphenylphosphine)palladium(II) (0.053 g) and lithium chloride (0.47 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was crudely purified by silica gel chromatography (hexane-ethyl acetate). A mixture of the crudely purified product (0.41 g), sodium periodate (1.69 g) and osmium oxide (immobilized catalyst I) (0.20 g), and acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.14 g) was dissolved in THF (2 mL), (2-fluoro-4-(1-methyl-1H-1,2,3-triazol-4-yl)phenyl)methanamine (0.10 g) obtained in Reference Example 154 and anhydrous magnesium sulfate (0.117 g) were added, and the mixture was stirred under an argon atmosphere at room temperature for 20 min. The insoluble material was filtered off, and the filtrate was concentrated. To a solution of the residue in acetic acid (2 mL) was added sodium triacetoxyhydroborate (0.15 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.004 g).

MS: [M+H]+ 408.1

$^1$H NMR (300 MHz, CDCl$_3$) δ 0.12-0.19 (2H, m), 0.43-0.52 (2H, m), 0.89 (1H, brs), 1.79 (2H, q, J=7.1 Hz), 4.15 (3H, s), 4.32 (2H, s), 4.56 (2H, t, J=7.0 Hz), 4.82 (2H, s), 6.93 (1H, d, J=5.3 Hz), 7.40-7.52 (2H, m), 7.62 (1H, dd, J=10.9, 1.2 Hz), 7.74 (1H, s), 8.24 (1H, d, J=5.3 Hz).

Example 261

7-(2-hydroxybutoxy)-2-(4-(1-methyl-1H-pyrazol-4-yl)benzyl)isoindolin-1-one

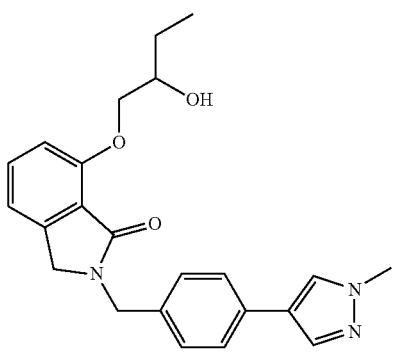 [SMILES: CCC(O)COc1cccc2c1C(=O)N(Cc1ccc(-c3cnn(C)c3)cc1)C2]

To a solution of 7-hydroxy-2-(4-(1-methyl-1H-pyrazol-4-yl)benzyl)isoindolin-1-one (0.30 g) obtained in Reference Example 6 in ethanol (9 mL) were added 2-ethyloxirane (0.68 g) and pyridine (0.74 g), and the mixture was stirred under a nitrogen atmosphere at 90° C. for 4 hr. The reaction mixture was concentrated, and the residue was purified by NH silica gel chromatography (hexane-ethyl acetate), and solidified with diisopropyl ether-ethyl acetate to give the title compound (0.22 g).

MS: [M+H]+ 392.2

$^1$H NMR (300 MHz, DMSO-d$_6$) δ 0.93 (3H, t, J=7.5 Hz), 1.35-1.51 (1H, m), 1.58-1.74 (1H, m), 3.67-3.79 (1H, m), 3.85 (3H, s), 3.92-4.04 (2H, m), 4.29 (2H, s), 4.63 (2H, s), 4.84 (1H, d, J=4.9 Hz), 7.07 (2H, t, J=7.9 Hz), 7.24 (2H, d, J=8.1 Hz), 7.44-7.56 (3H, m), 7.82 (1H, s), 8.10 (1H, s).

Example 262

2-(4-(1,3-dimethyl-1H-pyrazol-4-yl)-2-fluorobenzyl)-4-((tetrahydro-2H-pyran-4-yl)methoxy)-1,2-dihydro-3H-pyrrolo[3,4-c]pyridin-3-one

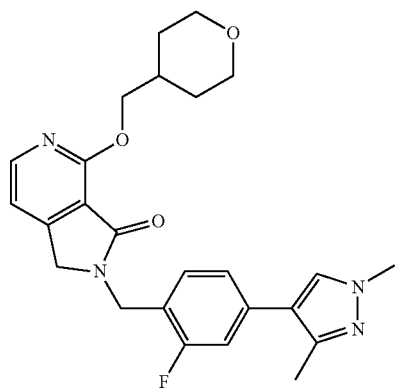 [SMILES: Cc1nn(C)cc1-c1ccc(CN2Cc3ccnc(OCC4CCOCC4)c3C2=O)c(F)c1]

To a solution of ethyl 4-iodo-2-((tetrahydro-2H-pyran-4-yl)methoxy)nicotinate (0.35 g) obtained in Reference Example 113 in DMF (8 mL) were added tributyl(vinyl)tin (0.42 g), trans-dichlorobis(triphenylphosphine)palladium (II) (0.031 g) and lithium chloride (0.28 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was crudely purified by silica gel chromatography (hexane-ethyl acetate). A mixture of the crudely purified product (0.26 g), sodium periodate (0.94 g) and osmium oxide (immobilized catalyst I) (0.11 g), and acetonitrile (7 mL)-acetone (7 mL)-water (7 mL) was stirred under a nitrogen atmosphere at room temperature overnight. The insoluble material was filtered off, and the filtrate was diluted with ethyl acetate. The organic layer was separated, washed with saturated brine, dried over anhydrous sodium sulfate, and concentrated. The residue (0.082 g) was dissolved in THF (3 mL), (4-(1,3-dimethyl-1H-pyrazol-4-yl)-2-fluorophenyl)methanamine (0.061 g) and anhydrous magnesium sulfate (0.067 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.089 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.032 g).

MS: [M+H]+ 451.1

¹H NMR (300 MHz, DMSO-d₆) δ 1.26-1.46 (2H, m), 1.69 (2H, d, J=10.8 Hz), 1.95-2.13 (1H, m), 2.29 (3H, s), 3.32-3.40 (2H, m), 3.77 (3H, s), 3.88 (2H, dd, J=11.1, 2.8 Hz), 4.25 (2H, d, J=6.6 Hz), 4.42 (2H, s), 4.69 (2H, s), 7.17-7.35 (4H, m), 7.95 (1H, s), 8.27 (1H, d, J=5.1 Hz).

Example 263

4-(cyclobutylmethoxy)-2-(2-fluoro-4-(1-methyl-1H-1,2,3-triazol-4-yl)benzyl)-1,2-dihydro-3H-pyrrolo[3,4-c]pyridin-3-one

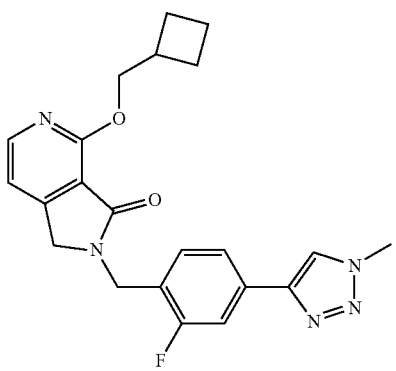 [SMILES: Cn1cc(-c2ccc(CN3Cc4ccnc(OCC5CCC5)c4C3=O)c(F)c2)nn1]

To a solution of ethyl 2-fluoro-4-iodonicotinate (0.50 g) obtained by a known method (Organic Letters, 7(10), 1943-1946; 2005) and cyclobutylmethanol (0.44 g) in THF (10 mL) was added 60% sodium hydride (0.27 g) at 0° C., and the mixture was stirred under an argon atmosphere at the same temperature for 1 hr. The reaction solution was neutralized with 1N hydrochloric acid, and diluted with ethyl acetate. The organic layer was separated, washed with water and saturated brine, dried over anhydrous sodium sulfate, and concentrated. The residue was crudely purified by silica gel chromatography (hexane-ethyl acetate). To a solution of the crudely purified product (0.51 g) in DMF (10 mL) were added tributyl(vinyl)tin (0.67 g), trans-dichlorobis(triphenylphosphine)palladium(II) (0.049 g) and lithium chloride (0.44 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was crudely purified by silica gel chromatography (hexane-ethyl acetate). A mixture of the crudely purified product (0.36 g), sodium periodate (1.48 g) and osmium oxide (immobilized catalyst I) (0.18 g), and acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.18 g) was dissolved in THF (3 mL), (2-fluoro-4-(1-methyl-1H-1,2,3-triazol-4-yl)phenyl)methanamine (0.14 g) obtained in Reference Example 154 and anhydrous magnesium sulfate (0.17 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.22 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.004 g).

MS: [M+H]⁺ 408.1

¹H NMR (300 MHz, CDCl₃) δ 1.90-1.98 (4H, m), 2.10-2.22 (2H, m), 2.83-2.97 (1H, m), 4.15 (3H, s), 4.32 (2H, s), 4.48 (2H, d, J=6.6 Hz), 4.81 (2H, s), 6.93 (1H, d, J=5.1 Hz), 7.41-7.52 (2H, m), 7.62 (1H, dd, J=10.8, 1.3 Hz), 7.74 (1H, s), 8.23 (1H, d, J=5.1 Hz).

Example 264

7-(2,6-difluorophenoxy)-2-((5-fluoro-2'-methyl-3,4'-bipyridin-6-yl)methyl)isoindolin-1-one

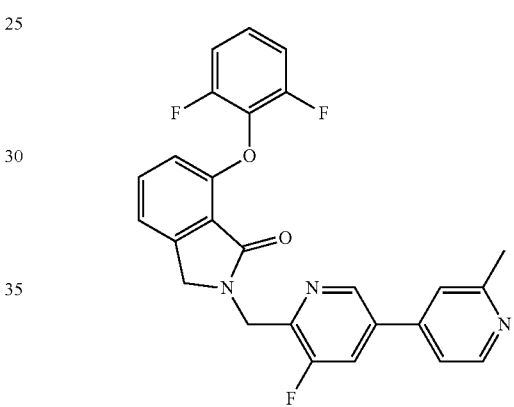

A solution of 5-fluoro-2'-methyl-(3,4'-bipyridine)-6-carbonitrile (0.33 g) obtained in Reference Example 114, Raney cobalt (0.30 g) and 8 mol/L ammonia (methanol solution) (1.94 mL) in ethanol (10 mL) was stirred under a hydrogen atmosphere at room temperature overnight, the insoluble material was filtered off through Celite, and the filtrate was concentrated. To a solution of the residue (0.11 g) in ethanol (5 mL) were added ethyl 2-(bromomethyl)-6-(2,6-difluorophenoxy)benzoate (0.14 g) obtained in Reference Example 115 and potassium carbonate (0.10 g), and the mixture was stirred at room temperature overnight. The reaction solution was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with THF-hexane to give the title compound (0.054 g).

MS: [M+H]⁺ 462.1

¹H NMR (300 MHz, DMSO-d₆) δ 2.54 (3H, s), 4.60 (2H, s), 4.98 (2H, d, J=1.5 Hz), 6.66 (1H, d, J=8.3 Hz), 7.28-7.44 (4H, m), 7.47-7.55 (1H, m), 7.59-7.64 (1H, m), 7.72 (1H, s), 8.24 (1H, dd, J=11.1, 1.9 Hz), 8.55 (1H, d, J=5.3 Hz), 8.85 (1H, t, J=1.5 Hz).

Example 265

2-(4-(1,3-dimethyl-1H-pyrazol-4-yl)benzyl)-4-((tetrahydrofuran-3-yl)methoxy)-1,2-dihydro-3H-pyrrolo[3,4-c]pyridin-3-one

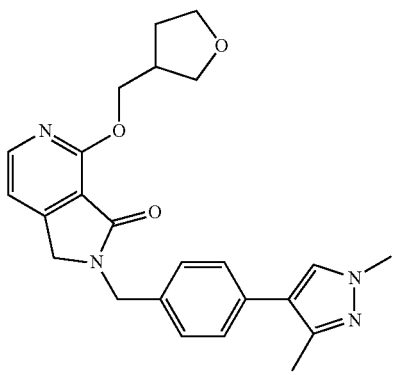 [SMILES: Cc1nn(C)cc1-c1ccc(CN2Cc3ccnc(OCC4CCOC4)c3C2=O)cc1]

To a solution of ethyl 2-fluoro-4-iodonicotinate (0.50 g) obtained by a known method (Organic Letters, 7(10), 1943-1946; 2005) and (tetrahydrofuran-3-yl)methanol (0.52 g) in THF (10 mL) was added 60% sodium hydride (0.27 g) at 0° C., and the mixture was stirred under an argon atmosphere at the same temperature for 1 hr. The reaction solution was neutralized with 1N hydrochloric acid, and diluted with ethyl acetate. The organic layer was separated, washed with water and saturated brine, dried over anhydrous sodium sulfate, and concentrated. The residue was crudely purified by silica gel chromatography (hexane-ethyl acetate). To a solution of the crudely purified product (0.59 g) in DMF (10 mL) were added tributyl(vinyl)tin (0.65 g), trans-dichlorobis(triphenylphosphine)palladium(II) (0.048 g) and lithium chloride (0.43 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was crudely purified by silica gel chromatography (hexane-ethyl acetate). A mixture of the crudely purified product (0.37 g), sodium periodate (1.44 g) and osmium oxide (immobilized catalyst I) (0.17 g), and acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.12 g) was dissolved in THF (3 mL), (4-(1,3-dimethyl-1H-pyrazol-4-yl)phenyl)methanamine (0.09 g) and anhydrous magnesium sulfate (0.10 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.14 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diethyl ether to give the title compound (0.054 g).

MS: [M+H]$^+$ 419.2

$^1$H NMR (300 MHz, DMSO-d$_6$) δ 1.64-1.78 (1H, m), 1.93-2.09 (1H, m), 2.27 (3H, s), 2.62-2.77 (1H, m), 3.58 (1H, dd, J=8.7, 5.5 Hz), 3.63-3.72 (1H, m), 3.74-3.85 (5H, m), 4.25-4.34 (1H, m), 4.36-4.45 (3H, m), 4.65 (2H, s), 7.19 (1H, d, J=5.3 Hz), 7.24-7.31 (2H, m), 7.36-7.42 (2H, m), 7.85 (1H, s), 8.27 (1H, d, J=5.3 Hz).

Example 266

2-(4-(2-methylpyridin-4-yl)benzyl)-4-((tetrahydrofuran-3-yl)methoxy)-1,2-dihydro-3H-pyrrolo[3,4-c]pyridin-3-one hydrochloride

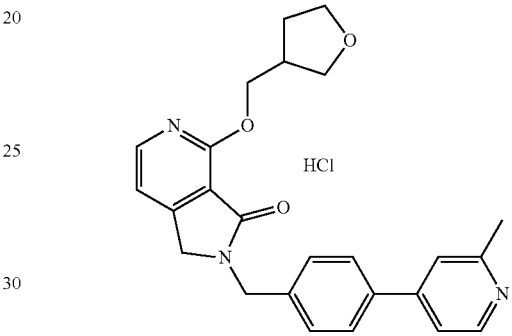

To a solution of ethyl 2-fluoro-4-iodonicotinate (0.50 g) obtained by a known method (Organic Letters, 7(10), 1943-1946; 2005) and (tetrahydrofuran-3-yl)methanol (0.52 g) in THF (10 mL) was added 60% sodium hydride (0.27 g) at 0° C., and the mixture was stirred under an argon atmosphere at the same temperature for 1 hr. The reaction solution was neutralized with 1N hydrochloric acid, and diluted with ethyl acetate. The organic layer was separated, washed with water and saturated brine, dried over anhydrous sodium sulfate, and concentrated. The residue was crudely purified by silica gel chromatography (hexane-ethyl acetate). To a solution of the crudely purified product (0.59 g) in DMF (10 mL) were added tributyl(vinyl)tin (0.65 g), trans-dichlorobis(triphenylphosphine)palladium(II) (0.048 g) and lithium chloride (0.43 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was crudely purified by silica gel chromatography (hexane-ethyl acetate). A mixture of the crudely purified product (0.37 g), sodium periodate (1.44 g) and osmium oxide (immobilized catalyst I) (0.17 g), and acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.12 g) was dissolved in THF (3 mL), (4-(2-methylpyridin-4-yl)phenyl)methanamine (0.085 g) obtained in Reference Example 63 and anhydrous magnesium sulfate (0.10 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.14 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate). The obtained oil was dissolved in diethyl ether, 4N hydrochloric acid (ethyl acetate solution) (0.005 mL) was added, and the resulting precipitate was collected by filtration, and dried to give the title compound (0.059 g).

MS: $[M+H]^+$ 416.1

$^1$H NMR (300 MHz, DMSO-$d_6$) δ 1.63-1.79 (1H, m), 2.00-2.09 (1H, m), 2.63-2.81 (4H, m), 3.57-3.60 (1H, m), 3.64-3.70 (1H, m), 3.74-3.85 (2H, m), 4.25-4.48 (4H, m), 4.77 (2H, s), 7.21 (1H, d, J=5.1 Hz), 7.52 (2H, d, J=8.3 Hz), 7.99 (2H, d, J=8.3 Hz), 8.14 (1H, d, J=6.2 Hz), 8.22-8.32 (2H, m), 8.78 (1H, d, J=6.2 Hz), HCl proton was merged with $H_2O$ signal.

Example 267

2-(4-(1,3-dimethyl-1H-pyrazol-4-yl)benzyl)-4-((trans-2-hydroxycyclohexyl)oxy)-1,2-dihydro-3H-pyrrolo[3,4-c]pyridin-3-one

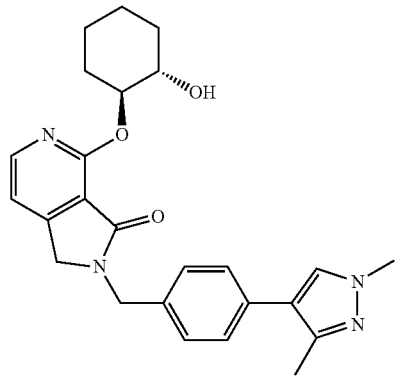 [SMILES: Cc1nn(C)cc1-c1ccc(CN2Cc3ccnc(O[C@H]4CCCC[C@@H]4O)c3C2=O)cc1]

A mixture of ethyl 2-((trans-2-hydroxycyclohexyl)oxy)-4-vinylnicotinate (0.82 g) obtained in Reference Example 116, sodium periodate (3.0 g) and osmium oxide (immobilized catalyst I) (0.36 g), and acetonitrile (10 mL)-acetone (10 mL)-water (10 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.10 g) was dissolved in THF (4 mL), (4-(1,3-dimethyl-1H-pyrazol-4-yl)phenyl)methanamine (0.069 g) and anhydrous magnesium sulfate (0.082 g) were added, and the mixture was stirred under an argon atmosphere at room temperature for 20 min. The insoluble material was filtered off, and the filtrate was concentrated. To a solution of the residue in acetic acid (4 mL) was added sodium triacetoxyhydroborate (0.11 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with THF-ethyl acetate-hexane to give the title compound (0.033 g).

MS: $[M+H]^+$ 433.1

$^1$H NMR (300 MHz, DMSO-$d_6$) δ 1.19-1.50 (4H, m), 1.66 (2H, brs), 1.83-2.07 (2H, m), 2.27 (3H, s), 3.57-3.69 (1H, m), 3.77 (3H, s), 4.37 (2H, s), 4.57-4.71 (2H, m), 4.76 (1H, d, J=4.5 Hz), 5.11 (1H, td, J=8.4, 4.1 Hz), 7.14 (1H, d, J=5.1 Hz), 7.24-7.32 (2H, m), 7.35-7.43 (2H, m), 7.85 (1H, s), 8.25 (1H, d, J=5.1 Hz).

Example 268, Example 269

Optically active 1,5-anhydro-3-O-(2-(4-bromobenzyl)-3-oxo-2,3-dihydro-1H-isoindol-4-yl)-2-deoxy-threo-pentitol and Example 270, Example 271

Optically active 1,5-anhydro-2-O-(2-(4-bromobenzyl)-3-oxo-2,3-dihydro-1H-isoindol-4-yl)-4-deoxy-threo-pentitol

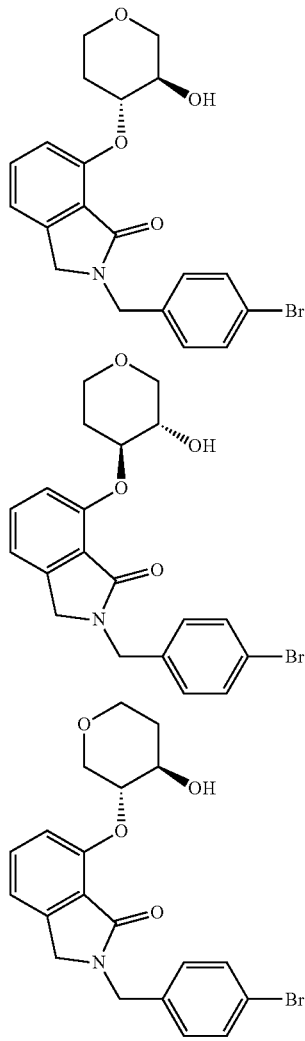

-continued

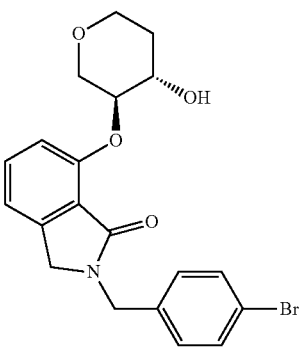

To a solution of 2-(4-bromobenzyl)-7-hydroxyisoindolin-1-one (0.86 g) obtained in Reference Example 3 in ethanol (16 mL) were added 3,7-dioxabicyclo[4.1.0]heptane (1.35 g) and pyridine (2.13 g), and the mixture was stirred under an argon atmosphere at 90° C. overnight. The reaction mixture was concentrated, and the residue was purified by NH silica gel chromatography (hexane-ethyl acetate) and chiral HPLC (column: CHIRALPAK AD (trade name), 50 mmID×500 mmL, manufactured by Dicel Corporation, mobile phase: hexane/2-propanol=300/700) to give the title compound.

retention time: tR2 (Example 268, yield 0.25 g)

MS: [M+H]$^+$ 418.0

$^1$H NMR (300 MHz, DMSO-$d_6$) δ 1.53-1.70 (1H, m), 2.06-2.19 (1H, m), 3.20 (1H, dd, J=11.2, 7.8 Hz), 3.40-3.46 (1H, m), 3.55-3.64 (1H, m), 3.76-3.93 (2H, m), 4.27-4.44 (3H, m), 4.64 (2H, s), 7.07-7.18 (2H, m), 7.24 (2H, d, J=8.3 Hz), 7.45-7.58 (3H, m), OH proton was merged with H$_2$O signal.

retention time: tR3 (Example 269, yield 0.26 g)

MS: [M+H]$^+$ 418.0

$^1$H NMR (300 MHz, DMSO-$d_6$) δ 1.54-1.68 (1H, m), 2.07-2.17 (1H, m), 3.20 (1H, dd, J=11.3, 7.7 Hz), 3.40-3.46 (1H, m), 3.54-3.64 (1H, m), 3.76-3.90 (2H, m), 4.28-4.41 (3H, m), 4.64 (2H, s), 7.09-7.18 (2H, m), 7.24 (2H, d, J=8.3 Hz), 7.45-7.58 (3H, m), OH proton was merged with H$_2$O signal.

retention time: tR1 (Example 270, yield 0.071 g)

MS: [M+H]$^+$ 417.9

$^1$H NMR (300 MHz, DMSO-$d_6$) δ 1.41-1.56 (1H, m), 1.96-2.07 (1H, m), 3.40-3.49 (3H, m), 3.72-3.84 (2H, m), 3.94-4.04 (1H, m), 4.05-4.16 (1H, m), 4.31 (2H, s), 4.64 (2H, s), 7.09-7.18 (2H, m), 7.24 (2H, d, J=8.5 Hz), 7.44-7.60 (3H, m).

retention time: tR4 (Example 271, yield 0.068 g)

MS: [M+H]$^+$ 418.0

$^1$H NMR (300 MHz, DMSO-$d_6$) δ 1.40-1.55 (1H, m), 1.96-2.08 (1H, nm), 3.40-3.47 (2H, m), 3.78 (2H, dd, J=11.4, 4.4 Hz), 3.99 (1H, dd, J=11.4, 3.9 Hz), 4.11 (1H, d, J=3.8 Hz), 4.31 (2H, s), 4.64 (2H, s), 7.14 (2H, dd, J=7.7, 3.4 Hz), 7.24 (2H, d, J=8.5 Hz), 7.45-7.60 (3H, m, OH proton was merged with H$_2$O signal.)

Example 272

Optically active 1,5-anhydro-2-deoxy-3-O-(2-(4-(1-methyl-1H-pyrazol-3-yl)benzyl)-3-oxo-2,3-dihydro-1H-isoindol-4-yl)-threo-pentitol

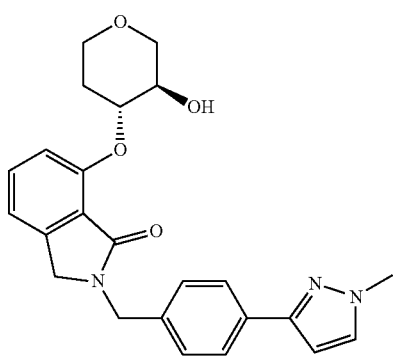 [SMILES: Cn1ccc(-c2ccc(CN3Cc4cccc(O[C@@H]5CCOC[C@H]5O)c4C3=O)cc2)n1]

To a solution of optically active 1,5-anhydro-3-O-(2-(4-bromobenzyl)-3-oxo-2,3-dihydro-1H-isoindol-4-yl)-2-deoxy-threo-pentitol (tR2) (0.12 g) obtained in Example 268 in DME (3 mL)-water (1 mL) were added 1-methyl-3-(4,4,5,5-tetramethyl-1,3,2-dioxaborolan-2-yl)-1H-pyrazole (0.072 g), sodium carbonate (0.061 g) and (1,1-bis(diphenylphosphino)ferrocene)dichloropalladium(II) (0.021 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.040 g).

MS: [M+H]$^+$ 420.2

$^1$H NMR (300 MHz, DMSO-$d_6$) δ 1.55-1.71 (1H, m), 2.07-2.18 (1H, m), 3.16-3.23 (1H, m), 3.41-3.45 (1H, m), 3.54-3.65 (1H, m), 3.78-3.92 (5H, m), 4.30-4.42 (3H, m), 4.68 (2H, s), 6.65 (1H, d, J=2.3 Hz), 7.14 (2H, t, J=7.6 Hz), 7.29 (2H, d, J=8.1 Hz), 7.44-7.54 (1H, m), 7.69-7.79 (3H, m), OH proton was merged with H$_2$O signal.

Example 273

Optically active 1,5-anhydro-2-deoxy-4-O-(2-(4-(1-methyl-1H-pyrazol-3-yl)benzyl)-3-oxo-2,3-dihydro-1H-isoindol-4-yl)-threo-pentitol

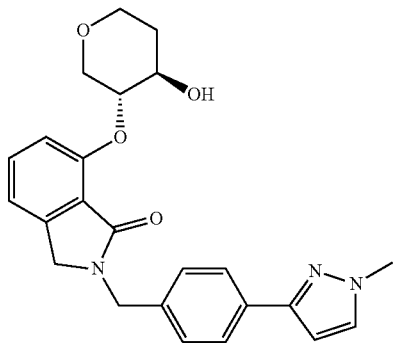 [SMILES: Cn1ccc(-c2ccc(CN3Cc4cccc(O[C@@H]5COCC[C@H]5O)c4C3=O)cc2)n1]

To a solution of optically active 1,5-anhydro-2-O-(2-(4-bromobenzyl)-3-oxo-2,3-dihydro-1H-isoindol-4-yl)-4-deoxy-threo-pentitol (tR4) (0.065 g) obtained in Example 271 in DME (3 mL)-water (1 mL) were added 1-methyl-3-(4,4,5,5-tetramethyl-1,3,2-dioxaborolan-2-yl)-1H-pyrazole (0.039 g), sodium carbonate (0.033 g) and (1,1-bis(diphenylphosphino)ferrocene)dichloropalladium(II) (0.011 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with THF-ethyl acetate-hexane to give the title compound (0.024 g).

MS: [M+H]$^+$ 420.2

$^1$H NMR (300 MHz, DMSO-d$_6$) δ1.42-1.56 (1H, m), 1.96-2.09 (1H, m), 3.41-3.50 (2H, m), 3.73-3.89 (5H, m), 3.97-4.05 (1H, m), 4.07-4.15 (1H, m), 4.32 (2H, s), 4.67 (2H, s), 6.65 (1H, d, J=2.3 Hz), 7.10-7.19 (2H, m), 7.25-7.33 (2H, m), 7.44-7.54 (1H, m), 7.67-7.79 (3H, m), OH proton was merged with H$_2$O signal.

Example 274, 275

Optically active 2-(4-(1,3-dimethyl-1H-pyrazol-4-yl)benzyl)-4-((1-hydroxybutan-2-yl)oxy)-1,2-dihydro-3H-pyrrolo[3,4-c]pyridin-3-one and Example 276, 277

Optically active 2-(4-(1,3-dimethyl-1H-pyrazol-4-yl)benzyl)-4-(2-hydroxybutoxy)-1,2-dihydro-3H-pyrrolo[3,4-c]pyridin-3-one

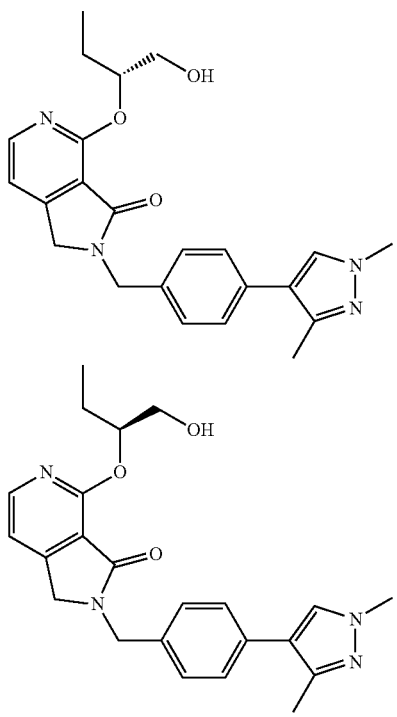

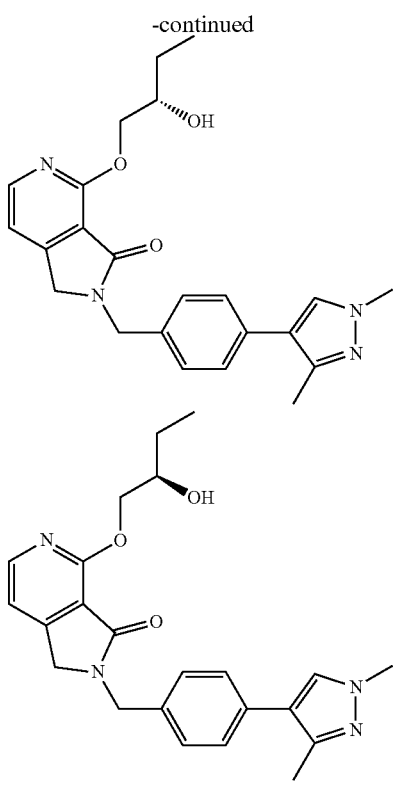

To a solution of ethyl 2-fluoro-4-iodonicotinate (1.0 g) obtained by a known method (Organic Letters, 7(10), 1943-1946; 2005) and butane-1,2-diol (0.92 g) in THF (50 mL) was added 60% sodium hydride (0.54 g) at 0° C., and the mixture was stirred under an argon atmosphere at the same temperature for 1 hr. The reaction solution was neutralized with 1N hydrochloric acid, and diluted with ethyl acetate. The organic layer was separated, washed with water and saturated brine, dried over anhydrous sodium sulfate, and concentrated. The residue was crudely purified by silica gel chromatography (hexane-ethyl acetate). To a solution of the crudely purified product (0.35 g) in DMF (10 mL) were added tributyl(vinyl)tin (0.46 g), trans-dichlorobis(triphenylphosphine)palladium(II) (0.034 g) and lithium chloride (0.30 g), and the mixture was stirred under an argon atmosphere at 90° C. for 2 hr. To the reaction solution was added saturated aqueous potassium fluoride solution, the resulting precipitate was filtered off through Celite, and the filtrate was diluted with water and ethyl acetate. The organic layer was separated, washed with saturated brine, dried over anhydrous sodium sulfate, and concentrated. The residue was crudely purified by silica gel chromatography (hexane-ethyl acetate). A mixture of the crudely purified product (0.23 g), sodium periodate (0.92 g) and osmium oxide (immobilized catalyst I) (0.11 g), and acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.23 g) was dissolved in THF (3 mL), (4-(1,3-dimethyl-1H-pyrazol-4-yl)phenyl)methanamine (0.17 g) and anhydrous magnesium sulfate (0.21 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.27 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK AD (trade name), 50 mmID×500 mmL, manufactured by Dicel Corporation, mobile phase: hexane/ethanol=500/500) to give the title compound.

retention time: tR1 (Example 274, yield 0.025 g)
MS: $[M+H]^+$ 407.1
$^1$H NMR (300 MHz, CDCl$_3$) δ 1.08 (3H, t, J=7.5 Hz), 1.76-2.03 (2H, m), 2.38 (3H, s), 3.78-3.97 (5H, m), 4.17-4.42 (3H, m), 4.66-4.84 (2H, m), 5.04-5.14 (1H, m), 6.97 (1H, d, J=5.3 Hz), 7.29-7.38 (4H, m), 7.41 (1H, s), 8.22 (1H, d, J=5.1 Hz).

retention time: tR2 (Example 275, yield 0.012 g)
MS: $[M+H]^+$ 407.2
$^1$H NMR (300 MHz, CDCl$_3$) δ 1.08 (3H, t, J=7.5 Hz), 1.76-2.03 (2H, m), 2.37 (3H, s), 3.83-3.90 (5H, m), 4.27 (3H, s), 4.67-4.84 (2H, m), 5.09 (1H, brs), 6.97 (1H, d, J=5.1 Hz), 7.28-7.37 (4H, m), 7.41 (1H, s), 8.22 (1H, d, J=5.1 Hz).

retention time: tR3 (Example 276, yield 0.047 g)
MS: $[M+H]^+$ 407.2
$^1$H NMR (300 MHz, CDCl$_3$) δ 1.05 (3H, t, J=7.5 Hz), 1.59-1.67 (2H, m), 2.37 (3H, s), 3.87 (3H, s), 3.94-4.17 (2H, m), 4.27 (2H, s), 4.36-4.45 (1H, m), 4.57 (1H, dd, J=11.1, 2.3 Hz), 4.75 (2H, s), 6.97 (1H, d, J=5.3 Hz), 7.29-7.38 (4H, m), 7.41 (1H, s), 8.23 (1H, d, J=5.3 Hz).

retention time: tR4 (Example 277, yield 0.052 g)
MS: $[M+H]^+$ 407.2
$^1$H NMR (300 MHz, CDCl$_3$) δ 1.05 (3H, t, J=7.5 Hz), 1.60 (2H, brs), 2.37 (3H, s), 3.87 (3H, s), 4.02 (2H, brs), 4.27 (2H, s), 4.35-4.46 (1H, m), 4.57 (1H, dd, J=11.1, 2.3 Hz), 4.75 (2H, s), 6.97 (1H, d, J=5.3 Hz), 7.28-7.38 (4H, m), 7.40 (1H, s), 8.23 (1H, d, J=5.1 Hz).

Example 278

2-(4-bromobenzyl)-4-(2-chloro-6-fluorophenoxy)-1,2-dihydro-3H-pyrrolo[3,4-c]pyridin-3-one

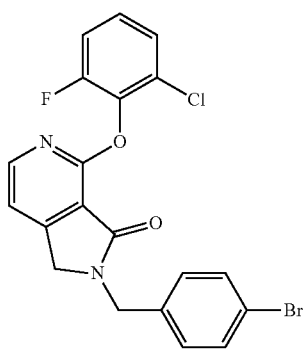 [SMILES: O=C1c2c(ccnc2Oc2c(F)cccc2Cl)CN1Cc1ccc(Br)cc1]

A mixture of ethyl 2-(2-chloro-6-fluorophenoxy)-4-vinylnicotinate (0.25 g) obtained in Reference Example 119, sodium periodate (1.84 g) and osmium oxide (immobilized catalyst I) (0.22 g), and acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.25 g) was dissolved in THF (3 mL), (4-bromophenyl)methanamine (0.14 g) and anhydrous magnesium sulfate (0.19 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.25 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.21 g).

MS: $[M+H]^+$ 446.9
$^1$H NMR (300 MHz, DMSO-d$_6$) δ 4.51 (2H, s), 4.70 (2H, s), 7.30 (2H, d, J=8.3 Hz), 7.40 (2H, d, J=5.3 Hz), 7.43-7.51 (2H, m), 7.54-7.60 (2H, m), 8.20 (1H, d, J=5.1 Hz).

Example 279

2-(4-bromo-2-fluorobenzyl)-4-(2-chloro-6-fluorophenoxy)-1,2-dihydro-3H-pyrrolo[3,4-c]pyridin-3-one

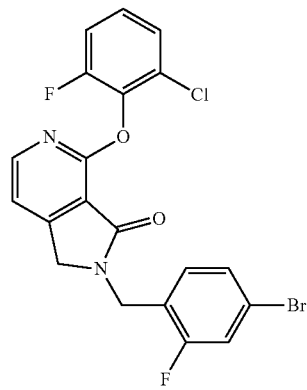

A mixture of ethyl 2-(2-chloro-6-fluorophenoxy)-4-vinylnicotinate (0.25 g) obtained in Reference Example 119, sodium periodate (1.84 g) and osmium oxide (immobilized catalyst I) (0.22 g), and acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.30 g) was dissolved in THF (3 mL), (4-bromo-2-fluorophenyl)methanamine (0.19 g) and anhydrous magnesium sulfate (0.22 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.30 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.31 g).

MS: $[M+H]^+$ 464.9

$^1$H NMR (300 MHz, DMSO-d$_6$) δ 4.54 (2H, s), 4.75 (2H, s), 7.33-7.52 (6H, m), 7.60 (1H, dd, J=9.6, 1.9 Hz), 8.21 (1H, d, J=5.3 Hz).

Example 280

4-(2-chloro-6-fluorophenoxy)-2-(4-(1,3-dimethyl-1H-pyrazol-4-yl)-2-fluorobenzyl)-1,2-dihydro-3H-pyrrolo[3,4-c]pyridin-3-one

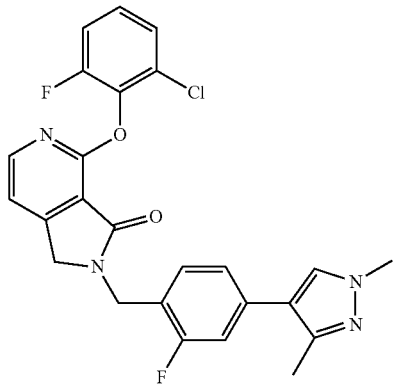 [SMILES: Cc1nn(C)cc1-c1ccc(CN2Cc3ccnc(Oc4c(F)cccc4Cl)c3C2=O)c(F)c1]

To a solution of 2-(4-bromo-2-fluorobenzyl)-4-(2-chloro-6-fluorophenoxy)-1,2-dihydro-3H-pyrrolo[3,4-c]pyridin-3-one (0.31 g) obtained in Example 279 in DME (3 mL)-water (3 mL) were added 1,3-dimethyl-4-(4,4,5,5-tetramethyl-1,3,2-dioxaborolan-2-yl)-1H-pyrazole (0.16 g), sodium carbonate (0.28 g) and (1,1-bis(diphenylphosphino)ferrocene)dichloropalladium(II) (0.048 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.049 g).

MS: [M+H]$^+$ 481.1

$^1$H NMR (300 MHz, DMSO-d$_6$) δ 2.30 (3H, s), 3.78 (3H, s), 4.56 (2H, s), 4.77 (2H, s), 7.24-7.31 (2H, m), 7.34-7.51 (5H, m), 7.97 (1H, s), 8.20 (1H, d, J=5.1 Hz).

Example 281

4-(2-chloro-6-fluorophenoxy)-2-(4-(1,3-dimethyl-1H-pyrazol-4-yl)benzyl)-1,2-dihydro-3H-pyrrolo[3,4-c]pyridin-3-one

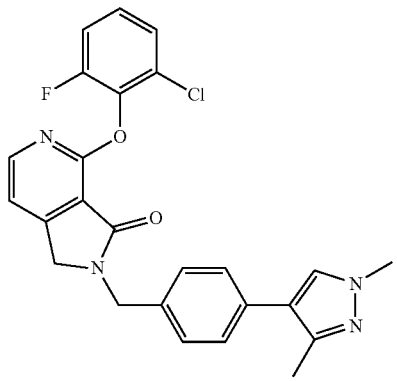

To a solution of 2-(4-bromobenzyl)-4-(2-chloro-6-fluorophenoxy)-1,2-dihydro-3H-pyrrolo[3,4-c]pyridin-3-one (0.20 g) obtained in Example 278 in DME (2 mL)-water (2 mL) were added 1,3-dimethyl-4-(4,4,5,5-tetramethyl-1,3,2-dioxaborolan-2-yl)-1H-pyrazole (0.11 g), sodium carbonate (0.19 g) and (1,1-bis(diphenylphosphino)ferrocene)dichloropalladium(II) (0.033 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.10 g).

MS: [M+H]$^+$ 463.1

$^1$H NMR (300 MHz, DMSO-d$_6$) δ 2.28 (3H, s), 3.78 (3H, s), 4.52 (2H, s), 4.72 (2H, s), 7.29-7.53 (8H, m), 7.87 (1H, s), 8.20 (1H, d, J=5.1 Hz).

Example 282

2-(4-bromo-2-fluorobenzyl)-4-(2,6-difluoro-3-methoxyphenoxy)-1,2-dihydro-3H-pyrrolo[3,4-c]pyridin-3-one

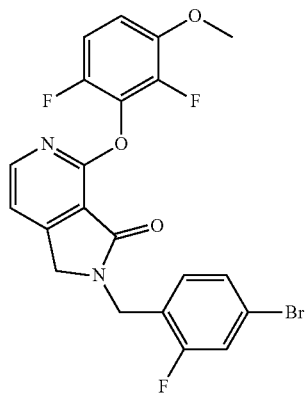 [SMILES: COc1ccc(F)c(Oc2nccc3c2C(=O)N(Cc2ccc(Br)cc2F)C3)c1F]

A mixture of ethyl 2-(2,6-difluoro-3-methoxyphenoxy)-4-vinylnicotinate (0.31 g) obtained in Reference Example 120, sodium periodate (0.98 g) and osmium oxide (immobilized catalyst I) (0.12 g), and acetonitrile (5 mL)-acetone (5 mL)-water (5 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.16 g) was dissolved in THF (3 mL), (4-bromo-2-fluorophenyl)methanamine (0.097 g) and anhydrous magnesium sulfate (0.11 g) were added, and the mixture was stirred under an argon atmosphere at room temperature for 30 min. The insoluble material was filtered off, and the filtrate was concentrated. To a solution of the residue in acetic acid (3 mL) was added sodium triacetoxyhydroborate (0.15 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (0.13 g).

MS: [M+H]$^+$ 478.9

¹H NMR (300 MHz, DMSO-d₆) δ 3.88 (3H, s), 4.54 (2H, s), 4.74 (2H, s), 7.08-7.29 (2H, m), 7.32-7.47 (3H, m), 7.59 (1H, dd, J=9.6, 1.9 Hz), 8.22 (1H, d, J=5.1 Hz).

Example 283

4-(2,6-difluoro-3-methoxyphenoxy)-2-(4-(1,3-dimethyl-1H-pyrazol-4-yl)-2-fluorobenzyl)-1,2-dihydro-3H-pyrrolo[3,4-c]pyridin-3-one

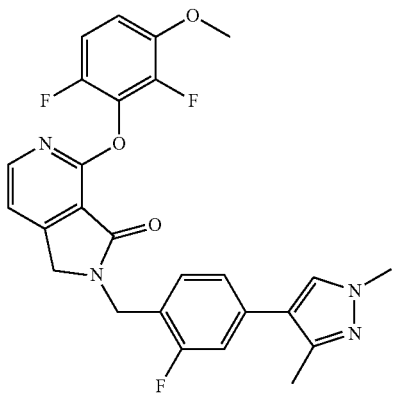 [SMILES: COc1ccc(F)c(Oc2nccc3c2C(=O)N(Cc2ccc(-c4cn(C)nc4C)cc2F)C3)c1F]

To a solution of 2-(4-bromo-2-fluorobenzyl)-4-(2,6-difluoro-3-methoxyphenoxy)-1,2-dihydro-3H-pyrrolo[3,4-c]pyridin-3-one (0.12 g) obtained in Example 282 in DME (2 mL)-water (2 mL) were added 1,3-dimethyl-4-(4,4,5,5-tetramethyl-1,3,2-dioxaborolan-2-yl)-1H-pyrazole (0.088 g), sodium carbonate (0.11 g) and (1,1-bis(diphenylphosphino)ferrocene)dichloropalladium(II) (0.019 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with THF-hexane to give the title compound (0.11 g).

MS: [M+H]⁺ 495.2

¹H NMR (300 MHz, DMSO-d₆) δ 2.30 (3H, s), 3.78 (3H, s), 3.88 (3H, s), 4.55 (2H, s), 4.77 (2H, s), 7.07-7.18 (1H, m), 7.20-7.31 (3H, m), 7.34-7.46 (2H, m), 7.97 (1H, s), 8.22 (1H, d, J=5.3 Hz).

Example 284

2-(4-bromobenzyl)-4-((tetrahydrofuran-2-yl)methoxy)-1,2-dihydro-3H-pyrrolo[3,4-c]pyridin-3-one

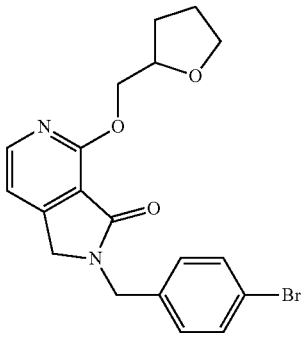 [SMILES: O=C1c2c(ccnc2OCC2CCCO2)CN1Cc1ccc(Br)cc1]

Isopropyl 4-formyl-2-((tetrahydrofuran-2-yl)methoxy)nicotinate (2.1 g) obtained in Reference Example 123 was dissolved in THF (15 mL), (4-bromophenyl)methanamine (1.33 g) and anhydrous magnesium sulfate (1.72 g) were added, and the mixture was stirred under an argon atmosphere at room temperature for 20 min. The insoluble material was filtered off, and the filtrate was concentrated. To a solution of the residue in acetic acid (15 mL) was added sodium triacetoxyhydroborate (2.27 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) to give the title compound (2.01 g).

MS: [M+H]⁺ 403.0

¹H NMR (300 MHz, DMSO-d₆) δ 1.67-1.89 (2H, m), 1.91-2.06 (2H, m), 3.60-3.72 (1H, m), 3.77-3.88 (1H, m), 4.17-4.27 (1H, m), 4.32-4.43 (4H, m), 4.63 (2H, s), 7.15-7.28 (3H, m), 7.49-7.57 (2H, m), 8.27 (1H, d, J=5.3 Hz).

Example 285

2-(4-(1-methyl-1H-pyrazol-4-yl)benzyl)-4-(tetrahydrofuran-2-yl)methoxy)-1,2-dihydro-3H-pyrrolo[3,4-c]pyridin-3-one

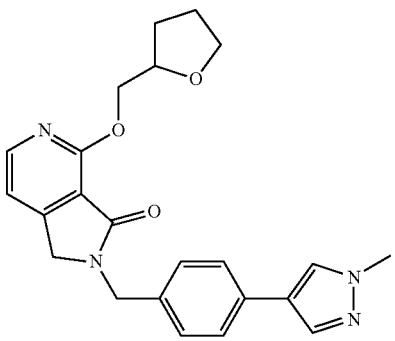 [SMILES: Cn1cc(-c2ccc(CN3Cc4ccnc(OCC5CCCO5)c4C3=O)cc2)cn1]

To a solution of 2-(4-bromobenzyl)-4-((tetrahydrofuran-2-yl)methoxy)-1,2-dihydro-3H-pyrrolo[3,4-c]pyridin-3-one (0.61 g) obtained in Example 284 in DME (6 mL)-water (6 mL) were added 1-methyl-4-(4,4,5,5-tetramethyl-1,3,2-dioxaborolan-2-yl)-1H-pyrazole (0.35 g), sodium carbonate (0.64 g) and (1,1-bis(diphenylphosphino)ferrocene)dichloropalladium(II) (0.11 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with THF-hexane to give the title compound (0.44 g).

MS: [M+H]⁺ 405.1

¹H NMR (300 MHz, DMSO-d₆) δ 1.69-1.89 (2H, m), 1.93-2.08 (2H, m), 3.61-3.72 (1H, m), 3.79-3.89 (4H, m), 4.19-4.28 (1H, m), 4.32-4.43 (4H, m), 4.64 (2H, s), 7.18 (1H, d, J=5.1 Hz), 7.25 (2H, d, J=8.1 Hz), 7.53 (2H, d, J=8.3 Hz), 7.82 (1H, s), 8.10 (1H, s), 8.26 (1H, d, J=5.1 Hz).

Example 286

2-(4-(1H-pyrazol-4-yl)benzyl)-4-((tetrahydrofuran-2-yl)methoxy)-1,2-dihydro-3H-pyrrolo[3,4-c]pyridin-3-one

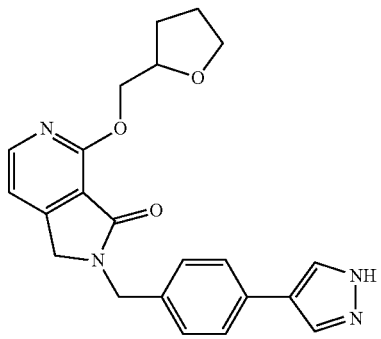

To a solution of 2-(4-bromobenzyl)-4-((tetrahydrofuran-2-yl)methoxy)-1,2-dihydro-3H-pyrrolo[3,4-c]pyridin-3-one (0.51 g) obtained in Example 284 in DME (5 mL)-water (5 mL) were added tert-butyl 4-(4,4,5,5-tetramethyl-1,3,2-dioxaborolan-2-yl)-1H-pyrazole-1-carboxylate (0.41 g), sodium carbonate (0.53 g) and (1,1-bis(diphenylphosphino)ferrocene)dichloropalladium(II) (0.046 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.26 g).

MS: [M+H]$^+$ 391.1

$^1$H NMR (300 MHz, DMSO-d$_6$) δ1.70-1.89 (2H, m), 1.92-2.08 (2H, m), 3.60-3.73 (1H, m), 3.78-3.91 (1H, m), 4.17-4.30 (1H, m), 4.31-4.46 (4H, m), 4.64 (2H, s), 7.18 (1H, d, J=5.1 Hz), 7.25 (2H, d, J=8.1 Hz), 7.58 (2H, d, J=8.1 Hz), 7.80-8.20 (2H, m), 8.26 (1H, d, J=5.3 Hz), 12.92 (1H, brs).

Example 287

4-((tetrahydrofuran-2-yl)methoxy)-2-(4-(1-(2,2,2-trifluoroethyl)-1H-pyrazol-4-yl)benzyl)-1,2-dihydro-3H-pyrrolo[3,4-c]pyridin-3-one

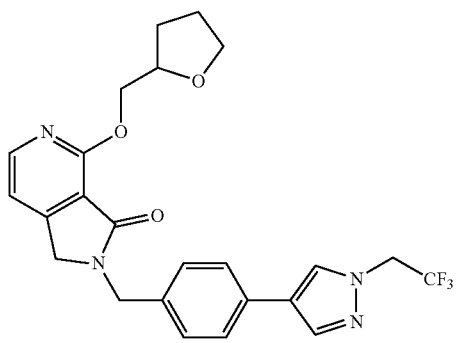 [SMILES: O=C1c2c(ccnc2OCC2CCCO2)CN1Cc1ccc(-c2cnn(CC(F)(F)F)c2)cc1]

A solution of 2-(4-(1H-pyrazol-4-yl)benzyl)-4-((tetrahydrofuran-2-yl)methoxy)-1,2-dihydro-3H-pyrrolo[3,4-c]pyridin-3-one (0.10 g) obtained in Example 286, 2,2,2-trifluoroethyl trifluoromethanesulfonate (0.095 g) and potassium carbonate (0.071 g) in acetonitrile (4 mL) was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with diethyl ether to give the title compound (0.055 g).

MS: [M+H]$^+$ 473.1

$^1$H NMR (300 MHz, DMSO-d$_6$) δ 1.69-1.89 (2H, m), 1.92-2.08 (2H, m), 3.62-3.72 (1H, m), 3.78-3.89 (1H, m), 4.16-4.29 (1H, m), 4.32-4.43 (4H, m), 4.65 (2H, s), 5.14 (2H, q, J=9.1 Hz), 7.18 (1H, d, J=5.1 Hz), 7.28 (2H, d, J=8.3 Hz), 7.58 (2H, d, J 8.1 Hz), 8.02 (1H, s), 8.23-8.31 (2H, m).

Example 288

2-(4-(1-(cyclopropylmethyl)-1H-pyrazol-4-yl)benzyl)-4-((tetrahydrofuran-2-yl) methoxy)-1,2-dihydro-3H-pyrrolo[3,4-c]pyridin-3-one

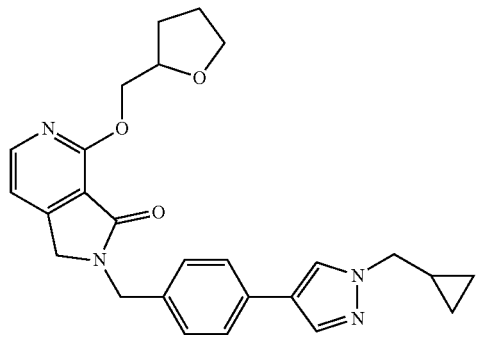 [SMILES: O=C1c2c(ccnc2OCC2CCCO2)CN1Cc1ccc(-c2cnn(CC3CC3)c2)cc1]

To a solution of 2-(4-bromobenzyl)-4-((tetrahydrofuran-2-yl)methoxy)-1,2-dihydro-3H-pyrrolo[3,4-c]pyridin-3-one (0.10 g) obtained in Example 284 in DME (3 mL)-water (3 mL) were added 1-(cyclopropylmethyl)-4-(4,4,5,5-tetramethyl-1,3,2-dioxaborolan-2-yl)-1H-pyrazole (0.068 g), sodium carbonate (0.11 g) and (1,1-bis(diphenylphosphino)ferrocene)dichloropalladium(II) (0.010 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.025 g).

MS: [M+H]$^+$ 445.2

$^1$H NMR (300 MHz, DMSO-d$_6$) δ 0.33-0.42 (2H, m), 0.48-0.58 (2H, m), 1.17-1.32 (1H, m), 1.69-1.89 (2H, m), 1.93-2.07 (2H, m), 3.62-3.72 (1H, m), 3.79-3.89 (1H, m), 3.97 (2H, d, J=7.0 Hz), 4.18-4.28 (1H, m), 4.32-4.44 (4H, m), 4.64 (2H, s), 7.18 (1H, d, J=5.1 Hz), 7.25 (2H, d, J=8.1 Hz), 7.54 (2H, d, J=8.1 Hz), 7.83 (1H, s), 8.17 (1H, s), 8.26 (1H, d, J=5.1 Hz).

Example 289

2-(4-(pyrazolo[1,5-a]pyridin-3-yl)benzyl)-4-((tetrahydrofuran-2-yl)methoxy)-1,2-dihydro-3H-pyrrolo[3,4-c]pyridin-3-one

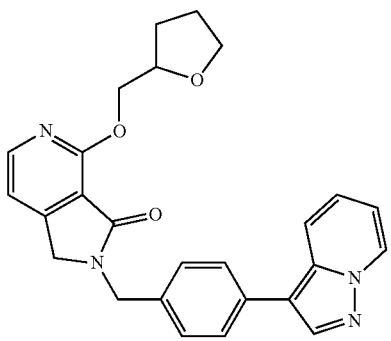 [SMILES: O=C1c2c(ccnc2OCC2CCCO2)CN1Cc1ccc(-c2cnn3ccccc23)cc1]

To a solution of 2-(4-bromobenzyl)-4-((tetrahydrofuran-2-yl)methoxy)-1,2-dihydro-3H-pyrrolo[3,4-c]pyridin-3-one (0.15 g) obtained in Example 284 in DME (4 mL)-water (4 mL) were added 3-(4,4,5,5-tetramethyl-1,3,2-dioxaborolan-2-yl)pyrazolo[1,5-a]pyridine (0.10 g), sodium carbonate (0.16 g) and (1,1-bis(diphenylphosphino)ferrocene)dichloropalladium(II) (0.014 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether to give the title compound (0.032 g).

MS: [M+H]$^+$ 441.1

$^1$H NMR (300 MHz, DMSO-$d_6$) δ 1.72-1.89 (2H, m), 1.96-2.05 (2H, m), 3.61-3.74 (1H, m), 3.77-3.90 (1H, m), 4.17-4.28 (1H, m), 4.34-4.45 (4H, m), 4.70 (2H, s), 6.87-7.00 (1H, m), 7.19 (1H, d, J=5.1 Hz), 7.27-7.41 (3H, m), 7.67 (2H, d, J=8.1 Hz), 7.95 (1H, d, J=8.9 Hz), 8.27 (1H, d, J=5.3 Hz), 8.35 (1H, s), 8.73 (1H, d, J=7.0 Hz).

Example 290

4-(2-fluoro-5-(hydroxymethyl)phenoxy)-2-(4-(2-methylpyridin-4-yl)benzyl)-1,2-dihydro-3H-pyrrolo[3,4-c]pyridin-3-one

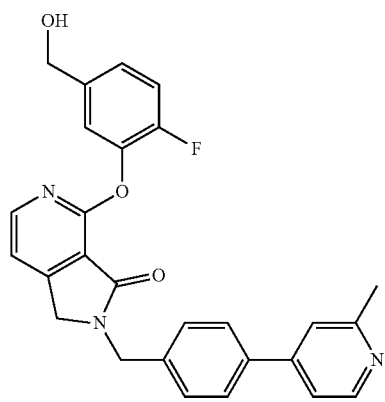 [SMILES: Cc1cc(-c2ccc(CN3Cc4ccnc(Oc5cc(CO)ccc5F)c4C3=O)cc2)ccn1]

A mixture of ethyl 2-(2-fluoro-5-(hydroxymethyl)phenoxy)-4-vinylnicotinate (0.21 g) obtained in Reference Example 261, sodium periodate (0.71 g) and osmium oxide (immobilized catalyst I) (0.084 g) and acetonitrile (4 mL)-acetone (4 mL)-water (4 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.079 g) was dissolved in THF (3 mL), (4-(2-methylpyridin-4-yl)phenyl)methanamine (0.049 g) obtained in Reference Example 63 and anhydrous magnesium sulfate (0.060 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.079 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with THF-ethyl acetate-hexane to give the title compound (0.022 g).

MS: [M+H]$^+$ 456.1

$^1$H NMR (300 MHz, DMSO-$d_6$) δ 2.53 (3H, s), 4.48-4.56 (4H, m), 4.79 (2H, s), 5.30 (1H, t, J=5.9 Hz), 7.21-7.38 (4H, m), 7.43-7.51 (3H, m), 7.57 (1H, s), 7.79 (2H, d, J=8.3 Hz), 8.21 (1H, d, J=5.1 Hz), 8.49 (1H, d, J=5.3 Hz)

Example 291

4-(2-fluoro-5-(methoxymethyl)phenoxy)-2-(4-(2-methylpyridin-4-yl)benzyl)-1,2-dihydro-3H-pyrrolo[3,4-c]pyridin-3-one

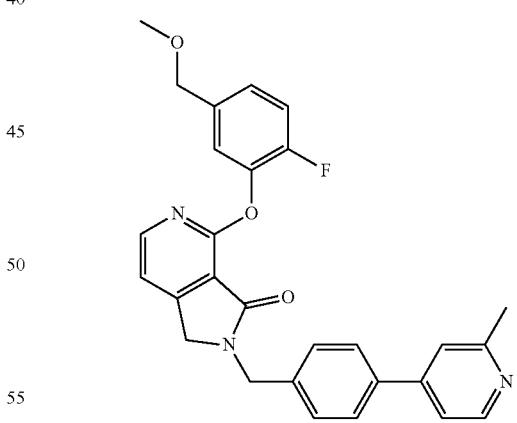

A mixture of ethyl 2-(2-fluoro-5-(methoxymethyl)phenoxy)-4-vinylnicotinate (0.28 g) obtained in Reference Example 124, sodium periodate (0.90 g) and osmium oxide (immobilized catalyst I) (0.11 g) and acetonitrile (4 mL)-acetone (4 mL)-water (4 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.10 g) was dissolved in THF (3 mL), (4-(2-methylpyridin- 4-yl)phenyl)methanamine (0.060 g) obtained in Reference Example 63 and anhydrous magnesium sulfate (0.072 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.095 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.067 g).

MS: [M+H]$^+$ 470.1

$^1$H NMR (300 MHz, DMSO-d$_6$) δ 2.53 (3H, s), 3.31 (3H, s), 4.42 (2H, s), 4.52 (2H, s), 4.79 (2H, s), 7.23-7.40 (4H, m), 7.43-7.52 (3H, m), 7.57 (1H, s), 7.79 (2H, d, J=8.3 Hz), 8.21 (1H, d, J=5.3 Hz), 8.49 (1H, d, J=5.3 Hz).

Example 292, Example 293

Optically active 1,5-anhydro-3-O-(2-(4-chlorobenzyl)-3-oxo-2,3-dihydro-1H-isoindol-4-yl)-2-deoxy-threo-pentitol and Example 294, Example 295

Optically active 1,5-anhydro-2-O-(2-(4-chlorobenzyl)-3-oxo-2,3-dihydro-1H-isoindol-4-yl)-4-deoxy-threo-pentitol

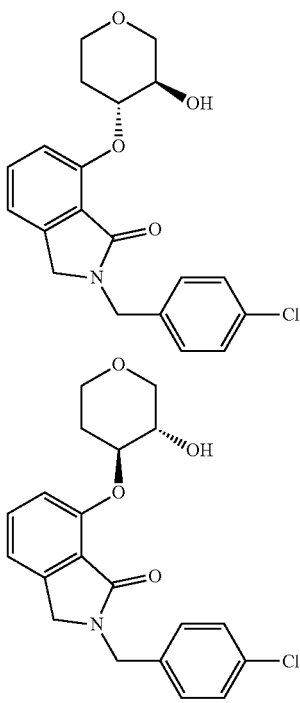

-continued

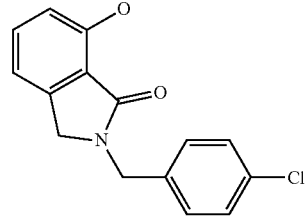

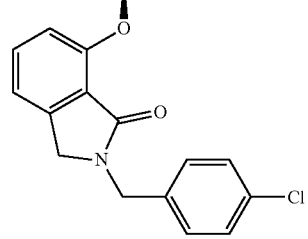

To a solution of 2-(4-chlorobenzyl)-7-hydroxyisoindolin-1-one (0.47 g) obtained in Reference Example 126 in ethanol (5 mL) were added 3,7-dioxabicyclo[4.1.0]heptane (0.69 g) and pyridine (1.1 g), and the mixture was stirred under an argon atmosphere at 100° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK IC (trade name), 50 mmID×500 mmL, manufactured by Dicel Corporation, mobile phase: hexane/2-propanol=300/700) to give the title compound.

retention time: tR3 (Example 292, yield 0.063 g)
MS: [M+H]$^+$ 374.1

$^1$H NMR (300 MHz, DMSO-d$_6$) δ1.54-1.68 (1H, m), 2.05-2.17 (1H, m), 3.15-3.25 (1H, m), 3.36-3.47 (1H, m), 3.54-3.65 (1H, m), 3.76-3.92 (2H, m), 4.26-4.42 (3H, m), 4.66 (2H, s), 5.38 (1H, d, J=4.3 Hz), 7.08-7.19 (2H, m), 7.26-7.34 (2H, m), 7.38-7.44 (2H, m), 7.46-7.53 (1H, m).

retention time: tR4 (Example 293, yield 0.058 g)
MS: [M+H]$^+$ 374.0

$^1$H NMR (300 MHz, DMSO-d$_6$) δ 1.54-1.69 (1H, m), 2.04-2.19 (1H, m), 3.20 (1H, dd, J=11.3, 7.7 Hz), 3.36-3.46 (1H, m), 3.53-3.66 (1H, m), 3.77-3.91 (2H, m), 4.25-4.42 (3H, m), 4.66 (2H, s), 5.38 (1H, d, J=4.5 Hz), 7.08-7.18 (2H, m), 7.26-7.33 (2H, m), 7.38-7.44 (2H, m), 7.45-7.54 (1H, m).

retention time: tR1 (Example 294, yield 0.058 g)
MS: [M+H]$^+$ 374.1

$^1$H NMR (300 MHz, DMSO-d$_6$) δ 1.42-1.57 (1H, m), 1.96-2.09 (1H, m), 3.36-3.49 (2H, m), 3.72-3.84 (2H, m), 3.99 (1H, dd, J=11.5, 4.0 Hz), 4.06-4.15 (1H, m), 4.31 (2H, s), 4.66 (2H, s), 5.33 (1H, d, J=4.0 Hz), 7.14 (2H, dd, J=7.7, 3.4 Hz), 7.26-7.33 (2H, m), 7.38-7.44 (2H, m), 7.45-7.53 (1H, m).

retention time: tR2 (Example 295, yield 0.058 g)
MS: [M+H]$^+$ 374.0

¹H NMR (300 MHz, DMSO-d₆) δ 1.41-1.57 (1H, m), 1.95-2.09 (1H, m), 3.35-3.50 (2H, m), 3.70-3.86 (2H, m), 3.99 (1H, dd, J=11.4, 3.9 Hz), 4.10 (1H, dt, J=7.0, 3.6 Hz), 4.31 (2H, s), 4.66 (2H, s), 5.33 (1H, d, J=4.0 Hz), 7.14 (2H, dd, J=7.7, 3.4 Hz), 7.26-7.34 (2H, m), 7.37-7.44 (2H, m), 7.45-7.53 (1H, m).

Example 296

4-((tetrahydrofuran-2-yl)methoxy)-2-(4-(4,5,6,7-tetrahydropyrazolo[1,5-a]pyridin-3-yl)benzyl)-1,2-dihydro-3H-pyrrolo[3,4-c]pyridin-3-one

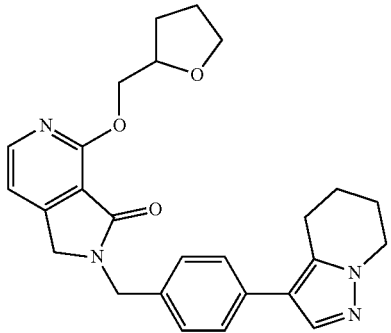 [SMILES: O=C1c2c(ccnc2OCC2CCCO2)CN1Cc1ccc(-c2cnn3c2CCCC3)cc1]

A solution of 2-(4-(pyrazolo[1,5-a]pyridin-3-yl)benzyl)-4-((tetrahydrofuran-2-yl)methoxy)-1,2-dihydro-3H-pyrrolo[3,4-c]pyridin-3-one (0.027 g) obtained in Example 289 and 10% palladium carbon (0.020 g) in ethanol (2 mL) was stirred under a hydrogen atmosphere at room temperature overnight. The insoluble material was filtered off, and the filtrate was concentrated. The residue was purified by NH silica gel chromatography (hexane-ethyl acetate), and solidified with ethyl acetate-hexane to give the title compound (0.018 g).
MS: [M+H]⁺ 445.2
¹H NMR (300 MHz, DMSO-d₆) δ 1.71-1.87 (4H, m), 1.93-2.07 (4H, m), 2.89 (2H, t, J=6.3 Hz), 3.62-3.72 (1H, m), 3.79-3.89 (1H, m), 4.08 (2H, t, J=6.0 Hz), 4.18-4.27 (1H, m), 4.32-4.44 (4H, m), 4.65 (2H, s), 7.18 (1H, d, J=5.1 Hz), 7.27 (2H, d, J=8.3 Hz), 7.38-7.45 (2H, m), 7.68 (1H, s), 8.26 (1H, d, J=5.1 Hz).

Example 297

4-fluoro-3-((2-(4-(1-methyl-1H-pyrazol-4-yl)benzyl)-3-oxo-2,3-dihydro-1H-pyrrolo[3,4-c]pyridin-4-yl)oxy)benzonitrile

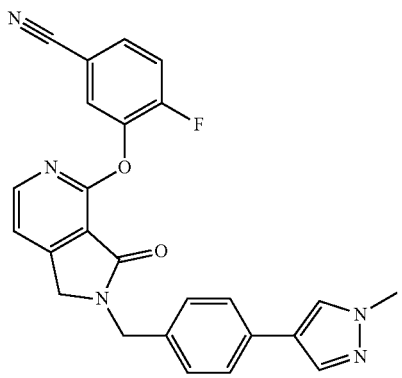 [SMILES: Cn1cc(-c2ccc(CN3Cc4ccnc(Oc5cc(C#N)ccc5F)c4C3=O)cc2)cn1]

To a solution of 3-((2-(4-bromobenzyl)-3-oxo-2,3-dihydro-1H-pyrrolo[3,4-c]pyridin-4-yl)oxy)-4-fluorobenzonitrile (0.10 g) obtained in Reference Example 128 in DME (3 mL)-water (3 mL) were added 1-methyl-4-(4,4,5,5-tetramethyl-1,3,2-dioxaborolan-2-yl)-1H-pyrazole (0.052 g), sodium carbonate (0.097 g) and (1,1-bis(diphenylphosphino)ferrocene)dichloropalladium(II) (0.008 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether to give the title compound (0.031 g).
MS: [M+H]⁺ 440.0
¹H NMR (300 MHz, DMSO-d₆) δ 3.85 (3H, s), 4.50 (2H, s), 4.70 (2H, s), 7.30 (2H, d, J=8.3 Hz), 7.41 (1H, d, J=5.3 Hz), 7.55 (2H, d, J=8.1 Hz), 7.66 (1H, dd, J=10.4, 8.7 Hz), 7.84 (1H, s), 7.86-7.93 (1H, m), 8.04-8.14 (2H, m), 8.22 (1H, d, J=5.1 Hz).

Example 298, Example 299

Optically active 1,5-anhydro-2-deoxy-3-O-(2-(2,4-difluorobenzyl)-3-oxo-2,3-dihydro-1H-isoindol-4-yl)-threo-pentitol and Example 300, Example 301

Optically active 1,5-anhydro-2-deoxy-4-O-(2-(2,4-difluorobenzyl)-3-oxo-2,3-dihydro-1H-isoindol-4-yl)-threo-pentitol

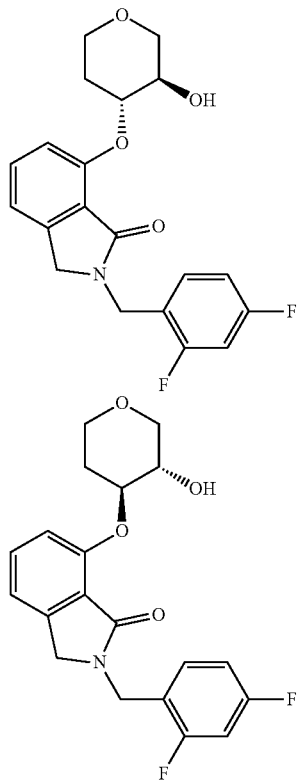

-continued

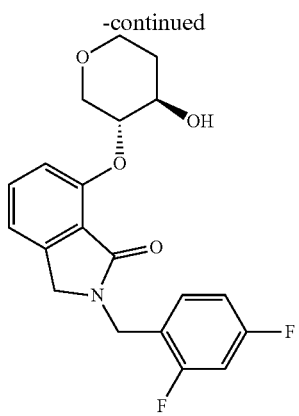

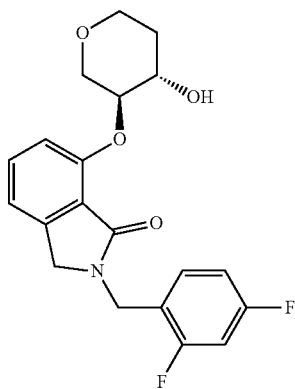

To a solution of 2-(2,4-difluorobenzyl)-7-hydroxyisoindolin-1-one (0.41 g) obtained in Reference Example 130 in ethanol (5 mL) were added 3,7-dioxabicyclo[4.1.0]heptane (0.60 g) and pyridine (0.95 g), and the mixture was stirred under an argon atmosphere at 100° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK IA (trade name), 50 mmID×500 mmL, manufactured by Dicel Corporation, mobile phase: hexane/2-propanol=900/100) to give the title compound.

retention time: tR2 (Example 298, yield 0.057 g)

MS: [M+H]$^+$ 376.1

$^1$H NMR (300 MHz, DMSO-d$_6$) δ 1.52-1.69 (1H, m), 2.04-2.19 (1H, m), 3.20 (1H, dd, J=11.3, 7.7 Hz), 3.37-3.48 (1H, m), 3.54-3.66 (1H, m), 3.76-3.92 (2H, m), 4.28-4.43 (3H, m), 4.69 (2H, s), 5.37 (1H, d, J=4.5 Hz), 7.03-7.19 (3H, m), 7.22-7.32 (1H, m), 7.34-7.45 (1H, m), 7.46-7.55 (1H, m).

retention time: tR3 (Example 299, yield 0.060 g)

MS: [M+H]$^+$ 376.1

$^1$H NMR (300 MHz, DMSO-d$_6$) δ 1.50-1.68 (1H, m), 2.04-2.18 (1H, m), 3.20 (1H, dd, J=11.3, 7.7 Hz), 3.36-3.48 (1H, m), 3.53-3.65 (1H, m), 3.75-3.91 (2H, m), 4.28-4.43 (3H, m), 4.69 (2H, s), 5.37 (1H, d, J=4.7 Hz), 7.02-7.19 (3H, m), 7.22-7.32 (1H, m), 7.33-7.44 (1H, m), 7.45-7.54 (1H, m).

retention time: tR1 (Example 300, yield 0.023 g)

MS: [M+H]$^+$ 376.1

$^1$H NMR (300 MHz, DMSO-d$_6$) δ1.40-1.57 (1H, m), 1.94-2.09 (1H, m), 3.36-3.49 (2H, m), 3.72-3.84 (2H, m), 3.94-4.03 (1H, m), 4.05-4.16 (1H, m), 4.33 (2H, s), 4.69 (2H, s), 5.32 (1H, d, J=4.2 Hz), 7.01-7.19 (3H, m), 7.21-7.32 (1H, m), 7.33-7.43 (1H, m), 7.45-7.53 (1H, m).

retention time: tR4 (Example 301, yield 0.023 g)

MS: [M+H]$^+$ 376.1

$^1$H NMR (300 MHz, DMSO-d$_6$) δ 1.39-1.55 (1H, m), 1.95-2.08 (1H, m), 3.37-3.50 (2H, m), 3.71-3.87 (2H, m), 3.99 (1H, dd, J=11.5, 4.0 Hz), 4.05-4.15 (1H, m), 4.33 (2H, s), 4.69 (2H, s), 5.32 (1H, d, J=4.0 Hz), 7.01-7.19 (3H, m), 7.22-7.32 (1H, m), 7.33-7.43 (1H, m), 7.45-7.53 (1H, m).

Example 302

4-(2-fluoro-5-(methoxymethyl)phenoxy)-2-(4-(1-methyl-1H-pyrazol-4-yl)benzyl)-1,2-dihydro-3H-pyrrolo[3,4-c]pyridin-3-one

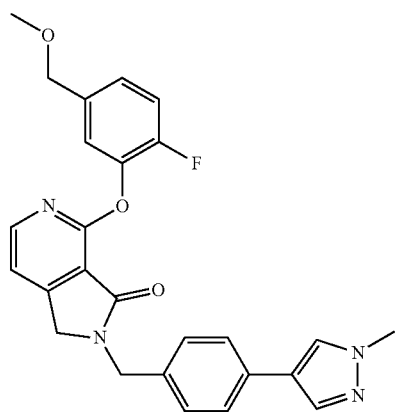 [SMILES: COCc1ccc(F)c(Oc2nccc3c2C(=O)N(Cc2ccc(-c4cnn(C)c4)cc2)C3)c1]

To a solution of 2-(4-bromobenzyl)-4-(2-fluoro-5-(methoxymethyl)phenoxy)-1H-pyrrolo[3,4-c]pyridin-3 (2H)-one (0.09 g) obtained in Reference Example 131 in DME (3 mL)-water (3 mL) were added 1-methyl-4-(4,4,5,5-tetramethyl-1,3,2-dioxaborolan-2-yl)-1H-pyrazole (0.045 g), sodium carbonate (0.083 g) and (1,1-bis(diphenylphosphino)ferrocene)dichloropalladium(II) (0.007 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether to give the title compound (0.0050 g).

MS: [M+H]$^+$ 459.1

$^1$H NMR (300 MHz, CDCl$_3$) δ 3.38 (3H, s), 3.95 (3H, s), 4.31 (2H, s), 4.45 (2H, s), 4.79 (2H, s), 7.04 (1H, d, J=5.3 Hz), 7.12-7.22 (2H, m), 7.29-7.39 (3H, m), 7.41-7.50 (2H, m), 7.61 (1H, s), 7.75 (1H, d, J=0.6 Hz), 8.18 (1H, d, J=5.1 Hz).

Example 303

4-(2-fluoro-4-(trifluoromethyl)phenoxy)-2-(4-(6-methylpyridazin-4-yl)benzyl)-1,2-dihydro-3H-pyrrolo[3,4-c]pyridin-3-one

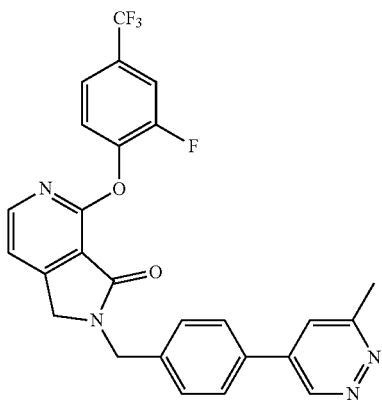 [SMILES: Cc1cc(-c2ccc(CN3Cc4ccnc(Oc5ccc(C(F)(F)F)cc5F)c4C3=O)cc2)cnn1]

To a solution of 2-(4-bromobenzyl)-4-(2-fluoro-4-(trifluoromethyl)phenoxy)-1H-pyrrolo[3,4-c]pyridin-3(2H)-one (0.10 g) obtained in Reference Example 132 in DME (3 mL)-water (3 mL) were added 3-methyl-5-(4,4,5,5-tetramethyl-1,3,2-dioxaborolan-2-yl)pyridazine (0.050 g), sodium carbonate (0.088 g) and (1,1-bis(diphenylphosphino)ferrocene)dichloropalladium(II) (0.0076 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.050 g).

MS: [M+H]$^+$ 495.1

$^1$H NMR (300 MHz, DMSO-d$_6$) δ 2.68 (3H, s), 4.55 (2H, s), 4.81 (2H, s), 7.43 (1H, d, J=5.1 Hz), 7.51 (2H, d, J=8.3 Hz), 7.61-7.75 (2H, m), 7.86-7.98 (4H, m), 8.24 (1H, d, J=5.1 Hz), 9.46 (1H, d, J=2.3 Hz).

Example 304

4-(2-fluoro-4-(trifluoromethyl)phenoxy)-2-(4-(1-methyl-1H-pyrazol-4-yl)benzyl)-1,2-dihydro-3H-pyrrolo[3,4-c]pyridin-3-one

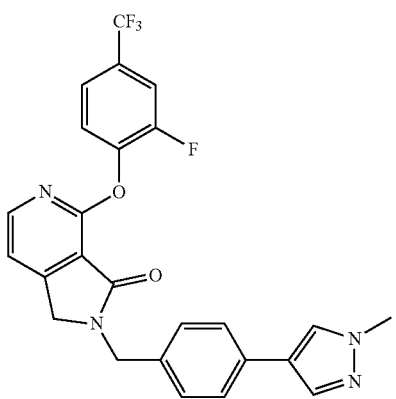 [SMILES: Cn1cc(-c2ccc(CN3Cc4ccnc(Oc5ccc(C(F)(F)F)cc5F)c4C3=O)cc2)cn1]

To a solution of 2-(4-bromobenzyl)-4-(2-fluoro-4-(trifluoromethyl)phenoxy)-1H-pyrrolo[3,4-c]pyridin-3(2H)-one (0.10 g) obtained in Reference Example 132 in DME (3 mL)-water (3 mL) were added 1-methyl-4-(4,4,5,5-tetramethyl-1,3,2-dioxaborolan-2-yl)-1H-pyrazole (0.048 g), sodium carbonate (0.088 g) and (1,1-bis(diphenylphosphino)ferrocene)dichloropalladium(II) (0.0076 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether to give the title compound (0.031 g).

MS: [M+H]$^+$ 483.1

$^1$H NMR (300 MHz, DMSO-d$_6$) δ 3.85 (3H, s), 4.50 (2H, s), 4.70 (2H, s), 7.30 (2H, d, J=8.1 Hz), 7.41 (1H, d, J=5.1 Hz), 7.55 (2H, d, J=8.1 Hz), 7.60-7.75 (2H, m), 7.84 (1H, s), 7.89-7.98 (1H, m), 8.12 (1H, s), 8.22 (1H, d, J=5.1 Hz).

Example 305

4-(2-fluoro-4-(trifluoromethyl)phenoxy)-2-(4-(1-methyl-1H-pyrazol-3-yl)benzyl)-1,2-dihydro-3H-pyrrolo[3,4-c]pyridin-3-one

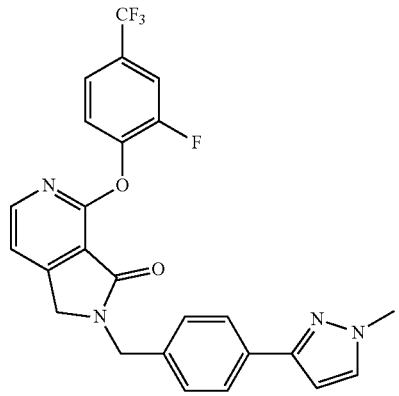 [SMILES: Cn1ccc(-c2ccc(CN3Cc4ccnc(Oc5ccc(C(F)(F)F)cc5F)c4C3=O)cc2)n1]

To a solution of 2-(4-bromobenzyl)-4-(2-fluoro-4-(trifluoromethyl)phenoxy)-1H-pyrrolo[3,4-c]pyridin-3(2H)-one (0.16 g) obtained in Reference Example 132 in DME (3 mL)-water (3 mL) were added 1-methyl-3-(4,4,5,5-tetramethyl-1,3,2-dioxaborolan-2-yl)-1H-pyrazole (0.076 g), sodium carbonate (0.14 g) and (1,1-bis(diphenylphosphino)ferrocene)dichloropalladium(II) dichloromethane adduct (0.027 g), and the mixture was stirred under an argon atmosphere at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether to give the title compound (0.014 g).

MS: [M+H]$^+$ 483.1

$^1$H NMR (300 MHz, DMSO-d$_6$) δ 3.87 (3H, s), 4.51 (2H, s), 4.73 (2H, s), 6.67 (1H, d, J=2.3 Hz), 7.34 (2H, d, J=8.1 Hz), 7.42 (1H, d, J=5.1 Hz), 7.61-7.81 (5H, m), 7.92 (1H, d, J=10.8 Hz), 8.23 (1H, d, J=5.1 Hz).

Example 306

4-(2-fluoro-4-(trifluoromethyl)phenoxy)-6-(4-(1-methyl-1H-pyrazol-4-yl)benzyl)-6,7-dihydro-5H-pyrrolo[3,4-d]pyrimidin-5-one

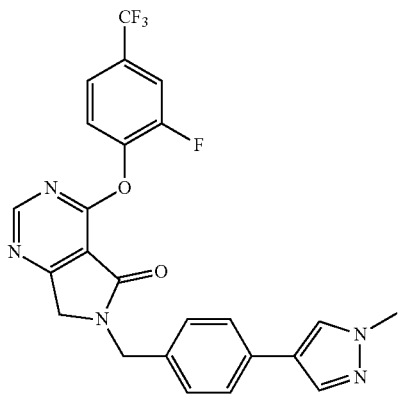 [SMILES: Cn1cc(-c2ccc(CN3Cc4ncnc(Oc5ccc(C(F)(F)F)cc5F)c4C3=O)cc2)cn1]

A mixed solution of methyl 4-(2-fluoro-4-(trifluoromethyl)phenoxy)-6-vinylpyrimidine-5-carboxylate (0.22 g) obtained in Reference Example 134, sodium periodate (0.69 g) and osmium oxide (immobilized catalyst I) (0.082 g) in acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.10 g) was dissolved in THF (3 mL), (4-(1-methyl-1H-pyrazol-4-yl)phenyl)methanamine (0.054 g) and anhydrous magnesium sulfate (0.070 g) were added, and the mixture was stirred under an argon atmosphere at room temperature for 20 min. The insoluble material was filtered off, and the filtrate was concentrated. To a solution of the residue in THF (3 mL) were added sodium triacetoxyhydroborate (0.30 g) and methanol (0.3 mL), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and solidified with ethyl acetate-hexane to give the title compound (0.023 g).

MS: [M+H]$^+$ 484.1

$^1$H NMR (300 MHz, DMSO-d$_6$) δ 3.86 (3H, s), 4.56 (2H, s), 4.73 (2H, s), 7.33 (2H, d, J=8.1 Hz), 7.55 (2H, d, J=8.1 Hz), 7.70-7.78 (2H, m), 7.84 (1H, s), 8.00 (1H, d, J=11.0 Hz), 8.12 (1H, s), 8.89 (1H, s).

Example 307

4-(4-(difluoromethyl)-2-fluorophenoxy)-6-(4-(1-methyl-1H-pyrazol-4-yl)benzyl)-6,7-dihydro-5H-pyrrolo[3,4-d]pyrimidin-5-one

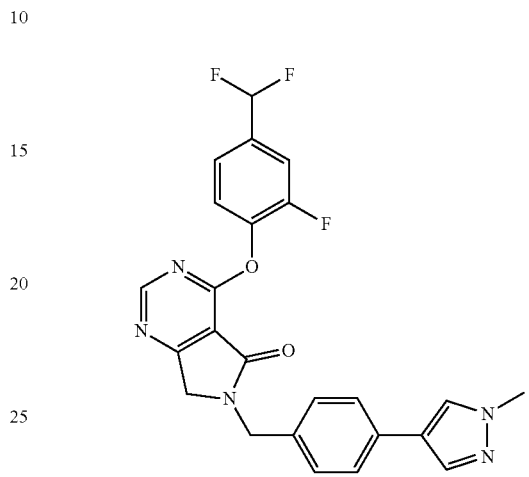

A mixed solution of methyl 4-(4-(difluoromethyl)-2-fluorophenoxy)-6-vinylpyrimidine-5-carboxylate (0.29 g) obtained in Reference Example 136, sodium periodate (0.94 g) and osmium oxide (immobilized catalyst I) (0.11 g) in acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.10 g) was dissolved in THF (3 mL), (4-(1-methyl-1H-pyrazol-4-yl)phenyl)methanamine (0.057 g) and anhydrous magnesium sulfate (0.074 g) were added, and the mixture was stirred under an argon atmosphere at room temperature for 20 min. The insoluble material was filtered off, and the filtrate was concentrated. To a solution of the residue in THF (3 mL) were added sodium triacetoxyhydroborate (0.33 g) and methanol (1 mL), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and solidified with THF-ethyl acetate-hexane to give the title compound (0.049 g).

MS: [M+H]$^+$ 466.1

$^1$H NMR (300 MHz, DMSO-d$_6$) δ 3.86 (3H, s), 4.55 (2H, s), 4.73 (2H, s), 6.88-7.40 (3H, m), 7.48-7.60 (3H, m), 7.61-7.76 (2H, m), 7.84 (1H, s), 8.12 (1H, s), 8.87 (1H, s).

Example 308

4-(2-fluoro-5-(2-hydroxypropan-2-yl)phenoxy)-2-(4-(1-methyl-1H-pyrazol-4-yl)benzyl)-1,2-dihydro-3H-pyrrolo[3,4-c]pyridin-3-one

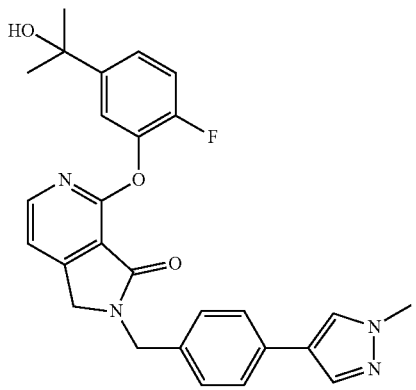 [SMILES: Cn1cc(-c2ccc(CN3Cc4ccnc(Oc5cc(C(C)(C)O)ccc5F)c4C3=O)cc2)cn1]

A mixed solution of ethyl 2-(2-fluoro-5-(2-hydroxypropan-2-yl)phenoxy)-4-vinylnicotinate (0.50 g) obtained in Reference Example 138, sodium periodate (1.55 g) and osmium oxide (immobilized catalyst I) (0.18 g) in acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.10 g) was dissolved in THF (3 mL), (4-(1-methyl-1H-pyrazol-4-yl)phenyl)methanamine (0.054 g) and anhydrous magnesium sulfate (0.069 g) were added, and the mixture was stirred under an argon atmosphere at room temperature for 20 min. The insoluble material was filtered off, and the filtrate was concentrated. To a solution of the residue in THF (3 mL) were added sodium triacetoxyhydroborate (0.29 g) and methanol (0.3 mL), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and solidified with ethyl acetate-hexane to give the title compound (0.035 g).

MS: [M+H]$^+$ 473.2

$^1$H NMR (300 MHz, DMSO-d$_6$) δ 1.44 (6H, s), 3.85 (3H, s), 4.48 (2H, s), 4.70 (2H, s), 5.13 (1H, s), 7.17-7.45 (6H, m), 7.55 (2H, d, J=8.3 Hz), 7.84 (1H, s), 8.11 (1H, s), 8.20 (1H, d, J=5.1 Hz).

Example 309

4-(2-fluoro-4-(trifluoromethyl)phenoxy)-2-(4-(pyridazin-4-yl)benzyl)-1,2-dihydro-3H-pyrrolo[3,4-c]pyridin-3-one

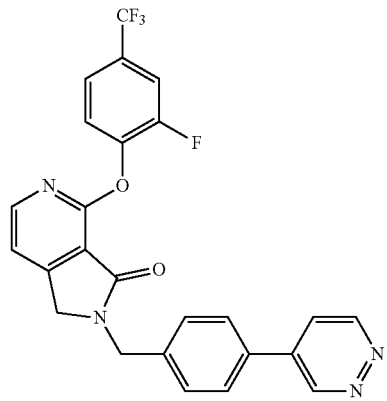 [SMILES: O=C1c2c(ccnc2Oc2ccc(C(F)(F)F)cc2F)CN1Cc1ccc(-c2ccnnc2)cc1]

Ethyl 2-(2-fluoro-4-(trifluoromethyl)phenoxy)-4-formylnicotinate (0.10 g) obtained in Reference Example 282 was dissolved in THF (3 mL), (4-(pyridazin-4-yl)phenyl)methanamine (0.052 g) and anhydrous magnesium sulfate (0.067 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.089 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.042 g).

MS: [M+H]$^+$ 481.1

$^1$H NMR (300 MHz, DMSO-d$_6$) δ 4.55 (2H, s), 4.82 (2H, s), 7.43 (1H, d, J=5.1 Hz), 7.52 (2H, d, J=8.3 Hz), 7.60-7.75 (2H, m), 7.87-8.04 (4H, m), 8.24 (1H, d, J=5.1 Hz), 9.27 (1H, dd, J=5.5, 1.1 Hz), 9.64 (1H, dd, J=2.5, 1.1 Hz).

Example 310

4-(4-(difluoromethyl)-2-fluorophenoxy)-6-(4-(1-methyl-1H-pyrazol-3-yl)benzyl)-6,7-dihydro-5H-pyrrolo[3,4-d]pyrimidin-5-one

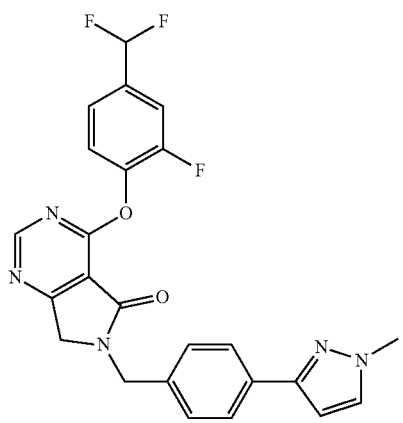 [SMILES: Cn1ccc(-c2ccc(CN3Cc4ncnc(Oc5ccc(C(F)F)cc5F)c4C3=O)cc2)n1]

A mixed solution of methyl 4-(4-(difluoromethyl)-2-fluorophenoxy)-6-vinylpyrimidine-5-carboxylate (0.29 g) obtained in Reference Example 136, sodium periodate (0.94 g) and osmium oxide (immobilized catalyst I) (0.11 g) in acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.06 g) was dissolved in THF (3 mL), (4-(1-methyl-1H-pyrazol-3-yl)phenyl)methanamine (0.034 g) and anhydrous magnesium sulfate (0.044 g) were added, and the mixture was stirred under an argon atmosphere at room temperature for 20 min. The insoluble material was filtered off, and the filtrate was concentrated. To a solution of the residue in THF (3 mL) were added sodium triacetoxyhydroborate (0.78 g) and methanol (1 mL), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and solidified with diethyl ether to give the title compound (0.030 g).

MS: [M+H]$^+$ 466.1

$^1$H NMR (300 MHz, DMSO-d$_6$) δ 3.88 (3H, s), 4.57 (2H, s), 4.76 (2H, s), 6.67 (1H, d, J=2.3 Hz), 6.89-7.31 (1H, m), 7.37 (2H, d, J=8.3 Hz), 7.50-7.85 (6H, m), 8.88 (1H, s).

Example 311

4-(2-fluoro-4-(trifluoromethyl)phenoxy)-6-(4-(6-methylpyridazin-4-yl)benzyl)-6,7-dihydro-5H-pyrrolo[3,4-d]pyrimidin-5-one

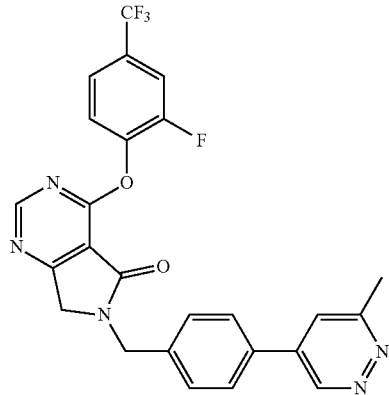 [SMILES: Cc1cc(-c2ccc(CN3Cc4ncnc(Oc5ccc(C(F)(F)F)cc5F)c4C3=O)cc2)cnn1]

A mixed solution of methyl 4-(2-fluoro-4-(trifluoromethyl)phenoxy)-6-vinylpyrimidine-5-carboxylate (0.22 g) obtained in Reference Example 134, sodium periodate (0.69 g) and osmium oxide (immobilized catalyst I) (0.082 g) in acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.10 g) was dissolved in THF (3 mL), (4-(6-methylpyridazin-4-yl)phenyl)methanamine (0.047 g) obtained in Reference Example 147 and anhydrous magnesium sulfate (0.071 g) were added, and the mixture was stirred under an argon atmosphere at room temperature for 20 min. The insoluble material was filtered off, and the filtrate was concentrated. To a solution of the residue in THF (3 mL) were added sodium triacetoxyhydroborate (0.87 g) and methanol (1 mL), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and solidified with ethyl acetate-hexane to give the title compound (0.041 g).

MS: [M+H]$^+$ 496.1

$^1$H NMR (300 MHz, DMSO-d$_6$) δ 2.68 (3H, s), 4.62 (2H, s), 4.84 (2H, s), 7.55 (2H, d, J=8.3 Hz), 7.70-7.80 (2H, m), 7.86-7.95 (3H, m), 8.01 (1H, d, J=11.0 Hz), 8.90 (1H, s), 9.46 (1H, d, J=2.1 Hz).

Example 312

2-(4-(1,3-dimethyl-1H-pyrazol-4-yl)benzyl)-4-(2-fluoro-5-(2-hydroxypropan-2-yl) phenoxy)-1,2-dihydro-3H-pyrrolo[3,4-c]pyridin-3-one

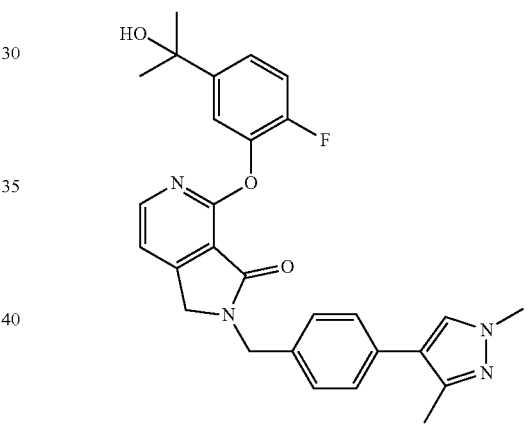

A mixed solution of ethyl 2-(2-fluoro-5-(2-hydroxypropan-2-yl)phenoxy)-4-vinylnicotinate (0.50 g) obtained in Reference Example 138, sodium periodate (1.55 g) and osmium oxide (immobilized catalyst I) (0.18 g) in acetonitrile (9 mL)-acetone (9 mL)-water (9 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.10 g) was dissolved in THF (3 mL), (4-(1,3-dimethyl-1H-pyrazol-4-yl)phenyl)methanamine (0.058 g) and anhydrous magnesium sulfate (0.069 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.12 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.024 g).

MS: [M+H]$^+$ 487.2

$^1$H NMR (300 MHz, DMSO-d$_6$) δ 1.44 (6H, s), 2.28 (3H, s), 3.77 (3H, s), 4.50 (2H, s), 4.72 (2H, s), 5.13 (1H, s), 7.20-7.47 (8H, m), 7.86 (1H, s), 8.20 (1H, d, J=5.1 Hz).

Example 313

4-(2-fluoro-4-(trifluoromethyl)phenoxy)-6-(4-(pyridazin-4-yl)benzyl)-6,7-dihydro-5H-pyrrolo[3,4-d]pyrimidin-5-one

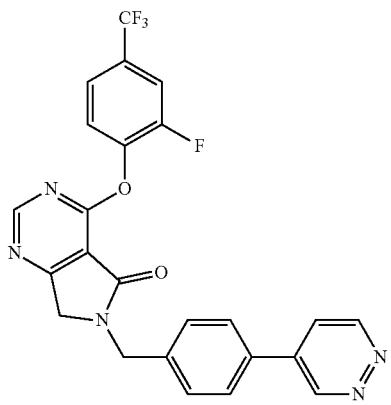

A mixed solution of methyl 4-(2-fluoro-4-(trifluoromethyl)phenoxy)-6-vinylpyrimidine-5-carboxylate (0.22 g) obtained in Reference Example 134, sodium periodate (0.69 g) and osmium oxide (immobilized catalyst I) (0.082 g) in acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.058 g) was dissolved in THF (3 mL), (4-(pyridazin-4-yl)phenyl)methanamine (0.040 g) and anhydrous magnesium sulfate (0.052 g) were added, and the mixture was stirred under an argon atmosphere at room temperature for 20 min. The insoluble material was filtered off, and the filtrate was concentrated. To a solution of the residue in THF (3 mL) were added sodium triacetoxyhydroborate (0.46 g) and methanol (1 mL), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and solidified with ethyl acetate-hexane to give the title compound (0.024 g).

MS: [M+H]$^+$ 482.2

$^1$H NMR (300 MHz, DMSO-d$_6$) δ 4.62 (2H, s), 4.85 (2H, s), 7.56 (2H, d, J=8.3 Hz), 7.69-7.80 (2H, m), 7.90-8.07 (4H, m), 8.90 (1H, s), 9.28 (1H, dd, J=5.5, 1.1 Hz), 9.65 (1H, dd, J=2.5, 1.1 Hz).

Example 314

4-(2-fluoro-4-(trifluoromethyl)phenoxy)-6-(4-(1-methyl-1H-pyrazol-3-yl)benzyl)-6,7-dihydro-5H-pyrrolo[3,4-d]pyrimidin-5-one

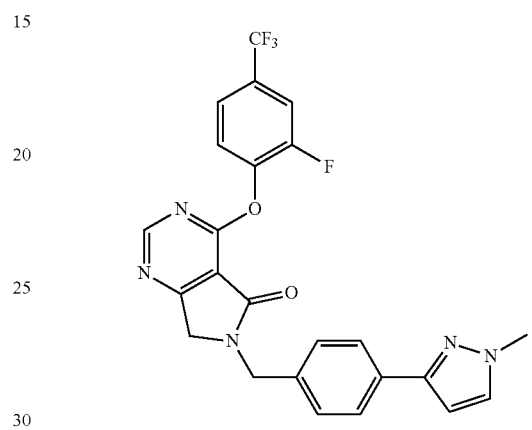

A mixed solution of methyl 4-(2-fluoro-4-(trifluoromethyl)phenoxy)-6-vinylpyrimidine-5-carboxylate (0.22 g) obtained in Reference Example 134, sodium periodate (0.69 g) and osmium oxide (immobilized catalyst I) (0.082 g) in acetonitrile (6 mL)-acetone (6 mL)-water (6 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.085 g) was dissolved in THF (3 mL), (4-(1-methyl-1H-pyrazol-3-yl)phenyl)methanamine (0.046 g) and anhydrous magnesium sulfate (0.059 g) were added, and the mixture was stirred under an argon atmosphere at room temperature for 20 min. The insoluble material was filtered off, and the filtrate was concentrated. To a solution of the residue in THF (3 mL) were added sodium triacetoxyhydroborate (0.52 g) and methanol (1 mL), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and solidified with diethyl ether to give the title compound (0.039 g).

MS: [M+H]$^+$ 484.2

$^1$H NMR (300 MHz, DMSO-d$_6$) δ 3.87 (3H, s), 4.57 (2H, s), 4.76 (2H, s), 6.67 (1H, d, J=2.3 Hz), 7.37 (2H, d, J=8.3 Hz), 7.66-7.83 (5H, m), 8.00 (1H, d, J=11.1 Hz), 8.89 (1H, s).

Example 315 and Example 316

Optically active 4-((trans-2-hydroxycyclohexyl)oxy)-2-(2,4,6-trifluorobenzyl)-1,2-dihydro-3H-pyrrolo[3,4-c]pyridin-3-one

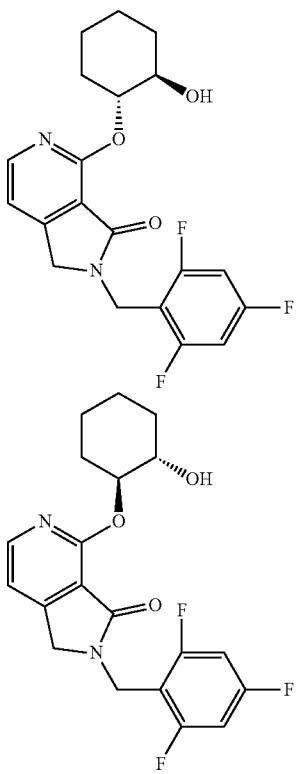

A mixed solution of ethyl 2-((trans-2-hydroxycyclohexyl)oxy)-4-vinylnicotinate (1.0 g) obtained in Reference Example 116, sodium periodate (3.7 g) and osmium oxide (immobilized catalyst I) (0.44 g) in acetonitrile (15 mL)-acetone (15 mL)-water (15 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.21 g) was dissolved in THF (3 mL), (2,4,6-trifluorophenyl)methanamine (0.12 g) and anhydrous magnesium sulfate (0.18 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.23 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK IA (trade name), 50 mmID×500 mmL, manufactured by Dicel Corporation, mobile phase: hexane/ethanol=650/350), and solidified with ethyl acetate-diisopropyl ether to give the title compound.

retention time: tR1 (Example 315, yield 0.056 g)
MS: [M+H]$^+$ 393.2

$^1$H NMR (300 MHz, DMSO-d$_6$) δ 1.20-1.45 (4H, m), 1.65 (2H, brs), 1.85-2.04 (2H, m), 3.55-3.67 (1H, m), 4.36 (2H, s), 4.61-4.71 (2H, m), 4.73 (1H, d, J=4.5 Hz), 5.09 (1H, td, J=8.4, 4.1 Hz), 7.13 (1H, d, J=5.3 Hz), 7.16-7.28 (2H, m), 8.24 (1H, d, J=5.3 Hz).

retention time: tR2 (Example 316, yield 0.052 g)
MS: [M+H]$^+$ 393.1

$^1$H NMR (300 MHz, DMSO-d$_6$) δ 1.22-1.46 (4H, m), 1.64 (2H, brs), 1.83-2.05 (2H, m), 3.55-3.67 (1H, m), 4.36 (2H, s), 4.60-4.71 (2H, m), 4.73 (1H, d, J=4.5 Hz), 5.09 (1H, td, J=8.3, 4.0 Hz), 7.13 (1H, d, J=5.3 Hz), 7.17-7.29 (2H, m), 8.18-8.28 (1H, m), 8.24 (1H, d, J=5.1 Hz).

Example 317 and Example 318

Optically active 1,5-anhydro-2-deoxy-3-O-(3-oxo-2-(2,4,6-trifluorobenzyl)-2,3-dihydro-1H-isoindol-4-yl)-threo-pentitol

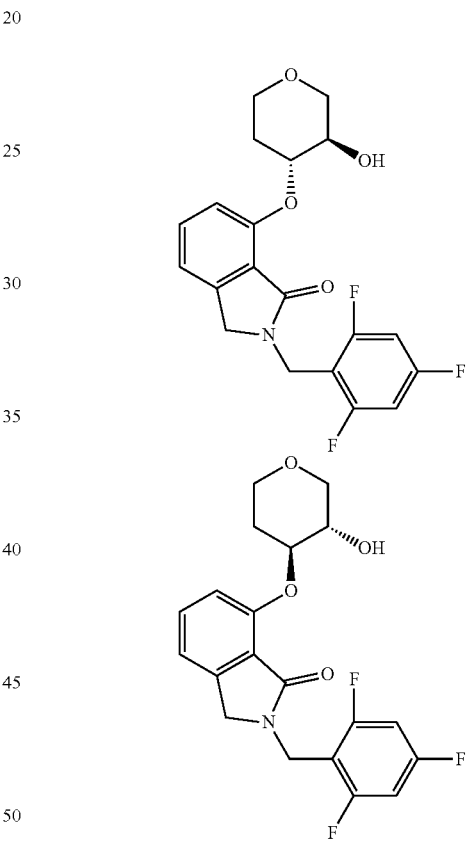

To a solution of 7-hydroxy-2-(2,4,6-trifluorobenzyl)isoindolin-1-one (0.51 g) obtained in Reference Example 139 in ethanol (5 mL) were added 3,7-dioxabicyclo[4.1.0]heptane (0.70 g) and pyridine (1.10 g), and the mixture was stirred under an argon atmosphere at 100° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK AD (trade name), 50 mmID×500 mmL, manufactured by Dicel Corporation, mobile phase: hexane/2-propanol=650/350) to give the title compound.

retention time: tR1 (Example 317, yield 0.070 g)
MS: [M+H]$^+$ 394.1

$^1$H NMR (300 MHz, DMSO-d$_6$) δ 1.51-1.69 (1H, m), 2.05-2.17 (1H, m), 3.19 (1H, dd, J=11.1, 7.7 Hz), 3.35-3.47 (1H, m), 3.53-3.65 (1H, m), 3.75-3.91 (2H, m), 4.25-4.42 (3H, m), 4.71 (2H, s), 5.35 (1H, d, J=4.7 Hz), 7.12 (2H, dd, J=7.6, 5.7 Hz), 7.18-7.30 (2H, m), 7.41-7.53 (1H, m).

retention time: tR2 (Example 318, yield 0.070 g)

MS: [M+H]$^+$ 394.1

$^1$H NMR (300 MHz, DMSO-d$_6$) δ 1.60 (1H, dt, J=13.3, 4.5 Hz), 2.05-2.17 (1H, m), 3.19 (1H, dd, J=11.2, 7.8 Hz), 3.40 (1H, ddd, J=11.7, 9.2, 2.9 Hz), 3.53-3.64 (1H, m), 3.75-3.91 (2H, m), 4.24-4.40 (3H, m), 4.71 (2H, s), 5.34 (1H, d, J=4.7 Hz), 7.12 (2H, dd, J=7.6, 5.6 Hz), 7.18-7.31 (2H, m), 7.43-7.53 (1H, m).

Example 319 and Example 320

Optically active 2-(2,5-difluorobenzyl)-4-((trans-2-hydroxycyclohexyl)oxy)-1,2-dihydro-3H-pyrrolo[3,4-c]pyridin-3-one

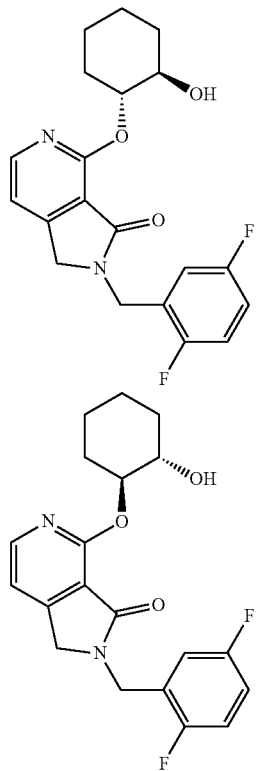

A mixed solution of ethyl 2-((trans-2-hydroxycyclohexyl)oxy)-4-vinylnicotinate (1.01 g) obtained in Reference Example 116, sodium periodate (3.71 g) and osmium oxide (immobilized catalyst I) (0.44 g) in acetonitrile (15 mL)-acetone (15 mL)-water (15 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.20 g) was dissolved in THF (3 mL), (2,5-difluorophenyl)methanamine (0.098 g) and anhydrous magnesium sulfate (0.16 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.22 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK IA (trade name), 50 mmID× 500 mmL, manufactured by Dicel Corporation, mobile phase: hexane/ethanol=600/400), and solidified with ethyl acetate-hexane to give the title compound.

retention time: tR1 (Example 319, yield 0.035 g)

MS: [M+H]$^+$ 375.1

$^1$H NMR (300 MHz, DMSO-d$_6$) δ 1.22-1.46 (4H, m), 1.65 (2H, brs), 1.85-2.06 (2H, m), 3.57-3.69 (1H, m), 4.43 (2H, s), 4.69 (2H, s), 4.74 (1H, d, J=4.5 Hz), 5.06-5.16 (1H, m), 7.11-7.34 (4H, m), 8.26 (1H, d, J=5.3 Hz).

retention time: tR2 (Example 320, yield 0.029 g)

MS: [M+H]$^+$ 375.1

$^1$H NMR (300 MHz, DMSO-d$_6$) δ 1.23-1.47 (4H, m), 1.65 (2H, brs), 1.85-2.05 (2H, m), 3.57-3.69 (1H, m), 4.43 (2H, s), 4.69 (2H, s), 4.74 (1H, d, J=4.5 Hz), 5.06-5.17 (1H, m), 7.10-7.34 (4H, m), 8.26 (1H, d, J=5.1 Hz).

Example 321 and Example 322

Optically active 2-(3-fluorobenzyl)-4-((trans-2-hydroxycyclohexyl)oxy)-1,2-dihydro-3H-pyrrolo[3,4-c]pyridin-3-one

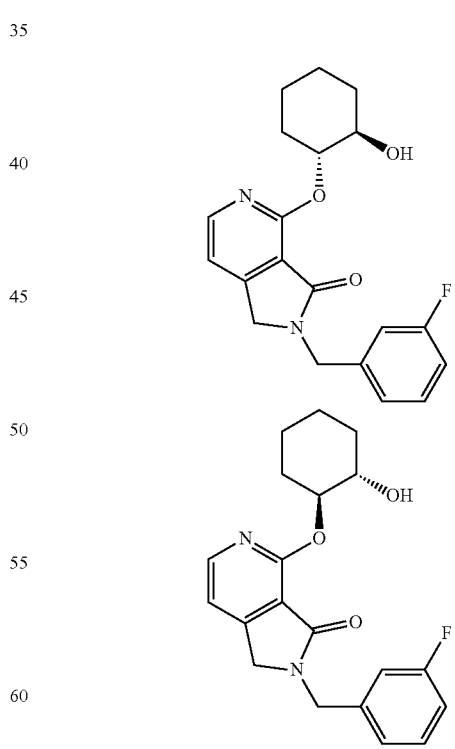

A mixed solution of ethyl 2-((trans-2-hydroxycyclohexyl)oxy)-4-vinylnicotinate (1.01 g) obtained in Reference Example 116, sodium periodate (3.71 g) and osmium oxide (immobilized catalyst I) (0.44 g) in acetonitrile (15 mL)- acetone (15 mL)-water (15 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.22 g) was dissolved in THF (3 mL), (3-fluorophenyl)methanamine (0.092 g) and anhydrous magnesium sulfate (0.18 g) were added, and the mixture was stirred under an argon atmosphere at room temperature for 20 min. The insoluble material was filtered off, and the filtrate was concentrated. To a solution of the residue in acetic acid (3 mL) was added sodium triacetoxyhydroborate (0.23 g), and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate) and chiral HPLC (column: CHIRALPAK IA (trade name), 50 mmID× 500 mmL, manufactured by Dicel Corporation, mobile phase: hexane/ethanol=650/350), and solidified with ethyl acetate-hexane to give the title compound.

retention time: tR1 (Example 321, yield 0.036 g)
MS: [M+H]$^+$ 357.2
$^1$H NMR (300 MHz, DMSO-$d_6$) δ 1.24-1.49 (4H, m), 1.66 (2H, brs), 1.84-2.06 (2H, m), 3.54-3.70 (1H, m), 4.38 (2H, s), 4.58-4.72 (2H, m), 4.75 (1H, d, J=4.5 Hz), 5.05-5.17 (1H, m), 7.04-7.19 (4H, m), 7.34-7.47 (1H, m), 8.25 (1H, d, J=5.1 Hz).

retention time: tR2 (Example 322, yield 0.033 g)
MS: [M+H]$^+$ 357.1
$^1$H NMR (300 MHz, DMSO-$d_6$) δ 1.22-1.48 (4H, m), 1.65 (2H, brs), 1.84-2.07 (2H, m), 3.57-3.69 (1H, m), 4.38 (2H, s), 4.59-4.73 (2H, m), 4.75 (1H, d, J=4.5 Hz), 5.06-5.16 (1H, m), 7.04-7.18 (4H, m), 7.34-7.46 (1H, m), 8.25 (1H, d, J=5.1 Hz).

Example 323

4-(cyclobutyloxy)-6-(4-(1,3-dimethyl-1H-pyrazol-4-yl)benzyl)-6,7-dihydro-5H-pyrrolo[3,4-d]pyrimidin-5-one

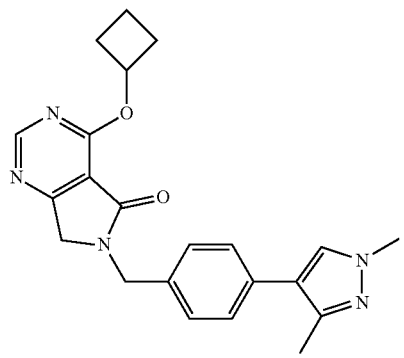 [SMILES: Cc1nn(C)cc1-c1ccc(CN2Cc3ncnc(OC4CCC4)c3C2=O)cc1]

A mixed solution of methyl 4-cyclobutoxy-6-vinylpyrimidine-5-carboxylate (1.69 g) obtained in Reference Example 141, sodium periodate (6.17 g) and osmium oxide (immobilized catalyst I) (0.37 g) in acetonitrile (15 mL)-acetone (15 mL)-water (15 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.20 g) was dissolved in THF (3 mL), (4-(1,3-dimethyl-1H-pyrazol-4-yl)phenyl)methanamine (0.17 g) was added, and the mixture was stirred under an argon atmosphere at room temperature for 20 min. To the reaction solution were added sodium triacetoxyhydroborate (0.90 g) and methanol (1 mL), and the mixture was stirred under an argon atmosphere at room temperature for 1 hr. Sodium triacetoxyhydroborate (0.090 g) was added, and the mixture was further stirred for 1 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether-ethyl acetate to give the title compound (0.15 g).

MS: [M+H]$^+$ 390.2
$^1$H NMR (300 MHz, DMSO-$d_6$) δ 1.60-1.92 (2H, m), 2.09-2.23 (2H, m), 2.27 (3H, s), 2.44 (2H, brs), 3.77 (3H, s), 4.42 (2H, s), 4.67 (2H, s), 5.35 (1H, quin, J=7.3 Hz), 7.24-7.33 (2H, m), 7.36-7.43 (2H, m), 7.85 (1H, s), 8.86 (1H, s).

Example 324

4-(cyclobutyloxy)-6-(4-(1-ethyl-1H-pyrazol-4-yl)benzyl)-6,7-dihydro-5H-pyrrolo[3,4-d]pyrimidin-5-one

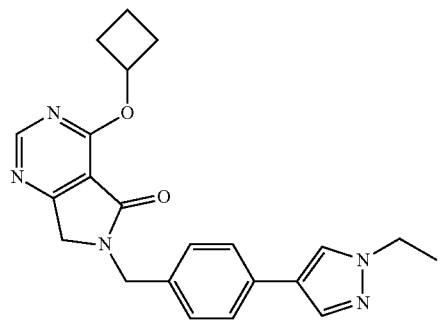 [SMILES: CCn1cc(-c2ccc(CN3Cc4ncnc(OC5CCC5)c4C3=O)cc2)cn1]

A mixed solution of methyl 4-cyclobutoxy-6-vinylpyrimidine-5-carboxylate (1.69 g) obtained in Reference Example 141, sodium periodate (6.17 g) and osmium oxide (immobilized catalyst I) (0.37 g) in acetonitrile (15 mL)-acetone (15 mL)-water (15 mL) was stirred at room temperature overnight. The insoluble material was filtered off, and the filtrate was diluted with ethyl acetate. The organic layer was separated, washed with saturated brine, dried over anhydrous sodium sulfate, and concentrated. The residue (0.20 g) was dissolved in THF (3 mL), (4-(1-ethyl-1H-pyrazol-4-yl)phenyl)methanamine (0.17 g) was added, and the mixture was stirred under an argon atmosphere at room temperature for 20 min. To the reaction solution were added sodium triacetoxyhydroborate (0.90 g) and methanol (1 mL), and the mixture was stirred under an argon atmosphere at room temperature for 1 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with diisopropyl ether-ethyl acetate to give the title compound (0.16 g).

MS: [M+H]$^+$ 390.2

$^1$H NMR (300 MHz, DMSO-d$_6$) δ 1.39 (3H, t, J=7.3 Hz), 1.60-1.91 (2H, m), 2.07-2.27 (2H, m), 2.44 (2H, brs), 4.13 (2H, q, J=7.4 Hz), 4.33-4.44 (2H, m), 4.66 (2H, s), 5.35 (1H, quin, J=7.3 Hz), 7.27 (2H, d, J=8.1 Hz), 7.53 (2H, d, J=8.3 Hz), 7.83 (1H, s), 8.16 (1H, s), 8.86 (1H, s).

Example 325

4-((tetrahydrofuran-2-yl)methoxy)-2-(4-(2-(trifluoromethyl)pyridin-4-yl)benzyl)-1,2-dihydro-3H-pyrrolo[3,4-c]pyridin-3-one

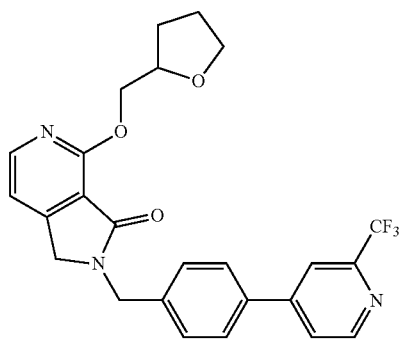 [SMILES: O=C1c2c(ccnc2OCC2CCCO2)CN1Cc1ccc(-c2ccnc(C(F)(F)F)c2)cc1]

To a solution of methyl 4-formyl-2-((tetrahydrofuran-2-yl)methoxy)nicotinate (0.10 g) obtained in Reference Example 142 and (4-(2-(trifluoromethyl)pyridin-4-yl)phenyl)methanamine (0.095 g) obtained in Reference Example 143 in methanol (2 mL)-THF (1 mL) was added tetra(isopropoxy)titanium (0.118 g) at 0° C., and the mixture was stirred under a nitrogen atmosphere at room temperature for 1 hr. Sodium tetrahydroborate (0.019 g) was added to the reaction mixture under ice-cooling, and the mixture was stirred under a nitrogen atmosphere at room temperature for 3 hr. The reaction mixture was diluted with saturated aqueous ammonium chloride solution and ethyl acetate, and the organic layer was separated, washed with saturated brine, dried over anhydrous magnesium sulfate and concentrated. The residue was purified by NH silica gel chromatography (hexane-ethyl acetate) to give the title compound (0.072 g).

MS: [M+H]$^+$ 470.2

$^1$H NMR (300 MHz, CDCl$_3$) δ 1.85-2.00 (2H, m), 2.05-2.19 (2H, m), 3.72-3.89 (1H, m), 3.94-4.07 (1H, m), 4.25 (2H, s), 4.42 (1H, d, J=4.7 Hz), 4.52 (2H, d, J=4.7 Hz), 4.80 (2H, s), 6.93 (1H, d, J=5.3 Hz), 7.45 (2H, d, J=8.1 Hz), 7.57-7.72 (3H, m), 7.84 (1H, s), 8.23 (1H, d, J=5.1 Hz), 8.75 (1H, d, J=5.1 Hz).

Example 326

2-(4-(6-methylpyridazin-4-yl)benzyl)-4-((tetrahydrofuran-2-yl)methoxy)-1,2-dihydro-3H-pyrrolo[3,4-c]pyridin-3-one

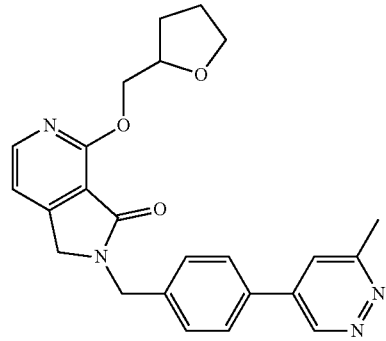 [SMILES: Cc1cc(-c2ccc(CN3Cc4ccnc(OCC5CCCO5)c4C3=O)cc2)cnn1]

To a solution of methyl 4-formyl-2-((tetrahydrofuran-2-yl)methoxy)nicotinate (0.10 g) obtained in Reference Example 142 and (4-(6-methylpyridazin-4-yl)phenyl)methanamine (0.15 g) obtained in Reference Example 147 in methanol (2 mL)-THF (1 mL) was added tetra(isopropoxy)titanium (0.12 g) at 0° C., and the mixture was stirred under a nitrogen atmosphere at room temperature for 1 hr. Sodium tetrahydroborate (0.019 g) was added to the reaction mixture under ice-cooling, and the mixture was stirred under a nitrogen atmosphere at room temperature for 3 hr. The reaction mixture was diluted with water, ethyl acetate and 1N hydrochloric acid, and the organic layer was separated, washed with saturated brine, dried over anhydrous magnesium sulfate and concentrated. The residue was purified by NH silica gel chromatography (hexane-ethyl acetate), and solidified with diisopropyl ether-ethyl acetate to give the title compound (0.023 g).

MS: [M+H]$^+$ 417.2

$^1$H NMR (300 MHz, CDCl$_3$) δ 1.83-2.02 (2H, m), 2.04-2.24 (2H, m), 2.78 (3H, s), 3.73-3.90 (1H, m), 3.93-4.09 (1H, m), 4.26 (2H, s), 4.35-4.49 (1H, m), 4.54 (2H, d, J=0.9 Hz), 4.81 (2H, s), 6.94 (1H, d, J=5.1 Hz), 7.40-7.52 (3H, m), 7.62 (2H, d, J=8.3 Hz), 8.25 (1H, d, J=5.1 Hz), 9.27 (1H, d, J=2.1 Hz).

Example 327

4-((2-fluorobenzyl)oxy)-2-(2-fluoro-4-(1-methyl-1H-1,2,3-triazol-4-yl)benzyl)-1,2-dihydro-3H-pyrrolo[3,4-c]pyridin-3-one

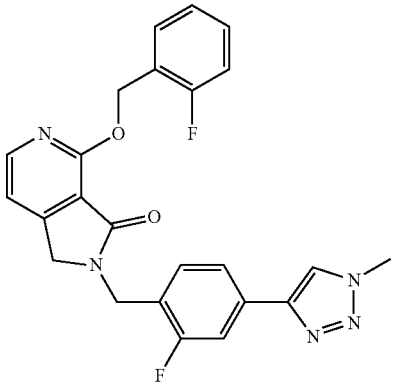 [SMILES: Cn1cc(-c2ccc(CN3Cc4ccnc(OCc5ccccc5F)c4C3=O)c(F)c2)nn1]

To a solution of methyl 2-((2-fluorobenzyl)oxy)-4-formylnicotinate (0.15 g) obtained in Reference Example 150 and (2-fluoro-4-(1-methyl-1H-1,2,3-triazol-4-yl)phenyl)methanamine (0.13 g) obtained in Reference Example 154 in methanol (3 mL)-THF (1.5 mL) was added tetra(isopropoxy)titanium (0.19 g) at room temperature, and the mixture was stirred under a nitrogen atmosphere at room temperature for 1 hr. Sodium tetrahydroborate (0.019 g) was added to the reaction mixture at 0° C., and the mixture was stirred under a nitrogen atmosphere at room temperature for 2 hr. The reaction mixture was diluted with water, ethyl acetate and 1N hydrochloric acid, and the organic layer was separated, washed with saturated brine, dried over anhydrous magnesium sulfate and concentrated. The residue was purified by NH silica gel chromatography (hexane-ethyl acetate), and solidified with diisopropyl ether-ethyl acetate to give the title compound (0.015 g).

MS: [M+H]+ 448.2

$^1$H NMR (300 MHz, CDCl$_3$) δ 4.15 (3H, s), 4.35 (2H, s), 4.83 (2H, s), 5.67 (2H, s), 6.99 (1H, d, J=5.3 Hz), 7.01-7.10 (1H, m), 7.11-7.20 (1H, m), 7.26 (1H, s), 7.39-7.54 (2H, m), 7.57-7.67 (1H, m), 7.67-7.78 (2H, m), 8.27 (1H, d, J=5.1 Hz).

Example 328

2-(2,6-difluoro-4-(1-methyl-1H-pyrazol-3-yl)benzyl)-4-((trans-2-hydroxycyclopentyl)oxy)-1,2-dihydro-3H-pyrrolo[3,4-c]pyridin-3-one

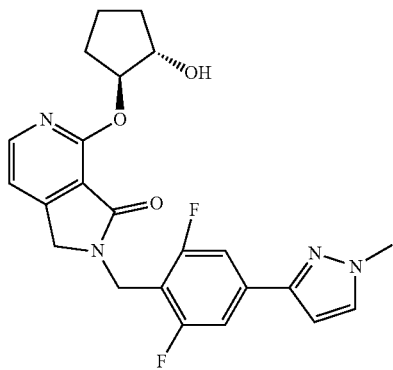 [SMILES: Cn1ccc(-c2cc(F)c(CN3Cc4ccnc(O[C@H]5CCC[C@@H]5O)c4C3=O)c(F)c2)n1]

A mixed solution of methyl 2-((trans-2-hydroxycyclopentyl)oxy)-4-vinylnicotinate (0.11 g) obtained in Reference Example 61, sodium periodate (0.43 g) and osmium oxide (immobilized catalyst I) (0.051 g) in acetonitrile (1.5 mL)-acetone (1.5 mL)-water (1.5 mL) was stirred at room temperature overnight. The insoluble material was filtered off, the filtrate was diluted with ethyl acetate and saturated aqueous sodium thiosulfate solution, and the organic layer was separated, washed with saturated brine, dried over anhydrous sodium sulfate, and concentrated. To a solution of the residue (0.11 g) obtained in the same manner and (2,6-difluoro-4-(1-methyl-1H-pyrazol-3-yl)phenyl)methanamine (0.11 g) obtained in Reference Example 156 in methanol (3 mL)-THF (1.5 mL) was added tetra(isopropoxy)titanium (0.23 g) at room temperature, and the mixture was stirred under a nitrogen atmosphere at room temperature for 1 hr. Sodium tetrahydroborate (0.030 g) was added to the reaction mixture at room temperature, and the mixture was stirred under a nitrogen atmosphere at room temperature for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate to give the title compound (0.010 g).

MS: [M+H]+ 441.3

$^1$H NMR (300 MHz, CDCl$_3$) δ 1.67-1.90 (3H, m), 2.06-2.20 (2H, m), 2.21-2.37 (1H, m), 3.95 (3H, s), 4.14-4.25 (1H, m), 4.30 (2H, s), 4.75-4.94 (2H, m), 4.95-5.09 (2H, m), 6.50 (1H, d, J=2.3 Hz), 6.97 (1H, d, J=5.3 Hz), 7.29-7.45 (3H, m), 8.20 (1H, d, J=5.3 Hz).

Example 329

2-(4-(1,3-dimethyl-1H-pyrazol-4-yl)-2-fluorobenzyl)-4-((3-fluoropyridin-2-yl)methoxy)-1,2-dihydro-3H-pyrrolo[3,4-c]pyridin-3-one

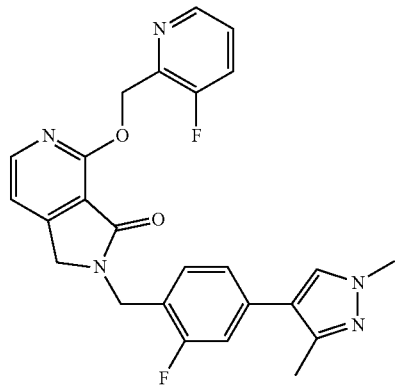 [SMILES: Cc1nn(C)cc1-c1ccc(CN2Cc3ccnc(OCc4ncccc4F)c3C2=O)c(F)c1]

To a solution of methyl 2-((3-fluoropyridin-2-yl)methoxy)-4-formylnicotinate (0.20 g) obtained in Reference Example 159 and (4-(1,3-dimethyl-1H-pyrazol-4-yl)-2-fluorophenyl)methanamine (0.18 g) in methanol (3 mL)-THF (1.5 mL) was added tetra(isopropoxy)titanium (0.26 g) at room temperature, and the mixture was stirred under a nitrogen atmosphere at room temperature for 1 hr. Sodium tetrahydroborate (0.039 g) was added to the reaction mixture at 0° C., and the mixture was stirred under a nitrogen atmosphere at room temperature for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate-diisopropyl ether to give the title compound (0.14 g).

MS: [M+H]+ 462.1

$^1$H NMR (300 MHz, CDCl$_3$) δ 2.37 (3H, s), 3.86 (3H, s), 4.34 (2H, s), 4.79 (2H, s), 5.78 (2H, d, J=1.9 Hz), 6.97 (1H, d, J=5.1 Hz), 7.03-7.14 (2H, m), 7.21-7.31 (1H, m), 7.34-7.47 (3H, m), 8.24 (1H, d, J=5.1 Hz), 8.36-8.44 (1H, m).

Example 330

2-(2-fluoro-4-(1-methyl-1H-1,2,3-triazol-4-yl)benzyl)-7-((tetrahydrofuran-2-yl)methoxy)isoindolin-1-one

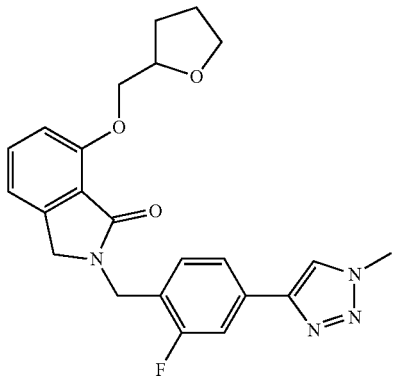 [SMILES: Cn1cc(-c2ccc(CN3Cc4cccc(OCC5CCCO5)c4C3=O)c(F)c2)nn1]

To a solution of methyl 2-formyl-6-((tetrahydrofuran-2-yl)methoxy)benzoate (0.10 g) obtained in Reference Example 205 and (2-fluoro-4-(1-methyl-1H-1,2,3-triazol-4-yl)phenyl)methanamine (0.094 g) obtained in Reference Example 154 in methanol (3 mL)-THF (1.5 mL) was added tetra(isopropoxy)titanium (0.14 g) at room temperature, and the mixture was stirred under a nitrogen atmosphere at room temperature for 1 hr. Sodium tetrahydroborate (0.021 g) was added to the reaction mixture at 0° C., and the mixture was stirred under a nitrogen atmosphere at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate) and recrystallization (ethyl acetate-diisopropyl ether) to give the title compound (0.017 g).

MS: [M+H]$^+$ 423.2

$^1$H NMR (300 MHz, CDCl$_3$) δ 1.84-2.23 (4H, m), 3.78-3.89 (1H, m), 3.95-4.07 (1H, m), 4.09-4.22 (5H, m), 4.29 (2H, s), 4.32-4.45 (1H, m), 4.83 (2H, s), 6.94 (2H, dd, J=11.5, 7.9 Hz), 7.35-7.53 (3H, m), 7.60 (1H, dd, J=10.8, 1.3 Hz), 7.73 (1H, s).

Example 331

4-(cyclopropylmethoxy)-2-(2-fluoro-4-(1-methyl-TH-1,2,3-triazol-4-yl)benzyl)-1,2-dihydro-3H-pyrrolo[3,4-c]pyridin-3-one

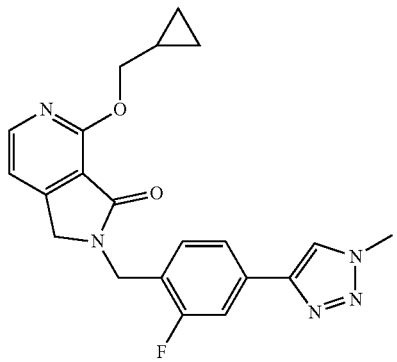 [SMILES: Cn1cc(-c2ccc(CN3Cc4ccnc(OCC5CC5)c4C3=O)c(F)c2)nn1]

To a solution of methyl 2-(cyclopropylmethoxy)-4-formylnicotinate (0.30 g) obtained in Reference Example 160 and (2-fluoro-4-(1-methyl-1H-1,2,3-triazol-4-yl)phenyl)methanamine (0.32 g) obtained in Reference Example 154 in methanol (6 mL)-THF (3 mL) was added tetra(isopropoxy)titanium (0.47 g) at room temperature, and the mixture was stirred under a nitrogen atmosphere at room temperature for 1 hr. Sodium tetrahydroborate (0.072 g) was added to the reaction mixture under ice-cooling, and the mixture was stirred under a nitrogen atmosphere at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with THF-diisopropyl ether to give the title compound (0.034 g).

MS: [M+H]$^+$ 394.1

$^1$H NMR (300 MHz, CDCl$_3$) δ 0.36-0.46 (2H, m), 0.56-0.66 (2H, m), 1.34-1.49 (1H, m), 4.15 (3H, s), 4.29-4.40 (4H, m), 4.82 (2H, s), 6.86-6.97 (1H, m), 7.38-7.53 (2H, m), 7.57-7.67 (1H, m), 7.74 (1H, s), 8.22 (1H, d, J=5.1 Hz).

Example 332

4-((2-fluorobenzyl)oxy)-2-(4-(1-methyl-1H-1,2,3-triazol-4-yl)benzyl)-1,2-dihydro-3H-pyrrolo[3,4-c]pyridin-3-one

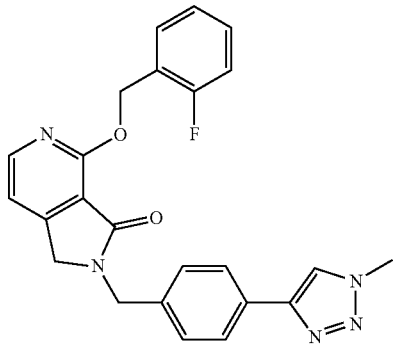 [SMILES: Cn1cc(-c2ccc(CN3Cc4ccnc(OCc5ccccc5F)c4C3=O)cc2)nn1]

To a solution of methyl 2-((2-fluorobenzyl)oxy)-4-formylnicotinate (0.17 g) obtained in Reference Example 150 and (4-(1-methyl-1H-1,2,3-triazol-4-yl)phenyl)methanamine (0.13 g) obtained in Reference Example 162 in methanol (3 mL)-THF (1.5 mL) was added tetra(isopropoxy)titanium (0.22 g) at room temperature, and the mixture was stirred under a nitrogen atmosphere at room temperature for 1 hr. Sodium tetrahydroborate (0.033 g) was added to the reaction mixture under ice-cooling, and the mixture was stirred under a nitrogen atmosphere at room temperature for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with THF-ethyl acetate to give the title compound (0.078 g).

MS: [M+H]$^+$ 430.2

$^1$H NMR (300 MHz, CDCl$_3$) δ 4.14 (3H, s), 4.26 (2H, s), 4.78 (2H, s), 5.69 (2H, s), 6.96 (1H, d, J=5.3 Hz), 7.01-7.10 (1H, m), 7.12-7.21 (1H, m), 7.23-7.31 (1H, m), 7.37 (2H, d, J=8.3 Hz), 7.68-7.84 (4H, m), 8.26 (1H, d, J=5.1 Hz).

Example 333

2-(4-(1H-pyrazol-3-yl)benzyl)-4-((tetrahydrofuran-2-yl)methoxy)-1,2-dihydro-3H-pyrrolo[3,4-c]pyridin-3-one

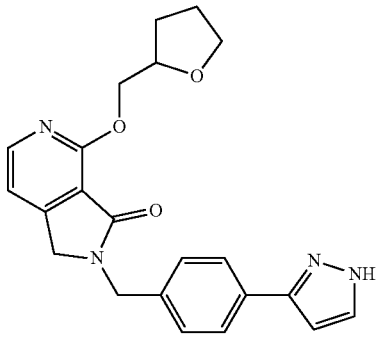 [SMILES: O=C1c2c(ccnc2OCC2CCCO2)CN1Cc1ccc(-c2cc[nH]n2)cc1]

To a solution of methyl 4-formyl-2-((tetrahydrofuran-2-yl)methoxy)nicotinate (1.30 g) obtained in Reference Example 142 and (4-(1H-pyrazol-3-yl)phenyl)methanamine (0.93 g) in methanol (15 mL)-THF (7.5 mL) was added tetra(isopropoxy)titanium (1.81 g) at room temperature, and the mixture was stirred under a nitrogen atmosphere at room temperature for 1 hr. Sodium tetrahydroborate (0.46 g) was added to the reaction mixture under ice-cooling, and the mixture was stirred under a nitrogen atmosphere at room temperature for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with THF-ethyl acetate-diisopropyl ether to give the title compound (0.33 g).

MS: [M+H]⁺ 391.1

¹H NMR (300 MHz, CDCl₃) δ 1.88-2.00 (2H, m), 2.06-2.19 (2H, m), 3.78-3.88 (1H, m), 3.95-4.07 (1H, m), 4.21 (2H, s), 4.36-4.47 (1H, m), 4.49-4.56 (2H, m), 4.76 (2H, s), 6.60 (1H, d, J=2.3 Hz), 6.92 (1H, d, J=5.3 Hz), 7.34 (2H, d, J=8.1 Hz), 7.62 (1H, d, J=2.3 Hz), 7.73 (2H, d, J=8.1 Hz), 8.22 (1H, d, J=5.1 Hz).

Example 334

2-(2-fluoro-4-(1-methyl-1H-1,2,3-triazol-4-yl)benzyl)-4-(1-(2-fluorophenyl)ethoxy)-1,2-dihydro-3H-pyrrolo[3,4-c]pyridin-3-one

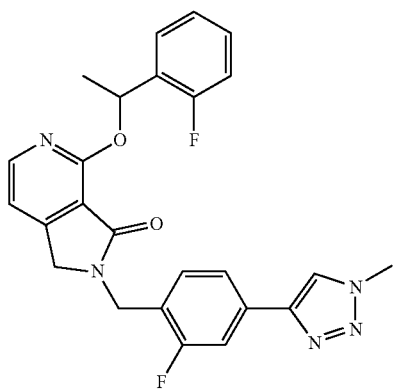 [SMILES: CC(Oc1nccc2c1C(=O)N(Cc1ccc(-c3cn(C)nn3)cc1F)C2)c1ccccc1F]

To a solution of ethyl 2-(1-(2-fluorophenyl)ethoxy)-4-formylnicotinate (0.25 g) obtained in Reference Example 165 and (2-fluoro-4-(1-methyl-1H-1,2,3-triazol-4-yl)phenyl)methanamine (0.20 g) obtained in Reference Example 154 in methanol (4 mL)-THF (2 mL) was added tetra(isopropoxy)titanium (0.29 g) at room temperature, and the mixture was stirred under a nitrogen atmosphere at room temperature for 1 hr. Sodium tetrahydroborate (0.089 g) was added to the reaction mixture under ice-cooling, and the mixture was stirred under a nitrogen atmosphere at room temperature for 4 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with THF-diisopropyl ether to give the title compound (0.056 g).

MS: [M+H]⁺ 462.1

¹H NMR (300 MHz, CDCl₃) δ 1.73 (3H, d, J=6.6 Hz), 4.15 (3H, s), 4.32 (2H, s), 4.68-4.97 (2H, m), 6.65-6.75 (1H, m), 6.92 (1H, d, J=5.1 Hz), 7.02 (1H, ddd, J=10.1, 8.3, 1.3 Hz), 7.10-7.24 (2H, m), 7.41-7.55 (2H, m), 7.62 (1H, dd, J=10.8, 1.3 Hz), 7.74 (1H, s), 7.81 (1H, td, J=7.6, 1.9 Hz), 8.20 (1H, d, J=5.1 Hz).

Example 335

4-(cyclobutyloxy)-2-(4-(1-methyl-1H-1,2,3-triazol-4-yl)benzyl)-1,2-dihydro-3H-pyrrolo[3,4-c]pyridin-3-one

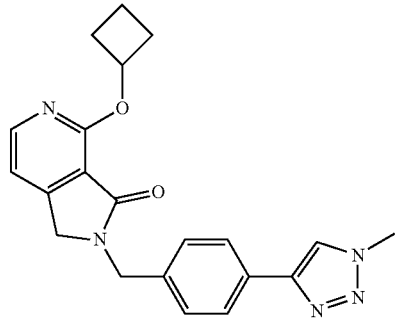 [SMILES: Cn1cc(-c2ccc(CN3Cc4ccnc(OC5CCC5)c4C3=O)cc2)nn1]

To a solution of cyclobutanol (0.025 g) in THF (2 mL) was added n-butyllithium (1.6M hexane solution, 0.19 mL) under ice-cooling, and the mixture was stirred under a nitrogen atmosphere for 20 min. A solution of 4-fluoro-2-(4-(1-methyl-1H-1,2,3-triazol-4-yl)benzyl)-1H-pyrrolo[3,4-c]pyridin-3(2H)-one (0.10 g) obtained in Reference Example 167 in THF (1 mL) was added to the reaction mixture at 0° C., and the mixture was stirred under a nitrogen atmosphere at 0° C. for 3 hr. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with ethyl acetate-diisopropyl ether to give the title compound (0.0095 g).

MS: [M+H]⁺ 376.1

¹H NMR (300 MHz, CDCl₃) δ 1.62-1.95 (2H, m), 2.24-2.43 (2H, m), 2.43-2.59 (2H, m), 4.14 (3H, s), 4.23 (2H, s), 4.76 (2H, s), 5.27-5.44 (1H, m), 6.90 (1H, d, J=5.1 Hz), 7.37 (2H, d, J=8.3 Hz), 7.73 (1H, s), 7.78 (2H, d, J=8.3 Hz), 8.21 (1H, d, J=5.1 Hz).

Example 336

4-((2,4-difluorobenzyl)oxy)-2-(4-(1-methyl-1H-1,2,3-triazol-4-yl)benzyl)-1,2-dihydro-3H-pyrrolo[3,4-c]pyridin-3-one

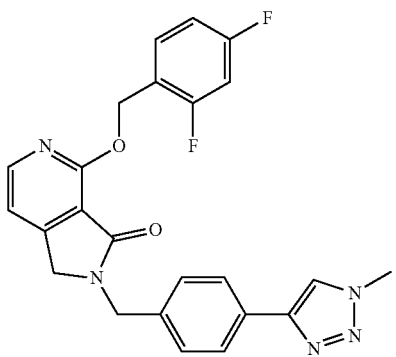 [SMILES: Cn1cc(-c2ccc(CN3Cc4ccnc(OCc5ccc(F)cc5F)c4C3=O)cc2)nn1]

To a solution of (2,4-difluorophenyl)methanol (0.087 g) in THF (2 mL) was added n-butyllithium (1.6M hexane solution, 0.32 mL) under ice-cooling, and the mixture was stirred under a nitrogen atmosphere for 20 min. A solution of 4-fluoro-2-(4-(1-methyl-1H-1,2,3-triazol-4-yl)benzyl)-1H-pyrrolo[3,4-c]pyridin-3(2H)-one (0.15 g) obtained in Reference Example 167 in THF (1 mL) was added to the reaction mixture at 0° C., and the mixture was stirred under a nitrogen atmosphere at 0° C. overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with THF-diisopropyl ether to give the title compound (0.017 g).

MS: [M+H]$^+$ 448.2

$^1$H NMR (300 MHz, CDCl$_3$) δ 4.15 (3H, s), 4.26 (2H, s), 4.78 (2H, s), 5.63 (2H, s), 6.77-6.95 (2H, m), 6.98 (1H, s), 7.37 (2H, d, J=8.1 Hz), 7.68-7.76 (2H, m), 7.79 (2H, d, J=8.1 Hz), 8.26 (1H, d, J=5.1 Hz).

Example 337

4-(cyclopropylmethoxy)-2-(4-(1-methyl-1H-1,2,3-triazol-4-yl)benzyl)-1,2-dihydro-3H-pyrrolo[3,4-c]pyridin-3-one

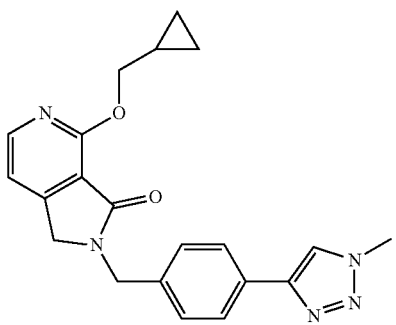 [SMILES: Cn1cc(-c2ccc(CN3Cc4ccnc(OCC5CC5)c4C3=O)cc2)nn1]

To a solution of ethyl 2-(cyclopropylmethoxy)-4-formylnicotinate (0.20 g) obtained in Reference Example 170 and (4-(1-methyl-1H-1,2,3-triazol-4-yl)phenyl)methanamine (0.18 g) obtained in Reference Example 162 in methanol (4 mL)-THF (2 mL) was added tetra(isopropoxy)titanium (0.25 g) at room temperature, and the mixture was stirred under a nitrogen atmosphere at room temperature for 1 hr. Sodium tetrahydroborate (0.091 g) was added to the reaction mixture at 0° C., and the mixture was stirred under a nitrogen atmosphere at room temperature overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with THF-diisopropyl ether to give the title compound (0.086 g).

MS: [M+H]$^+$ 376.2

$^1$H NMR (300 MHz, CDCl$_3$) δ 0.37-0.48 (2H, m), 0.56-0.69 (2H, m), 1.34-1.53 (1H, m), 4.15 (3H, s), 4.23 (2H, s), 4.37 (2H, d, J=7.2 Hz), 4.77 (2H, s), 6.91 (1H, d, J=5.1 Hz), 7.37 (2H, d, J=8.1 Hz), 7.73 (1H, s), 7.78 (2H, d, J=8.1 Hz), 8.22 (1H, d, J=5.1 Hz).

Example 338

4-(cyclobutyloxy)-2-(2-fluoro-4-(1-methyl-1H-1,2,3-triazol-4-yl)benzyl)-1,2-dihydro-3H-pyrrolo[3,4-c]pyridin-3-one

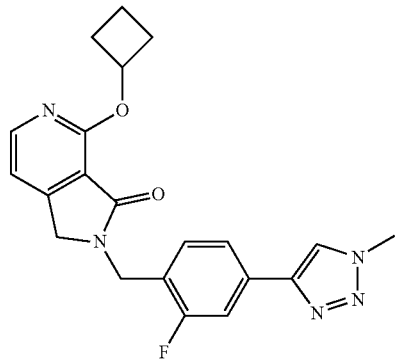 [SMILES: Cn1cc(-c2ccc(CN3Cc4ccnc(OC5CCC5)c4C3=O)c(F)c2)nn1]

To a solution of ethyl 2-cyclobutoxy-4-formylnicotinate (0.50 g) obtained in Reference Example 173 and (2-fluoro-4-(1-methyl-1H-1,2,3-triazol-4-yl)phenyl)methanamine (0.50 g) obtained in Reference Example 154 in methanol (10 mL)-THF (5 mL) was added tetra(isopropoxy)titanium (0.63 g) at room temperature, and the mixture was stirred under a nitrogen atmosphere at room temperature for 1 hr. Sodium tetrahydroborate (0.23 g) was added to the reaction mixture at 0° C., and the mixture was stirred under a nitrogen atmosphere at room temperature overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with THF-diisopropyl ether to give the title compound (0.088 g).

MS: [M+H]$^+$ 394.1

$^1$H NMR (300 MHz, CDCl$_3$) δ 1.61-1.94 (2H, m), 2.23-2.41 (2H, m), 2.43-2.58 (2H, m), 4.15 (3H, s), 4.32 (2H, s), 4.82 (2H, s), 5.34 (1H, quin, J=7.5 Hz), 6.92 (1H, d, J=5.1 Hz), 7.39-7.52 (2H, m), 7.57-7.66 (1H, m), 7.74 (1H, s), 8.22 (1H, d, J=5.3 Hz).

Example 339

4-(cyclopropylmethoxy)-2-(4-(2-methylpyridin-4-yl)benzyl)-1,2-dihydro-3H-pyrrolo[3,4-c]pyridin-3-one

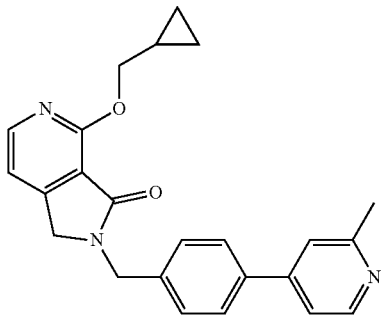 [SMILES: Cc1cc(-c2ccc(CN3Cc4ccnc(OCC5CC5)c4C3=O)cc2)ccn1]

To a solution of ethyl 2-(cyclopropylmethoxy)-4-formylnicotinate (0.20 g) obtained in Reference Example 170 and (4-(2-methylpyridin-4-yl)phenyl)methanamine (0.19 g) obtained in Reference Example 63 in methanol (4 mL)-THF (2 mL) was added tetra(isopropoxy)titanium (0.25 g) at room temperature, and the mixture was stirred under a nitrogen atmosphere at room temperature for 1 hr. Sodium tetrahydroborate (0.091 g) was added to the reaction mixture at 0° C., and the mixture was stirred under a nitrogen atmosphere at room temperature overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with ethyl acetate-diisopropyl ether to give the title compound (0.079 g).

MS: [M+H]$^+$ 386.2

$^1$H NMR (300 MHz, CDCl$_3$) δ 0.35-0.49 (2H, m), 0.55-0.68 (2H, m), 1.34-1.53 (1H, m), 2.62 (3H, s), 4.25 (2H, s), 4.37 (2H, d, J=7.0 Hz), 4.80 (2H, s), 6.92 (1H, d, J=5.3 Hz), 7.22-7.30 (1H, m), 7.34 (1H, s), 7.42 (2H, d, J=8.3 Hz), 7.59 (2H, d, J=8.3 Hz), 8.23 (1H, d, J=5.1 Hz), 8.53 (1H, d, J=5.3 Hz).

Example 340

4-((2,4-difluorobenzyl)oxy)-6-(4-(1-methyl-1H-1,2,3-triazol-4-yl)benzyl)-6,7-dihydro-5H-pyrrolo[3,4-d]pyrimidin-5-one

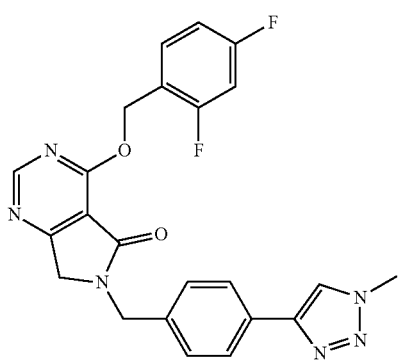 [SMILES: Cn1cc(-c2ccc(CN3Cc4ncnc(OCc5ccc(F)cc5F)c4C3=O)cc2)nn1]

To a solution of methyl 4-((2,4-difluorobenzyl)oxy)-6-formylpyrimidine-5-carboxylate (0.60 g) obtained in Reference Example 176 and (4-(1-methyl-1H-1,2,3-triazol-4-yl)phenyl)methanamine (0.39 g) obtained in Reference Example 162 in methanol (4 mL)-THF (4 mL) was added magnesium sulfate (0.47 g) at room temperature, and the mixture was stirred under a nitrogen atmosphere at room temperature for 1 hr. The insoluble material was filtered off, and the filtrate was concentrated. To a solution of the residue in acetic acid (4 mL) was added sodium triacetoxyhydroborate (0.62 g) at room temperature, and the mixture was stirred under a nitrogen atmosphere at room temperature for 3 hr. Water was added to the reaction mixture, and the mixture was concentrated. To the residue were added saturated aqueous sodium hydrogen carbonate solution and ethyl acetate, and the organic layer was separated, washed with saturated brine, dried over anhydrous magnesium sulfate and concentrated. The residue was purified by silica gel chromatography (hexane-ethyl acetate), and solidified with ethyl acetate-diisopropyl ether to give the title compound (0.088 g).

MS: [M+H]$^+$ 449.2

$^1$H NMR (300 MHz, CDCl$_3$) δ 4.15 (3H, s), 4.29 (2H, s), 4.79 (2H, s), 5.68 (2H, s), 6.76-6.99 (2H, m), 7.37 (2H, d, J=8.3 Hz), 7.56-7.68 (1H, m), 7.73 (1H, s), 7.80 (2H, d, J=8.1 Hz), 8.84 (1H, s).

Example 341

2-(4-(1,3-dimethyl-1H-pyrazol-4-yl)-2-fluorobenzyl)-4-((1-methylcyclopropyl)methoxy)-1,2-dihydro-3H-pyrrolo[3,4-c]pyridin-3-one

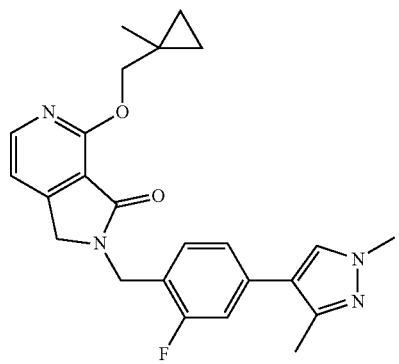 [SMILES: Cc1nn(C)cc1-c1ccc(CN2Cc3ccnc(OCC4(C)CC4)c3C2=O)c(F)c1]

To a solution of 2-(4-bromo-2-fluorobenzyl)-4-((1-methylcyclopropyl)methoxy)-1H-pyrrolo[3,4-c]pyridin-3(2H)-one (0.15 g) obtained in Reference Example 180 in DME (1.5 mL)-water (1.5 mL) were added 1,3-dimethyl-4-(4,4,5,5-tetramethyl-1,3,2-dioxaborolan-2-yl)-1H-pyrazole (0.11 g), sodium carbonate (0.15 g), and (1,1-bis(diphenylphosphino)ferrocene)dichloropalladium(II) methylene chloride adduct (0.030 g), and the mixture was stirred under a nitrogen atmosphere at 90° C. for 3 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate-diisopropyl ether to give the title compound (0.082 g).

MS: [M+H]$^+$ 421.2

$^1$H NMR (300 MHz, CDCl$_3$) δ 0.39-0.47 (2H, m), 0.58-0.68 (2H, m), 1.30 (3H, s), 2.38 (3H, s), 3.87 (3H, s), 4.31 (2H, s), 4.33 (2H, s), 4.81 (2H, s), 6.92 (1H, d, J=5.3 Hz), 7.04-7.17 (2H, m), 7.35-7.47 (2H, m), 8.20 (1H, d, J=5.3 Hz).

Example 342

4-((2-fluorobenzyl)oxy)-2-(2-fluoro-4-(1-methyl-1H-pyrazol-3-yl)benzyl)-1,2-dihydro-3H-pyrrolo[3,4-c]pyridin-3-one

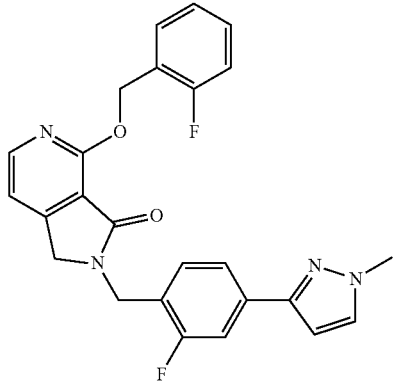 [SMILES: Cn1ccc(-c2ccc(CN3Cc4ccnc(OCc5ccccc5F)c4C3=O)c(F)c2)n1]

To a solution of 2-(4-bromo-2-fluorobenzyl)-4-((2-fluorobenzyl)oxy)-1H-pyrrolo[3,4-c]pyridin-3(2H)-one (0.30 g) obtained in Reference Example 184 in DME (2 mL)-water (2 mL) were added 1-methyl-3-(4,4,5,5-tetramethyl-1,3,2-dioxaborolan-2-yl)-1H-pyrazole (0.18 g), sodium carbonate (0.29 g), and (1,1-bis(diphenylphosphino)ferrocene)dichloropalladium(II) methylene chloride adduct (0.055 g), and the mixture was stirred under a nitrogen atmosphere at 90° C. for 3 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate-diisopropyl ether to give the title compound (0.11 g).

MS: [M+H]$^+$ 447.1

$^1$H NMR (300 MHz, CDCl$_3$) δ 3.94 (3H, s), 4.32 (2H, s), 4.83 (2H, s), 5.68 (2H, s), 6.50 (1H, d, J=2.3 Hz), 6.97 (1H, d, J=5.3 Hz), 7.05 (1H, t, J=9.3 Hz), 7.11-7.20 (1H, m), 7.22-7.31 (1H, m), 7.34-7.45 (2H, m), 7.47-7.57 (2H, m), 7.74 (1H, t, J=7.0 Hz), 8.26 (1H, d, J=5.1 Hz).

Example 343

2-(4-(1,3-dimethyl-1H-pyrazol-4-yl)-2-fluorobenzyl)-4-((2-fluorobenzyl)oxy)-1,2-dihydro-3H-pyrrolo[3,4-c]pyridin-3-one

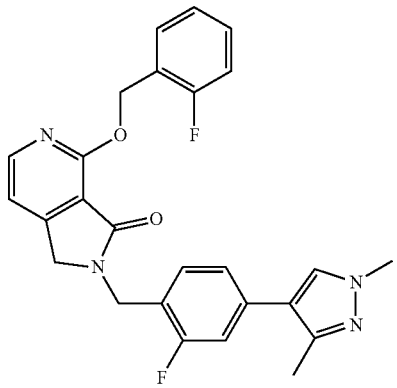 [SMILES: Cc1nn(C)cc1-c1ccc(CN2Cc3ccnc(OCc4ccccc4F)c3C2=O)c(F)c1]

To a solution of 2-(4-bromo-2-fluorobenzyl)-4-((2-fluorobenzyl)oxy)-1H-pyrrolo[3,4-c]pyridin-3(2H)-one (0.30 g) obtained in Reference Example 184 in DME (2 mL)-water (2 mL) were added 1,3-dimethyl-4-(4,4,5,5-tetramethyl-1,3,2-dioxaborolan-2-yl)-1H-pyrazole (0.20 g), sodium carbonate (0.29 g), and (1,1-bis(diphenylphosphino)ferrocene)dichloropalladium(II) methylene chloride adduct (0.055 g), and the mixture was stirred under a nitrogen atmosphere at 90° C. for 3 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate-diisopropyl ether to give the title compound (0.14 g).

MS: [M+H]$^+$ 461.1

$^1$H NMR (300 MHz, CDCl$_3$) δ 2.38 (3H, s), 3.87 (3H, s), 4.36 (2H, s), 4.82 (2H, s), 5.67 (2H, s), 6.95-7.20 (5H, m), 7.21-7.32 (1H, m), 7.34-7.46 (2H, m), 7.74 (1H, t, J=6.8 Hz), 8.26 (1H, d, J=5.3 Hz).

Example 344

4-((2-fluorobenzyl)oxy)-2-(2-fluoro-4-(6-methylpyridazin-4-yl)benzyl)-1,2-dihydro-3H-pyrrolo[3,4-c]pyridin-3-one

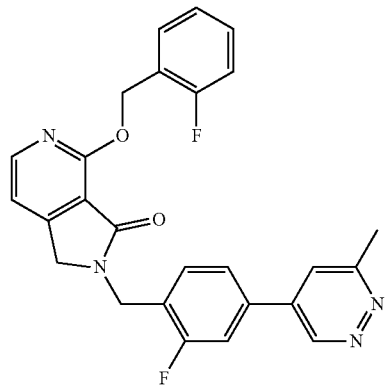 [SMILES: Cc1cc(-c2ccc(CN3Cc4ccnc(OCc5ccccc5F)c4C3=O)c(F)c2)cnn1]

To a solution of 2-(4-bromo-2-fluorobenzyl)-4-((2-fluorobenzyl)oxy)-1H-pyrrolo[3,4-c]pyridin-3(2H)-one (0.30 g) obtained in Reference Example 184 in DME (2 mL)-water (2 mL) were added 3-methyl-5-(4,4,5,5-tetramethyl-1,3,2-dioxaborolan-2-yl)pyridazine (0.19 g), sodium carbonate (0.29 g), and (1,1-bis(diphenylphosphino)ferrocene)dichloropalladium(II) methylene chloride adduct (0.055 g), and the mixture was stirred under a nitrogen atmosphere at 90° C. for 3 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with THF-diisopropyl ether to give the title compound (0.090 g).

MS: [M+H]$^+$ 459.1

$^1$H NMR (300 MHz, CDCl$_3$) δ 2.79 (3H, s), 4.39 (2H, s), 4.88 (2H, s), 5.68 (2H, s), 7.00 (1H, d, J=5.1 Hz), 7.02-7.10 (1H, m), 7.11-7.20 (1H, m), 7.23-7.32 (1H, m), 7.34-7.46 (3H, m), 7.53-7.64 (1H, m), 7.67-7.78 (1H, m), 8.29 (1H, d, J=5.1 Hz), 9.24 (1H, d, J=2.3 Hz).

Example 345

2-((2-(4-(1-ethyl-1H-pyrazol-4-yl)benzyl)-3-oxo-2,3-dihydro-1H-pyrrolo[3,4-c]pyridin-4-yl)oxy)-N-methoxy-N-methylacetamide

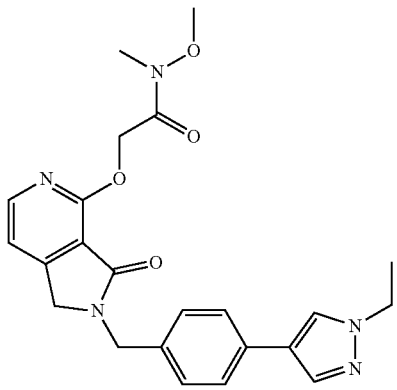 [SMILES: CCn1cc(-c2ccc(CN3Cc4ccnc(OCC(=O)N(C)OC)c4C3=O)cc2)cn1]

To a solution of ((2-(4-(1-ethyl-1H-pyrazol-4-yl)benzyl)-3-oxo-2,3-dihydro-1H-pyrrolo[3,4-c]pyridin-4-yl)oxy) acetic acid (1.3 g) obtained in Reference Example 255, 0-(7-azabenzotriazol-1-yl)-N,N,N',N'-tetramethyluronium hexafluorophosphate (3.15 g), and N,O-dimethylhydroxylamine (0.97 g) in DMF was added triethylamine (2.7 mL), and the mixture was stirred at room temperature overnight. Water was added to the reaction mixture, and the mixture was diluted with ethyl acetate. The organic layer was separated, washed with saturated aqueous sodium hydrogen carbonate solution and saturated brine, dried over anhydrous sodium sulfate, and concentrated. The residue was purified by NH silica gel chromatography (hexane-ethyl acetate) and recrystallization (ethyl acetate) to give the title compound (0.382 g).

MS: [M+H]$^+$ 436.1

$^1$H NMR (300 MHz, CDCl$_3$) 51.52 (2H, t, J=7.4 Hz), 3.22 (2H, s), 3.31 (1H, s), 3.72 (1H, s), 3.83 (3H, s), 4.11-4.24 (4H, m), 4.74 (2H, s), 5.35 (2H, s), 6.89-6.96 (1H, m), 7.27-7.32 (2H, m), 7.40-7.47 (2H, m), 7.63 (1H, s), 7.75 (1H, s), 8.18 (1H, d, J=5.3 Hz).

Example 346

4-(6,7-dihydro-5H-cyclopenta[b]pyridin-7-yloxy)-2-(4-(1,3-dimethyl-1H-pyrazol-4-yl)-2-fluorobenzyl)-1,2-dihydro-3H-pyrrolo[3,4-c]pyridin-3-one

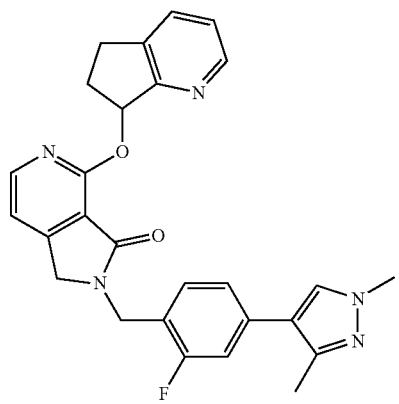 [SMILES: Cc1nn(C)cc1-c1ccc(CN2Cc3ccnc(OC4CCc5cccnc54)c3C2=O)c(F)c1]

To a solution of 2-(4-bromo-2-fluorobenzyl)-4-((6,7-dihydro-5H-cyclopenta[b]pyridin-7-yl)oxy)-1H-pyrrolo[3,4-c]pyridin-3(2H)-one (0.25 g) obtained in Reference Example 189 in DME (2 mL)-water (2 mL) were added 1,3-dimethyl-4-(4,4,5,5-tetramethyl-1,3,2-dioxaborolan-2-yl)-1H-pyrazole (0.16 g), sodium carbonate (0.23 g), and (1,1-bis(diphenylphosphino)ferrocene)dichloropalladium (II) methylene chloride adduct (0.045 g), and the mixture was stirred under a nitrogen atmosphere at 90° C. for 3 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with THF-diisopropyl ether to give the title compound (0.11 g).

MS: [M+H]$^+$ 470.2

$^1$H NMR (300 MHz, CDCl$_3$) δ 2.24-2.47 (4H, m), 2.66-2.81 (1H, m), 2.84-3.03 (1H, m), 3.11-3.30 (1H, m), 3.86 (3H, s), 4.33 (2H, s), 4.76 (2H, s), 6.81 (1H, dd, J=7.6, 5.1 Hz), 6.97 (1H, d, J=5.1 Hz), 7.03-7.11 (2H, m), 7.16 (1H, dd, J=7.6, 4.9 Hz), 7.31-7.39 (1H, m), 7.41 (1H, s), 7.58 (1H, d, J=6.8 Hz), 8.31 (1H, d, J=5.1 Hz), 8.48 (1H, d, J=4.9 Hz).

Example 347

4-(2,2-difluoro-2-(pyridin-2-yl)ethoxy)-2-(4-(1,3-dimethyl-1H-pyrazol-4-yl)-2-fluorobenzyl)-1,2-dihydro-3H-pyrrolo[3,4-c]pyridin-3-one

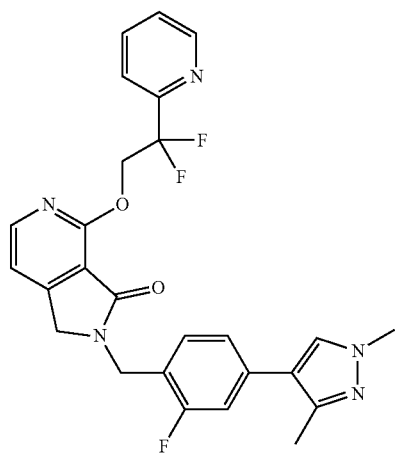 [SMILES: Cc1nn(C)cc1-c1ccc(CN2Cc3ccnc(OCC(F)(F)c4ccccn4)c3C2=O)c(F)c1]

To a solution of 2-(4-bromo-2-fluorobenzyl)-4-(2,2-difluoro-2-(pyridin-2-yl)ethoxy)-1H-pyrrolo[3,4-c]pyridin-3(2H)-one (0.30 g) obtained in Reference Example 193 in DME (3 mL)-water (3 mL) were added 1,3-dimethyl-4-(4,4,5,5-tetramethyl-1,3,2-dioxaborolan-2-yl)-1H-pyrazole (0.18 g), sodium carbonate (0.20 g), and (1,1-bis(diphenylphosphino)ferrocene)dichloropalladium(II) methylene chloride adduct (0.051 g), and the mixture was stirred under a nitrogen atmosphere at 90° C. for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate-diisopropyl ether to give the title compound (0.22 g).

MS: [M+H]$^+$ 494.2

$^1$H NMR (300 MHz, CDCl$_3$) δ 2.37 (3H, s), 3.86 (3H, s), 4.29 (2H, s), 4.77 (2H, s), 5.18 (2H, t, J=12.4 Hz), 6.98 (1H, d, J=5.1 Hz), 7.03-7.15 (2H, m), 7.30-7.46 (3H, m), 7.80-7.98 (2H, m), 8.22 (1H, d, J=5.1 Hz), 8.66 (1H, d, J=4.3 Hz).

Example 348

4-(cyclobutyloxy)-2-(4-(1-methyl-1H-pyrazol-4-yl)benzyl)-1,2-dihydro-3H-pyrrolo[3,4-c]pyridin-3-one

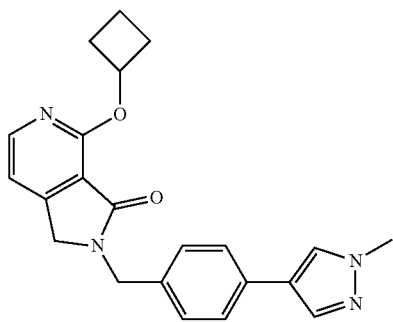 [SMILES: Cn1cc(-c2ccc(CN3Cc4ccnc(OC5CCC5)c4C3=O)cc2)cn1]

To a solution of 4-cyclobutoxy-2-(4-iodobenzyl)-1H-pyrrolo[3,4-c]pyridin-3(2H)-one (0.24 g) obtained in Reference Example 194 in DME (2.5 mL)-water (2.5 mL) were added 1-methyl-4-(4,4,5,5-tetramethyl-1,3,2-dioxaborolan-2-yl)-1H-pyrazole (0.15 g), sodium carbonate (0.18 g), and (1,1-bis(diphenylphosphino)ferrocene)dichloropalladium(II) methylene chloride adduct (0.046 g), and the mixture was stirred under a nitrogen atmosphere at 90° C. for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with methanol-diisopropyl ether to give the title compound (0.077 g).

MS: [M+H]$^+$ 375.2

$^1$H NMR (300 MHz, CDCl$_3$) δ 1.63-1.94 (2H, m), 2.23-2.43 (2H, m), 2.44-2.61 (2H, m), 3.94 (3H, s), 4.22 (2H, s), 4.73 (2H, s), 5.35 (1H, quin, J=7.5 Hz), 6.89 (1H, d, J=5.3 Hz), 7.27-7.33 (2H, m), 7.38-7.45 (2H, m), 7.59 (1H, s), 7.73 (1H, s), 8.21 (1H, d, J=0.5 Hz).

Example 349

4-((6,6-dimethyl-6,7-dihydro-5H-cyclopenta[b]pyridin-7-yl)oxy)-2-(4-(1-methyl-1H-pyrazol-4-yl)benzyl)-1,2-dihydro-3H-pyrrolo[3,4-c]pyridin-3-one

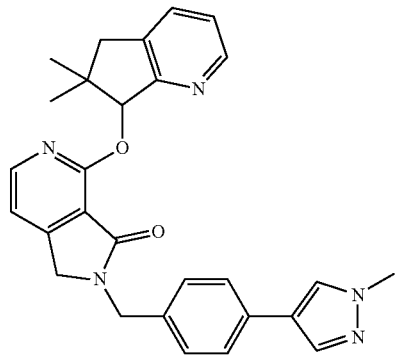 [SMILES: Cn1cc(-c2ccc(CN3Cc4ccnc(OC5c6ncccc6CC5(C)C)c4C3=O)cc2)cn1]

To a solution of 2-(4-bromobenzyl)-4-((6,6-dimethyl-6,7-dihydro-5H-cyclopenta[b]pyridin-7-yl)oxy)-1H-pyrrolo[3,4-c]pyridin-3(2H)-one (0.18 g) obtained in Reference Example 200 in DME (1.5 mL)-water (1.5 mL) were added 1,3-dimethyl-4-(4,4,5,5-tetramethyl-1,3,2-dioxaborolan-2-yl)-1H-pyrazole (0.11 g), sodium carbonate (0.12 g), and (1,1-bis(diphenylphosphino)ferrocene)dichloropalladium (II) methylene chloride adduct (0.032 g), and the mixture was stirred under a nitrogen atmosphere at 90° C. for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with THF-diisopropyl ether to give the title compound (0.080 g).

MS: [M+H]$^+$ 466.3

$^1$H NMR (300 MHz, CDCl$_3$) δ 1.26 (3H, s), 1.32 (3H, s), 2.73 (1H, d, J=15.7 Hz), 3.08 (1H, d, J=15.7 Hz), 3.93 (3H, s), 4.20 (2H, s), 4.56 (1H, d, J=14.9 Hz), 4.84 (1H, d, J=14.7 Hz), 6.58 (1H, s), 6.93 (1H, d, J=5.3 Hz), 7.12 (1H, dd, J=7.6, 4.9 Hz), 7.23-7.29 (2H, m), 7.41 (2H, d, J=8.1 Hz), 7.53 (1H, d, J=7.7 Hz), 7.58 (1H, s), 7.73 (1H, s), 8.32 (1H, d, J=5.1 Hz), 8.42 (1H, d, J=4.0 Hz).

Example 350

6-bromo-2-(4-(1-methyl-1H-pyrazol-4-yl)benzyl)-7-((tetrahydrofuran-2-yl)methoxy)isoindolin-1-one

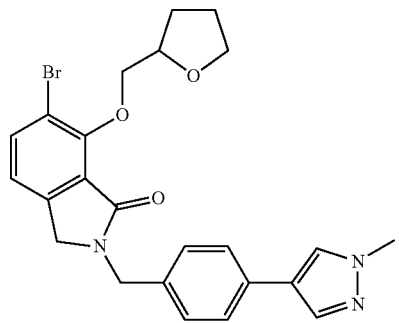 [SMILES: Cn1cc(-c2ccc(CN3Cc4ccc(Br)c(OCC5CCCO5)c4C3=O)cc2)cn1]

To a solution of 6-bromo-7-hydroxy-2-(4-(1-methyl-1H-pyrazol-4-yl)benzyl)isoindolin-1-one (0.13 g) obtained in Reference Example 57, (tetrahydrofuran-2-yl)methanol (0.17 g) and tributylphosphine (0.34 g) in THF (10 mL) was added ADDP (0.42 g), and the mixture was stirred at 60° C. for 5 hr. The reaction mixture was allowed to cool to room temperature, and the insoluble material was filtered off. The filtrate was diluted with ethyl acetate, washed with water and saturated brine, dried over anhydrous sodium sulfate, and concentrated.

The residue was purified by NH silica gel chromatography (hexane-ethyl acetate) to give the title compound (0.047 g).

MS: [M+H]+ 482.1

1H NMR (300 MHz, DMSO-d6) δ 1.77-2.04 (4H, m), 3.61-3.70 (1H, m), 3.73-3.82 (1H, m), 3.85 (3H, s), 4.15-4.26 (2H, m), 4.27-4.36 (3H, m), 4.67 (2H, s), 7.17-7.29 (3H, m), 7.53 (2H, d, J=8.1 Hz), 7.79 (1H, d, J=7.9 Hz), 7.82 (1H, d, J=0.6 Hz), 8.10 (1H, s).

Example 351

6-methyl-2-(4-(1-methyl-1H-pyrazol-4-yl)benzyl)-7-((tetrahydrofuran-2-yl)methoxy)isoindolin-1-one

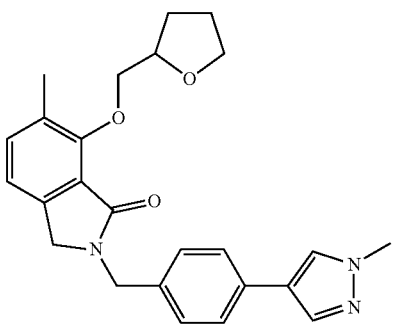 [SMILES: Cc1ccc2c(c1OCC1CCCO1)C(=O)N(Cc1ccc(-c3cnn(C)c3)cc1)C2]

To a solution of 6-bromo-2-(4-(1-methyl-1H-pyrazol-4-yl)benzyl)-7-((tetrahydrofuran-2-yl)methoxy)isoindolin-1-one (0.042 g) obtained in Example 350, methylzinc chloride (0.065 mL, 2M THF solution) and 1,2,3,4,5-pentaphenyl-1'-(di-tert-butylphosphino)ferrocene (0.0062 g) in THF was added tris(dibenzylideneacetone)dipalladium (0.0040 g), and the mixture was stirred under microwave irradiation at 100° C. for 1 hr. The reaction mixture was diluted with ethyl acetate, and the insoluble material was filtered off. The filtrate was washed with water and saturated brine, dried over anhydrous sodium sulfate, and concentrated. The residue was purified by NH silica gel chromatography (hexane-ethyl acetate) to give the title compound (0.022 g).

MS: [M+H]+ 418.2

1H NMR (300 MHz, DMSO-d6) δ 1.68-2.02 (4H, m), 2.27 (3H, s), 3.61-3.82 (2H, m), 3.85 (3H, s), 4.11-4.25 (3H, m), 4.27 (2H, s), 4.65 (2H, s), 7.12 (1H, d, J=7.5 Hz), 7.24 (2H, d, J=8.3 Hz), 7.39 (1H, d, J=7.5 Hz), 7.53 (2H, d, J=7.9 Hz), 7.82 (1H, s), 8.10 (1H, s).

Example 352

7-((trans-2-hydroxycyclohexyl)oxy)-2-(4-(pyridazin-4-yl)benzyl)isoindolin-1-one

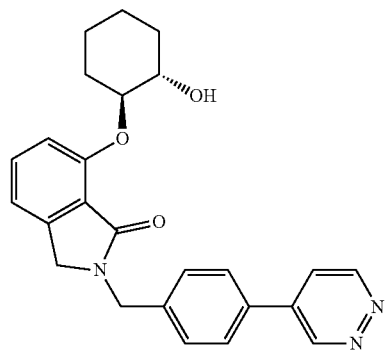 [SMILES: O=C1c2c(cccc2O[C@H]2CCCC[C@@H]2O)CN1Cc1ccc(-c2ccnnc2)cc1]

To a solution of methyl 2-formyl-6-((trans-2-hydroxycyclohexyl)oxy)benzoate (0.20 g) obtained in Reference Example 203 and (4-(pyridazin-4-yl)phenyl)methanamine (0.17 g) in THF (4 mL) was added anhydrous magnesium sulfate (0.17 g), and the mixture was stirred for 1 hr. The insoluble material was filtered off, and the filtrate was concentrated. The residue was dissolved in acetic acid (4 mL), sodium triacetoxyborohydride (0.31 g) was added, and the mixture was stirred for 1 hr. The reaction mixture was diluted with ethyl acetate and saturated aqueous sodium hydrogen carbonate solution, and the organic layer was separated, washed with saturated brine, dried over anhydrous sodium sulfate, and concentrated. The residue was purified by NH silica gel chromatography (hexane-ethyl acetate) to give the title compound (0.065 g).

MS: [M+H]+ 416.2

1H NMR (300 MHz, DMSO-d6) δ 1.21-1.75 (6H, m), 1.85-1.98 (1H, m), 2.02-2.15 (1H, m), 3.62 (1H, brs), 4.01-4.13 (1H, m), 4.36 (2H, s), 4.76 (2H, s), 5.15 (1H, brs), 7.12 (2H, dd, J=7.7, 3.4 Hz), 7.42-7.54 (3H, m), 7.92 (2H, d, J=8.3 Hz), 7.99 (1H, dd, J=5.5, 2.5 Hz), 9.26 (1H, dd, J=5.5, 1.1 Hz), 9.63 (1H, dd, J=2.5, 1.1 Hz).

Example 353

2-(4-(2-methylpyridin-4-yl)benzyl)-7-((tetrahydrofuran-2-yl)methoxy)isoindolin-1-one hydrochloride

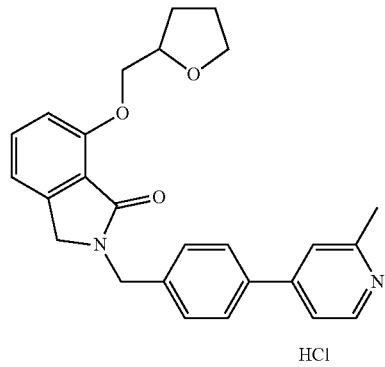 [SMILES: Cc1cc(-c2ccc(CN3Cc4cccc(OCC5CCCO5)c4C3=O)cc2)ccn1 ; Cl]

To a solution of methyl 2-formyl-6-((tetrahydrofuran-2-yl)methoxy)benzoate (0.20 g) obtained in Reference Example 205 and (4-(2-methylpyridin-4-yl)phenyl)methanamine (0.15 g) obtained in Reference Example 63 in THF (4 mL) was added anhydrous magnesium sulfate (0.18 g), and the mixture was stirred at room temperature for 1 hr. The insoluble material was filtered off, and the filtrate was concentrated. The residue was dissolved in acetic acid, sodium triacetoxyborohydride (0.32 g) was added, and the mixture was stirred for 1 hr. The reaction mixture was diluted with ethyl acetate and saturated aqueous sodium hydrogen carbonate solution, and the organic layer was separated, washed with saturated brine, dried over anhydrous sodium sulfate, and concentrated. The residue was purified by NH silica gel chromatography (hexane-ethyl acetate). The obtained product was dissolved in ethyl acetate, 4N hydrochloric acid-ethyl acetate was added, and the precipitate was collected by filtration to give the title compound (0.14 g).

MS: [M+H]+ 415.2

1H NMR (300 MHz, DMSO-d6) δ 1.73-1.91 (2H, m), 2.00-2.09 (2H, m), 2.78 (3H, s), 3.79-3.91 (2H, m), 4.06-4.13 (2H, m), 4.13-4.28 (1H, m), 4.35 (2H, s), 4.77 (2H, s), 7.07 (2H, dd, J=14.1, 7.8 Hz), 7.44-7.57 (3H, m), 8.01 (2H, d, J=8.3 Hz), 8.20 (1H, dd, J=6.4, 1.5 Hz), 8.31 (1H, s), 8.80 (1H, d, J=6.2 Hz).

Example 354

2-(4-(1,3-dimethyl-1H-pyrazol-4-yl)benzyl)-7-((7-oxabicyclo[2.2.1]hept-1-yl)methoxy)isoindolin-1-one

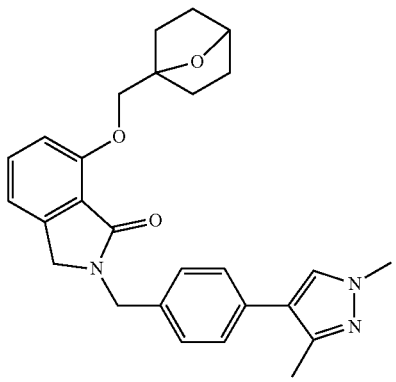 [SMILES: Cc1nn(C)cc1-c1ccc(CN2Cc3cccc(OCC45CCC(CC4)O5)c3C2=O)cc1]

To a solution of 7-((7-oxabicyclo[2.2.1]hept-1-yl)methoxy)-2-(4-bromobenzyl)isoindolin-1-one (0.070 g) obtained in Reference Example 329, 1,3-dimethyl-4-(4,4,5,5-tetramethyl-1,3,2-dioxaborolan-2-yl)-1H-pyrazole (0.054 g) in DME (2 mL) were added 2M aqueous sodium carbonate solution (0.5 mL) and [1,1'-bis(diphenylphosphino)ferrocene]dichloropalladium(II) (0.013 g), and the mixture was stirred under an argon atmosphere at 100° C. overnight. The reaction mixture was diluted with water, extracted with ethyl acetate, washed with saturated aqueous sodium hydrogen carbonate solution and saturated brine, dried over anhydrous sodium sulfate, and concentrated. The residue was purified by NH silica gel chromatography (hexane-ethyl acetate) to give the title compound (0.054 g).

MS: [M+H]+ 444.3

1H NMR (300 MHz, DMSO-d6) δ 1.46-1.86 (8H, m), 2.26 (3H, s), 3.77 (3H, s), 4.30 (2H, s), 4.39 (2H, s), 4.50 (1H, t, J=4.5 Hz), 4.64 (2H, s), 7.01-7.13 (2H, m), 7.21-7.32 (2H, m), 7.34-7.43 (2H, m), 7.43-7.54 (1H, m), 7.84 (1H, s).

Example 355

7-((trans-2-hydroxycyclohexyl)oxy)-2-(4-(6-methylpyridazin-4-yl)benzyl)isoindolin-1-one

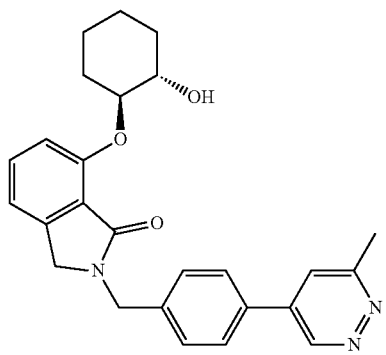 [SMILES: Cc1cc(-c2ccc(CN3Cc4cccc(O[C@H]5CCCC[C@@H]5O)c4C3=O)cc2)cnn1]

To a solution of 2-(4-bromobenzyl)-7-((trans-2-hydroxycyclohexyl)oxy)isoindolin-1-one (0.10 g) obtained in Example 25 and 3-methyl-5-(4,4,5,5-tetramethyl-1,3,2-dioxaborolan-2-yl)pyridazine (0.079 g) in DME (4 mL) were added 2M aqueous sodium carbonate solution (1 mL) and [1,1'-bis(diphenylphosphino)ferrocene]dichloropalladium(II) (0.0084 g), and the mixture was stirred under microwave irradiation at 100° C. for 1 hr. The reaction mixture was diluted with ethyl acetate, and the insoluble material was filtered off. The filtrate was washed with water and saturated brine, dried over anhydrous sodium sulfate, and concentrated. The residue was purified by NH silica gel chromatography (hexane-ethyl acetate, ethyl acetate/methanol) to give the title compound (0.025 g).

MS: [M+H]+ 430.2

1H NMR (300 MHz, DMSO-d6) δ 1.19-1.73 (6H, m), 1.91 (1H, brs), 2.08 (1H, d, J=11.9 Hz), 2.67 (3H, s), 3.53-3.66 (1H, m), 4.07 (1H, td, J=8.1, 3.4 Hz), 4.35 (2H, s), 4.75 (2H, s), 7.12 (2H, dd, J=7.8, 3.5 Hz), 7.41-7.54 (3H, m), 7.84-7.95 (3H, m), 9.45 (1H, d, J=2.1 Hz).

Example 356

2-(4-(6-methylpyridazin-4-yl)benzyl)-7-((tetrahydrofuran-2-yl)methoxy)isoindolin-1-one

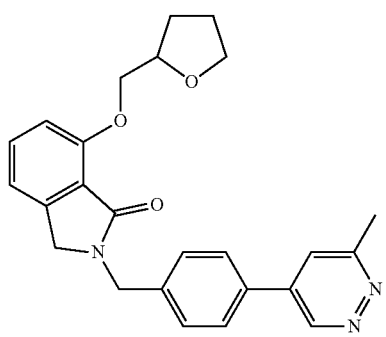 [SMILES: Cc1cc(-c2ccc(CN3Cc4cccc(OCC5CCCO5)c4C3=O)cc2)cnn1]

To a solution of 2-(4-bromobenzyl)-7-((tetrahydrofuran-2-yl)methoxy)isoindolin-1-one (0.10 g) obtained in Reference Example 331 and 3-methyl-5-(4,4,5,5-tetramethyl-1,3,2-dioxaborolan-2-yl)pyridazine (0.082 g) in 1,2-dimethoxyethane (4 mL) were added 2M aqueous sodium carbonate solution (1 mL) and [1,1'-bis(diphenylphosphino)ferrocene]dichloropalladium(II) (0.0087 g), and the mixture was stirred under microwave irradiation at 100° C. for 1 hr. The reaction mixture was diluted with ethyl acetate, and the insoluble material was filtered off. The filtrate was washed with water and saturated brine, dried over anhydrous sodium sulfate, and concentrated. The residue was purified by NH silica gel chromatography (hexane-ethyl acetate, ethyl acetate-methanol) to give the title compound (0.026 g).

MS: [M+H]$^+$ 416.2

$^1$H NMR (300 MHz, DMSO-d$_6$) δ 1.74-2.14 (4H, m), 2.67 (3H, s), 3.62-3.74 (1H, m), 3.80-3.91 (1H, min), 4.03-4.11 (2H, m), 4.14-4.26 (1H, m), 4.29-4.35 (2H, m), 4.73 (2H, s), 6.99-7.12 (2H, m), 7.40-7.53 (3H, m), 7.85-7.94 (3H, m), 9.44 (1H, d, J=2.3 Hz).

Example 357

2-(4-(1,3-dimethyl-1H-pyrazol-4-yl)benzyl)-4-(2-fluoro-6-methoxyphenoxy)-1,2-dihydro-3H-pyrrolo[3,4-c]pyridin-3-one

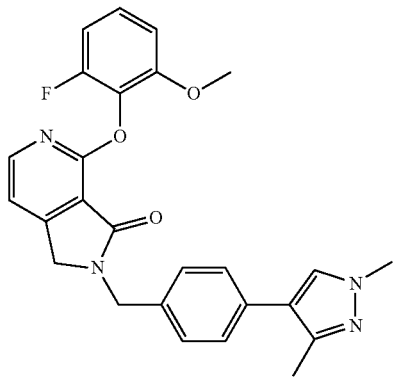 [SMILES: COc1cccc(F)c1Oc1nccc2c1C(=O)N(Cc1ccc(-c3cn(C)nc3C)cc1)C2]

To a solution of 2-(4-bromobenzyl)-4-(2-fluoro-6-methoxyphenoxy)-1H-pyrrolo[3,4-c]pyridin-3(2H)-one (0.10 g) obtained in Reference Example 330 and 1,3-dimethyl-4-(4,4,5,5-tetramethyl-1,3,2-dioxaborolan-2-yl)-1H-pyrazole (0.075 g) in 1,2-dimethoxyethane (3 mL) were added 2M aqueous sodium carbonate solution (0.6 mL) and [1,1'-bis(diphenylphosphino)ferrocene]dichloropalladium(II) (0.0092 g), and the mixture was stirred under microwave irradiation at 150° C. for 1 hr. The reaction mixture was diluted with water, extracted with ethyl acetate, washed with saturated aqueous sodium hydrogen carbonate solution and saturated brine, dried over anhydrous sodium sulfate, and concentrated. The residue was purified by NH silica gel chromatography (hexane-ethyl acetate) to give the title compound (0.045 g).

MS: [M+H]$^+$ 459.2

$^1$H NMR (300 MHz, DMSO-d$_6$) δ 2.28 (3H, s), 3.75 (3H, s), 3.78 (3H, s), 4.49 (2H, s), 4.71 (2H, s), 6.92-7.05 (2H, m), 7.22-7.37 (4H, m), 7.38-7.45 (2H, m), 7.86 (1H, s), 8.16 (1H, d, J=5.1 Hz).

Example 358

4-(2,4-difluoro-6-methylphenoxy)-2-(4-(6-methylpyridazin-4-yl)benzyl)-1,2-dihydro-3H-pyrrolo[3,4-c]pyridin-3-one

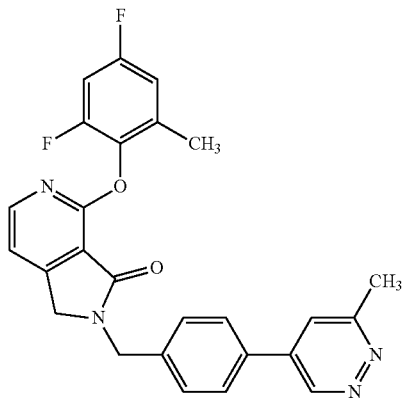 [SMILES: Cc1cc(-c2ccc(CN3Cc4ccnc(Oc5c(C)cc(F)cc5F)c4C3=O)cc2)cnn1]

To a solution of 2-(4-bromobenzyl)-4-(2,4-difluoro-6-methylphenoxy)-1H-pyrrolo[3,4-c]pyridin-3(2H)-one (0.10 g) obtained in Reference Example 213 and 3-methyl-5-(4,4,5,5-tetramethyl-1,3,2-dioxaborolan-2-yl)pyridazine (0.054 g) in DME (3 mL) were added 2M aqueous sodium carbonate solution (0.5 mL) and [1,1'-bis(diphenylphosphino)ferrocene]dichloropalladium(II) (0.0092 g), and the mixture was stirred under microwave irradiation at 150° C. for 1 hr. The reaction mixture was diluted with water, extracted with ethyl acetate, washed with saturated aqueous sodium hydrogen carbonate solution and saturated brine, dried over anhydrous sodium sulfate, and concentrated. The residue was purified by NH silica gel chromatography (hexane-ethyl acetate) to give the title compound (0.014 g).

MS: [M+H]$^+$ 459.1

$^1$H NMR (300 MHz, DMSO-d$_6$) δ 2.15 (3H, s), 2.68 (3H, s), 4.53 (2H, s), 4.81 (2H, s), 7.11 (1H, d, J=9.1 Hz), 7.21-7.31 (1H, m), 7.37 (1H, d, J=5.3 Hz), 7.52 (2H, d, J=8.3 Hz), 7.86-7.97 (3H, m), 8.20 (1H, d, J=5.1 Hz), 9.46 (1H, d, J=2.3 Hz).

Example 359

4-(2,4-difluoro-6-methylphenoxy)-2-(4-(1-methyl-1H-pyrazol-3-yl)benzyl)-1,2-dihydro-3H-pyrrolo[3,4-c]pyridin-3-one

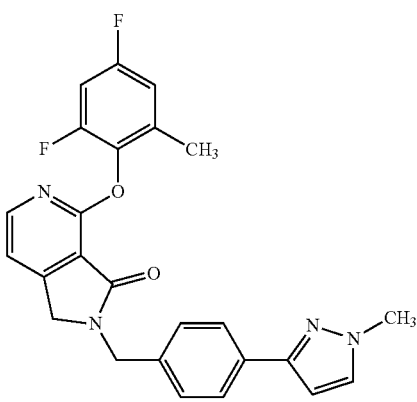 [SMILES: Cc1cc(F)cc(F)c1Oc1nccc2c1C(=O)N(Cc1ccc(-c3ccn(C)n3)cc1)C2]

To a solution of 2-(4-bromobenzyl)-4-(2,4-difluoro-6-methylphenoxy)-1H-pyrrolo[3,4-c]pyridin-3(2H)-one (0.10 g) obtained in Reference Example 213 and 1-methyl-3-(4,4,5,5-tetramethyl-1,3,2-dioxaborolan-2-yl)-1H-pyrazole (0.070 g) in DME (3 mL) were added 2M aqueous sodium carbonate solution (0.5 mL) and [1,1'-bis(diphenylphosphino)ferrocene]dichloropalladium(II) (0.0092 g), and the mixture was stirred under microwave irradiation at 150° C. for 1 hr. The reaction mixture was diluted with water, extracted with ethyl acetate, washed with saturated aqueous sodium hydrogen carbonate solution and saturated brine, dried over anhydrous sodium sulfate, and concentrated. The residue was purified by NH silica gel chromatography (hexane-ethyl acetate) to give the title compound (0.055 g).

MS: [M+H]$^+$ 447.0

$^1$H NMR (300 MHz, DMSO-d$_6$) δ 2.14 (3H, s), 3.87 (3H, s), 4.49 (2H, s), 4.73 (2H, s), 6.67 (1H, d, J=2.3 Hz), 7.11 (1H, d, J=9.4 Hz), 7.21-7.31 (1H, m), 7.31-7.39 (3H, m), 7.72 (1H, d, J=2.3 Hz), 7.78 (2H, d, J=8.1 Hz), 8.19 (1H, d, J=5.3 Hz).

Example 360

4-(2-fluoro-6-methoxyphenoxy)-2-(4-(1-methyl-1H-pyrazol-4-yl)benzyl)-1,2-dihydro-3H-pyrrolo[3,4-c]pyridin-3-one

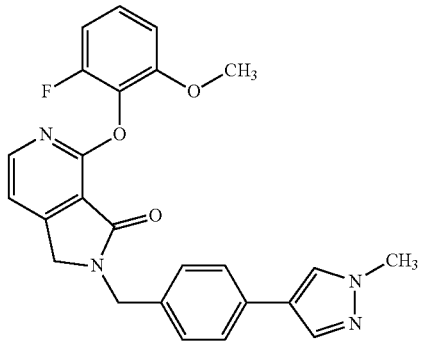 [SMILES: COc1cccc(F)c1Oc1nccc2c1C(=O)N(Cc1ccc(-c3cnn(C)c3)cc1)C2]

To a solution of 2-(4-bromobenzyl)-4-(2-fluoro-6-methoxyphenoxy)-1H-pyrrolo[3,4-c]pyridin-3(2H)-one (0.095 g) obtained in Reference Example 330 and 1-methyl-4-(4,4,5,5-tetramethyl-1,3,2-dioxaborolan-2-yl)-1H-pyrazole (0.054 g) in DME (3 mL) were added 2M aqueous sodium carbonate solution (0.6 mL) and [1,1'-bis(diphenylphosphino)ferrocene]dichloropalladium(II) (0.0088 g), and the mixture was stirred under microwave irradiation at 150° C. for 1 hr. The reaction mixture was diluted with water, extracted with ethyl acetate, washed with saturated aqueous sodium hydrogen carbonate solution and saturated brine, dried over anhydrous sodium sulfate, and concentrated. The residue was purified by NH silica gel chromatography (hexane-ethyl acetate) to give the title compound (0.035 g).

MS: [M+H]$^+$ 445.1

$^1$H NMR (300 MHz, DMSO-d$_6$) δ 3.31 (3H, s), 3.75 (3H, s), 4.47 (2H, s), 4.69 (2H, s), 6.91-7.05 (2H, m), 7.21-7.35 (4H, m), 7.56 (2H, d, J=8.3 Hz), 7.84 (1H, s), 8.12 (1H, s), 8.16 (1H, d, J=5.1 Hz).

Example 361

4-(2-cyclopropyl-4,6-difluorophenoxy)-2-(4-(6-methylpyridazin-4-yl)benzyl)-1,2-dihydro-3H-pyrrolo[3,4-c]pyridin-3-one

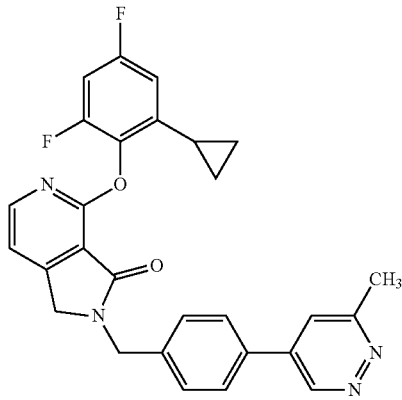 [SMILES: Cc1cc(-c2ccc(CN3Cc4ccnc(Oc5c(F)cc(F)cc5C5CC5)c4C3=O)cc2)cnn1]

To a solution of 2-(4-bromobenzyl)-4-(2-cyclopropyl-4,6-difluorophenoxy)-1H-pyrrolo[3,4-c]pyridin-3(2H)-one (0.072 g) obtained in Reference Example 214 and 3-methyl-5-(4,4,5,5-tetramethyl-1,3,2-dioxaborolan-2-yl)pyridazine (0.040 g) in DME (3 mL) were added 2M aqueous sodium carbonate solution (0.5 mL) and [1,1'-bis(diphenylphosphino)ferrocene]dichloropalladium(II) (0.0062 g), and the mixture was stirred under microwave irradiation at 150° C. for 1 hr. The reaction mixture was diluted with water, extracted with ethyl acetate, washed with saturated aqueous sodium hydrogen carbonate solution and saturated brine, dried over anhydrous sodium sulfate, and concentrated. The residue was purified by NH silica gel chromatography (hexane-ethyl acetate) to give the title compound (0.013 g).

MS: [M+H]$^+$ 485.1

$^1$H NMR (300 MHz, DMSO-d$_6$) δ 0.74 (2H, d, J=3.0 Hz), 0.87 (2H, d, J=7.7 Hz), 1.87-1.98 (1H, m), 2.68 (3H, s), 4.53 (2H, s), 4.80 (2H, s), 6.68-6.76 (1H, m), 7.14-7.26 (1H, m), 7.37 (1H, d, J=5.3 Hz), 7.52 (2H, d, J=8.3 Hz), 7.85-7.97 (3H, m), 8.22 (1H, d, J=5.1 Hz), 9.46 (1H, d, J=2.3 Hz).

Example 362

4-(2-fluoro-4-(trifluoromethoxy)phenoxy)-2-(4-(1-methyl-1H-pyrazol-4-yl)benzyl)-1,2-dihydro-3H-pyrrolo[3,4-c]pyridin-3-one

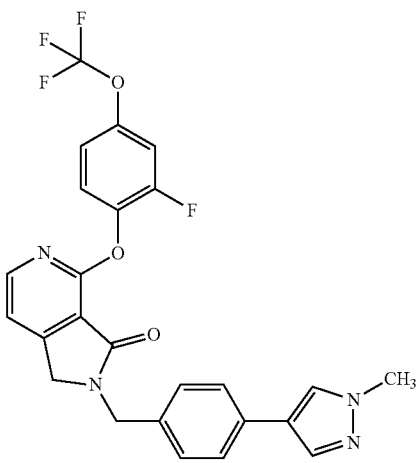 [SMILES: Cn1cc(-c2ccc(CN3Cc4ccnc(Oc5ccc(OC(F)(F)F)cc5F)c4C3=O)cc2)cn1]

To a solution of 2-(4-bromobenzyl)-4-(2-fluoro-4-(trifluoromethoxy)phenoxy)-1H-pyrrolo[3,4-c]pyridin-3(2H)-one (0.10 g) obtained in Reference Example 256 and 1-methyl-4-(4,4,5,5-tetramethyl-1,3,2-dioxaborolan-2-yl)-1H-pyrazole (0.050 g) in DME (3 mL) were added 2M aqueous sodium carbonate solution (0.6 mL) and [1,1'-bis(diphenylphosphino)ferrocene]dichloropalladium(II) (0.0082 g), and the mixture was stirred under microwave irradiation at 150° C. for 1 hr. The reaction mixture was diluted with water, extracted with ethyl acetate, washed with saturated aqueous sodium hydrogen carbonate solution and saturated brine, dried over anhydrous sodium sulfate, and concentrated. The residue was purified by NH silica gel chromatography (hexane-ethyl acetate) to give the title compound (0.016 g).

MS: [M+H]$^+$ 499.1

$^1$H NMR (300 MHz, DMSO-d$_6$) δ 3.85 (3H, s), 4.49 (2H, s), 4.70 (2H, s), 7.25-7.41 (4H, m), 7.51-7.67 (4H, m), 7.83 (1H, s), 8.11 (1H, s), 8.22 (1H, d, J=5.1 Hz).

Example 363

2-((2-(4-(1-methyl-1H-pyrazol-4-yl)benzyl)-3-oxo-2,3-dihydro-1H-pyrrolo[3,4-c]pyridin-4-yl)oxy)-5-(trifluoromethoxy)benzonitrile

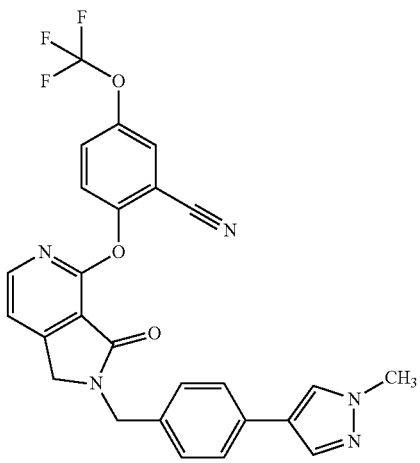 [SMILES: Cn1cc(-c2ccc(CN3Cc4ccnc(Oc5ccc(OC(F)(F)F)cc5C#N)c4C3=O)cc2)cn1]

To a solution of ethyl 2-(2-cyano-4-(trifluoromethoxy)phenoxy)-4-vinylnicotinate (0.094 g) obtained in Reference Example 212 in acetone-acetonitrile-water (1:1:1, 6 mL) were added sodium periodate (0.27 g) and osmium oxide (immobilized catalyst I) (0.032 g), and the mixture was stirred at room temperature overnight. The insoluble material was filtered off, and the filtrate was concentrated. The residue was dissolved in THF (10 mL), (4-(1-methyl-1H-pyrazol-4-yl)phenyl)methanamine (0.047 g) and anhydrous magnesium sulfate (0.50 g) were added, and the mixture was stirred for 1 hr. The insoluble material was filtered off, and the filtrate was concentrated. The residue was dissolved in acetic acid (10 mL), sodium triacetoxyborohydride (0.11 g) was added, and the mixture was stirred for 1 hr. The reaction mixture was diluted with ethyl acetate and saturated aqueous sodium hydrogen carbonate solution, and the organic layer was separated, washed with saturated brine, dried over anhydrous sodium sulfate, and concentrated. The residue was purified by NH silica gel chromatography (hexane-ethyl acetate) to give the title compound (0.014 g).

MS: [M+H]$^+$ 506.1

$^1$H NMR (300 MHz, DMSO-d$_6$) δ 3.85 (3H, s), 4.52 (2H, s), 4.71 (2H, s), 7.30 (2H, d, J=8.1 Hz), 7.46 (1H, d, J=5.3 Hz), 7.51-7.62 (3H, m), 7.81-7.89 (2H, m), 8.11 (1H, s), 8.18 (1H, d, J=2.8 Hz), 8.28 (1H, d, J=5.3 Hz).

Example 364

3,5-difluoro-4-((3-oxo-2-(4-(1H-pyrazol-1-yl)benzyl)-2,3-dihydro-1H-isoindol-4-yl)oxy)benzonitrile

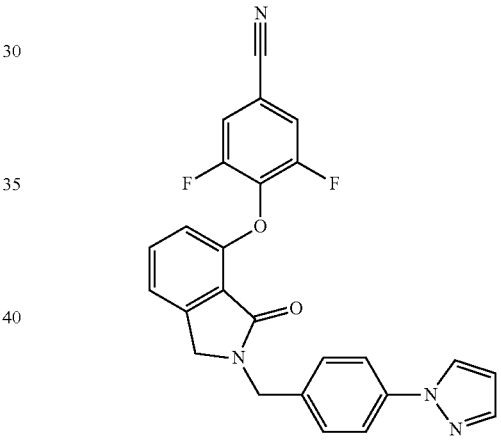

To a solution of 2-(4-(1H-pyrazol-1-yl)benzyl)-7-hydroxyisoindolin-1-one (0.20 g) obtained in Reference Example 14 in DMF (2 mL) was added potassium carbonate (0.27 g), and the mixture was stirred under an argon atmosphere at room temperature for 5 min. To the reaction solution was added 3,4,5-trifluorobenzonitrile (0.11 g) in DMF (2 mL), and the mixture was stirred at 90° C. overnight. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate), and solidified with hexane-ethyl acetate to give the title compound (0.014 g).

MS: [M+H]$^+$ 443.1

$^1$H NMR (300 MHz, CDCl$_3$) δ 4.29 (2H, s), 4.77 (2H, s), 6.45-6.49 (1H, m), 6.83 (1H, d, J=8.3 Hz), 7.17 (1H, d, J=7.5 Hz), 7.34 (2H, d, J=7.2 Hz), 7.37-7.48 (3H, m), 7.64-7.70 (2H, m), 7.72 (1H, d, J=1.9 Hz), 7.91 (1H, d, J=2.3 Hz).

Example 365

2-(4-(1-methyl-1H-pyrazol-3-yl)benzyl)-4-(2,4,6-trifluorophenoxy)-1H-pyrrolo[3,4-c]pyridin-3(2H)-one

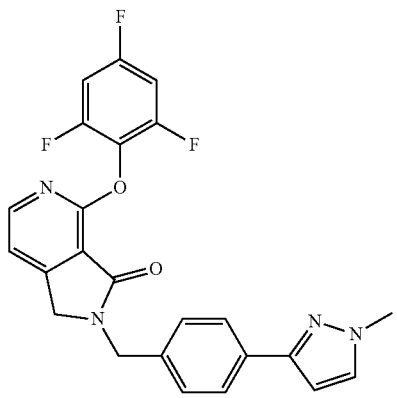 [SMILES: Cn1ccc(-c2ccc(CN3Cc4ccnc(Oc5c(F)cc(F)cc5F)c4C3=O)cc2)n1]

A mixture of methyl 2-(2,4,6-trifluorophenoxy)-4-vinyl-nicotinate (0.13 g) obtained in Reference Example 215, sodium periodate (0.45 g) and osmium oxide (immobilized catalyst I) (0.053 g) and acetonitrile (2 mL)-acetone (2 mL)-water (2 mL) was stirred at room temperature for 3 days. The insoluble material was filtered off, and the filtrate was diluted with ethyl acetate. The organic layer was separated, washed with saturated brine, dried over anhydrous magnesium sulfate, and concentrated.

To a mixed solution of the residue, (4-(1-methyl-1H-pyrazol-3-yl)phenyl)methanamine (0.079 g) and anhydrous magnesium sulfate (0.10 g) in THF (2 mL)-acetic acid (2 mL) was added sodium triacetoxyhydroborate (0.13 g), and the mixture was stirred under an argon atmosphere at room temperature for 3 hr. The reaction mixture was diluted with saturated aqueous sodium hydrogen carbonate solution and ethyl acetate, and the organic layer was separated, washed with saturated brine, dried over anhydrous magnesium sulfate and concentrated. The residue was purified by NH silica gel chromatography (hexane-ethyl acetate), and solidified with hexane-ethyl acetate to give the title compound (0.0023 g).

MS: [M+H]$^+$ 451.1

$^1$H NMR (300 MHz, CDCl$_3$) δ 3.96 (3H, s), 4.31 (2H, s), 4.83 (2H, s), 6.54 (1H, d, J=2.3 Hz), 6.81 (2H, dd, J=8.5, 7.3 Hz), 7.10 (1H, d, J=5.3 Hz), 7.34-7.41 (3H, m), 7.79 (2H, d, J=7.9 Hz), 8.17 (1H, d, J=4.9 Hz).

Example 366

6-(4-(1-methyl-1H-pyrazol-3-yl)benzyl)-4-(2,4,6-trifluorophenoxy)-6,7-dihydro-5H-pyrrolo[3,4-d]pyrimidin-5-one

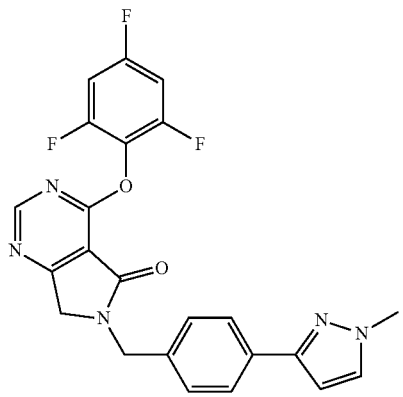 [SMILES: Cn1ccc(-c2ccc(CN3Cc4ncnc(Oc5c(F)cc(F)cc5F)c4C3=O)cc2)n1]

To a mixed solution of methyl 4-formyl-6-(2,4,6-trifluorophenoxy)pyrimidine-5-carboxylate (0.23 g) obtained in Reference Example 218 and (4-(1-methyl-1H-pyrazol-3-yl)phenyl)methanamine (0.14 g) in THF (4 mL)-acetic acid (4 mL) was added anhydrous magnesium sulfate (0.17 g), and the mixture was stirred under an argon atmosphere at 0° C. for 10 min. Sodium triacetoxyhydroborate (0.23 g) was added to the reaction mixture at 0° C., and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.0032 g).

MS: [M+H]$^+$ 452.2

$^1$H NMR (300 MHz, CDCl$_3$) δ 3.96 (3H, s), 4.37 (2H, s), 4.85 (2H, s), 6.54 (1H, d, J=2.3 Hz), 6.78-6.90 (2H, m), 7.36-7.41 (3H, m), 7.78-7.84 (2H, m), 8.78 (1H, s).

Example 367

6-(4-(2-methylpyridin-4-yl)benzyl)-4-(2,4,6-trifluorophenoxy)-6,7-dihydro-5H-pyrrolo[3,4-d]pyrimidin-5-one

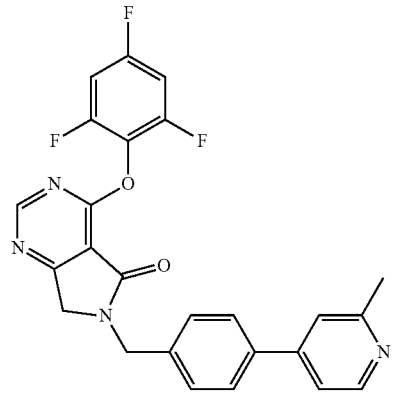 [SMILES: Cc1cc(-c2ccc(CN3Cc4ncnc(Oc5c(F)cc(F)cc5F)c4C3=O)cc2)ccn1]

A solution of methyl 4-formyl-6-(2,4,6-trifluorophenoxyl)pyrimidine-5-carboxylate (0.20 g) obtained in Reference Example 218, (4-(2-methylpyridin-4-yl)phenyl)methanamine (0.13 g) obtained in Reference Example 63 and anhydrous magnesium sulfate (0.15 g) in THF (4 mL) was stirred at room temperature for 1 hr. The insoluble material of the reaction mixture was filtered off, and the filtrate was concentrated. To a solution of the residue in acetic acid (4 mL) was added sodium triacetoxyhydroborate (0.20 g) at room temperature, and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.012 g).

MS: [M+H]$^+$ 463.1

$^1$H NMR (300 MHz, CDCl$_3$) δ 2.63 (3H, s), 4.41 (2H, s), 4.90 (2H, s), 6.84 (2H, dd, J=8.4, 7.5 Hz), 7.30 (1H, dd, J=5.3, 1.5 Hz), 7.36 (1H, s), 7.48 (2H, d, J=8.1 Hz), 7.64 (2H, d, J=8.3 Hz), 8.56 (1H, d, J=5.1 Hz), 8.80 (1H, s).

Example 368

3-fluoro-4-((2-(4-(2-methylpyridin-4-yl)benzyl)-3-oxo-2,3-dihydro-1H-pyrrolo[3,4-c]pyridin-4-yl)oxy)benzonitrile

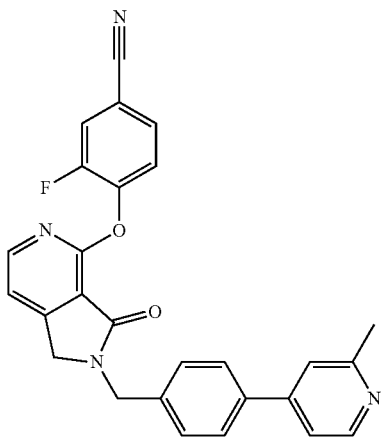 [SMILES: Cc1cc(-c2ccc(CN3Cc4ccnc(Oc5ccc(C#N)cc5F)c4C3=O)cc2)ccn1]

A solution of ethyl 2-(4-cyano-2-fluorophenoxy)-4-formylnicotinate (0.22 g) obtained in Reference Example 220, (4-(2-methylpyridin-4-yl)phenyl)methanamine (0.14 g) obtained in Reference Example 63 and anhydrous magnesium sulfate (0.17 g) in THF (4 mL) was stirred at room temperature for 1 hr. The insoluble material of the reaction mixture was filtered off, and the filtrate was concentrated. To a solution of the residue in acetic acid (4 mL) was added sodium triacetoxyhydroborate (0.22 g) at room temperature, and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and solidified with ethanol to give the title compound (0.11 g).

MS: [M+H]$^+$ 451.2

$^1$H NMR (300 MHz, CDCl$_3$) δ 2.63 (3H, s), 4.38 (2H, s), 4.87 (2H, s), 7.15 (1H, d, J=5.1 Hz), 7.30 (1H, dd, J=5.2, 1.4 Hz), 7.35 (1H, s), 7.43-7.58 (5H, m), 7.63 (2H, d, J=8.3 Hz), 8.19 (1H, d, J=5.3 Hz), 8.55 (1H, d, J=5.3 Hz).

Example 369

6-(4-(pyridazin-4-yl)benzyl)-4-(2,4,6-trifluorophenoxy)-6,7-dihydro-5H-pyrrolo[3,4-d]pyrimidin-5-one

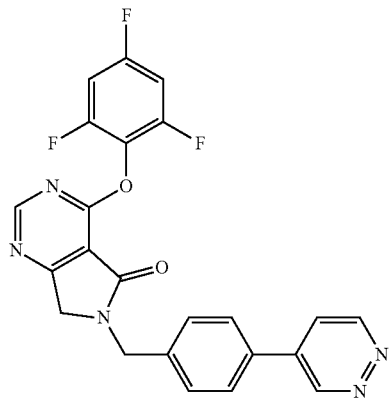 [SMILES: O=C1c2c(ncnc2Oc2c(F)cc(F)cc2F)CN1Cc1ccc(-c2ccnnc2)cc1]

A solution of methyl 4-formyl-6-(2,4,6-trifluorophenoxyl)pyrimidine-5-carboxylate (0.17 g) obtained in Reference Example 218, (4-(pyridazin-4-yl)phenyl)methanamine (0.10 g) and anhydrous magnesium sulfate (0.13 g) in THF (4 mL) was stirred under an argon atmosphere at room temperature for 1 hr. The insoluble material of the reaction mixture was filtered off, and the filtrate was concentrated. To a solution of the residue in acetic acid (4 mL) was added sodium triacetoxyhydroborate (0.17 g) at room temperature, and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethanol to give the title compound (0.026 g).

MS: [M+H]$^+$ 450.1

$^1$H NMR (300 MHz, CDCl$_3$) δ 4.43 (2H, s), 4.92 (2H, s), 6.80-6.89 (2H, m), 7.56 (2H, d, J=8.1 Hz), 7.65 (1H, dd, J=5.5, 2.5 Hz), 7.70 (2H, d, J=8.1 Hz), 8.80 (1H, s), 9.25 (1H, dd, J=5.5, 1.1 Hz), 9.47 (1H, dd, J=2.5, 1.1 Hz).

Example 370

6-(4-(1-methyl-1H-1,2,3-triazol-4-yl)benzyl)-4-(2,4,6-trifluorophenoxy)-6,7-dihydro-5H-pyrrolo[3,4-d]pyrimidin-5-one

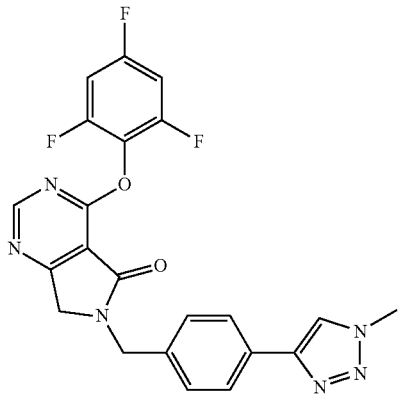 [SMILES: Cn1cc(-c2ccc(CN3Cc4ncnc(Oc5c(F)cc(F)cc5F)c4C3=O)cc2)nn1]

A solution of methyl 4-formyl-6-(2,4,6-trifluorophenoxyl)pyrimidine-5-carboxylate (0.14 g) obtained in Reference Example 218, (4-(1-methyl-1H-1,2,3-triazol-4-yl)phenyl)methanamine (0.10 g) obtained in Reference Example 162 and anhydrous magnesium sulfate (0.11 g) in THF (4 mL) was stirred under an argon atmosphere at room temperature for 1 hr. The insoluble material of the reaction mixture was filtered off, and the filtrate was concentrated. To a solution of the residue in acetic acid (4 mL) was added sodium triacetoxyhydroborate (0.14 g) at room temperature, and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was crudely purified by NH silica gel chromatography (hexane-ethyl acetate), and solidified with ethanol to give the title compound (0.0048 g).

MS: [M+H]$^+$ 453.1

$^1$H NMR (300 MHz, CDCl$_3$) δ 4.17 (3H, s), 4.39 (2H, s), 4.86 (2H, s), 6.78-6.89 (2H, m), 7.43 (2H, d, J=8.1 Hz), 7.76 (1H, s), 7.84 (2H, d, J=8.3 Hz), 8.79 (1H, s).

Example 371

3-fluoro-4-((6-(4-(1-methyl-1H-pyrazol-3-yl)benzyl)-5-oxo-6,7-dihydro-5H-pyrrolo[3,4-d]pyrimidin-4-yl)oxy)benzonitrile

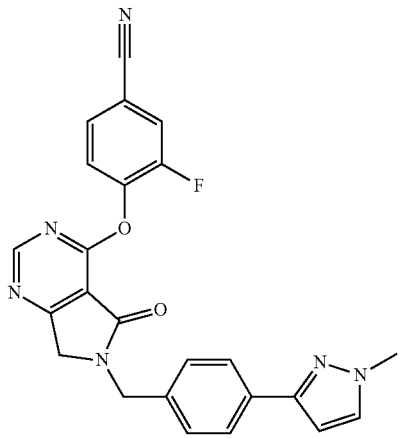 [SMILES: Cn1ccc(-c2ccc(CN3Cc4ncnc(Oc5ccc(C#N)cc5F)c4C3=O)cc2)n1]

A solution of methyl 4-(4-cyano-2-fluorophenoxy)-6-formylpyrimidine-5-carboxylate (0.072 g) obtained in Reference Example 223, (4-(1-methyl-1H-pyrazol-3-yl)phenyl)methanamine (0.047 g) and anhydrous magnesium sulfate (0.058 g) in THF (12 mL) was stirred under an argon atmosphere at room temperature for 2 hr. The insoluble material of the reaction mixture was filtered off, and the filtrate was concentrated. To a solution of the residue in acetic acid (3 mL) was added sodium triacetoxyhydroborate (0.061 g) at room temperature, and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was crudely purified by NH silica gel chromatography (hexane-ethyl acetate). Furthermore, the residue was purified by mass-triggered purification apparatus (water-0.1% TFA acetonitrile), and solidified with ethyl acetate-hexane to give the title compound (0.0022 g).

MS: [M+H]$^+$ 441.1

$^1$H NMR (300 MHz, CDCl$_3$) δ 3.96 (3H, s), 4.39 (2H, s), 4.85 (2H, s), 6.54 (1H, d, J=2.3 Hz), 7.36-7.41 (3H, m), 7.43-7.50 (1H, m), 7.52-7.61 (2H, m), 7.81 (2H, d, J=8.3 Hz), 8.77 (1H, s).

Example 372

4-(2,6-difluorophenoxy)-6-(4-(1,3-dimethyl-1H-pyrazol-4-yl)-2-fluorobenzyl)-6,7-dihydro-5H-pyrrolo[3,4-d]pyrimidin-5-one

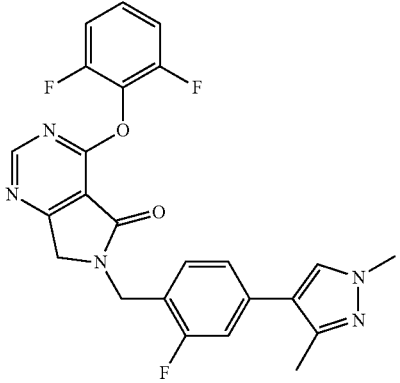 [SMILES: Cc1nn(C)cc1-c1ccc(CN2Cc3ncnc(Oc4c(F)cccc4F)c3C2=O)c(F)c1]

A solution of methyl 4-(2,6-difluorophenoxy)-6-formylpyrimidine-5-carboxylate (0.070 g) obtained in Reference Example 226, (4-(1,3-dimethyl-1H-pyrazol-4-yl)-2-fluorophenyl)methanamine (0.057 g) and anhydrous magnesium sulfate (0.057 g) in THF (4 mL) was stirred at room temperature for 2 hr. The insoluble material of the reaction mixture was filtered off, and the filtrate was concentrated. To a solution of the residue in acetic acid (4 mL) was added sodium triacetoxyhydroborate (0.061 g) at room temperature, and the mixture was stirred under an argon atmosphere at room temperature for 3 days. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), and solidified with ethyl acetate-hexane to give the title compound (0.0047 g).

MS: [M+H]$^+$ 466.1

¹H NMR (300 MHz, CDCl₃) δ 2.39 (3H, s), 3.88 (3H, s), 4.48 (2H, s), 4.89 (2H, s), 7.00-7.08 (2H, m), 7.10-7.19 (2H, m), 7.22-7.29 (1H, m), 7.41-7.48 (2H, m), 8.78 (1H, s).

Example 373

3-fluoro-4-((2-(4-(3-methyl-1,2-oxazol-5-yl)benzyl)-3-oxo-2,3-dihydro-1H-pyrrolo[3,4-c]pyridin-4-yl)oxy)benzonitrile

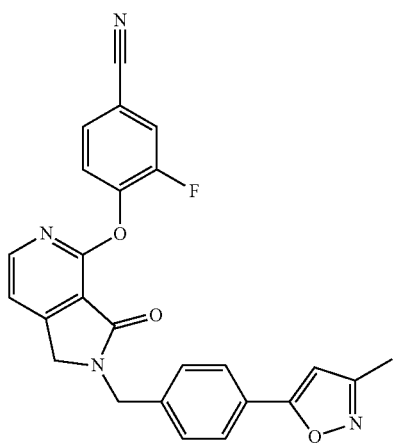 [SMILES: Cc1cc(-c2ccc(CN3Cc4ccnc(Oc5ccc(C#N)cc5F)c4C3=O)cc2)on1]

To a solution of 2-(4-ethynylbenzyl)isoindoline-1,3-dione (0.50 g) obtained in Reference Example 251, isocyanatobenzene (0.62 mL) and triethylamine (0.80 mL) in THF (10 mL) was added dropwise nitroethane (0.41 mL) at 50° C. over 6 hr, and the mixture was stirred at the same temperature overnight. Water was added to the reaction mixture, and the mixture was stirred at room temperature for 30 min. The precipitate was collected by filtration, and washed with ethyl acetate. To a solution of the obtained precipitate (0.51 g) in ethanol (5 mL) was added hydrazine monohydrate (5 mL) at room temperature, and the mixture was stirred at the same temperature for 2 hr. The reaction mixture was diluted with saturated aqueous sodium hydrogen carbonate solution and ethyl acetate. The organic layer was separated, washed with saturated brine, dried over anhydrous magnesium sulfate and concentrated. A solution of the obtained residue (0.15 g), ethyl 2-(4-cyano-2-fluorophenoxy)-4-formylnicotinate (0.075 g) obtained in Reference Example 220 and anhydrous magnesium sulfate (0.077 g) in THF (4 mL) was stirred under an argon atmosphere at room temperature for 2 hr. The insoluble material of the reaction mixture was filtered off, and the filtrate was concentrated. To a solution of the residue in acetic acid (4 mL) was added sodium triacetoxyhydroborate (0.10 g) at room temperature, and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous sodium sulfate, and concentrated. The residue was crudely purified by NH silica gel chromatography (hexane-ethyl acetate). Furthermore, the residue was purified by mass-triggered purification apparatus (water-0.1% TFA acetonitrile), and solidified with ethyl acetate-hexane to give the title compound (0.0060 g).

MS: [M+H]⁺ 441.1

¹H NMR (300 MHz, CDCl₃) δ 2.36 (3H, s), 4.36 (2H, s), 4.84 (2H, s), 6.37 (1H, s), 7.14 (1H, d, J=5.1 Hz), 7.22 (1H, s), 7.41-7.55 (4H, m), 7.75 (2H, d, J=8.3 Hz), 8.18 (1H, d, J=5.1 Hz).

Example 374

3-fluoro-4-((2-(4-(1-methyl-1H-pyrazol-3-yl)benzyl)-3-oxo-2,3-dihydro-1H-pyrrolo[3,4-c]pyridin-4-yl)oxy)benzonitrile

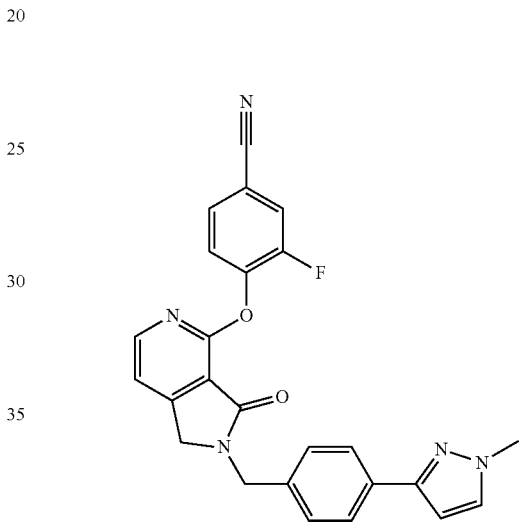

A solution of ethyl 2-(4-cyano-2-fluorophenoxy)-4-formylnicotinate (0.12 g) obtained in Reference Example 220, (4-(1-methyl-1H-pyrazol-3-yl)phenyl)methanamine (0.079 g) and anhydrous magnesium sulfate (0.092 g) in THF (8 mL) was stirred at room temperature for 3 hr. The insoluble material of the reaction mixture was filtered off, and the filtrate was concentrated. To a solution of the residue in acetic acid (3 mL) was added sodium triacetoxyhydroborate (0.12 g) at room temperature, and the mixture was stirred under an argon atmosphere at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was crudely purified by NH silica gel chromatography (hexane-ethyl acetate), and solidified with ethyl acetate to give the title compound (0.012 g).

MS: [M+H]⁺ 440.2

¹H NMR (300 MHz, CDCl₃) δ 3.96 (3H, s), 4.33 (2H, s), 4.82 (2H, s), 6.54 (1H, d, J=2.3 Hz), 7.13 (1H, d, J=5.1 Hz), 7.35-7.41 (3H, m), 7.43-7.58 (3H, m), 7.79 (2H, d, J=8.1 Hz), 8.17 (1H, d, J=5.1 Hz)

Example 375

3,5-difluoro-4-((2-(4-(1-methyl-1H-pyrazol-3-yl)benzyl)-3-oxo-2,3-dihydro-1H-pyrrolo[3,4-c]pyridin-4-yl)oxy)benzonitrile

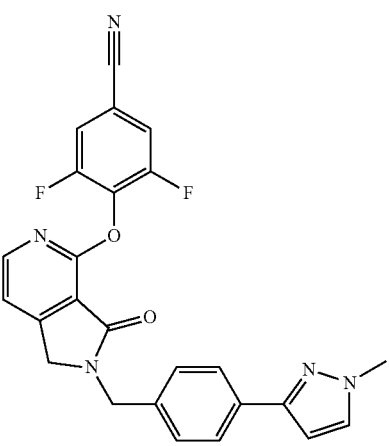 [SMILES: Cn1ccc(-c2ccc(CN3Cc4ccnc(Oc5c(F)cc(C#N)cc5F)c4C3=O)cc2)n1]

A solution of ethyl 2-(4-cyano-2,6-difluorophenoxy)-4-formylnicotinate (0.14 g) obtained in Reference Example 229, (4-(1-methyl-1H-pyrazol-3-yl)phenyl)methanamine (0.095 g) and anhydrous magnesium sulfate (0.10 g) in THF (8 mL) was stirred under an argon atmosphere at room temperature for 1 hr. The insoluble material of the reaction mixture was filtered off, and the filtrate was concentrated. To a solution of the residue in acetic acid (5 mL) was added sodium triacetoxyhydroborate (0.13 g) at room temperature, and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate-hexane to give the title compound (0.0038 g).

MS: [M+H]$^+$ 458.1

$^1$H NMR (300 MHz, CDCl$_3$) δ 3.96 (3H, s), 4.33 (2H, s), 4.83 (2H, s), 6.54 (1H, d, J=2.3 Hz), 7.15 (1H, d, J=5.1 Hz), 7.34-7.41 (5H, m), 7.79 (2H, d, J=8.3 Hz), 8.15 (1H, d, J=5.1 Hz).

Example 376

3,5-difluoro-4-((2-(4-(2-methylpyridin-4-yl)benzyl)-3-oxo-2,3-dihydro-1H-pyrrolo[3,4-c]pyridin-4-yl)oxy)benzonitrile

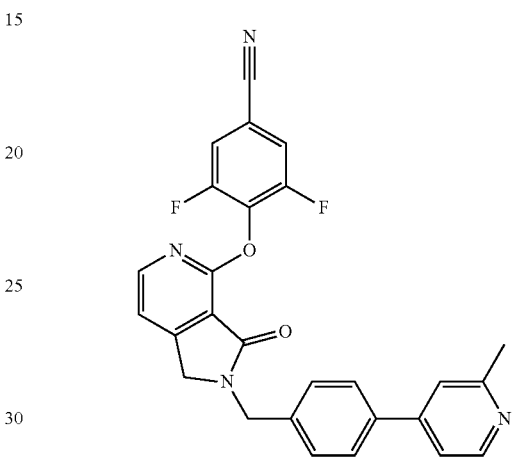

A solution of ethyl 2-(4-cyano-2,6-difluorophenoxy)-4-formylnicotinate (0.090 g) obtained in Reference Example 229, (4-(2-methylpyridin-4-yl)phenyl)methanamine (0.059 g) obtained in Reference Example 63 and anhydrous magnesium sulfate (0.065 g) in THF (8 mL) was stirred under an argon atmosphere at room temperature overnight. The insoluble material of the reaction mixture was filtered off, and the filtrate was concentrated. To a solution of the residue in acetic acid (2 mL) was added sodium triacetoxyhydroborate (0.086 g) at room temperature, and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by NH silica gel chromatography (hexane-ethyl acetate), and solidified with ethyl acetate-hexane to give the title compound (0.035 g).

MS: [M+H]$^+$ 469.1

$^1$H NMR (300 MHz, CDCl$_3$) δ 2.63 (3H, s), 4.39 (2H, s), 4.87 (2H, s), 7.17 (1H, d, J=5.3 Hz), 7.30 (1H, dd, J=5.3, 1.9 Hz), 7.37 (3H, d, J=6.6 Hz), 7.47 (2H, d, J=8.1 Hz), 7.64 (2H, d, J=8.1 Hz), 8.17 (1H, d, J=5.1 Hz), 8.56 (1H, d, J=5.1 Hz).

Example 377

3,5-difluoro-4-((2-((5-(1-methyl-1H-pyrazol-4-yl)pyridin-2-yl)methyl)-3-oxo-2,3-dihydro-1H-isoindol-4-yl)oxy)benzonitrile

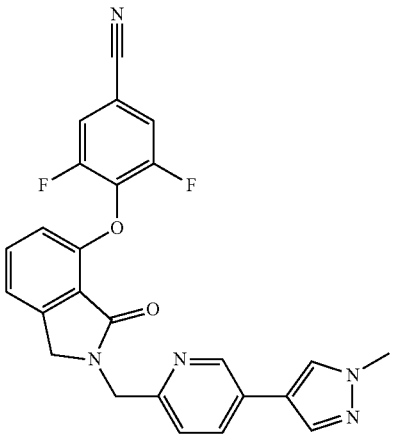 [SMILES: Cn1cc(-c2ccc(CN3Cc4cccc(Oc5c(F)cc(C#N)cc5F)c4C3=O)nc2)cn1]

To a solution of (5-(1-methyl-1H-pyrazol-4-yl)pyridin-2-yl)methanamine dihydrochloride (0.073 g) obtained in Reference Example 28 and ethyl 2-(bromomethyl)-6-(4-cyano-2,6-difluorophenoxy)benzoate (0.10 g) obtained in Reference Example 231 in ethanol (2 mL) was added potassium carbonate (0.11 g), and the mixture was stirred under an argon atmosphere at room temperature overnight. The reaction mixture was diluted with water and ethyl acetate. The organic layer was separated, washed with saturated brine, dried over anhydrous sodium sulfate, and concentrated. The residue was purified by silica gel chromatography (hexane-ethyl acetate), and solidified with ethyl acetate to give the title compound (0.017 g).

MS: [M+H]$^+$ 458.1

$^1$H NMR (300 MHz, CDCl$_3$) δ 3.97 (3H, s), 4.50 (2H, s), 4.87 (2H, s), 6.83 (1H, d, J=8.1 Hz), 7.21 (1H, d, J=7.6 Hz), 7.31-7.39 (3H, m), 7.42-7.50 (1H, m), 7.65 (1H, s), 7.72 (1H, dd, J=8.1, 2.3 Hz), 7.77 (1H, s), 8.66-8.70 (1H, m).

Example 378

3,5-difluoro-4-((2-((6-(1-methyl-1H-pyrazol-4-yl)pyridin-3-yl)methyl)-3-oxo-2,3-dihydro-1H-isoindol-4-yl)oxy)benzonitrile

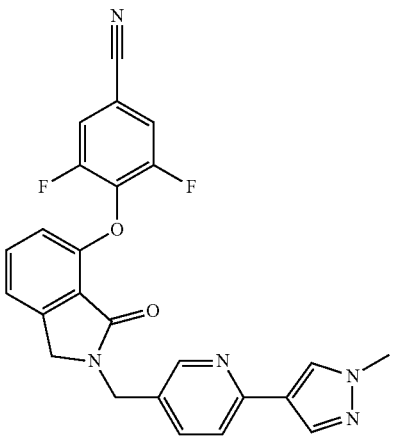 [SMILES: Cn1cc(-c2ccc(CN3Cc4cccc(Oc5c(F)cc(C#N)cc5F)c4C3=O)cn2)cn1]

To a solution of (6-(1-methyl-1H-pyrazol-4-yl)pyridin-3-yl)methanamine dihydrochloride (0.073 g) obtained in Reference Example 25 and ethyl 2-(bromomethyl)-6-(4-cyano-2,6-difluorophenoxy)benzoate (0.10 g) obtained in Reference Example 231 in ethanol (2 mL) was added potassium carbonate (0.11 g), and the mixture was stirred under an argon atmosphere at room temperature overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with ethyl acetate to give the title compound (0.019 g).

MS: [M+H]$^+$ 458.1

$^1$H NMR (300 MHz, CDCl$_3$) δ 3.96 (3H, s), 4.32 (2H, s), 4.75 (2H, s), 6.83 (1H, d, J=8.3 Hz), 7.18 (1H, d, J=7.4 Hz), 7.35 (2H, d, J=7.0 Hz), 7.41-7.50 (2H, m), 7.66 (1H, dd, J=8.1, 2.3 Hz), 7.93 (2H, d, J=7.4 Hz), 8.50 (1H, d, J=1.7 Hz).

Example 379

4-(4-(difluoromethyl)-2-fluorophenoxy)-2-(4-(2-methylpyridin-4-yl)benzyl)-1,2-dihydro-3H-pyrrolo[3,4-c]pyridin-3-one

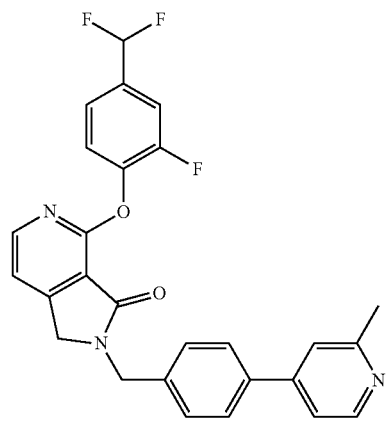 [SMILES: Cc1cc(-c2ccc(CN3Cc4ccnc(Oc5ccc(C(F)F)cc5F)c4C3=O)cc2)ccn1]

A solution of ethyl 2-(4-(difluoromethyl)-2-fluorophenoxy)-4-formylnicotinate (0.20 g) obtained in Reference Example 234, (4-(2-methylpyridin-4-yl)phenyl)methanamine (0.13 g) obtained in Reference Example 63 and anhydrous magnesium sulfate (0.14 g) in THF (4 mL) was stirred under an argon atmosphere at room temperature for 2 hr. The insoluble material of the reaction mixture was filtered off, and the filtrate was concentrated. To a solution of the residue in acetic acid (4 mL) was added sodium triacetoxyhydroborate (0.19 g) at room temperature, and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous magnesium sulfate and concentrated. The residue was crudely purified by NH silica gel chromatography (hexane-ethyl acetate), further purified by silica gel chromatography (hexane-ethyl acetate), and solidified with ethyl acetate to give the title compound (0.039 g).

MS: [M+H]+ 476.1

1H NMR (300 MHz, CDCl3) δ 2.63 (3H, s), 4.37 (2H, s), 4.87 (2H, s), 6.46-6.88 (1H, m), 7.11 (1H, d, J=5.1 Hz), 7.30 (1H, d, J=5.3 Hz), 7.35-7.50 (6H, m), 7.60-7.66 (2H, m), 8.20 (1H, d, J=5.1 Hz), 8.55 (1H, d, J=5.3 Hz).

Example 380

4-(4-(difluoromethyl)-2-fluorophenoxy)-2-(4-(1-methyl-1H-pyrazol-3-yl)benzyl)-1,2-dihydro-3H-pyrrolo[3,4-c]pyridin-3-one

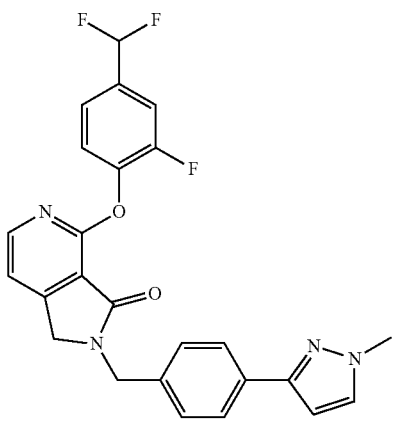 [SMILES: Cn1ccc(-c2ccc(CN3Cc4ccnc(Oc5ccc(C(F)F)cc5F)c4C3=O)cc2)n1]

A solution of ethyl 2-(4-(difluoromethyl)-2-fluorophenoxy)-4-formylnicotinate (0.20 g) obtained in Reference Example 234, (4-(1-methyl-1H-pyrazol-3-yl)phenyl)methanamine (0.12 g) and anhydrous magnesium sulfate (0.14 g) in THF (4 mL) was stirred under an argon atmosphere at room temperature overnight. The insoluble material of the reaction mixture was filtered off, and the filtrate was concentrated. To a solution of the residue in acetic acid (4 mL) was added sodium triacetoxyhydroborate (0.19 g) at room temperature, and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was crudely purified by NH silica gel chromatography (hexane-ethyl acetate), and solidified with ethyl acetate to give the title compound (0.012 g).

MS: [M+H]+ 465.1

1H NMR (300 MHz, CDCl3) δ 3.96 (3H, s), 4.32 (2H, s), 4.83 (2H, s), 6.46-6.87 (2H, m), 7.09 (1H, d, J=5.3 Hz), 7.33-7.48 (6H, m), 7.79 (2H, d, J=8.3 Hz), 8.18 (1H, d, J=5.3 Hz).

Example 381

4-(4-(difluoromethyl)-2-fluorophenoxy)-2-(4-(1,3-dimethyl-1H-pyrazol-4-yl)-2-fluorobenzyl)-1,2-dihydro-3H-pyrrolo[3,4-c]pyridin-3-one

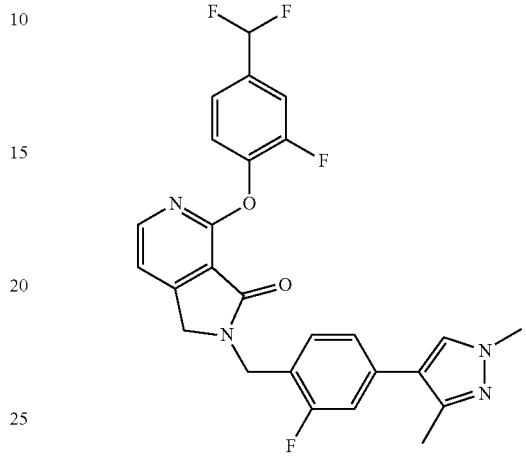

A solution of ethyl 2-(4-(difluoromethyl)-2-fluorophenoxy)-4-formylnicotinate (0.32 g) obtained in Reference Example 234, (4-bromo-2-fluorophenyl)methanamine (0.21 g) and anhydrous magnesium sulfate (0.23 g) in THF (6 mL) was stirred under an argon atmosphere at room temperature overnight. The insoluble material of the reaction mixture was filtered off, and the filtrate was concentrated. To a solution of the residue in acetic acid (6 mL) was added sodium triacetoxyhydroborate (0.30 g) at room temperature, and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous magnesium sulfate and concentrated. The residue was crudely purified by NH silica gel chromatography (hexane-ethyl acetate). To a solution of the obtained crudely purified product (0.13 g), 1,3-dimethyl-4-(4,4,5,5-tetramethyl-1,3,2-dioxaborolan-2-yl)-1H-pyrazole (0.071 g) and 2M aqueous sodium carbonate solution (0.27 mL) in DME (3 mL) was added [1,1-bis(diphenylphosphino)ferrocene]dichloropalladium(II) (0.019 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was crudely purified by silica gel chromatography (hexane-ethyl acetate), further purified by mass-triggered purification apparatus (water-0.1% TFA acetonitrile), and solidified with ethyl acetate to give the title compound (0.025 g).

MS: [M+H]+ 497.2

1H NMR (300 MHz, CDCl3) δ 2.40 (3H, s), 3.88 (3H, s), 4.45 (2H, s), 4.88 (2H, s), 6.46-6.87 (1H, m), 7.09-7.20 (3H, m), 7.33-7.49 (5H, m), 8.19 (1H, d, J=5.1 Hz).

Example 382

3,5-difluoro-4-((2-((6-(1-isopropyl-1H-pyrazol-4-yl)pyridin-3-yl)methyl)-3-oxo-2,3-dihydro-1H-isoindol-4-yl)oxy)benzonitrile

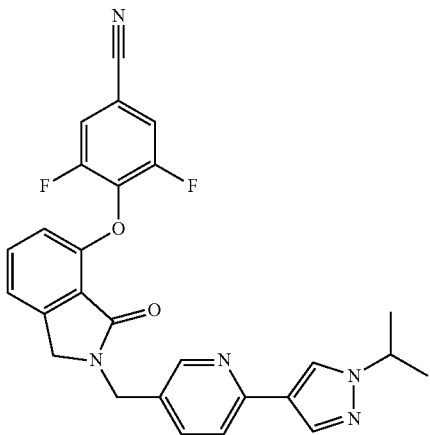 [SMILES: CC(C)n1cc(-c2ccc(CN3Cc4cccc(Oc5c(F)cc(C#N)cc5F)c4C3=O)cn2)cn1]

To a solution of (6-chloropyridin-3-yl)methanamine (0.22 g) and ethyl 2-(bromomethyl)-6-(4-cyano-2,6-difluorophenoxy)benzoate (0.50 g) obtained in Reference Example 231 in THF (10 mL) was added potassium carbonate (0.52 g), and the mixture was stirred under an argon atmosphere at room temperature for 3 days. The reaction mixture was diluted with water and ethyl acetate. The organic layer was separated, washed with saturated brine, dried over anhydrous magnesium sulfate and concentrated. The residue were collected by filtration, and washed with ethyl acetate. To a solution of the obtained residue (0.20 g), (1-isopropyl-1H-pyrazol-4-yl)boronic acid (0.090 g) and 2M aqueous sodium carbonate solution (0.49 mL) in DME (4 mL) was added [1,1-bis(diphenylphosphino)ferrocene]dichloropalladium(II) (0.036 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with ethyl acetate to give the title compound (0.079 g).

MS: [M+H]$^+$ 486.2

$^1$H NMR (300 MHz, CDCl$_3$) δ 1.56 (6H, d, J=6.8 Hz), 4.31 (2H, s), 4.55 (1H, quin, J=6.7 Hz), 4.75 (2H, s), 6.84 (1H, d, J=8.1 Hz), 7.18 (1H, d, J=7.6 Hz), 7.35 (2H, d, J=7.0 Hz), 7.42-7.50 (2H, m), 7.65 (1H, dd, J=8.1, 2.3 Hz), 7.95 (1H, s), 8.01 (1H, s), 8.50 (1H, d, J=2.1 Hz).

Example 383

4-(4-chloro-2-fluorophenoxy)-2-(4-(2-methylpyridin-4-yl)benzyl)-1,2-dihydro-3H-pyrrolo[3,4-c]pyridin-3-one

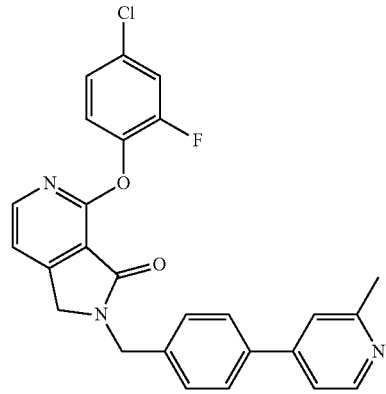 [SMILES: Cc1cc(-c2ccc(CN3Cc4ccnc(Oc5ccc(Cl)cc5F)c4C3=O)cc2)ccn1]

A solution of ethyl 2-(4-chloro-2-fluorophenoxy)-4-formylnicotinate (0.30 g) obtained in Reference Example 236 and (4-(2-methylpyridin-4-yl)phenyl)methanamine (0.22 g) obtained in Reference Example 63 in THF (6 mL) was stirred at room temperature for 1 hr. The reaction mixture was concentrated, to a solution of the residue in acetic acid (6 mL) was added sodium triacetoxyhydroborate (0.30 g) at room temperature, and the mixture was stirred under an argon atmosphere at room temperature for 3 hr. The reaction mixture was neutralized with saturated aqueous sodium hydrogen carbonate solution, and the mixture was diluted with ethyl acetate. The organic layer was separated, washed with saturated brine, dried over anhydrous magnesium sulfate and concentrated. The residue was purified by silica gel chromatography (hexane-ethyl acetate), and solidified with ethyl acetate to give the title compound (0.13 g).

MS: [M+H]$^+$ 460.1

$^1$H NMR (300 MHz, CDCl$_3$) δ 2.63 (3H, s), 4.36 (2H, s), 4.86 (2H, s), 7.09 (1H, d, J=5.3 Hz), 7.16-7.32 (4H, m), 7.35 (1H, s), 7.46 (2H, d, J=8.1 Hz), 7.60-7.65 (2H, m), 8.20 (1H, d, J=5.1 Hz), 8.55 (1H, d, J=5.3 Hz).

Example 384

3,5-difluoro-4-((2-(4-(1-isopropyl-1H-pyrazol-4-yl)benzyl)-3-oxo-2,3-dihydro-1H-pyrrolo[3,4-c]pyridin-4-yl)oxy)benzonitrile

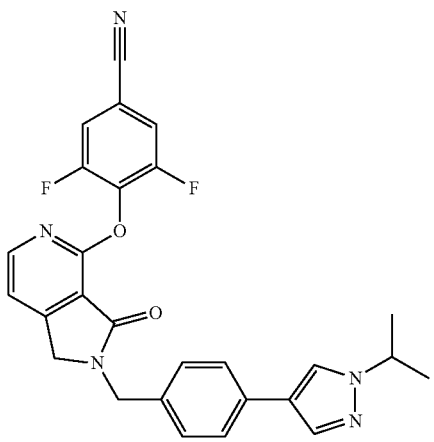 [SMILES: CC(C)n1cc(-c2ccc(CN3Cc4ccnc(Oc5c(F)cc(C#N)cc5F)c4C3=O)cc2)cn1]

A solution of ethyl 2-(4-cyano-2,6-difluorophenoxy)-4-formylnicotinate (0.30 g) obtained in Reference Example 229 and (4-bromophenyl)methanamine (0.19 g) in THF (6 mL) was stirred at room temperature for 4 hr. The reaction mixture was concentrated, to a solution of the residue in acetic acid (6 mL) was added sodium triacetoxyhydroborate (0.29 g) at room temperature, and the mixture was stirred under an argon atmosphere at room temperature for 2 hr. The reaction mixture was neutralized with saturated aqueous sodium hydrogen carbonate solution, and the mixture was diluted with ethyl acetate. The organic layer was separated, washed with saturated brine, dried over anhydrous sodium sulfate, and concentrated. To a solution of the obtained residue (0.15 g), (1-isopropyl-1H-pyrazol-4-yl)boronic acid (0.056 g) and 2M aqueous sodium carbonate solution (0.49 mL) in DME (3 mL) was added [1,1-bis(diphenylphosphino)ferrocene]dichloropalladium(II) (0.024 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was crudely purified by silica gel chromatography (hexane-ethyl acetate), and further purified by reversed-phase preparative HPLC (water-0.1% TFA acetonitrile).

The residue was solidified with ethyl acetate to give the title compound (0.0041 g).

MS: [M+H]$^+$ 486.2

$^1$H NMR (300 MHz, CDCl$_3$) δ 1.54-1.58 (6H, m), 4.35 (2H, s), 4.54 (1H, quin, J=6.7 Hz), 4.81 (2H, s), 7.16 (1H, d, J=5.1 Hz), 7.32-7.39 (4H, m), 7.45-7.51 (2H, m), 7.67 (1H, s), 7.77 (1H, s), 8.15 (1H, d, J=5.1 Hz).

Example 385

4-((2-(4-(1,3-dimethyl-1H-pyrazol-4-yl)benzyl)-3-oxo-2,3-dihydro-1H-pyrrolo[3,4-c]pyridin-4-yl)oxy)-3,5-difluorobenzonitrile

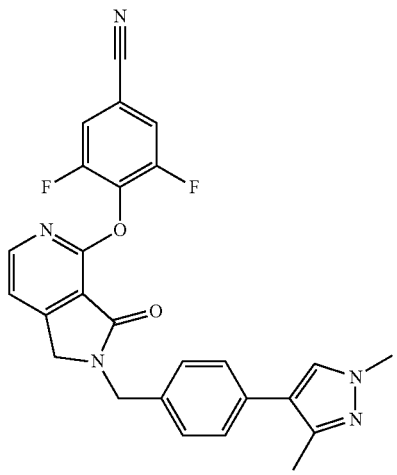 [SMILES: Cc1nn(C)cc1-c1ccc(CN2Cc3ccnc(Oc4c(F)cc(C#N)cc4F)c3C2=O)cc1]

A solution of ethyl 2-(4-cyano-2,6-difluorophenoxy)-4-formylnicotinate (0.30 g) obtained in Reference Example 229 and (4-bromophenyl)methanamine (0.19 g) in THF (6 mL) was stirred at room temperature for 4 hr. The reaction mixture was concentrated, to a solution of the residue in acetic acid (6 mL) was added sodium triacetoxyhydroborate (0.29 g) at room temperature, and the mixture was stirred under an argon atmosphere at room temperature for 2 hr. The reaction mixture was neutralized with saturated aqueous sodium hydrogen carbonate solution, and the mixture was diluted with ethyl acetate. The organic layer was separated, washed with saturated brine, dried over anhydrous sodium sulfate, and concentrated. To a solution of the obtained residue (0.11 g), 1,3-dimethyl-4-(4,4,5,5-tetramethyl-1,3,2-dioxaborolan-2-yl)-1H-pyrazole (0.054 g) and 2M aqueous sodium carbonate solution (0.36 mL) in DME (3 mL) was added [1,1-bis(diphenylphosphino)ferrocene]dichloropalladium(II) (0.018 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was crudely purified by silica gel chromatography (hexane-ethyl acetate), and solidified with ethyl acetate to give the title compound (0.012 g).

MS: [M+H]$^+$ 472.2

$^1$H NMR (300 MHz, CDCl$_3$) δ 2.40 (3H, s), 3.88 (3H, s), 4.38 (2H, s), 4.82 (2H, s), 7.17 (1H, d, J=5.3 Hz), 7.34-7.40 (6H, m), 7.43 (1H, s), 8.16 (1H, d, J=5.1 Hz).

Example 386

3,5-difluoro-4-((2-(2-fluoro-4-(1-methyl-1H-pyrazol-4-yl)benzyl)-3-oxo-2,3-dihydro-1H-pyrrolo[3,4-c]pyridin-4-yl)oxy)benzonitrile

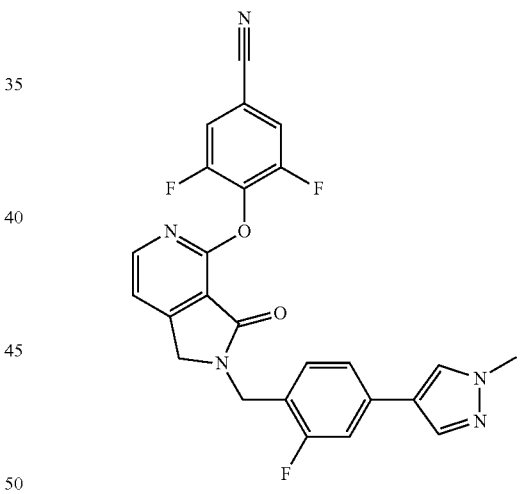

A solution of ethyl 2-(4-cyano-2,6-difluorophenoxy)-4-formylnicotinate (0.30 g) obtained in Reference Example 229 and (4-bromo-2-fluorophenyl)methanamine (0.20 g) in THF (6 mL) was stirred at room temperature for 4 hr. The reaction mixture was concentrated, to a solution of the residue in acetic acid (6 mL) was added sodium triacetoxyhydroborate (0.29 g) at room temperature, and the mixture was stirred under an argon atmosphere at room temperature for 2 hr. The reaction mixture was neutralized with saturated aqueous sodium hydrogen carbonate solution, and the mixture was diluted with ethyl acetate. The organic layer was separated, washed with saturated brine, dried over anhydrous magnesium sulfate and concentrated. To a solution of the obtained 4-((2-(4-bromo-2-fluorobenzyl)-3-oxo-2,3-dihydro-1H-pyrrolo[3,4-c]pyridin-4-yl)oxy)-3,5-difluorobenzonitrile (0.20 g), ((1-methyl-1H-pyrazol-4-yl)boronic acid (0.058 g) and 2M aqueous sodium carbonate solution (0.63 mL) in DME (4 mL) was added [1,1-bis(diphenylphosphino)ferrocene]dichloropalladium(II) (0.031 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with ethyl acetate to give the title compound (0.017 g).

MS: [M+H]⁺ 476.1

¹H NMR (300 MHz, CDCl₃) δ 3.96 (3H, s), 4.45 (2H, s), 4.86 (2H, s), 7.16-7.20 (1H, m), 7.22 (1H, d, J=4.2 Hz), 7.26 (1H, brs), 7.36 (2H, d, J=6.6 Hz), 7.40-7.47 (1H, m), 7.62 (1H, s), 7.74 (1H, s), 8.16 (1H, d, J=5.1 Hz).

Example 387

3,5-difluoro-4-((2-(2-fluoro-4-(1-methyl-1H-pyrazol-3-yl)benzyl)-3-oxo-2,3-dihydro-1H-pyrrolo[3,4-c]pyridin-4-yl)oxy)benzonitrile

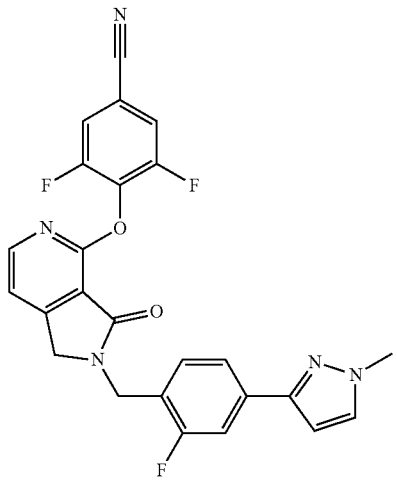 [SMILES: Cn1ccc(-c2ccc(CN3Cc4ccnc(Oc5c(F)cc(C#N)cc5F)c4C3=O)c(F)c2)n1]

A solution of ethyl 2-(4-cyano-2,6-difluorophenoxy)-4-formylnicotinate (0.30 g) obtained in Reference Example 229 and (4-bromo-2-fluorophenyl)methanamine (0.20 g) in THF (6 mL) was stirred at room temperature for 4 hr. The reaction mixture was concentrated, to a solution of the residue in acetic acid (6 mL) was added sodium triacetoxyhydroborate (0.29 g) at room temperature, and the mixture was stirred under an argon atmosphere at room temperature for 2 hr. The reaction mixture was neutralized with saturated aqueous sodium hydrogen carbonate solution, and the mixture was diluted with ethyl acetate. The organic layer was separated, washed with saturated brine, dried over anhydrous magnesium sulfate and concentrated. To a solution of the obtained residue (0.23 g), 1-methyl-3-(4,4,5,5-tetramethyl-1,3,2-dioxaborolan-2-yl)-1H-pyrazole (0.11 g) and 2M aqueous sodium carbonate solution (0.73 mL) in DME (4 mL) was added [1,1-bis(diphenylphosphino)ferrocene]dichloropalladium(II) (0.036 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was crudely purified by silica gel chromatography (hexane-ethyl acetate), and solidified with ethyl acetate to give the title compound (0.0081 g).

MS: [M+H]⁺ 476.1

¹H NMR (300 MHz, CDCl₃) δ 3.95 (3H, s), 4.42 (2H, s), 4.87 (2H, s), 6.52 (1H, d, J=2.3 Hz), 7.17 (1H, d, J=5.3 Hz), 7.35 (2H, d, J=6.6 Hz), 7.39 (1H, d, J=2.1 Hz), 7.41-7.48 (1H, m), 7.53 (1H, s), 7.55-7.58 (1H, m), 8.14 (1H, d, J=5.1 Hz).

Example 388

4-(4-chloro-2-fluorophenoxy)-2-(4-(1-methyl-1H-pyrazol-4-yl)benzyl)-1,2-dihydro-3H-pyrrolo[3,4-c]pyridin-3-one

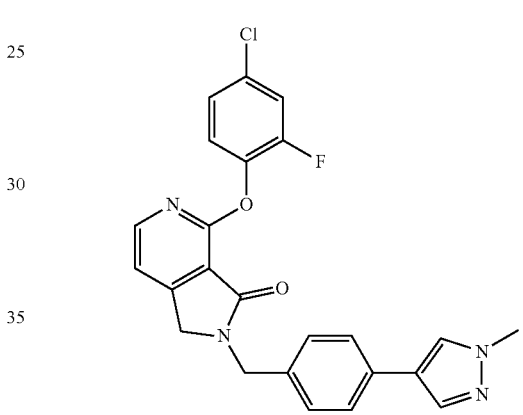

A solution of ethyl 2-(4-chloro-2-fluorophenoxy)-4-formylnicotinate (1.00 g) obtained in Reference Example 236 and (4-bromophenyl)methanamine (0.63 g) in THF (20 mL) was stirred at room temperature for 2 hr. The reaction mixture was concentrated, to a solution of the residue in acetic acid (20 mL) was added sodium triacetoxyhydroborate (0.98 g) at room temperature, and the mixture was stirred under an argon atmosphere at room temperature for 3 hr. The reaction mixture was neutralized with saturated aqueous sodium hydrogen carbonate solution, and the mixture was diluted with ethyl acetate. The organic layer was separated, washed with saturated brine, dried over anhydrous sodium sulfate, and concentrated. To a solution of the obtained residue (0.50 g), 1-methyl-4-(4,4,5,5-tetramethyl-1,3,2-dioxaborolan-2-yl)-1H-pyrazole (0.26 g) and 2M aqueous sodium carbonate solution (1.12 mL) in DME (10 mL) was added [1,1-bis(diphenylphosphino)ferrocene]dichloropalladium(II) (0.082 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with ethyl acetate to give the title compound (0.037 g).

MS: [M+H]+ 449.1

$^1$H NMR (300 MHz, CDCl$_3$) δ 3.95 (3H, s), 4.33 (2H, s), 4.80 (2H, s), 7.08 (1H, d, J=5.1 Hz), 7.16-7.32 (3H, m), 7.32-7.37 (2H, m), 7.44-7.49 (2H, m), 7.61 (1H, s), 7.75 (1H, s), 8.18 (1H, d, J=5.1 Hz).

Example 389

7-(2-fluoro-4-(2,2,2-trifluoro-1-hydroxyethyl)phenoxy)-2-((5-(1-methyl-1H-pyrazol-4-yl)pyridin-2-yl)methyl)isoindolin-1-one

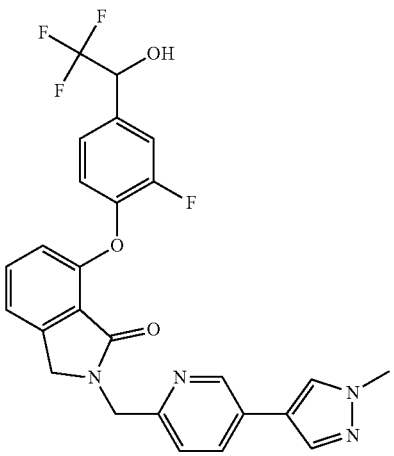 [SMILES: Cn1cc(-c2ccc(CN3Cc4cccc(Oc5ccc(C(O)C(F)(F)F)cc5F)c4C3=O)nc2)cn1]

To a solution of (5-(1-methyl-1H-pyrazol-4-yl)pyridin-2-yl)methanamine dihydrochloride (0.11 g) obtained in Reference Example 28 and ethyl 2-(bromomethyl)-6-(2-fluoro-4-(2,2,2-trifluoro-1-hydroxyethyl)phenoxy)benzoate (0.19 g) obtained in Reference Example 241 in ethanol (4 mL) was added potassium carbonate (0.18 g), and the mixture was stirred under an argon atmosphere at room temperature for 2 days. The reaction mixture was diluted with water and ethyl acetate. The organic layer was separated, washed with saturated brine, dried over anhydrous sodium sulfate, and concentrated. The residue was crudely purified by NH silica gel chromatography (hexane-ethyl acetate), and solidified with ethyl acetate to give the title compound (0.085 g).

MS: [M+H]+ 513.2

$^1$H NMR (300 MHz, CDCl$_3$) δ 3.51 (1H, d, J=4.9 Hz), 3.97 (3H, s), 4.49 (2H, s), 4.89 (2H, s), 5.02-5.11 (1H, m), 6.76 (1H, d, J=8.3 Hz), 7.07-7.16 (2H, m), 7.18-7.22 (1H, m), 7.32 (1H, dd, J=11.1, 1.7 Hz), 7.37-7.46 (2H, m), 7.65 (1H, s), 7.72 (1H, dd, J=8.3, 2.3 Hz), 7.76 (1H, s), 8.67 (1H, d, J=1.5 Hz).

Example 390

7-(2-fluoro-4-(2,2,2-trifluoro-1-hydroxyethyl)phenoxy)-2-((6-(1-methyl-1H-pyrazol-4-yl)pyridin-3-yl)methyl)isoindolin-1-one

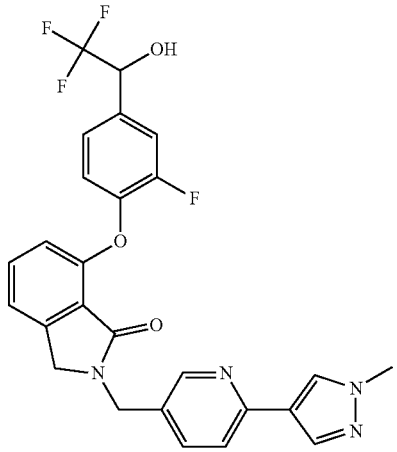 [SMILES: Cn1cc(-c2ccc(CN3Cc4cccc(Oc5ccc(C(O)C(F)(F)F)cc5F)c4C3=O)cn2)cn1]

To a solution of (6-(1-methyl-1H-pyrazol-4-yl)pyridin-3-yl)methanamine dihydrochloride (0.29 g) obtained in Reference Example 25 and ethyl 2-(bromomethyl)-6-(2-fluoro-4-(2,2,2-trifluoro-1-hydroxyethyl)phenoxy)benzoate (0.50 g) obtained in Reference Example 241 in ethanol (10 mL) was added potassium carbonate (0.46 g), and the mixture was stirred under an argon atmosphere at room temperature for 3 days. The reaction mixture was diluted with water and ethyl acetate. The organic layer was separated, washed with saturated brine, dried over anhydrous sodium sulfate, and concentrated. The residue was purified by NH silica gel chromatography (hexane-ethyl acetate) to give the title compound (0.20 g).

MS: [M+H]+ 513.2

$^1$H NMR (300 MHz, CDCl$_3$) δ 3.75 (1H, d, J=4.7 Hz), 3.97 (3H, s), 4.33 (2H, s), 4.70-4.83 (2H, m), 5.04-5.10 (1H, m), 6.80 (1H, d, J=8.3 Hz), 7.06-7.15 (2H, m), 7.22 (1H, d, J=8.7 Hz), 7.29-7.37 (1H, m), 7.40-7.47 (2H, m), 7.68 (1H, dd, J=8.1, 2.3 Hz), 7.94 (2H, s), 8.47 (1H, d, J=1.9 Hz).

Example 391

4-(4-(difluoromethyl)-2-fluorophenoxy)-2-(4-(1-methyl-1H-pyrazol-4-yl)benzyl)-1,2-dihydro-3H-pyrrolo[3,4-c]pyridin-3-one

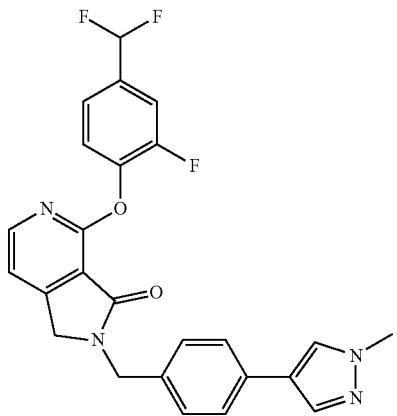 [SMILES: Cn1cc(-c2ccc(CN3Cc4ccnc(Oc5ccc(C(F)F)cc5F)c4C3=O)cc2)cn1]

A mixture of ethyl 2-(4-(difluoromethyl)-2-fluorophenoxy)-4-vinylnicotinate (0.50 g) obtained in Reference Example 233, sodium periodate (1.59 g) and osmium oxide (immobilized catalyst I) (0.19 g), and acetonitrile (10 mL)-acetone (10 mL)-water (10 mL) was stirred under an argon atmosphere at room temperature overnight. The insoluble material was filtered off, and the filtrate was diluted with ethyl acetate. The organic layer was separated, washed with saturated brine, dried over anhydrous magnesium sulfate, and concentrated. To a solution of the residue in THF (10 mL) was added (4-bromophenyl)methanamine (0.28 g) at room temperature, and the mixture was stirred under an argon atmosphere at room temperature for 3 hr. The reaction mixture was concentrated, to a solution of the residue in acetic acid (10 mL) was added sodium triacetoxyhydroborate (0.38 g) at room temperature, and the mixture was stirred under an argon atmosphere at room temperature for 2 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was crudely purified by NH silica gel chromatography (hexane-ethyl acetate). To a solution of the obtained crudely purified product (0.20 g), 1-methyl-4-(4,4,5,5-tetramethyl-1,3,2-dioxaborolan-2-yl)-1H-pyrazole (0.099 g) and 2M aqueous sodium carbonate solution (0.43 mL) in DME (4 mL) was added [1,1-bis(diphenylphosphino)ferrocene]dichloropalladium(II) (0.032 g), and the mixture was stirred under an argon atmosphere at 80° C. for 7 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate to give the title compound (0.053 g).

MS: [M+H]$^+$ 465.1

$^1$H NMR (300 MHz, CDCl$_3$) δ 3.96 (3H, s), 4.34 (2H, s), 4.81 (2H, s), 6.47-6.87 (1H, m), 7.09 (1H, d, J=5.1 Hz), 7.32-7.49 (7H, m), 7.62 (1H, s), 7.76 (1H, s), 8.18 (1H, d, J=5.1 Hz).

Example 392

4-(4-(difluoromethyl)-2-fluorophenoxy)-2-(4-(6-methylpyridazin-4-yl)benzyl)-1,2-dihydro-3H-pyrrolo[3,4-c]pyridin-3-one A mixture of ethyl 2-(4-(difluoromethyl)-2-fluorophenoxy)-4-vinylnicotinate (0.50 g) obtained in Reference Example 233, sodium periodate (1.59 g) and osmium oxide (immobilized catalyst I) (0.19 g), and acetonitrile (10 mL)-acetone (10 mL)-water (10 mL) was stirred under an argon atmosphere at room temperature overnight. The insoluble material was filtered off, and the filtrate was diluted with ethyl acetate. The organic layer was separated, washed with saturated brine, dried over anhydrous magnesium sulfate, and concentrated.

To a solution of the residue in THF (10 mL) was added (4-bromophenyl)methanamine (0.28 g) at room temperature, and the mixture was stirred under an argon atmosphere at room temperature for 3 hr. The reaction mixture was concentrated, to a solution of the residue in acetic acid (10 mL) was added sodium triacetoxyhydroborate (0.38 g) at room temperature, and the mixture was stirred under an argon atmosphere at room temperature for 2 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was crudely purified by NH silica gel chromatography (hexane-ethyl acetate). To a solution of the obtained crudely purified product (0.088 g), 3-methyl-5-(4,4,5,5-tetramethyl-1,3,2-dioxaborolan-2-yl)pyridazine (0.050 g) and 2M aqueous sodium carbonate solution (0.19 mL) in DME (2 mL) was added [1,1-bis(diphenylphosphino)ferrocene]dichloropalladium(II) (0.014 g), and the mixture was stirred under an argon atmosphere at 80° C. for 7 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate to give the title compound (0.0043 g).

MS: [M+H]$^+$ 477.0

$^1$H NMR (300 MHz, CDCl$_3$) δ 2.80 (3H, s), 4.38 (2H, s), 4.89 (2H, s), 6.47-6.88 (1H, m), 7.12 (1H, d, J=5.1 Hz), 7.35-7.47 (3H, m), 7.48 (1H, d, J=2.3 Hz), 7.53 (2H, d, J=8.3 Hz), 7.64-7.69 (2H, m), 8.21 (1H, d, J=5.3 Hz), 9.29 (1H, d, J=2.3 Hz).

Example 393

4-(2-fluoro-4-(2,2,2-trifluoro-1-hydroxyethyl)phenoxy)-2-(4-(1-methyl-1H-pyrazol-4-yl)benzyl)-1,2-dihydro-3H-pyrrolo[3,4-c]pyridin-3-one

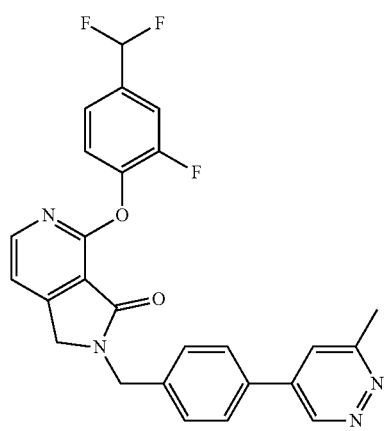 [SMILES: Cc1cc(-c2ccc(CN3Cc4ccnc(Oc5ccc(C(F)F)cc5F)c4C3=O)cc2)cnn1]

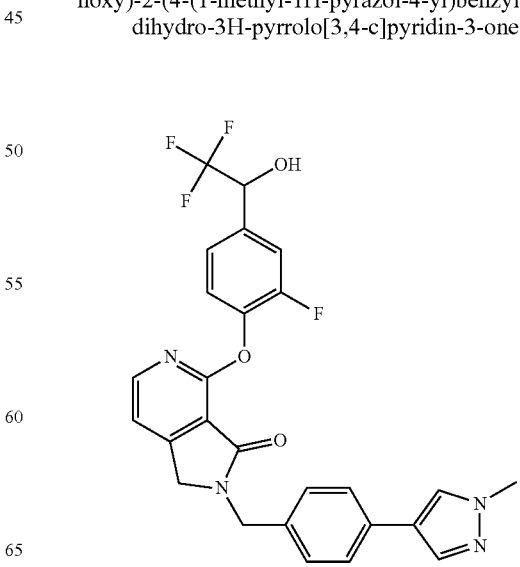

A mixture of ethyl 2-(2-fluoro-4-(2,2,2-trifluoro-1-hydroxyethyl)phenoxy)-4-vinylnicotinate (0.31 g) obtained in Reference Example 242, sodium periodate (0.86 g) and osmium oxide (immobilized catalyst I) (0.10 g), and acetonitrile (6 mL)-acetone (6 mL)-water (6 mL) was stirred under an argon atmosphere at room temperature overnight. The insoluble material was filtered off, and the filtrate was diluted with ethyl acetate. The organic layer was separated, washed with saturated brine, dried over anhydrous magnesium sulfate, and concentrated. To a solution of the residue in THF (6 mL) was added (4-bromophenyl)methanamine (0.31 g), and the mixture was stirred under an argon atmosphere at room temperature for 2 hr. The reaction mixture was concentrated, to a solution of the residue in acetic acid (6 mL) was added sodium triacetoxyhydroborate (0.19 g) at room temperature, and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was crudely purified by NH silica gel chromatography (hexane-ethyl acetate). To a solution of the obtained crudely purified product (0.35 g), 1-methyl-4-(4,4,5,5-tetramethyl-1,3,2-dioxaborolan-2-yl)-1H-pyrazole (0.17 g) and 2M aqueous sodium carbonate solution (0.69 mL) in DME (7 mL) was added [1,1-bis(diphenylphosphino)ferrocene]dichloropalladium(II) (0.17 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate to give the title compound (0.024 g).

MS: [M+H]$^+$ 513.2

$^1$H NMR (300 MHz, DMSO-d$_6$) δ 3.85 (3H, s), 4.48 (2H, s), 4.70 (2H, s), 5.29 (1H, t, J=5.9 Hz), 7.04 (1H, d, J=5.3 Hz), 7.30 (2H, d, J=8.3 Hz), 7.37 (1H, d, J=5.1 Hz), 7.41-7.44 (2H, m), 7.48 (1H, d, J=11.5 Hz), 7.55 (2H, d, J=8.1 Hz), 7.84 (1H, s), 8.12 (1H, s), 8.21 (1H, d, J=5.1 Hz).

Example 394

4-(2-fluoro-4-(1-hydroxyethyl)phenoxy)-2-(4-(1-methyl-1H-pyrazol-4-yl)benzyl)-1,2-dihydro-3H-pyrrolo[3,4-c]pyridin-3-one

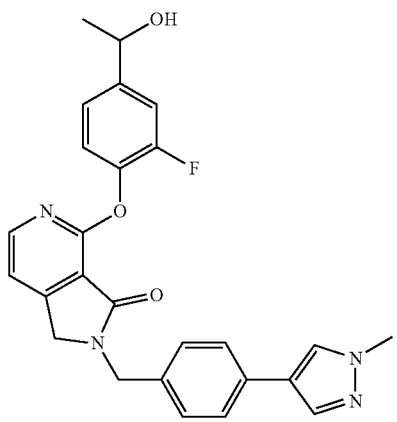 [SMILES: CC(O)c1ccc(Oc2nccc3c2C(=O)N(Cc2ccc(-c4cnn(C)c4)cc2)C3)c(F)c1]

To a solution of ethyl 2-(2-fluoro-4-(1-hydroxyethyl)phenoxy)-4-formylnicotinate (0.46 g) obtained in Reference Example 245 and (4-bromophenyl)methanamine (0.26 g) in THF (9 mL) was stirred at room temperature for 2 hr. The reaction mixture was concentrated, to a solution of the residue in acetic acid (9 mL) was added sodium triacetoxyhydroborate (0.19 g) at room temperature, and the mixture was stirred under an argon atmosphere at room temperature for 3 hr. The reaction mixture was neutralized with saturated sodium hydrogen carbonate solution, and diluted with ethyl acetate. The organic layer was separated, washed with saturated brine, dried over anhydrous magnesium sulfate and concentrated. The residue was crudely purified by NH silica gel chromatography (hexane-ethyl acetate). To a solution of the obtained crudely purified product (0.35 g), 1-methyl-4-(4,4,5,5-tetramethyl-1,3,2-dioxaborolan-2-yl)-1H-pyrazole (0.18 g) and 2M aqueous sodium carbonate solution (0.77 mL) in DME (7 mL) was added [1,1-bis(diphenylphosphino)ferrocene]dichloropalladium(II) (0.056 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate-ethanol to give the title compound (0.058 g).

MS: [M+H]$^+$ 459.2

$^1$H NMR (300 MHz, CDCl$_3$) δ 1.52 (3H, d, J=6.4 Hz), 1.85 (1H, d, J=3.8 Hz), 3.94 (3H, s), 4.31 (2H, s), 4.79 (2H, s), 4.93 (1H, dd, J=6.6, 3.8 Hz), 7.05 (1H, d, J=5.1 Hz), 7.16-7.24 (1H, m), 7.27-7.36 (4H, m), 7.43-7.48 (2H, m), 7.60 (1H, s), 7.74 (1H, s), 8.18 (1H, d, J=5.3 Hz).

Example 395

4-(2,6-difluorophenoxy)-6-(4-(1-methyl-1H-pyrazol-3-yl)benzyl)-6,7-dihydro-5H-pyrrolo[3,4-d]pyrimidin-5-one

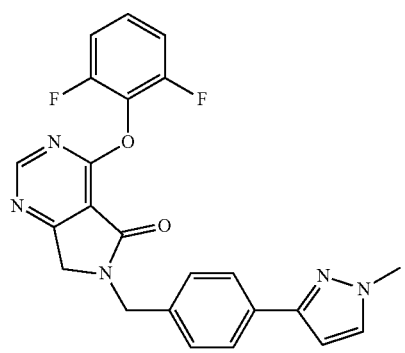 [SMILES: Cn1ccc(-c2ccc(CN3Cc4ncnc(Oc5c(F)cccc5F)c4C3=O)cc2)n1]

A solution of methyl 4-(2,6-difluorophenoxy)-6-formylpyrimidine-5-carboxylate (0.040 g) obtained in Reference Example 226 and (4-(1-methyl-1H-pyrazol-3-yl)phenyl)methanamine (0.025 g) in THF (1 mL) was stirred under an argon atmosphere at room temperature for 2 hr. The reaction mixture was concentrated, to a mixed solution of the residue in THF (1 mL)-methanol (0.3 mL) was added sodium triacetoxyhydroborate (0.14 g) at room temperature, and the mixture was stirred under an argon atmosphere at room temperature for 2 hr. Sodium triacetoxyhydroborate (0.14 g)

was further added to the reaction mixture at room temperature, and the mixture was stirred under an argon atmosphere at room temperature for 1 hr. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by silica gel chromatography (hexane-ethyl acetate), and solidified with ethyl acetate to give the title compound (0.021 g).

MS: [M+H]⁺ 434.2

¹H NMR (300 MHz, CDCl₃) δ 3.96 (3H, s), 4.37 (2H, s), 4.85 (2H, s), 6.54 (1H, d, J=2.3 Hz), 7.00-7.10 (2H, m), 7.21-7.31 (1H, m), 7.39 (3H, dd, J=5.1, 2.8 Hz), 7.81 (2H, d, J=8.3 Hz), 8.78 (1H, s).

Example 396

4-(2-chloro-6-fluorophenoxy)-6-(4-(1-methyl-TH-pyrazol-4-yl)benzyl)-6,7-dihydro-5H-pyrrolo[3,4-d]pyrimidin-5-one

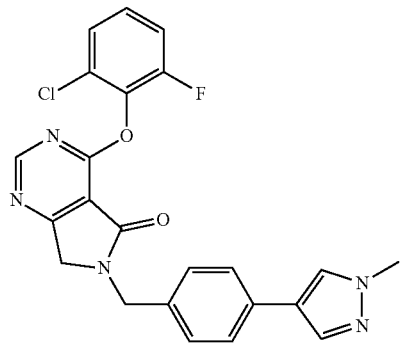 [SMILES: Cn1cc(-c2ccc(CN3Cc4ncnc(Oc5c(F)cccc5Cl)c4C3=O)cc2)cn1]

A solution of methyl 4-(2-chloro-6-fluorophenoxy)-6-formylpyrimidine-5-carboxylate (0.19 g) obtained in Reference Example 248 and (4-bromophenyl)methanamine (0.11 g) in THF (4 mL) was stirred under an argon atmosphere at room temperature for 2 hr. The reaction mixture was concentrated, to a mixed solution of the residue in THF (6 mL)-methanol (2 mL) was added sodium triacetoxyhydroborate (1.30 g) at room temperature, and the mixture was stirred under an argon atmosphere at room temperature overnight. The reaction mixture was diluted with water and ethyl acetate. The organic layer was separated, washed with saturated brine, dried over anhydrous magnesium sulfate and concentrated. To a solution of the obtained residue, 1-methyl-4-(4,4,5,5-tetramethyl-1,3,2-dioxaborolan-2-yl)-1H-pyrazole (0.13 g) and 2M aqueous sodium carbonate solution (0.61 mL) in DME (4 mL) was added [1,1-bis(diphenylphosphino)ferrocene]dichloropalladium(II) (0.050 g), and the mixture was stirred under an argon atmosphere at 80° C. for 2 hr. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with ethyl acetate to give the title compound (0.015 g).

MS: [M+H]⁺ 450.1

¹H NMR (300 MHz, CDCl₃) δ 3.96 (3H, s), 4.38 (2H, s), 4.83 (2H, s), 7.12-7.20 (1H, m), 7.21-7.29 (2H, m), 7.29-7.34 (1H, m), 7.34-7.39 (1H, m), 7.46-7.51 (2H, m), 7.62 (1H, s), 7.76 (1H, s), 8.77 (1H, s).

Example 397

4-(2-chloro-6-fluorophenoxy)-2-(4-(1-methyl-1H-pyrazol-4-yl)benzyl)-1,2-dihydro-3H-pyrrolo[3,4-c]pyridin-3-one

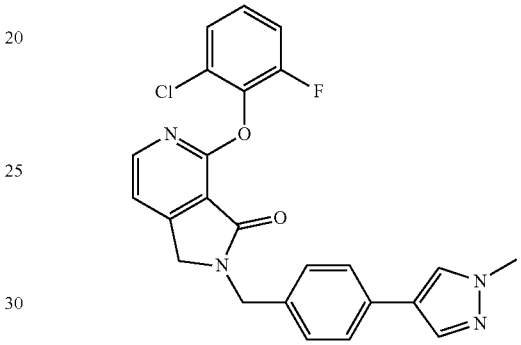

A solution of ethyl 2-(2-chloro-6-fluorophenoxy)-4-formylnicotinate (0.32 g) obtained in Reference Example 250 and (4-bromophenyl)methanamine (0.19 g) in THF (6 mL) was stirred under an argon atmosphere at room temperature for 2 hr. The reaction mixture was concentrated, to a solution of the residue in acetic acid (6 mL) was added sodium triacetoxyhydroborate (0.31 g) at room temperature, and the mixture was stirred under an argon atmosphere at room temperature overnight. The reaction mixture was diluted with water and ethyl acetate. The organic layer was separated, washed with saturated brine, dried over anhydrous magnesium sulfate and concentrated. The residue was crudely purified by silica gel chromatography (hexane-ethyl acetate). To a solution of the obtained crudely purified product (0.19 g), 1-methyl-4-(4,4,5,5-tetramethyl-1,3,2-dioxaborolan-2-yl)-1H-pyrazole (0.097 g) and 2M aqueous sodium carbonate solution (0.42 mL) in DME (4 mL) was added [1,1-bis(diphenylphosphino)ferrocene]dichloropalladium(II) (0.035 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was purified by silica gel chromatography (hexane-ethyl acetate), and solidified with ethyl acetate to give the title compound (0.013 g).

MS: [M+H]⁺ 449.1

¹H NMR (300 MHz, CDCl₃) δ 3.96 (3H, s), 4.33 (2H, s), 4.81 (2H, s), 7.07-7.23 (3H, m), 7.27-7.32 (1H, m), 7.33-7.39 (2H, m), 7.44-7.50 (2H, m), 7.62 (1H, s), 7.76 (1H, d, J=0.8 Hz), 8.17 (1H, d, J=5.3 Hz).

Example 398

3,5-difluoro-4-((2-(4-(6-methylpyridazin-4-yl)benzyl)-3-oxo-2,3-dihydro-1H-isoindol-4-yl)oxy)benzonitrile

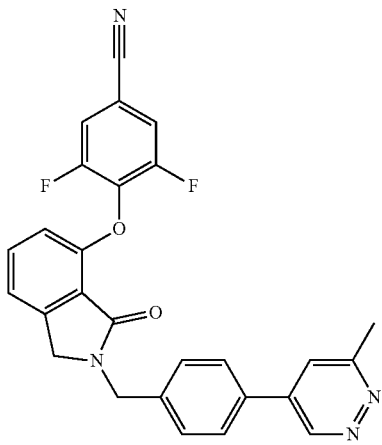 [SMILES: Cc1cc(-c2ccc(CN3Cc4cccc(Oc5c(F)cc(C#N)cc5F)c4C3=O)cc2)cnn1]

To a solution of ethyl 2-(bromomethyl)-6-(4-cyano-2,6-difluorophenoxy)benzoate (0.50 g) obtained in Reference Example 231 and (4-bromophenyl)methanamine (0.25 g) in ethanol (20 mL) was added potassium carbonate (0.52 g), and the mixture was stirred under an argon atmosphere at room temperature overnight.

The reaction mixture was diluted with water and ethyl acetate.

The organic layer was separated, washed with saturated brine, dried over anhydrous magnesium sulfate and concentrated. The residue was crudely purified by silica gel chromatography (hexane-ethyl acetate). The crudely purified product was diluted with water and ethyl acetate. The organic layer was separated, washed with saturated brine, dried over anhydrous magnesium sulfate and concentrated. To a solution of the obtained residue (0.19 g), (6-methylpyridazin-4-yl)boronic acid (0.058 g) and 2M aqueous sodium carbonate solution (0.42 mL) in DME (4 mL) was added [1,1-bis(diphenylphosphino)ferrocene]dichloropalladium(II) (0.034 g), and the mixture was stirred under an argon atmosphere at 80° C. overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and solidified with ethyl acetate-hexane to give the title compound (0.060 g).

MS: [M+H]$^+$ 469.0

$^1$H NMR (300 MHz, CDCl$_3$) δ 2.79 (3H, s), 4.33 (2H, s), 4.82 (2H, s), 6.84 (1H, d, J=8.3 Hz), 7.18 (1H, d, J=7.6 Hz), 7.34 (2H, d, J=7.2 Hz), 7.42-7.51 (4H, m), 7.64 (2H, d, J=8.3 Hz), 9.27 (1H, d, J=2.3 Hz).

Example 399

4-((trans-2-hydroxycyclohexyl)oxy)-2-(2-thienylmethyl)-1,2-dihydro-3H-pyrrolo[3,4-c]pyridin-3-one

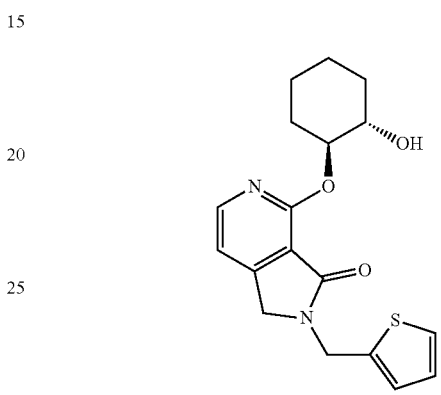

A mixture of ethyl 2-((trans-2-hydroxycyclohexyl)oxy)-4-vinylnicotinate (0.82 g) obtained in Reference Example 116, sodium periodate (3.0 g) and osmium oxide (immobilized catalyst I) (0.36 g), and acetonitrile (10 mL)-acetone (10 mL)-water (10 mL) was stirred at room temperature overnight. The insoluble material was filtered off, and the filtrate was diluted with ethyl acetate. The organic layer was separated, washed with saturated brine, dried over anhydrous sodium sulfate, and concentrated. To a solution of the residue (0.40 g) and 1-(2-thienyl)methanamine (0.16 g) in THF (3 mL) was added anhydrous magnesium sulfate (0.33 g), and the mixture was stirred at room temperature for 1 hr. The reaction mixture was filtered, concentrated, and dissolved in acetic acid (3 mL). Sodium triacetoxyhydroborate (0.43 g) was added, and the mixture was stirred at room temperature overnight. The reaction mixture was neutralized with saturated aqueous sodium hydrogen carbonate solution, and diluted with water and ethyl acetate.

The organic layer was separated, washed with saturated aqueous sodium hydrogen carbonate solution and saturated brine, dried over anhydrous magnesium sulfate and concentrated. The residue was purified by silica gel chromatography (hexane-ethyl acetate) to give the title compound (0.25 g).

MS: [M+H]$^+$ 345.1

$^1$H NMR (300 MHz, CDCl$_3$) δ 1.38 (4H, brs), 1.71-1.84 (2H, m), 2.08-2.20 (1H, m), 2.31-2.44 (1H, m), 3.82-3.96 (1H, m), 4.01 (1H, brs), 4.30 (2H, s), 4.81 (1H, ddd, J=15.2, 8.9, 4.5 Hz), 4.91 (2H, d, J=3.4 Hz), 6.93-6.99 (2H, m), 7.00-7.06 (1H, m), 7.24 (1H, dd, J=5.1, 1.1 Hz), 8.23 (1H, d, J=5.1 Hz).

Example 400

2-((5-bromo-2-thienyl)methyl)-4-((trans-2-hydroxy-cyclohexyl)oxy)-1,2-dihydro-3H-pyrrolo[3,4-c]pyridin-3-one

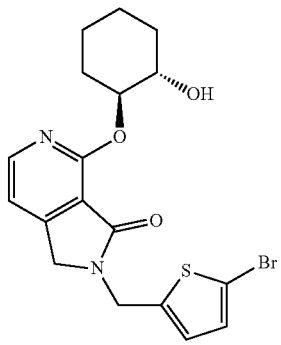 [SMILES: O=C1c2c(ccnc2O[C@H]2CCCC[C@@H]2O)CN1Cc1ccc(Br)s1]

To a solution of 4-((trans-2-hydroxycyclohexyl)oxy)-2-(2-thienylmethyl)-1,2-dihydro-3H-pyrrolo[3,4-c]pyridin-3-one (0.11 g) obtained in Example 399 in acetonitrile (3 mL) was added NBS (0.059 g), and the mixture was stirred at room temperature overnight. The reaction mixture was diluted with water and ethyl acetate. The organic layer was separated, saturated aqueous sodium hydrogen carbonate solution, washed with saturated brine, dried over anhydrous sodium sulfate, and concentrated. The residue was purified by silica gel chromatography (hexane-ethyl acetate) to give the title compound (0.096 g).

MS: [M+H]$^+$ 423.0

$^1$H NMR (300 MHz, CDCl$_3$) δ 1.24-1.55 (4H, m), 1.68-1.89 (2H, m), 2.07-2.20 (1H, m), 2.25-2.44 (1H, m), 3.84-3.96 (2H, m), 4.31 (2H, s), 4.73-4.89 (3H, m), 6.80 (1H, d, J=3.6 Hz), 6.91 (1H, d, J=3.6 Hz), 6.97 (1H, d, J=5.3 Hz), 8.24 (1H, d, J=5.3 Hz).

Example 401

2-((5-chloro-2-thienyl)methyl)-4-((trans-2-hydroxy-cyclohexyl)oxy)-1,2-dihydro-3H-pyrrolo[3,4-c]pyridin-3-one

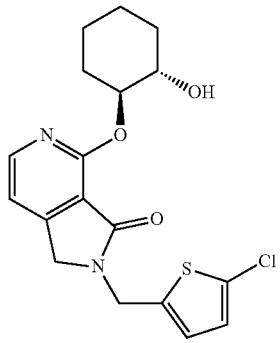 [SMILES: O=C1c2c(ccnc2O[C@H]2CCCC[C@@H]2O)CN1Cc1ccc(Cl)s1]

To a solution of 4-((trans-2-hydroxycyclohexyl)oxy)-2-(2-thienylmethyl)-1,2-dihydro-3H-pyrrolo[3,4-c]pyridin-3-one (0.060 g) obtained in Example 399 in acetonitrile (3 mL) was added N-chlorosuccinimide (0.023 g), and the mixture was stirred at 90° C. for 5 hr. The reaction mixture was diluted with water and ethyl acetate. The organic layer was separated, washed with saturated aqueous sodium hydrogen carbonate solution and saturated brine, dried over anhydrous sodium sulfate, and concentrated. The residue was purified by silica gel chromatography (hexane-ethyl acetate) to give the title compound (0.019 g).

MS: [M+H]$^+$ 379.1

$^1$H NMR (300 MHz, CDCl$_3$) δ 1.29-1.58 (4H, m), 1.67-1.85 (2H, m), 2.06-2.21 (1H, m), 2.27-2.45 (1H, m), 3.83-3.95 (2H, m), 4.31 (2H, s), 4.79 (3H, d, J=5.1 Hz), 6.74-6.78 (1H, m), 6.79-6.83 (1H, m), 6.97 (1H, d, J=5.1 Hz), 8.24 (1H, d, J=5.3 Hz).

Example 402

2-((5-(1,3-dimethyl-1H-pyrazol-4-yl)-2-thienyl)methyl)-4-((trans-2-hydroxycyclohexyl)oxy)-1,2-dihydro-3H-pyrrolo[3,4-c]pyridin-3-one

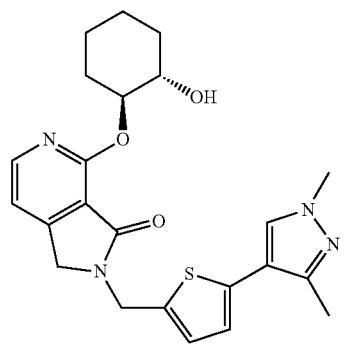 [SMILES: Cc1nn(C)cc1-c1ccc(CN2Cc3ccnc(O[C@H]4CCCC[C@@H]4O)c3C2=O)s1]

To a solution of 2-((5-bromo-2-thienyl)methyl)-4-((trans-2-hydroxycyclohexyl)oxy)-1,2-dihydro-3H-pyrrolo[3,4-c]pyridin-3-one (0.050 g) obtained in Example 400, 1,3-dimethyl-4-(4,4,5,5-tetramethyl-1,3,2-dioxaborolan-2-yl)-1H-pyrazole (0.032 g) and 2M aqueous sodium carbonate solution (0.12 mL) in DME (3 mL) was added (1,1-bis(diphenylphosphino)ferrocene)dichloropalladium(II) (0.0030 g), and the mixture was stirred under an argon atmosphere at 90° C. overnight. The reaction mixture was diluted with ethyl acetate and water. The organic layer was washed with water and saturated brine, dried over anhydrous magnesium sulfate and concentrated. The residue was purified by silica gel column chromatography (hexane-ethyl acetate, ethyl acetate-methanol) and recrystallization (ethyl acetate-diisopropyl ether) to give the title compound (0.025 g).

MS: [M+H]$^+$ 439.2

$^1$H NMR (300 MHz, CDCl$_3$) δ 1.32-1.60 (4H, m), 1.68-1.84 (3H, m), 2.07-2.20 (1H, m), 2.37 (3H, s), 2.38-2.41 (1H, m), 3.83 (3H, s), 3.84-3.96 (1H, m), 4.34 (2H, s), 4.75-4.95 (3H, m), 6.74-7.00 (3H, m), 7.40 (1H, s), 8.23 (1H, d, J=5.3 Hz).

Example 403

4-(cyclobutyloxy)-2-(4-(1,3-dimethyl-1H-pyrazol-4-yl)benzyl)-1,2-dihydro-3H-pyrrolo[3,4-c]pyridin-3-one

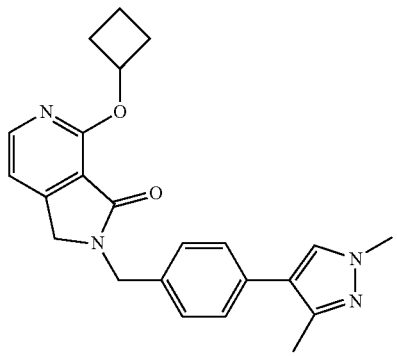 [SMILES: Cc1nn(C)cc1-c1ccc(CN2Cc3ccnc(OC4CCC4)c3C2=O)cc1]

To a solution of ethyl 2-cyclobutoxy-4-formylnicotinate (0.50 g) obtained in Reference Example 173 in THF (3 mL) was added (4-(1,3-dimethyl-1H-pyrazol-4-yl)phenyl)methanamine (0.42 g), and the mixture was stirred at room temperature for 1 hr. To the reaction mixture were added methanol (0.5 mL) and sodium triacetoxyhydroborate (2.13 g), and the mixture was stirred at room temperature for 1 hr. The reaction mixture was neutralized with saturated aqueous sodium hydrogen carbonate solution, and diluted with water and ethyl acetate. The organic layer was separated, washed with saturated aqueous sodium hydrogen carbonate solution and saturated brine, dried over anhydrous sodium sulfate, and concentrated. The residue was purified by silica gel chromatography (hexane-ethyl acetate) to give the title compound (0.38 g).

MS: [M+H]$^+$ 389.2

$^1$H NMR (300 MHz, CDCl$_3$) 51.60-1.94 (2H, m), 2.23-2.42 (5H, m), 2.45-2.60 (2H, m), 3.86 (3H, s), 4.24 (2H, s), 4.75 (2H, s), 5.26-5.42 (1H, m), 6.90 (1H, d, J=5.3 Hz), 7.32 (4H, d, J=1.1 Hz), 7.40 (1H, s), 8.21 (1H, d, J=4.9 Hz).

Example 404

4-(cyclobutyloxy)-2-(4-(1-ethyl-1H-pyrazol-4-yl)benzyl)-1,2-dihydro-3H-pyrrolo[3,4-c]pyridin-3-one

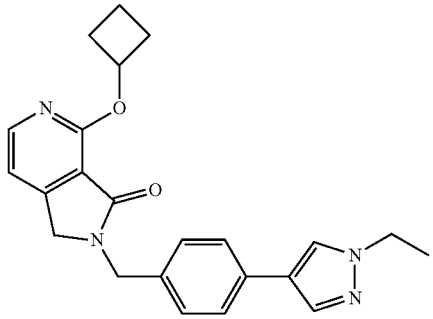 [SMILES: CCn1cc(-c2ccc(CN3Cc4ccnc(OC5CCC5)c4C3=O)cc2)cn1]

To a solution of ethyl 2-cyclobutoxy-4-formylnicotinate (0.20 g) obtained in Reference Example 173 in THF (3 mL) was added (4-(1-ethyl-1H-pyrazol-4-yl)phenyl)methanamine (0.17 g), and the mixture was stirred at room temperature for 1 hr. To the reaction mixture were added methanol (0.5 mL) and sodium triacetoxyhydroborate (0.85 g), and the mixture was stirred at room temperature for 1 hr. Thereafter, sodium triacetoxyhydroborate (0.51 g) was further added, and the mixture was stirred at room temperature for 2 hr. The reaction mixture was neutralized with saturated aqueous sodium hydrogen carbonate solution, and diluted with water and ethyl acetate. The organic layer was separated, washed with saturated aqueous sodium hydrogen carbonate solution and saturated brine, dried over anhydrous sodium sulfate, and concentrated. The residue was purified by silica gel chromatography (hexane-ethyl acetate) to give the title compound (0.13 g).

MS: [M+H]$^+$ 389.2

$^1$H NMR (300 MHz, CDCl$_3$) δ1.52 (3H, t, J=7.4 Hz), 1.61-1.76 (1H, m), 1.79-1.96 (1H, m), 2.25-2.43 (2H, m), 2.45-2.61 (2H, m), 4.14-4.26 (4H, m), 4.73 (2H, s), 5.28-5.42 (1H, m), 6.89 (1H, d, J=5.3 Hz), 7.27-7.32 (2H, m), 7.39-7.46 (2H, m), 7.62 (1H, s), 7.74 (1H, s), 8.21 (1H, d, J=5.1 Hz).

Example 405

(3-fluoro-4-((2-(4-(1-methyl-1H-pyrazol-4-yl)benzyl)-3-oxo-2,3-dihydro-1H-pyrrolo[3,4-c]pyridin-4-yl)oxy)phenyl)acetonitrile

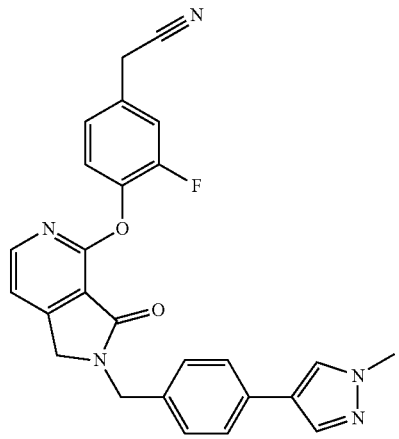 [SMILES: Cn1cc(-c2ccc(CN3Cc4ccnc(Oc5ccc(CC#N)cc5F)c4C3=O)cc2)cn1]

Ethyl 2-(4-(cyanomethyl)-2-fluorophenoxy)-4-formylnicotinate (0.32 g) obtained in Reference Example 259 was dissolved in methanol (5 mL), (4-(1-methyl-1H-pyrazol-4-yl)phenyl)methanamine (0.18 g) and acetic acid (0.058 g) were added, and the mixture was stirred under an argon atmosphere at room temperature for 20 min. To the reaction mixture was added sodium triacetoxyhydroborate (1.02 g), and the mixture was stirred at room temperature for 1 hr. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by silica gel chromatography (hexane-ethyl acetate), and solidified with hexane-ethyl acetate to give the title compound (0.098 g).

MS: [M+H]$^+$ 454.1

$^1$H NMR (300 MHz, DMSO-d$_6$) δ3.85 (3H, s), 4.11 (2H, s), 4.48 (2H, s), 4.70 (2H, s), 7.24-7.37 (4H, m), 7.37-7.45 (2H, m), 7.51-7.59 (2H, m), 7.83 (1H, d, J=0.6 Hz), 8.11 (1H, s), 8.19 (1H, d, J=5.1 Hz).

Example 406

(4-fluoro-3-((2-(4-(1-methyl-1H-pyrazol-4-yl)benzyl)-3-oxo-2,3-dihydro-1H-pyrrolo[3,4-c]pyridin-4-yl)oxy)phenyl)acetonitrile

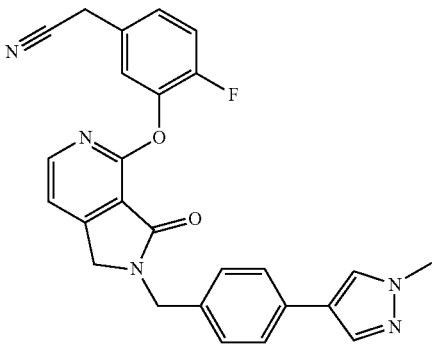 [SMILES: Cn1cc(-c2ccc(CN3Cc4ccnc(Oc5cc(CC#N)ccc5F)c4C3=O)cc2)cn1]

Ethyl 2-(5-(cyanomethyl)-2-fluorophenoxy)-4-formylnicotinate (0.36 g) obtained in Reference Example 263 was dissolved in methanol (5 mL), (4-(1-methyl-1H-pyrazol-4-yl)phenyl)methanamine (0.20 g) and acetic acid (0.065 g) were added, and the mixture was stirred under an argon atmosphere at room temperature for 20 min. Sodium triacetoxyhydroborate (1.15 g) was added to the reaction mixture, and the mixture was stirred at room temperature for 1 hr. The reaction mixture was neutralized with saturated sodium hydrogen carbonate solution, and diluted with ethyl acetate. The organic layer was separated, washed with saturated brine, dried over anhydrous sodium sulfate, and concentrated. The residue was purified by silica gel chromatography (hexane-ethyl acetate), the obtained solid was washed with methanol to give the title compound (0.077 g).

MS: [M+H]$^+$ 454.1
$^1$H NMR (300 MHz, DMSO-d$_6$) δ 3.85 (3H, s), 4.08 (2H, s), 4.48 (2H, s), 4.70 (2H, s), 7.26-7.35 (3H, m), 7.35-7.46 (3H, m), 7.55 (2H, d, J=8.1 Hz), 7.84 (1H, s), 8.11 (1H, s), 8.20 (1H, d, J=5.1 Hz).

Example 407

2-(4-(6-methylpyridazin-4-yl)benzyl)-4-(2-methyl-4-(trifluoromethyl)phenoxy)-1,2-dihydro-3H-pyrrolo[3,4-c]pyridin-3-one

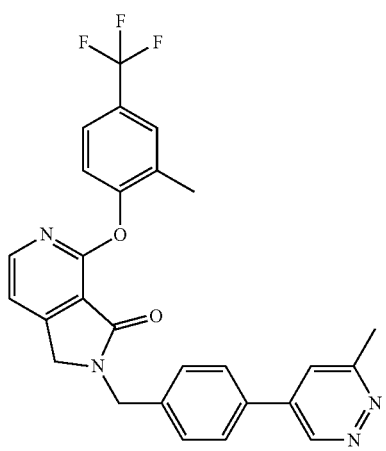 [SMILES: Cc1cc(-c2ccc(CN3Cc4ccnc(Oc5ccc(C(F)(F)F)cc5C)c4C3=O)cc2)cnn1]

A solution of 2-(4-bromobenzyl)-4-(2-methyl-4-(trifluoromethyl)phenoxy)-1H-pyrrolo[3,4-c]pyridin-3(2H)-one (0.13 g) obtained in Reference Example 266, 3-methyl-5-(4,4,5,5-tetramethyl-1,3,2-dioxaborolan-2-yl)pyridazine (0.077 g), 1,1'-bis(diphenylphosphino)ferrocene-palladium(II) dichloride dichloromethane complex (0.022 g) and 2M aqueous sodium carbonate solution (0.18 mL) in DME (2 mL) was subjected to microwave irradiation at 120° C. for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate) to give the title compound (0.012 g).

MS: [M+H]$^+$ 491.1
$^1$H NMR (300 MHz, DMSO-d$_6$) δ 2.19 (3H, s), 2.68 (3H, s), 4.53 (2H, s), 4.81 (2H, s), 7.30-7.41 (2H, m), 7.51 (2H, d, J=8.3 Hz), 7.63 (1H, d, J=8.9 Hz), 7.74 (1H, s), 7.89 (1H, d, J=2.3 Hz), 7.93 (2H, d, J=8.3 Hz), 8.22 (1H, d, J=5.1 Hz), 9.46 (1H, d, J=2.3 Hz).

Example 408

4-(2-fluoro-4-(2-hydroxypropan-2-yl)phenoxy)-2-(4-(1-methyl-1H-pyrazol-4-yl)benzyl)-1,2-dihydro-3H-pyrrolo[3,4-c]pyridin-3-one

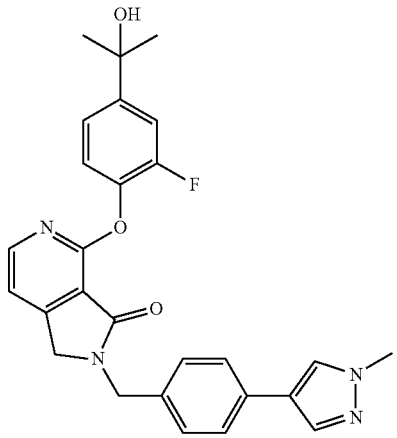 [SMILES: Cn1cc(-c2ccc(CN3Cc4ccnc(Oc5ccc(C(C)(C)O)cc5F)c4C3=O)cc2)cn1]

Ethyl 2-(2-fluoro-4-(2-hydroxypropan-2-yl)phenoxy)-4-formylnicotinate (0.17 g) obtained in Reference Example 268 was dissolved in methanol (2.5 mL), (4-(1-methyl-1H-pyrazol-4-yl)phenyl)methanamine (0.094 g) and anhydrous magnesium sulfate (0.060 g) were added, and the mixture was stirred at room temperature for 30 min. The solvent was evaporated, to the residue were added acetic acid (2.5 mL) and sodium triacetoxyhydroborate (0.21 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by silica gel chromatography (hexane-ethyl acetate), and the obtained solid was washed with hexane-ethyl acetate to give the title compound (0.038 g).

MS: [M+H]$^+$ 473.2
$^1$H NMR (300 MHz, DMSO-d$_6$) δ 1.46 (6H, s), 3.85 (3H, s), 4.47 (2H, s), 4.70 (2H, s), 5.18 (1H, s), 7.22-7.36 (5H, m), 7.41 (1H, dd, J=12.4, 2.0 Hz), 7.55 (2H, d, J=8.1 Hz), 7.83 (1H, s), 8.11 (1H, s), 8.19 (1H, d, J=5.3 Hz).

Example 409

2-(3-fluoro-4-((2-(4-(1-methyl-1H-pyrazol-4-yl)benzyl)-3-oxo-2,3-dihydro-1H-pyrrolo[3,4-c]pyridin-4-yl)oxy)phenyl)-2-methylpropanenitrile

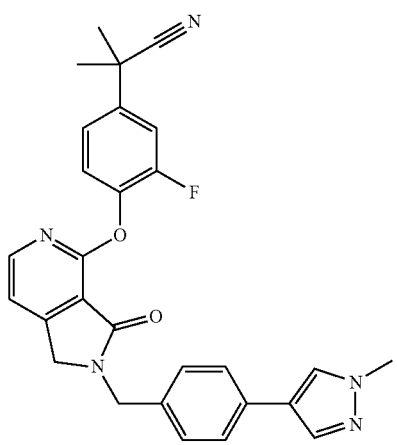 [SMILES: Cn1cc(-c2ccc(CN3Cc4ccnc(Oc5ccc(C(C)(C)C#N)cc5F)c4C3=O)cc2)cn1]

Ethyl 2-(4-(2-cyanopropan-2-yl)-2-fluorophenoxy)-4-formylnicotinate (0.029 g) obtained in Reference Example 270 was dissolved in THF (2.5 mL), (4-(1-methyl-1H-pyrazol-4-yl)phenyl)methanamine (0.023 g) was added, and the mixture was stirred at room temperature for 30 min. The solvent was evaporated, to the residue were added acetic acid (2.5 mL) and sodium triacetoxyhydroborate (0.035 g), and the mixture was stirred at room temperature overnight. The reaction mixture was concentrated, neutralized with saturated sodium hydrogen carbonate solution, and diluted with ethyl acetate. The organic layer was separated, washed with saturated brine, dried over anhydrous magnesium sulfate and concentrated. The residue was purified by silica gel chromatography (hexane-ethyl acetate), and the obtained solid was washed with hexane-ethyl acetate to give the title compound (0.0073 g).

MS: [M+H]+ 482.2

$^1$H NMR (300 MHz, DMSO-$d_6$) δ1.74 (6H, s), 3.85 (3H, s), 4.48 (2H, s), 4.70 (2H, s), 7.30 (2H, d, J=8.1 Hz), 7.36 (1H, d, J=5.1 Hz), 7.41-7.48 (2H, m), 7.52-7.61 (3H, m), 7.83 (1H, s), 8.11 (1H, s), 8.21 (1H, d, J=5.1 Hz).

Example 410

4-(2-fluoro-4-(2-fluoropropan-2-yl)phenoxy)-2-(4-(6-methylpyridazin-4-yl)benzyl)-1,2-dihydro-3H-pyrrolo[3,4-c]pyridin-3-one and Example 411

4-(2-fluoro-4-(prop-1-en-2-yl)phenoxy)-2-(4-(6-methylpyridazin-4-yl)benzyl)-1,2-dihydro-3H-pyrrolo[3,4-c]pyridin-3-one

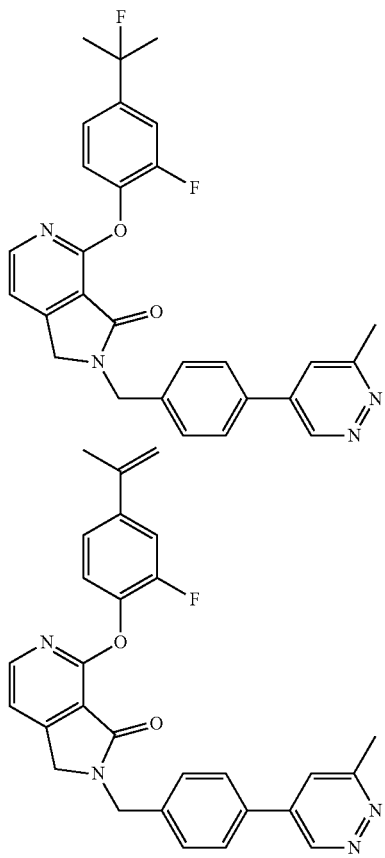

To a solution of 2-(4-bromobenzyl)-4-(2-fluoro-4-(2-hydroxypropan-2-yl)phenoxy)-1H-pyrrolo[3,4-c]pyridin-3(2H)-one (0.20 g) obtained in Reference Example 271 in THF (3 mL) was added diethylaminosulfur trifluoride (0.14 mg) under ice-cooling, and the mixture was stirred for 1 hr. The reaction mixture was neutralized with saturated sodium hydrogen carbonate solution, and diluted with ethyl acetate. The organic layer was separated, washed with saturated brine, dried over anhydrous magnesium sulfate and concentrated. The residue was crudely purified by silica gel chromatography (hexane-ethyl acetate). To a solution of the obtained crudely purified product in DME (3 mL) were added 3-methyl-5-(4,4,5,5-tetramethyl-1,3,2-dioxaborolan-2-yl)pyridazine (0.093 g), 1,1'-bis(diphenylphosphino)ferrocene-palladium(II)dichloride dichloromethane complex (0.035 g) and 2M aqueous sodium carbonate solution (0.28 mL), and the mixture was stirred under an argon atmosphere at 90° C. for 1 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate) to give 4-(2-fluoro-4-(2-fluoropropan-2-yl)phenoxy)-2-(4-(6-methylpyridazin-4-yl)benzyl)-1,2-dihydro-3H-pyrrolo[3,4-c]pyridin-3-one (0.051 g), and 4-(2-fluoro-4-(prop-1-en-2-yl)

phenoxy)-2-(4-(6-methylpyridazin-4-yl)benzyl)-1,2-dihydro-3H-pyrrolo[3,4-c]pyridin-3-one (0.025 g).

4-(2-fluoro-4-(2-fluoropropan-2-yl) phenoxy)-2-(4-(6-methylpyridazin-4-yl)benzyl)-1,2-dihydro-3H-pyrrolo[3,4-c]pyridin-3-one

MS: [M+H]$^+$ 487.2

$^1$H NMR (300 MHz, DMSO-d$_6$) δ 1.62-1.78 (6H, m), 2.68 (3H, s), 4.53 (2H, s), 4.81 (2H, s), 7.28-7.47 (4H, m), 7.51 (2H, d, J=8.3 Hz), 7.89 (1H, d, J=2.3 Hz), 7.92 (2H, d, J=8.3 Hz), 8.22 (1H, d, J=5.1 Hz), 9.45 (1H, d, J=2.3 Hz).

4-(2-fluoro-4-(prop-1-en-2-yl)phenoxy)-2-(4-(6-methylpyridazin-4-yl)benzyl)-1,2-dihydro-3H-pyrrolo[3,4-c]pyridin-3-one

MS: [M+H]$^+$ 467.2

$^1$H NMR (300 MHz, DMSO-d$_6$) 52.14 (3H, s), 2.68 (3H, s), 4.53 (2H, s), 4.81 (2H, s), 5.18 (1H, s), 5.53 (1H, s), 7.29-7.44 (3H, m), 7.48-7.56 (3H, m), 7.89 (1H, d, J=2.1 Hz), 7.92 (2H, d, J=8.3 Hz), 8.21 (1H, d, J=5.1 Hz), 9.46 (1H, d, J=2.3 Hz).

Example 412

2-(4-(1,3-dimethyl-1H-pyrazol-4-yl)benzyl)-4-(2-fluoro-4-(2-hydroxypropan-2-yl)phenoxy)-1,2-dihydro-3H-pyrrolo[3,4-c]pyridin-3-one

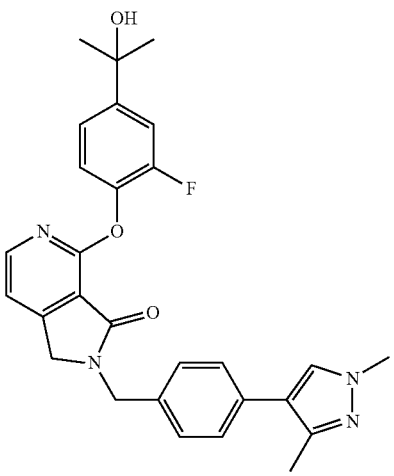 [SMILES: Cc1nn(C)cc1-c1ccc(CN2Cc3ccnc(Oc4ccc(C(C)(C)O)cc4F)c3C2=O)cc1]

A solution of 2-(4-bromobenzyl)-4-(2-fluoro-4-(2-hydroxypropan-2-yl)phenoxy)-1H-pyrrolo[3,4-c]pyridin-3 (2H)-one (0.070 g) obtained in Reference Example 271, 1,3-dimethyl-4-(4,4,5,5-tetramethyl-1,3,2-dioxaborolan-2-yl)-1H-pyrazole (0.043 g), 1,1'-bis(diphenylphosphino)ferrocene-palladium(II) dichloride dichloromethane complex (0.012 g) and 2M aqueous sodium carbonate solution (0.095 mL) in DME (1.5 mL) was stirred under an argon atmosphere at 90° C. for 1 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate). The obtained solid was washed with hexane-ethyl acetate to give the title compound (0.020 g).

MS: [M+H]$^+$ 487.2

$^1$H NMR (300 MHz, DMSO-d$_6$) δ1.46 (6H, s), 2.28 (3H, s), 3.77 (3H, s), 4.49 (2H, s), 4.71 (2H, s), 7.21-7.30 (1H, m), 7.30-7.37 (4H, m), 7.37-7.46 (3H, m), 7.86 (1H, s), 8.20 (1H, d, J=5.1 Hz), 1H not detected.

Example 413

4-(2-fluoro-4-(2-hydroxypropan-2-yl)phenoxy)-2-(4-(1-methyl-1H-pyrazol-3-yl)benzyl)-1,2-dihydro-3H-pyrrolo[3,4-c]pyridin-3-one

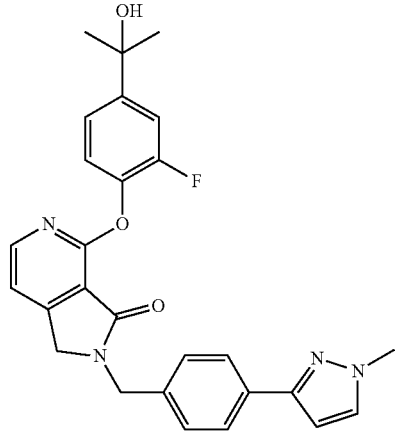 [SMILES: Cn1ccc(-c2ccc(CN3Cc4ccnc(Oc5ccc(C(C)(C)O)cc5F)c4C3=O)cc2)n1]

A solution of 2-(4-bromobenzyl)-4-(2-fluoro-4-(2-hydroxypropan-2-yl)phenoxy)-1H-pyrrolo[3,4-c]pyridin-3 (2H)-one (0.070 g) obtained in Reference Example 271, 1-methyl-3-(4,4,5,5-tetramethyl-1,3,2-dioxaborolan-2-yl)-1H-pyrazole (0.040 g), 1,1'-bis(diphenylphosphino)ferrocene-palladium(II) dichloride dichloromethane complex (0.012 g) and 2M aqueous sodium carbonate solution (0.28 mL) in DME (2 mL) was stirred under an argon atmosphere at 90° C. for 1 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate).

The obtained solid was recrystallized from hexane-ethyl acetate to give the title compound (0.027 g).

MS: [M+H]$^+$ 473.2

$^1$H NMR (300 MHz, DMSO-d$_6$) δ1.46 (6H, s), 3.87 (3H, s), 4.49 (2H, s), 4.72 (2H, s), 5.18 (1H, s), 6.67 (1H, d, J=2.3 Hz), 7.23-7.31 (1H, m), 7.31-7.37 (4H, m), 7.41 (1H, dd, J=12.4, 2.0 Hz), 7.72 (1H, d, J=2.3 Hz), 7.77 (2H, d, J=8.3 Hz), 8.20 (1H, d, J=5.1 Hz).

Example 414

4-(2-fluoro-4,6-dimethylphenoxy)-2-(4-(1-methyl-1H-pyrazol-3-yl)benzyl)-1,2-dihydro-3H-pyrrolo[3,4-c]pyridin-3-one

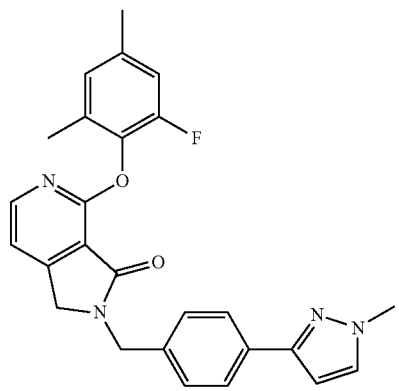 [SMILES: Cc1cc(C)c(Oc2nccc3c2C(=O)N(Cc2ccc(-c4ccn(C)n4)cc2)C3)c(F)c1]

Ethyl 2-(2-fluoro-4,6-dimethylphenoxy)-4-formylnicotinate (0.10 g) obtained in Reference Example 276 was dissolved in THF (2.5 mL), (4-(1-methyl-1H-pyrazol-3-yl)phenyl)methanamine (0.065 g) was added, and the mixture was stirred at room temperature for 30 min. The solvent was evaporated, and acetic acid (2.5 mL) and sodium triacetoxyhydroborate (0.13 g) were added to the residue, and the mixture was stirred at room temperature overnight. The reaction mixture was concentrated, neutralized with saturated sodium hydrogen carbonate solution, and diluted with ethyl acetate. The organic layer was separated, washed with saturated brine, dried over anhydrous magnesium sulfate and concentrated. The residue was purified by silica gel chromatography (hexane-ethyl acetate), and the obtained solid was washed with hexane-ethyl acetate to give the title compound (0.047 g).

MS: [M+H]+ 443.1

$^1$H NMR (300 MHz, DMSO-d$_6$) δ2.08 (3H, s), 2.31 (3H, s), 3.87 (3H, s), 4.48 (2H, s), 4.72 (2H, s), 6.67 (1H, d, J=2.3 Hz), 6.97 (1H, s), 7.00 (1H, d, J=11.0 Hz), 7.30-7.37 (3H, m), 7.72 (1H, d, J=2.3 Hz), 7.78 (2H, d, J=8.1 Hz), 8.16 (1H, d, J=5.1 Hz).

Example 415

4-(2-fluoro-4,6-dimethylphenoxy)-2-(4-(1-methyl-1H-pyrazol-4-yl)benzyl)-1,2-dihydro-3H-pyrrolo[3,4-c]pyridin-3-one

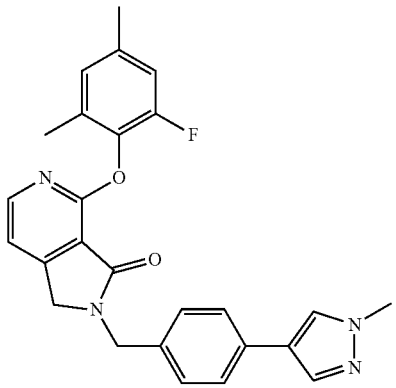 [SMILES: Cc1cc(C)c(Oc2nccc3c2C(=O)N(Cc2ccc(-c4cnn(C)c4)cc2)C3)c(F)c1]

Ethyl 2-(2-fluoro-4,6-dimethylphenoxy)-4-formylnicotinate (0.10 g) obtained in Reference Example 276 was dissolved in THF (2.5 mL), (4-(1-methyl-1H-pyrazol-4-yl)phenyl)methanamine (0.065 g) was added, and the mixture was stirred at room temperature for 30 min. The solvent was evaporated, acetic acid (2.5 mL) and sodium triacetoxyhydroborate (0.13 g) were added to the residue, and the mixture was stirred at room temperature overnight. The reaction mixture was concentrated, neutralized with saturated sodium hydrogen carbonate solution, and diluted with ethyl acetate. The organic layer was separated, washed with saturated brine, dried over anhydrous magnesium sulfate and concentrated. The residue was purified by silica gel chromatography (hexane-ethyl acetate), and the obtained solid was washed with hexane-ethyl acetate to give the title compound (0.047 g).

MS: [M+H]+ 443.2

$^1$H NMR (300 MHz, DMSO-d$_6$) δ2.08 (3H, s), 2.31 (3H, s), 3.85 (3H, s), 4.47 (2H, s), 4.69 (2H, s), 6.93-7.04 (2H, m), 7.27-7.34 (3H, m), 7.55 (2H, d, J=8.3 Hz), 7.83 (1H, s), 8.11 (1H, s), 8.16 (1H, d, J=5.3 Hz).

Example 416

2-((2-(4-(1-methyl-1H-pyrazol-3-yl)benzyl)-3-oxo-2,3-dihydro-1H-pyrrolo[3,4-c]pyridin-4-yl)oxy)-5-(trifluoromethyl)benzonitrile

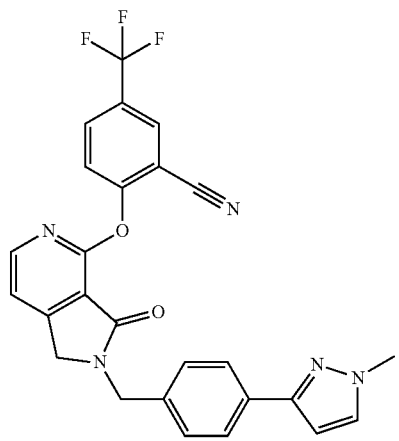 [SMILES: Cn1ccc(-c2ccc(CN3Cc4ccnc(Oc5ccc(C(F)(F)F)cc5C#N)c4C3=O)cc2)n1]

Ethyl 2-(2-cyano-4-(trifluoromethyl)phenoxy)-4-formylnicotinate (0.090 g) obtained in Reference Example 27B was dissolved in THF (2.5 mL), (4-(1-methyl-1H-pyrazol-3-yl)phenyl)methanamine (0.060 g) was added, and the mixture was stirred at room temperature for 30 min. The solvent was evaporated, acetic acid (2.5 mL) and sodium triacetoxyhydroborate (0.11 g) were added to the residue, and the mixture was stirred at room temperature overnight. The reaction mixture was concentrated, neutralized with saturated sodium hydrogen carbonate solution, and diluted with ethyl acetate. The organic layer was separated, washed with saturated brine, dried over anhydrous magnesium sulfate and concentrated. The residue was purified by silica gel chromatography (hexane-ethyl acetate) and reversed-phase preparative HPLC (L-column2 ODS, mobile phase:

water/acetonitrile (ammonium carbonate system)), and the obtained crystals were recrystallized from hexane-ethyl acetate to give the title compound (0.011 g).

MS: [M+H]+ 490.1

$^1$H NMR (300 MHz, DMSO-d$_6$) δ 3.87 (3H, s), 4.54 (2H, s), 4.73 (2H, s), 6.67 (1H, d, J=2.3 Hz), 7.33 (2H, d, J=8.3 Hz), 7.51 (1H, d, J=5.3 Hz), 7.63 (1H, d, J=8.7 Hz), 7.72 (1H, d, J=2.3 Hz), 7.77 (2H, d, J=8.3 Hz), 8.15 (1H, dd, J=8.9, 1.9 Hz), 8.31 (1H, d, J=5.3 Hz), 8.52 (1H, d, J=2.1 Hz).

Example 417

3-fluoro-5-methyl-4-((2-(4-(1-methyl-1H-pyrazol-3-yl)benzyl)-3-oxo-2,3-dihydro-1H-pyrrolo[3,4-c]pyridin-4-yl)oxy)benzonitrile

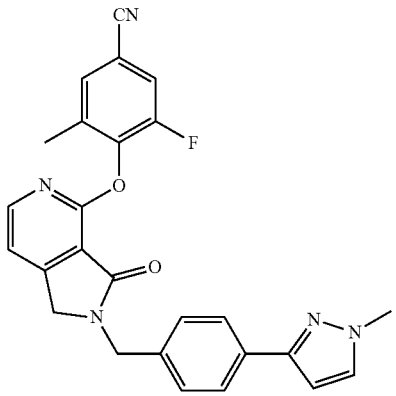 [SMILES: Cc1cc(C#N)cc(F)c1Oc1nccc2c1C(=O)N(Cc1ccc(-c3ccn(C)n3)cc1)C2]

Ethyl 2-(4-cyano-2-fluoro-6-methylphenoxy)-4-formylnicotinate (0.057 g) obtained in Reference Example 280 was dissolved in THF (1.5 mL), (4-(1-methyl-1H-pyrazol-3-yl)phenyl)methanamine (0.036 g) was added, and the mixture was stirred at room temperature for 30 min. The solvent was evaporated, acetic acid (2.5 mL) and sodium triacetoxyhydroborate (0.074 g) were added to the residue, and the mixture was stirred at room temperature overnight. The reaction mixture was concentrated, neutralized with saturated sodium hydrogen carbonate solution, and diluted with ethyl acetate. The organic layer was separated, washed with saturated brine, dried over anhydrous magnesium sulfate and concentrated. The residue was purified by silica gel chromatography (hexane-ethyl acetate), and the obtained solid was washed with hexane-ethyl acetate to give the title compound (0.010 g).

MS: [M+H]+ 454.1

$^1$H NMR (300 MHz, DMSO-d$_6$) δ2.20 (3H, s), 3.87 (3H, s), 4.51 (2H, s), 4.73 (2H, s), 6.67 (1H, d, J=2.3 Hz), 7.35 (2H, d, J=8.3 Hz), 7.41 (1H, d, J=5.1 Hz), 7.72 (1H, d, J=2.1 Hz), 7.75-7.81 (3H, m), 7.90 (1H, dd, J=9.9, 1.6 Hz), 8.19 (1H, d, J=5.1 Hz).

Example 418

4-(2-fluoro-4-(trifluoromethyl)phenoxy)-2-(4-(4-methyl-1H-imidazol-1-yl)benzyl)-1,2-dihydro-3H-pyrrolo[3,4-c]pyridin-3-one

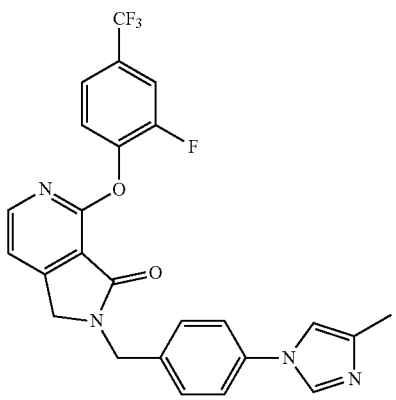 [SMILES: Cc1cn(-c2ccc(CN3Cc4ccnc(Oc5ccc(C(F)(F)F)cc5F)c4C3=O)cc2)cn1]

Ethyl 2-(2-fluoro-4-(trifluoromethyl)phenoxy)-4-formylnicotinate (0.14 g) obtained in Reference Example 282 was dissolved in methanol (2 mL), (4-(4-methyl-1H-imidazol-1-yl)phenyl)methanamine dihydrochloride (0.10 g) obtained in Reference Example 285, acetic acid (0.024 g) and triethylamine (0.10 g) were added, and the mixture was stirred under an argon atmosphere at room temperature for 30 min. Sodium triacetoxyhydroborate (0.85 g) was added to the reaction mixture, and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and the obtained solid was washed with ethyl acetate to give the title compound (0.060 g)

MS: [M+H]+ 483.1

$^1$H NMR (300 MHz, DMSO-d$_6$) δ2.16 (3H, d, J=0.6 Hz), 4.53 (2H, s), 4.76 (2H, s), 7.39-7.47 (4H, m), 7.56-7.75 (4H, m), 7.92 (1H, dd, J=10.6, 1.7 Hz), 8.11 (1H, d, J=1.3 Hz), 8.23 (1H, d, J=5.1 Hz).

Example 419

4-(2-fluoro-4-(trifluoromethyl)phenoxy)-2-(4-(1-methyl-1H-imidazol-4-yl)benzyl)-1,2-dihydro-3H-pyrrolo[3,4-c]pyridin-3-one

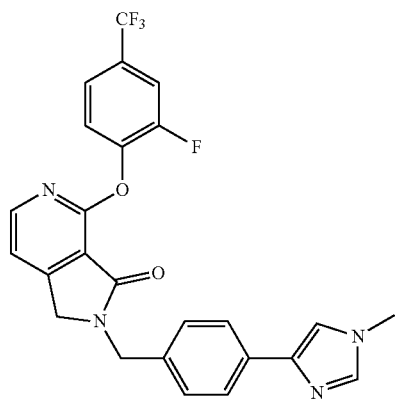 [SMILES: Cn1cnc(-c2ccc(CN3Cc4ccnc(Oc5ccc(C(F)(F)F)cc5F)c4C3=O)cc2)c1]

Ethyl 2-(2-fluoro-4-(trifluoromethyl)phenoxy)-4-formylnicotinate (0.11 g) obtained in Reference Example 282 was dissolved in methanol (2 mL), (4-(1-methyl-1H-imidazol-4-yl)phenyl)methanamine dihydrochloride (0.12 g) obtained in Reference Example 286, acetic acid (0.018 g) and triethylamine (0.091 g) were added, and the mixture was stirred under an argon atmosphere at room temperature for 30 min. Sodium triacetoxyhydroborate (0.64 g) was added to the reaction mixture, and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and the obtained solid was washed with ethyl acetate to give the title compound (0.013 g).

MS: [M+H]+ 483.1

¹H NMR (300 MHz, DMSO-d₆) δ3.68 (3H, s), 4.51 (2H, s), 4.71 (2H, s), 7.30 (2H, d, J=8.3 Hz), 7.41 (1H, d, J=5.1 Hz), 7.57-7.78 (6H, m), 7.88-7.98 (1H, m), 8.22 (1H, d, J=5.3 Hz).

Example 420

4-(2-fluoro-4-methylphenoxy)-2-(4-(1-methyl-1H-pyrazol-3-yl)benzyl)-1,2-dihydro-3H-pyrrolo[3,4-c]pyridin-3-one

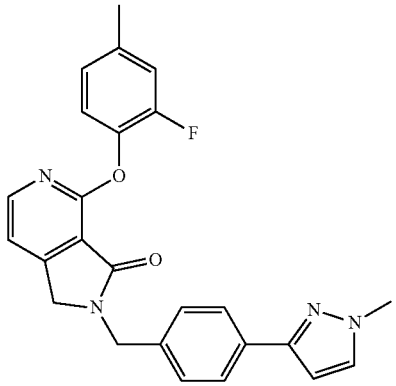 [SMILES: Cc1ccc(Oc2nccc3c2C(=O)N(Cc2ccc(-c4ccn(C)n4)cc2)C3)c(F)c1]

Ethyl 2-(2-fluoro-4-methylphenoxy)-4-formylnicotinate (0.12 g) obtained in Reference Example 288 was dissolved in THF (2 mL), (4-(1-methyl-1H-pyrazol-3-yl)phenyl)methanamine (0.075 g) and anhydrous magnesium sulfate (0.048 g) were added, and the mixture was stirred at room temperature for 30 min. The solvent was evaporated, acetic acid (2 mL) and sodium triacetoxyhydroborate (0.17 g) were added to the residue, and the mixture was stirred at room temperature overnight. The reaction mixture was concentrated, neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and the obtained crystals were recrystallized from ethyl acetate-methanol. The obtained crystals were collected by filtration, and dried to give the title compound (0.065 g).

MS: [M+H]⁺ 429.1

¹H NMR (300 MHz, DMSO-d₆) δ2.35 (3H, s), 3.87 (3H, s), 4.48 (2H, s), 4.72 (2H, s), 6.66 (1H, d, J=2.3 Hz), 7.07 (1H, d, J=9.3 Hz), 7.15-7.28 (2H, m), 7.29-7.38 (3H, m), 7.72 (1H, d, J=2.1 Hz), 7.77 (2H, d, J=8.3 Hz), 8.18 (1H, d, J=5.1 Hz).

Example 421

4-(2-fluoro-6-methyl-4-(trifluoromethyl)phenoxy)-2-(4-(1-methyl-1H-pyrazol-3-yl)benzyl)-1,2-dihydro-3H-pyrrolo[3,4-c]pyridin-3-one

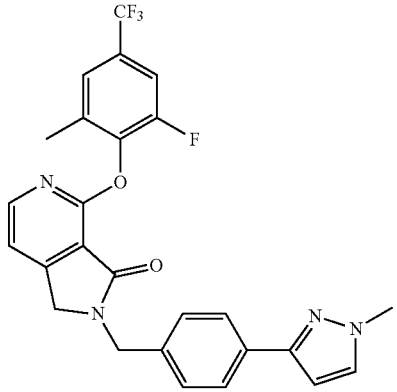 [SMILES: Cc1cc(C(F)(F)F)cc(F)c1Oc1nccc2c1C(=O)N(Cc1ccc(-c3ccn(C)n3)cc1)C2]

Ethyl 2-(2-fluoro-6-methyl-4-(trifluoromethyl)phenoxy)-4-formylnicotinate (0.037 g) obtained in Reference Example 294 was dissolved in THF (2 mL), (4-(1-methyl-1H-pyrazol-3-yl)phenyl)methanamine (0.021 g) and anhydrous magnesium sulfate (0.012 g) were added, and the mixture was stirred at room temperature for 30 min. The solvent was evaporated, acetic acid (2 mL) and sodium triacetoxyhydroborate (0.042 g) were added to the residue, and the mixture was stirred at room temperature overnight. The reaction mixture was concentrated, neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and the obtained crystals were recrystallized from ethyl acetate-methanol. The obtained crystals were collected by filtration, and dried to give the title compound (0.014 g).

MS: [M+H]⁺ 497.1

¹H NMR (300 MHz, DMSO-d₆) δ2.24 (3H, s), 3.87 (3H, s), 4.51 (2H, s), 4.74 (2H, s), 6.67 (1H, d, J=2.3 Hz), 7.35 (2H, d, J=8.3 Hz), 7.40 (1H, d, J=5.3 Hz), 7.65 (1H, s), 7.68-7.75 (2H, m), 7.75-7.81 (2H, m), 8.19 (1H, d, J=5.1 Hz).

Example 422

4-((4-(2-fluoro-4-(trifluoromethyl)phenoxy)-3-oxo-1,3-dihydro-2H-pyrrolo[3,4-c]pyridin-2-yl)methyl)benzamide

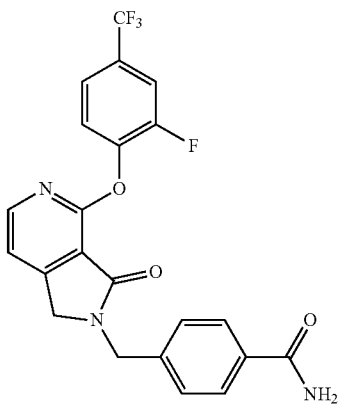 [SMILES: NC(=O)c1ccc(CN2Cc3ccnc(Oc4ccc(C(F)(F)F)cc4F)c3C2=O)cc1]

A solution of methyl 4-((4-(2-fluoro-4-(trifluoromethyl)phenoxy)-3-oxo-1H-pyrrolo[3,4-c]pyridin-2(3H)-yl)methyl)benzoate (0.34 g) obtained in Reference Example 295 and 1N aqueous sodium hydroxide solution (1.11 mL) in THF (5 mL)-methanol (5 mL) was stirred at room temperature for 1 hr, sodium triacetoxyhydroborate (2.09 g) was added, and the mixture was stirred at room temperature for 5 hr. After evaporation of the solvent, the residue was neutralized with 1N hydrochloric acid, and extracted twice with ethyl acetate. The combined organic layer was washed with saturated brine, dried over anhydrous magnesium sulfate and concentrated. To a solution of the obtained residue (0.28 g) in THF (2 mL)-methanol (2 mL) were added ammonium chloride (0.14 g), triethylamine (0.71 g) and 4-(4,6-dimethoxy[1,3,5]triazin-2-yl)-4-methylmorpholinium chloride hydrate (0.35 g), and the mixture was stirred at room temperature for 2 hr. After evaporation of the solvent, the residue was diluted with ethyl acetate and water. The organic layer was washed with water and saturated brine, dried over anhydrous magnesium sulfate and concentrated. The residue was purified by silica gel column chromatography (hexane-ethyl acetate), and the obtained crystals were recrystallized from ethyl acetate-methanol to give the title compound (0.056 g).

MS: [M+H]$^+$ 446.1

$^1$H NMR (300 MHz, DMSO-d$_6$) δ 4.52 (2H, s), 4.78 (2H, s), 7.33 (1H, brs), 7.37-7.44 (3H, m), 7.59-7.73 (2H, m), 7.87 (2H, d, J=8.3 Hz), 7.90-7.99 (2H, m), 8.23 (1H, d, J=5.1 Hz).

Example 423

2-(4-chlorobenzyl)-4-(((2R,3R)-3-hydroxybutan-2-yl)oxy)-1,2-dihydro-3H-pyrrolo[3,4-c]pyridin-3-one

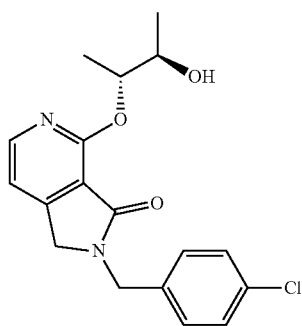 [SMILES: C[C@@H](O)[C@@H](C)Oc1nccc2c1C(=O)N(Cc1ccc(Cl)cc1)C2]

A solution of ethyl 4-formyl-2-(((2R,3R)-3-hydroxybutan-2-yl)oxy)nicotinate (0.16 g) obtained in Reference Example 297 and (4-chlorophenyl)methanamine (0.11 g) in THF (0.5 mL) was stirred at room temperature for 30 min. Acetic acid (1.5 mL) and sodium triacetoxyhydroborate (0.25 g) were added to the reaction mixture, and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate) to give the title compound (0.046 g).

MS: [M+H]$^+$ 345.0

$^1$H NMR (300 MHz, DMSO-d$_6$) δ1.12 (3H, d, J=6.4 Hz), 1.23 (3H, d, J=6.4 Hz), 3.85 (1H, quin, J=6.0 Hz), 4.36 (2H, s), 4.55-4.84 (3H, m), 5.20-5.32 (1H, m), 7.15 (1H, d, J=5.1 Hz), 7.26-7.34 (2H, m), 7.36-7.45 (2H, m), 8.26 (1H, d, J=5.1 Hz).

Example 424

2-(2,4-difluorobenzyl)-4-(((2R,3R)-3-hydroxybutan-2-yl)oxy)-1,2-dihydro-3H-pyrrolo[3,4-c]pyridin-3-one

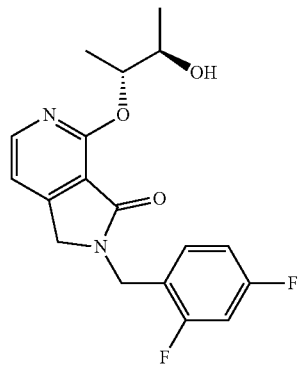 [SMILES: C[C@@H](O)[C@@H](C)Oc1nccc2c1C(=O)N(Cc1ccc(F)cc1F)C2]

A solution of ethyl 4-formyl-2-(((2R,3R)-3-hydroxybutan-2-yl)oxy)nicotinate (0.16 g) obtained in Reference Example 297 and (2,4-difluorophenyl)methanamine (0.12 g) in THF (0.5 mL) was stirred at room temperature for 30 min. To the reaction mixture were added acetic acid (1.5 mL) and sodium triacetoxyhydroborate (0.25 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate) to give the title compound (0.087 g).

MS: [M+H]$^+$ 349.1

$^1$H NMR (300 MHz, DMSO-d$_6$) δ1.11 (3H, d, J=6.4 Hz), 1.22 (3H, d, J=6.2 Hz), 3.77-3.89 (1H, m), 4.38 (2H, s), 4.67 (2H, s), 4.71 (1H, d, J=4.7 Hz), 5.20-5.31 (1H, m), 7.02-7.12 (1H, m), 7.15 (1H, d, J=5.1 Hz), 7.21-7.31 (1H, m), 7.39 (1H, td, J=8.6, 6.7 Hz), 8.26 (1H, d, J=5.3 Hz).

Example 425

4-(((2R,3R)-3-hydroxybutan-2-yl)oxy)-2-(2,4,6-trifluorobenzyl)-1,2-dihydro-3H-pyrrolo[3,4-c]pyridin-3-one

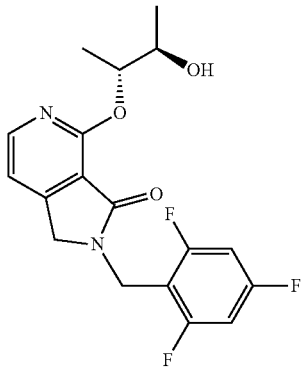 [SMILES: C[C@@H](O)[C@@H](C)Oc1nccc2c1C(=O)N(Cc1c(F)cc(F)cc1F)C2]

A solution of ethyl 4-formyl-2-(((2R,3R)-3-hydroxybutan-2-yl)oxy)nicotinate (0.16 g) obtained in Reference Example 297, (2,4,6-trifluorophenyl)methanamine (0.13 g) and magnesium sulfate (0.072 g) in THF (0.5 mL) was stirred at room temperature for 30 min. To the reaction mixture were added acetic acid (1.5 mL) and sodium triacetoxyhydroborate (0.25 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate) to give the title compound (0.10 g).

MS: [M+H]$^+$ 367.0

$^1$H NMR (300 MHz, DMSO-d) δ1.11 (3H, d, J=6.2 Hz), 1.21 (3H, d, J=6.2 Hz), 3.78-3.89 (1H, m), 4.36 (2H, s), 4.61-4.75 (3H, m), 5.18-5.30 (1H, m), 7.14 (1H, d, J=5.3 Hz), 7.18-7.28 (2H, m), 8.24 (1H, d, J=5.1 Hz).

Example 426

4-(((2R,3R)-3-hydroxybutan-2-yl)oxy)-2-(4-(1-methyl-1H-pyrazol-3-yl)benzyl)-1,2-dihydro-3H-pyrrolo[3,4-c]pyridin-3-one

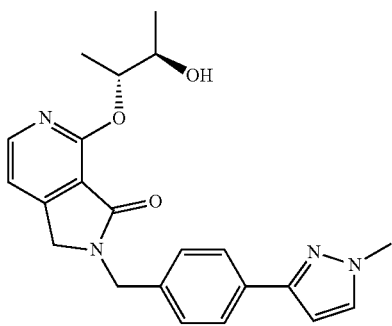 [SMILES: C[C@@H](O)[C@@H](C)Oc1nccc2c1C(=O)N(Cc1ccc(-c3ccn(C)n3)cc1)C2]

A solution of ethyl 4-formyl-2-(((2R,3R)-3-hydroxybutan-2-yl)oxy)nicotinate (0.16 g) obtained in Reference Example 297, (4-(1-methyl-1H-pyrazol-3-yl)phenyl)methanamine (0.124 g) and magnesium sulfate (0.072 g) in THF (0.5 mL) was stirred at room temperature for 30 min. To the reaction mixture were added acetic acid (1.5 mL) and sodium triacetoxyhydroborate (0.19 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate) to give the title compound (0.049 g).

MS: [M+H]$^+$ 393.2

$^1$H NMR (300 MHz, DMSO-d$_6$) δ1.13 (3H, d, J=6.4 Hz), 1.24 (3H, d, J=6.4 Hz), 3.80-3.91 (4H, m), 4.36 (2H, s), 4.65 (2H, d, J=2.6 Hz), 4.72 (1H, d, J=4.5 Hz), 5.26 (1H, quin, J=6.0 Hz), 6.65 (1H, d, J=2.3 Hz), 7.15 (1H, d, J=5.1 Hz), 7.29 (2H, d, J=8.3 Hz), 7.69-7.79 (3H, m), 8.26 (1H, d, J=5.1 Hz).

Example 427

4-(2-fluoro-4-methylphenoxy)-2-(4-(4-methyl-1H-imidazol-1-yl)benzyl)-1,2-dihydro-3H-pyrrolo[3,4-c]pyridin-3-one

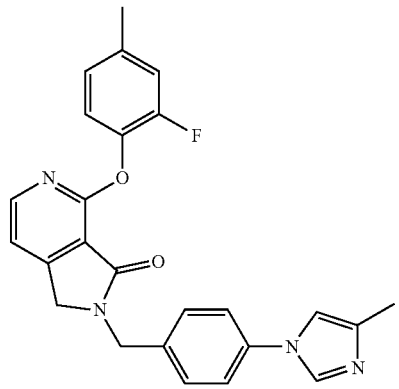 [SMILES: Cc1ccc(Oc2nccc3c2C(=O)N(Cc2ccc(-n4cnc(C)c4)cc2)C3)c(F)c1]

Ethyl 2-(2-fluoro-4-methylphenoxy)-4-formylnicotinate (0.15 g) obtained in Reference Example 288 was dissolved in methanol (5 mL), (4-(4-methyl-1H-imidazol-1-yl)phenyl)methanamine dihydrochloride (0.13 g) obtained in Reference Example 285, acetic acid (0.029 g) and triethylamine (0.13 g) were added, and the mixture was stirred at room temperature for 30 min. To the reaction mixture was added sodium triacetoxyhydroborate (1.06 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and the obtained solid was washed with ethyl acetate to give the title compound (0.087 g).

MS: [M+H]$^+$ 429.1

$^1$H NMR (300 MHz, DMSO-d$_6$) δ2.16 (3H, s), 2.35 (3H, s), 4.50 (2H, s), 4.74 (2H, s), 7.07 (1H, d, J=8.3 Hz), 7.14-7.26 (2H, m), 7.34 (1H, d, J=5.1 Hz), 7.38-7.47 (3H, m), 7.56-7.63 (2H, m), 8.10 (1H, d, J=1.3 Hz), 8.19 (1H, d, J=5.1 Hz).

Example 428

4-(2,6-difluoro-4-methylphenoxy)-2-(4-(4-methyl-1H-imidazol-1-yl)benzyl)-1,2-dihydro-3H-pyrrolo[3,4-c]pyridin-3-one

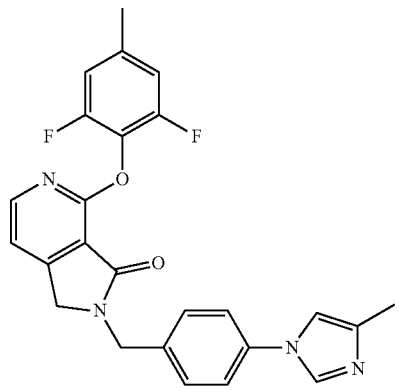 [SMILES: Cc1cc(F)c(Oc2nccc3c2C(=O)N(Cc2ccc(-n4cnc(C)c4)cc2)C3)c(F)c1]

Ethyl 2-(2,6-difluoro-4-methylphenoxy)-4-formylnicotinate (0.090 g) obtained in Reference Example 299 was dissolved in methanol (3 mL), (4-(4-methyl-1H-imidazol-1-yl)phenyl)methanamine dihydrochloride (0.080 g) obtained in Reference Example 285, acetic acid (0.017 g) and triethylamine (0.071 g) were added, and the mixture was stirred at room temperature for 30 min. To the reaction mixture was added sodium triacetoxyhydroborate (0.59 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and the obtained solid was washed with ethyl acetate to give the title compound (0.052 g).

MS: [M+H]$^+$ 447.0

$^1$H NMR (300 MHz, DMSO-d$_6$) δ2.16 (3H, d, J=0.8 Hz), 2.37 (3H, s), 4.52 (2H, s), 4.75 (2H, s), 7.08-7.17 (2H, m), 7.37-7.49 (4H, m), 7.55-7.63 (2H, m), 8.10 (1H, d, J=1.5 Hz), 8.21 (1H, d, J=5.1 Hz).

Example 429

4-(4-ethyl-2,6-difluorophenoxy)-2-(4-(4-methyl-1H-imidazol-1-yl)benzyl)-1,2-dihydro-3H-pyrrolo[3,4-c]pyridin-3-one

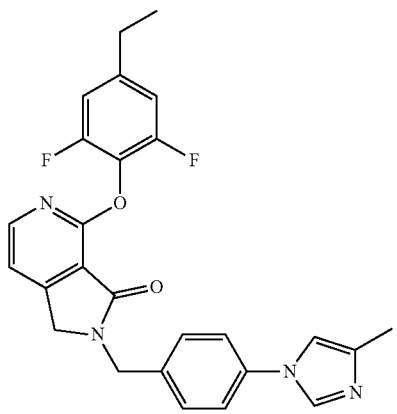 [SMILES: CCc1cc(F)c(Oc2nccc3c2C(=O)N(Cc2ccc(-n4cnc(C)c4)cc2)C3)c(F)c1]

Ethyl 2-(4-ethyl-2,6-difluorophenoxy)-4-formylnicotinate (0.15 g) obtained in Reference Example 301 was dissolved in methanol (3 mL), (4-(4-methyl-1H-imidazol-1-yl)phenyl)methanamine dihydrochloride (0.13 g) obtained in Reference Example 285, acetic acid (0.027 g) and triethylamine (0.12 g) were added, and the mixture was stirred at room temperature for 30 min. To the reaction mixture was added sodium triacetoxyhydroborate (0.97 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and the obtained solid was washed with ethyl acetate to give the title compound (0.063 g).

MS: [M+H]$^+$ 461.1

$^1$H NMR (300 MHz, DMSO-d$_6$) δ1.22 (3H, t, J=7.6 Hz), 2.16 (3H, d, J=0.6 Hz), 2.67 (2H, q, J=7.7 Hz), 4.52 (2H, s), 4.75 (2H, s), 7.10-7.22 (2H, m), 7.37-7.49 (4H, m), 7.55-7.63 (2H, m), 8.10 (1H, d, J=1.3 Hz), 8.22 (1H, d, J=5.3 Hz).

Example 430

4-(4-ethyl-2,6-difluorophenoxy)-2-(4-(1-methyl-1H-pyrazol-3-yl)benzyl)-1,2-dihydro-3H-pyrrolo[3,4-c]pyridin-3-one

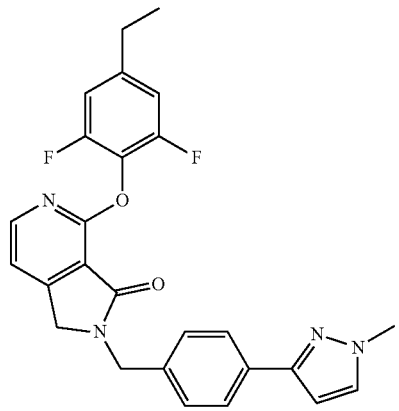 [SMILES: CCc1cc(F)c(Oc2nccc3c2C(=O)N(Cc2ccc(-c4ccn(C)n4)cc2)C3)c(F)c1]

Ethyl 2-(4-ethyl-2,6-difluorophenoxy)-4-formylnicotinate (0.14 g) obtained in Reference Example 301 was dissolved in methanol (3 mL), (4-(1-methyl-1H-pyrazol-3-yl)phenyl)methanamine (0.086 g) and acetic acid (0.025 g) were added, and the mixture was stirred at room temperature for 30 min. To the reaction mixture was added sodium triacetoxyhydroborate (0.89 g), and the mixture was stirred at room temperature overnight. The reaction mixture was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate to give the title compound (0.062 g).

MS: [M+H]$^+$ 461.1

$^1$H NMR (300 MHz, DMSO-d$_6$) δ1.22 (3H, t, J=7.6 Hz), 2.67 (2H, q, J=7.6 Hz), 3.87 (3H, s), 4.50 (2H, s), 4.73 (2H, s), 6.66 (1H, d, J=2.3 Hz), 7.12-7.22 (2H, m), 7.31-7.37 (2H, m), 7.40 (1H, d, J=5.1 Hz), 7.72 (1H, d, J=2.3 Hz), 7.74-7.81 (2H, m), 8.21 (1H, d, J=5.3 Hz).

Example 431

4-((4-(2-fluoro-4-(trifluoromethyl)phenoxy)-3-oxo-1,3-dihydro-2H-pyrrolo[3,4-c]pyridin-2-yl)methyl)-N-methylbenzamide

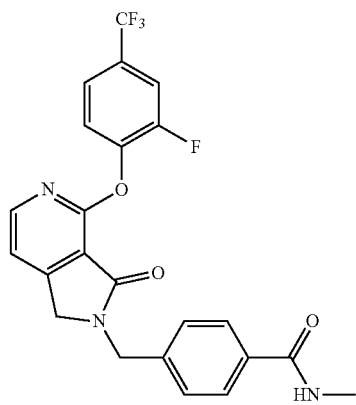

Ethyl 2-(2-fluoro-4-(trifluoromethyl)phenoxy)-4-formylnicotinate (0.18 g) obtained in Reference Example 282 was dissolved in methanol (5 mL), 4-(aminomethyl)-N-methylbenzamide hydrochloride (0.10 g), acetic acid (0.0060 g) and triethylamine (0.056 g) were added, and the mixture was stirred at room temperature for 1 hr. To the reaction mixture was added sodium triacetoxyhydroborate (0.53 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from hexane-ethyl acetate to give the title compound (0.031 g).

MS: [M+H]$^+$ 460.1

$^1$H NMR (300 MHz, DMSO-d$_6$) δ2.78 (3H, d, J=4.5 Hz), 4.52 (2H, s), 4.77 (2H, s), 7.35-7.45 (3H, m), 7.59-7.73 (2H, m), 7.83 (2H, d, J=8.3 Hz), 7.92 (1H, dd, J=10.6, 1.5 Hz), 8.23 (1H, d, J=5.1 Hz), 8.40 (1H, q, J=4.5 Hz).

Example 432

N-ethyl-4-((4-(2-fluoro-4-(trifluoromethyl)phenoxy)-3-oxo-1,3-dihydro-2H-pyrrolo[3,4-c]pyridin-2-yl)methyl)benzamide

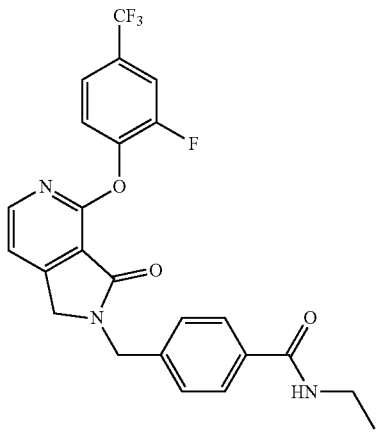 [SMILES: CCNC(=O)c1ccc(CN2Cc3ccnc(Oc4ccc(C(F)(F)F)cc4F)c3C2=O)cc1]

Ethyl 2-(2-fluoro-4-(trifluoromethyl)phenoxy)-4-formylnicotinate (0.18 g) obtained in Reference Example 282 was dissolved in methanol (5 mL), 4-(aminomethyl)-N-ethylbenzamide hydrochloride (0.11 g), acetic acid (0.0060 g) and triethylamine (0.056 g) were added, and the mixture was stirred at room temperature for 1 hr. To the reaction mixture was added sodium triacetoxyhydroborate (0.53 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from hexane-ethyl acetate to give the title compound (0.029 g).

MS: [M+H]$^+$ 474.2

$^1$H NMR (300 MHz, DMSO-d$_6$) δ1.11 (3H, t, J=7.2 Hz), 3.23-3.30 (2H, m), 4.51 (2H, s), 4.77 (2H, s), 7.34-7.45 (3H, m), 7.59-7.74 (2H, m), 7.84 (2H, d, J=8.1 Hz), 7.92 (1H, dd, J=10.9, 1.6 Hz), 8.23 (1H, d, J=5.1 Hz), 8.44 (1H, t, J=5.4 Hz).

Example 433

4-((4-(2-fluoro-4-methylphenoxy)-3-oxo-1,3-dihydro-2H-pyrrolo[3,4-c]pyridin-2-yl)methyl)-N-methylbenzamide

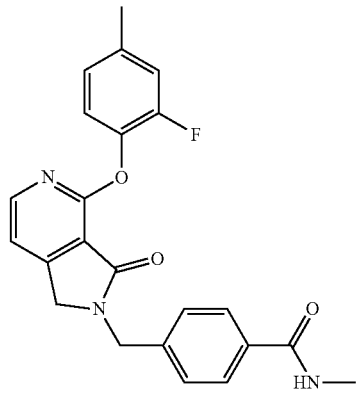 [SMILES: CNC(=O)c1ccc(CN2Cc3ccnc(Oc4ccc(C)cc4F)c3C2=O)cc1]

Ethyl 2-(2-fluoro-4-methylphenoxy)-4-formylnicotinate (0.15 g) obtained in Reference Example 288 was dissolved in methanol (5 mL), 4-(aminomethyl)-N-methylbenzamide hydrochloride (0.10 g), acetic acid (0.0060 g) and triethylamine (0.056 g) were added, and the mixture was stirred at room temperature for 1 hr. To the reaction mixture was added sodium triacetoxyhydroborate (0.53 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate to give the title compound (0.037 g).

MS: [M+H]$^+$ 406.1

$^1$H NMR (300 MHz, DMSO-d$_6$) δ 2.35 (3H, s), 2.78 (3H, d, J=4.5 Hz), 4.48 (2H, s), 4.76 (2H, s), 7.07 (1H, dd, J=7.9, 1.9 Hz), 7.15-7.27 (2H, m), 7.34 (1H, d, J=5.3 Hz), 7.39 (2H, d, J=8.3 Hz), 7.83 (2H, d, J=8.3 Hz), 8.19 (1H, d, J=4.9 Hz), 8.41 (1H, q, J=4.0 Hz).

Example 434

N-ethyl-4-((4-(2-fluoro-4-methylphenoxy)-3-oxo-1,3-dihydro-2H-pyrrolo[3,4-c]pyridin-2-yl)methyl)benzamide

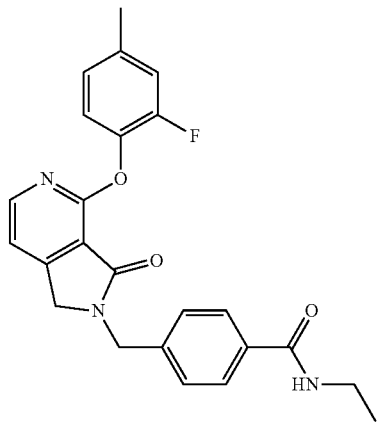 [SMILES: CCNC(=O)c1ccc(CN2Cc3ccnc(Oc4ccc(C)cc4F)c3C2=O)cc1]

Ethyl 2-(2-fluoro-4-methylphenoxy)-4-formylnicotinate (0.15 g) obtained in Reference Example 288 was dissolved in methanol (5 mL), 4-(aminomethyl)-N-ethylbenzamide hydrochloride (0.11 g), acetic acid (0.0060 g) and triethylamine (0.056 g) were added, and the mixture was stirred at room temperature for 1 hr. To the reaction mixture was added sodium triacetoxyhydroborate (0.53 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from hexane-ethyl acetate to give the title compound (0.036 g).

MS: [M+H]$^+$ 420.1

$^1$H NMR (300 MHz, DMSO-d$_6$) δ1.11 (3H, t, J=7.2 Hz), 2.35 (3H, s), 3.22-3.30 (2H, m), 4.48 (2H, s), 4.76 (2H, s), 7.07 (1H, d, J=8.7 Hz), 7.16-7.27 (2H, m), 7.34 (1H, d, J=4.9 Hz), 7.39 (2H, d, J=8.3 Hz), 7.83 (2H, d, J=8.3 Hz), 8.19 (1H, d, J=4.9 Hz), 8.44 (1H, t, J=5.7 Hz).

Example 435

2-fluoro-4-((4-(2-fluoro-4-(trifluoromethyl)phenoxy)-3-oxo-1,3-dihydro-2H-pyrrolo[3,4-c]pyridin-2-yl)methyl)-N-methylbenzamide

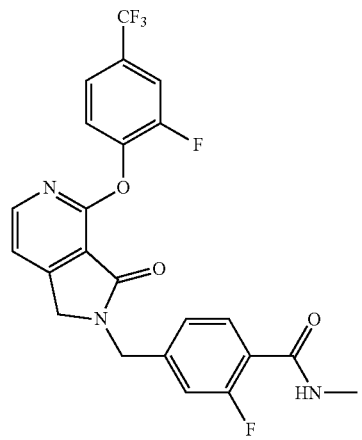 [SMILES: CNC(=O)c1ccc(CN2Cc3ccnc(Oc4ccc(C(F)(F)F)cc4F)c3C2=O)cc1F]

Ethyl 2-(2-fluoro-4-(trifluoromethyl)phenoxy)-4-formylnicotinate (0.14 g) obtained in Reference Example 282 was dissolved in methanol (5 mL), 4-(aminomethyl)-2-fluoro-N-methylbenzamide hydrochloride (0.096 g) obtained in Reference Example 303, acetic acid (0.024 g) and triethylamine (0.061 g) were added, and the mixture was stirred at room temperature for 1 hr. To the reaction mixture was added sodium triacetoxyhydroborate (0.42 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from hexane-ethyl acetate to give the title compound (0.052 g).

MS: [M+H]$^+$ 478.0

$^1$H NMR (300 MHz, DMSO-d$_6$) δ2.77 (3H, d, J=4.5 Hz), 4.55 (2H, s), 4.77 (2H, s), 7.16-7.30 (2H, m), 7.43 (1H, d, J=5.1 Hz), 7.57-7.74 (3H, m), 7.92 (1H, dd, J=10.6, 1.7 Hz), 8.12-8.22 (1H, m), 8.24 (1H, d, J=5.1 Hz).

Example 436

N-ethyl-2-fluoro-4-((4-(2-fluoro-4-(trifluoromethyl)phenoxy)-3-oxo-1,3-dihydro-2H-pyrrolo[3,4-c]pyridin-2-yl)methyl)benzamide

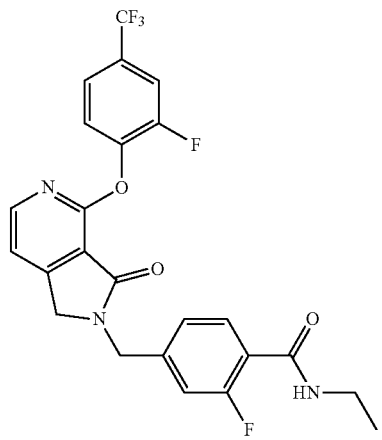 [SMILES: CCNC(=O)c1ccc(CN2Cc3ccnc(Oc4ccc(C(F)(F)F)cc4F)c3C2=O)cc1F]

Ethyl 2-(2-fluoro-4-(trifluoromethyl)phenoxy)-4-formylnicotinate (0.14 g) obtained in Reference Example 282 was dissolved in methanol (5 mL), 4-(aminomethyl)-N-ethyl-2-fluorobenzamide hydrochloride (0.10 g) obtained in Reference Example 305, acetic acid (0.024 g) and triethylamine (0.061 g) were added, and the mixture was stirred at room temperature for 1 hr. To the reaction mixture was added sodium triacetoxyhydroborate (0.42 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from hexane-ethyl acetate to give the title compound (0.058 g).

MS: [M+H]$^+$ 492.2

$^1$H NMR (300 MHz, DMSO-d$_6$) δ1.10 (3H, t, J=7.2 Hz), 3.20-3.29 (2H, m), 4.55 (2H, s), 4.77 (2H, s), 7.17-7.28 (2H, m), 7.43 (1H, d, J=5.3 Hz), 7.54-7.74 (3H, m), 7.92 (1H, dd, J=10.6, 1.9 Hz), 8.16-8.31 (2H, m).

Example 437

2-fluoro-4-((4-(2-fluoro-4-methylphenoxy)-3-oxo-1,3-dihydro-2H-pyrrolo[3,4-c]pyridin-2-yl)methyl)-N-methylbenzamide

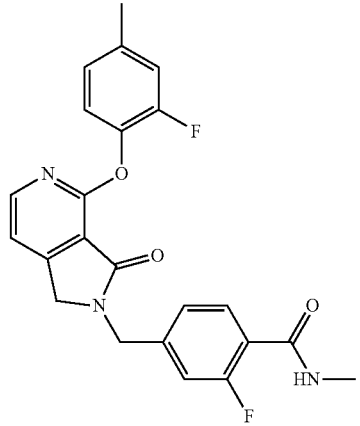 [SMILES: CNC(=O)c1ccc(CN2Cc3ccnc(Oc4ccc(C)cc4F)c3C2=O)cc1F]

Ethyl 2-(2-fluoro-4-methylphenoxy)-4-formylnicotinate (0.12 g) obtained in Reference Example 288 was dissolved in methanol (5 mL), 4-(aminomethyl)-2-fluoro-N-methylbenzamide hydrochloride (0.096 g) obtained in Reference Example 303, acetic acid (0.024 g) and triethylamine (0.061 g) were added, and the mixture was stirred at room temperature for 1 hr. To the reaction mixture was added sodium triacetoxyhydroborate (0.42 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate to give the title compound (0.059 g).

MS: [M+H]+ 424.1

$^1$H NMR (300 MHz, DMSO-d$_6$) δ2.35 (3H, s), 2.77 (3H, d, J=4.5 Hz), 4.52 (2H, s), 4.76 (2H, s), 7.07 (1H, d, J=8.5 Hz), 7.15-7.27 (4H, m), 7.35 (1H, d, J=5.1 Hz), 7.62 (1H, t, J=7.9 Hz), 8.13-8.23 (2H, m).

Example 438

2-fluoro-4-((4-(2-fluoro-4-(trifluoromethyl)phenoxy)-3-oxo-1,3-dihydro-2H-pyrrolo[3,4-c]pyridin-2-yl)methyl)benzamide

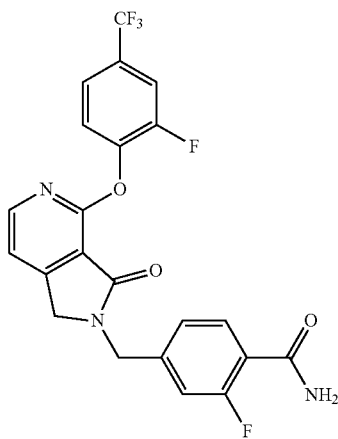 [SMILES: NC(=O)c1ccc(CN2Cc3ccnc(Oc4ccc(C(F)(F)F)cc4F)c3C2=O)cc1F]

Ethyl 2-(2-fluoro-4-(trifluoromethyl)phenoxy)-4-formylnicotinate (0.18 g) obtained in Reference Example 282 was dissolved in methanol (5 mL), 4-(aminomethyl)-2-fluorobenzamide hydrochloride (0.15 g) obtained in Reference Example 307, acetic acid (0.030 g) and triethylamine (0.076 g) were added, and the mixture was stirred at room temperature for 1 hr. To the reaction mixture was added sodium triacetoxyhydroborate (1.06 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from hexane-ethyl acetate to give the title compound (0.065 g).

MS: [M+H]+ 464.1

$^1$H NMR (300 MHz, DMSO-d$_6$) δ4.55 (2H, s), 4.77 (2H, s), 7.17-7.28 (2H, m), 7.43 (1H, d, J=5.3 Hz), 7.56-7.74 (5H, m), 7.92 (1H, dd, J=10.6, 1.7 Hz), 8.24 (1H, d, J=5.1 Hz).

Example 439

4-((7-(2-fluoro-4-(trifluoromethyl)phenoxy)-1-oxo-1,3-dihydro-2H-isoindol-2-yl)methyl)-N-methylbenzamide

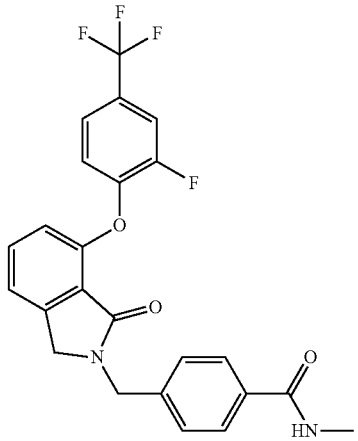 [SMILES: CNC(=O)c1ccc(CN2Cc3cccc(Oc4ccc(C(F)(F)F)cc4F)c3C2=O)cc1]

To a solution of ethyl 2-(bromomethyl)-6-(2-fluoro-4-(trifluoromethyl)phenoxy)benzoate (0.44 g) obtained in Reference Example 328 in ethanol (3.5 mL) were added 4-(aminomethyl)-N-methylbenzamide hydrochloride (0.12 g) and potassium carbonate (0.19 g), and the mixture was stirred at 60° C. for 2 hr. The reaction mixture was diluted with water and ethyl acetate. The organic layer was separated, washed with saturated brine, dried over anhydrous sodium sulfate, and concentrated. The obtained solid was recrystallized from ethanol to give the title compound (0.22 g).

MS: [M+H]+ 459.1

$^1$H NMR (300 MHz, DMSO-d$_6$) δ 2.77 (3H, d, J=4.5 Hz), 4.43 (2H, s), 4.68 (2H, s), 7.04 (1H, t, J=8.4 Hz), 7.15 (1H, d, J=7.9 Hz), 7.32 (2H, d, J=8.3 Hz), 7.46 (1H, d, J=7.6 Hz), 7.51 (1H, d, J=8.7 Hz), 7.61-7.70 (1H, m), 7.80 (2H, d, J=8.3 Hz), 7.88 (1H, dd, J=11.1, 2.1 Hz), 8.39 (1H, q, J=3.9 Hz).

Example 440

2-fluoro-4-((4-(2-fluoro-4-methylphenoxy)-3-oxo-1,3-dihydro-2H-pyrrolo[3,4-c]pyridin-2-yl)methyl)benzamide

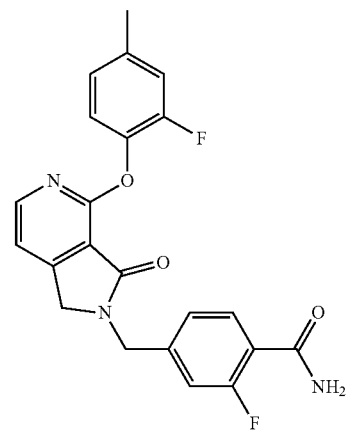 [SMILES: Cc1ccc(Oc2nccc3c2C(=O)N(Cc2ccc(C(N)=O)c(F)c2)C3)c(F)c1]

Ethyl 2-(2-fluoro-4-methylphenoxy)-4-formylnicotinate (0.15 g) obtained in Reference Example 288 was dissolved in methanol (5 mL), 4-(aminomethyl)-2-fluorobenzamide hydrochloride (0.15 g) obtained in Reference Example 307, acetic acid (0.030 g) and triethylamine (0.076 g) were added, and the mixture was stirred at room temperature for 1 hr. To the reaction mixture was added sodium triacetoxyhydroborate (1.06 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from hexane-ethyl acetate to give the title compound (0.065 g).

MS: [M+H]+ 410.1

$^1$H NMR (300 MHz, DMSO-d$_6$) 52.35 (3H, s), 4.52 (2H, s), 4.76 (2H, s), 7.07 (1H, d, J=8.1 Hz), 7.15-7.26 (4H, m), 7.35 (1H, d, J=5.1 Hz), 7.53-7.72 (3H, m), 8.20 (1H, d, J=5.1 Hz).

Example 441

N-ethyl-3-fluoro-4-((4-(2-fluoro-4-methylphenoxy)-3-oxo-1,3-dihydro-2H-pyrrolo[3,4-c]pyridin-2-yl)methyl)benzamide

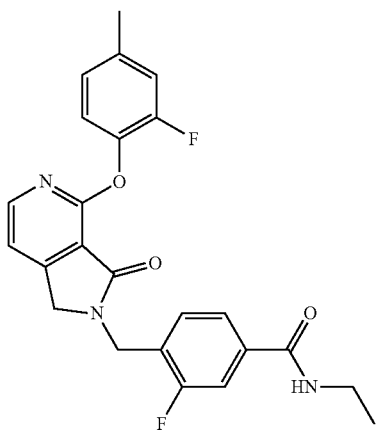 [SMILES: CCNC(=O)c1ccc(CN2Cc3ccnc(Oc4ccc(C)cc4F)c3C2=O)c(F)c1]

Ethyl 2-(2-fluoro-4-methylphenoxy)-4-formylnicotinate (0.15 g) obtained in Reference Example 288 was dissolved in methanol (5 mL), 4-(aminomethyl)-N-ethyl-3-fluorobenzamide hydrochloride (0.13 g) obtained in Reference Example 309, acetic acid (0.030 g) and triethylamine (0.076 g) were added, and the mixture was stirred at room temperature for 1 hr. To the reaction mixture was added sodium triacetoxyhydroborate (1.06 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate-ethanol to give the title compound (0.057 g).

MS: [M+H]+ 438.1

$^1$H NMR (300 MHz, DMSO-d$_6$) δ1.12 (3H, t, J=7.2 Hz), 2.35 (3H, s), 3.22-3.30 (2H, m), 4.52 (2H, s), 4.81 (2H, s), 7.02-7.10 (1H, m), 7.16-7.25 (2H, m), 7.35 (1H, d, J=5.3 Hz), 7.45 (1H, s), 7.64-7.68 (1H, m), 7.70 (1H, s), 8.19 (1H, d, J=5.1 Hz), 8.45-8.60 (1H, m).

Example 442

4-((4-(4-bromo-2-fluorophenoxy)-3-oxo-1,3-dihydro-2H-pyrrolo[3,4-c]pyridin-2-yl)methyl)-2-fluoro-N-methylbenzamide

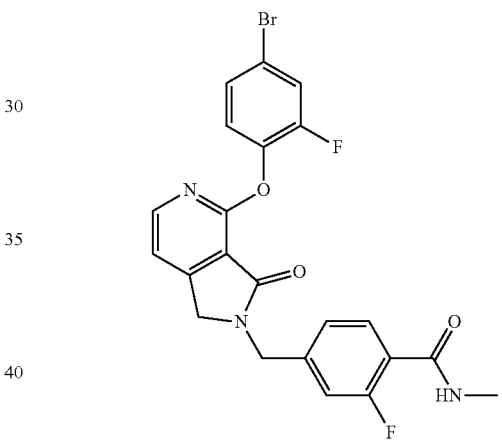

Ethyl 2-(4-bromo-2-fluorophenoxy)-4-formylnicotinate (0.37 g) obtained in Reference Example 311 was dissolved in methanol (5 mL), 4-(aminomethyl)-2-fluoro-N-methylbenzamide hydrochloride (0.24 g) obtained in Reference Example 303, acetic acid (0.060 g) and triethylamine (0.15 g) were added, and the mixture was stirred at room temperature for 1 hr. To the reaction mixture was added sodium triacetoxyhydroborate (1.06 g), and the mixture was stirred at room temperature overnight. After evaporation of the solvent, the residue was neutralized with saturated sodium hydrogen carbonate solution, and diluted with ethyl acetate. The organic layer was separated, washed with saturated brine, dried over anhydrous magnesium sulfate and concentrated. The residue was purified by NH silica gel chromatography (hexane-ethyl acetate), and the obtained solid was washed with ethyl acetate to give the title compound (0.19 g).

MS: [M+H]+ 488.0

$^1$H NMR (300 MHz, DMSO-d$_6$) δ2.77 (3H, d, J=4.5 Hz), 4.53 (2H, s), 4.76 (2H, s), 7.17-7.28 (2H, m), 7.33-7.42 (2H, m), 7.46-7.53 (1H, m), 7.62 (1H, t, J=7.9 Hz), 7.75 (1H, dd, J=10.2, 2.3 Hz), 8.10-8.26 (2H, m).

Example 443

2-(4-(1,3-dimethyl-1H-pyrazol-4-yl)benzyl)-4-(2-fluoro-4-(2-hydroxypropan-2-yl)phenoxy)-1,2-dihydro-3H-pyrrolo[3,4-c]pyridin-3-one

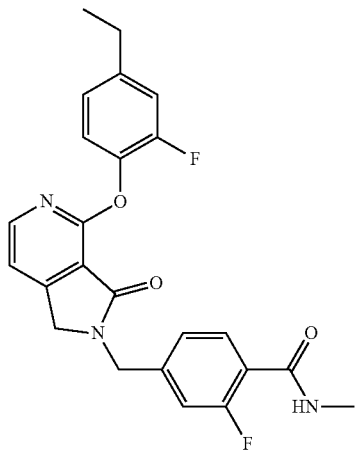 [SMILES: CCc1ccc(Oc2nccc3c2C(=O)N(Cc2ccc(C(=O)NC)c(F)c2)C3)c(F)c1]

A solution of 4-((4-(4-bromo-2-fluorophenoxy)-3-oxo-1,3-dihydro-2H-pyrrolo[3,4-c]pyridin-2-yl)methyl)-2-fluoro-N-methylbenzamide (0.070 g) obtained in Example 442, 1,1'-bis(diphenylphosphino)ferrocene-palladium(II)dichloride dichloromethane complex (0.033 g) and 1 M diethylzinc hexane solution (0.41 mL) in DMF (1 mL) was stirred under an argon atmosphere at 80° C. for 2 hr. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate-ethanol to give the title compound (0.061 g).

MS: [M+H]$^+$ 438.1

$^1$H NMR (300 MHz, DMSO-d$_6$) δ1.22 (3H, t, J=7.6 Hz), 2.66 (2H, q, J=7.6 Hz), 2.77 (3H, d, J=4.7 Hz), 4.52 (2H, s), 4.76 (2H, s), 7.10 (1H, dd, J=8.3, 1.5 Hz), 7.17-7.28 (4H, m), 7.35 (1H, d, J=5.3 Hz), 7.62 (1H, t, J=7.9 Hz), 8.10-8.26 (2H, m).

Example 444

4-((4-(4-ethyl-2-fluorophenoxy)-3-oxo-1,3-dihydro-2H-pyrrolo[3,4-c]pyridin-2-yl)methyl)-N-methylbenzamide

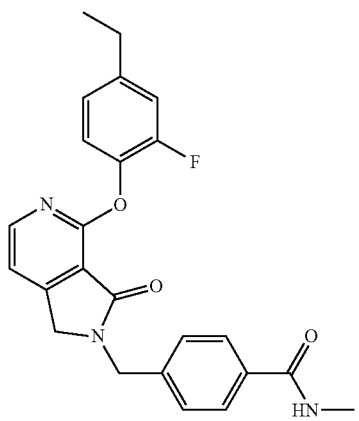 [SMILES: CCc1ccc(Oc2nccc3c2C(=O)N(Cc2ccc(C(=O)NC)cc2)C3)c(F)c1]

Ethyl 2-(4-ethyl-2-fluorophenoxy)-4-formylnicotinate (0.13 g) obtained in Reference Example 313 was dissolved in methanol (3 mL), 4-(aminomethyl)-N-methylbenzamide hydrochloride (0.096 g), acetic acid (0.024 g) and triethylamine (0.061 g) were added, and the mixture was stirred at room temperature for 1 hr. To the reaction mixture was added sodium tetrahydroborate (0.15 g), and the mixture was stirred at room temperature overnight. After evaporation of the solvent, the residue was diluted with water and ethyl acetate. The organic layer was separated, washed with saturated brine, dried over anhydrous magnesium sulfate and concentrated. The obtained solid was recrystallized from ethyl acetate-ethanol to give the title compound (0.058 g).

MS: [M+H]$^+$ 420.1

$^1$H NMR (300 MHz, DMSO-d$_6$) δ1.22 (3H, t, J=7.6 Hz), 2.66 (2H, q, J=7.5 Hz), 2.78 (3H, d, J=4.7 Hz), 4.49 (2H, s), 4.76 (2H, s), 7.10 (1H, dd, J=8.2, 1.4 Hz), 7.19-7.29 (2H, m), 7.34 (1H, d, J=5.1 Hz), 7.39 (2H, d, J=8.3 Hz), 7.83 (2H, d, J=8.3 Hz), 8.20 (1H, d, J=5.3 Hz), 8.35-8.45 (1H, m).

Example 445

4-((4-(4-ethyl-2-fluorophenoxy)-3-oxo-1,3-dihydro-2H-pyrrolo[3,4-c]pyridin-2-yl)methyl)-2-fluorobenzamide

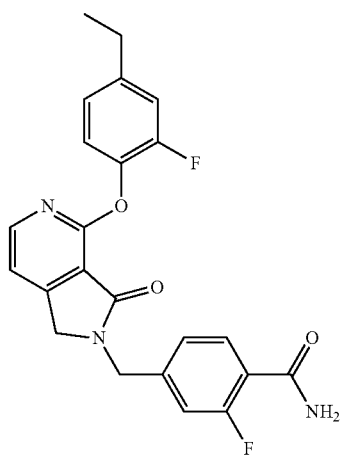 [SMILES: CCc1ccc(Oc2nccc3c2C(=O)N(Cc2ccc(C(N)=O)c(F)c2)C3)c(F)c1]

Ethyl 2-(4-ethyl-2-fluorophenoxy)-4-formylnicotinate (0.13 g) obtained in Reference Example 313 was dissolved in methanol (4 mL), 4-(aminomethyl)-2-fluorobenzamide hydrochloride (0.090 g) obtained in Reference Example 307, acetic acid (0.024 g) and triethylamine (0.061 g) were added, and the mixture was stirred at room temperature for 1 hr. To the reaction mixture was added sodium tetrahydroborate (0.076 g), and the mixture was stirred at room temperature for 3 days. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate-ethanol to give the title compound (0.054 g).

MS: [M+H]$^+$ 424.0

$^1$H NMR (300 MHz, DMSO-d$_6$) δ1.22 (3H, t, J=7.6 Hz), 2.66 (2H, q, J=7.6 Hz), 4.52 (2H, s), 4.76 (2H, s), 7.05-7.15 (1H, m), 7.17-7.29 (4H, m), 7.35 (1H, d, J=5.1 Hz), 7.65 (3H, q, J=8.1 Hz), 8.20 (1H, d, J=5.1 Hz).

Example 446

4-((4-(4-cyclopropyl-2-fluorophenoxy)-3-oxo-1,3-dihydro-2H-pyrrolo[3,4-c]pyridin-2-yl)methyl)-2-fluorobenzamide

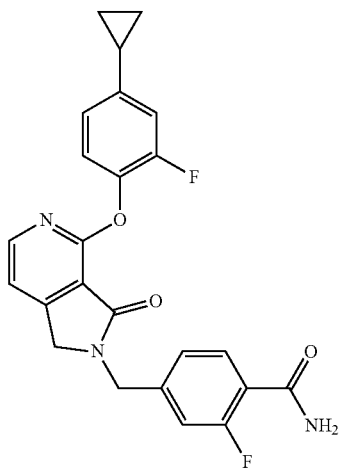 [SMILES: NC(=O)c1ccc(CN2Cc3ccnc(Oc4ccc(C5CC5)cc4F)c3C2=O)cc1F]

Ethyl 2-(4-cyclopropyl-2-fluorophenoxy)-4-formylnicotinate (0.13 g) obtained in Reference Example 317 was dissolved in methanol (3 mL), 4-(aminomethyl)-2-fluorobenzamide hydrochloride (0.090 g) obtained in Reference Example 307, acetic acid (0.024 g) and triethylamine (0.061 g) were added, and the mixture was stirred at room temperature for 1 hr. To the reaction mixture was added sodium tetrahydroborate (0.076 g)), and the mixture was stirred at room temperature 3 days. The reaction mixture was diluted with water and ethyl acetate. The organic layer was separated, washed with saturated brine, dried over anhydrous magnesium sulfate and concentrated. The obtained solid was recrystallized from ethyl acetate-ethanol to give the title compound (0.068 g).

MS: [M+H]$^+$ 436.0

$^1$H NMR (300 MHz, DMSO-d$_6$) δ0.68-0.77 (2H, m), 0.93-1.04 (2H, m), 1.93-2.04 (1H, m), 4.52 (2H, s), 4.76 (2H, s), 7.00 (1H, dd, J=8.1, 1.9 Hz), 7.06 (1H, dd, J=12.1, 2.1 Hz), 7.16-7.26 (3H, m), 7.35 (1H, d, J=5.1 Hz), 7.65 (3H, q, J=7.9 Hz), 8.19 (1H, d, J=5.1 Hz).

Example 447

4-((4-(4-cyclopropyl-2-fluorophenoxy)-3-oxo-1,3-dihydro-2H-pyrrolo[3,4-c]pyridin-2-yl)methyl)-N-methylbenzamide

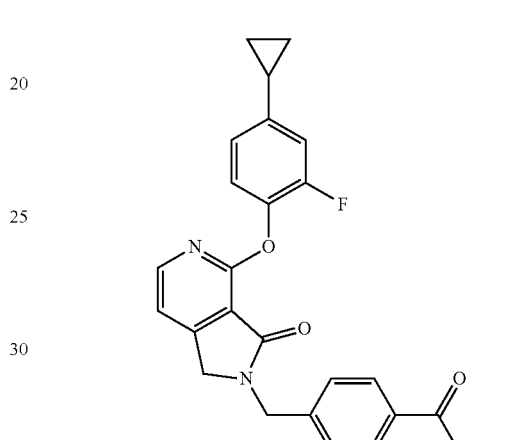

Ethyl 2-(4-cyclopropyl-2-fluorophenoxy)-4-formylnicotinate (0.13 g) obtained in Reference Example 317 was dissolved in methanol (3 mL), 4-(aminomethyl)-N-methylbenzamide hydrochloride (0.088 g), acetic acid (0.024 g) and triethylamine (0.061 g) were added, and the mixture was stirred at room temperature for 1 hr. To the reaction mixture was added sodium tetrahydroborate (0.076 g), and the mixture was stirred at room temperature overnight. The reaction mixture was diluted with water and ethyl acetate. The organic layer was separated, washed with saturated brine, dried over anhydrous magnesium sulfate and concentrated. The obtained solid was recrystallized from ethyl acetate-ethanol to give the title compound (0.071 g).

MS: [M+H]$^+$ 432.0

$^1$H NMR (300 MHz, DMSO-d$_6$) δ0.68-0.78 (2H, m), 0.93-1.03 (2H, m), 1.92-2.03 (1H, m), 2.77 (3H, d, J=4.5 Hz), 4.48 (2H, s), 4.76 (2H, s), 7.00 (1H, dd, J=8.3, 2.1 Hz), 7.06 (1H, dd, J=12.1, 2.1 Hz), 7.21 (1H, t, J=8.3 Hz), 7.34 (1H, d, J=5.1 Hz), 7.38 (2H, d, J=8.1 Hz), 7.82 (2H, d, J=8.3 Hz), 8.19 (1H, d, J=5.3 Hz), 8.40 (1H, q, J=4.7 Hz).

Example 448

4-((4-(4-cyclopropyl-2-fluorophenoxy)-3-oxo-1,3-dihydro-2H-pyrrolo[3,4-c]pyridin-2-yl)methyl)benzamide

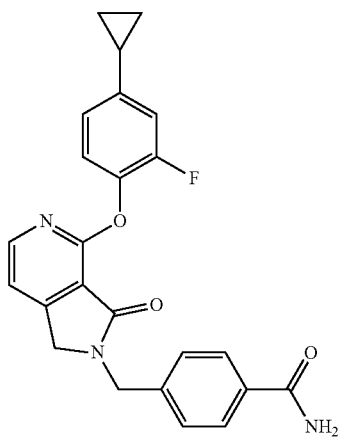 [SMILES: NC(=O)c1ccc(CN2Cc3ccnc(Oc4ccc(C5CC5)cc4F)c3C2=O)cc1]

Ethyl 2-(4-cyclopropyl-2-fluorophenoxy)-4-formylnicotinate (0.13 g) obtained in Reference Example 317 was dissolved in methanol (3 mL), 4-(aminomethyl)benzamide hydrochloride (0.082 g), acetic acid (0.024 g) and triethylamine (0.061 g) were added, and the mixture was stirred at room temperature for 1 hr. To the reaction mixture was added sodium tetrahydroborate (0.076 g), and the mixture was stirred at room temperature 3 days was stirred. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate-ethanol to give the title compound (0.075 g).

MS: [M+H]$^+$ 418.2

$^1$H NMR (300 MHz, DMSO-$d_6$) δ0.66-0.81 (2H, m), 0.92-1.05 (2H, m), 1.90-2.05 (1H, m), 4.48 (2H, s), 4.76 (2H, s), 7.00 (1H, dd, J=8.2, 2.0 Hz), 7.06 (1H, dd, J=12.1, 2.1 Hz), 7.16-7.25 (1H, m), 7.33 (2H, d, J=5.1 Hz), 7.38 (2H, d, J=8.3 Hz), 7.87 (2H, d, J=8.1 Hz), 7.94 (1H, brs), 8.19 (1H, d, J=5.3 Hz).

Example 449

4-((4-(4-ethyl-2-fluorophenoxy)-3-oxo-1,3-dihydro-2H-pyrrolo[3,4-c]pyridin-2-yl)methyl)benzamide

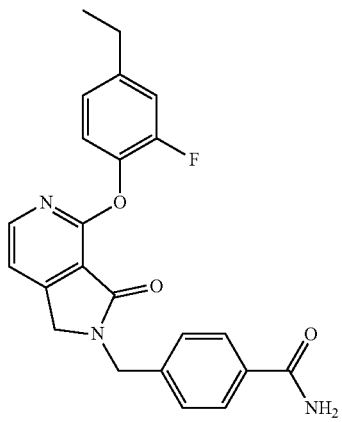 [SMILES: CCc1ccc(Oc2nccc3c2C(=O)N(Cc2ccc(C(N)=O)cc2)C3)c(F)c1]

Ethyl 2-(4-ethyl-2-fluorophenoxy)-4-formylnicotinate (0.13 g) obtained in Reference Example 313 was dissolved in methanol (3 mL), 4-(aminomethyl)benzamide hydrochloride (0.082 g), acetic acid (0.024 g) and triethylamine (0.061 g) were added, and the mixture was stirred at room temperature for 1 hr. To the reaction mixture was added sodium tetrahydroborate (0.076 g), and the mixture was stirred at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate-ethanol to give the title compound (0.068 g).

MS: [M+H]$^+$ 406.2

$^1$H NMR (300 MHz, DMSO-$d_6$) δ1.22 (3H, t, J=7.6 Hz), 2.66 (2H, q, J=7.6 Hz), 4.49 (2H, s), 4.76 (2H, s), 7.11 (1H, d, J=8.3 Hz), 7.19-7.29 (2H, m), 7.34 (2H, d, J=5.1 Hz), 7.38 (2H, d, J=8.1 Hz), 7.87 (2H, d, J=8.1 Hz), 7.95 (1H, brs), 8.20 (1H, d, J=5.1 Hz).

Example 450

4-((4-(2-fluoro-4-propylphenoxy)-3-oxo-1,3-dihydro-2H-pyrrolo[3,4-c]pyridin-2-yl)methyl)benzamide

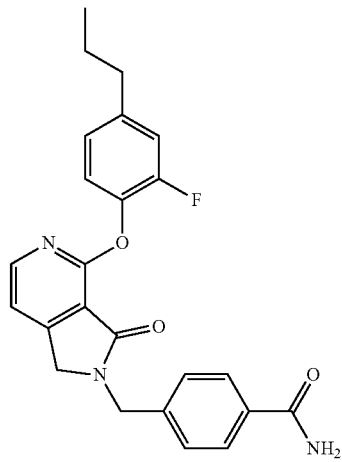 [SMILES: CCCc1ccc(Oc2nccc3c2C(=O)N(Cc2ccc(C(N)=O)cc2)C3)c(F)c1]

Ethyl 2-(2-fluoro-4-propylphenoxy)-4-formylnicotinate (0.13 g) obtained in Reference Example 319 was dissolved in methanol (3 mL), 4-(aminomethyl)benzamide hydrochloride (0.082 g), acetic acid (0.024 g) and triethylamine (0.061 g) were added, and the mixture was stirred at room temperature for 1 hr. To the reaction mixture was added sodium tetrahydroborate (0.15 g), and the mixture was stirred at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate-ethanol to give the title compound (0.079 g).

MS: [M+H]$^+$ 420.2

$^1$H NMR (300 MHz, DMSO-$d_6$) δ0.93 (3H, t, J=7.3 Hz), 1.63 (2H, sxt, J=7.4 Hz), 2.56-2.65 (2H, m), 4.48 (2H, s), 4.76 (2H, s), 7.02-7.14 (1H, m), 7.16-7.28 (2H, m), 7.34

(2H, d, J=5.1 Hz), 7.38 (2H, d, J=8.3 Hz), 7.87 (2H, d, J=8.3 Hz), 7.94 (1H, brs), 8.20 (1H, d, J=5.1 Hz).

Example 451

4-((4-(2-fluoro-4-propylphenoxy)-3-oxo-1,3-dihydro-2H-pyrrolo[3,4-c]pyridin-2-yl)methyl)-N-methylbenzamide

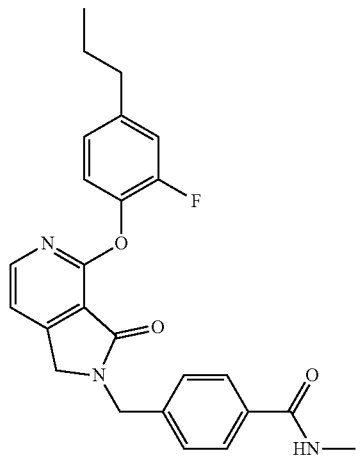 [SMILES: CCCc1ccc(Oc2nccc3c2C(=O)N(Cc2ccc(C(=O)NC)cc2)C3)c(F)c1]

Ethyl 2-(2-fluoro-4-propylphenoxy)-4-formylnicotinate (0.13 g) obtained in Reference Example 319 was dissolved in methanol (3 mL), 4-(aminomethyl)-N-methylbenzamide hydrochloride (0.088 g), acetic acid (0.024 g) and triethylamine (0.061 g) were added, and the mixture was stirred at room temperature for 1 hr. To the reaction mixture was added sodium tetrahydroborate (0.15 g), and the mixture was stirred at room temperature overnight. The reaction mixture was diluted with water and ethyl acetate. The organic layer was separated, washed with saturated brine, dried over anhydrous magnesium sulfate and concentrated. The obtained solid was washed with methanol, and dried to give the title compound (0.079 g).

MS: [M+H]⁺ 434.2

¹H NMR (300 MHz, DMSO-d₆) δ0.93 (3H, t, J=7.3 Hz), 1.63 (2H, sxt, J=7.6 Hz), 2.56-2.64 (2H, m), 2.78 (3H, d, J=4.5 Hz), 4.49 (2H, s), 4.76 (2H, s), 7.08 (1H, d, J=7.9 Hz), 7.17-7.27 (2H, m), 7.34 (1H, d, J=5.3 Hz), 7.39 (2H, d, J=8.3 Hz), 7.83 (2H, d, J=8.1 Hz), 8.20 (1H, d, J=5.1 Hz), 8.35-8.45 (1H, m).

Example 452

2-fluoro-4-((4-(2-fluoro-4-propylphenoxy)-3-oxo-1,3-dihydro-2H-pyrrolo[3,4-c]pyridin-2-yl)methyl)benzamide

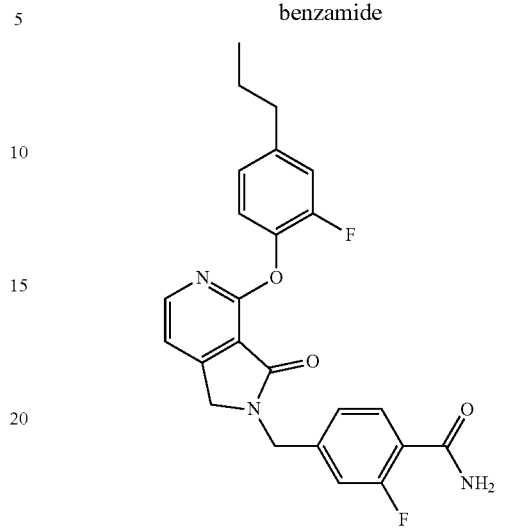

Ethyl 2-(2-fluoro-4-propylphenoxy)-4-formylnicotinate (0.13 g) obtained in Reference Example 319 was dissolved in methanol (3 mL), 4-(aminomethyl)-2-fluorobenzamide hydrochloride (0.090 g) obtained in Reference Example 307, acetic acid (0.024 g) and triethylamine (0.061 g) were added, and the mixture was stirred at room temperature for 1 hr. To the reaction mixture was added sodium tetrahydroborate (0.15 g), and the mixture was stirred at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and the obtained solid was recrystallized from ethyl acetate-ethanol to give the title compound (0.081 g).

MS: [M+H]⁺ 438.2

¹H NMR (300 MHz, DMSO-d₆) δ0.93 (3H, t, J=7.4 Hz), 1.63 (2H, sxt, J=7.5 Hz), 2.55-2.65 (2H, m), 4.52 (2H, s), 4.76 (2H, s), 7.04-7.11 (1H, m), 7.16-7.28 (4H, m), 7.35 (1H, d, J=5.1 Hz), 7.65 (3H, q, J=7.8 Hz), 8.21 (1H, d, J=5.3 Hz).

Example 453

5-((4-(4-ethyl-2-fluorophenoxy)-3-oxo-1,3-dihydro-2H-pyrrolo[3,4-c]pyridin-2-yl)methyl)-N-methylpyridine-2-carboxamide

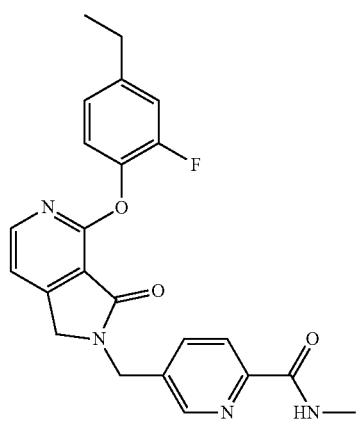 [SMILES: CCc1ccc(Oc2nccc3c2C(=O)N(Cc2ccc(C(=O)NC)nc2)C3)c(F)c1]

Ethyl 2-(4-ethyl-2-fluorophenoxy)-4-formylnicotinate (0.13 g) obtained in Reference Example 313 was dissolved in methanol (3 mL), 5-(aminomethyl)-N-methylpicolinamide hydrochloride (0.089 g) obtained in Reference Example 321, acetic acid (0.024 g) and triethylamine (0.061 g) were added, and the mixture was stirred at room temperature for 1 hr. To the reaction mixture was added sodium tetrahydroborate (0.15 g), and the mixture was stirred at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from ethanol to give the title compound (0.050 g).

MS: [M+H]$^+$ 421.2

$^1$H NMR (300 MHz, DMSO-d$_6$) δ1.22 (3H, t, J=7.6 Hz), 2.66 (2H, q, J=7.7 Hz), 2.82 (3H, d, J=4.7 Hz), 4.54 (2H, s), 4.83 (2H, s), 7.10 (1H, dd, J=8.3, 1.5 Hz), 7.18-7.28 (2H, m), 7.35 (1H, d, J=5.1 Hz), 7.87-7.95 (1H, m), 7.97-8.05 (1H, m), 8.20 (1H, d, J=5.1 Hz), 8.63 (1H, d, J=1.7 Hz), 8.68-8.80 (1H, m)

Example 454

5-((4-(4-cyclopropyl-2-fluorophenoxy)-3-oxo-1,3-dihydro-2H-pyrrolo[3,4-c]pyridin-2-yl)methyl)-N-methylpyridine-2-carboxamide

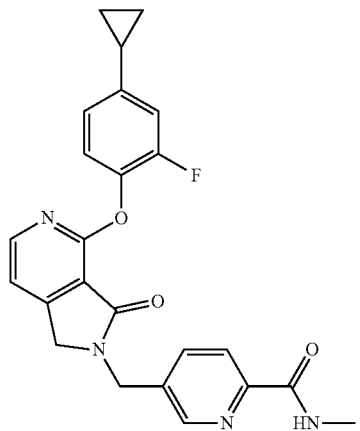 [SMILES: CNC(=O)c1ccc(CN2Cc3ccnc(Oc4ccc(C5CC5)cc4F)c3C2=O)cn1]

Ethyl 2-(4-cyclopropyl-2-fluorophenoxy)-4-formylnicotinate (0.17 g) obtained in Reference Example 317 was dissolved in methanol (3 mL), 5-(aminomethyl)-N-methylpicolinamide hydrochloride (0.11 g) obtained in Reference Example 321, acetic acid (0.030 g) and triethylamine (0.076 g) were added, and the mixture was stirred at room temperature for 1 hr. To the reaction mixture was added sodium tetrahydroborate (0.19 g), and the mixture was stirred at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from ethanol to give the title compound (0.060 g).

MS: [M+H]$^+$ 433.2

$^1$H NMR (300 MHz, DMSO-d$_6$) δ0.68-0.77 (2H, m), 0.93-1.03 (2H, m), 1.91-2.04 (1H, m), 2.82 (3H, d, J=4.9 Hz), 4.54 (2H, s), 4.83 (2H, s), 6.99 (1H, dd, J=8.3, 1.7 Hz), 7.06 (1H, dd, J=12.1, 1.9 Hz), 7.14-7.25 (1H, m), 7.34 (1H, d, J=5.3 Hz), 7.90 (1H, dd, J=8.0, 2.2 Hz), 7.98-8.05 (1H, m), 8.19 (1H, d, J=5.1 Hz), 8.62 (1H, d, J=1.5 Hz), 8.73 (1H, q, J=4.7 Hz).

Example 455

5-((4-(2-fluoro-4-propylphenoxy)-3-oxo-1,3-dihydro-2H-pyrrolo[3,4-c]pyridin-2-yl)methyl)-N-methylpyridine-2-carboxamide

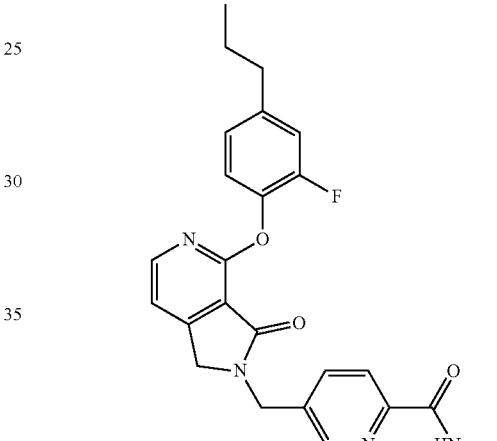

Ethyl 2-(2-fluoro-4-propylphenoxy)-4-formylnicotinate (0.17 g) obtained in Reference Example 319 was dissolved in methanol (3 mL), 5-(aminomethyl)-N-methylpicolinamide hydrochloride (0.089 g) obtained in Reference Example 321, acetic acid (0.024 g) and triethylamine (0.101 g) were added, and the mixture was stirred at room temperature for 1 hr. To the reaction mixture was added sodium tetrahydroborate (0.15 g), and the mixture was stirred at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from ethyl acetate-ethanol to give the title compound (0.025 g).

MS: [M+H]$^+$ 435.2

$^1$H NMR (300 MHz, DMSO-d$_6$) δ0.93 (3H, t, J=7.3 Hz), 1.63 (2H, sxt, J=7.4 Hz), 2.56-2.64 (2H, m), 2.82 (3H, d, J=4.9 Hz), 4.54 (2H, s), 4.83 (2H, s), 7.08 (1H, dd, J=8.2, 1.6 Hz), 7.16-7.28 (2H, m), 7.35 (1H, d, J=5.1 Hz), 7.91 (1H, dd, J=8.1, 2.1 Hz), 7.98-8.04 (1H, m), 8.20 (1H, d, J=5.1 Hz), 8.63 (1H, d, J=1.7 Hz), 8.68-8.80 (1H, m).

Example 456

5-((4-(2-fluoro-4-(trifluoromethyl)phenoxy)-3-oxo-1,3-dihydro-2H-pyrrolo[3,4-c]pyridin-2-yl)methyl)-N-methylpyridine-2-carboxamide

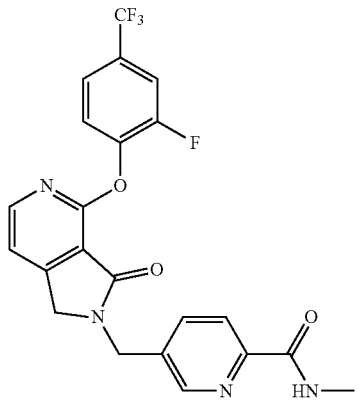 [SMILES: CNC(=O)c1ccc(CN2Cc3ccnc(Oc4ccc(C(F)(F)F)cc4F)c3C2=O)cn1]

Ethyl 2-(2-fluoro-4-(trifluoromethyl)phenoxy)-4-formylnicotinate (0.14 g) obtained in Reference Example 282 was dissolved in methanol (3 mL), 5-(aminomethyl)-N-methylpicolinamide hydrochloride (0.089 g) obtained in Reference Example 321, acetic acid (0.024 g) and triethylamine (0.061 g) were added, and the mixture was stirred at room temperature for 1 hr. To the reaction mixture was added sodium tetrahydroborate (0.15 g), and the mixture was stirred at room temperature overnight. The reaction mixture was diluted with water and ethyl acetate. The organic layer was separated, washed with saturated brine, dried over anhydrous magnesium sulfate and concentrated. The residue was purified by NH silica gel chromatography (hexane-ethyl acetate), and recrystallized from hexane-ethyl acetate to give the title compound (0.029 g).

MS: [M+H]$^+$ 461.1

$^1$H NMR (300 MHz, DMSO-d$_6$) δ2.82 (3H, d, J=4.9 Hz), 4.57 (2H, s), 4.84 (2H, s), 7.43 (1H, d, J=5.1 Hz), 7.59-7.74 (2H, m), 7.87-7.96 (2H, m), 7.98-8.05 (1H, m), 8.24 (1H, d, J=5.3 Hz), 8.63 (1H, d, J=1.5 Hz), 8.74 (1H, q, J=5.1 Hz).

Example 457

4-((4-(2-fluoro-4-(2,2,2-trifluoroethyl)phenoxy)-3-oxo-1,3-dihydro-2H-pyrrolo[3,4-c]pyridin-2-yl)methyl)-N-methylbenzamide

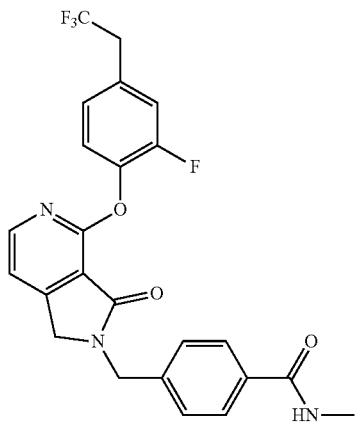 [SMILES: CNC(=O)c1ccc(CN2Cc3ccnc(Oc4ccc(CC(F)(F)F)cc4F)c3C2=O)cc1]

Ethyl 2-(2-fluoro-4-(2,2,2-trifluoroethyl)phenoxy)-4-formylnicotinate (0.074 g) obtained in Reference Example 326 was dissolved in methanol (1.5 mL), 4-(aminomethyl)-N-methylbenzamide hydrochloride (0.044 g), acetic acid (0.012 g) and triethylamine (0.030 g) were added, and the mixture was stirred at room temperature for 1 hr. To the reaction mixture was added sodium tetrahydroborate (0.076 g), and the mixture was stirred at room temperature overnight. The reaction mixture was diluted with water and ethyl acetate. The organic layer was separated, washed with saturated brine, dried over anhydrous magnesium sulfate and concentrated. The obtained solid was washed with methanol and dried to give the title compound (0.049 g).

MS: [M+H]$^+$ 474.1

$^1$H NMR (300 MHz, DMSO-d$_6$) δ2.78 (3H, d, J=4.5 Hz), 3.74 (2H, q, J=11.6 Hz), 4.50 (2H, s), 4.77 (2H, s), 7.24-7.31 (1H, m), 7.35-7.45 (5H, m), 7.78-7.87 (2H, m), 8.22 (1H, d, J=5.1 Hz), 8.35-8.44 (1H, m).

Example 458

4-((4-(2-fluoro-4-(2,2,2-trifluoroethyl)phenoxy)-3-oxo-1,3-dihydro-2H-pyrrolo[3,4-c]pyridin-2-yl)methyl)benzamide

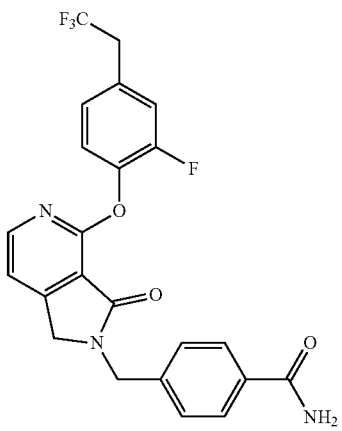 [SMILES: NC(=O)c1ccc(CN2Cc3ccnc(Oc4ccc(CC(F)(F)F)cc4F)c3C2=O)cc1]

Ethyl 2-(2-fluoro-4-(2,2,2-trifluoroethyl)phenoxy)-4-formylnicotinate (0.15 g) obtained in Reference Example 326 was dissolved in methanol (3 mL), 4-(aminomethyl)benzamide hydrochloride (0.082 g), acetic acid (0.024 g) and triethylamine (0.061 g) were added, and the mixture was stirred at room temperature for 1 hr. To the reaction mixture was added sodium tetrahydroborate (0.15 g), and the mixture was stirred at room temperature overnight. The precipitate was collected by filtration, and washed with methanol and water. The obtained solid was recrystallized from methanol-water to give the title compound (0.094 g).

MS: [M+H]$^+$ 460.1

$^1$H NMR (300 MHz, DMSO-d$_6$) δ3.74 (2H, q, J=11.5 Hz), 4.50 (2H, s), 4.77 (2H, s), 7.24-7.30 (1H, m), 7.33 (1H, brs), 7.36-7.44 (5H, m), 7.87 (2H, d, J=8.3 Hz), 7.95 (1H, brs), 8.22 (1H, d, J=5.1 Hz).

Example 459

2-fluoro-4-((4-(2-fluoro-4-(2,2,2-trifluoroethyl)phenoxy)-3-oxo-1,3-dihydro-2H-pyrrolo[3,4-c]pyridin-2-yl)methyl)benzamide

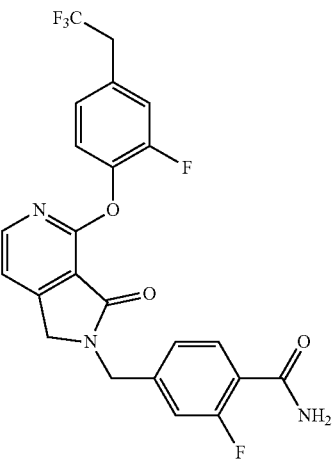 [SMILES: NC(=O)c1ccc(CN2Cc3ccnc(Oc4ccc(CC(F)(F)F)cc4F)c3C2=O)cc1F]

Ethyl 2-(2-fluoro-4-(2,2,2-trifluoroethyl)phenoxy)-4-formylnicotinate (0.15 g) obtained in Reference Example 326 was dissolved in methanol (3 mL), 4-(aminomethyl)-2-fluorobenzamide hydrochloride (0.090 g) obtained in Reference Example 307, acetic acid (0.024 g) and triethylamine (0.061 g) were added, and the mixture was stirred at room temperature for 1 hr. To the reaction mixture was added sodium tetrahydroborate (0.15 g), and the mixture was stirred at room temperature overnight. The precipitate was collected by filtration, washed with methanol and water, and dried to give the title compound (0.080 g).

MS: [M+H]$^+$ 478.1

$^1$H NMR (300 MHz, DMSO-d$_6$) δ 3.74 (2H, q, J=11.5 Hz), 4.53 (2H, s), 4.76 (2H, s), 7.17-7.31 (3H, m), 7.36-7.45 (2H, m), 7.55-7.70 (4H, m), 8.22 (1H, d, J=5.1 Hz).

Example 460

4-((7-(2-fluoro-4-(trifluoromethyl)phenoxy)-1-oxo-1,3-dihydro-2H-isoindol-2-yl)methyl)benzamide

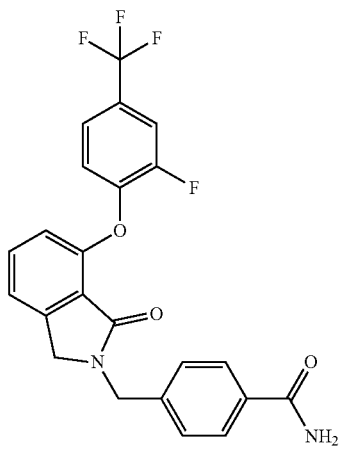 [SMILES: NC(=O)c1ccc(CN2Cc3cccc(Oc4ccc(C(F)(F)F)cc4F)c3C2=O)cc1]

To a solution of ethyl 2-(bromomethyl)-6-(2-fluoro-4-(trifluoromethyl)phenoxy)benzoate (0.21 g) obtained in Reference Example 328 in ethanol (2 mL) were added 4-(aminomethyl)benzamide hydrochloride (0.11 g) and potassium carbonate (0.14 g), and the mixture was stirred at 45° C. overnight. The reaction mixture was diluted with water and ethyl acetate. The organic layer was separated, washed with saturated brine, dried over anhydrous sodium sulfate, and concentrated. The residue was purified by silica gel chromatography (hexane-ethyl acetate), and the obtained solid was recrystallized from ethyl acetate-ethanol. The obtained crystals were collected by filtration and dried to give the title compound (0.055 g).

MS: [M+H]$^+$ 445.1

$^1$H NMR (300 MHz, DMSO-d$_6$) δ 4.42 (2H, s), 4.68 (2H, s), 7.04 (1H, t, J=8.4 Hz), 7.15 (1H, d, J=7.9 Hz), 7.31 (3H, d, J=8.1 Hz), 7.46 (1H, d, J=7.6 Hz), 7.51 (1H, d, J=8.5 Hz), 7.62-7.69 (1H, m), 7.81-7.96 (4H, m).

Example 461

2-fluoro-4-((7-(2-fluoro-4-(trifluoromethyl)phenoxy)-1-oxo-1,3-dihydro-2H-isoindol-2-yl)methyl)benzamide

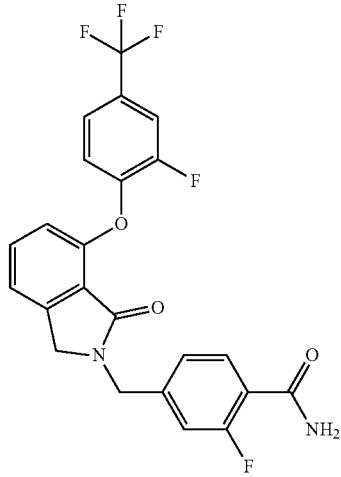 [SMILES: NC(=O)c1ccc(CN2Cc3cccc(Oc4ccc(C(F)(F)F)cc4F)c3C2=O)cc1F]

To a solution of ethyl 2-(bromomethyl)-6-(2-fluoro-4-(trifluoromethyl)phenoxy)benzoate (0.21 g) obtained in Reference Example 328 in ethanol (2 mL) were added 4-(aminomethyl)-2-fluorobenzamide hydrochloride (0.068 g) obtained in Reference Example 307 and potassium carbonate (0.14 g), and the mixture was stirred at 45° C. overnight. The reaction mixture was diluted with water and ethyl acetate. The organic layer was separated, washed with saturated brine, dried over anhydrous sodium sulfate, and concentrated. The obtained crystals were recrystallized from ethanol. The obtained crystals were collected by filtration, and dried to give the title compound (0.072 g).

MS: [M+H]$^+$ 463.1

$^1$H NMR (300 MHz, DMSO-d$_6$) δ 4.46 (2H, s), 4.68 (2H, s), 7.05 (1H, t, J=8.3 Hz), 7.11-7.20 (3H, m), 7.44-7.53 (2H, m), 7.53-7.73 (4H, m), 7.88 (1H, dd, J=11.0, 2.0 Hz).

Example compounds produced according to the above-mentioned methods or a method analogous thereto and using commercially available reagents or the compounds obtained in Reference Examples are shown in the following Tables. In the Tables, MS shows measured values.

TABLE 1-1

| Ex. No. | compound name | structure | stereo-chemistry | MS |
|---|---|---|---|---|
| 87 | 7-(2-methoxy-4-nitrophenoxy)-2-(4-(1-methyl-1H-pyrazol-4-yl)benzyl)isoindolin-1-one | 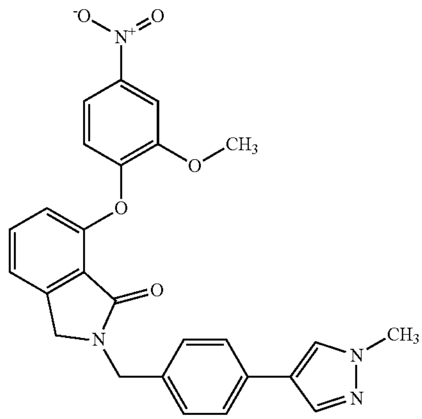 | | 471.2 |

1H NMR (300 MHz, DMSO-d6) δ 3.85 (3H, s), 3.96 (3H, s), 4.40 (2H, s), 4.61 (2H, s), 6.90 (1H, d, J = 8.9 Hz), 7.00 (1H, d, J = 7.7 Hz), 7.24 (2H, d, J = 8.1 Hz), 7.41 (1H, d, J = 7.0 Hz), 7.49-7.64 (3H, m), 7.78-7.87 (2H, m), 7.94 (1H, d, J = 2.6 Hz), 8.10 (1H, s).

| 88 | 2-(4-fluorobenzyl)-7-((trans-2-hydroxycyclohexyl)oxy)isoindolin-1-one | | racemate | 356.2 |

1H NMR (400 MHz, DMSO-d6) δ 1.24-1.37 (3H, m), 1.41-1.54 (1H, m), 1.57-1.72 (2H, m), 1.86-1.96 (1H, m), 2.04-2.12 (1H, m), 3.56-3.66 (1H, m), 4.04-4.09 (1H, m), 4.30 (2H, s), 4.65 (2H, s), 5.16 (1H, d, J = 3.7 Hz), 7.08-7.14 (2H, m), 7.15-7.21 (2H, m), 7.29-7.36 (2H, m), 7.48 (1H, t, J = 7.8 Hz).

| 89 | 7-(4-amino-2-methoxyphenoxy)-2-(4-(1-methyl-1H-pyrazol-4-yl)benzyl)isoindolin-1-one | | | 441.2 |

1H NMR (300 MHz, DMSO-d6) δ 3.63 (3H, s), 3.85 (3H, s), 4.32 (2H, s), 4.66 (2H, s), 5.11 (2H, s), 6.18 (1H, dd, J = 8.3, 2.5 Hz), 6.34-6.46 (2H, m), 6.76 (1H, d, J = 8.5 Hz), 7.05 (1H, d, J = 7.0 Hz), 7.23-7.40 (3H, m), 7.55 (2H, d, J = 8.1 Hz), 7.83 (1H, d, J = 0.8 Hz), 8.11 (1H, s).

TABLE 1-1-continued

| Ex. No. | compound name | structure | stereo-chemistry | MS |
|---|---|---|---|---|
| 90 | 7-(2-(piperidin-1-yl)ethoxy)-2-(4-(1H-pyrazol-5-yl)benzyl)isoindolin-1-one | 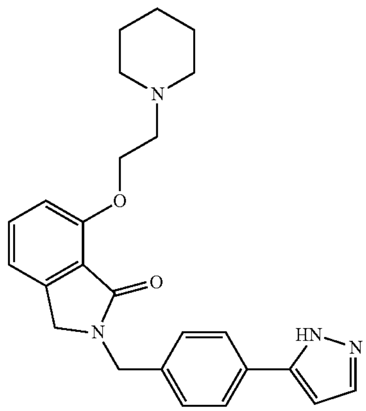 [SMILES: O=C1c2c(cccc2OCCN2CCCCC2)CN1Cc1ccc(-c2ccn[nH]2)cc1] | | 417.2 |

1H NMR (300 MHz, DMSO-d6) δ 1.29-1.77 (6H, m), 2.51-3.09 (6H, m), 4.10-4.46 (4H, m), 4.66 (2H, s), 6.67 (1H, s), 7.07 (2H, t, J = 8.6 Hz), 7.28 (2H, d, J = 7.9 Hz), 7.42-7.94 (4H, m), 12.67-13.48 (1H, m).

TABLE 1-2

| Ex. No. | compound name | structure | stereo-chemistry | MS |
|---|---|---|---|---|
| 91 | N-cyclopropyl-4-((1-oxo-7-((tetrahydrofuran-2-yl)methoxy)-1,3-dihydro-2H-isoindol-2-yl)methyl)benzamide | 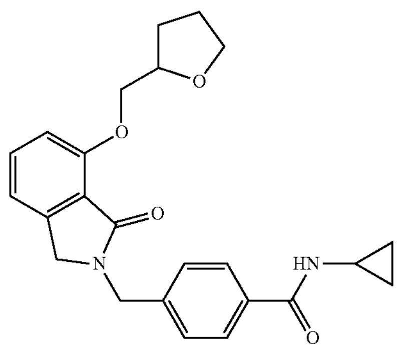 [SMILES: O=C(NC1CC1)c1ccc(CN2Cc3cccc(OCC4CCCO4)c3C2=O)cc1] | racemate | 407.3 |

1H NMR (300 MHz, DMSO-d6) δ 0.48-0.60 (2H, m), 0.62-0.73 (2H, m), 1.75-1.91 (2H, m), 1.94-2.09 (2H, m), 2.82 (1H, td, J = 7.3, 4.0 Hz), 3.60-3.73 (1H, m), 3.79-3.90 (1H, m), 4.01-4.12 (2H, m), 4.15-4.24 (1H, m), 4.28 (2H, s), 4.69 (2H, s), 7.05 (2H, dd, J = 11.9, 7.7 Hz), 7.31 (2H, d, J = 8.3 Hz), 7.49 (1H, dd, J = 8.1, 7.6 Hz), 7.78 (2H, d, J = 8.3 Hz), 8.39 (1H, d, J = 4.2 Hz).

| 92 | 3-fluoro-2-((2-((5-(1-methyl-1H-pyrazol-4-yl)-2-thienyl)methyl)-3-oxo-2,3-dihydro-1H-isoindol-4-yl)oxy)benzonitrile | | | 445.1 |

1H NMR (300 MHz, DMSO-d6) δ 3.82 (3H, s), 4.47 (2H, s), 4.82 (2H, s), 6.83 (1H, d, J = 8.1 Hz), 6.94-7.09 (2H, m), 7.36 (1H, d, J = 7.6 Hz), 7.42-7.60 (2H, m), 7.66 (1H, d, J = 0.8 Hz), 7.74-7.89 (2H, m), 7.98 (1H, s).

TABLE 1-2-continued

| Ex. No. | compound name | structure | stereo-chemistry | MS |
|---|---|---|---|---|
| 93 | 2-((2-(4-(1-methyl-1H-pyrazol-4-yl)benzyl)-3-oxo-2,3-dihydro-1H-isoindol-4-yl)oxy)benzonitrile | 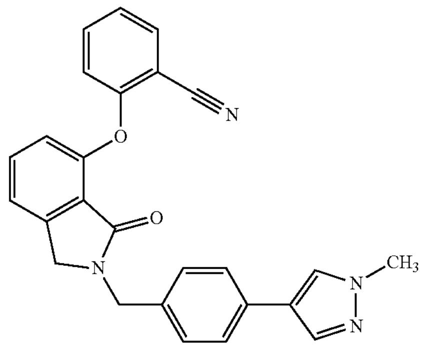 [SMILES: Cn1cc(-c2ccc(CN3Cc4cccc(Oc5ccccc5C#N)c4C3=O)cc2)cn1] | | 421.2 |

1H NMR (300 MHz, DMSO-d6) δ 3.85 (3H, s), 4.41 (2H, s), 4.60 (2H, s), 6.77 (1H, d, J = 7.9 Hz), 7.12-7.32 (4H, m), 7.44-7.72 (5H, m), 7.82 (1H, d, J = 0.8 Hz), 7.89 (1H, dd, J = 7.7, 1.7 Hz), 8.10 (1H, s).

| Ex. No. | compound name | structure | stereo-chemistry | MS |
|---|---|---|---|---|
| 94 | 7-((2-fluorobenzyl)oxy)-2-(4-(1-methyl-1H-pyrazol-4-yl)benzyl)isoindolin-1-one | | | 428.2 |

1H NMR (400 MHz, DMSO-d6) δ 3.85 (3H, s), 4.31 (2H, s), 4.64 (2H, s), 5.31 (2H, s), 7.09-7.19 (2H, m), 7.22-7.31 (4H, m), 7.38-7.47 (1H, m), 7.49-7.55 (3H, m), 7.73-7.79 (1H, m), 7.82 (1H, s), 8.10 (1H, s).

TABLE 1-3

| Ex. No. | compound name | structure | stereo-chemistry | MS |
|---|---|---|---|---|
| 95 | 2-(4-(1-methyl-1H-pyrazol-3-yl)benzyl)-7-(2-(piperidin-1-yl)ethoxy)isoindolin-1-one | 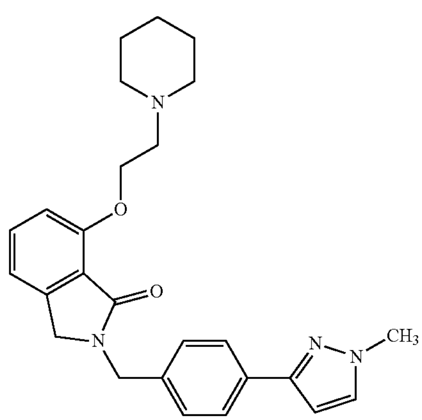 | | 431.3 |

1H NMR (300 MHz, DMSO-d6) δ 1.31-1.57 (6H, m), 2.46 (4H, brs), 2.69 (2H, t, J = 6.0 Hz), 3.86 (3H, s), 4.19 (2H, t, J = 6.0 Hz), 4.28 (2H, s), 4.65 (2H, s), 6.65 (1H, d, J = 2.3 Hz), 7.05 (2H, d, J = 7.7 Hz), 7.27 (2H, d, J = 8.3 Hz), 7.48 (1H, t, J = 7.9 Hz), 7.67-7.81 (3H, m).

TABLE 1-3-continued

| Ex. No. | compound name | structure | stereo-chemistry | MS |
|---|---|---|---|---|
| 96 | 7-(cyclohexyloxy)-2-(4-(1-methyl-1H-pyrazol-4-yl)benzyl)isoindolin-1-one | 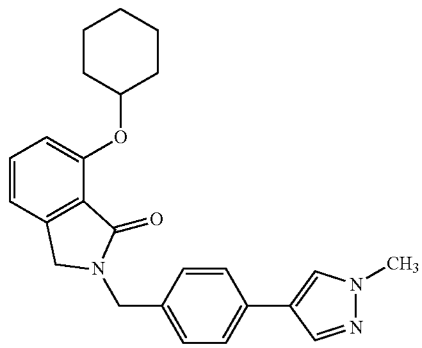 [SMILES: Cn1cc(-c2ccc(CN3Cc4cccc(OC5CCCOC5)c4C3=O)cc2)cn1] | | 402.3 |

1H NMR (400 MHz, DMSO-d6) δ 1.29-1.42 (3H, m), 1.45-1.60 (3H, m), 1.73-1.93 (4H, m), 3.85 (3H, s), 4.27 (2H, s), 4.50-4.59 (1H, m), 4.62 (2H, s), 7.04 (2H, dd, J = 7.8, 2.7 Hz), 7.24 (2H, d, J = 8.1 Hz), 7.45 (1H, t, J = 7.9 Hz), 7.53 (2H, d, J = 8.1 Hz), 7.83 (1H, s), 8.11 (1H, s).

| 97 | 2-(4-(1-methyl-1H-pyrazol-4-yl)benzyl)-7-(2-(2-oxopyrrolidin-1-yl)ethoxy)isoindolin-1-one | | | 431.2 |

1H NMR (300 MHz, DMSO-d6) δ 1.82-2.04 (2H, m), 2.14-2.29 (2H, m), 3.57 (2H, t, J = 5.1 Hz), 3.70 (2H, t, J = 7.0 Hz), 3.85 (3H, s), 4.19 (2H, t, J = 5.3 Hz), 4.28 (2H, s), 4.63 (2H, s), 6.95-7.14 (2H, m), 7.24 (2H, d, J = 8.3 Hz), 7.43-7.60 (3H, m), 7.82 (1H, d, J = 0.8 Hz), 8.10 (1H, s).

| 98 | 7-((3-chloropyridin-2-yl)oxy)-2-(4-(1-methyl-1H-pyrazol-4-yl)benzyl)isoindolin-1-one | | | 431.2 |

1H NMR (300 MHz, DMSO-d6) δ 3.84 (3H, s), 4.38 (2H, s), 4.55 (2H, s), 6.98-7.32 (4H, m), 7.43 (1H, d, J = 7.9 Hz), 7.52 (2H, d, J = 8.3 Hz), 7.59-7.68 (1H, m), 7.82 (1H, s), 7.95 (1H, dd, J = 4.9, 1.5 Hz), 8.03 (1H, dd, J = 7.7, 1.7 Hz), 8.10 (1H, s).

TABLE 1-4

| Ex. No. | compound name | structure | stereo-chemistry | MS |
|---|---|---|---|---|
| 99 | 2-(4-(1-methyl-1H-pyrazol-4-yl)benzyl)-7-(tetrahydro-2H-pyran-3-yloxy)isoindolin-1-one | 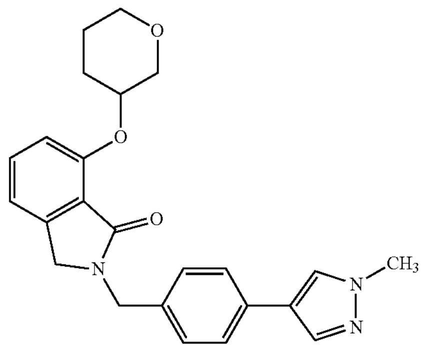 | racemate | 404.2 |

1H NMR (300 MHz, DMSO-d6) δ 1.43-1.61 (1H, m), 1.64-1.79 (1H, m), 1.80-1.95 (1H, m), 1.96-2.12 (1H, m), 3.44-3.57 (2H, m), 3.58-3.71 (1H, m), 3.75-3.91 (4H, m), 4.28 (2H, s), 4.47-4.58 (1H, m), 4.63 (2H, s), 7.08 (2H, dd, J = 10.5, 7.8 Hz), 7.25 (2H, d, J = 8.3 Hz), 7.40-7.59 (3H, m), 7.82 (1H, d, J = 0.8 Hz), 8.10 (1H, s).

| 100 | 2-(4-(1-methyl-1H-pyrazol-4-yl)benzyl)-7-((tetrahydro-2H-pyran-3-yl)methoxy)isoindolin-1-one | | racemate | 418.2 |

1H NMR (300 MHz, DMSO-d6) δ 1.35-1.67 (3H, m), 1.81-1.94 (1H, m), 2.03 (1H, brs), 3.33-3.44 (2H, m), 3.71-3.80 (1H, m), 3.85 (3H, s), 3.90-4.07 (3H, m), 4.27 (2H, s), 4.62 (2H, s), 6.92-7.12 (2H, m), 7.24 (2H, d, J = 8.3 Hz), 7.40-7.59 (3H, m), 7.82 (1H, d, J = 0.8 Hz), 8.10 (1H, s).

| 101 | 4-((1-oxo-7-((tetrahydrofuran-2-yl)methoxy)-1,3-dihydro-2H-isoindol-2-yl)methyl)-N-(2,2,2-trifluoroethyl)benzamide | | racemate | 449.2 |

1H NMR (300 MHz, DMSO-d6) δ 1.75-1.90 (2H, m), 1.93-2.10 (2H, m), 3.61-3.73 (1H, m), 3.80-3.91 (1H, m), 4.00-4.15 (4H, m), 4.16-4.26 (1H, m), 4.30 (2H, s), 4.72 (2H, s), 7.05 (2H, dd, J = 11.9, 7.7 Hz), 7.37 (2H, d, J = 8.3 Hz), 7.49 (1H, dd, J = 8.3, 7.6 Hz), 7.87 (2H, d, J = 8.3 Hz), 9.06 (1H, t, J = 6.2 Hz).

TABLE 1-4-continued

| Ex. No. | compound name | structure | stereo-chemistry | MS |
|---|---|---|---|---|
| 102 | 2-(4-(1-methyl-1H-pyrazol-4-yl)benzyl)-7-((oxetan-2-yl)methoxy)isoindolin-1-one | 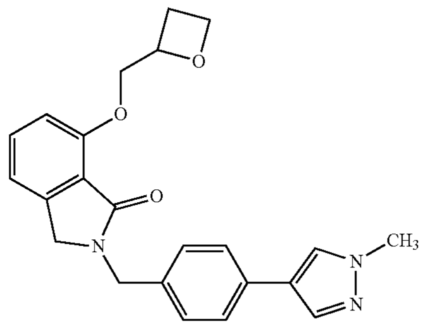 [SMILES: Cn1cc(-c2ccc(CN3Cc4cccc(OCC5CCO5)c4C3=O)cc2)cn1] | racemate | 390.2 |

1H NMR (300 MHz, DMSO-d6) δ 2.72 (2H, q, J = 7.6 Hz), 3.85 (3H, s), 4.20-4.26 (2H, m), 4.30 (2H, s), 4.45-4.56 (1H, m), 4.59-4.71 (3H, m), 4.94-5.09 (1H, m), 7.07 (2H, t, J = 7.5 Hz), 7.25 (2H, d, J = 8.1 Hz), 7.44-7.56 (3H, m), 7.82 (1H, d, J = 0.8 Hz), 8.10 (1H, s).

TABLE 1-5

| Ex. No. | compound name | structure | stereo-chemistry | MS |
|---|---|---|---|---|
| 103 | N-(2-fluorobenzyl)-4-((1-oxo-7-((tetrahydrofuran-2-yl)methoxy)-1,3-dihydro-2H-isoindol-2-yl)methyl)benzamide | 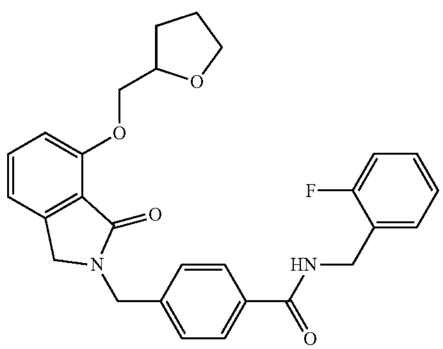 [SMILES: O=C(NCc1ccccc1F)c1ccc(CN2Cc3cccc(OCC4CCCO4)c3C2=O)cc1] | racemate | 475.3 |

1H NMR (300 MHz, DMSO-d6) δ 1.73-1.91 (2H, m), 1.92-2.10 (2H, m), 3.61-3.74 (1H, m), 3.79-3.92 (1H, m), 4.00-4.14 (2H, m), 4.16-4.25 (1H, m), 4.30 (2H, s), 4.51 (2H, d, J = 5.9 Hz), 4.71 (2H, s), 7.05 (2H, dd, J = 12.1, 7.7 Hz), 7.12-7.22 (2H, m), 7.25-7.40 (4H, m), 7.49 (1H, dd, J = 8.1, 7.6 Hz), 7.88 (2H, d, J = 8.3 Hz), 9.00 (1H, t, J = 5.9 Hz).

| | | | | |
|---|---|---|---|---|
| 104 | 7-(4-amino-2-(trifluoromethyl)phenoxy)-2-(4-(1-methyl-1H-pyrazol-4-yl)benzyl)isoindolin-1-one | | | 479.3 |

1H NMR (300 MHz, DMSO-d6) δ 3.85 (3H, s), 4.35 (2H, s), 4.65 (2H, s), 5.49 (2H, s), 6.56 (1H, d, J = 8.3 Hz), 6.73-6.91 (2H, m), 6.95 (1H, d, J = 2.5 Hz), 7.18 (1H, d, J = 7.6 Hz), 7.28 (2H, d, J = 8.3 Hz), 7.36-7.50 (1H, m), 7.55 (2H, d, J = 8.3 Hz), 7.83 (1H, d, J = 0.6 Hz), 8.11 (1H, s).

TABLE 1-5-continued

| Ex. No. | compound name | structure | stereo-chemistry | MS |
|---|---|---|---|---|
| 105 | 7-(4-amino-2-(difluoromethyl)phenoxy)-2-(4-(1-methyl-1H-pyrazol-4-yl)benzyl)isoindolin-1-one | 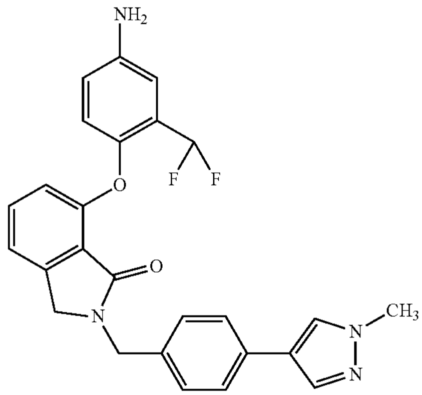 [SMILES: Cn1cc(-c2ccc(CN3Cc4cccc(Oc5ccc(N)cc5C(F)F)c4C3=O)cc2)cn1] | | 461.2 |

1H NMR (300 MHz, DMSO-d6) δ 3.85 (3H, s), 4.38 (2H, s), 4.62 (2H, s), 6.84 (1H, d, J = 8.7 Hz), 6.96-7.43 (7H, m), 7.46-7.64 (3H, m), 7.82 (1H, d, J = 0.6 Hz), 8.10 (1H, s). NH$_2$ protons were not observed.

| Ex. No. | compound name | structure | stereo-chemistry | MS |
|---|---|---|---|---|
| 106 | 2-(4-(1-methyl-1H-pyrazol-4-yl)benzyl)-7-((tetrahydro-2H-pyran-4-yl)methoxy)isoindolin-1-one | | | 418.2 |

1H NMR (300 MHz, DMSO-d6) δ 1.29-1.47 (2H, m), 1.68-1.81 (2H, m), 2.04 (1H, brs), 3.33-3.44 (2H, m), 3.80-4.04 (7H, m), 4.28 (2H, s), 4.62 (2H, s), 6.96-7.12 (2H, m), 7.24 (2H, d, J = 8.3 Hz), 7.42-7.59 (3H, m), 7.82 (1H, d, J = 0.8 Hz), 8.10 (1H, s).

TABLE 1-6

| Ex. No. | compound name | structure | stereo-chemistry | MS |
|---|---|---|---|---|
| 107 | 2-(4-(1-methyl-1H-pyrazol-4-yl)benzyl)-7-((pyridin-2-yl)methoxy)isoindolin-1-one | 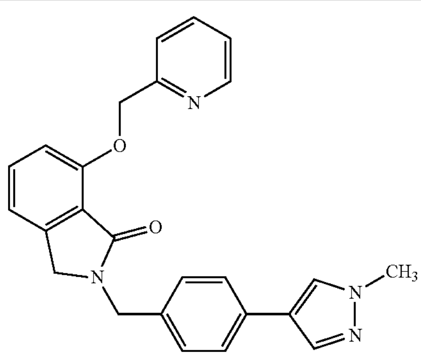 [SMILES: Cn1cc(-c2ccc(CN3Cc4cccc(OCc5ccccn5)c4C3=O)cc2)cn1] | | 411.3 |

1H NMR (400 MHz, DMSO-d6) δ 3.85 (3H, s), 4.32 (2H, s), 4.66 (2H, s), 5.32 (2H, s), 7.09-7.14 (2H, m), 7.26 (2H, d, J = 8.3 Hz), 7.33-7.38 (1H, m), 7.48-7.56 (3H, m), 7.78-7.85 (2H, m), 7.86-7.92 (1H, m), 8.11 (1H, s), 8.58 (1H, d, J = 4.2 Hz).

TABLE 1-6-continued

| Ex. No. | compound name | structure | stereo-chemistry | MS |
|---|---|---|---|---|
| 108 | 2-(4-(1-methyl-1H-pyrazol-4-yl)benzyl)-7-((5,6,7,8-tetrahydroimidazo[1,5-a]pyridin-3-yl)methoxy)isoindolin-1-one | 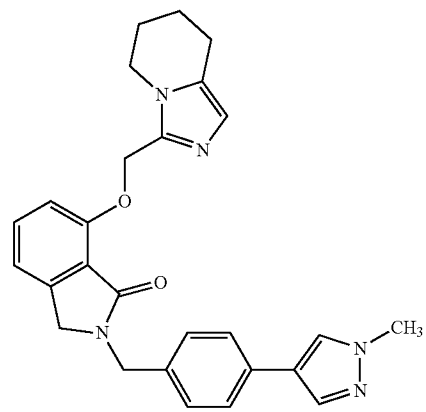 [SMILES: Cn1cc(-c2ccc(CN3Cc4cccc(OCc5ncc6n5CCCC6)c4C3=O)cc2)cn1] | | 454.2 |

1H NMR (300 MHz, DMSO-d6) δ 1.67-1.80 (2H, m), 1.83-1.94 (2H, m), 2.64-2.77 (2H, m), 3.84 (3H, s), 4.12 (2H, t, J = 6.1 Hz), 4.28 (2H, s), 4.62 (2H, s), 5.23 (2H, s), 6.62 (1H, s), 7.09 (1H, d, J = 7.4 Hz), 7.17-7.32 (3H, m), 7.43-7.60 (3H, m), 7.82 (1H, d, J = 0.8 Hz), 8.10 (1H, s).

| 109 | 7-(2-methoxyphenoxy)-2-(4-(1-methyl-1H-pyrazol-4-yl)benzyl)isoindolin-1-one | | | 426.2 |

1H NMR (300 MHz, DMSO-d6) δ 3.75 (3H, s), 3.85 (3H, s), 4.36 (2H, s), 4.66 (2H, s), 6.46 (1H, d, J = 8.1 Hz), 6.95-7.10 (2H, m), 7.12-7.32 (5H, m), 7.35-7.46 (1H, m), 7.55 (2H, d, J = 8.1 Hz), 7.83 (1H, d, J = 0.8 Hz), 8.11 (1H, s).

| 110 | 2-((5-(1-methyl-1H-pyrazol-4-yl)-2-thienyl)methyl)-7-(2-(piperidin-1-yl)ethoxy)isoindolin-1-one | | | 437.2 |

1H NMR (300 MHz, DMSO-d6) δ 1.32-1.55 (6H, m), 2.39-2.49 (4H, m), 2.65-2.75 (2H, m), 3.81 (3H, s), 4.19 (2H, t, J = 6.0 Hz), 4.33 (2H, s), 4.77 (2H, s), 6.94-7.11 (4H, m), 7.42-7.54 (1H, m), 7.64 (1H, d, J = 0.8 Hz), 7.96 (1H, s).

TABLE 1-7

| Ex. No. | compound name | structure | stereo-chemistry | MS |
|---|---|---|---|---|
| 111 | N-(cyclopropylmethyl)-4-((1-oxo-7-((tetrahydrofuran-2-yl)methoxy)-1,3-dihydro-2H-isoindol-2-yl)methyl)benzamide | 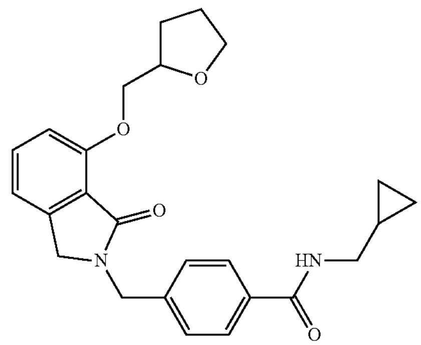 [SMILES: O=C(NCC1CC1)c1ccc(CN2Cc3cccc(OCC4CCCO4)c3C2=O)cc1] | racemate | 421.2 |

1H NMR (300 MHz, DMSO-d6) δ 0.15-0.27 (2H, m), 0.35-0.47 (2H, m), 0.93-1.10 (1H, m), 1.75-1.91 (2H, m), 1.96-2.11 (2H, m), 3.13 (2H, t, J = 6.2 Hz), 3.57-3.74 (1H, m), 3.79-3.92 (1H, m), 4.04-4.12 (2H, m), 4.15-4.25 (1H, m), 4.29 (2H, s), 4.70 (2H, s), 7.05 (2H, dd, J = 12.2, 7.6 Hz), 7.33 (2H, d, J = 8.5 Hz), 7.42-7.55 (1H, m), 7.83 (2H, d, J = 8.5 Hz), 8.52 (1H, t, J = 5.7 Hz).

| 112 | 2-(4-(1-methyl-1H-pyrazol-4-yl)benzyl)-7-(2-(morpholin-4-yl)ethoxy)isoindolin-1-one | | | 433.2 |

1H NMR (300 MHz, DMSO-d6) δ 2.52-2.60 (4H, m), 2.73 (2H, t, J = 5.8 Hz), 3.50-3.64 (4H, m), 3.85 (3H, s), 4.14-4.34 (4H, m), 4.62 (2H, s), 6.98-7.12 (2H, m), 7.23 (2H, d, J = 8.3 Hz), 7.41-7.58 (3H, m), 7.82 (1H, d, J = 0.8 Hz), 8.09 (1H, s).

| 113 | 2-(4-(1-methyl-1H-pyrazol-4-yl)benzyl)-7-(tetrahydro-2H-pyran-4-yloxy)isoindolin-1-one | | | 404.3 |

1H NMR (400 MHz, DMSO-d6) δ 1.58-1.74 (2H, m), 1.89-2.03 (2H, m), 3.39-3.57 (2H, m), 3.79-3.98 (5H, m), 4.28 (2H, s), 4.63 (2H, s), 4.78 (1H, brs), 7.00-7.14 (2H, m), 7.25 (2H, d, J = 7.8 Hz), 7.44-7.57 (3H, m), 7.83 (1H, s), 8.11 (1H, s).

TABLE 1-7-continued

| Ex. No. | compound name | structure | stereo-chemistry | MS |
|---|---|---|---|---|
| 114 | 7-((1-methyl-1H-imidazol-2-yl)methoxy)-2-(4-(1-methyl-1H-pyrazol-4-yl)benzyl)isoindolin-1-one | 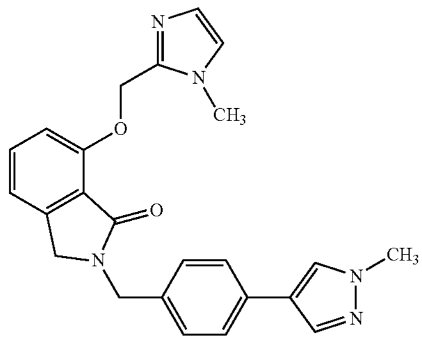 [SMILES: Cn1cc(-c2ccc(CN3Cc4cccc(OCc5nccn5C)c4C3=O)cc2)cn1] | | 414.2 |

1H NMR (300 MHz, DMSO-d6) δ 3.78 (3H, s), 3.84 (3H, s), 4.29 (2H, s), 4.62 (2H, s), 5.29 (2H, s), 6.86 (1H, d, J = 1.1 Hz), 7.11 (1H, d, J = 7.4 Hz), 7.17-7.29 (4H, m), 7.43-7.57 (3H, m), 7.82 (1H, d, J = 0.8 Hz), 8.09 (1H, s).

TABLE 1-8

| Ex. No. | compound name | structure | stereo-chemistry | MS |
|---|---|---|---|---|
| 115 | 2-((2-(4-(1-methyl-1H-pyrazol-4-yl)benzyl)-3-oxo-2,3-dihydro-1H-isoindol-4-yl)oxy)nicotinonitrile | 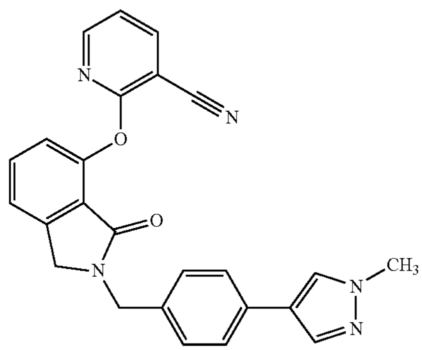 [SMILES: Cn1cc(-c2ccc(CN3Cc4cccc(Oc5ncccc5C#N)c4C3=O)cc2)cn1] | | 422.2 |

1H NMR (300 MHz, DMSO-d6) δ 3.84 (3H, s), 4.40 (2H, s), 4.55 (2H, s), 7.18 (2H, d, J = 8.3 Hz), 7.24-7.39 (2H, m), 7.45-7.56 (3H, m), 7.62-7.73 (1H, m), 7.82 (1H, d, J = 0.8 Hz), 8.09 (1H, s), 8.29 (1H, dd, J = 5.1, 1.9 Hz), 8.43 (1H, dd, J = 7.6, 2.0 Hz).

| 116 | 2-(4-(1-methyl-1H-pyrazol-4-yl)benzyl)-7-(4-nitro-2-(trifluoromethyl)phenoxy)isoindolin-1-one | | | 509.2 |

1H NMR (300 MHz, DMSO-d6) δ 3.85 (3H, s), 4.43 (2H, s), 4.59 (2H, s), 6.97 (1H, d, J = 9.3 Hz), 7.22 (2H, d, J = 8.3 Hz), 7.31 (1H, d, J = 7.6 Hz), 7.47-7.62 (3H, m), 7.68-7.79 (1H, m), 7.82 (1H, d, J = 0.8 Hz), 8.10 (1H, s), 8.39 (1H, dd, J = 9.3, 2.8 Hz), 8.53 (1H, d, J = 2.8 Hz).

TABLE 1-8-continued

| Ex. No. | compound name | structure | stereo-chemistry | MS |
|---|---|---|---|---|
| 117 | 2-(4-bromobenzyl)-7-((trans-2-hydroxycyclopentyl)oxy)isoindolin-1-one | 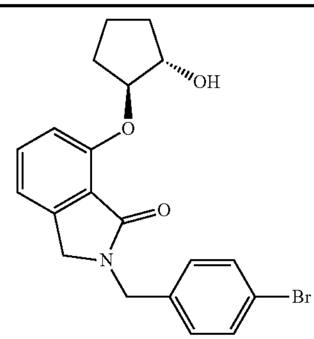 | racemate | 402.0 404.0 |

1H NMR (300 MHz, DMSO-d6) δ 1.47-1.58 (1H, m), 1.61-1.78 (3H, m), 1.84-1.96 (1H, m), 2.02-2.16 (1H, m), 4.08-4.15 (1H, m), 4.27 (2H, s), 4.53-4.65 (3H, m), 4.94 (1H, d, J = 4.0 Hz), 6.97-7.13 (2H, m), 7.23 (2H, d, J = 8.5 Hz), 7.43-7.58 (3H, m).

| 118 | 7-(1,1-difluoro-2-oxo-2-(piperidin-1-yl)ethoxy)-2-(4-(1-methyl-1H-pyrazol-4-yl)benzyl)isoindolin-1-one | | | 481.2 |

1H NMR (300 MHz, DMSO-d6) δ 1.41-1.73 (6H, m), 3.46-3.59 (2H, m), 3.85 (3H, s), 3.86-3.95 (2H, m), 4.38 (2H, s), 4.67 (2H, s), 7.19-7.35 (3H, m), 7.44-7.58 (3H, m), 7.59-7.69 (1H, m), 7.83 (1H, d, J = 0.8 Hz), 8.10 (1H, s).

TABLE 1-9

| Ex. No. | compound name | structure | stereo-chemistry | MS |
|---|---|---|---|---|
| 119 | 7-((cis-2-fluorocyclohexyl)oxy)-2-(4-(1-methyl-1H-pyrazol-4-yl)benzyl)isoindolin-1-one | 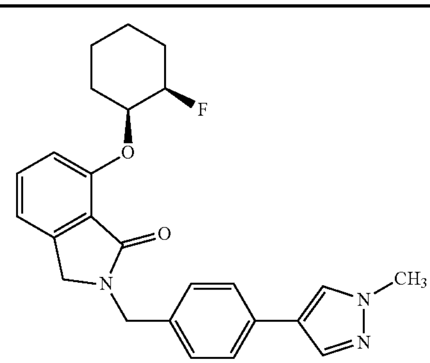 | racemate | 420.2 |

1H NMR (300 MHz, DMSO-d6) δ 1.26-1.50 (2H, m), 1.53-1.79 (4H, m), 1.80-1.96 (1H, m), 2.04-2.24 (1H, m), 3.85 (3H, s), 4.29 (2H, s), 4.56-4.71 (2H, m), 4.74-5.01 (2H, m), 7.00-7.15 (2H, m), 7.25 (2H, d, J = 8.1 Hz), 7.41-7.58 (3H, m), 7.82 (1H, d, J = 0.8 Hz), 8.10 (1H, s).

TABLE 1-9-continued

| Ex. No. | compound name | structure | stereo-chemistry | MS |
|---|---|---|---|---|
| 120 | 7-((trans-2-hydroxycyclohexyl)oxy)-2-(4-(trifluoromethoxy)benzyl)isoindolin-1-one | 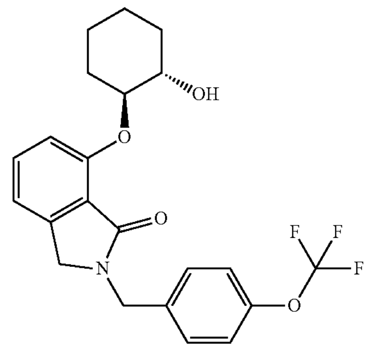 [SMILES: O=C1c2c(cccc2O[C@H]2CCCC[C@@H]2O)CN1Cc1ccc(OC(F)(F)F)cc1] | racemate | 422.3 |

1H NMR (400 MHz, DMSO-d6) δ 1.27-1.34 (3H, m), 1.49 (1H, brs), 1.56-1.72 (2H, m), 1.84-1.96 (1H, m), 2.03-2.13 (1H, m), 3.57-3.65 (1H, m), 4.01-4.12 (1H, m), 4.33 (2H, s), 4.70 (2H, s), 5.14 (1H, d, J = 3.4 Hz), 7.12 (2H, dd, J = 7.3, 6.1 Hz), 7.32-7.44 (4H, m), 7.46-7.53 (1H, m).

| 121 | 7-((1-bromo-5,6,7,8-tetrahydroimidazo[1,5-a]pyridin-3-yl)methoxy)-2-(4-(1-methyl-1H-pyrazol-4-yl)benzyl)isoindolin-1-one | | | 532.2 534.2 |

1H NMR (300 MHz, DMSO-d6) δ 1.71-1.95 (4H, m), 2.58 (2H, t, J = 6.1 Hz), 3.84 (3H, s), 4.15 (2H, t, J = 5.9 Hz), 4.29 (2H, s), 4.62 (2H, s), 5.24 (2H, s), 7.12 (1H, d, J = 7.6 Hz), 7.18-7.28 (3H, m), 7.43-7.60 (3H, m), 7.82 (1H, d, J = 0.8 Hz), 8.09 (1H, s).

| 122 | 7-(2-(difluoromethyl)-4-nitrophenoxy)-2-(4-(1-methyl-1H-pyrazol-4-yl)benzyl)isoindolin-1-one | | | 491.2 |

1H NMR (300 MHz, DMSO-d6) δ 3.84 (3H, s), 4.42 (2H, s), 4.58 (2H, s), 6.88 (1H, d, J = 9.1 Hz), 7.21 (2H, d, J = 8.1 Hz), 7.25-7.67 (5H, m), 7.68-7.77 (1H, m), 7.82 (1H, d, J = 0.6 Hz), 8.10 (1H, s), 8.30 (1H, dd, J = 9.3, 2.8 Hz), 8.44 (1H, d, J = 2.8 Hz).

TABLE 1-10

| Ex. No. | compound name | structure | stereo-chemistry | MS |
|---|---|---|---|---|
| 123 | 3-fluoro-2-((2-(3-(1-methyl-1H-pyrazol-4-yl)benzyl)-3-oxo-2,3-dihydro-1H-isoindol-4-yl)oxy)benzonitrile | 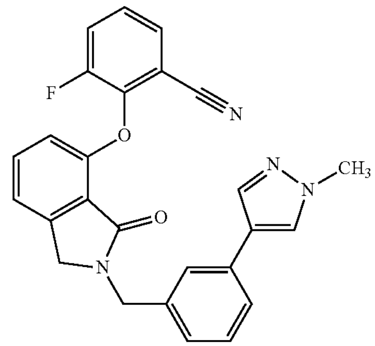 [SMILES: Cn1cc(-c2cccc(CN3Cc4cccc(Oc5c(F)cccc5C#N)c4C3=O)c2)cn1] | | 439.2 |

1H NMR (300 MHz, DMSO-d6) δ 3.85 (3H, s), 4.43 (2H, s), 4.69 (2H, s), 6.84 (1H, d, J = 8.1 Hz), 7.09 (1H, d, J = 7.6 Hz), 7.26-7.40 (2H, m), 7.44-7.58 (4H, m), 7.74-7.89 (3H, m), 8.11 (1H, s).

| 124 | 2-(4-(1-methyl-1H-pyrazol-4-yl)benzyl)-7-(2-(trifluoromethyl)phenoxy)isoindolin-1-one | | | 464.2 |

1H NMR (300 MHz, DMSO-d6) δ 3.85 (3H, s), 4.40 (2H, s), 4.62 (2H, s), 6.93 (2H, dd, J = 17.2, 8.1 Hz), 7.20-7.34 (3H, m), 7.40 (1H, d, J = 7.6 Hz), 7.48-7.67 (4H, m), 7.71-7.92 (2H, m), 8.11 (1H, s).

| 125 | 2-(4-(1-methyl-1H-pyrazol-4-yl)benzyl)-7-(((2R)-5-oxopyrrolidin-2-yl)methoxy)isoindolin-1-one | | R | 417.2 |

1H NMR (300 MHz, DMSO-d6) δ 1.92-2.22 (3H, m), 2.61-2.75 (1H, m), 3.85 (3H, s), 3.88-4.03 (2H, m), 4.16 (1H, dd, J = 9.8, 4.0 Hz), 4.29 (2H, s), 4.64 (2H, s), 7.07 (2H, dd, J = 15.7, 7.7 Hz), 7.25 (2H, d, J = 8.1 Hz), 7.44-7.57 (3H, m), 7.61 (1H, s), 7.82 (1H, d, J = 0.6 Hz), 8.09 (1H, s).

TABLE 1-10-continued

| Ex. No. | compound name | structure | stereo-chemistry | MS |
|---|---|---|---|---|
| 126 | 7-(2-(difluoromethyl)phenoxy)-2-(4-(1-methyl-1H-pyrazol-4-yl)benzyl)isoindolin-1-one | 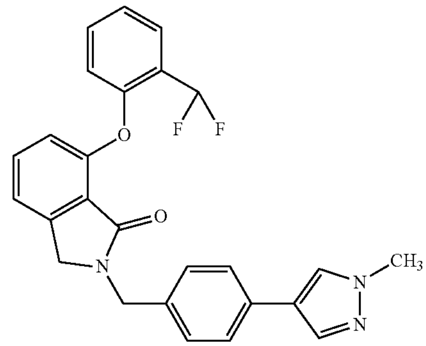 [SMILES: Cn1cc(-c2ccc(CN3Cc4cccc(Oc5ccccc5C(F)F)c4C3=O)cc2)cn1] | | 446.2 |

1H NMR (300 MHz, DMSO-d6) δ 3.85 (3H, s), 4.39 (2H, s), 4.62 (2H, s), 6.80 (1H, d, J = 7.6 Hz), 7.01-7.75 (11H, m), 7.82 (1H, d, J = 0.6 Hz), 8.10 (1H, s).

TABLE 1-11

| Ex. No. | compound name | structure | stereo-chemistry | MS |
|---|---|---|---|---|
| 127 | 2-(((2-(4-(1-methyl-1H-pyrazol-4-yl)benzyl)-3-oxo-2,3-dihydro-1H-isoindol-4-yl)oxy)methyl)benzonitrile | 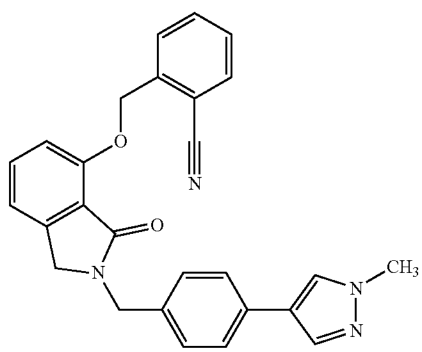 [SMILES: Cn1cc(-c2ccc(CN3Cc4cccc(OCc5ccccc5C#N)c4C3=O)cc2)cn1] | | 435.3 |

1H NMR (300 MHz, DMSO-d6) δ 3.84 (3H, s), 4.32 (2H, s), 4.65 (2H, s), 5.42 (2H, s), 7.15 (2H, d, J = 7.7 Hz), 7.25 (2H, d, J = 8.3 Hz), 7.50-7.62 (4H, m), 7.77-7.84 (2H, m), 7.89-7.98 (2H, m), 8.09 (1H, s).

| 128 | 2-((2-(3-bromobenzyl)-3-oxo-2,3-dihydro-1H-isoindol-4-yl)oxy)-3-fluorobenzonitrile | | | 437.0 439.0 |

1H NMR (300 MHz, DMSO-d6) δ 4.44 (2H, s), 4.69 (2H, s), 6.85 (1H, d, J = 8.1 Hz), 7.24-7.40 (3H, m), 7.43-7.61 (4H, m), 7.73-7.88 (2H, m).

TABLE 1-11-continued

| Ex. No. | compound name | structure | stereo-chemistry | MS |
|---|---|---|---|---|
| 129 | 2-(4-(1-methyl-1H-pyrazol-4-yl)benzyl)-7-(2-phenoxyethoxy)isoindolin-1-one | 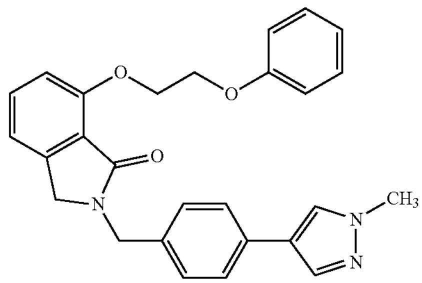 [SMILES: Cn1cc(-c2ccc(CN3Cc4cccc(OCCOc5ccccc5)c4C3=O)cc2)cn1] | | 440.1 |

1H NMR (300 MHz, DMSO-d6) δ 3.84 (3H, s), 4.29 (2H, s), 4.35 (2H, d, J = 4.9 Hz), 4.42-4.52 (2H, m), 4.62 (2H, s), 6.92-7.05 (3H, m), 7.10 (2H, d, J = 7.6 Hz), 7.19-7.37 (4H, m), 7.47-7.57 (3H, m), 7.81 (1H, s), 8.10 (1H, s).

| 130 | 3-((2-(4-(1-methyl-1H-pyrazol-4-yl)benzyl)-3-oxo-2,3-dihydro-1H-isoindol-4-yl)oxy)propanamide | | | 391.0 |

1H NMR (300 MHz, CDCl3) δ 1.58 (3H, brs), 1.74 (2H, td, J = 8.9, 6.0 Hz), 2.21-2.36 (1H, m), 2.44 (1H, dd, J = 9.3, 5.1 Hz), 3.94 (3H, s), 4.23 (1H, d, J = 15.1 Hz), 4.58 (1H, t, J = 3.8 Hz), 5.15 (2H, d, J = 15.1 Hz), 6.87 (2H, dd, J = 9.8, 7.9 Hz), 7.28-7.36 (2H, m), 7.37-7.46 (3H, m), 7.59 (1H, s), 7.72 (1H, s).

TABLE 1-12

| Ex. No. | compound name | structure | stereo-chemistry | MS |
|---|---|---|---|---|
| 131 | 3-fluoro-2-((2-(3-fluoro-4-(1-methyl-1H-pyrazol-4-yl)benzyl)-3-oxo-2,3-dihydro-1H-isoindol-4-yl)oxy)benzonitrile | 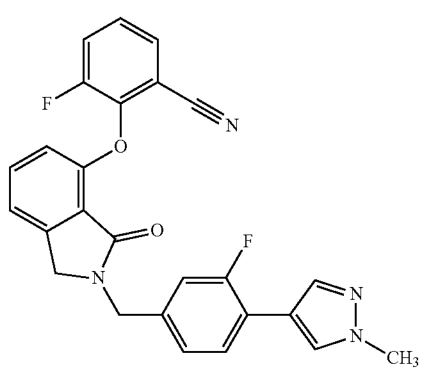 [SMILES: Cn1cc(-c2ccc(CN3Cc4cccc(Oc5c(F)cccc5C#N)c4C3=O)cc2F)cn1] | | 457.2 |

1H NMR (300 MHz, CDCl3) δ 3.96 (3H, s), 4.32 (2H, s), 4.75 (2H, s), 6.77 (1H, d, J = 8.3 Hz), 7.06-7.14 (2H, m), 7.17 (1H, d, J = 6.8 Hz), 7.23-7.32 (1H, m), 7.38-7.48 (2H, m), 7.49-7.55 (2H, m), 7.77 (1H, d, J = 2.6 Hz), 7.84 (1H, s).

TABLE 1-12-continued

| Ex. No. | compound name | structure | stereo-chemistry | MS |
|---|---|---|---|---|
| 132 | 3-fluoro-2-((2-(4-(1-methyl-1H-pyrazol-3-yl)benzyl)-3-oxo-2,3-dihydro-1H-isoindol-4-yl)oxy)benzonitrile | 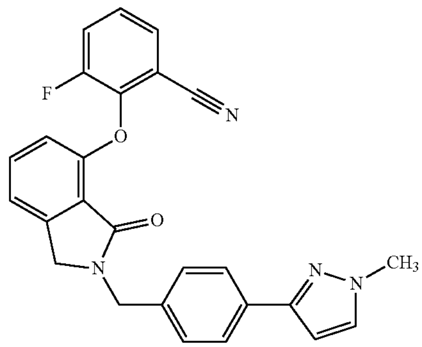 [SMILES: Cn1ccc(-c2ccc(CN3Cc4cccc(Oc5c(F)cccc5C#N)c4C3=O)cc2)n1] | | 439.2 |

1H NMR (300 MHz, CDCl3) δ 3.96 (3H, s), 4.28 (2H, s), 4.78 (2H, s), 6.53 (1H, d, J = 2.3 Hz), 6.78 (1H, d, J = 8.3 Hz), 7.14 (1H, d, J = 7.5 Hz), 7.22-7.31 (1H, m), 7.32-7.46 (5H, m), 7.50 (1H, dt, J = 7.8, 1.4 Hz), 7.77 (2H, d, J = 8.3 Hz).

| 133 | 2-((2-(3-chloro-4-(1-methyl-1H-pyrazol-4-yl)benzyl)-3-oxo-2,3-dihydro-1H-isoindol-4-yl)oxy)-3-fluorobenzonitrile | | | 473.1 |

1H NMR (300 MHz, CDCl3) δ 3.97 (3H, s), 4.32 (2H, s), 4.74 (2H, s), 6.78 (1H, d, J = 8.3 Hz), 7.17 (1H, d, J = 7.5 Hz), 7.21-7.32 (2H, m), 7.38-7.48 (4H, m), 7.48-7.54 (1H, m), 7.79 (2H, d, J = 2.6 Hz).

| 134 | 3-fluoro-2-((2-(4-(1H-imidazol-1-yl)benzyl)-3-oxo-2,3-dihydro-1H-isoindol-4-yl)oxy)benzonitrile | | | 425.2 |

1H NMR (300 MHz, CDCl3) δ 4.33 (2H, s), 4.82 (2H, s), 6.76 (1H, d, J = 8.3 Hz), 7.17 (1H, dd, J = 7.6, 0.6 Hz), 7.24 (1H, s), 7.26-7.34 (2H, m), 7.36-7.49 (6H, m), 7.49-7.54 (1H, m), 7.92 (1H, s).

TABLE 1-13

| Ex. No. | compound name | structure | stereo-chemistry | MS |
|---|---|---|---|---|
| 135 | 3-fluoro-2-((2-(3-fluoro-4-(1H-pyrazol-1-yl)benzyl)-3-oxo-2,3-dihydro-1H-isoindol-4-yl)oxy)benzonitrile | 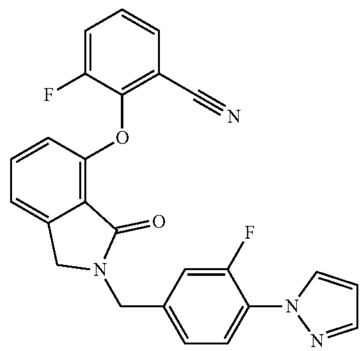 [SMILES: N#Cc1cccc(F)c1Oc1cccc2c1C(=O)N(Cc1ccc(-n3cccn3)c(F)c1)C2] | | 443.2 |

1H NMR (300 MHz, CDCl3) δ 4.32 (2H, s), 4.78 (2H, s), 6.48 (1H, dd, J = 2.6, 1.9 Hz), 6.77 (1H, d, J = 8.3 Hz), 7.15-7.32 (4H, m), 7.38-7.48 (2H, m), 7.50 (1H, dt, J = 7.8, 1.4 Hz), 7.74 (1H, d, J = 1.9 Hz), 7.89 (1H, t, J = 8.1 Hz), 7.99 (1H, t, J = 2.6 Hz).

| 136 | 3-fluoro-2-((2-((5-(1-methyl-1H-pyrazol-4-yl)pyridin-2-yl)methyl)-3-oxo-2,3-dihydro-1H-isoindol-4-yl)oxy)benzonitrile | | | 440.2 |

1H NMR (300 MHz, CDCl3) δ 3.97 (3H, s), 4.49 (2H, s), 4.89 (2H, s), 6.76 (1H, d, J = 7.9 Hz), 7.19 (1H, d, J = 7.5 Hz), 7.23-7.32 (1H, m), 7.34-7.53 (4H, m), 7.65 (1H, s), 7.72 (1H, dd, J = 8.1, 2.4 Hz), 7.77 (1H, s), 8.68 (1H, d, J = 1.5 Hz).

| 137 | 3-fluoro-2-((2-(4-(1-methyl-1H-pyrazol-5-yl)benzyl)-3-oxo-2,3-dihydro-1H-isoindol-4-yl)oxy)benzonitrile | | | 439.2 |

1H NMR (300 MHz, CDCl3) δ 3.90 (3H, s), 4.35 (2H, s), 4.82 (2H, s), 6.30 (1H, d, J = 1.9 Hz), 6.77 (1H, d, J = 7.9 Hz), 7.17 (1H, d, J = 7.5 Hz), 7.25-7.33 (1H, m), 7.38-7.48 (6H, m), 7.49-7.54 (2H, m).

TABLE 1-13-continued

| Ex. No. | compound name | structure | stereo-chemistry | MS |
|---|---|---|---|---|
| 138 | 2-((2-(2-chloro-4-(1H-pyrazol-1-yl)benzyl)-3-oxo-2,3-dihydro-1H-isoindol-4-yl)oxy)-3-fluorobenzonitrile | 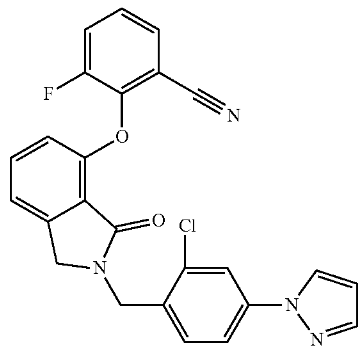 [SMILES: N#Cc1cccc(F)c1Oc1cccc2c1C(=O)N(Cc1ccc(-n3cccn3)cc1Cl)C2] | | 459.1 |

1H NMR (300 MHz, CDCl3) δ 4.39 (2H, s), 4.92 (2H, s), 6.46-6.50 (1H, m), 6.76 (1H, d, J = 8.3 Hz), 7.18 (1H, d, J = 7.2 Hz), 7.27-7.31 (1H, m), 7.37-7.57 (5H, m), 7.72 (1H, d, J = 1.5 Hz), 7.84 (1H, d, J = 2.3 Hz), 7.90 (1H, d, J = 2.3 Hz).

TABLE 1-14

| Ex. No. | compound name | structure | stereo-chemistry | MS |
|---|---|---|---|---|
| 139 | 3-fluoro-2-((2-(4-(3-furyl)benzyl)-3-oxo-2,3-dihydro-1H-isoindol-4-yl)oxy)benzonitrile | 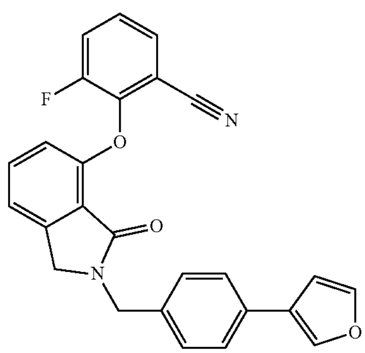 [SMILES: N#Cc1cccc(F)c1Oc1cccc2c1C(=O)N(Cc1ccc(-c3ccoc3)cc1)C2] | | 425.1 |

1H NMR (300 MHz, CDCl3) δ 4.29 (2H, s), 4.77 (2H, s), 6.70 (1H, dd, J = 1.8, 0.8 Hz), 6.77 (1H, d, J = 8.1 Hz), 7.15 (1H, d, J = 7.6 Hz), 7.24-7.36 (3H, m), 7.38-7.47 (3H, m), 7.47-7.53 (3H, m), 7.73 (1H, t, J = 1.1 Hz).

| 140 | 3-fluoro-2-((2-((5-(1-methyl-1H-pyrazol-4-yl)-2-furyl)methyl)-3-oxo-2,3-dihydro-1H-isoindol-4-yl)oxy)benzonitrile | | | 429.2 |

1H NMR (300 MHz, CDCl3) δ 1.25 (1.5H, t, J = 7.0 Hz), 3.68-3.79 (1H, m), 3.92 (3H, s), 4.40 (2H, s), 4.77 (2H, s), 6.26 (1H, d, J = 3.4 Hz), 6.34 (1H, d, J = 3.4 Hz), 6.76 (1H, d, J = 8.3 Hz), 7.18 (1H, d, J = 7.5 Hz), 7.22-7.31 (3H, m), 7.36-7.46 (2H, m), 7.50 (1H, dt, J = 7.9, 1.5 Hz), 7.61 (1H, s), 7.67 (1H, s).

TABLE 1-14-continued

| Ex. No. | compound name | structure | stereo-chemistry | MS |
|---|---|---|---|---|
| 141 | 3-fluoro-2-((2-(4-(2-furyl)benzyl)-3-oxo-2,3-dihydro-1H-isoindol-4-yl)oxy)benzonitrile | 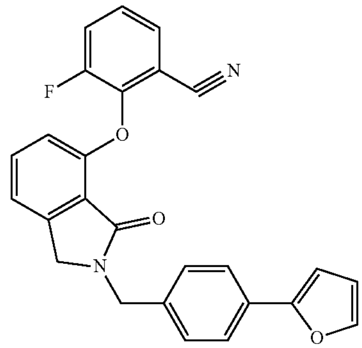 [SMILES: N#Cc1cccc(F)c1Oc1cccc2c1C(=O)N(Cc1ccc(-c3ccco3)cc1)C2] | | 425.1 |

1H NMR (300 MHz, CDCl3) δ 4.29 (2H, s), 4.77 (2H, s), 6.48 (1H, dd, J = 3.4, 1.9 Hz), 6.65 (1H, dd, J = 3.3, 0.7 Hz), 6.77 (1H, d, J = 8.3 Hz), 7.15 (1H, dd, J = 7.6, 0.6 Hz), 7.24-7.32 (1H, m), 7.34 (2H, d, J = 8.5 Hz), 7.38-7.48 (3H, m), 7.51 (1H, dt, J = 7.9, 1.4 Hz), 7.63-7.68 (2H, m).

| Ex. No. | compound name | structure | stereo-chemistry | MS |
|---|---|---|---|---|
| 142 | 3-fluoro-2-((2-(3-methoxy-4-(1H-pyrazol-1-yl)benzyl)-3-oxo-2,3-dihydro-1H-isoindol-4-yl)oxy)benzonitrile | | | 455.2 |

1H NMR (300 MHz, CDCl3) δ 3.87 (3H, s), 4.31 (2H, s), 4.78 (2H, s), 6.43 (1H, t, J = 2.1 Hz), 6.77 (1H, d, J = 8.3 Hz), 7.01 (1H, dd, J = 8.1, 1.7 Hz), 7.04 (1H, d, J = 1.5 Hz), 7.17 (1H, d, J = 7.5 Hz), 7.24-7.32 (1H, m), 7.38-7.47 (2H, m), 7.51 (1H, dt, J = 7.8, 1.4 Hz), 7.70 (2H, dd, J = 5.1, 3.2 Hz), 8.03 (1H, d, J = 2.6 Hz).

TABLE 1-15

| Ex. No. | compound name | structure | stereo-chemistry | MS |
|---|---|---|---|---|
| 143 | 3-fluoro-2-((3-oxo-2-(4-(1H-1,2,4-triazol-1-yl)benzyl)-2,3-dihydro-1H-isoindol-4-yl)oxy)benzonitrile | 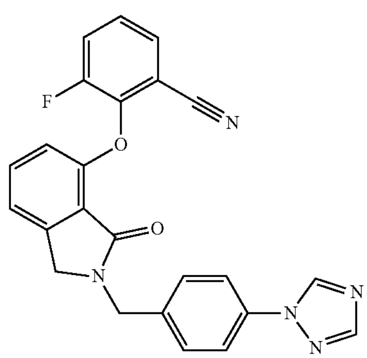 [SMILES: N#Cc1cccc(F)c1Oc1cccc2c1C(=O)N(Cc1ccc(-n3cncn3)cc1)C2] | | 426.2 |

1H NMR (300 MHz, CDCl3) δ 4.31 (2H, s), 4.82 (2H, s), 6.76 (1H, d, J = 8.3 Hz), 7.16 (1H, d, J = 7.5 Hz), 7.22-7.33 (1H, m), 7.38-7.53 (5H, m), 7.63-7.70 (2H, m), 8.10 (1H, s), 8.54 (1H, s).

TABLE 1-15-continued

| Ex. No. | compound name | structure | stereo-chemistry | MS |
|---|---|---|---|---|
| 144 | 3-fluoro-2-((3-oxo-2-(4-(2-oxopyrrolidin-1-yl)benzyl)-2,3-dihydro-1H-isoindol-4-yl)oxy)benzonitrile | 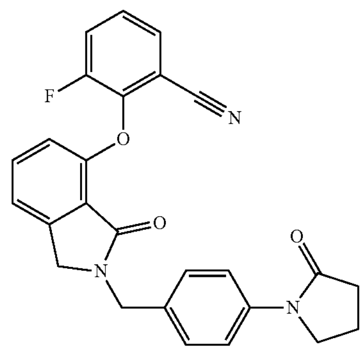 [SMILES: N#Cc1cccc(F)c1Oc1cccc2c1C(=O)N(Cc1ccc(N3CCCC3=O)cc1)C2] | | 442.2 |

1H NMR (300 MHz, CDCl3) δ 2.17 (2H, quin, J = 7.6 Hz), 2.62 (2H, t, J = 8.1 Hz), 3.86 (2H, t, J = 7.0 Hz), 4.26 (2H, s), 4.74 (2H, s), 6.76 (1H, d, J = 7.9 Hz), 7.14 (1H, d, J = 7.5 Hz), 7.22-7.36 (3H, m), 7.37-7.46 (2H, m), 7.50 (1H, dt, J = 7.8, 1.4 Hz), 7.56-7.63 (2H, m).

| 145 | 3-fluoro-2-((3-oxo-2-(4-(2-thienyl)benzyl)-2,3-dihydro-1H-isoindol-4-yl)oxy)benzonitrile | | | 441.2 |

1H NMR (300 MHz, CDCl3) δ 4.30 (2H, s), 4.77 (2H, s), 6.77 (1H, d, J = 8.3 Hz), 7.08 (1H, dd, J = 5.1, 3.6 Hz), 7.15 (1H, d, J = 7.5 Hz), 7.23-7.34 (4H, m), 7.35 (1H, s), 7.38-7.46 (2H, m), 7.51 (1H, dt, J = 7.6, 1.5 Hz), 7.57-7.62 (2H, m).

| 146 | 3-fluoro-2-((3-oxo-2-(4-(3-thienyl)benzyl)-2,3-dihydro-1H-isoindol-4-yl)oxy)benzonitrile | | | 441.2 |

1H NMR (300 MHz, CDCl3) δ 4.30 (2H, s), 4.78 (2H, s), 6.77 (1H, d, J = 8.3 Hz), 7.15 (1H, d, J = 7.5 Hz), 7.24-7.32 (1H, m), 7.33-7.47 (7H, m), 7.51 (1H, dt, J = 7.8, 1.4 Hz), 7.56-7.61 (2H, m).

TABLE 1-16

| Ex. No. | compound name | structure | stereo-chemistry | MS |
|---|---|---|---|---|
| 147 | 3-fluoro-2-((2-((4'-methoxybiphenyl-4-yl)methyl)-3-oxo-2,3-dihydro-1H-isoindol-4-yl)oxy)benzonitrile | 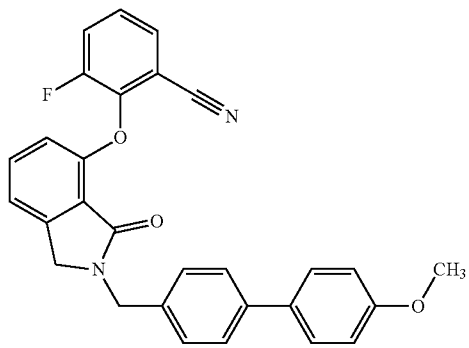 [SMILES: COc1ccc(-c2ccc(CN3Cc4cccc(Oc5c(F)cccc5C#N)c4C3=O)cc2)cc1] | | 465.2 |

1H NMR (300 MHz, CDCl3) δ 3.85 (3H, s), 4.30 (2H, s), 4.78 (2H, s), 6.76 (1H, d, J = 8.3 Hz), 6.94-7.00 (2H, m), 7.15 (1H, d, J = 6.8 Hz), 7.22-7.31 (1H, m), 7.33-7.46 (4H, m), 7.47-7.55 (5H, m).

| 148 | 2-((2-(4-(3,5-dimethyl-1,2-oxazol-4-yl)benzyl)-3-oxo-2,3-dihydro-1H-isoindol-4-yl)oxy)-3-fluorobenzonitrile | | | 454.2 |

1H NMR (300 MHz, CDCl3) δ 2.26 (3H, s), 2.40 (3H, s), 4.34 (2H, s), 4.80 (2H, s), 6.76 (1H, d, J = 7.9 Hz), 7.16 (1H, d, J = 7.5 Hz), 7.21-7.25 (2H, m), 7.27-7.32 (1H, m), 7.36-7.47 (4H, m), 7.50 (1H, dt, J = 7.6, 1.5 Hz).

| 149 | 3-fluoro-2-((3-oxo-2-(4-(pyrimidin-5-yl)benzyl)-2,3-dihydro-1H-isoindol-4-yl)oxy)benzonitrile | | | 437.0 |

1H NMR (400 MHz, DMSO-d6) δ 4.46 (2H, s), 4.76 (2H, s), 6.85 (1H, d, J = 8.31 Hz), 7.35 (1H, d, J = 7.58 Hz), 7.40-7.62 (4H, m), 7.76-7.91 (4H, m), 9.08-9.24 (3H, m).

TABLE 1-16-continued

| Ex. No. | compound name | structure | stereo-chemistry | MS |
|---|---|---|---|---|
| 150 | 2-((2-(4-(2,4-dimethyl-1,3-thiazol-5-yl)benzyl)-3-oxo-2,3-dihydro-1H-isoindol-4-yl)oxy)-3-fluorobenzonitrile | 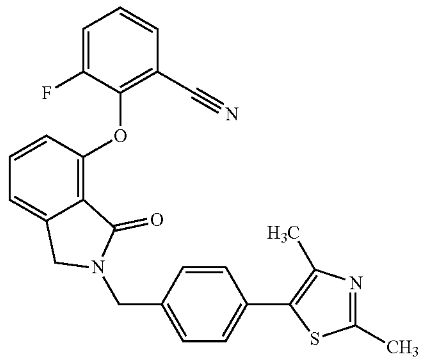 [SMILES: Cc1nc(C)c(-c2ccc(CN3Cc4cccc(Oc5c(F)cccc5C#N)c4C3=O)cc2)s1] | | 470.1 |

1H NMR (400 MHz, DMSO-d6) δ 2.37 (3H, s), 2.61 (3H, s), 4.45 (2H, s), 4.72 (2H, s), 6.84 (1H, d, J = 8.31 Hz), 7.26-7.41 (3H, m), 7.41-7.58 (4H, m), 7.74-7.89 (2H, m).

TABLE 1-17

| Ex. No. | compound name | structure | stereo-chemistry | MS |
|---|---|---|---|---|
| 151 | 6-bromo-7-((trans-2-hydroxycyclohexyl)oxy)-2-(4-(1-methyl-1H-pyrazol-4-yl)benzyl)isoindolin-1-one | 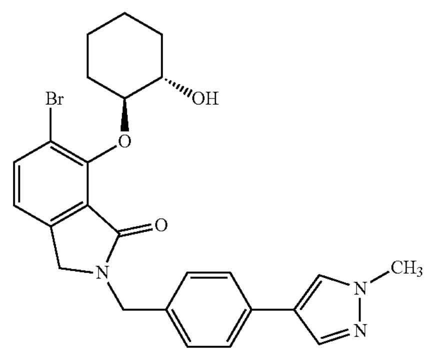 [SMILES: Cn1cc(-c2ccc(CN3Cc4ccc(Br)c(O[C@H]5CCCC[C@@H]5O)c4C3=O)cc2)cn1] | racemate | 496.1 498.1 |

1H NMR (300MHz, DMSO-d6) δ 1.11-1.30 (3H, m), 1.48-1.71 (3H, m), 1.87-2.08 (2H, m), 3.60-3.73 (1H, m), 3.85 (3H, s), 4.31 (2H, s), 4.41-4.52 (1H, m), 4.68 (2H, s), 4.96 (1H, d, J = 5.1 Hz), 7.15 (1H, d, J = 8.1 Hz), 7.27 (2H, d, J = 8.3 Hz), 7.54 (2H, d, J = 8.3 Hz), 7.77 (1H, d, J = 7.9 Hz), 7.83 (1H, d, J = 0.6 Hz), 8.11 (1H, s).

| 152 | 2-((2-((6-(1,3-dimethyl-1H-pyrazol-4-yl)pyridin-3-yl)methyl)-3-oxo-2,3-dihydro-1H-isoindol-4-yl)oxy)-3-fluorobenzonitrile | | | 454.2 |

1H NMR (300 MHz, CDCl3) δ 2.52 (3H, s), 3.88 (3H, s), 4.32 (2H, s), 4.77 (2H, s), 6.76 (1H, d, J = 8.3 Hz), 7.17 (1H, d, J = 7.2 Hz), 7.24-7.33 (1H, m), 7.39-7.47 (3H, m), 7.51 (1H, dt, J = 7.9, 1.5 Hz), 7.69 (1H, dd, J = 8.1, 2.4 Hz), 7.80 (1H, s), 8.54 (1H, d, J = 1.9 Hz).

TABLE 1-17-continued

| Ex. No. | compound name | structure | stereo-chemistry | MS |
|---|---|---|---|---|
| 153 | 3-fluoro-2-((3-oxo-2-(4-(1,2-thiazol-4-yl)benzyl)-2,3-dihydro-1H-isoindol-4-yl)oxy)benzonitrile | 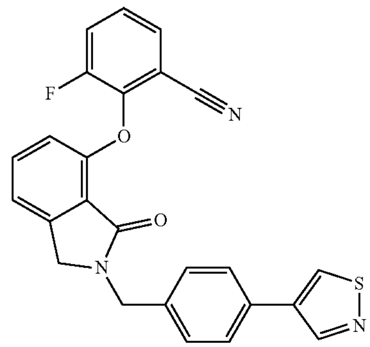 [SMILES: N#Cc1cccc(F)c1Oc1cccc2c1C(=O)N(Cc1ccc(-c3cnsc3)cc1)C2] | | 442.1 |

1H NMR (300 MHz, CDCl3) δ 4.31 (2H, s), 4.80 (2H, s), 6.76 (1H, d, J = 7.9 Hz), 7.15 (1H, d, J = 7.5 Hz), 7.23-7.32 (1H, m), 7.38-7.46 (4H, m), 7.50 (1H, dt, J = 7.8, 1.4 Hz), 7.55-7.61 (2H, m), 8.70 (1H, s), 8.76 (1H, s).

| 154 | 3-fluoro-2-((3-oxo-2-(4-(1,2-thiazol-5-yl)benzyl)-2,3-dihydro-1H-isoindol-4-yl)oxy)benzonitrile | | | 442.1 |

1H NMR (300 MHz, CDCl3) δ 4.32 (2H, s), 4.81 (2H, s), 6.77 (1H, d, J = 8.3 Hz), 7.16 (1H, d, J = 7.5 Hz), 7.25-7.33 (1H, m), 7.39-7.47 (5H, m), 7.51 (1H, dt, J = 7.8, 1.4 Hz), 7.59 (1H, s), 7.62 (1H, s), 8.48 (1H, d, J = 1.9 Hz).

TABLE 1-18

| Ex. No. | compound name | structure | stereo-chemistry | MS |
|---|---|---|---|---|
| 155 | 3-fluoro-2-((3-oxo-2-(4-(pyridazin-4-yl)benzyl)-2,3-dihydro-1H-isoindol-4-yl)oxy)benzonitrile | 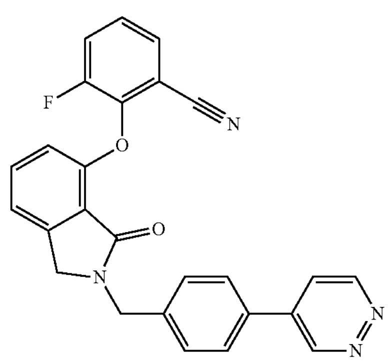 [SMILES: N#Cc1cccc(F)c1Oc1cccc2c1C(=O)N(Cc1ccc(-c3ccnnc3)cc1)C2] | | 437.2 |

1H NMR (300 MHz, CDCl3) δ 4.34 (2H, s), 4.85 (2H, s), 6.77 (1H, d, J = 8.3 Hz), 7.17 (1H, d, J = 7.2 Hz), 7.25-7.34 (1H, m), 7.40-7.48 (2H, m), 7.52 (3H, d, J = 7.9 Hz), 7.60-7.70 (3H, m), 9.24 (1H, dd, J = 5.3, 1.1 Hz), 9.46 (1H, dd, J = 2.3, 1.1 Hz).

TABLE 1-18-continued

| Ex. No. | compound name | structure | stereo-chemistry | MS |
|---|---|---|---|---|
| 156 | 3-fluoro-2-((2-(4-(6-methylpyridin-3-yl)benzyl)-3-oxo-2,3-dihydro-1H-isoindol-4-yl)oxy)benzonitrile | 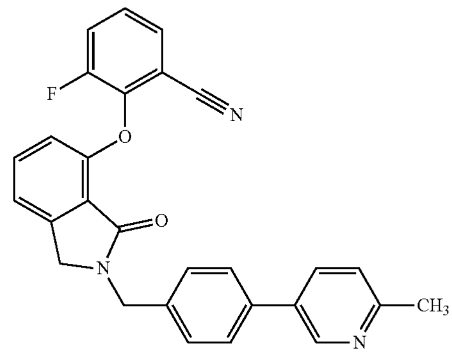 [SMILES: Cc1ccc(-c2ccc(CN3Cc4cccc(Oc5c(F)cccc5C#N)c4C3=O)cc2)cn1] | | 450.2 |

1H NMR (300 MHz, CDCl3) δ 2.61 (3H, s), 4.32 (2H, s), 4.82 (2H, s), 6.77 (1H, d, J = 8.3 Hz), 7.16 (1H, d, J = 7.2 Hz), 7.20-7.33 (2H, m), 7.37-7.47 (4H, m), 7.48-7.58 (3H, m), 7.76 (1H, dd, J = 8.1, 2.4 Hz), 8.72 (1H, d, J = 1.9 Hz).

| 157 | 3-fluoro-2-((2-(4-(6-methoxypyridin-3-yl)benzyl)-3-oxo-2,3-dihydro-1H-isoindol-4-yl)oxy)benzonitrile | | | 466.2 |

1H NMR (300 MHz, CDCl3) δ 3.98 (3H, s), 4.31 (2H, s), 4.80 (2H, s), 6.76 (1H, d, J = 8.3 Hz), 6.81 (1H, dd, J = 8.7, 0.8 Hz), 7.15 (1H, d, J = 7.5 Hz), 7.22-7.31 (1H, m), 7.37-7.46 (4H, m), 7.47-7.53 (3H, m), 7.77 (1H, dd, J = 8.7, 2.6 Hz), 8.37 (1H, d, J = 2.6 Hz).

| 158 | 3,5-difluoro-2-((3-oxo-2-(4-(1H-pyrazol-1-yl)benzyl)-2,3-dihydro-1H-isoindol-4-yl)oxy)benzonitrile | | | 443.2 |

1H NMR (300 MHz, CDCl3) δ 4.30 (2H, s), 4.79 (2H, s), 6.47 (1H, t, J = 2.1 Hz), 6.78 (1H, d, J = 8.3 Hz), 7.14-7.29 (3H, m), 7.39-7.48 (3H, m), 7.66-7.71 (2H, m), 7.73 (1H, d, J = 1.9 Hz), 7.92 (1H, d, J = 2.6 Hz).

TABLE 1-19

| Ex. No. | compound name | structure | stereo-chemistry | MS |
|---|---|---|---|---|
| 159 | 7-(2-fluoro-6-nitrophenoxy)-2-(4-(1H-pyrazol-1-yl)benzyl)isoindolin-1-one | 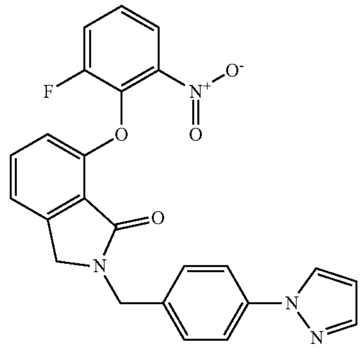 [SMILES: O=C1c2c(cccc2Oc2c(F)cccc2[N+](=O)[O-])CN1Cc1ccc(-n2cccn2)cc1] | | 445.2 |

1H NMR (300 MHz, CDCl3) δ 4.30 (2H, s), 4.81 (2H, s), 6.48 (1H, dd, J = 2.6, 1.9 Hz), 6.70 (1H, d, J = 8.3 Hz), 7.12 (1H, d, J = 7.5 Hz), 7.32-7.52 (5H, m), 7.66-7.72 (2H, m), 7.73 (1H, d, J = 1.5 Hz), 7.87 (1H, dt, J = 8.3, 1.7 Hz), 7.93 (1H, d, J = 3.0 Hz).

| 160 | 7-(2-chloro-6-fluorophenoxy)-2-(4-(1H-pyrazol-1-yl)benzyl)isoindolin-1-one | | | 434.2 |

1H NMR (300 MHz, CDCl3) δ 4.30 (2H, s), 4.84 (2H, s), 6.46-6.50 (1H, m), 6.53 (1H, d, J = 8.3 Hz), 7.07 (1H, d, J = 7.5 Hz), 7.10-7.23 (2H, m), 7.28-7.39 (2H, m), 7.44-7.49 (2H, m), 7.66-7.72 (2H, m), 7.73 (1H, d, J = 1.5 Hz), 7.91-7.94 (1H, m).

| 161 | 3-fluoro-2-((3-oxo-2-((6-(1H-pyrazol-1-yl)pyridin-3-yl)methyl)-2,3-dihydro-1H-isoindol-4-yl)oxy)benzonitrile | | | 426.2 |

1H NMR (300 MHz, CDCl3) δ 4.33 (2H, s), 4.80 (2H, s), 6.47 (1H, dd, J = 2.6, 1.5 Hz), 6.77 (1H, d, J = 8.3 Hz), 7.17 (1H, d, J = 7.5 Hz), 7.24-7.33 (1H, m), 7.38-7.48 (2H, m), 7.51 (1H, dt, J = 7.9, 1.5 Hz), 7.73-7.75 (1H, m), 7.83 (1H, dd, J = 8.5, 2.4 Hz), 7.98 (1H, d, J = 8.3 Hz), 8.39 (1H, d, J = 1.9 Hz), 8.55 (1H, dd, J = 2.6, 0.8 Hz).

TABLE 1-19-continued

| Ex. No. | compound name | structure | stereo-chemistry | MS |
|---|---|---|---|---|
| 162 | 3-fluoro-2-((2-((2'-methoxy-3,4'-bipyridin-6-yl)methyl)-3-oxo-2,3-dihydro-1H-isoindol-4-yl)oxy)benzonitrile | 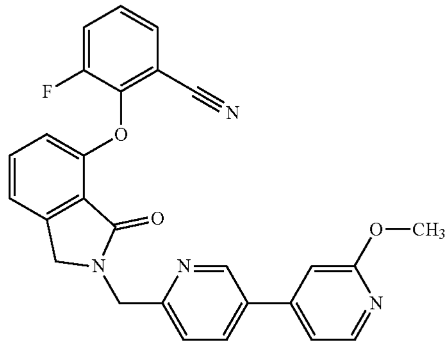 [SMILES: COc1cc(-c2ccc(CN3Cc4cccc(Oc5c(F)cccc5C#N)c4C3=O)nc2)ccn1] | | 467.2 |

1H NMR (300 MHz, CDCl3) δ 4.00 (3H, s), 4.53 (2H, s), 4.95 (2H, s), 6.76 (1H, d, J = 8.3 Hz), 6.94 (1H, s), 7.08 (1H, dd, J = 5.3, 1.5 Hz), 7.20 (1H, d, J = 7.5 Hz), 7.28-7.32 (1H, m), 7.38-7.54 (4H, m), 7.89 (1H, dd, J = 8.1, 2.4 Hz), 8.26 (1H, dd, J = 5.3, 0.8 Hz), 8.80 (1H, dd, J = 2.3, 0.8 Hz).

TABLE 1-20

| Ex. No. | compound name | structure | stereo-chemistry | MS |
|---|---|---|---|---|
| 163 | 3-fluoro-2-((2-((2'-methyl-3,4'-bipyridin-6-yl)methyl)-3-oxo-2,3-dihydro-1H-isoindol-4-yl)oxy)benzonitrile | 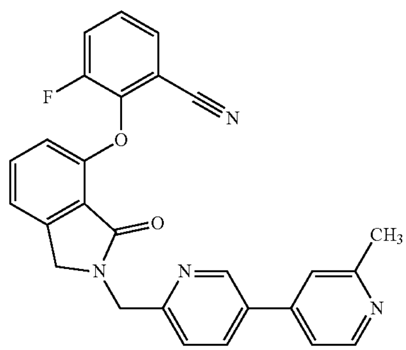 [SMILES: Cc1cc(-c2ccc(CN3Cc4cccc(Oc5c(F)cccc5C#N)c4C3=O)nc2)ccn1] | | 451.2 |

1H NMR (300 MHz, CDCl3) δ 2.64 (3H, s), 4.52 (2H, s), 4.95 (2H, s), 6.75 (1H, d, J = 8.3 Hz), 7.19 (1H, dd, J = 7.5, 0.8 Hz), 7.23-7.31 (2H, m), 7.34 (1H, s), 7.37-7.53 (4H, m), 7.85-7.92 (1H, m), 8.59 (1H, d, J = 4.9 Hz), 8.80 (1H, d, J = 1.9 Hz).

| 164 | 7-(2-chloro-6-fluorophenoxy)-2-((6-(1-methyl-1H-pyrazol-4-yl)pyridin-3-yl)methyl)isoindolin-1-one | | | 449.1 |

1H NMR (300 MHz, CDCl3) δ 3.97 (3H, s), 4.31 (2H, s), 4.81 (2H, s), 6.53 (1H, d, J = 8.3 Hz), 7.07 (1H, d, J = 7.5 Hz), 7.10-7.24 (2H, m), 7.28-7.39 (2H, m), 7.45 (1H, d, J = 8.3 Hz), 7.73 (1H, dd, J = 8.3, 2.3 Hz), 7.94 (2H, d, J = 8.3 Hz), 8.54 (1H, d, J = 1.5 Hz).

TABLE 1-20-continued

| Ex. No. | compound name | structure | stereo-chemistry | MS |
|---|---|---|---|---|
| 165 | 7-(2-chloro-6-fluorophenoxy)-2-((5-(1-methyl-1H-pyrazol-4-yl)pyridin-2-yl)methyl)isoindolin-1-one | 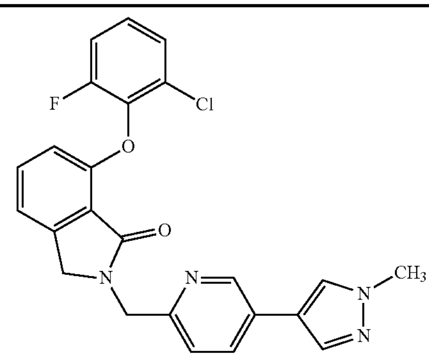 | | 449.2 |

1H NMR (300 MHz, CDCl3) δ 3.98 (3H, s), 4.48 (2H, s), 4.93 (2H, s), 6.52 (1H, d, J = 8.3 Hz), 7.06-7.23 (3H, m), 7.27-7.32 (1H, m), 7.36 (1H, t, J = 7.7 Hz), 7.43 (1H, d, J = 7.9 Hz), 7.66 (1H, s), 7.73 (1H, dd, J = 8.3, 2.3 Hz), 7.78 (1H, d, J = 0.8 Hz), 8.69 (1H, dd, J = 2.3, 0.8 Hz).

| 166 | 3-fluoro-2-((2-((5-(1-methyl-1H-pyrazol-4-yl)-2-thienyl)methyl)-3-oxo-2,3-dihydro-1H-isoindol-4-yl)oxy)benzamide | | | 463.2 |

1H NMR (300MHz, DMSO-d6) δ 3.82 (3H, s), 4.47 (2H, s), 4.85 (2H, s), 6.59 (1H, dd, J = 8.1, 1.7 Hz), 6.99-7.05 (2H, m), 7.26 (1H, d, J = 7.4 Hz), 7.38-7.51 (2H, m), 7.53-7.71 (4H, m), 7.81 (1H, s), 7.99 (1H, s).

TABLE 1-21

| Ex. No. | compound name | structure | stereo-chemistry | MS |
|---|---|---|---|---|
| 167 | 7-((trans-2-fluorocyclohexyl)oxy)-2-(4-(1-methyl-1H-pyrazol-4-yl)benzyl)isoindolin-1-one | 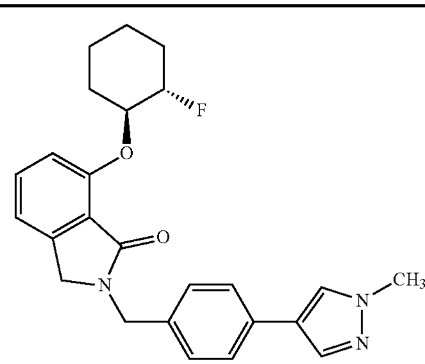 | racemate | 420.2 |

1H NMR (300 MHz, DMSO-d6) δ 1.31-1.73 6H, m), 2.02-2.19 (2H, m), 3.85 (3H, s), 4.28 (2H, s), 4.51-4.84 (4H, m), 7.03-7.16 (2H, m), 7.25 (2H, d, J = 8.3 Hz), 7.40-7.58 (3H, m), 7.81 (1H, s), 8.09 (1H, s).

TABLE 1-21-continued

| Ex. No. | compound name | structure | stereo-chemistry | MS |
|---|---|---|---|---|
| 168 | 2-((2-(4-(3-(benzyloxy)-1H-pyrazol-1-yl)benzyl)-3-oxo-2,3-dihydro-1H-isoindol-4-yl)oxy)-3-fluorobenzonitrile | 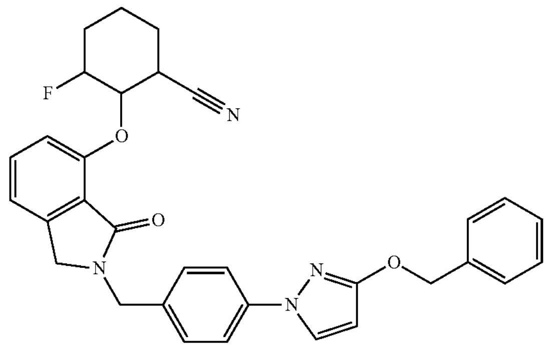 [SMILES: N#CC1CCCC(F)C1Oc1cccc2c1C(=O)N(Cc1ccc(-n3ccc(OCc4ccccc4)n3)cc1)C2] | | 531.3 |

1H NMR (300 MHz, DMSO-d6) δ 4.42 (2H, s), 4.70 (2H, s), 5.25 (2H, s), 6.07 (1H, d, J = 2.6 Hz), 6.84 (1H, d, J = 8.3 Hz), 7.31-7.43 (6H, m), 7.45-7.57 (4H, m), 7.70-7.86 (4H, m), 8.32 (1H, d, J = 2.6 Hz).

| 169 | 2-((2-(4-(5-(benzyloxy)-1H-pyrazol-1-yl)benzyl)-3-oxo-2,3-dihydro-1H-isoindol-4-yl)oxy)-3-fluorobenzonitrile | | | 531.3 |

1H NMR (300 MHz, LMSC-d6) δ 4.43 (2H, s), 4.71 (2H, s), 5.24 (2H, s), 5.97 (1H, d, J = 1.9 Hz), 6.84 (1H, d, J = 8.1 Hz), 7.31-7.57 (11H, m), 7.67 (2H, d, J = 8.7 Hz), 7.74-7.86 (2H, m).

| 170 | 3-fluoro-2-((2-(4-(3-hydroxy-1H-pyrazol-1-yl)benzyl)-3-oxo-2,3-dihydro-1H-isoindol-4-yl)oxy)benzonitrile | | | 441.2 |

1H NMR (300 MHz, DMSO-d6) δ 4.42 (2H, s), 4.69 (2H, s), 5.80 (1H, d, J = 2.6 Hz), 6.84 (1H, d, J = 8.3 Hz), 7.31-7.40 (3H, m), 7.45-7.57 (2H, m), 7.66 (2H, d, J = 8.7 Hz), 7.75-7.87 (2H, m), 8.19 (1H, d, J = 2.6 Hz), 10.10-10.33 (1H, m).

TABLE 1-22

| Ex. No. | compound name | structure | stereo-chemistry | MS |
|---|---|---|---|---|
| 171 | 3-fluoro-2-((2-(4-(5-hydroxy-1H-pyrazol-1-yl)benzyl)-3-oxo-2,3-dihydro-1H-isoindol-4-yl)oxy)benzonitrile | 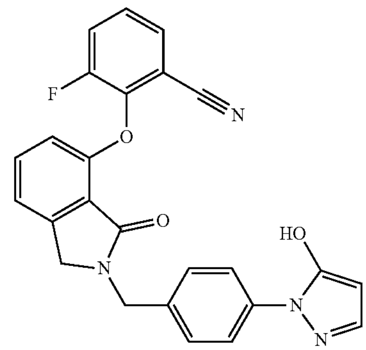 [SMILES: N#Cc1cccc(F)c1Oc1cccc2c1C(=O)N(Cc1ccc(-n3nccc3O)cc1)C2] | | 441.2 |

1H NMR (300 MHz, DMSO-d6) δ 4.43 (2H, s), 4.71 (2H, s), 5.50 (1H, s), 6.84 (1H, d, J = 7.9 Hz), 7.28-7.42 (4H, m), 7.44-7.59 (2H, m), 7.66-7.88 (4H, m), 11.64 (1H, brs).

| 172 | 3-fluoro-2-((2-(4-(3-methoxy-1H-pyrazol-1-yl)benzyl)-3-oxo-2,3-dihydro-1H-isoindol-4-yl)oxy)benzonitrile | | | 455.2 |

1H NMR (300 MHz, DMSO-d6) δ 3.87 (3H, s), 4.42 (2H, s), 4.69 (2H, s), 6.01 (1H, d, J = 2.6 Hz), 6.84 (1H, d, J = 8.3 Hz), 7.30-7.42 (3H, m), 7.44-7.58 (2H, m), 7.71 (2H, d, J = 8.5 Hz), 7.76-7.86 (2H, m), 8.31 (1H, d, J = 2.6 Hz).

| 173 | 3-fluoro-2-((2-(4-(5-methoxy-1H-pyrazol-1-yl)benzyl)-3-oxo-2,3-dihydro-1H-isoindol-4-yl)oxy)benzonitrile | | | 455.2 |

1H NMR (300 MHz, DMSO-d6) δ 3.92 (3H, s), 4.44 (2H, s), 4.72 (2H, s), 5.88 (1H, d, J = 1.9 Hz), 6.84 (1H, d, J = 8.3 Hz), 7.32-7.43 (3H, m), 7.45-7.58 (3H, m), 7.64 (2H, d, J = 8.5 Hz), 7.75-7.87 (2H, m).

TABLE 1-22-continued

| Ex. No. | compound name | structure | stereo-chemistry | MS |
|---|---|---|---|---|
| 174 | 2-(4-(1-methyl-1H-pyrazol-4-yl)benzyl)-7-(((2S)-tetrahydrofuran-2-yl)methoxy)isoindolin-1-one | 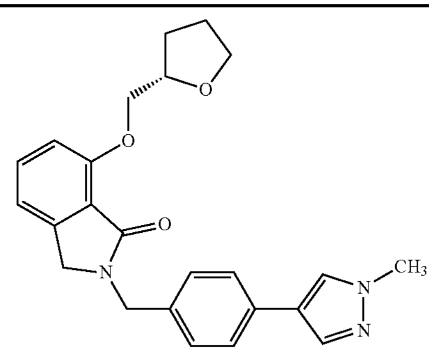 | S | 404.2 |

1H NMR (300 MHz, DMSO-d6) δ 1.75-1.91 (2H, m), 1.95-2.09 (2H, m), 3.61-3.74 (1H, m), 3.79-3.91 (4H, m), 4.02-4.13 (2H, m), 4.16-4.24 (1H, m), 4.28 (2H, s), 4.63(2H, s), 7.04 (2H, dd, J = 12.4, 7.8 Hz), 7.24 (2H, d, J = 8.1 Hz), 7.42-7.57 (3H, m), 7.82 (1H, s), 8.09 (1H, s).

TABLE 1-23

| Ex. No. | compound name | structure | stereo-chemistry | MS |
|---|---|---|---|---|
| 175 | 7-(4-methoxyphenoxy)-2-(4-(1-methyl-1H-pyrazol-4-yl)benzyl)isoindolin-1-one | 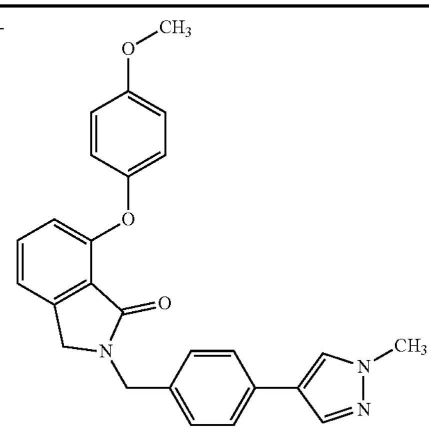 | | 426.2 |

1H NMR (300MHz, DMSO-d6) δ 3.76 (3H, s), 3.85 (3H, s), 4.36 (2H, s), 4.65 (2H, s), 6.69 (1H, d, J = 7.9 Hz), 6.95-7.07 (4H, m), 7.18-7.30 (3H, m), 7.43-7.50 (1H, m), 7.54 (2H, d, J = 8.3 Hz), 7.83 (1H, d, J = 0.6 Hz), 8.10 (1H, s).

| 176 | 7-(3-methoxyphenoxy)-2-(4-(1-methyl-1H-pyrazol-4-yl)benzyl)isoindolin-1-one | | | 426.2 |

1H NMR (300MHz, DMSO-d6) δ 3.75 (3H, s), 3.85 (3H, s), 4.38 (2H, s), 4.64 (2H, s), 6.49-6.66 (2H, m), 6.73 (1H, d, J = 7.9 Hz), 6.89 (1H, d, J = 7.9 Hz), 7.28 (4H, dd, J = 12.6, 8.1 Hz), 7.53 (3H, d, J = 7.2 Hz), 7.83 (1H, s), 8.11 (1H, s).

TABLE 1-23-continued

| Ex. No. | compound name | structure | stereo-chemistry | MS |
|---|---|---|---|---|
| 177 | 7-((1-azabicyclo[2.2.1]hept-2-yl)methoxy)-2-(4-(1H-pyrazol-1-yl)benzyl)isoindolin-1-one | 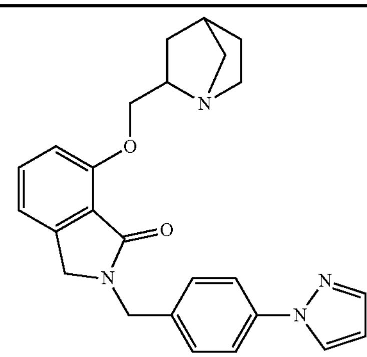 | racemate, single diastereomer | 415.3 |

1H NMR (300 MHz, DMSO-d6) δ 1.30-1.43 (1H, m), 1.53-1.82 (3H, m), 2.54-2.76 (2H, m), 2.81-3.06 (2H, m), 3.36-3.48 (2H, m), 4.15 (2H, d, J = 4.7 Hz), 4.34 (2H, s), 4.71 (2H, s), 6.48-6.57 (1H, m), 7.06 (1H, d, J = 8.5 Hz), 7.13 (1H, d, J = 7.2 Hz), 7.38 (2H, d, J = 8.7 Hz), 7.48-7.57 (1H, m), 7.73 (1H, d, J = 1.5 Hz), 7.82 (2H, d, J = 8.5 Hz), 8.46 (1H, d, J = 2.5 Hz).

| Ex. No. | compound name | structure | stereo-chemistry | MS |
|---|---|---|---|---|
| 178 | 4-(2-chloro-6-fluorophenoxy)-2-(4-(1H-pyrazol-1-yl)benzyl)-1,2-dihydro-3H-pyrrolo[3,4-c]pyridin-3-one | | | 435.1 |

1H NMR (300 MHz, DMSO-d6) δ 4.53 (2H, s), 4.76 (2H, s), 6.54 (1H, t, J = 2.1 Hz), 7.35-7.52 (6H, m), 7.74 (1H, d, J = 1.5 Hz), 7.85 (2H, d, J = 8.7 Hz), 8.21 (1H, d, J = 5.3 Hz), 8.49 (1H, d, J = 2.3 Hz).

TABLE 1-24

| Ex. No. | compound name | structure | stereo-chemistry | MS |
|---|---|---|---|---|
| 179 | 4-methyl-2-(4-(1-methyl-1H-pyrazol-4-yl)benzyl)-7-((tetrahydrofuran-2-yl)methoxy)-2,3-dihydro-1H-isoindol-1-one | 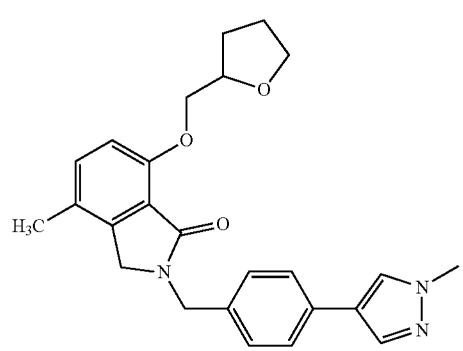 | | 418.3 |

1H NMR (300 MHz, DMSO-d6) δ 1.74-1.89 (2H, m), 1.91-2.08 (2H, m), 2.16 (3H, s), 3.61-3.72 (1H, m), 3.79-3.89 (4H, m), 4.01-4.08 (2H, m), 4.14-4.26 (3H, m), 4.64 (2H, s), 6.94 (1H, d, J = 8.3 Hz), 7.20-7.30 (3H, m), 7.53 (2H, d, J = 8.1 Hz), 7.82 (1H, d, J = 0.4 Hz), 8.09 (1H, s).

TABLE 1-24-continued

| Ex. No. | compound name | structure | stereo-chemistry | MS |
|---|---|---|---|---|
| 180 | 2-(4-(1-methyl-1H-pyrazol-4-yl)benzyl)-4-phenyl-7-((tetrahydrofuran-2-yl)methoxy)-2,3-dihydro-1H-isoindol-1-one | | | 480.3 |

1H NMR (300 MHz, DMSO-d6) δ 1.77-1.93 (2H, m), 1.95-2.12 (2H, m), 3.65-3.74 (1H, m), 3.81-3.92 (4H, m), 4.10-4.16 (2H, m), 4.19-4.29 (1H, m), 4.39 (2H, s), 4.63 (2H, s), 7.17 (1H, d, J = 8.7 Hz), 7.24 (2H, d, J = 8.3 Hz), 7.30-7.57 (8H, m), 7.79 (1H, s), 8.07 (1H, s).

| Ex. No. | compound name | structure | stereo-chemistry | MS |
|---|---|---|---|---|
| 181 | 2-(4-(1-methyl-1H-pyrazol-4-yl)benzyl)-7-(3-(1H-pyrrol-1-yl)propoxy)isoindolin-1-one | 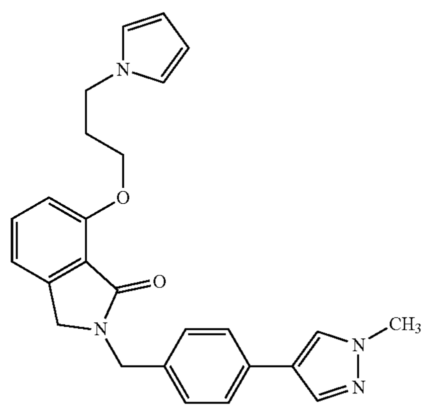 [SMILES: Cn1cc(-c2ccc(CN3Cc4cccc(OCCCn5cccc5)c4C3=O)cc2)cn1] | | 427.1 |
| 182 | 2-(4-(1-methyl-1H-pyrazol-4-yl)benzyl)-7-(2-oxo-2-phenylethoxy)isoindolin-1-one | 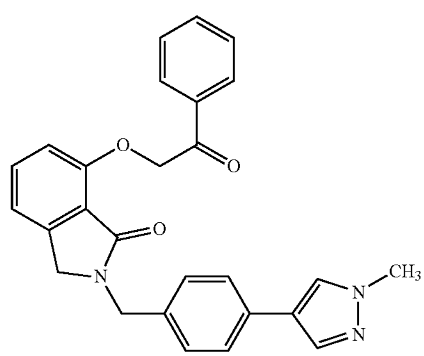 [SMILES: Cn1cc(-c2ccc(CN3Cc4cccc(OCC(=O)c5ccccc5)c4C3=O)cc2)cn1] | | 438.1 |
| 183 | 7-(3-(benzyloxy)propoxy)-2-(4-(1-methyl-1H-pyrazol-4-yl)benzyl)isoindolin-1-one | 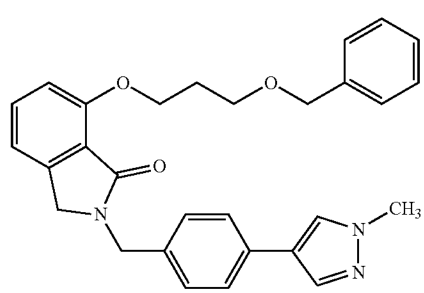 [SMILES: Cn1cc(-c2ccc(CN3Cc4cccc(OCCCOCc5ccccc5)c4C3=O)cc2)cn1] | | 468.1 |

TABLE 1-25

| Ex. No. | compound name | structure | stereo-chemistry | MS |
|---|---|---|---|---|
| 184 | 2-((2-(4-(1-methyl-1H-pyrazol-4-yl)benzyl)-3-oxo-2,3-dihydro-1H-isoindol-4-yl)oxy)acetamide | 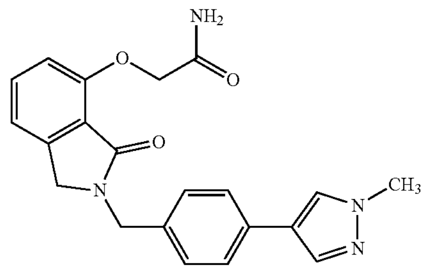 [SMILES: Cn1cc(-c2ccc(CN3Cc4cccc(OCC(N)=O)c4C3=O)cc2)cn1] | | 377.0 |
| 185 | 7-(2-ethoxyethoxy)-2-(4-(1-methyl-1H-pyrazol-4-yl)benzyl)isoindolin-1-one | 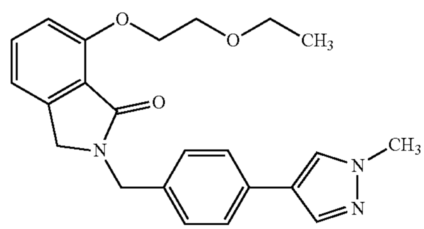 [SMILES: CCOCCOc1cccc2c1C(=O)N(Cc1ccc(-c3cnn(C)c3)cc1)C2] | | 392.0 |
| 186 | 7-(2-(azetidin-1-yl)-2-oxoethoxy)-2-(4-(1-methyl-1H-pyrazol-4-yl)benzyl)isoindolin-1-one | 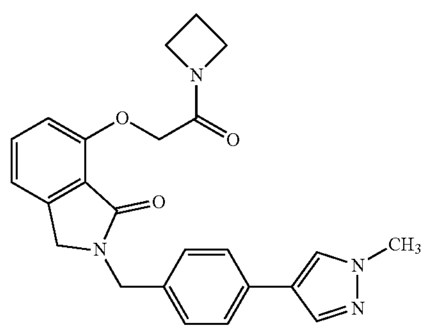 [SMILES: Cn1cc(-c2ccc(CN3Cc4cccc(OCC(=O)N5CCC5)c4C3=O)cc2)cn1] | | 417.0 |
| 187 | 7-(cyclopropylmethoxy)-2-(4-(1-methyl-1H-pyrazol-4-yl)benzyl)isoindolin-1-one | 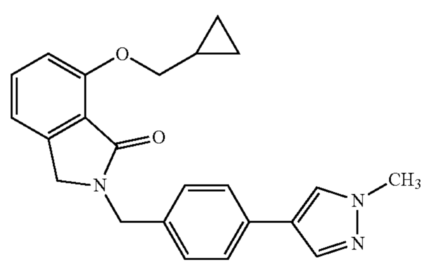 [SMILES: Cn1cc(-c2ccc(CN3Cc4cccc(OCC5CC5)c4C3=O)cc2)cn1] | | 373.9 |
| 188 | 2-(4-(1-methyl-1H-pyrazol-4-yl)benzyl)-7-(2-phenylethoxy)isoindolin-1-one | 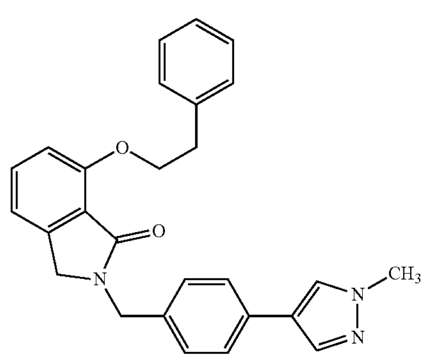 [SMILES: Cn1cc(-c2ccc(CN3Cc4cccc(OCCc5ccccc5)c4C3=O)cc2)cn1] | | 424.1 |

TABLE 1-26

| Ex. No. | compound name | structure | stereo-chemistry | MS |
|---|---|---|---|---|
| 189 | 2-(4-(1-methyl-1H-pyrazol-4-yl)benzyl)-7-(1-phenylethoxy)isoindolin-1-one | 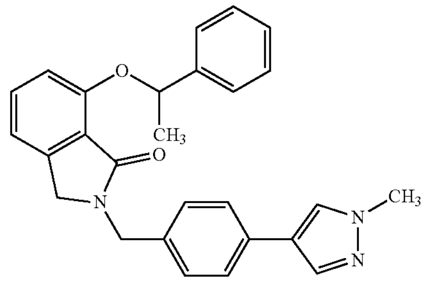 [SMILES: CC(Oc1cccc2c1C(=O)N(Cc1ccc(-c3cnn(C)c3)cc1)C2)c1ccccc1] | racemate | 424.1 |
| 190 | 7-(cyclohexylmethoxy)-2-(4-(1-methyl-1H-pyrazol-4-yl)benzyl)isoindolin-1-one | 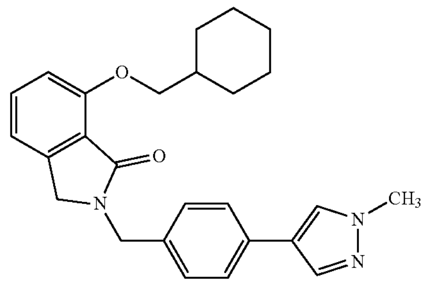 [SMILES: Cn1cc(-c2ccc(CN3Cc4cccc(OCC5CCCCC5)c4C3=O)cc2)cn1] | | 416.1 |
| 191 | 2-(4-(1-methyl-1H-pyrazol-4-yl)benzyl)-7-((pyridin-3-yl)methoxy)isoindolin-1-one | 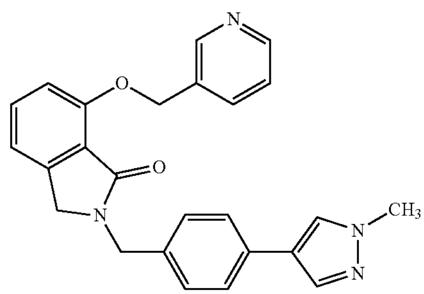 [SMILES: Cn1cc(-c2ccc(CN3Cc4cccc(OCc5cccnc5)c4C3=O)cc2)cn1] | | 411.0 |
| 192 | 7-(imidazo[1,2-a]pyridin-2-ylmethoxy)-2-(4-(1-methyl-1H-pyrazol-4-yl)benzyl)isoindolin-1-one | 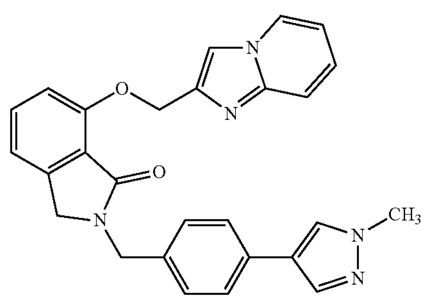 [SMILES: Cn1cc(-c2ccc(CN3Cc4cccc(OCc5cn6ccccc6n5)c4C3=O)cc2)cn1] | | 450.1 |
| 193 | 7-((biphenyl-4-yl)methoxy)-2-(4-(1-methyl-1H-pyrazol-4-yl)benzyl)isoindolin-1-one | 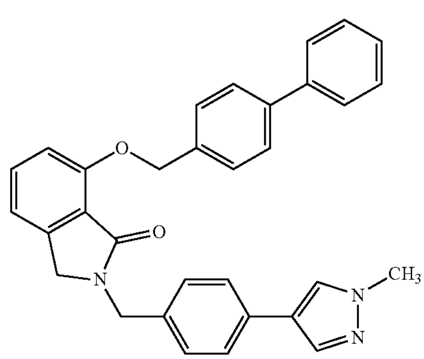 [SMILES: Cn1cc(-c2ccc(CN3Cc4cccc(OCc5ccc(-c6ccccc6)cc5)c4C3=O)cc2)cn1] | | 486.1 |

TABLE 1-27

| Ex. No. | compound name | structure | stereo-chemistry | MS |
|---|---|---|---|---|
| 194 | 7-(2-cyclohexylethoxy)-2-(4-(1-methyl-1H-pyrazol-4-yl)benzyl)isoindolin-1-one | 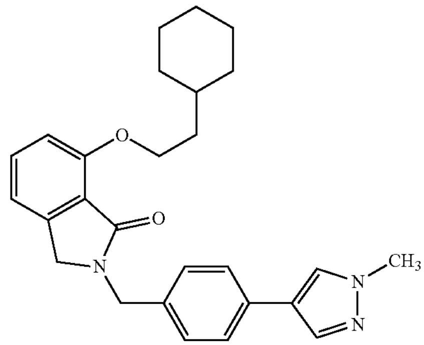 [SMILES: Cn1cc(-c2ccc(CN3Cc4cccc(OCCC5CCCCC5)c4C3=O)cc2)cn1] | | 430.1 |
| 195 | 2-(4-(1-methyl-1H-pyrazol-4-yl)benzyl)-7-(3-phenylpropoxy)isoindolin-1-one | 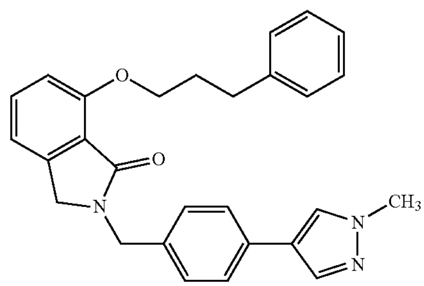 [SMILES: Cn1cc(-c2ccc(CN3Cc4cccc(OCCCc5ccccc5)c4C3=O)cc2)cn1] | | 438.1 |
| 196 | 2-(4-(1-methyl-1H-pyrazol-4-yl)benzyl)-7-((3-(trifluoromethyl)benzyl)oxy)isoindolin-1-one | 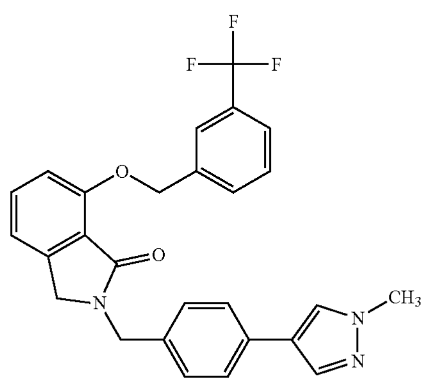 [SMILES: Cn1cc(-c2ccc(CN3Cc4cccc(OCc5cccc(C(F)(F)F)c5)c4C3=O)cc2)cn1] | | 478.1 |
| 197 | 2-(4-(1-methyl-1H-pyrazol-4-yl)benzyl)-7-((4-(trifluoromethyl)benzyl)oxy)isoindolin-1-one | 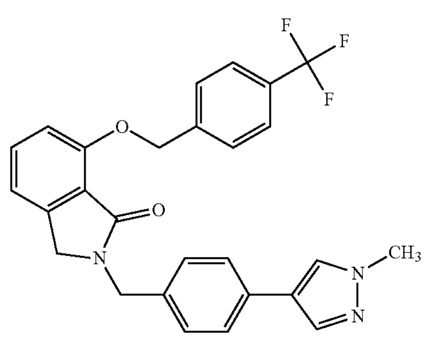 [SMILES: Cn1cc(-c2ccc(CN3Cc4cccc(OCc5ccc(C(F)(F)F)cc5)c4C3=O)cc2)cn1] | | 478.1 |

TABLE 1-27-continued

| Ex. No. | compound name | structure | stereo-chemistry | MS |
|---|---|---|---|---|
| 198 | methyl((2-(4-(1-methyl-1H-pyrazol-4-yl)benzyl)-3-oxo-2,3-dihydro-1H-isoindol-4-yl)oxy)(phenyl)acetate | 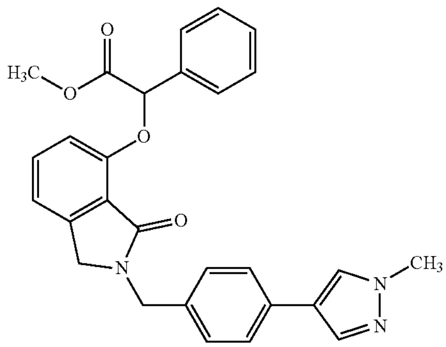 [SMILES: COC(=O)C(Oc1cccc2c1C(=O)N(Cc1ccc(-c3cnn(C)c3)cc1)C2)c1ccccc1] | racemate | 468.1 |

TABLE 1-28

| Ex. No. | compound name | structure | stereo-chemistry | MS |
|---|---|---|---|---|
| 199 | 2-(4-(1-methyl-1H-pyrazol-4-yl)benzyl)-7-((2-(trifluoromethyl)benzyl)oxy)isoindolin-1-one | 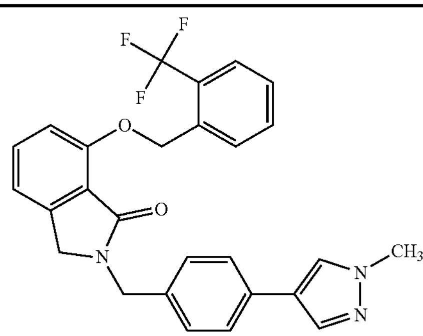 | | 478.1 |
| 200 | 3-fluoro-2-((3-oxo-2-(4-(1H-pyrazol-4-yl)benzyl)-2,3-dihydro-1H-isoindol-4-yl)oxy)benzonitrile | 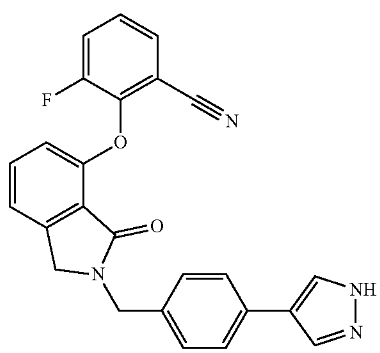 [SMILES: N#Cc1cccc(F)c1Oc1cccc2c1C(=O)N(Cc1ccc(-c3cn[nH]c3)cc1)C2] | | 425.0 |
| 201 | 3-fluoro-2-((3-oxo-2-(4-(pyridin-3-yl)benzyl)-2,3-dihydro-1H-isoindol-4-yl)oxy)benzonitrile | 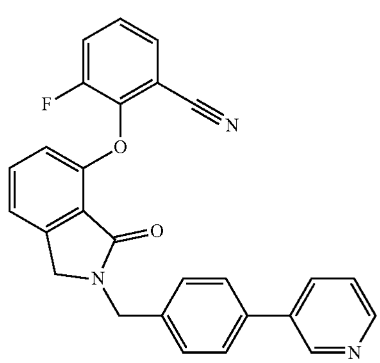 [SMILES: N#Cc1cccc(F)c1Oc1cccc2c1C(=O)N(Cc1ccc(-c3cccnc3)cc1)C2] | | 436.0 |

TABLE 1-28-continued

| Ex. No. | compound name | structure | stereo-chemistry | MS |
|---|---|---|---|---|
| 202 | 3-fluoro-2-((3-oxo-2-(4-(pyridin-4-yl)benzyl)-2,3-dihydro-1H-isoindol-4-yl)oxy)benzonitrile | 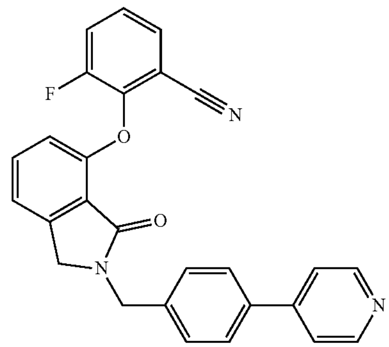 [SMILES: N#Cc1cccc(F)c1Oc1cccc2c1C(=O)N(Cc1ccc(-c3ccncc3)cc1)C2] | | 436.0 |
| 203 | 3-fluoro-2-((2-(4-(1-isopropyl-1H-pyrazol-4-yl)benzyl)-3-oxo-2,3-dihydro-1H-isoindol-4-yl)oxy)benzonitrile | 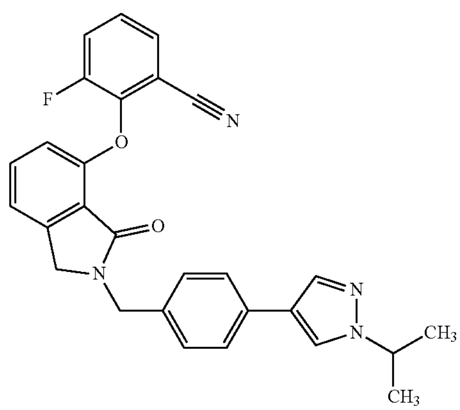 [SMILES: CC(C)n1cc(-c2ccc(CN3Cc4cccc(Oc5c(F)cccc5C#N)c4C3=O)cc2)cn1] | | 467.1 |

TABLE 1-29

| Ex. No. | compound name | structure | stereo-chemistry | MS |
|---|---|---|---|---|
| 204 | 3-fluoro-2-((3-oxo-2-(4-(pyridin-2-yl)benzyl)-2,3-dihydro-1H-isoindol-4-yl)oxy)benzonitrile | 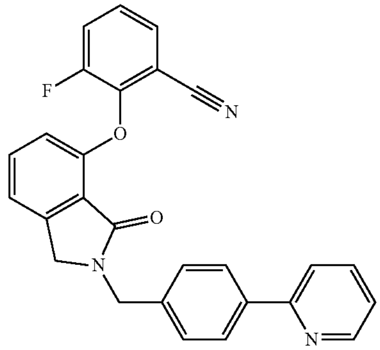 [SMILES: N#Cc1cccc(F)c1Oc1cccc2c1C(=O)N(Cc1ccc(-c3ccccn3)cc1)C2] | | 436.0 |

TABLE 1-29-continued

| Ex. No. | compound name | structure | stereo-chemistry | MS |
|---|---|---|---|---|
| 205 | 2-((2-(4-(1,5-dimethyl-1H-pyrazol-4-yl)benzyl)-3-oxo-2,3-dihydro-1H-isoindol-4-yl)oxy)-3-fluorobenzonitrile | 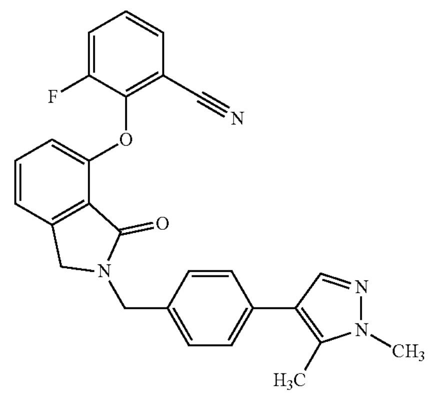 [SMILES: Cc1c(-c2ccc(CN3Cc4cccc(Oc5c(F)cccc5C#N)c4C3=O)cc2)cnn1C] | | 453.1 |
| 206 | 4'-((7-(2-cyano-6-fluorophenoxy)-1-oxo-1,3-dihydro-2H-isoindol-2-yl)methyl)biphenyl-4-carbonitrile | 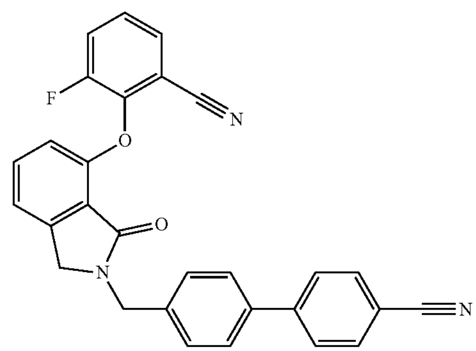 [SMILES: N#Cc1ccc(-c2ccc(CN3Cc4cccc(Oc5c(F)cccc5C#N)c4C3=O)cc2)cc1] | | 460.1 |
| 207 | 4'-((7-(2-cyano-6-fluorophenoxy)-1-oxo-1,3-dihydro-2H-isoindol-2-yl)methyl)biphenyl-3-carbonitrile | 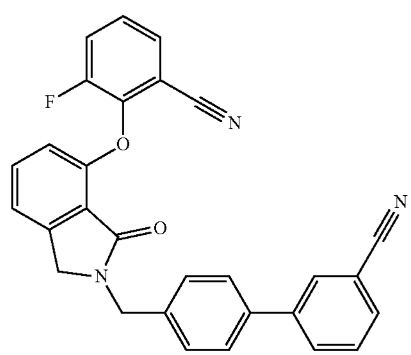 [SMILES: N#Cc1cccc(-c2ccc(CN3Cc4cccc(Oc5c(F)cccc5C#N)c4C3=O)cc2)c1] | | 460.1 |
| 208 | 2-((2-(4-((E)-2-(4-chlorophenyl)vinyl)benzyl)-3-oxo-2,3-dihydro-1H-isoindol-4-yl)oxy)-3-fluorobenzonitrile | 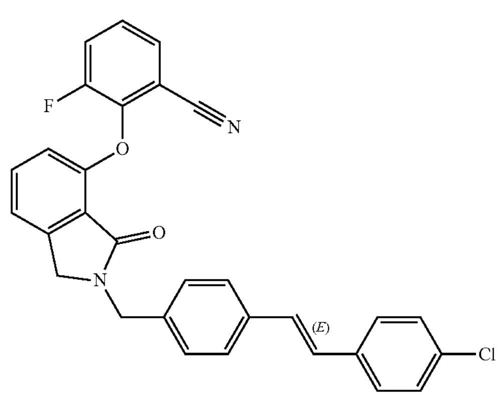 [SMILES: N#Cc1cccc(F)c1Oc1cccc2c1C(=O)N(Cc1ccc(/C=C/c3ccc(Cl)cc3)cc1)C2] | | 495.1 |

TABLE 1-30

| Ex. No. | compound name | structure | stereo-chemistry | MS |
|---|---|---|---|---|
| 209 | 2-((2-(biphenyl-4-ylmethyl)-3-oxo-2,3-dihydro-1H-isoindol-4-yl)oxy)-3-fluorobenzonitrile | 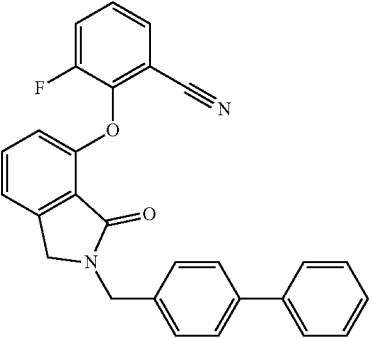 [SMILES: N#Cc1cccc(F)c1Oc1cccc2c1C(=O)N(Cc1ccc(-c3ccccc3)cc1)C2] | | 435.0 |
| 210 | 2-((2-((4'-chlorobiphenyl-4-yl)methyl)-3-oxo-2,3-dihydro-1H-isoindol-4-yl)oxy)-3-fluorobenzonitrile | 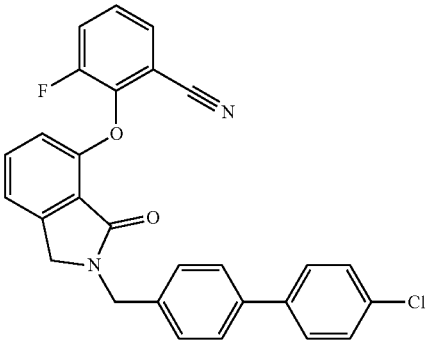 [SMILES: N#Cc1cccc(F)c1Oc1cccc2c1C(=O)N(Cc1ccc(-c3ccc(Cl)cc3)cc1)C2] | | 469.0 |
| 211 | 2-((2-((3'-chlorobiphenyl-4-yl)methyl)-3-oxo-2,3-dihydro-1H-isoindol-4-yl)oxy)-3-fluorobenzonitrile | 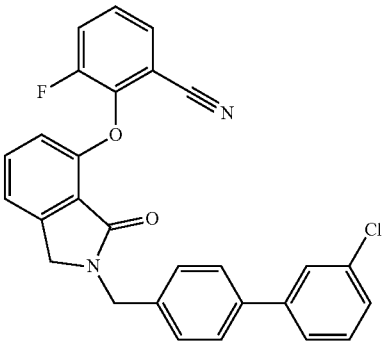 [SMILES: N#Cc1cccc(F)c1Oc1cccc2c1C(=O)N(Cc1ccc(-c3cccc(Cl)c3)cc1)C2] | | 469.0 |
| 212 | 3-fluoro-2-((2-((3'-methoxybiphenyl-4-yl)methyl)-3-oxo-2,3-dihydro-1H-isoindol-4-yl)oxy)benzonitrile | 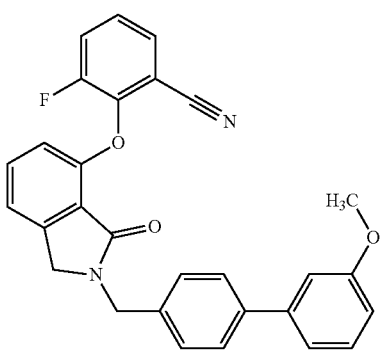 [SMILES: COc1cccc(-c2ccc(CN3Cc4cccc(Oc5c(F)cccc5C#N)c4C3=O)cc2)c1] | | 465.1 |

TABLE 1-30-continued

| Ex. No. | compound name | structure | stereo-chemistry | MS |
|---|---|---|---|---|
| 213 | 3-fluoro-2-((2-((2'-methoxybiphenyl-4-yl)methyl)-3-oxo-2,3-dihydro-1H-isoindol-4-yl)oxy)benzonitrile | 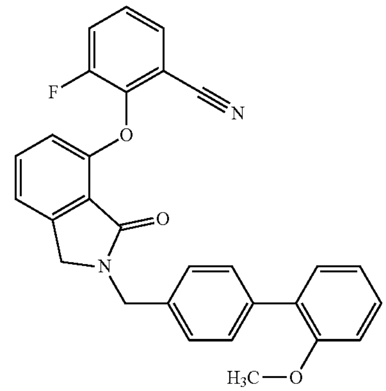 [SMILES: COc1ccccc1-c1ccc(CN2Cc3cccc(Oc4c(F)cccc4C#N)c3C2=O)cc1] | | 465.1 |

TABLE 1-31

| Ex. No. | compound name | structure | stereo-chemistry | MS |
|---|---|---|---|---|
| 214 | 2-((2-((2'-chlorobiphenyl-4-yl)methyl)-3-oxo-2,3-dihydro-1H-isoindol-4-yl)oxy)-3-fluorobenzonitrile | 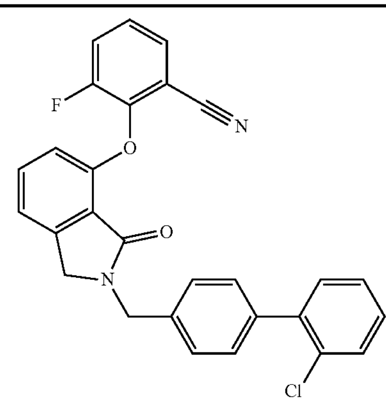 | | 469.0 |
| 215 | 4'-((7-(2-cyano-6-fluorophenoxy)-1-oxo-1,3-dihydro-2H-isoindol-2-yl)methyl)biphenyl-2-carbonitrile | 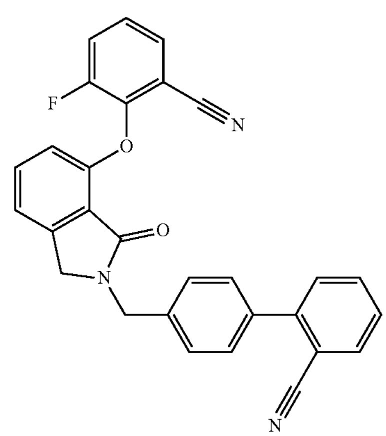 [SMILES: N#Cc1ccccc1-c1ccc(CN2Cc3cccc(Oc4c(F)cccc4C#N)c3C2=O)cc1] | | 460.1 |

TABLE 1-31-continued

| Ex. No. | compound name | structure | stereo-chemistry | MS |
|---|---|---|---|---|
| 216 | 3-fluoro-2-((2-(4-(1-methyl-1,2,3,6-tetrahydropyridin-4-yl)benzyl)-3-oxo-2,3-dihydro-1H-isoindol-4-yl)oxy)benzonitrile | 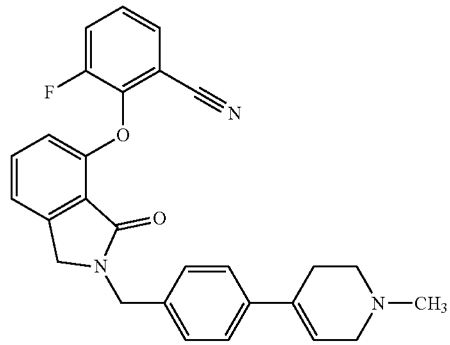 [SMILES: CN1CC=C(c2ccc(CN3Cc4cccc(Oc5c(F)cccc5C#N)c4C3=O)cc2)CC1] | | 454.1 |
| 217 | 3-fluoro-2-((2-(4-(1-methyl-1H-pyrrol-2-yl)benzyl)-3-oxo-2,3-dihydro-1H-isoindol-4-yl)oxy)benzonitrile | 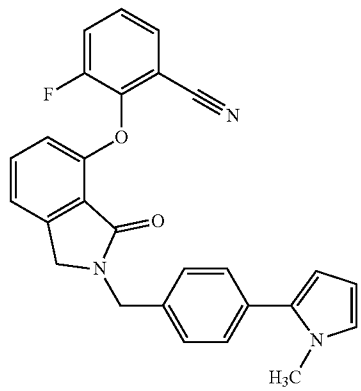 [SMILES: Cn1cccc1-c1ccc(CN2Cc3cccc(Oc4c(F)cccc4C#N)c3C2=O)cc1] | | 438.0 |
| 218 | 4-bromo-7-((trans-2-hydroxycyclohexyl)oxy)-2-(4-(1-methyl-1H-pyrazol-4-yl)benzyl)isoindolin-1-one | 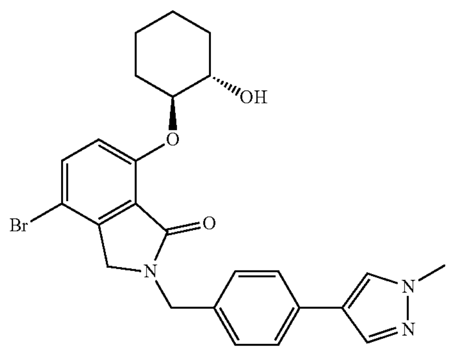 [SMILES: Cn1cc(-c2ccc(CN3Cc4c(Br)ccc(O[C@H]5CCCC[C@@H]5O)c4C3=O)cc2)cn1] | racemate | 496.2 498.2 |

TABLE 1-32

| Ex. No. | compound name | structure | stereo-chemistry | MS |
|---|---|---|---|---|
| 219 | 5-bromo-7-((trans-2-hydroxycyclohexyl)oxy)-2-(4-(1-methyl-1H-pyrazol-4-yl)benzyl)isoindolin-1-one | 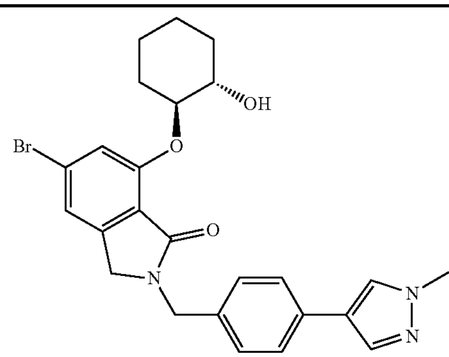 | racemate | 496.2 498.2 |

TABLE 1-32-continued

| Ex. No. | compound name | structure | stereo-chemistry | MS |
|---|---|---|---|---|
| 220 | 2-(4-(1-methyl-1H-pyrazol-4-yl)benzyl)-7-((tetrahydro-2H-pyran-2-yl)methoxy)isoindolin-1-one | 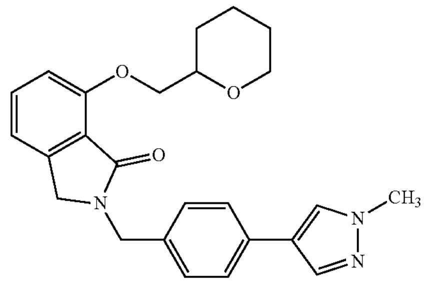 [SMILES: Cn1cc(-c2ccc(CN3Cc4cccc(OCC5CCCCO5)c4C3=O)cc2)cn1] | racemate | 418.1 |
| 221 | 2-(2-((2-(4-(1-methyl-1H-pyrazol-4-yl)benzyl)-3-oxo-2,3-dihydro-1H-isoindol-4-yl)oxy)ethyl)-1H-isoindole-1,3(2H)-dione | 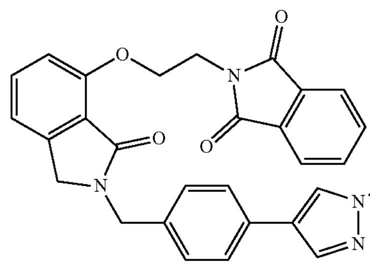 | | 493.1 |
| 222 | 2-((2-(4-(1,3-dimethyl-1H-pyrazol-4-yl)benzyl)-3-oxo-2,3-dihydro-1H-isoindol-4-yl)oxy)-3-fluorobenzonitrile | 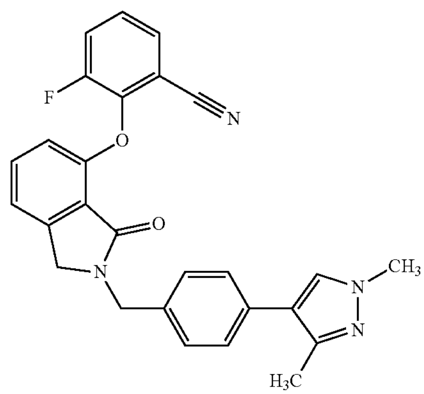 [SMILES: Cc1nn(C)cc1-c1ccc(CN2Cc3cccc(Oc4c(F)cccc4C#N)c3C2=O)cc1] | | 453.1 |

TABLE 1-33

| Ex. No. | compound name | structure | salt, stereo-chemistry | MS |
|---|---|---|---|---|
| 466 | 4-fluoro-2-(4-(1H-pyrazol-1-yl)benzyl)-7-((tetrahydrofuran-2-yl)methoxy)isoindolin-1-one | 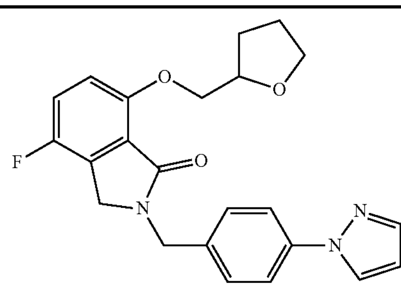 | racemate | 408.1 |

1HNMR (400 MHz, CDCl3) δ 1.88-2.02 (2H, m), 2.03-2.22 (2H, m), 3.80-3.90 (1H, m), 3.93-4.06 (1H, m), 4.14 (2H, d, J = 5.2 Hz), 4.25 (2H, s), 4.32-4.43 (1H, m), 4.77 (2H, s), 6.46 (1H, t, J = 2.0 Hz), 6.91 (1H, dd, J = 8.8, 3.6 Hz), 7.12 (1H, t, J = 8.8 Hz), 7.40 (2H, d, J = 8.4 Hz), 7.66 (2H, d, J = 8.4 Hz), 7.72 (1H, d, J = 1.2 Hz), 7.91 (1H, d, J = 2.4 Hz).

TABLE 1-33-continued

| Ex. No. | compound name | structure | salt, stereo-chemistry | MS |
|---|---|---|---|---|
| 467 | 2-(4-(1H-pyrazol-1-yl)benzyl)-7-(2-(pyridin-2-yl)ethoxy)isoindolin-1-one | 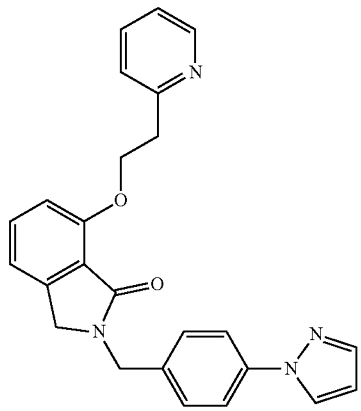 [SMILES: O=C1c2c(cccc2OCCc2ccccn2)CN1Cc1ccc(-n2cccn2)cc1] | | 411.2 |

1H NMR (300 MHz, DMSO-d6) δ 3.24 (2H, t, J = 6.7 Hz), 4.30 (2H, s), 4.46 (2H, t, J = 6.7 Hz), 4.68 (2H,s), 6.51-6.56 (1H, m), 7.01-7.12 (2H, m), 7.20-7.28 (1H, m), 7.38 (2H, d, J = 8.5 Hz), 7.44-7.56 (2H, m), 7.68-7.77 (2H, m), 7.81 (2H, d, J = 8.7 Hz), 8.46 (1H, d, J = 2.5 Hz), 8.49-8.54 (1H, m).

| 468 | 6-((3-oxo-2-(4-(1H-pyrazol-1-yl)benzyl)-2,3-dihydro-1H-isoindol-4-yl)oxy)pyridine-2-carbonitrile | | | 408.1 |

1H NMR (300 MHz, CDCl3) δ 4.32 (2H, s), 4.69 (2H, s), 6.36-6.52 (1H, m), 7.20 (1H, d, J = 8.1 Hz), 7.28-7.44 (5H, m), 7.59 (1H, t, J = 7.8 Hz), 7.63-7.69 (2H, m), 7.71 (1H, d, J = 1.5 Hz), 7.85 (1H, dd, J = 8.3, 7.4 Hz), 7.90 (1H, d, J = 2.5 Hz).

| 469 | 7-(2,6-difluoro-4-nitrophenoxy)-2-(4-(1H-pyrazol-1-yl)benzyl)isoindolin-1-one | | | 463.1 |

1H NMR (300 MHz, CDCl3) δ 4.30 (2H, s), 4.76 (2H, s), 6.45-6.49 (1H, m), 6.90 (1H, d, J = 8.3 Hz), 7.20 (1H, d, J = 7.2 Hz), 7.39 (2H, d, J = 8.7 Hz), 7.43-7.51 (1H, m), 7.65-7.70 (2H, m), 7.72 (1H, d, J = 1.5 Hz), 7.91 (1H, d, J = 2.6 Hz), 7.95 (2H, d, J = 7.9 Hz).

TABLE 1-34

| Ex. No. | compound name | structure | salt, stereochemistry | MS |
|---|---|---|---|---|
| 470 | 3-fluoro-2-((7-fluoro-3-oxo-2-(4-(1H-pyrazol-1-yl)benzyl)-2,3-dihydro-1H-isoindol-4-yl)oxy)benzonitrile | 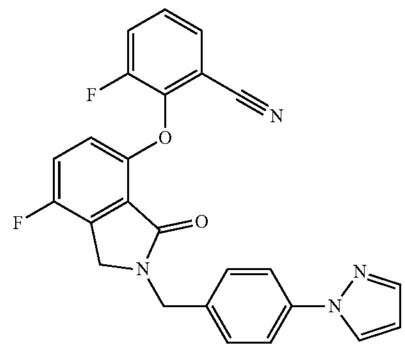 [SMILES: N#Cc1cccc(F)c1Oc1ccc(F)c2c1C(=O)N(Cc1ccc(-n3cccn3)cc1)C2] | | 443.1 |

1HNMR (400 MHz, DMSO-d6) δ 4.53 (2H, s), 4.72 (2H, s), 6.54 (1H, dd, J = 2.4, 2.0 Hz), 7.00 (1H, dd, J = 9.2, 3.2 Hz), 7.38-7.46 (3H, m), 7.47-7.53 (1H, m), 7.72-7.88 (5H, m), 8.48 (1H, d, J = 2.4 Hz).

| 471 | 3-((3-oxo-2-(4-(1H-pyrazol-1-yl)benzyl)-2,3-dihydro-1H-isoindol-4-yl)oxy)benzonitrile | | | 407.1 |

1H NMR (300 MHz, CDCl3) δ 4.32 (2H, s), 4.75 (2H, s), 6.46 (1H, t, J = 2.1 Hz), 6.99 (1H, d, J = 8.1 Hz), 7.17-7.24 (2H, m), 7.33-7.42 (4H, m), 7.42-7.57 (2H, m), 7.63-7.70 (2H, m), 7.71 (1H, d, J = 1.7 Hz), 7.90 (1H, d, J = 2.5 Hz).

| 472 | 3-((3-oxo-2-(4-(1H-pyrazol-1-yl)benzyl)-2,3-dihydro-1H-isoindol-4-yl)oxy)propanenitrile | | | 359.1 |

1H NMR (300 MHz, CDCl3) δ 2.98 (1H, t, J = 6.9 Hz), 4.25 (1H, s), 4.47 (1H, t, J = 6.9 Hz), 4.78 (1H, s), 6.40-6.50 (1H, m), 6.96 (1H, d, J = 8.1 Hz), 7.06 (1H, d, J = 7.6 Hz), 7.40 (2H, d, J = 8.5 Hz), 7.43-7.52 (1H, m), 7.63-7.69 (2H, m), 7.71 (1H, d, J = 1.5 Hz), 7.90 (1H, d, J = 2.6 Hz).

TABLE 1-34-continued

| Ex. No. | compound name | structure | salt, stereochemistry | MS |
|---|---|---|---|---|
| 473 | ((3-oxo-2-(4-(1H-pyrazol-1-yl)benzyl)-2,3-dihydro-1H-isoindol-4-yl)oxy)acetonitrile | 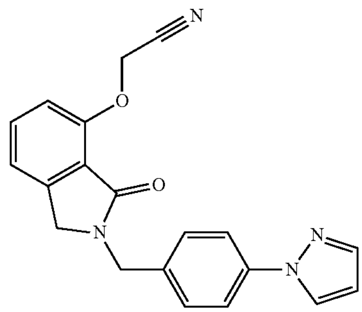 [SMILES: N#CCOc1cccc2c1C(=O)N(Cc1ccc(-n3cccn3)cc1)C2] | | 345.2 |

1H NMR (300 MHz, CDCl3) δ 4.29 (2H, s), 4.79 (2H, s), 5.19 (2H, s), 6.37-6.51 (1H, m), 7.13 (2H, dd, J = 16.3, 7.8 Hz), 7.40 (2H, d, J = 8.7 Hz), 7.46-7.58 (1H, m), 7.64-7.70 (2H, m), 7.72 (1H, d, J = 1.5 Hz), 7.90 (1H, d, J = 2.5 Hz).

TABLE 1-35

| Ex. No. | compound name | structure | salt, stereochemistry | MS |
|---|---|---|---|---|
| 474 | 2-(4-(pyrimidin-2-yl)benzyl)-7-((tetrahydrofuran-2-yl)methoxy)isoindolin-1-one | 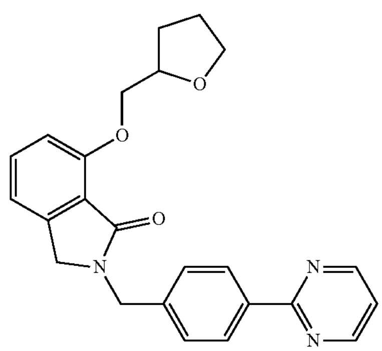 [SMILES: O=C1c2c(cccc2OCC2CCCO2)CN1Cc1ccc(-c2ncccn2)cc1] | racemate | 402.1 |

1H NMR (300 MHz, CDCl3) δ 1.83-2.29 (4H, m), 3.75-3.91 (1H, m), 4.02 (1H, dt, J = 8.0, 6.2 Hz), 4.11-4.27 (4H, m), 4.29-4.49 (1H, m), 4.73-4.93 (2H, m), 6.85-7.02 (2H, m), 7.18 (1H, t, J = 4.8 Hz), 7.37-7.47 (3H, m), 8.40 (2H, d, J = 8.3 Hz), 8.79 (2H, d, J = 4.9 Hz).

| 475 | 7-((tetrahydrofuran-2-yl)methoxy)-2-(4-(5-(trifluoromethyl)-1,3,4-thiadiazol-2-yl)benzyl)isoindolin-1-one | | racemate | 476.2 |

1H NMR (300 MHz, CDCl3) δ 1.87-2.26 (4H, m), 3.78-3.90 (1H, m), 3.96-4.07 (1H, m), 4.18 (2H, dd, J = 4.5, 3.0 Hz), 4.25 (2H, s), 4.32-4.50 (1H, m), 4.82 (2H, s), 6.95 (2H, dd, J = 7.7, 4.5 Hz), 7.36-7.51 (3H, m), 7.96 (2H, d, J = 8.3 Hz).

TABLE 1-35-continued

| Ex. No. | compound name | structure | salt, stereochemistry | MS |
|---|---|---|---|---|
| 476 | 7-((1,1-dioxidotetrahydro-2H-thiopyran-4-yl)oxy)-2-(4-(1H-pyrazol-1-yl)benzyl)isoindolin-1-one | 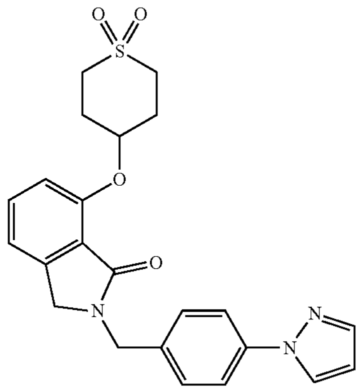 [SMILES: O=C1c2c(cccc2OC2CCS(=O)(=O)CC2)CN1Cc1ccc(-n2cccn2)cc1] | | 438.1 |

1H NMR (300 MHz, CDCl3) δ 2.29-2.48 (2H, m), 2.48-2.67 (2H, m), 2.93 (2H, dd, J = 14.9, 3.6 Hz), 3.73 (2H, td, J = 13.3, 3.6 Hz), 4.25 (2H, s), 4.78 (2H, s), 4.85-4.94 (1H, m), 6.39-6.52 (1H, m), 6.95 (1H, d, J = 8.1 Hz), 7.06 (1H, d, J = 7.4 Hz), 7.35-7.52 (3H, m), 7.61-7.75 (3H, m), 7.91 (1H, d, J = 2.3 Hz).

| 477 | 2-(4-(pyridazin-4-yl)benzyl)-7-((tetrahydrofuran-2-yl)methoxy)isoindolin-1-one | | racemate | 402.1 |

1H NMR (300 MHz, DMSO-d6) δ 1.77-1.92 (2H, m), 1.95-2.09 (2H, m), 3.63-3.73 (1H, m), 3.82-3.90 (1H, m), 4.06-4.11 (2H, m), 4.16-4.26 (1H, m), 4.33 (2H, s), 4.74 (2H, s), 7.00-7.11 (2H, m), 7.42-7.53 (3H, m), 7.92 (2H, d, J = 8.3 Hz), 7.99 (1H, dd, J = 5.7, 2.6 Hz), 9.26 (1H, d, J = 5.7 Hz), 9.60-9.64 (1H, m).

TABLE 1-36

| Ex. No. | compound name | structure | salt, stereochemistry | MS |
|---|---|---|---|---|
| 478 | 7-(2,6-difluorophenoxy)-2-(4-(1H-pyrazol-1-yl)benzyl)isoindolin-1-one | 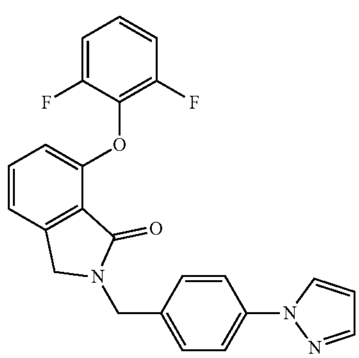 [SMILES: O=C1c2c(cccc2Oc2c(F)cccc2F)CN1Cc1ccc(-n2cccn2)cc1] | | 418.1 |

1H NMR (300 MHz, CDCl3) δ 4.29 (2H, s), 4.82 (2H, s), 6.45-6.49 (1H, m), 6.64 (1H, d, J = 8.3 Hz), 6.98-7.09 (3H, m), 7.13-7.21 (1H, m), 7.36 (1H, dd, J = 8.3, 7.5 Hz), 7.45 (2H, d, J = 8.7 Hz), 7.65-7.70 (2H, m), 7.72 (1H, d, J = 1.1 Hz), 7.91 (1H, d, J = 1.9 Hz).

TABLE 1-36-continued

| Ex. No. | compound name | structure | salt, stereochemistry | MS |
|---|---|---|---|---|
| 479 | 6-fluoro-2-(4-(1H-pyrazol-1-yl)benzyl)-7-((tetrahydrofuran-2-yl)methoxy)isoindolin-1-one | 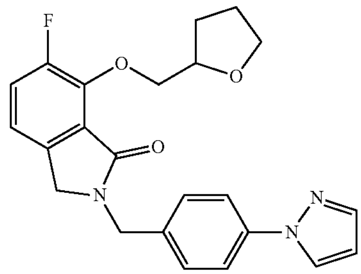 [SMILES: O=C1c2c(ccc(F)c2OCC2CCCO2)CN1Cc1ccc(-n2cccn2)cc1] | racemate | 408.2 |

1HNMR (400 MHz, CDCl3) δ 1.86-2.18 (4H, m), 3.78-3.87 (1H, m), 3.88-3.98 (1H, m), 4.19 (2H, s), 4.29-4.38 (1H, m), 4.38-4.44 (2H, m), 4.78 (2H, s), 6.46 (1H, t, J = 2.0 Hz), 6.98 (1H, dd, J = 8.4, 3.6 Hz), 7.23 (1H, dd, J = 11.2, 8.0 Hz), 7.39 (2H, d, J = 8.4 Hz), 7.66 (2H, d, J = 8.4 Hz), 7.72 (1H, d, J = 1.6 Hz), 7.90 (1H, d, J = 2.4 Hz).

| 480 | 3-fluoro-2-((2-(4-(5-methyl-1,3,4-oxadiazol-2-yl)benzyl)-3-oxo-2,3-dihydro-1H-isoindol-4-yl)oxy)benzonitrile | | | 441.1 |

1H NMR (300 MHz, CDCl3) δ 2.62 (3H, s), 4.31 (2H, s), 4.82 (2H, s), 6.76 (1H, d, J = 8.3 Hz), 7.16 (1H, d, J = 7.5 Hz), 7.27-7.33 (1H, m), 7.38-7.53 (5H, m), 8.01 (2H, d, J = 8.3 Hz).

| 481 | 2-(4-(2-methylpyrimidin-4-yl)benzyl)-4-((tetrahydrofuran-2-yl)methoxy)-1,2-dihydro-3H-pyrrolo[3,4-c]pyridin-3-one | | racemate | 417.1 |

1H NMR (300 MHz, CDCl3) δ 1.86-2.01 (2H, m), 2.06-2.19 (2H, m), 2.79 (3H, s), 3.78-3.90 (1H, m), 3.97-4.07 (1H, m), 4.22 (2H, s), 4.43 (1H, d, J = 4.9 Hz), 4.50-4.57 (2H, m), 4.81 (2H, s), 6.92 (1H, d, J = 5.3 Hz), 7.35-7.54 (3H, m), 7.96-8.09 (2H, m), 8.24 (1H, d, J = 5.1 Hz), 8.66 (1H, d, J = 5.5 Hz).

TABLE 1-37

| Ex. No. | compound name | structure | salt, stereochemistry | MS |
|---|---|---|---|---|
| 482 | 7-(3,5-difluorophenoxy)-2-(4-(1H-pyrazol-1-yl)benzyl)isoindolin-1-one | 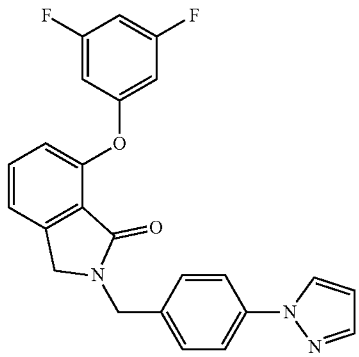 [SMILES: O=C1c2c(cccc2Oc2cc(F)cc(F)c2)CN1Cc1ccc(-n2cccn2)cc1] | | 418.1 |

1H NMR (300 MHz, CDCl3) δ 4.32 (2H, s), 4.77 (2H, s), 6.45-6.49 (1H, m), 6.51-6.61 (3H, m), 7.03 (1H, d, J = 7.5 Hz), 7.24 (1H, d, J = 7.5 Hz), 7.41 (2H, d, J = 8.3 Hz), 7.49-7.56 (1H, m), 7.67 (2H, d, J = 8.7 Hz), 7.73 (1H, d, J = 1.5 Hz), 7.91 (1H, d, J = 2.6 Hz).

| 483 | 2-(4-(1,3-dimethyl-1H-pyrazol-4-yl)benzyl)-7-((2-methyltetrahydrofuran-2-yl)methoxy)isoindolin-1-one | | racemate | 432.1 |

1H NMR (300 MHz, DMSO-d6) δ 1.29 (3H, s), 1.54-1.77 (1H, m), 1.79-1.98 (1H, m), 2.02-2.18 (2H, m), 2.27 (3H, s), 3.68-4.03 (7H, m), 4.29 (2H, s), 4.65 (2H, s), 7.04 (2H, dd, J = 13.3, 7.8 Hz), 7.21-7.32 (2H, m), 7.34-7.42 (2H, m), 7.48 (1H, t, J = 7.9 Hz), 7.84 (1H, s).

| 484 | 7-((trans-4-hydroxytetrahydrofuran-3-yl)oxy)-2-(4-(2-methylpyridin-4-yl)benzyl)isoindolin-1-one | | racemate | 417.1 |

1H NMR (300 MHz, DMSO-d6) δ 3.62 (1H, dd, J = 9.5, 1.9 Hz), 3.81 (1H, d, J = 10.2 Hz), 3.97 (1H, dd, J = 9.3, 4.4 Hz), 4.09 (1H, dd, J = 10.2, 4.2 Hz), 4.25 (1H, brs), 4.33 (2H, s), 4.71 (2H, s), 4.83 (1H, d, J = 4.2 Hz), 5.45 (1H, d, J = 3.8 Hz), 7.11 (2H, dd, J = 11.7, 8.0 Hz), 7.40 (2H, d, J = 8.3 Hz), 7.45-7.59 (3H, m), 7.77 (2H, d, J = 8.3 Hz), 8.48 (1H, d, J = 5.3 Hz).

TABLE 1-37-continued

| Ex. No. | compound name | structure | salt, stereochemistry | MS |
|---|---|---|---|---|
| 485 | 7-(((2S)-5-oxotetrahydrofuran-2-yl)methoxy)-2-(4-(1H-pyrazol-1-yl)benzyl)isoindolin-1-one | 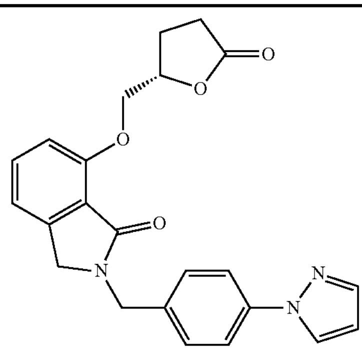 | chiral, (S) | 404.2 |

1H NMR (300 MHz, DMSO-d6) δ 2.16-2.55 (4H, m), 4.19 (1H, dd, J = 10.9, 3.4 Hz), 4.32 (2H, s), 4.38 (1H, dd, J = 10.9, 2.3 Hz), 4.70 (2H, s), 4.93 (1H, brs), 6.48-6.56 (1H, m), 7.03 (1H, d, J = 8.3 Hz), 7.11 (1H, d, J = 7.5 Hz), 7.38 (2H, d, J = 8.3 Hz), 7.48-7.56 (1H, m), 7.72 (1H, d, J = 1.9 Hz), 7.76-7.85 (2H, m), 8.46 (1H, d, J = 2.6 Hz).

TABLE 1-38

| Ex. No. | compound name | structure | salt, stereochemistry | MS |
|---|---|---|---|---|
| 486 | 2-(4-bromobenzyl)-7-((1,4-dioxan-2-yl)methoxy)isoindolin-1-one | 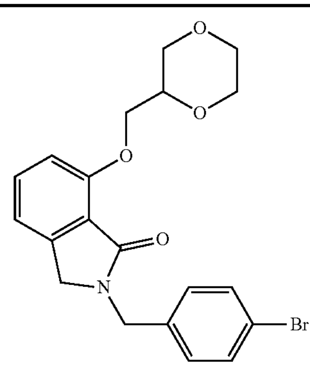 | racemate | 418.0 |

1H NMR (300 MHz, DMSO-d6) δ 3.43-3.57 (2H, m), 3.58-3.71 (2H, m), 3.73-3.82 (1H, m), 3.84-3.95 (2H, m), 4.00-4.08 (1H, m), 4.09-4.18 (1H, m), 4.29 (2H, s), 4.63 (2H, s), 7.06 (2H, dd, J = 16.5, 7.8 Hz), 7.23 (2H, d, J = 8.5 Hz), 7.48 (1H, d, J = 7.7 Hz), 7.54 (2H, d, J = 8.5 Hz).

| 487 | 2-(4-(1,3-dimethyl-1H-pyrazol-4-yl)benzyl)-7-((1,4-dioxan-2-yl)methoxy)isoindolin-1-one | | racemate | 434.2 |

1H NMR (300 MHz, DMSO-d6) δ 2.26 (3H, s), 3.45-3.57 (2H, m), 3.59-3.71 (2H, m), 3.73-3.82 (4H, m), 3.84-3.96 (2H, m), 4.01-4.10 (1H, m), 4.12-4.19 (1H, m), 4.30 (2H, s), 4.65 (2H, s), 7.06 (2H, dd, J = 17.0, 7.7 Hz), 7.23-7.30 (2H, m), 7.34-7.43 (2H, m), 7.49 (1H, t, J = 7.8 Hz), 7.84 (1H, s).

TABLE 1-38-continued

| Ex. No. | compound name | structure | salt, stereochemistry | MS |
|---|---|---|---|---|
| 488 | 7-((3-fluoropyridin-2-yl)oxy)-2-(4-(1H-pyrazol-1-yl)benzyl)isoindolin-1-one | 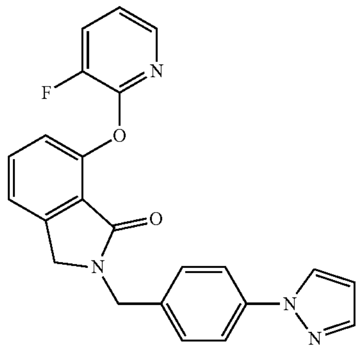 [SMILES: O=C1c2c(cccc2Oc2ncccc2F)CN1Cc1ccc(-n2cccn2)cc1] | | 401.1 |

1H NMR (300 MHz, CDCl3) δ 4.28 (2H, s), 4.69 (2H, s), 6.45-6.48 (1H, m), 7.00 (1H, ddd, J = 8.0, 4.9, 3.2 Hz), 7.24-7.30 (2H, m), 7.33 (2H, d, J = 8.5 Hz), 7.52 (1H, ddd, J = 9.7, 8.0, 1.5 Hz), 7.56-7.67 (3H, m), 7.72 (1H, d, J = 1.7 Hz), 7.84 (1H, dd, J = 4.9, 1.5 Hz), 7.90 (1H, d, J = 2.3 Hz).

| 489 | 7-((3,5-difluoropyridin-2-yl)oxy)-2-(4-(1H-pyrazol-1-yl)benzyl)isoindolin-1-one | | | 419.1 |

1H NMR (300 MHz, CDCl3) δ 4.29 (2H, s), 4.69 (2H, s), 6.47 (1H, t, J = 2.2 Hz), 7.23-7.41 (5H, m), 7.57-7.68 (3H, m), 7.73 (2H, t, J = 2.1 Hz), 7.90 (1H, d, J = 2.5 Hz).

TABLE 1-39

| Ex. No. | compound name | structure | salt, stereochemistry | MS |
|---|---|---|---|---|
| 490 | 7-((3,5-difluoropyridin-4-yl)oxy)-2-(4-(1H-pyrazol-1-yl)benzyl)isoindolin-1-one | 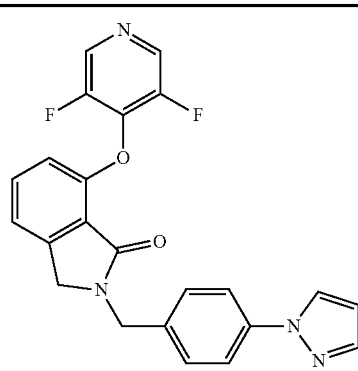 | | 419.1 |

1H NMR (300 MHz, CDCl3) δ 4.31 (2H, s), 4.78 (2H, s), 6.45-6.50 (1H, m), 6.93 (1H, d, J = 8.1 Hz), 7.21 (1H, d, J = 7.0 Hz), 7.41 (2H, d, J = 8.7 Hz), 7.44-7.51 (1H, m), 7.66-7.71 (2H, m), 7.73 (1H, d, J = 1.7 Hz), 7.92 (1H, d, J = 2.5 Hz), 8.41 (2H, s).

TABLE 1-39-continued

| Ex. No. | compound name | structure | salt, stereochemistry | MS |
|---|---|---|---|---|
| 491 | 5-fluoro-2-(4-(1H-pyrazol-1-yl)benzyl)-7-((tetrahydrofuran-2-yl)methoxy)isoindolin-1-one | 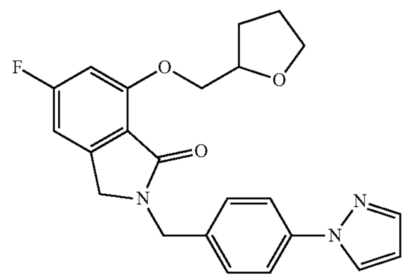 [SMILES: O=C1c2c(cc(F)cc2OCC2CCCO2)CN1Cc1ccc(-n2cccn2)cc1] | racemate | 408.2 |

1H NMR (400 MHz, DMSO-d6) δ 1.72-1.89 (2H, m), 1.92-2.13 (2H, m), 3.62-3.72 (1H, m), 3.80-3.89 (1H, m), 4.02-4.14 (2H, m), 4.17-4.25 (1H, m), 4.30 (2H, s), 4.66 (2H, s), 6.53 (1H, t, J = 2.0 Hz), 6.90-7.00 (2H, m), 7.37 (2H, d, J = 8.4 Hz), 7.72 (1H, d, J = 1.6 Hz), 7.80 (2H, d, J = 8.4 Hz), 8.45 (1H, d, J = 2.4 Hz).

| 492 | 3-fluoro-2-((6-fluoro-3-oxo-2-(4-(1H-pyrazol-1-yl)benzyl)-2,3-dihydro-1H-isoindol-4-yl)oxy)benzonitrile | | | 443.2 |

1H NMR (400 MHz, DMSO-d6) δ 4.43 (2H, s), 4.70 (2H, s), 6.53 (1H, t, J = 2.0 Hz), 6.88 (1H, d, J = 10.8 Hz), 7.25 (1H, dd, J = 8.0, 1.6 Hz), 7.40 (2H, d, J = 8.4 Hz), 7.47-7.55 (1H, m), 7.73 (1H, d, J = 1.6 Hz), 7.76-7.85 (4H, m), 8.47 (1H, d, J = 2.4 Hz).

| 493 | 7-((5-fluoropyrimidin-2-yl)oxy)-2-(4-(1H-pyrazol-1-yl)benzyl)isoindolin-1-one | | | 402.1 |

1H NMR (300 MHz, CDCl3) δ 4.30 (2H, s), 4.67 (2H, s), 6.45-6.48 (1H, m), 7.26-7.37 (4H, m), 7.57-7.68 (3H, m), 7.72 (1H, d, J = 1.5 Hz), 7.90 (1H, d, J = 2.3 Hz), 8.41 (2H, s).

TABLE 1-40

| Ex. No. | compound name | structure | salt, stereochemistry | MS |
|---|---|---|---|---|
| 494 | 7-((3-fluoro-5-(trifluoromethyl)pyridin-2-yl)oxy)-2-(4-(1H-pyrazol-1-yl)benzyl)isoindolin-1-one | 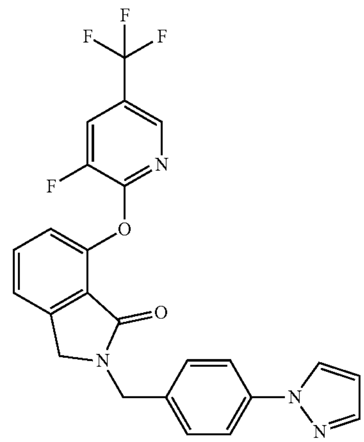 [SMILES: O=C1c2c(cccc2Oc2ncc(C(F)(F)F)cc2F)CN1Cc1ccc(-n2cccn2)cc1] | | 469.1 |

1H NMR (300 MHz, CDCl3) δ 4.31 (2H, s), 4.69 (2H, s), 6.47 (1H, t, J = 2.1 Hz), 7.25-7.30 (1H, m), 7.31-7.37 (3H, m), 7.59-7.67 (3H, m), 7.71-7.76 (2H, m), 7.90 (1H, d, J = 2.6 Hz), 8.10 (1H, d, J = 0.8 Hz).

| 495 | 3,5-difluoro-4-((3-oxo-2-(4-(1H-pyrazol-1-yl)benzyl)-2,3-dihydro-1H-isoindol-4-yl)oxy)benzaldehyde | | | 446.1 |

1H NMR (300 MHz, CDCl3) δ 4.31 (2H, s), 4.80 (2H, s), 6.46-6.50 (1H, m), 6.78-6.83 (1H, m), 7.14-7.21 (1H, m), 7.39-7.47 (3H, m), 7.57 (2H, d, J = 7.5 Hz), 7.69 (2H, d, J = 8.3 Hz), 7.73 (1H, d, J = 1.5 Hz), 7.92 (1H, d, J = 2.6 Hz), 9.93 (1H, t, J = 1.7 Hz).

| 496 | 2-(4-((1-methyl-1H-pyrazol-3-yl)oxy)benzyl)-4-((tetrahydrofuran-2-yl)methoxy)-1,2-dihydro-3H-pyrrolo[3,4-c]pyridin-3-one | | racemate | 421.2 |

1H NMR (300 MHz, DMSO-d6) δ 1.68-1.89 (2H, m), 1.92-2.07 (2H, m), 3.61-3.70 (1H, m), 3.72 (3H, s), 3.79-3.88 (1H, m), 4.18-4.28 (1H, m), 4.31-4.42 (4H, m), 4.62 (2H, s), 5.80 (1H, d, J = 2.5 Hz), 6.97-7.06 (2H, m), 7.18 (1H, d, J = 5.1 Hz), 7.25 (2H, d, J = 8.7 Hz), 7.61 (1H, d, J = 2.3 Hz), 8.26 (1H, d, J = 5.3 Hz).

TABLE 1-40-continued

| Ex. No. | compound name | structure | salt, stereochemistry | MS |
|---|---|---|---|---|
| 497 | 4-(cyclopropylmethoxy)-2-(4-(1-methyl-1H-pyrazol-3-yl)benzyl)-1,2-dihydro-3H-pyrrolo[3,4-c]pyridin-3-one | 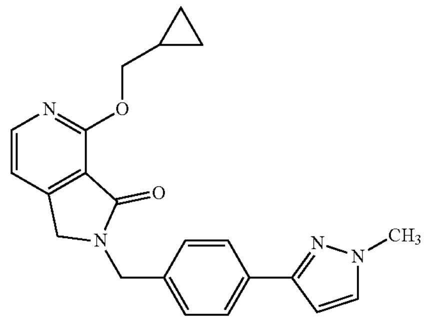 [SMILES: Cn1ccc(-c2ccc(CN3Cc4ccnc(OCC5CC5)c4C3=O)cc2)n1] | | 375.2 |

1H NMR (300 MHz, CDCl3) δ 0.37-0.47 (2H, m), 0.57-0.67 (2H, m), 1.36-1.53 (1H, m), 3.94 (3H, s), 4.20 (2H, s), 4.37 (2H, d, J = 7.0 Hz), 4.76 (2H, s), 6.51 (1H, d, J = 2.3 Hz), 6.89 (1H, d, J = 5.3 Hz), 7.33 (2H, d, J = 8.3 Hz), 7.37 (1H, d, J = 2.3 Hz), 7.68-7.80 (2H, m), 8.21 (1H, d, J = 5.1 Hz).

TABLE 1-41

| Ex. No. | compound name | structure | salt, stereochemistry | MS |
|---|---|---|---|---|
| 498 | 2-((2-(4-(1,3-dimethyl-1H-pyrazol-5-yl)benzyl)-3-oxo-2,3-dihydro-1H-isoindol-4-yl)oxy)-3-fluorobenzonitrile | 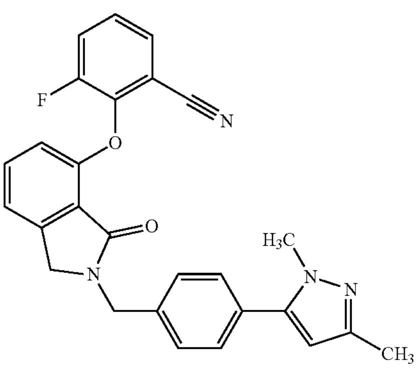 [SMILES: Cc1cc(-c2ccc(CN3Cc4cccc(Oc5c(F)cccc5C#N)c4C3=O)cc2)n(C)n1] | | 453.2 |

1H NMR (300 MHz, DMSO-d6) δ 2.15 (3H, s), 3.75 (3H, s), 4.46 (2H, s), 4.74 (2H, s), 6.15 (1H, s), 6.84 (1H, d, J = 7.9 Hz), 7.32-7.42 (1H, m), 7.45-7.59 (2H, m), 7.76-7.87 (1H, m).

| 499 | 2-((2-(4-(1,3-dimethyl-1H-pyrazol-4-yl)-3-fluorobenzyl)-3-oxo-2,3-dihydro-1H-isoindol-4-yl)oxy)-3-fluorobenzonitrile | | | 471.2 |

1H NMR (300 MHz, CDCl3) δ 2.35 (3H, s), 3.89 (3H, s), 4.34 (2H, s), 4.77 (2H, s), 6.77 (1H, d, J = 8.3 Hz), 7.05-7.20 (3H, m), 7.28-7.48 (4H, m), 7.49-7.54 (2H, m).

TABLE 1-41-continued

| Ex. No. | compound name | structure | salt, stereochemistry | MS |
|---|---|---|---|---|
| 500 | 2-(4-(1-methyl-1H-pyrazol-4-yl)benzyl)-7-((1,3-thiazol-4-yl)methoxy)isoindolin-1-one | 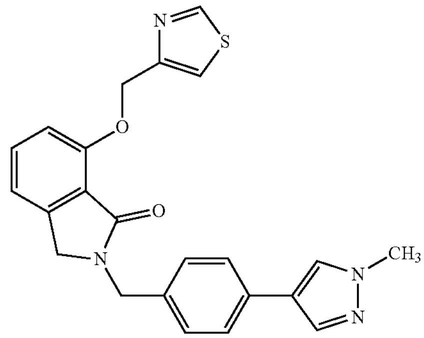 [SMILES: Cn1cc(-c2ccc(CN3Cc4cccc(OCc5cscn5)c4C3=O)cc2)cn1] | | 417.0 |

1H NMR (300 MHz, DMSO-d6) δ 3.84 (3H, s), 4.31 (2H, s), 4.64 (2H, s), 5.38 (2H, s), 7.10 (1H, d, J = 7.4 Hz), 7.18 (1H, d, J = 8.3 Hz), 7.25 (2H, d, J = 8.3 Hz), 7.46-7.56 (3H, m), 7.82 (1H, s), 7.86 (1H, d, J = 1.9 Hz), 8.10 (1H, s), 9.15 (1H, d, J = 1.9 Hz).

| 501 | 2-(4-(1,3-dimethyl-1H-pyrazol-4-yl)benzyl)-4-((tetrahydro-2H-pyran-4-yl)methoxy)-1,2-dihydro-3H-pyrrolo[3,4-c]pyridin-3-one | | | 433.1 |

1H NMR (300 MHz, DMSO-d6) δ 1.28-1.46 (2H, m), 1.71 (2H, d, J = 12.7 Hz), 1.97-2.14 (1H, m), 2.27 (3H, s), 3.32-3.40 (2H, m), 3.77 (3H, s), 3.88 (2H, dd, J = 11.3, 2.8 Hz), 4.26 (2H, d, J = 6.6 Hz), 4.38 (2H, s), 4.64 (2H, s), 7.17 (1H, d, J = 5.1 Hz), 7.24-7.31 (2H, m), 7.35-7.42 (2H, m), 7.85 (1H, s), 8.27 (1H, d, J = 5.1 Hz).

TABLE 1-42

| Ex. No. | compound name | structure | salt, stereochemistry | MS |
|---|---|---|---|---|
| 502 | 2-(4-(2-methylpyridin-4-yl)benzyl)-4-((tetrahydro-2H-pyran-4-yl)methoxy)-1,2-dihydro-3H-pyrrolo[3,4-c]pyridin-3-one | 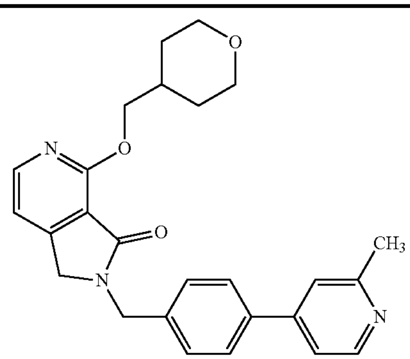 | | 430.2 |

1H NMR (300 MHz, DMSO-d6) δ 1.27-1.45 (2H, m), 1.71 (2H, d, J = 12.8 Hz), 1.97-2.15 (1H, m), 2.52 (3H, brs), 3.32-3.41 (2H, m), 3.89 (2H, dd, J = 11.6, 2.9 Hz), 4.27 (2H, d, J = 6.6 Hz), 4.40 (2H, s), 4.71 (2H, s), 7.18 (1H, d, J = 5.3 Hz), 7.41 (2H, d, J = 8.3 Hz), 7.47 (1H, dd, J = 5.1, 1.7 Hz), 7.56 (1H, s), 7.77 (2H, d, J = 8.3 Hz), 8.28 (1H, d, J = 5.1 Hz), 8.48 (1H, d, J = 5.3 Hz).

TABLE 1-42-continued

| Ex. No. | compound name | structure | salt, stereochemistry | MS |
|---|---|---|---|---|
| 503 | 5-fluoro-6-((3-oxo-2-(4-(1H-pyrazol-1-yl)benzyl)-2,3-dihydro-1H-isoindol-4-yl)oxy)nicotinonitrile | 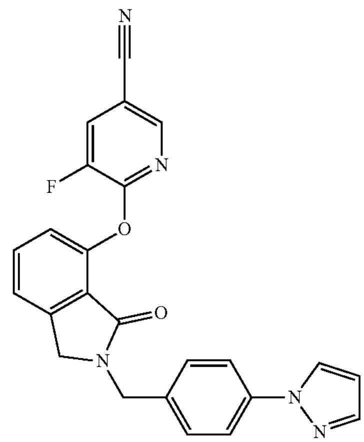 [SMILES: N#Cc1cnc(Oc2cccc3c2C(=O)N(Cc2ccc(-n4cccn4)cc2)C3)c(F)c1] | | 426.1 |

1H NMR (300 MHz, CDCl3) δ 4.31 (2H, s), 4.68 (2H, s), 6.47 (1H, t, J = 2.1 Hz), 7.29-7.38 (4H, m), 7.60-7.69 (3H, m), 7.71-7.78 (2H, m), 7.91 (1H, d, J = 2.5 Hz), 8.13 (1H, d, J = 1.9 Hz).

| 504 | 7-((1,5-dimethyl-1H-pyrazol-3-yl)methoxy)-2-(4-(1-methyl-1H-pyrazol-4-yl)benzyl)isoindolin-1-one | | | 428.2 |

1H NMR (300 MHz, DMSO-d6) δ 2.11 (3H, s), 3.78-3.87 (6H, m), 4.29 (2H, s), 4.62 (2H, s), 5.27 (2H, s), 6.16 (1H, s), 7.08-7.27 (4H, m), 7.47-7.56 (3H, m), 7.82 (1H, s), 8.10 (1H, s).

| 505 | 7-((1,3-dimethyl-1H-pyrazol-5-yl)methoxy)-2-(4-(1-methyl-1H-pyrazol-4-yl)benzyl)isoindolin-1-one | | | 428.2 |

1H NMR (300 MHz, DMSO-d6) δ 2.11 (3H, s), 3.79-3.89 (6H, m), 4.29 (2H, s), 4.63 (2H, s), 5.27 (2H, s), 6.16 (1H, s), 7.08-7.27 (4H, m), 7.46-7.58 (3H, m), 7.82 (1H, s), 8.10 (1H, s).

TABLE 1-43

| Ex. No. | compound name | structure | salt, stereochemistry | MS |
|---|---|---|---|---|
| 506 | 4-(((1,2-trans)-2-hydroxycyclohexyl)oxy)-2-((6-methylpyridin-3-yl)methyl)-1,2-dihydro-3H-pyrrolo[3,4-c]pyridin-3-one | 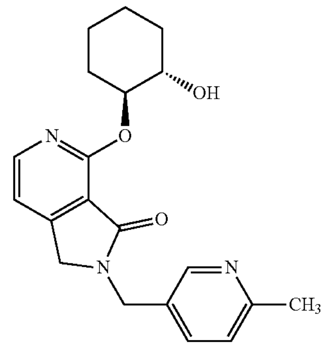 [SMILES: Cc1ccc(CN2Cc3ccnc(O[C@H]4CCCC[C@@H]4O)c3C2=O)cn1] | HCl salt, racemate | 354.1 |

1H NMR (300 MHz, DMSO-d6) δ 1.24-1.43 (4H, m), 1.65 (2H, brs), 1.88-2.05 (2H, m), 2.54 (1H, s), 2.67 (3H, s), 3.60-3.63 (1H, m), 4.47 (2H, s), 4.78 (2H, s), 5.07-5.17 (1H, m), 7.17 (1H, d, J = 5.1 Hz), 7.77 (1H, d, J = 8.3 Hz), 8.22-8.30 (2H, m), 8.70 (1H, d, J = 1.7 Hz), HCl proton was merged with H2O signal.

| 507 | 4-(cyclobutyloxy)-2-(4-(2-methylpyridin-4-yl)benzyl)-1,2-dihydro-3H-pyrrolo[3,4-c]pyridin-3-one | | | 386.1 |

1H NMR (300 MHz, CDCl3) δ 1.64-1.95 (2H, m), 2.27-2.42 (2H, m), 2.45-2.58 (2H, m), 2.61 (3H, s), 4.25 (2H, s), 4.80 (2H, s), 5.36 (1H, quin, J = 7.5 Hz), 6.91 (1H, d, J = 5.1 Hz), 7.24-7.30 (1H, m), 7.33 (1H, s), 7.38-7.46 (2H, m), 7.58 (2H, d, J = 8.3 Hz), 8.23 (1H, d, J = 5.3 Hz), 8.53 (1H, d, J = 5.1 Hz).

| 508 | 3-fluoro-2-((2-(4-(3-methyl-1,2-oxazol-5-yl)benzyl)-3-oxo-2,3-dihydro-1H-isoindol-4-yl)oxy)benzonitrile | | | 440.1 |

1H NMR (300 MHz, CDCl3) δ 2.36 (3H, s), 4.31 (2H, s), 4.81 (2H, s), 6.36 (1H, s), 6.77 (1H, d, J = 8.3 Hz), 7.16 (1H, d, J = 7.6 Hz), 7.24-7.33 (1H, m), 7.39-7.47 (4H, m), 7.51 (1H, dt, J = 7.7, 1.4 Hz), 7.74 (2H, d, J = 8.3 Hz).

TABLE 1-43-continued

| Ex. No. | compound name | structure | salt, stereochemistry | MS |
|---|---|---|---|---|
| 509 | 4-((2-(2,5-difluorobenzyl)-3-coxo-2,3-dihydro-1H-pyrrolo[3,4-c]pyridin-4-yl)oxy)-3,5-difluorobenzonitrile | 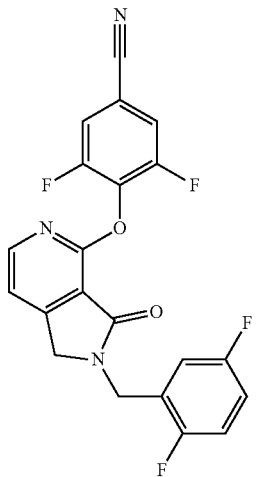 [SMILES: N#Cc1cc(F)c(Oc2nccc3c2C(=O)N(Cc2cc(F)ccc2F)C3)c(F)c1] | | 414.1 |

1H NMR (300 MHz, CDCl3) δ 4.44 (2H, s), 4.83 (2H, s), 6.94-7.21 (4H, m), 7.35 (2H, d, J = 6.6 Hz), 8.17 (1H, d, J = 5.3 Hz).

TABLE 1-44

| Ex. No. | compound name | structure | salt, stereochemistry | MS |
|---|---|---|---|---|
| 510 | 2-(4-bromo-2-fluorobenzyl)-4-(6,7-dihydro-5H-cyclopenta[b]pyridin-7-yloxy)-1,2-dihydro-3H-pyrrolo[3,4-c]pyridin-3-one | 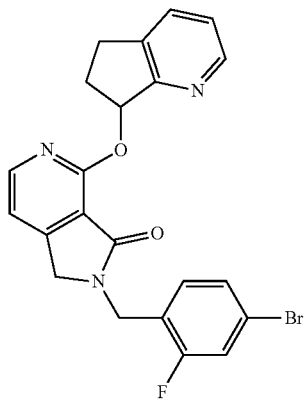 [SMILES: O=C1c2c(ccnc2OC2CCc3cccnc32)CN1Cc1ccc(Br)cc1F] | racemate | 453.9 |

1H NMR (300 MHz, CDCl3) δ 2.35 (1H, ddt, J = 14.0, 8.6, 5.6 Hz), 2.63-2.83 (1H, m), 2.84-3.04 (1H, m), 3.09-3.30 (1H, m), 4.29 (2H, s), 4.70 (2H, s), 6.82 (1H, dd, J = 7.4, 5.1 Hz), 6.97 (1H, d, J = 5.1 Hz), 7.15 (1H, dd, J = 7.6, 4.8 Hz), 7.20-7.32 (2H, m), 7.58 (1H, d, J = 7.9 Hz), 8.32 (1H, d, J = 5.1 Hz), 8.48 (1H, d, J = 4.3 Hz), TABLE 1-44-continued

| Ex. No. | compound name | structure | salt, stereochemistry | MS |
|---|---|---|---|---|
| 511 | 4-((2-((6-chloropyridin-3-yl)methyl)-3-oxo-2,3-dihydro-1H-isoindol-4-yl)oxy)-3,5-difluorobenzonitrile | 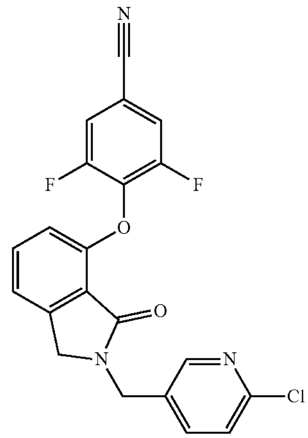 [SMILES: N#Cc1cc(F)c(Oc2cccc3c2C(=O)N(Cc2ccc(Cl)nc2)C3)c(F)c1] | | 412.0 |

1H NMR (300 MHz, CDCl3) δ 4.32 (2H, s), 4.75 (2H, s), 6.83 (1H, d, J = 8.1 Hz), 7.20 (1H, d, J = 7.4 Hz), 7.30-7.37 (3H, m), 7.44-7.51 (1H, m), 7.68 (1H, dd, J = 8.1, 2.5 Hz), 8.37 (1H, d, J = 2.3 Hz).

| 512 | 2-(4-bromobenzyl)-4-((2,2-dimethyl-2,3-dihydro-1-benzofuran-7-yl)oxy)-1,2-dihydro-3H-pyrrolo[3,4-c]pyridin-3-one | | | 465.0 |

1H NMR (300 MHz, DMSO-d6) δ 1.34 (6H, s), 3.06 (2H, s), 4.45 (2H, s), 4.69 (2H, s), 6.84 (1H, d, J = 7.5 Hz), 6.92 (1H, s), 7.04-7.12 (1H, m), 7.25-7.33 (3H, m), 7.51-7.61 (2H, m), 8.16 (1H, d, J = 5.3 Hz).

| 513 | 4-((2,2-dimethyl-2,3-dihydro-1-benzofuran-7-yl)oxy)-2-(4-(1-methyl-1H-pyrazol-4-yl)benzyl)-1,2-dihydro-3H-pyrrolo[3,4-c]pyridin-3-one | | | 467.2 |

1H NMR (300 MHz, DMSO-d6) δ 1.34 (6H, s), 3.06 (2H, s), 3.85 (3H, s), 4.45 (2H, s), 4.69 (2H, s), 6.79-6.88 (1H, m), 6.91-6.97 (1H, m), 7.08 (1H, d, J = 7.2 Hz), 7.24-7.34 (3H, m), 7.55 (2H, d, J = 8.1 Hz), 7.84 (1H, s), 8.12 (1H, s), 8.16 (1H, d, J = 5.1 Hz).

TABLE 1-45

| Ex. No. | compound name | structure | salt, stereochemistry | MS |
|---|---|---|---|---|
| 514 | 4-((2,2-dimethyl-2,3-dihydro-1-benzofuran-7-yl)oxy)-2-(4-(1-methyl-1H-pyrazol-3-yl)benzyl)-1,2-dihydro-3H-pyrrolo[3,4-c]pyridin-3-one | 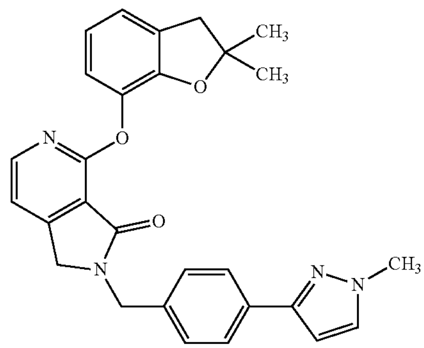 [SMILES: Cn1ccc(-c2ccc(CN3Cc4ccnc(Oc5cccc6c5OC(C)(C)C6)c4C3=O)cc2)n1] | | 467.2 |

1H NMR (300 MHz, DMSO-d6) δ 1.34 (6H, s), 3.06 (2H, s), 3.87 (3H, s), 4.46 (2H, s), 4.72 (2H, s), 6.67 (1H, d, J = 2.1 Hz), 6.78-6.88 (1H, m), 6.91-6.99 (1H, m), 7.08 (1H, d, J = 7.4 Hz), 7.28 (1H, d, J = 5.1 Hz), 7.33 (2H, d, J = 8.1 Hz), 7.72 (1H, d, J = 2.1 Hz), 7.77 (2H, d, J = 8.1 Hz), 8.16 (1H, d, J = 5.1 Hz).

| 515 | 4-(2-fluoro-3-(trifluoromethyl)phenoxy)-2-(4-(2-methylpyridin-4-yl)benzyl)-1,2-dihydro-3H-pyrrolo[3,4-c]pyridin-3-one | | | 494.1 |

1H NMR (300 MHz, DMSO-d6) δ 2.53 (3H, s), 4.54 (2H, s), 4.80 (2H, s), 7.40-7.60 (6H, m), 7.67-7.83 (4H, m), 8.24 (1H, d, J = 5.3 Hz), 8.49 (1H, d, J = 5.3 Hz).

| 516 | 4-(2-fluoro-5-(trifluoromethyl)phenoxy)-2-(4-(2-methylpyridin-4-yl)benzyl)-1,2-dihydro-3H-pyrrolo[3,4-c]pyridin-3-one | | | 494.1 |

1H NMR (300 MHz, DMSO-d6) δ 2.53 (3H, s), 4.54 (2H, s), 4.80 (2H, s), 7.39-7.51 (4H, m), 7.57 (1H, s), 7.62-7.71 (1H, m), 7.72-7.83 (3H, m), 7.86-7.98 (1H, m), 8.23 (1H, d, J = 5.1 Hz), 8.49 (1H, d, J = 5.3 Hz).

TABLE 1-45-continued

| Ex. No. | compound name | structure | salt, stereochemistry | MS |
|---|---|---|---|---|
| 517 | 4-(2-fluoro-5-methylphenoxy)-2-(4-(2-methylpyridin-4-yl)benzyl)-1,2-dihydro-3H-pyrrolo[3,4-c]pyridin-3-one | 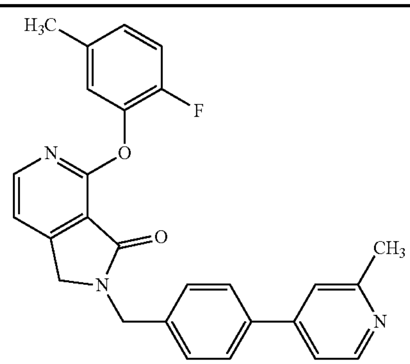 | | 440.1 |

1H NMR (300 MHz, DMSO-d6) δ 2.32 (3H, s), 2.53 (3H, s), 4.51 (2H, s), 4.78 (2H, s), 7.06-7.14 (1H, m), 7.15-7.29 (2H, m), 7.35 (1H, d, J = 5.3 Hz), 7.42-7.51 (3H, m), 7.57 (1H, s), 7.79 (2H, d, J = 8.3 Hz), 8.21 (1H, d, J = 5.1 Hz), 8.49 (1H, d, J = 5.3 Hz).

TABLE 1-46

| Ex. No. | compound name | structure | salt, stereochtemistry | MS |
|---|---|---|---|---|
| 518 | 1,5-anhydro-2-deoxy-4-O-(2-(4-methylbenzyl)-3-oxo-2,3-dihydro-1H-isoindol-4-yl)-threo-pentitol | 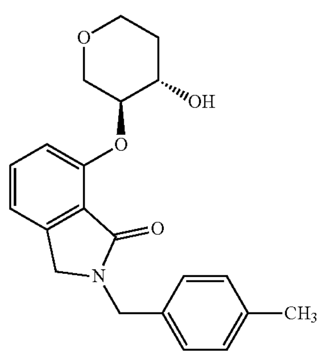 [SMILES: Cc1ccc(CN2Cc3cccc(O[C@H]4COCC[C@@H]4O)c3C2=O)cc1] | tR1 in Examples 53-56, optically active form, 3,4-trans | 354.1 |

1H NMR (300 MHz, DMSO-d6) δ 1.41-1.58 (1H, m), 1.95-2.09 (1H, m), 2.20-2.32 (3H, m), 3.37-3.49 (2H, m), 3.72-3.86 (2H, m), 3.95-4.15 (2H, m), 4.27 (2H, s), 4.61 (2H, s), 5.36 (1H, d, J = 4.0 Hz), 7.06-7.21 (6H, m), 7.40-7.55 (1H, m).

| 519 | 1,5-anhydro-2-deoxy-3-O-(2-(4-methylbenzyl)-3-oxo-2,3-dihydro-1H-isoindol-4-yl)-threo-pentitol | | tR2 in Examples 53-56, optically active form, 3,4-trans | 354.1 |

1H NMR (300 MHz, DMSO-d6) δ 1.54-1.69 (1H, m), 2.06-2.18 (1H, m), 2.28 (3H, s), 3.19 (1H, dd, J = 11.2, 7.8 Hz), 3.36-3.47 (1H, m), 3.53-3.65 (1H, m), 3.77-3.91 (2H, m), 4.27 (2H, s), 4.31-4.40 (1H, m), 4.62 (2H, s), 5.41 (1H, d, J = 4.5 Hz), 7.08-7.21 (6H, m), 7.43-7.53 (1H, m).

TABLE 1-46-continued

| Ex. No. | compound name | structure | salt, stereochemistry | MS |
|---|---|---|---|---|
| 520 | 1,5-anhydro-2-deoxy-3-O-(2-(4-methylbenzyl)-3-oxo-2,3-dihydro-1H-isoindol-4-yl)-threo-pentitol | 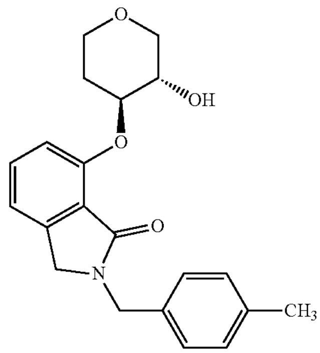 [SMILES: Cc1ccc(CN2Cc3cccc(O[C@H]4CCOC[C@@H]4O)c3C2=O)cc1] | tR3 on Examples 53-56, optically active form, 3,4-trans | 354.1 |

1H NMR (300 MHz, DMSO-d6) δ 1.53-1.71 (1H, m), 2.05-2.19 (1H, m), 2.28 (3H, s), 3.19 (1H, dd, J = 11.2, 7.8 Hz), 3.36-3.47 (1H, m), 3.54-3.67 (1H, m), 3.77-3.92 (2H, m), 4.27 (2H, s), 4.30-4.41 (1H, m), 4.62 (2H, s), 5.42 (1H, d, J = 4.3 Hz), 7.07-7.21 (6H, m), 7.44-7.53 (1H, m).

| 521 | 1,5-anhydro-2-deoxy-4-O-(2-(4-methylbenzyl)-3-oxo-2,3-dihydro-1H-isoindol-4-yl)-threo-pentitol | | tR4 on Examples 53-56, optically active form, 3,4-trans | 354.1 |

1H NMR (300 MHz, DMSO-d6) δ 1.43-1.57 (1H, m), 1.99-2.09 (1H, m), 2.28 (3H, s), 3.36-3.49 (2H, m), 3.72-3.85 (2H, m), 3.96-4.13 (2H, m), 4.27 (2H, s), 4.61 (2H, s), 5.36 (1H, d, J = 4.0 Hz), 7.10-7.19 (6H, m), 7.43-7.52 (1H, m).

TABLE 1-47

| Ex. No. | compound name | structure | salt, stereochemistry | MS |
|---|---|---|---|---|
| 522 | 6-(4-chlorobenzyl)-4-((tetrahydrofuran-2-yl)methoxy)-6,7-dihydro-5H-pyrrolo[3,4-d]pryimidin-5-one | 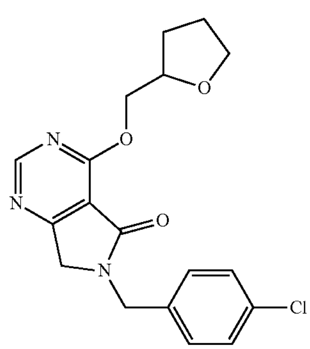 [SMILES: O=C1c2c(ncnc2OCC2CCCO2)CN1Cc1ccc(Cl)cc1] | racemate | 360.1 |

1H NMR (300 MHz, DMSO-d6) δ 1.64-1.89 (2H, m), 1.88-2.08 (2H, m), 3.61-3.72 (1H, m), 3.76-3.86 (1H, m), 4.17-4.30 (1H, m), 4.38-4.44 (2H, m), 4.45-4.56 (2H, m), 4.68 (2H, s), 7.28-7.35 (2H, m), 7.37-7.45 (2H, m), 8.89 (1H, s).

TABLE 1-47-continued

| Ex. No. | compound name | structure | salt, stereochemistry | MS |
|---|---|---|---|---|
| 523 | 4-(2,3-difluorophenoxy)-2-(4-(1-methyl-1H-pyrazol-3-yl)benzyl)-1,2-dihydro-3H-pyrrolo[3,4-c]pyridin-3-one | 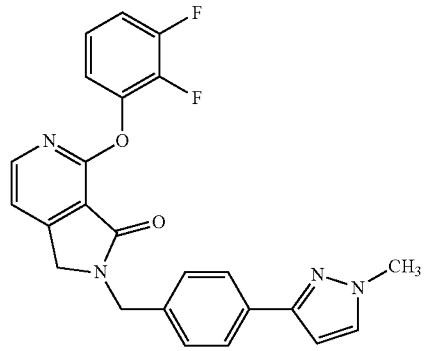 [SMILES: Cn1ccc(-c2ccc(CN3Cc4ccnc(Oc5cccc(F)c5F)c4C3=O)cc2)n1] | | 433.0 |

1H NMR (300 MHz, DMSO-d6) δ 3.87 (3H, s), 4.50 (2H, s), 4.73 (2H, s), 6.67 (1H, d, J = 2.3 Hz), 7.19-7.45 (6H, m), 7.72 (1H, d, J = 2.1 Hz), 7.77 (2H, d, J = 8.1 Hz), 8.23 (1H, d, J = 5.1 Hz).

| 524 | 4-(2,3-difluorophenoxy)-2-(4-(6-methylpyridazin-4-yl)benzyl)-1,2-dihydro-3H-pyrrolo[3,4-c]pyridin-3-one | | | 445.1 |

1H NMR (300 MHz, DMSO-d6) δ 2.68 (3H, s), 4.54 (2H, s), 4.81 (2H, s), 7.20-7.46 (4H, m), 7.51 (2H, d, J = 8.1 Hz), 7.85-7.97 (3H, m), 8.24 (1H, d, J = 5.3 Hz), 9.46 (1H, d, J = 2.3 Hz).

| 525 | 4-(2,5-difluorophenoxy)-2-(4-(1-methyl-1H-pyrazol-3-yl)benzyl)-1,2-dihydro-3H-pyrrolo[3,4-c]pyridin-3-one | | | 433.0 |

1H NMR (300 MHz, DMSO-d6) δ 3.87 (3H, s), 4.50 (2H, s), 4.73 (2H, s), 6.66 (1H, d, J = 2.3 Hz), 7.13-7.25 (1H, m), 7.33 (2H, d, J = 8.3 Hz), 7.37-7.51 (3H, m), 7.72 (1H, d, J = 2.1 Hz), 7.77 (2H, d, J = 8.1 Hz), 8.23 (1H, d, J = 5.3 Hz).

TABLE 1-48

| Ex. No. | compound name | structure | salt, stereochemistry | MS |
|---|---|---|---|---|
| 526 | 4-(2,5-difluorophenoxy)-2-(4-(6-methylpyridazin-4-yl)benzyl)-1,2-dihydro-3H-pyrrolo[3,4-c]pyridin-3-one | 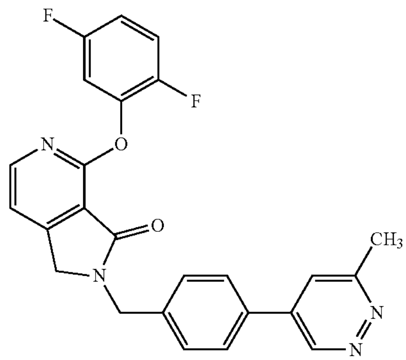 [SMILES: Cc1cc(-c2ccc(CN3Cc4ccnc(Oc5cc(F)ccc5F)c4C3=O)cc2)cnn1] | | 445.1 |

1H NMR (300 MHz, DMSO-d6) δ 2.68 (3H, s), 4.54 (2H, s), 4.81 (2H, s), 7.13-7.25 (1H, m), 7.36-7.55 (5H, m), 7.85-7.96 (3H, m), 8.24 (1H, d, J = 5.1 Hz), 9.46 (1H, d, J = 2.3 Hz).

| 527 | 4-(4-fluoro-2-methylphenoxy)-2-(4-(6-methylpyridazin-4-yl)benzyl)-1,2-dihydro-3H-pyrrolo[3,4-c]pyridin-3-one | | | 441.1 |

1H NMR (300 MHz, DMSO-d6) δ 2.08 (3H, s), 2.68 (3H, s), 4.51 (2H, s), 4.80 (2H, s), 7.02-7.12 (1H, m), 7.12-7.25 (2H, m), 7.32 (1H, d, J = 5.3 Hz), 7.51 (2H, d, J = 8.3 Hz), 7.84-7.97 (3H, m), 8.19 (1H, d, J = 5.3 Hz), 9.46 (1H, d, J = 2.3 Hz).

| 528 | 4-(4-chloro-2-methylphenoxy)-2-(4-(6-methylpyridazin-4-yl)benzyl)-1,2-dihydro-3H-pyrrolo[3,4-c]pyridin-3-one | | | 457.1 |

1H NMR (300 MHz, DMSO-d6) δ 2.08 (3H, s), 2.68 (3H, s), 4.51 (2H, s), 4.80 (2H, s), 7.16 (1H, d, J = 8.7 Hz), 7.27-7.37 (2H, m), 7.43 (1H, d, J = 2.4 Hz), 7.51 (2H, d, J = 8.3 Hz), 7.89 (1H, d, J = 2.3 Hz), 7.92 (2H, d, J = 8.5 Hz), 8.19 (1H, d, J = 5.3 Hz), 9.46 (1H, d, J = 2.1 Hz).

TABLE 1-48-continued

| Ex. No. | compound name | structure | salt, stereochemistry | MS |
|---|---|---|---|---|
| 529 | 4-(2,4-dimethylphenoxy)-2-(4-(6-methylpyridazin-4-yl)benzyl)-1,2-dihydro-3H-pyrrolo[3,4-c]pyridin-3-one | 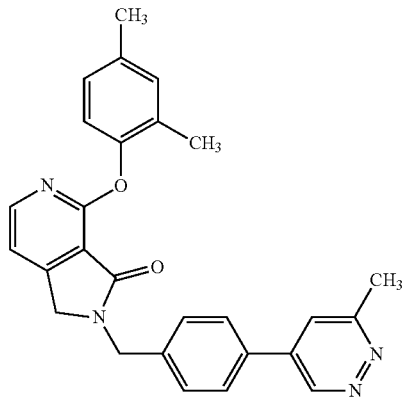 [SMILES: Cc1ccc(Oc2nccc3c2C(=O)N(Cc2ccc(-c4cnnc(C)c4)cc2)C3)c(C)c1] | | 437.2 |

1H NMR (300 MHz, DMSO-d6) δ 2.02 (3H, s), 2.30 (3H, s), 2.68 (3H, s), 4.50 (2H, s), 4.80 (2H, s), 6.94-7.00 (1H, m), 7.03-7.09 (1H, m), 7.12 (1H, s), 7.29 (1H, d, J = 5.3 Hz), 7.51 (2H, d, J = 8.3 Hz), 7.89 (1H, d, J = 2.3 Hz), 7.92 (2H, d, J = 8.3 Hz), 8.16 (1H, d, J = 4.9 Hz), 9.46 (1H, d, J = 2.3 Hz).

TABLE 1-49

| Ex. No. | compound name | structure | salt, stereochemistry | MS |
|---|---|---|---|---|
| 530 | 2-(4-bromobenzyl)-4-(2-fluoro-4-(2-hydroxypropan-2-yl)phenoxy)-1,2-dihydro-3H-pyrrolo[3,4-c]pyridin-3-one | 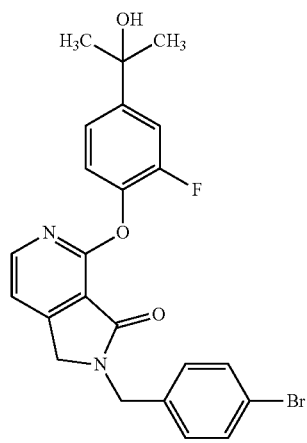 [SMILES: CC(C)(O)c1ccc(Oc2nccc3c2C(=O)N(Cc2ccc(Br)cc2)C3)c(F)c1] | | 471.0 |

1H NMR (300 MHz, DMSO-d6) δ 1.46 (6H, s), 4.48 (2H, s), 4.69 (2H, s), 5.17 (1H, s), 7.22-7.38 (5H, m), 7.41 (1H, dd, J = 12.4, 2.0 Hz), 7.52-7.60 (2H, m), 8.20 (1H, d, J = 5.1 Hz).

TABLE 1-49-continued

| Ex. No. | compound name | structure | salt, stereochemistry | MS |
|---|---|---|---|---|
| 531 | (4-((2-(2,4-difluorobenzyl)-3-oxo-2,3-dihydro-1H-pyrrolo[3,4-c]pyridin-4-yl)oxy)-3-fluorophenyl)acetonitrile | 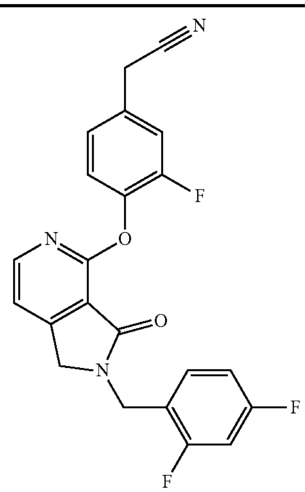 | | 410.1 |

1H NMR (300 MHz, DMSO-d6) δ 4.11 (2H, s), 4.51 (2H, s), 4.74 (2H, s), 7.10 (1H, td, J = 8.4, 2.2 Hz), 7.23-7.33 (2H, m), 7.34-7.51 (4H, m), 8.20 (1H, d, J = 5.3 Hz).

| 532 | (3-fluoro-4-((3-oxo-2-(4-(3-(trifluoromethyl)-1H-pyrazol-1-yl)benzyl)-2,3-dihydro-1H-pyrrolo[3,4-c]pyridin-4-yl)oxy)phenyl)acetonitrile | | | 508.2 |

1H NMR (300 MHz, DMSO-d6) δ 4.11 (2H, s), 4.52 (2H, s), 4.79 (2H, s), 7.04 (1H, d, J = 2.5 Hz), 7.28 (1H, d, J = 8.5 Hz), 7.35-7.46 (3H, m), 7.51 (2H, d, J = 8.7 Hz), 7.88 (2H, d, J = 8.5 Hz), 8.21 (1H, d, J = 5.1 Hz), 8.72 (1H, dd, J = 2.5, 0.9 Hz).

| 533 | 7-(2-fluoro-4-(trifluoromethyl)phenoxy)-2-(4-(1-methyl-1H-pyrazol-3-yl)benzyl)-2,3-dihydro-1H-pyrrolo[3,4-c]pyridin-1-one | | | 483.1 |

1H NMR (300 MHz, DMSO-d6) δ 3.87 (3H, s), 4.54 (2H, s), 4.67 (2H, s), 6.66 (1H, d, J = 2.3 Hz), 7.15 (1H, t, J = 8.6 Hz), 7.29 (2H, d, J = 8.3 Hz), 7.51 (1H, d, J = 8.3 Hz), 7.71 (1H, d, J = 2.1 Hz), 7.75 (2H, d, J = 8.3 Hz), 7.91 (1H, dd, J = 11.1, 2.1 Hz), 8.53 (1H, s), 8.77 (1H, s).

TABLE 1-50

| Ex. No. | compound name | structure | salt, stereochemistry | MS |
|---|---|---|---|---|
| 534 | 3-fluoro-4-((4-(2-fluoro-4-(trifluoromethyl)phenoxy)-3-oxo-1,3-dihydro-2H-pyrrolo[3,4-c]pyridin-2-yl)methyl)benzonitrile | 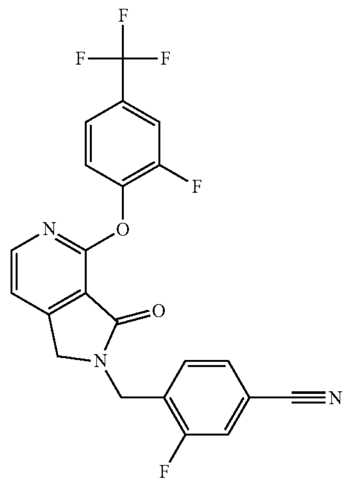 [SMILES: N#Cc1ccc(CN2Cc3ccnc(Oc4ccc(C(F)(F)F)cc4F)c3C2=O)c(F)c1] | | 446.0 |

1H NMR (300 MHz, DMSO-d6) δ 4.58 (2H, s), 4.85 (2H, s), 7.44 (1H, d, J = 5.1 Hz), 7.52-7.60 (1H, m), 7.60-7.67 (1H, m), 7.67-7.74 (2H, m), 7.87-7.97 (2H, m), 8.24 (1H, d, J = 5.1 Hz).

| 535 | (3-fluoro-4-((4-(2-fluoro-4-(trifluoromethyl)phenoxy)-3-oxo-1,3-dihydro-2H-pyrrolo[3,4-c]pyridin-2-yl)methyl)phenyl)acetonitrile | | | 460.1 |

1H NMR (300 MHz, DMSO-d6) δ 4.07 (2H, s), 4.53 (2H, s), 4.77 (2H, s), 7.18-7.30 (2H, m), 7.37-7.46 (2H, m), 7.58-7.74 (2H, m), 7.92 (1H, dd, J = 10.5, 1.8 Hz), 8.23 (1H, d, J = 5.1 Hz).

| 536 | 2-(4-fluorobenzyl)-4-(((2R,3R)-3-hydroxybutan-2-yl)oxy)-1,2-dihydro-3H-pyrrolo[3,4-c]pyridin-3-one | | (2R, 3R) | 331.2 |

1H NMR (300 MHz, DMSO-d6) δ 1.12 (3H, d, J = 6.4 Hz), 1.23 (3H, d, J = 6.4 Hz), 3.84 (1H, quin, J = 6.0 Hz), 4.34 (2H, s), 4.52-4.84 (3H, m), 5.20-5.31 (1H, m), 7.12-7.22 (3H, m), 7.27-7.38 (2H, m), 8.25 (1H, d, J = 5.1 Hz).

TABLE 1-50-continued

| Ex. No. | compound name | structure | salt, stereochemistry | MS |
|---|---|---|---|---|
| 537 | 2-(2,4-difluorobenzyl)-4-(((2,3-cis)-3-hydroxybutan-2-yl)oxy)-1,2-dihydro-3H-pyrrolo[3,4-c]pyridin-3-one | 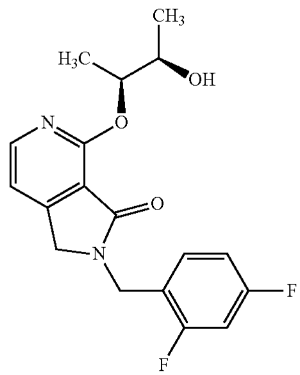 [SMILES: C[C@H](Oc1nccc2c1C(=O)N(Cc1ccc(F)cc1F)C2)[C@@H](C)O] | racemate | 349.1 |

1H NMR (300 MHz, DMSO-d6) δ 1.14 (3H, d, J = 6.4 Hz), 1.28 (3H, d, J = 6.2 Hz), 3.74 (1H, sxt, J = 5.9 Hz), 4.38 (2H, s), 4.59-4.76 (3H, m), 5.10 (1H, quin, J = 6.0 Hz), 7.07 (1H, td, J = 8.5, 1.7 Hz), 7.15 (1H, d, J = 5.1 Hz), 7.20-7.32 (1H, m), 7.33-7.46 (1H, m), 8.26 (1H, d, J = 5.3 Hz).

TABLE 1-51

| Ex. No. | compound name | structure | salt stereochemistry | MS |
|---|---|---|---|---|
| 538 | 4-(((2S)-2-aminobutyl)oxy)-2-(2,4-difluorobenzyl)-1,2-dihydro-3H-pyrrolo[3,4-c]pyridin-3-one | 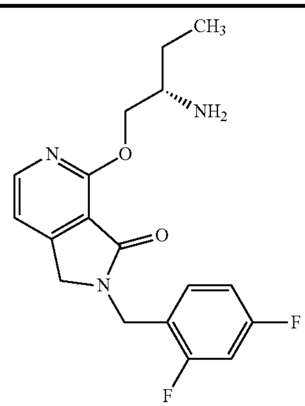 | HCl salt, (S) | 348.1 |

1H NMR (300 MHz, DMSO-d6) δ 1.74 (2H, d, J = 9.6 Hz), 3.45-3.54 (1H, m), 4.41-4.52 (3H, m), 4.57 (1H, d, J = 4.5 Hz), 4.70 (2H, s), 7.09 (1H, s), 7.28 (2H, d, J = 4.9 Hz), 7.39 (1H, d, J = 6.6 Hz), 7.98 (3H, brs), 8.31 (1H, d, J = 5.3 Hz).

| 539 | 4-(((2R)-2-aminobutyl)oxy)-2-(2,4-difluorobenzyl)-1,2-dihydro-3H-pyrrolo[3,4-c]pyridin-3-one | | HCl salt, (R) | 348.1 |

1H NMR (300 MHz, DMSO-d6) δ 1.00 (3H, t, J = 7.5 Hz), 1.62-1.84 (2H, m), 3.42-3.55 (1H, m), 4.45 (2H, s), 4.46-4.52 (1H, m), 4.54-4.64 (1H, m), 4.70 (2H, s), 7.09 (1H, td, J = 8.6, 2.4 Hz), 7.23-7.33 (2H, m), 7.39 (1H, td, J = 8.7, 6.8 Hz), 8.01 (3H, brs), 8.31 (1H, d, J = 5.3 Hz).

TABLE 1-51-continued

| Ex. No. | compound name | structure | salt stereochemistry | MS |
|---|---|---|---|---|
| 540 | N-ethyl-2-fluoro-4-((4-(2-fluoro-4-methylphenoxy)-3-oxo-1,3-dihydro-2H-pyrrolo[3,4-c]pyridin-2-yl)methyl)benzamide | 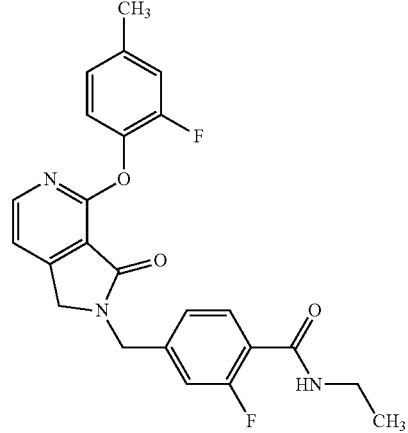 [SMILES: CCNC(=O)c1ccc(CN2Cc3ccnc(Oc4ccc(C)cc4F)c3C2=O)cc1F] | | 438.1 |

1H NMR (300 MHz, DMSO-d6) δ 1.10 (3H, t, J = 7.2 Hz), 2.35 (3H, s), 3.21-3.30 (2H, m), 4.51 (2H, s), 4.76 (2H, s), 7.07 (1H, d, J = 8.9 Hz), 7.15-7.27 (4H, m), 7.35 (1H, d, J = 5.1 Hz), 7.60 (1H, t, J = 7.8 Hz), 8.20 (1H, d, J = 5.1 Hz), 8.21-8.29 (1H, m),

| 541 | 2-(2,4-difluorobenzyl)-4-(((2R)-2-(dimethylamino)butyl)oxy)-1,2-dihydro-3H-pyrrolo[3,4-c]pyridin-3-one | 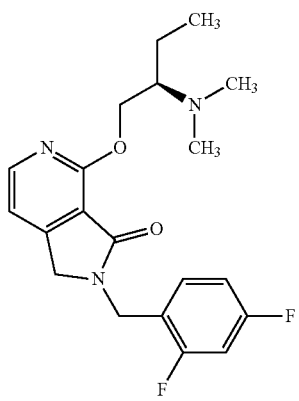 [SMILES: CC[C@H](COc1nccc2c1C(=O)N(Cc1ccc(F)cc1F)C2)N(C)C] | HCl salt, R | 376.1 |

1H NMR (300 MHz, DMSO-d6) δ 0.98 (3 H, t, J = 7.5 Hz), 1.70-1.91 (2 H, m), 2.76-3.03 (6 H, m), 3.63 (1 H, br. s.), 4.44 (2 H, s), 4.64-4.81 (4 H, m), 7.03-7.15 (1 H, m), 7.20-7.33 (2 H, m), 7.34-7.45 (1 H, m), 8.33 (1 H, d, J = 5.3 Hz), 10.26 (1 H, br. s.)

TABLE 1-52

| Ex. No. | compound name | structure | salt, stereochemistry | MS |
|---|---|---|---|---|
| 542 | 1,5-anyhdro-2-deoxy-3-O-(2-(4-fluorobenzyl)-3-oxo-2,3-dihydro-1H-isoindol-4-yl)-DL-threo-pentitol | 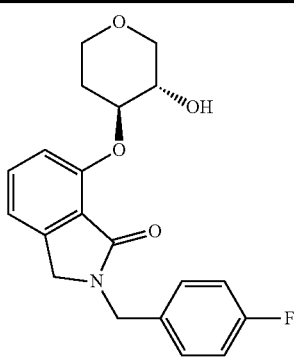 | racemate (3,4-trans) | 358.1 |

1H NMR (300 MHz, DMSO-d6) δ 1.49-1.72 (1H, m), 2.03-2.21 (1H, m), 3.20 (1H, dd, J = 11.1, 7.7 Hz), 3.37-3.48 (1H, m), 3.54-3.68 (1H, m), 3.74-3.93 (2H, m), 4.24-4.42 (3H, m), 4.65 (2H, s), 5.38 (1H, d, J = 4.5 Hz), 7.07-7.24 (4H, m), 7.28-7.37 (2H, m), 7.43-7.55 (1H, m).

TABLE 1-52-continued

| Ex. No. | compound name | structure | salt, stereochemistry | MS |
|---|---|---|---|---|
| 543 | 7-((1-methylpiperidin-4-yl)oxy)-2-(4-(1H-pyrazol-1-yl)benzyl)isoindolin-1-one | 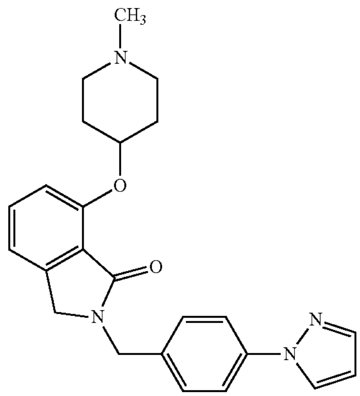 [SMILES: CN1CCC(Oc2cccc3c2C(=O)N(Cc2ccc(-n4cccn4)cc2)C3)CC1] | | 403.2 |

1H NMR (300MHz, DMSO-d6) δ 1.62-1.78 (2H, m), 1.85-1.98 (2H, m), 2.10-2.25 (5H, m), 2.66 (2H, ddd, J = 10.8, 6.4, 3.8 Hz), 4.30 (2H, s), 4.55 (1H, tt, J = 7.7, 3.8 Hz), 4.69 (2H, s), 6.50-6.56 (1H, m), 7.06 (2H, t, J = 7.7 Hz), 7.39 (2H, d, J = 8.5 Hz), 7.43-7.51 (1H, m), 7.73 (1H, d, J = 1.7 Hz), 7.81 (2H, d, J = 8.5 Hz), 8.46 (1H, d, J = 2.5 Hz).

| 544 | 5-((4-(2-fluoro-4-(2,2,2-trifluoroethyl)phenoxy)-3-oxo-1,3-dihydro-2H-pyrrolo[3,4-c]pyridin-2-yl)methyl)-N-methylpyridine-2-carboxamide | | | 475.1 |

1H NMR (300 MHz, DMSO-d6) δ 2.82 (3H, d, J = 4.9 Hz), 3.74 (2H, q, J = 11.4 Hz), 4.55 (2H, s), 4.84 (2H, s), 7.23-7.32 (1H, m), 7.34-7.46 (3H, m), 7.87-7.94 (1H, m), 7.98-8.05 (1H, m), 8.22 (1H, d, J = 5.3 Hz), 8.63 (1H, d, J = 1.5 Hz), 8.74 (1H, q, J = 4.6 Hz).

| 545 | 5-((4-(2-fluoro-4-(2,2,2-trifluoroethyl)phenoxy)-3-oxo-1,3-dihydro-2H-pyrrolo[3,4-c]pyridin-2-yl)methyl)pyridine-2-carboxamide | | | 461.1 |

1H NMR (300 MHz, DMSO-d6) δ 3.74 (2H, q, J = 11.3 Hz), 4.56 (2H, s), 4.84 (2H, s), 7.23-7.31 (1H, m), 7.34-7.46 (3H, m), 7.62 (1H, brs), 7.91 (1H, dd, J = 8.1, 2.1 Hz), 7.99-8.05 (1H, m), 8.09 (1H, brs), 8.22 (1H, d, J = 5.1 Hz), 8.57-8.67 (1H, m).

TABLE 1-53

| Ex. No. | compound name | structure | salt, stereochemistry | MS |
|---|---|---|---|---|
| 546 | 2-(2,4-dichlorobenzyl)-4-((tetrahydrofuran-2-yl)methoxy)-1,2-dihydro-3H-pyrrolo[3,4-c]pyridin-3-one | 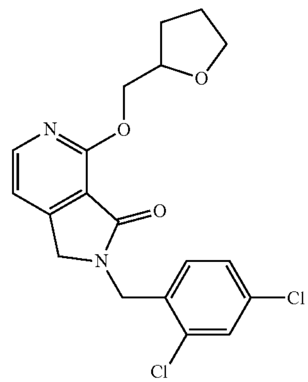 [SMILES: O=C1c2c(ccnc2OCC2CCCO2)CN1Cc1ccc(Cl)cc1Cl] | racemate | 393.0 |
| 547 | 2-(3-chloro-2,6-difluorobenzyl)-4-((tetrahydrofuran-2-yl)methoxy)-1,2-dihydro-3H-pyrrolo[3,4-c]pyridin-3-one | 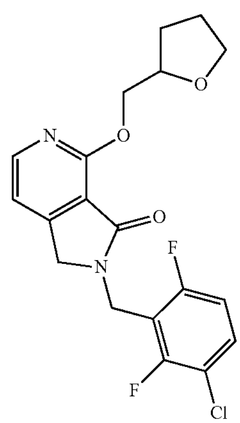 [SMILES: O=C1c2c(ccnc2OCC2CCCO2)CN1Cc1c(F)ccc(Cl)c1F] | racemate | 395.1 |
| 548 | 2-(2,4-dimethoxybenzyl)-4-((tetrahydrofuran-2-yl)methoxy)-1,2-dihydro-3H-pyrrolo[3,4-c]pyridin-3-one | 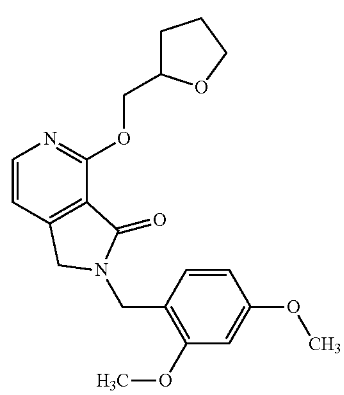 [SMILES: COc1ccc(CN2Cc3ccnc(OCC4CCCO4)c3C2=O)c(OC)c1] | racemate | 385.1 |

TABLE 1-53-continued

| Ex. No. | compound name | structure | salt, stereochemistry | MS |
|---|---|---|---|---|
| 549 | 3-fluoro-4-((3-oxo-2-(4-(1H-pyrazol-1-yl)benzyl)-2,3-dihydro-1H-isoindol-4-yl)oxy)benzonitrile | 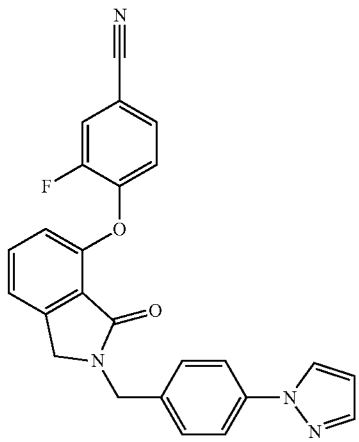 | | 425.1 |
| 550 | 2-(4-(1-methyl-1H-pyrazol-4-yl)benzyl)-7-(5,6,7,8-tetrahydroquinoline-8-yloxy)isoindolin-1-one | 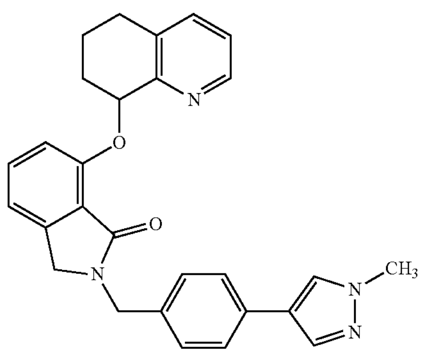 [SMILES: Cn1cc(-c2ccc(CN3Cc4cccc(OC5CCCc6cccnc65)c4C3=O)cc2)cn1] | racemate | 451.1 |

TABLE 1-54

| Ex. No.. | compound name | structure | salt, stereochemistry | MS |
|---|---|---|---|---|
| 551 | 3-(((2-(4-(1-methyl-1H-pyrazol-4-yl)benzyl)-3-oxo-2,3-dihydro-1H-isoindol-4-yl)oxy)methyl)benzonitrile | 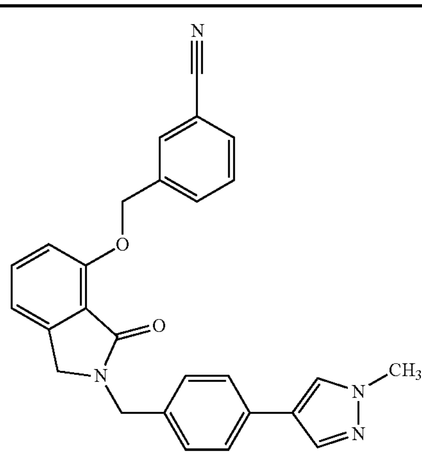 | | 435.1 |

TABLE 1-54-continued

| Ex. No.. | compound name | structure | salt, stereochemistry | MS |
|---|---|---|---|---|
| 552 | 7-((3-methoxybenzyl)oxy)-2-(4-(1-methyl-1H-pyrazol-4-yl)benzyl)isoindolin-1-one | 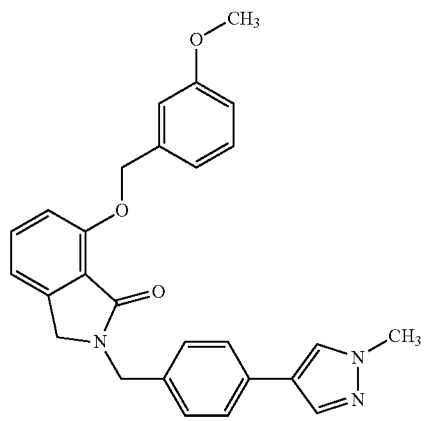 [SMILES: COc1cccc(COc2cccc3c2C(=O)N(Cc2ccc(-c4cnn(C)c4)cc2)C3)c1] | | 440.2 |
| 553 | 7-((2-methoxybenzyl)oxy)-2-(4-(1-methyl-1H-pyrazol-4-yl)benzyl)isoindolin-1-one | 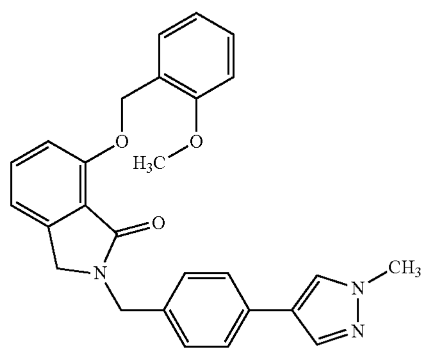 [SMILES: COc1ccccc1COc1cccc2c1C(=O)N(Cc1ccc(-c3cnn(C)c3)cc1)C2] | | 440.1 |
| 554 | 7-((2,6-difluorobenzyl)oxy-2-(4-(1-methyl-1H-pyrazol-4-yl)benzyl)isoindolin-1-one | 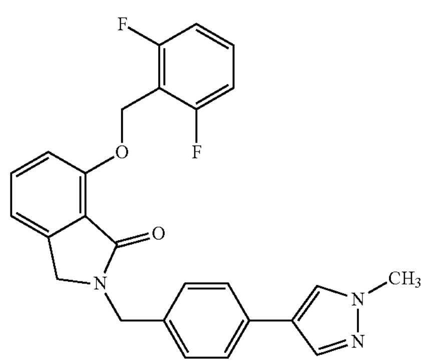 [SMILES: Cn1cc(-c2ccc(CN3Cc4cccc(OCc5c(F)cccc5F)c4C3=O)cc2)cn1] | | 446.0 |
| 555 | 7-((3-fluorobenzyl)oxy)-2-(4-(1-methyl-1H-pyrazol-4-yl)benzyl)isoindolin-1-one | 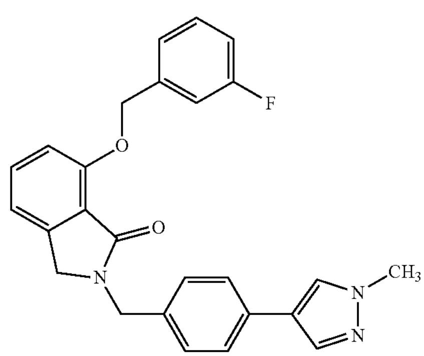 [SMILES: Cn1cc(-c2ccc(CN3Cc4cccc(OCc5cccc(F)c5)c4C3=O)cc2)cn1] | | 428.1 |

TABLE 1-55

| Ex. No. | compound name | structure | salt, stereochemistry | MS |
|---|---|---|---|---|
| 556 | 7-((4-fluorobenzyl)oxy)-2-(4-(1-methyl-1H-pyrazol-4-yl)benzyl)isoindolin-1-one | 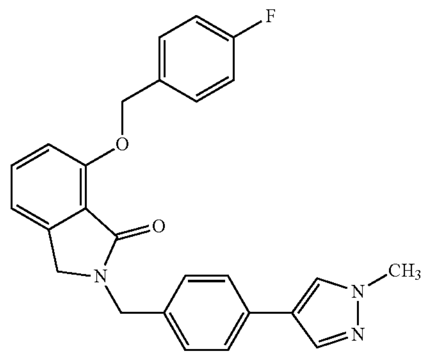 [SMILES: Cn1cc(-c2ccc(CN3Cc4cccc(OCc5ccc(F)cc5)c4C3=O)cc2)cn1] | | 428.2 |
| 557 | 7-((2,5-difluorobenzyl)oxy-2-(4-(1-methyl-1H-pyrazol-4-yl)benzyl)isoindolin-1-one | 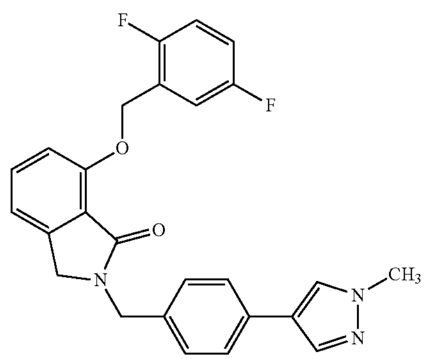 [SMILES: Cn1cc(-c2ccc(CN3Cc4cccc(OCc5cc(F)ccc5F)c4C3=O)cc2)cn1] | | 446.1 |
| 558 | 7-((3,4-difluorobenzyl)oxy)-2-(4-(1-methyl-1H-pyrazol-4-yl)benzyl)isoindolin-1-one | 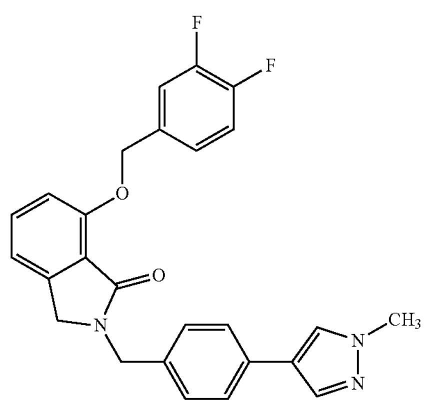 [SMILES: Cn1cc(-c2ccc(CN3Cc4cccc(OCc5ccc(F)c(F)c5)c4C3=O)cc2)cn1] | | 446.1 |
| 559 | 7-(2-(2-fluorophenyl)ethoxy)-2-(4-(1-methyl-1H-pyrazol-4-yl)benzyl)isoindolin-1-one | 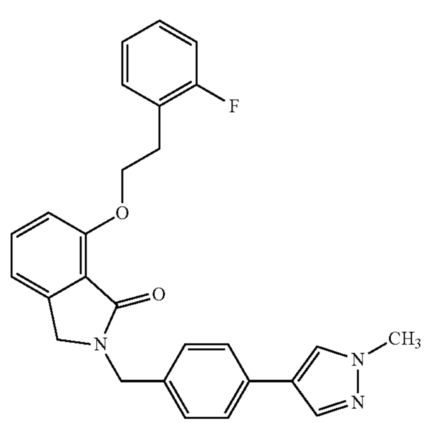 [SMILES: Cn1cc(-c2ccc(CN3Cc4cccc(OCCc5ccccc5F)c4C3=O)cc2)cn1] | | 442.1 |

TABLE 1-55-continued
| Ex. No. | compound name | structure | salt, stereochemistry | MS |
|---|---|---|---|---|
| 560 | 2-(4-(1-methyl-1H-pyrazol-4-yl)benzyl)-7-(2-(pyridin-2-yl)ethoxy)isoindolin-1-one | 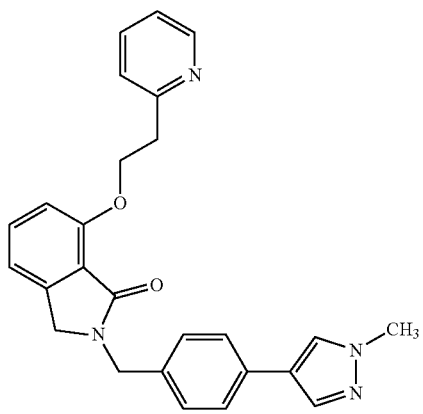 [SMILES: Cn1cc(-c2ccc(CN3Cc4cccc(OCCc5ccccn5)c4C3=O)cc2)cn1] | | 425.1 |
TABLE 1-56
| Ex. No. | compound name | structure | salt, stereochemistry | MS |
|---|---|---|---|---|
| 561 | 2-(4-(1-methyl-1H-pyrazol-4-yl)benzyl)-7-(1,2,3,4-tetrahydronaphthalen-1-yloxy)isoindolin-1-one | 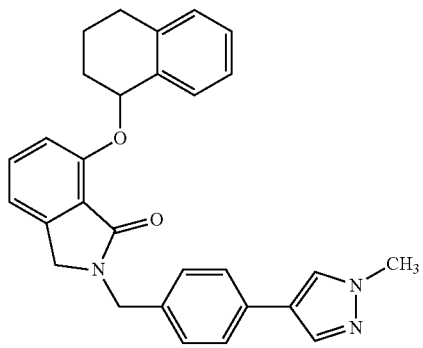 [SMILES: Cn1cc(-c2ccc(CN3Cc4cccc(OC5CCCc6ccccc65)c4C3=O)cc2)cn1] | racemate | 450.1 |
| 562 | 7-(2-methyl-1-phenylpropoxy)-2-(4-(1-methyl-1H-pyrazol-4-yl)benzyl)isoindolin-1-one | 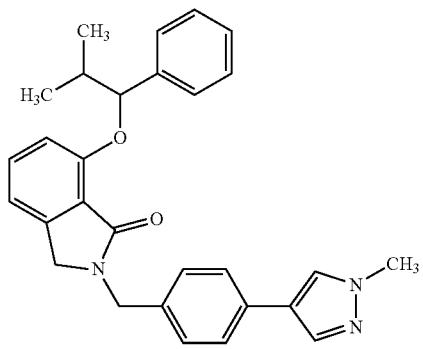 [SMILES: CC(C)C(Oc1cccc2c1C(=O)N(Cc1ccc(-c3cnn(C)c3)cc1)C2)c1ccccc1] | racemate | 452.2 |

TABLE 1-56-continued

| Ex. No. | compound name | structure | salt, stereochemistry | MS |
|---|---|---|---|---|
| 563 | 7-((2-chlorobenzyl)oxy)-2-(4-(1-methyl-1H-pyrazol-4-yl)benzyl)isoindolin-1-one | 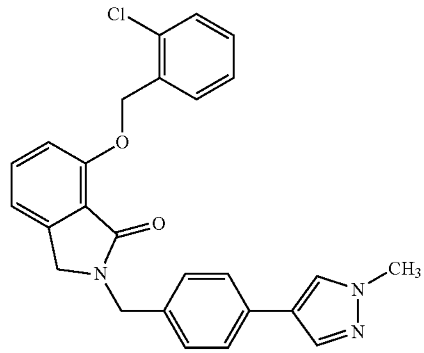 [SMILES: Cn1cc(-c2ccc(CN3Cc4cccc(OCc5ccccc5Cl)c4C3=O)cc2)cn1] | | 444.2 |
| 564 | 7-(3,4-dihydro-2H-chromen-4-yloxy)-2-(4-(1-methyl-1H-pyrazol-4-yl)benzyl)isoindolin-1-one | 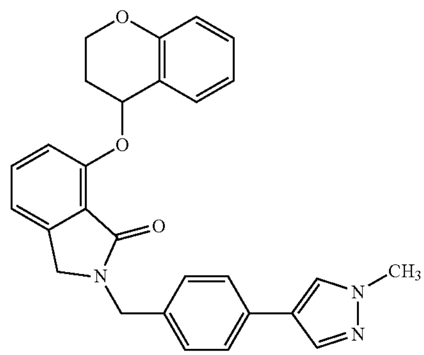 [SMILES: Cn1cc(-c2ccc(CN3Cc4cccc(OC5CCOc6ccccc65)c4C3=O)cc2)cn1] | racemate | 452.1 |

Formulation Example 1

| | |
|---|---|
| (1) compound obtained in Example 1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is passed through a 1 mm mesh sieve by using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of saccharose, titanium dioxide, talc and gum arabic. The coated tablets are glazed with beeswax to give 1000 coated tablets.

Formulation Example 2

| | |
|---|---|
| (1) compound obtained in Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

Experimental Example 1

Measurement of M1 Receptor Positive Allosteric Modulator (M1PAM) Activity

The activity of a test compound in the presence of acetylcholine at EC20 concentration (final concentration 0.6 nM), which affords an action corresponding to 20% of the maximum activity, was measured as PAM activity. The method is as follows. CHO-K1 cells forcibly expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and assay buffer A (Recording medium (DOJINDO LABORATORIES), 0.1% BSA (Wako Pure Chemical Industries, Ltd.), 2.5 µg/mL Fluo-4 AM (DOJINDO LABORATORIES), 0.08% Pluronic F127 (DOJINDO LABORATORIES), 1.25 mM probenecid (DOJINDO LABORATORIES)) containing a calcium indicator was added at 30 µL/well. The cells were left standing in the incubator at 37° C., 5% $CO_2$ for 30 min, and further left standing at room temperature for 30 min. A test compound prepared by diluting with assay buffer B (HBSS (Invitrogen), 20 mM HEPES (Invitrogen), 0.1% BSA) containing 2.4 nM acetylcholine was added at 10 µL/well, and the fluorescence was measured by FLIPRtetra (Molecular Devices) for 1 min every 1 second. With the definition that the amount of change in the fluorescence on addition of acetylcholine (final concentration 1 µM) is 100% and that on addition of DMSO instead of a test compound is 0%, the activity (%) of the test compound and the inflection point in the concentration-dependent curve of the test compound were calculated as IP values. The results are shown in Table 2.

TABLE 2

| Example No. | activity (%) at 10 μM | IP value (nM) |
|---|---|---|
| 1 | 102 | 7.0 |
| 2 | 105 | 8.7 |
| 3 | 104 | 9.1 |
| 4 | 101 | 13 |
| 5 | 102 | 20 |
| 6 | 90 | 31 |
| 7 | 114 | 32 |
| 8 | 99 | 33 |
| 9 | 93 | 34 |
| 10 | 103 | 54 |
| 11 | 102 | 65 |
| 12 | 57 | 36 |
| 13 | 102 | 43 |
| 16 | 106 | 47 |
| 17 | 118 | 120 |
| 18 | 107 | 60 |
| 19 | 91 | 110 |
| 20 | 100 | 80 |
| 21 | 105 | 96 |
| 22 | 103 | 190 |
| 25 | 113 | 190 |
| 26 | 96 | 4.1 |
| 27 | 97 | 6.4 |
| 28 | 120 | 7.0 |
| 29 | 89 | 7.5 |
| 30 | 104 | 190 |
| 31 | 105 | 8.5 |
| 32 | 110 | 10 |
| 33 | 98 | 77 |
| 34 | 92 | 10 |
| 35 | 134 | 14 |
| 38 | 118 | 44 |
| 39 | 97 | 58 |
| 40 | 117 | 64 |
| 42 | 107 | 85 |
| 43 | 99 | 210 |
| 48 | 100 | 360 |
| 53 | 90 | 270 |
| 54 | 106 | 160 |
| 59 | 136 | 57 |
| 60 | 115 | 320 |
| 61 | 113 | 37 |
| 65 | 76 | 63 |
| 66 | 101 | 69 |
| 68 | 109 | 72 |
| 69 | 103 | 410 |
| 72 | 102 | 88 |
| 73 | 99 | 24 |
| 76 | 108 | 7.2 |
| 77 | 103 | 39 |
| 78 | 104 | 10 |
| 79 | 114 | 29 |
| 80 | 100 | 5.6 |
| 81 | 57 | 170 |
| 86 | 104 | 17 |
| 223 | 103 | 19 |
| 224 | 107 | 38 |
| 225 | 104 | 51 |
| 226 | 98 | 30 |
| 227 | 99 | 10 |
| 228 | 118 | 94 |
| 229 | 117 | 6.1 |
| 230 | 113 | 10 |
| 231 | 106 | 24 |
| 234 | 91 | 38 |
| 235 | 105 | 14 |
| 236 | 109 | 10 |
| 237 | 108 | 23 |
| 239 | 109 | 6.1 |
| 241 | 101 | 13 |
| 242 | 110 | 8.2 |
| 243 | 104 | 37 |

TABLE 2-continued

| Example No. | activity (%) at 10 μM | IP value (nM) |
|---|---|---|
| 244 | 104 | 16 |
| 245 | 101 | 57 |
| 246 | 100 | 9.4 |
| 248 | 117 | 3.0 |
| 251 | 117 | 7.5 |
| 252 | 99 | 7.6 |
| 253 | 100 | 22 |
| 254 | 110 | 67 |
| 255 | 106 | 48 |
| 256 | 101 | 4.0 |
| 258 | 107 | 5.7 |
| 259 | 109 | 85 |
| 260 | 109 | 45 |
| 261 | 98 | 25 |
| 262 | 107 | 54 |
| 263 | 106 | 41 |
| 264 | 92 | 140 |
| 265 | 96 | 24 |
| 266 | 100 | 45 |
| 267 | 94 | 2.1 |
| 268 | 103 | 39 |
| 271 | 97 | 130 |
| 272 | 107 | 6.5 |
| 273 | 103 | 8.5 |
| 274 | 102 | 12 |
| 275 | 104 | 76 |
| 276 | 99 | 3.6 |
| 277 | 96 | 42 |
| 280 | 110 | 26 |
| 281 | 108 | 65 |
| 283 | 97 | 10 |
| 284 | 94 | 340 |
| 285 | 95 | 10 |
| 286 | 99 | 13 |
| 287 | 99 | 10 |
| 288 | 103 | 12 |
| 289 | 89 | 4.7 |
| 290 | 91 | 44 |
| 291 | 91 | 34 |
| 292 | 101 | 48 |
| 295 | 100 | 150 |
| 296 | 92 | 12 |
| 297 | 96 | 16 |
| 299 | 91 | 18 |
| 301 | 89 | 120 |
| 302 | 92 | 32 |
| 303 | 91 | 8.5 |
| 304 | 93 | 12 |
| 305 | 94 | 25 |
| 306 | 97 | 8.9 |
| 307 | 92 | 9.3 |
| 308 | 99 | 44 |
| 309 | 100 | 27 |
| 310 | 105 | 30 |
| 311 | 100 | 16 |
| 312 | 96 | 39 |
| 313 | 89 | 27 |
| 314 | 89 | 11 |
| 315 | 101 | 6.6 |
| 318 | 99 | 26 |
| 319 | 104 | 9.1 |
| 321 | 104 | 32 |
| 323 | 89 | 21 |
| 324 | 99 | 19 |
| 325 | 116 | 47 |
| 326 | 108 | 23 |
| 327 | 98 | 6.5 |
| 328 | 97 | 6.4 |
| 329 | 106 | 4.3 |
| 330 | 104 | 30 |
| 331 | 104 | 16 |
| 332 | 106 | 17 |
| 333 | 114 | 21 |
| 334 | 99 | 65 |
| 335 | 98 | 57 |
| 336 | 106 | 22 |
| 337 | 92 | 49 |
| 338 | 98 | 19 |

TABLE 2-continued

| Example No. | activity (%) at 10 μM | IP value (nM) |
|---|---|---|
| 339 | 106 | 70 |
| 340 | 106 | 3.8 |
| 341 | 93 | 63 |
| 342 | 96 | 73 |
| 343 | 94 | 29 |
| 344 | 97 | 55 |
| 346 | 85 | 2.1 |
| 347 | 97 | 10 |
| 348 | 97 | 74 |
| 349 | 104 | 12 |
| 352 | 94 | 4.4 |
| 353 | 97 | 46 |
| 354 | 93 | 270 |
| 355 | 95 | 4.3 |
| 356 | 101 | 49 |
| 357 | 90 | 51 |
| 358 | 91 | 77 |
| 359 | 96 | 93 |
| 360 | 105 | 72 |
| 361 | 100 | 76 |
| 362 | 98 | 30 |
| 363 | 94 | 6.6 |
| 364 | 86 | 31 |
| 365 | 104 | 44 |
| 366 | 104 | 42 |
| 367 | 101 | 28 |
| 368 | 99 | 10 |
| 369 | 103 | 54 |
| 370 | 97 | 14 |
| 371 | 99 | 13 |
| 372 | 109 | 46 |
| 373 | 103 | 45 |
| 374 | 103 | 16 |
| 375 | 99 | 10 |
| 376 | 106 | 6.9 |
| 377 | 83 | 7.6 |
| 378 | 98 | 33 |
| 379 | 90 | 14 |
| 380 | 102 | 22 |
| 381 | 103 | 7.8 |
| 382 | 99 | 70 |
| 383 | 86 | 48 |
| 384 | 91 | 7.8 |
| 385 | 85 | 2.6 |
| 386 | 86 | 1.4 |
| 387 | 102 | 7.1 |
| 388 | 102 | 30 |
| 389 | 93 | 32 |
| 390 | 90 | 71 |
| 391 | 100 | 10 |
| 392 | 105 | 16 |
| 393 | 89 | 5.0 |
| 394 | 109 | 7.1 |
| 395 | 96 | 65 |
| 396 | 95 | 33 |
| 397 | 95 | 25 |
| 398 | 99 | 20 |
| 399 | 94 | 97 |
| 400 | 88 | 56 |
| 401 | 92 | 48 |
| 402 | 104 | 4.6 |
| 403 | 102 | 57 |
| 404 | 87 | 53 |
| 405 | 95 | 1.8 |
| 406 | 97 | 40 |
| 407 | 89 | 74 |
| 408 | 99 | 5.6 |
| 409 | 96 | 3.4 |
| 410 | 99 | 19 |
| 411 | 102 | 61 |
| 412 | 101 | 8 |
| 413 | 104 | 10 |
| 414 | 103 | 69 |
| 415 | 106 | 16 |
| 416 | 98 | 13 |
| 417 | 96 | 16 |
| 418 | 95 | 9.1 |
| 419 | 102 | 7.3 |
| 420 | 101 | 39 |
| 421 | 112 | 39 |
| 422 | 107 | 12 |
| 423 | 96 | 90 |
| 424 | 106 | 88 |
| 425 | 102 | 86 |
| 426 | 102 | 8.8 |
| 427 | 111 | 31 |
| 428 | 106 | 14 |
| 429 | 109 | 11 |
| 430 | 110 | 17 |
| 431 | 103 | 6.8 |
| 432 | 92 | 52 |
| 433 | 101 | 10 |
| 434 | 95 | 26 |
| 435 | 102 | 30 |
| 436 | 106 | 41 |
| 437 | 98 | 78 |
| 438 | 101 | 14 |
| 439 | 96 | 13 |
| 440 | 100 | 70 |
| 441 | 100 | 44 |
| 442 | 100 | 38 |
| 443 | 101 | 31 |
| 444 | 100 | 17 |
| 445 | 100 | 28 |
| 446 | 107 | 26 |
| 447 | 93 | 5.2 |
| 448 | 102 | 6.1 |
| 449 | 99 | 9.3 |
| 450 | 102 | 10 |
| 451 | 105 | 11 |
| 452 | 102 | 45 |
| 453 | 97 | 56 |
| 454 | 86 | 30 |
| 455 | 86 | 60 |
| 456 | 91 | 46 |
| 457 | 91 | 8.6 |
| 458 | 93 | 12 |
| 459 | 93 | 32 |
| 460 | 96 | 17 |
| 461 | 95 | 50 |

INDUSTRIAL APPLICABILITY

The compound of the present invention is useful as medicaments such as a cholinergic muscarinic M1 receptor positive allosteric modulator, a prophylactic or therapeutic drug for Alzheimer's disease, schizophrenia, pain, sleep disorder and the like, and the like.

This application is based on a patent application No. 2012-253708 filed in Japan, the entire contents of which are incorporated by reference herein.

The invention claimed is:

1. A compound represented by formula (1)

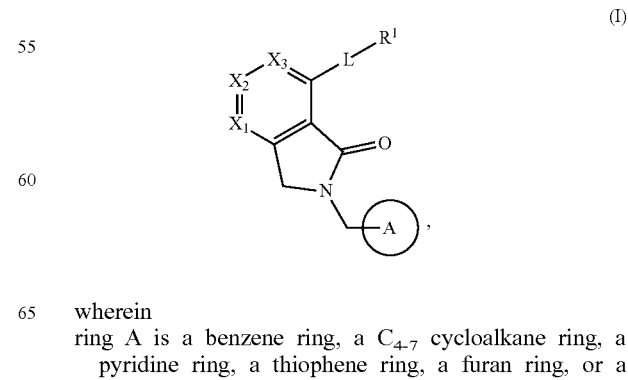

wherein
ring A is a benzene ring, a $C_{4-7}$ cycloalkane ring, a pyridine ring, a thiophene ring, a furan ring, or a piperidine ring, each of which is optionally substituted by from 1 to 3 substituents selected from the group consisting of
(1) a halogen atom,
(2) a cyano group,
(3) a carbamoyl group optionally mono-substituted by a $C_{1-6}$ alkyl group optionally substituted by from 1 to 3 tetrahydrofuryl groups,
(4) a $C_{1-6}$ alkoxy-carbonyl group,
(5) a $C_{3-6}$ cycloalkyl group, and
(6) a pyrazolyl group, a piperidyl group, a pyridyl group, a pyridazinyl group, a triazolyl group, an imidazolyl group, an isoxazolyl group, a pyrazolopyridyl group, or a 4,5,6,7-tetrahydropyrazolopyridyl group, each of which optionally has from 1 to 3 substituents selected from the group consisting of
(i) a halogen atom,
(ii) a $C_{1-6}$ alkyl group optionally substituted by from 1 to 3 substituents selected from the group consisting of a halogen atom and a $C_{3-6}$ cycloalkyl group, and
(iii) a tetrahydropyranyl group;
L is —O—,
$R^1$ is
(I) a $C_{3-8}$ cycloalkyl group, a phenyl group, a pyridyl group, a tetrahydropyranyl group, a 6,7-dihydro-5H-cyclopentapyridyl group, or a pyrazolyl group, each of which is optionally substituted by from 1 to 3 substituents selected from the group consisting of
(1) a halogen atom,
(2) a cyano group,
(3) a nitro group,
(4) an amino group,
(5) a hydroxy group,
(6) a $C_{1-6}$ alkyl group optionally having from 1 to 5 substituents selected from
(i) a halogen atom,
(ii) a cyano group,
(iii) a hydroxy group, and
(iv) a $C_{1-6}$ alkoxy group,
(7) a $C_{1-6}$ alkoxy group optionally having from 1 to 3 halogen atoms,
(8) a $C_{2-6}$ alkenyl group, and
(9) a $C_{3-6}$ cycloalkyl group; or
(II) a $C_{1-6}$ alkyl group substituted by from 1 to 3 substituents selected from the group consisting of
(1) a hydroxy group,
(2) a $C_{1-6}$ alkoxy-carbonyl group,
(3) a carboxy group,
(4) a piperidylcarbonyl group,
(5) a $C_{3-6}$ cycloalkyl group optionally substituted by from 1 to 3 $C_{1-6}$ alkyl groups,
(6) a phenyl group substituted by from 1 to 3 halogen atoms, and
(7) a tetrahydrofuryl group, a pyrrolidinyl group, a piperidyl group, a pyrazolyl group, a tetrahydropyranyl group, a pyridyl group, or a 7-oxabicyclo[2.2.1]heptyl group, each of which optionally has from 1 to 3 substituents selected from the group consisting of a halogen atom and a $C_{1-6}$ alkoxy-carbonyl group;
$X_1$, $X_2$, and $X_3$ are selected from following combinations:
(1) $X_1$ is —CH=, $X_2$ is —CH=, and $X_3$ is —N=;
(2) $X_1$ is —N=, $X_2$ is —CH=, and $X_3$ is —N=; and
(3) $X_1$ is —CH=, $X_2$ is —CH=, and $X_3$ is —CH=;
or a salt thereof.

2. The compound according to claim 1, wherein $R^1$ is a $C_{3-8}$ cycloalkyl group, a phenyl group, a pyridyl group, or a tetrahydropyranyl group, each of which is optionally substituted by from 1 to 3 substituents selected from the group consisting of
(1) a halogen atom,
(2) a cyano group,
(3) a hydroxy group,
(4) a $C_{1-6}$ alkyl group optionally having from 1 to 5 substituents selected from the group consisting of
(i) a halogen atom,
(ii) a cyano group,
(iii) a hydroxy group, and
(iv) a $C_{1-6}$ alkoxy group,
(5) a $C_{1-6}$ alkoxy group optionally having from 1 to 3 halogen atoms, and
(6) a $C_{3-6}$ cycloalkyl group; and
ring A is a benzene ring or a pyridine ring, each of which is substituted by from 1 to 3 substituents selected from
(1) a halogen atom,
(2) a carbamoyl group,
(3) a pyrazolyl group substituted by from 1 to 3 $C_{1-6}$ alkyl groups, and
(4) a triazolyl group substituted by from 1 or 2 $C_{1-6}$ alkyl groups;
or a salt thereof.

3. The compound according to claim 1, wherein $R^1$ is a phenyl group or a pyridyl group, each of which is optionally substituted by from 1 to 3 substituents selected from the group consisting of
(1) a halogen atom,
(2) a cyano group,
(3) a $C_{1-6}$ alkyl group optionally having from 1 to 3 halogen atoms,
(4) a $C_{1-6}$ alkoxy group optionally having from 1 to 3 halogen atoms, and
(5) a $C_{3-6}$ cycloalkyl group; and
ring A is a benzene ring or a pyridine ring, each of which is substituted by from 1 to 3 substituents selected from the group consisting of
(1) a halogen atom,
(2) a carbamoyl group,
(3) a pyrazolyl group substituted by from 1 to 3 $C_{1-6}$ alkyl groups, and
(4) a triazolyl group substituted by from 1 or 2 $C_{1-6}$ alkyl groups;
or a salt thereof.

4. The compound according to claim 1, wherein $R^1$ is (I) a $C_{3-8}$ cycloalkyl group, a phenyl group, a pyridyl group, or a tetrahydropyranyl group, each of which is substituted by from 1 to 3 substituents selected from the group consisting of
(1) a halogen atom,
(2) a cyano group,
(3) a hydroxy group, and
(4) a $C_{1-6}$ alkyl group substituted by from 1 to 3 halogen atoms; or
(II) a $C_{1-6}$ alkyl group substituted by from 1 to 3 substituents selected from the group consisting of
(1) a phenyl group substituted by from 1 to 3 halogen atoms, and
(2) a tetrahydrofuryl group; and
ring A is a benzene ring or a pyridine ring, each of which is substituted by from 1 to 3 substituents selected from the group consisting of
(1) a halogen atom,
(2) a carbamoyl group, (3) a pyrazolyl group substituted by from 1 to 3 $C_{1-6}$ alkyl groups, and
(4) a triazolyl group substituted by 1 or 2 $C_{1-6}$ alkyl groups;
or a salt thereof.

5. The compound according to claim 1, wherein $R^1$ is a phenyl group or a pyridyl group, each of which is substituted by from 1 to 3 substituents selected from the group consisting of
(1) a halogen atom,
(2) a cyano group, and
(3) a $C_{1-6}$ alkyl group substituted by from 1 to 3 halogen atoms;
ring A is a benzene ring or a pyridine ring, each of which is substituted by from 1 to 3 substituents selected from the group consisting of
(1) a halogen atom,
(2) a carbamoyl group,
(3) a pyrazolyl group substituted by from 1 to 3 $C_{1-6}$ alkyl groups, and
(4) a triazolyl group substituted by from 1 or 2 $C_{1-6}$ alkyl groups; and
$X_1$, $X_2$, and $X_3$ are selected from following combinations:
(1) $X_1$ is —CH=, $X_2$ is —CH=, and $X_3$ is —N=; and
(2) $X_1$ is —N=, $X_2$ is —CH=, and $X_3$ is —N=;
or a salt thereof.

6. 2-(4-(1-Methyl-1H-pyrazol-4-yl)benzyl)-7-((tetrahydrofuran-2-yl)methoxy)isoindolin-1-one, or a salt thereof.

7. 3-Fluoro-2-((2-(4-(1-methyl-1H-pyrazol-4-yl)benzyl)-3-oxo-2,3-dihydro-1H-isoindol-4-yl)oxy)benzonitrile, or a salt thereof.

8. 4-((2,4-Difluorobenzyl)oxy)-6-(4-(1-methyl-1H-1,2,3-triazol-4-yl)benzyl)-6,7-dihydro-5H-pyrrolo[3,4-d]pyrimidin-5-one, or a salt thereof.

9. 4-((4-(2-Fluoro-4-(trifluoromethyl)phenoxy)-3-oxo-1,3-dihydro-2H-pyrrolo[3,4-c]pyridin-2-yl)methyl)benzamide, or a salt thereof.

10. A pharmaceutical composition comprising the compound according to claim 1, or a salt thereof, and a pharmaceutically acceptable carrier.

11. The pharmaceutical composition according to claim 10, which is a cholinergic muscarinic M1 receptor positive allosteric modulator.

12. A method of cholinergic muscarinic M1 receptor positive allosteric modulation in a mammal, comprising administering an effective amount of the compound according to claim 1, or a salt thereof to said mammal.

* * * * *